US011993648B2

(12) United States Patent
Kuburas et al.

(10) Patent No.: US 11,993,648 B2
(45) **Date of Patent: *May 28, 2024**

(54) SCREENING METHOD FOR IDENTIFYING ANTI-PACAP ANTIBODIES OR ANTIBODY FRAGMENTS SUITABLE FOR USE IN TREATING OR PREVENTING PACAP-ASSOCIATED PHOTOPHOBIA OR LIGHT AVERSION

(71) Applicants: H. LUNDBECK A/S, Valby (DK); The University of Iowa Research Foundation, Iowa City, IA (US)

(72) Inventors: Adisa Kuburas, North Liberty, IA (US); Bianca Mason, Iowa City, IA (US); Levi P. Sowers, Iowa City, IA (US); Andrew F. Russo, Iowa City, IA (US); Maria-Cristina Loomis, Bothell, WA (US); Leon F. Garcia-Martinez, Woodinville, WA (US); Benjamin H. Dutzar, Seattle, WA (US); Daniel S. Allison, Lake Forest Park, WA (US); Katherine Lee Hendrix, Renton, WA (US); Ethan W. Ojala, Snohomish, WA (US); Pei Fan, Bothell, WA (US); Jeffrey T. L. Smith, Bellevue, WA (US); John A. Latham, Seattle, WA (US); Charlie Karasek, Seattle, WA (US); Jenny Mulligan, Lake Forest Park, WA (US); Michelle Scalley-Kim, Seattle, WA (US); Erica Stewart, Seattle, WA (US); Vanessa Lisbeth Rubin, Seattle, WA (US); Jens J. Billgren, Seattle, WA (US)

(73) Assignees: H. LUNDBECK A/S, Valby (DK); The University of Iowa Research Foundation

( * ) Notice: Subject to any disclaimer, the term of this patent is extended or adjusted under 35 U.S.C. 154(b) by 0 days.

This patent is subject to a terminal disclaimer.

(21) Appl. No.: 16/953,443

(22) Filed: Nov. 20, 2020

(65) Prior Publication Data

US 2021/0324068 A1 Oct. 21, 2021

Related U.S. Application Data

(62) Division of application No. 15/130,215, filed on Apr. 15, 2016, now Pat. No. 10,844,116.

(Continued)

(51) Int. Cl.

| | |
|---|---|
| ***A61K 39/395*** | (2006.01) |
| ***A61P 25/06*** | (2006.01) |
| ***C07K 16/26*** | (2006.01) |
| *A61K 39/00* | (2006.01) |
| *A61K 45/06* | (2006.01) |
| *A61K 49/00* | (2006.01) |
| *C07K 14/575* | (2006.01) |

(Continued)

(52) U.S. Cl.

CPC .......... *C07K 16/26* (2013.01); *A61K 39/3955* (2013.01); *A61P 25/06* (2018.01); *A61K 39/39566* (2013.01); *A61K 2039/505* (2013.01); *A61K 45/06* (2013.01); *A61K 49/0004* (2013.01); *A61K 49/0008* (2013.01); *C07K 14/57536* (2013.01); *C07K 14/57563* (2013.01); *C07K 16/4241* (2013.01); *C07K 2317/21* (2013.01); *C07K 2317/24* (2013.01); *C07K 2317/33* (2013.01); *C07K 2317/34* (2013.01); *C07K 2317/40* (2013.01); *C07K 2317/50* (2013.01); *C07K 2317/54* (2013.01); *C07K 2317/55* (2013.01); *C07K 2317/56* (2013.01); *C07K 2317/565* (2013.01); *C07K 2317/622* (2013.01); *C07K 2317/76* (2013.01); *C07K 2317/92* (2013.01); *G01N 33/5088* (2013.01); *G01N 33/74* (2013.01); *G01N 2333/5757* (2013.01); *Y02A 50/30* (2018.01)

(58) Field of Classification Search

CPC . A61K 39/3955; C07K 16/26; C07K 2317/76

See application file for complete search history.

(56) References Cited

U.S. PATENT DOCUMENTS 5,198,542 A 3/1993 Onda et al.
5,486,472 A 1/1996 Suzuki et al.

(Continued)

FOREIGN PATENT DOCUMENTS

EP 0522159 12/2001
EP 1731168 12/2006

(Continued)

OTHER PUBLICATIONS

Rossi et al., Apr. 2015 (Epub Mar. 19, 2015). Headache. 55(4): 600-604; pp. 1-8 as printed.*

(Continued)

*Primary Examiner* — Zachary C Howard

(74) *Attorney, Agent, or Firm* — Robin L. Teskin; Baker, Donelson, Bearman, Caldwell & Berkowitz PC

(57) ABSTRACT

This invention relates to methods of screening for anti-PACAP antibodies, or anti-PACAP receptor antibodies, and antigen binding fragments thereof, for potential use in treating or preventing PACAP-associated photophobia or light aversion, and therapeutic compositions containing and methods of using anti-PACAP antibodies, or anti-PACAP receptor antibodies, and antigen binding fragments thereof.

9 Claims, 33 Drawing Sheets

Specification includes a Sequence Listing.

Related U.S. Application Data

(60) Provisional application No. 62/148,583, filed on Apr. 16, 2015, provisional application No. 62/148,557, filed on Apr. 16, 2015, provisional application No. 62/148,643, filed on Apr. 16, 2015, provisional application No. 62/148,640, filed on Apr. 16, 2015, provisional application No. 62/148,562, filed on Apr. 16, 2015, provisional application No. 62/148,596, filed on Apr. 16, 2015, provisional application No. 62/148,550, filed on Apr. 16, 2015.

(51) Int. Cl.

| | |
|---|---|
| *C07K 16/42* | (2006.01) |
| *G01N 33/50* | (2006.01) |
| *G01N 33/74* | (2006.01) |

(56) References Cited

U.S. PATENT DOCUMENTS

| | | | |
|---|---|---|---|
| 5,858,787 | A | 1/1999 | Onda et al. |
| 5,892,004 | A | 4/1999 | Ohtaki et al. |
| 6,399,316 | B1 | 6/2002 | Onda et al. |
| 7,615,219 | B2 | 11/2009 | Freson et al. |
| 9,255,154 | B2 | 2/2016 | Feldhaus et al. |
| 9,290,567 | B2 | 3/2016 | Bohrmann et al. |
| 9,365,653 | B2 | 6/2016 | Xu et al. |
| 2002/0155533 | A1 | 10/2002 | Onda et al. |
| 2002/0182729 | A1 | 12/2002 | Dicicco-Bloom et al. |
| 2004/0014095 | A1 | 1/2004 | Gerber et al. |
| 2004/0038888 | A1 | 2/2004 | Mercer et al. |
| 2005/0129687 | A1 | 6/2005 | Vizzard et al. |
| 2006/0062785 | A1 | 3/2006 | Freson et al. |
| 2007/0054843 | A1 | 2/2007 | Yeomans et al. |
| 2007/0149439 | A1 | 6/2007 | Dicicco-Bloom et al. |
| 2007/0202099 | A1 | 8/2007 | Nooka et al. |
| 2010/0068208 | A1 | 3/2010 | Ogi et al. |
| 2010/0112601 | A1 | 5/2010 | Shirakawa et al. |
| 2010/0129372 | A1 | 5/2010 | Freson et al. |
| 2012/0294797 | A1 | 11/2012 | Kovacevich et al. |
| 2012/0294802 | A1 | 11/2012 | Russo et al. |
| 2012/0309696 | A1 | 12/2012 | Dores |
| 2013/0177568 | A1 | 7/2013 | Bhatt et al. |
| 2013/0267689 | A1 | 10/2013 | Latham et al. |
| 2013/0302399 | A1 | 11/2013 | Feldhaus et al. |
| 2013/0310541 | A1 | 11/2013 | Bohrmann et al. |
| 2014/0370019 | A1 | 12/2014 | Bruenker et al. |
| 2015/0010560 | A1 | 1/2015 | Xu et al. |
| 2016/0304604 | A1 | 10/2016 | Loomis et al. |
| 2016/0362488 | A1 | 12/2016 | Loomis et al. |
| 2016/0376363 | A1 | 12/2016 | Kuburas et al. |

FOREIGN PATENT DOCUMENTS

| | | |
|---|---|---|
| EP | 2009026 | 12/2008 |
| JP | H06-500001 A | 1/1994 |
| JP | 2002-510500 A | 4/2002 |
| WO | 199114786 | 10/1991 |
| WO | WO 91/14786 | 10/1991 |
| WO | WO 1996/039439 | 12/1996 |
| WO | WO 1998/024900 | 6/1998 |
| WO | 199951762 | 10/1999 |
| WO | WO 1999/051762 | 10/1999 |
| WO | WO 2001/023420 | 4/2001 |
| WO | WO 2003/092716 | 11/2003 |
| WO | WO 2004/006839 | 1/2004 |
| WO | WO 2004/062684 | 7/2004 |
| WO | WO 2005/041757 | 5/2005 |
| WO | WO 2005/072385 | 8/2005 |
| WO | WO 2006/052468 | 5/2006 |
| WO | 2006118328 | 11/2006 |
| WO | WO 2009/000894 | 12/2008 |
| WO | WO 2009/033489 | 3/2009 |
| WO | 2010/005068 | 1/2010 |
| WO | WO 2010/007175 | 1/2010 |
| WO | WO 2012/010647 | 1/2012 |
| WO | WO 2012/106407 | 8/2012 |
| WO | 2015058861 | 4/2015 |
| WO | WO 2015/127288 | 8/2015 |
| WO | WO 2016/168757 | 10/2016 |
| WO | WO 2016/168760 | 10/2016 |
| WO | WO 2016/168762 | 10/2016 |
| WO | WO 2016/168768 | 10/2016 |
| WO | 2017/106578 | 6/2017 |

OTHER PUBLICATIONS

Grider, J R et al. "Regulation of the descending relaxation phase of intestinal peristalsis by PACAP." Journal of the autonomic nervous system vol. 50,2 (1994): 151-9. doi:10.1016/0165-1838(94)90005-1.

Atsuro Miyata, Structure and function of PACAP as a brain gut peptide, Journal of Clinical and Experimental Medicine, vol. 2007, vol. 223, No. 7, pp. 569 to 572.

Seeliger, Stephan et al. "Pituitary adenylate cyclase activating polypeptide: an important vascular regulator in human skin in vivo." The American journal of pathology vol. 177,5 (2010): 2563-75. doi:10.2353/ajpath.2010.090941.

Alaoui-Ismaili et al. "Design of Second Generation Therapeutic Recombinant Bone Morphogenetic Proteins," Cytokine Growth Factor Rev. 2009; 20:501-507.

Bowie et al. "Deciphering the Message in Protein Sequences: Tolerance to Amino Acid Substitutions," Science. Mar. 16, 1990;247(4948):1306-10.

Burgess et al. "Possible Dissociation of the Heparin-Binding and Mitogenic Activities of Heparin-Binding (Acidic Fibroblast) Growth factor-1 From Its Receptor-Binding Activities by Site-Directed Mutagenesis of a Single Lysine Residue," J Cell Biol . Nov. 1990; 111(5 Pt 1):2129-38.

Casset et al., "A Peptide Mimetic of an anti-CD4 Monoclonal Antibody by Rational Design," Biochem Biophys Res Commun . Jul. 18, 2003;307(1):198-205.

Chen etal., "Selection and Analysis of an Optimized anti-VEGF Antibody: Crystal Structure of an Affinity-Matured Fab in Complex With Antigen," J Mol Biol. Nov. 5, 1999;293(4):865-81.

Csaba Z., et al. "Local effect of PACAP and VIP on testicular function in immature and adult rats," Peptides, 1997; 18 (10): 1561-7.

Dodick, "Migraine," Lancet. Mar. 31, 2018;391(10127):1315-1330.

Guo et al., "Protein Tolerance to Random Amino Acid Change," Proc Natl Acad Sci USA. Jun. 22, 2004;101 (25):9205-10.

Holm et al., "Functional Mapping and Single Chain Construction of the Anti-Cytokeratin 8 Monoclonal Antibody TS1," Mol Immunol. Feb. 2007;44(6):1075-84.

MacCallum et al. "Antibody-antigen Interactions: Contact Analysis and Binding Site Topography," J Mol Biol . Oct. 11, 1996;262(5):732-45.

Noseda et al., "Current Understanding of Photophobia, Visual Networks and Headaches," Cephalalgia Nov. 2019;39(13):1623-1634.

Pascalis et al. "Grafting of 'Abbreviated' Complementarity-Determining Regions Containing Specificity-Determining Residues Essential for Ligand Contact to Engineer a Less Immunogenic Humanized Monoclonal Antibody," J Immunol Sep. 15, 2002;169(6):3076-84.

Pawson et al. "Assembly of Cell Regulatory Systems Through Protein Interaction Domains," Science. Apr. 18, 2003;300(5618):445-52.

Sundrum et al., "Pituitary Adenylate Cyclase-Activating Polypeptide Receptors in the Trigeminovascular System: Implications for Migraine," Br J Pharmacol. Nov. 2018;175(21):4109-4120.

Vajdos et al., "Comprehensive Functional Maps of the Antigen-Binding Site of an anti-ErbB2 Antibody Obtained With Shotgun Scanning Mutagenesis," J Mol Biol . Jul. 5, 2002;320(2):415-28.

Wu et al., "Humanization of a Murine Monoclonal Antibody by Simultaneous Optimization of Framework and CDR Residues," J Mol Biol. Nov. 19, 1999;294(1):151-62.

(56) References Cited

OTHER PUBLICATIONS

Wu et al., "Photophobia in Neurologic Disorders," Transl Neurodegener. Sep. 20, 2017;6:26.
Nair DT, et al. "Epitope recognition by diverse antibodies suggests conformational convergence in an antibody response," J Immunol. Mar. 1, 2002;168(5):2371-82.
Ahmadzadeh V, et al. "Antibody humanization methods for development of therapeutic applications," Monoclon Antib Immunodiagn Immunother. Apr. 2014;33(2):67-73.
Almagro J, et al. "Antibody engineering: Humanization, affinity maturation, and selection techniques" Therapeutic Monoclonal Antibodies: From Bench to Clinic, Oct. 2009, Wiley, pp. 311-334.
Brown M, et al. "Tolerance of single, but not multiple, amino acid replacements in antibody VH CDR 2: a means of minimizing B cell wastage from somatic hypermutation?" J Immunol. May 1, 1996;156(9):3285-91.
Cochaud S, et al. "Neuropeptides of the VIP family inhibit glioblastoma cell invasion," J Neurooncol. Mar. 2015; 122(1):63-73.
Fleischer N, et al. "Studies of ACTH antibodies and their reactions with inactive analogues of ACTH," Endocrinology. May 1966;78(5): 1067-75.
Freson K, et al. "The pituitary adenylate cyclase-activating polypeptide is a physiological inhibitor of platelet activation," J Clin Invest. Mar. 2004;113(6):905-12.
Rubio-Beltrán E, et al. "PACAP38 and PAC1 receptor blockade: a new target for headache?" J Headache Pain. Aug. 7, 2018;19(1):64.
Shimazaki Y, et al. "Epitope analysis using membrane-immobilized avidin and protein A," Protein Expr Purif. Jun. 2012;83(2):177-81.
Walter S, et al. "TEV-48125: a review of a monoclonal CGRP antibody in development for the preventive treatment of migraine," Curr Pain Headache Rep. Mar. 2015;19(3):6.
Waschek JA, et al. "PACAP and migraine headache: immunomodulation of neural circuits in autonomic ganglia and brain parenchyma," J Headache Pain. Mar. 13, 2018;19(1):23.
White A, et al. "Characterisation of monoclonal antibodies to adrenocorticotrophin," J Immunol Methods. May 23, 1985;79(2):185-94.
Rudikoff, S. et al., "Single amino acid substitution altering antigen-binding specificity", PNAS, 1982; 79: 1979-1983.
Suzuki, N. et al., "Production of Immunoreactive Pituitary Adenylate Cyclase Activating Polypeptide (PACAP) by Human Neuroblastoma Cells, IMR-32: Detection and Characterization with Monoclonal and Polyclonal Antibodies against Different Epitopes of PACAP", J. Biochem., 1993; 113: 549-556.
Syed, A. et al., "Pituitary Adenylate Cyclase-Activating Polypeptide (PACAP) Potentially Dilates Middle Meningeal Arteries: Implications for Migraine", J. Mol. Neurosci., 2012; 48: 574-583.
Amin, F.M. et al., "Headache and prolonged dilation of the middle meningeal artery by PACAP 38 in healthy volunteers", Cephalalgia, 2011; 32(2): 140-149.
Amin, F.M. et al., "Investigation of the pathoshysiological mechanisms of migraine attacks induced by pituitary adenylate cyclase-activating polypeptide-38", Brain, 2014; 137: 779-794.
Baun, M. et al., "Pharmacological characterization and expression of VIP and PACAP receptors in isolated cranial arteries of the rat", European Journal of Pharmacology, 2011; 670: 186-194.
Bhatt, D.K. et al., "PACAP-38 infusion causes sustained vasodilation of the middle meningeal artery in the rat: Possible involvement of mast cells", Cephalalgia, 2014; 0(0): 1-10.
Boni, L.J. et al., "The in vivo effect of VIP, PACAP-38 and PACAP-27 and mRNA expression of their receptors in rat middle meningeal artery", Cephalalgia, 2009; 29: 837-847.
Botz, B. et al., "Role of pituitary Adenylate-Cyclase Activating Polypeptide and Tac1 gene derived tachykinins in sensory, motor and vascular functions under normal and neuropathic conditions", Peptides, 2013; 43: 105-112.
Chan, K.Y. et al., "Pharmacological characterization of VIP and PACAP receptors in the human meningeal and coronary artery", Cephalalgia, 2011; 31(2): 181-189.
Chen, D. et al., "Pituitary adenylyl cyclase-activating peptide: A pivotal modulator of glutamatergic regulation of the surachiasmatic circadian clock", PNAS, 1999; 96(23): 13468-13473.
Dickson, L. and Finlayson, K. "VPAC and PAC receptors: From ligands to function", Pharmacology & Therapeutics, 2009; 121: 294-316.
Edvinsson, L., "PACAP and its receptors in migraine pathophysiology: Commentary on Walker et al., Br J Pharmacol 171: 1521-1533", British Journal of Pharmacology, 2015; 172: 4782-4784.
Farnham, M.M.J. and Pilowsky, P.M., "The role of PACAP in central cardiorespiratory regulation", Respiratory Physiology and Neurobiology, 2010; 174: 65-75.
Freson, K. et al., "PACAP and its receptor VPACI regulate megakaryocyte maturation: therapeutic implications", Blood, Feb. 15, 2008; 111(4): 1885-1893.
Grände, G. et al., "Comparison of responses to vasoactive drugs in human and rat cerebral arteries using myography and pressurized cerebral artery method", Cephalalgia, 2012; 33(3): 152-159.
Harmar, A.J. et al., "Pharmacology and functions of receptors for vasoactive intestinal peptide and pituitary adenylate cyclase-activating polypeptide: IUPHAR Review 1", British Journal of Pharmacology, 2012; 166: 4-17.
Kaiser, E.A. and Russo, A.F., "CGRP and migraine: Could PACAP play a role too?", Neuropeptides, 2013; 47: 451-461.
Khan, S. et al., "Sphenopalatine ganglion neuromodulation in migraine: What is the rationale?", Cephalalgia, 2014; 34(5): 382-391.
Kumar, S. et al., "Crystal Structure of the PACIR Extracellular Domain Unifies a Consensus Fold for Hormone Recognition by Class B G-Protein Coupled Receptors", PLOS One, 2011; 6(5): 1-11.
Markovics, A. et al., "Pituitary adenylate cyclase-activating polypeptide plays a key role in nitroglycerol-induced trigeminovascular activation in mice", Neurobiology of Disease, 2012; 45: 633-644.
Moody, T.W. et al., "VIP and PACAP. Recent insights into their functions/roles in physiology and disease from molecular and genetic studies", Curr Opin Endocrinol Diabetes Obes., Feb. 2011; 18(1): 61-67.
Nassini, R. et al., "The 'headache tree' via umbellulone and TRPA1 activates the trigeminovascular system", Brain, 2012; 135: 376-390.
Ng, S.Y.L. et al., "Agnathan VIP, PACAP and Their Receptors: Ancestral Origins of Today's Highly Diversified Forms", PLOS One, Sep. 2012; 7(9): 1-15.
Noseda, R. et al., "A neural mechanism for exacerbation of headache by light", Nature Neuroscience, Feb. 2010; 13(2): 239-246.
Schmidt-Choudhury, A. et al., "Mast cells contribute to PACAP-induced dermal oedema in mice", Regulatory Peptides, 1999; 82: 65-69.
Schwarzhoff, R. et al., "Specific monoclonal antibodies neutralize the action of PACAP 1-27 or PACAP 1-38 on intestinal muscle strips in vitro", Regulatory Peptides, 1995; 55: 57-66.
Schytz, H.W. et al., "Cutaneous nociception and neurogenic inflammation evoked by PACAP38 and VIP", J Headache Pain, 2010; 11: 309-316.
Schytz, H.W. et al., "PACAP38 induces migraine-like attacks in patients with migraine without aura", Brain, 2009; 132: 16-25.
Schytz, H.W. et al., "The PACAP Receptor: A Novel Target for Migraine Treatment", Neurotherapeutics, 2010; 7(2): 191-196.
Schytz, H.W. et al., "What have we learnt from triggering migraine?", Curr Opin Neruol, 2010; 23: 259-265.
Sun, C. et al., "Solution structure and mutational analysis of pituitary adenylate cyclase-activating polypeptide binding to the extracellular domain of PACI-$R_S$", PNAS, 2007; 104(19): 7875-7880.
Tuka, B. et al., "Alterations in PACAP-38-like immunoreactivity in the plasma during ictal and interictal periods of migraine patients", Cephalalgia, 2013; 0(0): 1-11.
Tuka, B. et al., "Peripheral and central alterations of pituitary adenylate cyclase activating polypeptide-like immunoreactivity in the rat in response to activation of the trigeminovascular system", Peptides, 2012; 33: 307-316.
Vécsei, L. et al., "Role of PACAP in migraine headaches", Brain (Scientific Commentaries) 2014; 137: 650-651.

(56) References Cited

OTHER PUBLICATIONS

Wang, Z.-Y. et al., "Distribution and effects of pituitary adenylate cyclase-activating peptide in the rabbit eye", Neuroscience, 1995; 69(1): 297-308.
Warren, J.B. et al., "Pituitary Adenylate Cyclase Activating Polypeptide is a Potent Vasodilator in Humans", Journal of Cardiovascular Pharmacology, 1992; 20(1): 83-87.
Yada, T. et al., "Pituitary adenylate cyclase-activating polypeptide (PACAP) is an islet substance serving as an intra-islet amplifier of glucose-induced insulin secretion in rats", Journal of Physiology, 1997; 505.2: 319-328.
Zagami, A.S. et al., "Pituitary adenylate cyclase activating polypeptide and migraine", Annals of Clinical and Translational Neurology, 2014; 1(12): 1036-1040.
Zhang, Y. et al., "Capsaicin-evoked release of pituitary adenylate cyclase activating peptide (PACAP) and calcitonin gene-related peptide (CGRP) from rat spinal cord in vivo", Regulatory Peptides, 1997; 69: 83-87.

* cited by examiner

Figure 1A

Antibody Variable Heavy Chain Protein Features

| Sequence Name | FR1 | CDR1 | FR2 | CDR2 |
|---|---|---|---|---|
| Ab1 | QSVEESGGRLVTPGTPLTLTCTVSGFSLS | SAVMN | WVRQAPGKGLEWIG | SIVASGTTYYASWANG |
| Ab1.H | EVQLVESGGGLVQPGGSLRLSCAASGFTVS | SAVMN | WVRQAPGKGLEWIG | SIVASGTTYYASSANG |
| Ab2 | QSVEESGGRLVTPGTPLTLTCTVSGFSLS | GAAMN | WVRQAPGKGLEWIG | VIGNSGSTYYASWAKG |
| Ab3 | QEQLVESGGGLVQPEGSLTLTCTASGFSFS | SSDYMC | WVRQAPGKGLEWIG | CIDAGSSGDTYFASWAKG |
| Ab4 | QSVEESGGRLVTPGTPLTLTCTVSGFSLS | SYDMS | WVRQAPGKGLEYIG | IINTNDDTWYASWVKG |
| Ab5 | QSVEESGGRLVTPGTPLTLTCTVSGFSLS | SYAMI | WVRQAPGKGLEWIG | IIYDNGDTYYASWAKG |
| Ab6 | QQLEQSGGGAEGGLVKPGGSLELCCKASGFSLS | STYWMC | WVRQAPGKGLEWIG | CIYTGSGSTDYASWVNG |
| Ab7 | QSVEESGGRLVTPGTPLTLTCTASGIDLS | GYAMG | WVRQAPGKGLEWIG | DISTYGTTDYASWVNG |
| Ab8 | QQLEQSGGGAEGGLVKPGGSLELCCKASGFSLT | TSHWMC | WVRQAPGKGLNWIG | CISAGSGDADYATWVDA |
| Ab9 | QQLEQSGGGAEGGLVKPGGSLKLSCKASGFTIS | RDYWIC | WVRQAPGKGLEWIG | CISAGGGSTDYANWVNG |
| Ab11 | QSVEESGGRLVTPGTPLTLTCTASGFSLS | RYAMG | WVRQAPGKGLEWIG | DISTYGTTDYASWVNG |
| Ab12 | QSVEESGGRLVTPGTPLTLTCTASGFSLS | SYAMG | WVRQAPGKGLEWIG | DISTYGTTDYASWVYG |
| Ab13 | QSVEESGGRLVTPGTPLTLTCTVSGFSLS | SAAMN | WVRQAPGKGLEWIG | IIDNTAGTYYAPWAKG |
| Ab14 | QSVEASGGRLVTPGTPLTLTCTVSGFSLS | SAAMN | WVRQAPGKGLEWIG | FIEYSKNIVYASWAKG |
| Ab15 | QSVEASGGHLVTPGTPLTLTCTVSGFSLS | SAAMN | WVRQAPGKGLEWIG | SVDERQNKYYASWAKG |
| Ab16 | QSVEESGGRLVTPGTPLTLTCTVSGFSLS | SAAMS | WVRQAPGKGLEWIG | IIDDSGNTYYASWAKA |
| Ab17 | QSVEESGGRLVTPGTPLTLTCTVSGFSLS | SAAMN | WVRQAPGKGLEWIG | IFDPYSSTYYASWAKG |
| Ab18 | QSVEESGGRLVTPGTPLTLTCTVSGFSLS | SAALS | WVRQAPGKGLEWIG | IIDKGVMSYYASWAKG |
| Ab19 | QSVEASGGRLVTPGTPLTLTCTVSGFSLS | SATMN | WVRQAPGKGLEWIG | LIGGNDERYYASWAKG |

Figure 1B

Antibody Variable Heavy Chain Protein Features

| Sequence Name | FR3 | CDR3 | FR4 | |
|---|---|---|---|---|
| Ab1 | RFTISKTSSTTMDLKMTSPTTEDTATYFCAR | GGGEFFI | WGPGTLVTVSS | (SEQ ID NO: 2) |
| Ab1.H | RFTISRDNSKNTLYLQMNSLRAEDTAVYYCAR | GGGEFFI | WGQGTLVTVSS | (SEQ ID NO: 42) |
| Ab2 | RFTISKTSSTTVDLKMTSPTTEDTATYFCAR | GGGEFFI | WGQGTLVTVSS | (SEQ ID NO: 82) |
| Ab3 | RFTISKTSSTTVTLQMTSLTAADTATYFCAR | HLYGSITFAFGL | WGQGTLVTVSS | (SEQ ID NO: 682) |
| Ab4 | RFTISKTSSTTVDLKMTSLTTEDTATYFCAR | ISDAYVFDYAYYFTL | WGQGTLVTVSS | (SEQ ID NO: 642) |
| Ab5 | RFTISKTSTTVYLKIASPTTEDTATYFCAR | EPGSTTQNDL | WGQGTLVTVSS | (SEQ ID NO: 482) |
| Ab6 | QFTLSRDIDQSTGCLQLNSLTVADTAMYYCTK | NFDL | WGPGTLVTVSS | (SEQ ID NO: 722) |
| Ab7 | RFTISRTSTTVTLKMTSLTTEDTATYFCAR | DYWLSL | WGPGTLVTVSS | (SEQ ID NO: 522) |
| Ab8 | QFTLSRDIDQNTGCLQLNSLTPADTAMYYCTI | NFEL | WGQGTLVTVSS | (SEQ ID NO: 762) |
| Ab9 | RFTLSRDIDQSTGCLQLNSLTDADTAMYYCAG | NLEI | WGQGTLVTVSS | (SEQ ID NO: 802) |
| Ab11 | RFTISRTSTTVTLKMTSLTTEDTATYFCAR | DYWLSL | WGQGTLVTVSS | (SEQ ID NO: 562) |
| Ab12 | RFTISRTSTTVTLKMTSLTTEDTATYFCAR | DYWLSL | WGQGTLVTVSS | (SEQ ID NO: 602) |
| Ab13 | RFTISKTSSTTVDLKMTSPTTEDTATYFCAR | GGGEFFI | WGPGTLVTVSS | (SEQ ID NO: 122) |
| Ab14 | RFTISKVSSTTVDLKMTSPTTEDTATYFCAR | GGGEFFI | WGQGTLVTVSS | (SEQ ID NO: 162) |
| Ab15 | RFTISRTSSTTVNLKMTSPTTEDTATYFCAR | GGGEFFI | WGQGTLVTVSS | (SEQ ID NO: 202) |
| Ab16 | RFTISKTSSTTVDLKMTSPTTEDTATYFCAR | GGGEFFI | WGPGTLVTVSS | (SEQ ID NO: 242) |
| Ab17 | RFTISKTSSTTVDLKMTSPTTEDTATYFCAR | GGGEFFI | WGPGTLVTVSS | (SEQ ID NO: 282) |
| Ab18 | RFTISKTSSTTVDLKVTSPTTEDTATYFCAR | GGGEFFI | WGQGTLVTVSS | (SEQ ID NO: 322) |
| Ab19 | RFTISKTSSTTVDLKMTSPTTEDTATYFCAR | GGGEFFI | WGPGTLVTVSS | (SEQ ID NO: 362) |

Figure 2A

Antibody Variable Light Chain Protein Features

| Sequence Name | FR1 | CDR1 | FR2 | CDR2 |
|---|---|---|---|---|
| Ab1 | DPVMTQTPSSTSAAVGGTVTISC | QSSESVYSNYLS | WYQQKPGQPPNFLIY | QASNLAS |
| Ab1.H | DIQMTQSPSTLSASVGDRVTITC | QSSESVYSNYLS | WYQQKPGKAPKFLIY | QASNLAS |
| Ab2 | AQVLTQTPSPVSAAVGGTVTINC | QSSESVYKNNYLS | WYQQKPGQPPKFLIY | QASNLAD |
| Ab3 | AAVLTQTPSPVSAAVGGTVTINC | QASQSIGSDLA | WYQQKPGQPPKLLIY | DASTLAS |
| Ab4 | ALVMTQTPSSVSAAVGGTVTINC | LASQNIYNSLA | WYQQKPGQPPKLLIY | RASTLAS |
| Ab5 | DVVMTQTPASVSEPVGGTVTIKC | QASENIYNSLL | WYQQKPGQPPKLLIY | RASTLAS |
| Ab6 | AQVLTQTPSSVSAAVGGTVTINC | QSSPSVYSNNYLS | WFQQKPGQPPKGLIA | DASTLAS |
| Ab7 | AAVLTQTPSPVSAAVGGTVTIKC | QSSQSVYDNNALA | WYQQKPGQPPKLLIY | AASTLAS |
| Ab8 | AQVLTQTPSSVSAAVGGTVTINC | QSSPSVYSSYLS | WFQQKPGQPPKFLIY | EASKLAS |
| Ab9 | AQVLTQTPSSVSAAVGGTVTINC | QSSPSIYSGAFLS | WFQQKPGQPPKFLIY | EASKLAS |
| Ab11 | AAVLTQTPSPVSAAVGGTVTIKC | QSSQSVYDNNALA | WYQQKPGQPPKLLIY | AASNLAS |
| Ab12 | AAVLTQTPSPVSAAVGGTVTIKC | QSSQSVYDNNALA | WYQQKPGQPPKLLIY | AASTLAS |
| Ab13 | AQVLTQTPSSVSAAVGGTVTINC | QSSQSVHDGSYLS | WYQQKPGQPPNFLIY | QASNLAS |
| Ab14 | AQVLTQTPSSVSAAVGGTVTINC | QSSQSVYSNNRLS | YYQQKPGQPPKLLIY | EASSLAY |
| Ab15 | AQVLTQTPSSVSAAVGGTVTINC | QSSQSVYSNNRLS | WYQQKPGQPPNLLIY | EASSLAS |
| Ab16 | DPVLTQTPSSVSAAVGGTVTINC | QSSQSVYNNKWLS | WYQQKPGQSPKFLIY | QASNLAS |
| Ab17 | AQVLTQTPSSVSAAVGGTVTINC | QSSQSVYKNKYLS | WYQQKVGQPPKFLIY | QASNLAS |
| Ab18 | AQVLTQTPSSVSAAVGGTVTINC | QSSKSVYNNNWLS | WYQQKPGQPPKFLIY | QASNLAS |
| Ab19 | AQVLTQTPSSVSAAVGGTVTINC | QSSESVYTNDRLS | WYQQKPGQPPKLLIY | EASKLAS |

Figure 2B

Antibody Variable Light Chain Protein Features

| Sequence Name | FR3 | CDR3 | FR4 | |
|---|---|---|---|---|
| Ab1 | GVPSRFKGSGSGTQFTLTITDLECDDAATYYC | AGGYSENIVG | FGGGTEVVVKR | (SEQ ID NO: 22) |
| Ab1.H | GVPSRFSGSGSGTEFTLTISSLQPDDFATYYC | AGGYSENIVG | FGGGTKVEIKR | (SEQ ID NO: 62) |
| Ab2 | GVPSRFKGSGSGTQFTLTISDLECDDAATYYC | AGGYSTYMSG | FGGGTEVVVKR | (SEQ ID NO: 102) |
| Ab3 | GVPSRFSGSGSGTQFTLTISGVQCDDAATYYC | QGTYYSSGWYTA | FGGGTEVVVKR | (SEQ ID NO: 702) |
| Ab4 | GVSSRFKGSGSGTQFTLTISGVECADAATYYC | QQGAGADNIGNP | FGGGTEVVVKR | (SEQ ID NO: 662) |
| Ab5 | GVSSRFKGSGSGTEFTLTISDLECADAATYYC | QNYYNIWTNGAA | FGGGTEVVVKR | (SEQ ID NO: 502) |
| Ab6 | GVPSRFKGSGSGTQFTLTISGVQCDDAAAYYC | LGYYDCGSTDCHA | FGGGTEVVVKR | (SEQ ID NO: 742) |
| Ab7 | GVPSRFKGSGSGTQFTLTINGVQCDDAATYYC | LGGYDDPADNA | FGGGTEVVVKR | (SEQ ID NO: 542) |
| Ab8 | GVPSRFSGSGSGTQFTLTISGVQCSDAATYYC | LGAYDCGRTDCHA | FGGGTEVVVKR | (SEQ ID NO: 782) |
| Ab9 | GVPSRFSGSGSGTQFTLTISDVQCDDAATYYC | LGFYDCSSVDCHA | FGGGTEVVVKR | (SEQ ID NO: 822) |
| Ab11 | GVPDRFSGSGSGTQFTLTISGVQCDDAATYYC | LGGYDDAADNA | FGGGTEVVVKR | (SEQ ID NO: 582) |
| Ab12 | GVPSRFSGSGSGTEFTLTISGVQCDDAATYYC | LGGYYDPADNA | FGGGTEVVVKR | (SEQ ID NO: 622) |
| Ab13 | GVPSRFKGSGSGTQFTLTISDLECDDAATYYC | AGGYSSNICG | FGGGTEVVVKR | (SEQ ID NO: 142) |
| Ab14 | GVPSRFKGSGSGTQFTLTISDLECDDAATYYC | AGAYSNSIYS | FGGGTEVVVKR | (SEQ ID NO: 182) |
| Ab15 | GVPSRFSGSGSGTQFTLTISDLECDDAATYYC | AGAYNTGIYG | FGGGTEVVVKR | (SEQ ID NO: 222) |
| Ab16 | GVPSRFKGSGSGTQFTLTISDLECDDGATYYC | AGGYRGNVCG | FGGGTEVVVKR | (SEQ ID NO: 262) |
| Ab17 | GVPSRFKGSGSGTQFTLTISDLECDDAATYYC | AGGYSGNMVD | FGGGTEVVVKR | (SEQ ID NO: 302) |
| Ab18 | GVPSRFKGSGSGTQFTLTISDLECDDAATYYC | AGGYSGNIVG | FGGGTEVVVKR | (SEQ ID NO: 342) |
| Ab19 | GVPPRFSGSGSGTQFTLTISDLECDDAATYYC | AGAYSTSIHG | FGGGTEVVVKR | (SEQ ID NO: 382) |

Figure 3A

Antibody Variable Heavy Chain DNA Features

| Sequence Name | FR1 |
|---|---|
| Ab1 | cagtcggtggaggagtccgggggtcgcctggtcacgcctgggacacccctgacactcacctgcaccgtctctggat |
| Ab1.H | gaggtgcagcttgtggagtctgggggaggcttggtccagcctgggggtccctgagactctcctgtgcagcctctg |
| Ab2 | cagtcggtggaggagtccgggggtcgcctggtcacgcctgggacacccctgacactcacctgcaccgtctctggat |
| Ab3 | caggagcagctggtggagtccgggggaggcctggtccagcctgagggatccctgacactcacctgcacagcctctg |
| Ab4 | cagtcggtggaggagtccgggggtcgcctggtcacgcctgggacacccctgacactcacctgcaccgtctctggat |
| Ab5 | cagtcggtggaggagtccgggggtcgcctggtcacgcctgggacacccctgacactcacctgcacagtctctggat |
| Ab6 | cagcagctggagcagtccggaggaggagccgaaggaggcctggtcaagcctggggatccctggaactctgctgca |
| Ab7 | cagtcggtggaggagtccgggggtcgcctggtaacgcctgggacacccctgacactcacctgcacagcctctggaa |
| Ab8 | cagcagctggagcagtccggaggaggagccgaaggaggcctggtcaagcctggggatccctggaactctgctgca |
| Ab9 | cagcagctggagcagtccggaggaggagccgaaggaggcctggtcaagcctggggatccctgaaactctcctgca |
| Ab11 | cagtcggtggaggagtctgggggtcgcctggtcacgcctgggacacccctgacactcacctgcacagcctctggat |
| Ab12 | cagtcggtggaggagtccgggggtcgcctggtcacgcctgggacacccctgacactcacctgcacagcctctggat |
| Ab13 | cagtcggtggaggagtccgggggtcgcctggtcacgcctgggacacccctgacactcacctgcaccgtctctggat |
| Ab14 | cagtcggtggaggcgtccgggggtcgcctggtcacgcctgggacacccctgacactcacctgcaccgtctctggat |
| Ab15 | cagtcggtggaggcgtccgggggtcacctagtcacgcctgggacacccctgacactcacctgcaccgtctctggat |
| Ab16 | cagtcggtggaggagtccgggggtcgcctggtcacgcctgggacacccctgacactcacctgcaccgtctctggat |
| Ab17 | cagtcagtggaggagtccgggggtcgcctggtcacgcctgggacacccctaacactcacctgcaccgtctctggat |
| Ab18 | cagtcggtggaggagtccgggggtcgcctggtcacgcctgggacacccctgacactcacctgcaccgtctctggat |
| Ab19 | cagtcggtggaggcgtccgggggtcgcctggtcacgcctgggacacccctgacactcacctgcaccgtctctggat |

Figure 3B

Antibody Variable Heavy Chain DNA Features

| Sequence Name | FR1 | CDR1 | FR2 |
|---|---|---|---|
| Ab1 | tctccctcagt | agcgctgtaatgaat | tgggtccgccaggctccagggaaggggctggaat |
| Ab1.H | gattcaccgtcagt | agcgctgtaatgaat | tgggtccgtcaggctccagggaaggggctggagt |
| Ab2 | tctccctcagt | ggcgctgcgatgaac | tgggtccgccaggctccagggaaggggctggaat |
| Ab3 | gattctccttcagt | agcagcgactacatgtgc | tgggtccgccaggctccagggaaggggctggagt |
| Ab4 | tctccctcagc | agctacgacatgagc | tgggtccgccaggctccaggaaaggggctggaat |
| Ab5 | tctccctcagt | agctatgcgatgatc | tgggtccgccaggctccagggaaggggctggaat |
| Ab6 | aggcctctggattctccctcagt | agcacctactggatgtgc | tgggtccgccaggctccagggaaggggctggagt |
| Ab7 | tcgacctcagt | ggctatgcaatgggc | tgggtccgccaggctccagggaaggggctggaat |
| Ab8 | aagcctctggattctccctcact | acgagccactggatgtgt | tgggtccgccaggctccagggaaggggctgaatt |
| Ab9 | aagcctctggattcaccatcagt | agggactactggatatgt | tgggtccgccaggctccagggaaggggctggagt |
| Ab11 | tctccctcagt | agatatgcaatgggc | tgggtccgccaggctccagggaaggggctggaat |
| Ab12 | tctccctcagt | agctatgcaatgggc | tgggtccgccaggctccagggaaggggctggaat |
| Ab13 | tctccctcagt | agcgctgcaatgaac | tgggtccgccaggctccagggaaggggctggaat |
| Ab14 | tctccctcagt | agcgctgcaatgaac | tgggtccgccaggctccagggaaggggctggaat |
| Ab15 | tctccctcagt | agcgctgcaatgaac | tgggtccgccaggctccagggaaggggctggaat |
| Ab16 | tctccctcagt | agcgctgcaatgagc | tgggtccgccaggctccagggaaggggctggaat |
| Ab17 | tctccctcagt | agcgctgcaatgaac | tgggtccgccaggctccagggaaggggctggaat |
| Ab18 | tctccctcagt | agcgctgcattgagc | tgggtccgccaggctccagggaaggggctggaat |
| Ab19 | tctccctcagt | agcgctacaatgaac | tgggtccgccaggctccagggaaggggctggaat |

Figure 3C

Antibody Variable Heavy Chain DNA Features

| Sequence Name | FR2 | CDR2 |
|---|---|---|
| Ab1 | ggatcgga | agtattgttgctagtggtaccacatactacgcgagctgggcgaacggc |
| Ab1.H | ggatcgga | agtattgttgctagtggtaccacatactacgctagctctgctaacggc |
| Ab2 | ggatcgga | gttattggtaatagtggtagcacatactacgcgtcctgggcgaaaggc |
| Ab3 | ggatcgga | tgcattgatgctggtagtagtggtgacacttacttcgcgagctgggcgaaaggc |
| Ab4 | acatcggc | atcattaatactaatgatgacacatggtacgcgagctgggtgaaaggc |
| Ab5 | ggatcgga | atcatttatgataatggtgacacatactacgcgagctgggcgaaaggc |
| Ab6 | ggattgga | tgcatttatactggtagtggtagcacagactacgcgagctgggtgaatggc |
| Ab7 | ggatcgga | gacattagtacctatggtaccacagactacgcgagctgggtgaatggc |
| Ab8 | ggattgga | tgcattagtgccggtagtggtgacgcagactacgcgacctgggtggatgcc |
| Ab9 | ggattgga | tgcattagtgctggtggtggtagcacagactacgcgaactgggtgaatggc |
| Ab11 | ggatcgga | gacattagtacttatggtaccacagactacgcgagctgggtgaatggc |
| Ab12 | ggatcgga | gacattagtacttatggtaccacagactacgcgagctgggtgtatggc |
| Ab13 | ggatcgga | attattgataatactgctggcacatattacgcgccctgggcgaaaggc |
| Ab14 | ggatcgga | tttattgagtatagtaagaatatagtttacgcgtcctgggcgaaaggc |
| Ab15 | ggatcgga | tcggttgatgagcgtcagaataaatattacgcgtcctgggcgaaaggc |
| Ab16 | ggatcgga | attattgatgatagtggtaacacatactacgcgtcctgggcgaaagcc |
| Ab17 | ggatcggt | atttttgatccttatagtagtacatactacgcgtcctgggcgaaaggc |
| Ab18 | ggatcgga | attattgataagggtgttatgtcttactacgcgtcctgggcgaaaggc |
| Ab19 | ggatcggg | cttattggcggtaatgacgaaagatactacgcgtcctgggcgaaaggc |

Figure 3D

Antibody Variable Heavy Chain DNA Features

| Sequence Name | FR3 |
|---|---|
| Ab1 | cgattcaccatctccaaaacctcgtcgaccacgatggatctgaaaatgaccagtccgacaaccgaggacacggcca |
| Ab1.H | cgattcaccatctccagagacaattccaagaacaccctgtatcttcaaatgaacagcctgagagctgaggacactg |
| Ab2 | cgattcaccatctccaaaacctcgtcgaccacggtggatctgaaaatgaccagtccgacaaccgaggacacggcca |
| Ab3 | cgattcaccatctccaaaacctcgtcgaccacggtgactctgcaaatgaccagtctgacagccgcggacacggcca |
| Ab4 | cgattcaccatctccaaaacctcgtcgaccacggtggatctgaaaatgaccagtctgacaaccgaggacacggcca |
| Ab5 | cggttcaccatctccaaaacctcgaccacggtgtatctgaagatcgccagtccgacaaccgaggacacggccacct |
| Ab6 | caattcactctctccagagacatcgaccagagcacaggttgcctacaactgaacagtctgacagtcgcggacacgg |
| Ab7 | cgattcaccatctccagaacctcgaccacggtgactctgaaaatgaccagtctgacaaccgaggacacggccacct |
| Ab8 | caattcactctctccagagacatcgaccagaacacaggttgcctacaattgaacagtctgacacccgcggacacgg |
| Ab9 | cgattcactctctccagagacatcgaccagagcacaggttgccttcaactgaacagtctgacagacgcggacacgg |
| Ab11 | cgattcaccatctccagaacctcgaccacggtgactctgaaaatgaccagtctgacaaccgaggacacggccacct |
| Ab12 | cgattcaccatctccagaacctcgaccacggtgactctgaaaatgaccagtctgacaaccgaggacacggccacct |
| Ab13 | cgattcaccatctccaaaacctcgtcgaccacggtggatctgaaaatgaccagtccgacaaccgaggacacggcca |
| Ab14 | cgattcaccatctccaaagtctcgtcgaccacggtggatctgaaaatgaccagtccgacaaccgaggacacggcca |
| Ab15 | cgattcaccatctccagaacctcgtcgaccacggtgaatctgaaaatgaccagtccgacaaccgaggacacggcca |
| Ab16 | cgattcaccatctccaaaacctcgtcgaccacggtggatctgaaaatgaccagtccgacaaccgaggacacggcca |
| Ab17 | cgattcaccatctccaaaacctcgtcgaccacggtggatctgaaaatgaccagtccgacaaccgaggacacggcca |
| Ab18 | cgattcaccatctccaaaacctcgtcgaccacggtggatctaaaagtgaccagtccgacaaccgaggacacggcca |
| Ab19 | cgattcaccatctccaaaacctcgtcgaccacggtggatctgaaaatgaccagtccgacaaccgaggacacggcca |

Figure 3E

Antibody Variable Heavy Chain DNA Features

| Sequence Name | FR3 | CDR3 |
|---|---|---|
| Ab1 | cctatttctgtgccaga | gggggaggggaatttttcatc |
| Ab1.H | ctgtgtattactgtgctaga | gggggaggggaatttttcatc |
| Ab2 | cctatttctgtgccaga | gggggaggggaatttttcatc |
| Ab3 | cctatttctgtgcgaga | catctttatggtagtattactttcgcctttggcttg |
| Ab4 | cctatttctgtgccaga | atatccgatgcttatgtttttgattatgcgtattactttactttg |
| Ab5 | acttctgtgccaga | gagcctggtagtactactcagaatgacttg |
| Ab6 | ccatgtattactgtacgaaa | aattttgacttg |
| Ab7 | atttctgtgccaga | gactattggttgagcttg |
| Ab8 | ccatgtattactgtacgata | aattttgagttg |
| Ab9 | ccatgtattactgtgcggga | aatctagagatc |
| Ab11 | atttctgtgccaga | gactattggttgagcttg |
| Ab12 | atttctgtgccaga | gactattggttgagcttg |
| Ab13 | cctatttctgtgccaga | gggggaggggaatttttcatc |
| Ab14 | cctatttctgtgccagg | gggggaggggaatttttcatc |
| Ab15 | cctatttctgtgccaga | gggggaggggaatttttcatc |
| Ab16 | cctatttctgtgccaga | gggggaggggagtttttcatc |
| Ab17 | cctatttctgtgccaga | gggggaggggaatttttcatc |
| Ab18 | cctatttctgtgccaga | ggggggggggaatttttcatc |
| Ab19 | cctatttctgtgccaga | ggggggggggaatttttcatc |

Figure 3F

Antibody Variable Heavy Chain DNA Features

| Sequence Name | FR4 | |
|---|---|---|
| Ab1 | tggggcccggggaccctcgtcaccgtctcgagc | (SEQ ID NO: 12) |
| Ab1.H | tggggccaagggaccctcgtcaccgtctcgagc | (SEQ ID NO: 52) |
| Ab2 | tggggccaagggaccctggtcaccgtctcgagc | (SEQ ID NO: 92) |
| Ab3 | tggggccagggcaccctggtcaccgtctcgagc | (SEQ ID NO: 692) |
| Ab4 | tggggccaggggaccctggtcaccgtctcgagc | (SEQ ID NO: 652) |
| Ab5 | tggggccaagggaccctggtcaccgtctcgagc | (SEQ ID NO: 492) |
| Ab6 | tggggcccgggcaccctggtcaccgtctcgagc | (SEQ ID NO: 732) |
| Ab7 | tggggcccgggcaccctcgtcaccgtctcgagc | (SEQ ID NO: 532) |
| Ab8 | tggggccaaggcaccctggtcaccgtctcgagc | (SEQ ID NO: 772) |
| Ab9 | tggggccaagggaccctggtcaccgtctcgagc | (SEQ ID NO: 812) |
| Ab11 | tggggccaaggcaccctcgtcaccgtctcgagc | (SEQ ID NO: 572) |
| Ab12 | tggggccaaggcaccctggtcaccgtctcgagc | (SEQ ID NO: 612) |
| Ab13 | tggggcccgggcaccctcgtcaccgtctcgagc | (SEQ ID NO: 132) |
| Ab14 | tggggccaaggcaccctggtcaccgtctcgagc | (SEQ ID NO: 172) |
| Ab15 | tggggccagggcaccctcgtcaccgtctcgagc | (SEQ ID NO: 212) |
| Ab16 | tggggcccgggcaccctcgtcaccgtctcgagc | (SEQ ID NO: 252) |
| Ab17 | tggggcccaggcaccctcgtcaccgtctcgagc | (SEQ ID NO: 292) |
| Ab18 | tggggccagggcaccctcgtcaccgtctcgagc | (SEQ ID NO: 332) |
| Ab19 | tggggcccgggcaccctggtcaccgtctcgagc | (SEQ ID NO: 372) |

Figure 4A

Antibody Variable Light Chain DNA Features

| Sequence Name | FR1 |
|---|---|
| Ab1 | gaccctgtgatgacccagactccatcttccacgtctgcggctgtgggaggcacagtcaccatcagttgc |
| Ab1.H | gacatccagatgacccagtctccttccaccctgtctgcatctgtaggagacagagtcaccatcacttgt |
| Ab2 | gcccaagtgctgacccagactccatccccagtgtctgcagctgtgggaggcaccgtcaccatcaattgc |
| Ab3 | gcagccgtgctgacccagacaccatcgcccgtgtctgcagctgtgggaggcacagtcaccatcaattgc |
| Ab4 | gcccttgtgatgacccagactccatcctccgtgtctgcagctgtgggaggcacagtcaccatcaattgc |
| Ab5 | gatgttgtgatgacccagactccagcctccgtgtctgaacctgtgggaggcacagtcaccatcaagtgc |
| Ab6 | gcccaagtgctgacccagactccatcctccgtgtctgcagctgtgggaggcacagtcaccatcaattgc |
| Ab7 | gcagccgtgctgacccagacaccatcgcccgtgtctgcagctgtgggaggcacagtcaccatcaagtgc |
| Ab8 | gcccaagtgctgacccagactccatcctccgtgtctgcagctgtgggaggcacagtcaccatcaattgc |
| Ab9 | gcccaagtgctgacccagactccatcctccgtgtctgcagctgtgggaggcacagtcaccatcaattgc |
| Ab11 | gcagccgtgctgacccagacaccatcgcccgtgtctgcagctgtgggaggcacagtcaccatcaagtgc |
| Ab12 | gcagccgtgctgacccagacaccatcgcccgtgtctgcagctgtgggaggcacagtcaccatcaagtgc |
| Ab13 | gcgcaagtgctgacccagactccatcgtccgtgtctgcagctgtgggaggcacagtcaccatcaattgc |
| Ab14 | gcgcaagtgctgacccagactccatcgtccgtgtctgcagctgtgggaggcacagtcaccatcaattgc |
| Ab15 | gcgcaagtgctgacccagactccatcgtccgtgtctgcagctgtgggaggcacagtcaccatcaattgc |
| Ab16 | gaccctgtgctgacccagactccatcgtccgtgtctgcagctgtgggaggcacagtcaccatcaattgc |
| Ab17 | gcccaagtgctgacccagactccatcgtccgtgtctgcagctgtgggaggcacagtcaccatcaattgc |
| Ab18 | gcgcaagtgctgacccagactccatcgtccgtgtctgcagctgtgggaggcacagtcaccatcaattgc |
| Ab19 | gcgcaagtgctgacccagactccatcgtccgtgtctgcagctgtgggaggcacagtcaccatcaattgc |

Figure 4B

Antibody Variable Light Chain DNA Features

| Sequence Name | CDR1 | FR2 |
|---|---|---|
| Ab1 | cagtccagtgagagtgtttatagtaactacttatcc | tggtatcagcagaaaccagggcagcctcccaacttcc |
| Ab1.H | cagtccagtgagagtgtttatagtaactacttatcc | tggtatcagcagaaaccaggaaaagcccctaagttcc |
| Ab2 | cagtccagtgagagtgtttataagaacaactacttatcc | tggtatcagcagaaaccagggcagcctcccaagttcc |
| Ab3 | caggccagtcagagcattggtagcgacttagcc | tggtatcagcagaaaccagggcagcctcccaagctcc |
| Ab4 | ctggccagtcagaacatttacaattctttagcc | tggtatcagcagaaaccagggcagcctcccaagctcc |
| Ab5 | caggccagtgagaacatttacaactctttactc | tggtatcagcagaaaccagggcagcctcccaagctcc |
| Ab6 | cagtccagtccgagtgtttatagtaacaactacttatcc | tggtttcagcagaaaccagggcagcctcccaaaggcc |
| Ab7 | cagtccagtcagagtgtttatgataacaatgctttagcc | tggtatcagcagaaaccagggcagcctcccaagctcc |
| Ab8 | cagtccagtccgagtgtttatagtagctacttatcc | tggtttcagcagaaaccagggcagcctcccaagttcc |
| Ab9 | cagtccagtccgagtatttatagtggcgccttttatcc | tggtttcagcagaaaccagggcagcctcccaagttcc |
| Ab11 | cagtccagtcagagtgtttatgataacaatgctttagcc | tggtatcagcagaaaccaggacagcctcccaagctcc |
| Ab12 | cagtccagtcagagtgtttatgataacaatgctttagcc | tggtatcagcagaaaccagggcagcctcccaagctcc |
| Ab13 | cagtccagtcagagtgttcatgatggcagctacttatcc | tggtatcagcagaaaccagggcagcctcccaacttcc |
| Ab14 | cagtccagtcagagtgtttatagtaacaaccggttatcg | tactatcagcagaaaccagggcagcctcccaagctcc |
| Ab15 | cagtccagtcagagtgtttatagtaacaaccgcttatcc | tggtatcagcagaaaccagggcagcctcccaatctcc |
| Ab16 | cagtccagtcagagtgtttataataacaagtggttatcc | tggtatcagcagaaaccaggacagtctcccaagttcc |
| Ab17 | cagtccagtcagagtgtttataagaataagtacttatcc | tggtatcagcagaaagtagggcagcctcccaagttcc |
| Ab18 | cagtccagtaagagtgtttataacaacaattggttatcc | tggtatcaacagaaaccagggcagcctcccaagttcc |
| Ab19 | cagtccagtgagagtgtttatactaacgaccgcttatcc | tggtatcagcagaaaccagggcagcctcccaagctcc |

Figure 4C

Antibody Variable Light Chain DNA Features

| Sequence Name | FR2 | CDR2 | FR3 |
|---|---|---|---|
| Ab1 | tgatctac | caggcatccaatttggcatct | ggggtcccatcgcggttcaaaggcagtggatctgggacacagttca |
| Ab1.H | tgatctat | caggcatccaatttggcatct | ggagtcccatcaaggttcagcggcagtggatctggaacagaattca |
| Ab2 | tgatctac | caggcatccaatttggcagat | ggggtcccatcgcggttcaaaggcagtggatctgggacacagttca |
| Ab3 | tgatctat | gatgcatccactctggcatct | ggggtcccatcgcggttcagcggcagtggatctgggacacagttca |
| Ab4 | tgatctac | agggcatccactctggcatct | ggggtctcatcgcggttcaaaggcagtggatctgggacacagttca |
| Ab5 | tgatctat | agggcatccactctggcatct | ggggtctcatcgcggttcaaaggcagtggatctgggacagagttca |
| Ab6 | tgatcgct | gatgcatccactctggcatct | ggggtcccatcgcggttcaaaggcagtggatctgggacacagttca |
| Ab7 | tgatctat | gctgcatccactctggcatct | ggggtcccatcgcggttcaaaggcagtggatctgggacacagttca |
| Ab8 | tgatctac | gaagcatccaaactggcatct | ggggtcccatcgcggttcagcggcagtggatctgggacacagttca |
| Ab9 | tgatctac | gaagcctccaaactggcatct | ggggtcccatcgcggttcagtggcagtggatctgggacacagttca |
| Ab11 | tgatctat | gctgcatccaatctggcatct | ggggtcccagataggttcagcggcagtggatctgggacacagttca |
| Ab12 | tgatctat | gctgcatccactctggcatct | ggggtcccatcgcggttcagtggcagtggatctgggacagagttca |
| Ab13 | tgatctac | caggcatccaatttggcatct | ggggtcccatcgcggttcaaaggcagtggatctgggacacagttca |
| Ab14 | tgatctac | gaagcatccagtctggcatat | ggggtcccatcgcggttcaaaggcagtggatctgggacacagttca |
| Ab15 | tgatctac | gaagcatccagtctggcatct | ggggtcccatcgcggttcagcggcagtggatctgggacacagttca |
| Ab16 | tgatttac | caggcatccaatttggcatct | ggggtcccatcgcggttcaaaggcagtggatctgggacacagttca |
| Ab17 | tgatctac | caggcatccaatttggcatct | ggggtcccatcgcggttcaaaggcagtggatctgggacacagttca |
| Ab18 | tgatctac | caggcatccaatttggcatct | ggggtcccgtcgcggttcaaaggcagtggatctgggacacagttca |
| Ab19 | tgatctac | gaagcatccaagctggcatct | ggggtcccaccgcggttcagcggcagtggatctgggacacagttca |

Figure 4D

Antibody Variable Light Chain DNA Features

| Sequence Name | FR3 | CDR3 |
|---|---|---|
| Ab1 | ctctcaccatcaccgacctggagtgtgacgatgccgccacttattactgt | gcaggcggttatagtgaaaacattg |
| Ab1.H | ctctcaccatcagcagcctgcagcctgatgattttgcaacttactactgt | gcaggcggttatagtgaaaacattg |
| Ab2 | ctctcaccatcagcgacctggagtgtgacgatgccgccacttattactgt | gcaggcggttatagtacttatatgt |
| Ab3 | ctctcaccatcagcggcgtgcagtgtgacgatgctgccacttactactgt | caaggcacttattatagtagtggtt |
| Ab4 | ctctcaccatcagcggcgtggagtgtgccgatgctgccacttactactgt | caacagggtgctggtgctgataata |
| Ab5 | ctctcaccatcagcgacctggagtgtgccgatgctgccacttactactgt | caaaactattataatatatggacta |
| Ab6 | ctctcaccatcagcggcgtgcagtgtgacgatgctgccgcttactactgt | ctaggctattatgattgtggtagta |
| Ab7 | ctctcaccatcaacggcgtgcagtgtgacgatgctgccacttactactgt | ctaggcggttatgatgatcctgctg |
| Ab8 | ctctcaccatcagcggcgtgcagtgtagcgatgctgccacttactactgt | cttggcgcgtatgattgtggtcgta |
| Ab9 | ctctcaccatcagcgacgtacagtgtgacgatgctgccacttactactgt | ctaggcttttatgattgtagcagtg |
| Ab11 | ctctcaccatcagcggcgtgcagtgtgacgatgctgccacttactactgt | ctaggcggttatgatgatgctgctg |
| Ab12 | ctctcaccatcagcggcgtgcagtgtgacgatgctgccacttactactgt | ctaggcggttattatgatcctgctg |
| Ab13 | ctctcaccatcagcgacctggagtgtgacgatgccgccacttattactgt | gcaggcggttatagtagtaatattt |
| Ab14 | ctctcaccatcagcgacctggagtgtgacgatgccgccacttattactgt | gcaggtgcctatagtaatagtattt |
| Ab15 | ctctcaccatcagcgacctggagtgtgacgatgccgccacttattactgt | gcaggcgcttataatactgggattt |
| Ab16 | ctctcaccatcagcgacctggagtgtgacgatggcgccacttattactgt | gcaggcggctaccgtggtaatgttt |
| Ab17 | ctctcaccatcagcgacctggagtgtgacgatgccgccacttattactgt | gcaggcggttatagtggtaatatgg |
| Ab18 | ctctcaccatcagcgacctcgagtgtgacgatgccgccacttattactgt | gcaggcggttatagtggtaatattg |
| Ab19 | ctctcaccatcagcgacctggagtgtgacgatgccgccacttattactgt | gcaggcgcttatagtactagtatcc |

Figure 4E

Antibody Variable Light Chain DNA Features

| Sequence Name | CDR3 | FR4 | |
|---|---|---|---|
| Ab1 | ttggt | ttcggcggagggaccgaggtggtggtcaaacgt | (SEQ ID NO: 32) |
| Ab1.H | ttggt | ttcggcggaggaaccaaggtggaaatcaaacgt | (SEQ ID NO: 72) |
| Ab2 | ctggt | ttcggcggagggaccgaggtggtggtcaaacgt | (SEQ ID NO: 112) |
| Ab3 | ggtacactgct | ttcggcggagggaccgaggtggtggtcaaacgt | (SEQ ID NO: 712) |
| Ab4 | ttggtaatcct | ttcggcggagggaccgaggtggtggtcaaacgt | (SEQ ID NO: 672) |
| Ab5 | atggtgctgct | ttcggcggagggaccgaggtggtggtcaaacgt | (SEQ ID NO: 512) |
| Ab6 | ctgattgtcatgct | ttcggcggagggaccgaggtggtggtcaaacgt | (SEQ ID NO: 752) |
| Ab7 | ataatgct | ttcggcggagggaccgaggtggtggtcaaacgt | (SEQ ID NO: 552) |
| Ab8 | ctgattgtcatgct | ttcggcggagggaccgaggtggtggtcaaacgt | (SEQ ID NO: 792) |
| Ab9 | ttgattgccatgct | ttcggcggagggaccgaggtggtggtcaaacgt | (SEQ ID NO: 832) |
| Ab11 | ataatgct | ttcggcggagggaccgaggtggtggtcaaacgt | (SEQ ID NO: 592) |
| Ab12 | ataatgct | ttcggcggagggaccgaggtggtggtcaaacgt | (SEQ ID NO: 632) |
| Ab13 | gtggt | ttcggcggagggaccgaggtggtggtcaaacgt | (SEQ ID NO: 152) |
| Ab14 | atagt | ttcggcggagggaccgaggtggtggtcaaacgt | (SEQ ID NO: 192) |
| Ab15 | atggt | ttcggcggagggaccgaggtggtggtcaaacgt | (SEQ ID NO: 232) |
| Ab16 | gtggt | ttcggcggagggaccgaggtggtggtcaaacgt | (SEQ ID NO: 272) |
| Ab17 | ttgat | ttcggcggagggaccgaggtggtggtcaaacgt | (SEQ ID NO: 312) |
| Ab18 | ttggt | ttcggcggagggaccgaggtggtggtcaaacgt | (SEQ ID NO: 352) |
| Ab19 | atggt | ttcggcggagggaccgaggtggtggtcaaacgt | (SEQ ID NO: 392) |

Figure 5

Antibody Heavy Chain Protein Features

| Sequence Name | Variable region coordinates | SEQ ID NO: | CDR1 coordinates | SEQ ID NO: | CDR2 coordinates | SEQ ID NO: | CDR3 coordinates | SEQ ID NO: |
|---|---|---|---|---|---|---|---|---|
| Ab1 | 1-113 | 2 | 30-34 | 4 | 49-64 | 6 | 96-102 | 8 |
| Ab1.H | 1-115 | 42 | 31-35 | 44 | 50-65 | 46 | 98-104 | 48 |
| Ab2 | 1-113 | 82 | 30-34 | 84 | 49-64 | 86 | 96-102 | 88 |
| Ab3 | 1-122 | 682 | 31-36 | 684 | 51-68 | 686 | 100-111 | 688 |
| Ab4 | 1-121 | 642 | 30-34 | 644 | 49-64 | 646 | 96-110 | 648 |
| Ab5 | 1-115 | 482 | 30-34 | 484 | 49-64 | 486 | 95-104 | 488 |
| Ab6 | 1-117 | 722 | 34-39 | 724 | 54-70 | 726 | 103-106 | 728 |
| Ab7 | 1-111 | 522 | 30-34 | 524 | 49-64 | 526 | 95-100 | 528 |
| Ab8 | 1-117 | 762 | 34-39 | 764 | 54-70 | 766 | 103-106 | 768 |
| Ab9 | 1-117 | 802 | 34-39 | 804 | 54-70 | 806 | 103-106 | 808 |
| Ab11 | 1-111 | 562 | 30-34 | 564 | 49-64 | 566 | 95-100 | 568 |
| Ab12 | 1-111 | 602 | 30-34 | 604 | 49-64 | 606 | 95-100 | 608 |
| Ab13 | 1-113 | 122 | 30-34 | 124 | 49-64 | 126 | 96-102 | 128 |
| Ab14 | 1-113 | 162 | 30-34 | 164 | 49-64 | 166 | 96-102 | 168 |
| Ab15 | 1-113 | 202 | 30-34 | 204 | 49-64 | 206 | 96-102 | 208 |
| Ab16 | 1-113 | 242 | 30-34 | 244 | 49-64 | 246 | 96-102 | 248 |
| Ab17 | 1-113 | 282 | 30-34 | 284 | 49-64 | 286 | 96-102 | 288 |
| Ab18 | 1-113 | 322 | 30-34 | 324 | 49-64 | 326 | 96-102 | 328 |
| Ab19 | 1-113 | 362 | 30-34 | 364 | 49-64 | 366 | 96-102 | 368 |

Figure 6

Antibody Heavy Chain Protein Features

| Sequence Name | FR1 coordinates | SEQ ID NO: | FR2 coordinates | SEQ ID NO: | FR3 coordinates | SEQ ID NO: | FR4 coordinates | SEQ ID NO: | Constant region coordinates | SEQ ID NO: |
|---|---|---|---|---|---|---|---|---|---|---|
| Ab1 | 1-29 | 3 | 35-48 | 5 | 65-95 | 7 | 103-113 | 9 | 114-443 | 10 |
| Ab1.H | 1-30 | 43 | 36-49 | 45 | 66-97 | 47 | 105-115 | 49 | 116-445 | 50 |
| Ab2 | 1-29 | 83 | 35-48 | 85 | 65-95 | 87 | 103-113 | 89 | 114-443 | 90 |
| Ab3 | 1-30 | 683 | 37-50 | 685 | 69-99 | 687 | 112-122 | 689 | 123-452 | 690 |
| Ab4 | 1-29 | 643 | 35-48 | 645 | 65-95 | 647 | 111-121 | 649 | 122-451 | 650 |
| Ab5 | 1-29 | 483 | 35-48 | 485 | 65-94 | 487 | 105-115 | 489 | 116-445 | 490 |
| Ab6 | 1-33 | 723 | 40-53 | 725 | 71-102 | 727 | 107-117 | 729 | 118-447 | 730 |
| Ab7 | 1-29 | 523 | 35-48 | 525 | 65-94 | 527 | 101-111 | 529 | 112-441 | 530 |
| Ab8 | 1-33 | 763 | 40-53 | 765 | 71-102 | 767 | 107-117 | 769 | 118-447 | 770 |
| Ab9 | 1-33 | 803 | 40-53 | 805 | 71-102 | 807 | 107-117 | 809 | 118-447 | 810 |
| Ab11 | 1-29 | 563 | 35-48 | 565 | 65-94 | 567 | 101-111 | 569 | 112-441 | 570 |
| Ab12 | 1-29 | 603 | 35-48 | 605 | 65-94 | 607 | 101-111 | 609 | 112-441 | 610 |
| Ab13 | 1-29 | 123 | 35-48 | 125 | 65-95 | 127 | 103-113 | 129 | 114-443 | 130 |
| Ab14 | 1-29 | 163 | 35-48 | 165 | 65-95 | 167 | 103-113 | 169 | 114-443 | 170 |
| Ab15 | 1-29 | 203 | 35-48 | 205 | 65-95 | 207 | 103-113 | 209 | 114-443 | 210 |
| Ab16 | 1-29 | 243 | 35-48 | 245 | 65-95 | 247 | 103-113 | 249 | 114-443 | 250 |
| Ab17 | 1-29 | 283 | 35-48 | 285 | 65-95 | 287 | 103-113 | 289 | 114-443 | 290 |
| Ab18 | 1-29 | 323 | 35-48 | 325 | 65-95 | 327 | 103-113 | 329 | 114-443 | 330 |
| Ab19 | 1-29 | 363 | 35-48 | 365 | 65-95 | 367 | 103-113 | 369 | 114-443 | 370 |

Figure 7

Antibody Light Chain Protein Features

| Sequence Name | Variable region coordinates | SEQ ID NO: | CDR1 coordinates | SEQ ID NO: | CDR2 coordinates | SEQ ID NO: | CDR3 coordinates | SEQ ID NO: |
|---|---|---|---|---|---|---|---|---|
| Ab1 | 1-110 | 22 | 24-35 | 24 | 51-57 | 26 | 90-99 | 28 |
| Ab1.H | 1-110 | 62 | 24-35 | 64 | 51-57 | 66 | 90-99 | 68 |
| Ab2 | 1-111 | 102 | 24-36 | 104 | 52-58 | 106 | 91-100 | 108 |
| Ab3 | 1-111 | 702 | 24-34 | 704 | 50-56 | 706 | 89-100 | 708 |
| Ab4 | 1-111 | 662 | 24-34 | 664 | 50-56 | 666 | 89-100 | 668 |
| Ab5 | 1-111 | 502 | 24-34 | 504 | 50-56 | 506 | 89-100 | 508 |
| Ab6 | 1-114 | 742 | 24-36 | 744 | 52-58 | 746 | 91-103 | 748 |
| Ab7 | 1-112 | 542 | 24-36 | 544 | 52-58 | 546 | 91-101 | 548 |
| Ab8 | 1-113 | 782 | 24-35 | 784 | 51-57 | 786 | 90-102 | 788 |
| Ab9 | 1-114 | 822 | 24-36 | 824 | 52-58 | 826 | 91-103 | 828 |
| Ab11 | 1-112 | 582 | 24-36 | 584 | 52-58 | 586 | 91-101 | 588 |
| Ab12 | 1-112 | 622 | 24-36 | 624 | 52-58 | 626 | 91-101 | 628 |
| Ab13 | 1-111 | 142 | 24-36 | 144 | 52-58 | 146 | 91-100 | 148 |
| Ab14 | 1-111 | 182 | 24-36 | 184 | 52-58 | 186 | 91-100 | 188 |
| Ab15 | 1-111 | 222 | 24-36 | 224 | 52-58 | 226 | 91-100 | 228 |
| Ab16 | 1-111 | 262 | 24-36 | 264 | 52-58 | 266 | 91-100 | 268 |
| Ab17 | 1-111 | 302 | 24-36 | 304 | 52-58 | 306 | 91-100 | 308 |
| Ab18 | 1-111 | 342 | 24-36 | 344 | 52-58 | 346 | 91-100 | 348 |
| Ab19 | 1-111 | 382 | 24-36 | 384 | 52-58 | 386 | 91-100 | 388 |

Figure 8

Antibody Light Chain Protein Features

| Sequence Name | FR1 coordinates | SEQ ID NO: | FR2 coordinates | SEQ ID NO: | FR3 coordinates | SEQ ID NO: | FR4 coordinates | SEQ ID NO: | Constant region coordinates | SEQ ID NO: |
|---|---|---|---|---|---|---|---|---|---|---|
| Ab1 | 1-23 | 23 | 36-50 | 25 | 58-89 | 27 | 100-110 | 29 | 111-216 | 30 |
| Ab1.H | 1-23 | 63 | 36-50 | 65 | 58-89 | 67 | 100-110 | 69 | 111-216 | 70 |
| Ab2 | 1-23 | 103 | 37-51 | 105 | 59-90 | 107 | 101-111 | 109 | 112-217 | 110 |
| Ab3 | 1-23 | 703 | 35-49 | 705 | 57-88 | 707 | 101-111 | 709 | 112-217 | 710 |
| Ab4 | 1-23 | 663 | 35-49 | 665 | 57-88 | 667 | 101-111 | 669 | 112-217 | 670 |
| Ab5 | 1-23 | 503 | 35-49 | 505 | 57-88 | 507 | 101-111 | 509 | 112-217 | 510 |
| Ab6 | 1-23 | 743 | 37-51 | 745 | 59-90 | 747 | 104-114 | 749 | 115-220 | 750 |
| Ab7 | 1-23 | 543 | 37-51 | 545 | 59-90 | 547 | 102-112 | 549 | 113-218 | 550 |
| Ab8 | 1-23 | 783 | 36-50 | 785 | 58-89 | 787 | 103-113 | 789 | 114-219 | 790 |
| Ab9 | 1-23 | 823 | 37-51 | 825 | 59-90 | 827 | 104-114 | 829 | 115-220 | 830 |
| Ab11 | 1-23 | 583 | 37-51 | 585 | 59-90 | 587 | 102-112 | 589 | 113-218 | 590 |
| Ab12 | 1-23 | 623 | 37-51 | 625 | 59-90 | 627 | 102-112 | 629 | 113-218 | 630 |
| Ab13 | 1-23 | 143 | 37-51 | 145 | 59-90 | 147 | 101-111 | 149 | 112-217 | 150 |
| Ab14 | 1-23 | 183 | 37-51 | 185 | 59-90 | 187 | 101-111 | 189 | 112-217 | 190 |
| Ab15 | 1-23 | 223 | 37-51 | 225 | 59-90 | 227 | 101-111 | 229 | 112-217 | 230 |
| Ab16 | 1-23 | 263 | 37-51 | 265 | 59-90 | 267 | 101-111 | 269 | 112-217 | 270 |
| Ab17 | 1-23 | 303 | 37-51 | 305 | 59-90 | 307 | 101-111 | 309 | 112-217 | 310 |
| Ab18 | 1-23 | 343 | 37-51 | 345 | 59-90 | 347 | 101-111 | 349 | 112-217 | 350 |
| Ab19 | 1-23 | 383 | 37-51 | 385 | 59-90 | 387 | 101-111 | 389 | 112-217 | 390 |

Figure 9

Antibody Heavy Chain DNA Features

| Sequence Name | Variable region coordinates | SEQ ID NO: | CDR1 coordinates | SEQ ID NO: | CDR2 coordinates | SEQ ID NO: | CDR3 coordinates | SEQ ID NO: |
|---|---|---|---|---|---|---|---|---|
| Ab1 | 1-339 | 12 | 88-102 | 14 | 145-192 | 16 | 286-306 | 18 |
| Ab1.H | 1-345 | 52 | 91-105 | 54 | 148-195 | 56 | 292-312 | 58 |
| Ab2 | 1-339 | 92 | 88-102 | 94 | 145-192 | 96 | 286-306 | 98 |
| Ab3 | 1-366 | 692 | 91-108 | 694 | 151-204 | 696 | 298-333 | 698 |
| Ab4 | 1-363 | 652 | 88-102 | 654 | 145-192 | 656 | 286-330 | 658 |
| Ab5 | 1-345 | 492 | 88-102 | 494 | 145-192 | 496 | 283-312 | 498 |
| Ab6 | 1-351 | 732 | 100-117 | 734 | 160-210 | 736 | 307-318 | 738 |
| Ab7 | 1-333 | 532 | 88-102 | 534 | 145-192 | 536 | 283-300 | 538 |
| Ab8 | 1-351 | 772 | 100-117 | 774 | 160-210 | 776 | 307-318 | 778 |
| Ab9 | 1-351 | 812 | 100-117 | 814 | 160-210 | 816 | 307-318 | 818 |
| Ab11 | 1-333 | 572 | 88-102 | 574 | 145-192 | 576 | 283-300 | 578 |
| Ab12 | 1-333 | 612 | 88-102 | 614 | 145-192 | 616 | 283-300 | 618 |
| Ab13 | 1-339 | 132 | 88-102 | 134 | 145-192 | 136 | 286-306 | 138 |
| Ab14 | 1-339 | 172 | 88-102 | 174 | 145-192 | 176 | 286-306 | 178 |
| Ab15 | 1-339 | 212 | 88-102 | 214 | 145-192 | 216 | 286-306 | 218 |
| Ab16 | 1-339 | 252 | 88-102 | 254 | 145-192 | 256 | 286-306 | 258 |
| Ab17 | 1-339 | 292 | 88-102 | 294 | 145-192 | 296 | 286-306 | 298 |
| Ab18 | 1-339 | 332 | 88-102 | 334 | 145-192 | 336 | 286-306 | 338 |
| Ab19 | 1-339 | 372 | 88-102 | 374 | 145-192 | 376 | 286-306 | 378 |

Figure 10

Antibody Heavy Chain DNA Features

| Sequence Name | FR1 coordinates | SEQ ID NO: | FR2 coordinates | SEQ ID NO: | FR3 coordinates | SEQ ID NO: | FR4 coordinates | SEQ ID NO: | Constant region coordinates | SEQ ID NO: |
|---|---|---|---|---|---|---|---|---|---|---|
| Ab1 | 1-87 | 13 | 103-144 | 15 | 193-285 | 17 | 307-339 | 19 | 340-1329 | 20 |
| Ab1.H | 1-90 | 53 | 106-147 | 55 | 196-291 | 57 | 313-345 | 59 | 346-1335 | 60 |
| Ab2 | 1-87 | 93 | 103-144 | 95 | 193-285 | 97 | 307-339 | 99 | 340-1329 | 100 |
| Ab3 | 1-90 | 693 | 109-150 | 695 | 205-297 | 697 | 334-366 | 699 | 367-1356 | 700 |
| Ab4 | 1-87 | 653 | 103-144 | 655 | 193-285 | 657 | 331-363 | 659 | 364-1353 | 660 |
| Ab5 | 1-87 | 493 | 103-144 | 495 | 193-282 | 497 | 313-345 | 499 | 346-1335 | 500 |
| Ab6 | 1-99 | 733 | 118-159 | 735 | 211-306 | 737 | 319-351 | 739 | 352-1341 | 740 |
| Ab7 | 1-87 | 533 | 103-144 | 535 | 193-282 | 537 | 301-333 | 539 | 334-1323 | 540 |
| Ab8 | 1-99 | 773 | 118-159 | 775 | 211-306 | 777 | 319-351 | 779 | 352-1341 | 780 |
| Ab9 | 1-99 | 813 | 118-159 | 815 | 211-306 | 817 | 319-351 | 819 | 352-1341 | 820 |
| Ab11 | 1-87 | 573 | 103-144 | 575 | 193-282 | 577 | 301-333 | 579 | 334-1323 | 580 |
| Ab12 | 1-87 | 613 | 103-144 | 615 | 193-282 | 617 | 301-333 | 619 | 334-1323 | 620 |
| Ab13 | 1-87 | 133 | 103-144 | 135 | 193-285 | 137 | 307-339 | 139 | 340-1329 | 140 |
| Ab14 | 1-87 | 173 | 103-144 | 175 | 193-285 | 177 | 307-339 | 179 | 340-1329 | 180 |
| Ab15 | 1-87 | 213 | 103-144 | 215 | 193-285 | 217 | 307-339 | 219 | 340-1329 | 220 |
| Ab16 | 1-87 | 253 | 103-144 | 255 | 193-285 | 257 | 307-339 | 259 | 340-1329 | 260 |
| Ab17 | 1-87 | 293 | 103-144 | 295 | 193-285 | 297 | 307-339 | 299 | 340-1329 | 300 |
| Ab18 | 1-87 | 333 | 103-144 | 335 | 193-285 | 337 | 307-339 | 339 | 340-1329 | 340 |
| Ab19 | 1-87 | 373 | 103-144 | 375 | 193-285 | 377 | 307-339 | 379 | 340-1329 | 380 |

Figure 11

Antibody Light Chain DNA Features

| Sequence Name | Variable region coordinates | SEQ ID NO: | CDR1 coordinates | SEQ ID NO: | CDR2 coordinates | SEQ ID NO: | CDR3 coordinates | SEQ ID NO: |
|---|---|---|---|---|---|---|---|---|
| Ab1 | 1-330 | 32 | 70-105 | 34 | 151-171 | 36 | 268-297 | 38 |
| Ab1.H | 1-330 | 72 | 70-105 | 74 | 151-171 | 76 | 268-297 | 78 |
| Ab2 | 1-333 | 112 | 70-108 | 114 | 154-174 | 116 | 271-300 | 118 |
| Ab3 | 1-333 | 712 | 70-102 | 714 | 148-168 | 716 | 265-300 | 718 |
| Ab4 | 1-333 | 672 | 70-102 | 674 | 148-168 | 676 | 265-300 | 678 |
| Ab5 | 1-333 | 512 | 70-102 | 514 | 148-168 | 516 | 265-300 | 518 |
| Ab6 | 1-342 | 752 | 70-108 | 754 | 154-174 | 756 | 271-309 | 758 |
| Ab7 | 1-336 | 552 | 70-108 | 554 | 154-174 | 556 | 271-303 | 558 |
| Ab8 | 1-339 | 792 | 70-105 | 794 | 151-171 | 796 | 268-306 | 798 |
| Ab9 | 1-342 | 832 | 70-108 | 834 | 154-174 | 836 | 271-309 | 838 |
| Ab11 | 1-336 | 592 | 70-108 | 594 | 154-174 | 596 | 271-303 | 598 |
| Ab12 | 1-336 | 632 | 70-108 | 634 | 154-174 | 636 | 271-303 | 638 |
| Ab13 | 1-333 | 152 | 70-108 | 154 | 154-174 | 156 | 271-300 | 158 |
| Ab14 | 1-333 | 192 | 70-108 | 194 | 154-174 | 196 | 271-300 | 198 |
| Ab15 | 1-333 | 232 | 70-108 | 234 | 154-174 | 236 | 271-300 | 238 |
| Ab16 | 1-333 | 272 | 70-108 | 274 | 154-174 | 276 | 271-300 | 278 |
| Ab17 | 1-333 | 312 | 70-108 | 314 | 154-174 | 316 | 271-300 | 318 |
| Ab18 | 1-333 | 352 | 70-108 | 354 | 154-174 | 356 | 271-300 | 358 |
| Ab19 | 1-333 | 392 | 70-108 | 394 | 154-174 | 396 | 271-300 | 398 |

Figure 12

Antibody Light Chain DNA Features

| Sequence Name | FR1 coordinates | SEQ ID NO: | FR2 coordinates | SEQ ID NO: | FR3 coordinates | SEQ ID NO: | FR4 coordinates | SEQ ID NO: | Constant region coordinates | SEQ ID NO: |
|---|---|---|---|---|---|---|---|---|---|---|
| Ab1 | 1-69 | 33 | 106-150 | 35 | 172-267 | 37 | 298-330 | 39 | 331-648 | 40 |
| Ab1.H | 1-69 | 73 | 106-150 | 75 | 172-267 | 77 | 298-330 | 79 | 331-648 | 80 |
| Ab2 | 1-69 | 113 | 109-153 | 115 | 175-270 | 117 | 301-333 | 119 | 334-651 | 120 |
| Ab3 | 1-69 | 713 | 103-147 | 715 | 169-264 | 717 | 301-333 | 719 | 334-651 | 720 |
| Ab4 | 1-69 | 673 | 103-147 | 675 | 169-264 | 677 | 301-333 | 679 | 334-651 | 680 |
| Ab5 | 1-69 | 513 | 103-147 | 515 | 169-264 | 517 | 301-333 | 519 | 334-651 | 520 |
| Ab6 | 1-69 | 753 | 109-153 | 755 | 175-270 | 757 | 310-342 | 759 | 343-660 | 760 |
| Ab7 | 1-69 | 553 | 109-153 | 555 | 175-270 | 557 | 304-336 | 559 | 337-654 | 560 |
| Ab8 | 1-69 | 793 | 106-150 | 795 | 172-267 | 797 | 307-339 | 799 | 340-657 | 800 |
| Ab9 | 1-69 | 833 | 109-153 | 835 | 175-270 | 837 | 310-342 | 839 | 343-660 | 840 |
| Ab11 | 1-69 | 593 | 109-153 | 595 | 175-270 | 597 | 304-336 | 599 | 337-654 | 600 |
| Ab12 | 1-69 | 633 | 109-153 | 635 | 175-270 | 637 | 304-336 | 639 | 337-654 | 640 |
| Ab13 | 1-69 | 153 | 109-153 | 155 | 175-270 | 157 | 301-333 | 159 | 334-651 | 160 |
| Ab14 | 1-69 | 193 | 109-153 | 195 | 175-270 | 197 | 301-333 | 199 | 334-651 | 200 |
| Ab15 | 1-69 | 233 | 109-153 | 235 | 175-270 | 237 | 301-333 | 239 | 334-651 | 240 |
| Ab16 | 1-69 | 273 | 109-153 | 275 | 175-270 | 277 | 301-333 | 279 | 334-651 | 280 |
| Ab17 | 1-69 | 313 | 109-153 | 315 | 175-270 | 317 | 301-333 | 319 | 334-651 | 320 |
| Ab18 | 1-69 | 353 | 109-153 | 355 | 175-270 | 357 | 301-333 | 359 | 334-651 | 360 |
| Ab19 | 1-69 | 393 | 109-153 | 395 | 175-270 | 397 | 301-333 | 399 | 334-651 | 400 |

Ab1.H-mediated Inhibition of PACAP38-induced dermal vasodilation in rabbits

Ab10-mediated Inhibition of PACAP38-induced dermal vasodilation in rabbits

SEQUENCE LISTING

<160> NUMBER OF SEQ ID NOS: 1246

<210> SEQ ID NO 1
<211> LENGTH: 443
<212> TYPE: PRT
<213> ORGANISM: Artificial
<220> FEATURE:
<223> OTHER INFORMATION: Humanized Antibody Sequence

<400> SEQUENCE: 1

Gln Ser Val Glu Glu Ser Gly Gly Arg Leu Val Thr Pro Gly Thr Pro
1 5 10 15

Leu Thr Leu Thr Cys Thr Val Ser Gly Phe Ser Leu Ser Ser Ala Val
20 25 30

Met Asn Trp Val Arg Gln Ala Pro Gly Lys Gly Leu Glu Trp Ile Gly
35 40 45

Ser Ile Val Ala Ser Gly Thr Thr Tyr Tyr Ala Ser Trp Ala Asn Gly
50 55 60

Arg Phe Thr Ile Ser Lys Thr Ser Ser Thr Thr Met Asp Leu Lys Met
65 70 75 80

-continued

```
Thr Ser Pro Thr Thr Glu Asp Thr Ala Thr Tyr Phe Cys Ala Arg Gly
                85                  90                  95

Gly Gly Glu Phe Phe Ile Trp Gly Pro Gly Thr Leu Val Thr Val Ser
            100                 105                 110

Ser Ala Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Ala Arg Val Glu Pro Lys Ser Cys Asp Lys Thr His Thr Cys Pro Pro
    210                 215                 220

Cys Pro Ala Pro Glu Leu Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
        275                 280                 285

Glu Glu Gln Tyr Ala Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Ala Leu Pro Ala Pro Ile Glu Lys Thr Ile Ser Lys Ala Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
        435                 440
```

<210> SEQ ID NO 2
<211> LENGTH: 113
<212> TYPE: PRT
<213> ORGANISM: Artificial
<220> FEATURE:
<223> OTHER INFORMATION: Humanized Antibody Sequence

<400> SEQUENCE: 2

Gln Ser Val Glu Glu Ser Gly Gly Arg Leu Val Thr Pro Gly Thr Pro
1 5 10 15

Leu Thr Leu Thr Cys Thr Val Ser Gly Phe Ser Leu Ser Ser Ala Val
20 25 30

Met Asn Trp Val Arg Gln Ala Pro Gly Lys Gly Leu Glu Trp Ile Gly
35 40 45

Ser Ile Val Ala Ser Gly Thr Thr Tyr Tyr Ala Ser Trp Ala Asn Gly
50 55 60

Arg Phe Thr Ile Ser Lys Thr Ser Ser Thr Thr Met Asp Leu Lys Met
65 70 75 80

Thr Ser Pro Thr Thr Glu Asp Thr Ala Thr Tyr Phe Cys Ala Arg Gly
85 90 95

Gly Gly Glu Phe Phe Ile Trp Gly Pro Gly Thr Leu Val Thr Val Ser
100 105 110

Ser

<210> SEQ ID NO 3
<211> LENGTH: 29
<212> TYPE: PRT
<213> ORGANISM: Oryctolagus cuniculus

<400> SEQUENCE: 3

Gln Ser Val Glu Glu Ser Gly Gly Arg Leu Val Thr Pro Gly Thr Pro
1 5 10 15

Leu Thr Leu Thr Cys Thr Val Ser Gly Phe Ser Leu Ser
20 25

<210> SEQ ID NO 4
<211> LENGTH: 5
<212> TYPE: PRT
<213> ORGANISM: Oryctolagus cuniculus

<400> SEQUENCE: 4

Ser Ala Val Met Asn
1 5

<210> SEQ ID NO 5
<211> LENGTH: 14
<212> TYPE: PRT
<213> ORGANISM: Oryctolagus cuniculus

<400> SEQUENCE: 5

Trp Val Arg Gln Ala Pro Gly Lys Gly Leu Glu Trp Ile Gly
1 5 10

<210> SEQ ID NO 6
<211> LENGTH: 16
<212> TYPE: PRT
<213> ORGANISM: Oryctolagus cuniculus

<400> SEQUENCE: 6

Ser Ile Val Ala Ser Gly Thr Thr Tyr Tyr Ala Ser Trp Ala Asn Gly
1 5 10 15

<210> SEQ ID NO 7
<211> LENGTH: 31
<212> TYPE: PRT
<213> ORGANISM: Oryctolagus cuniculus

<400> SEQUENCE: 7

-continued

Arg Phe Thr Ile Ser Lys Thr Ser Ser Thr Thr Met Asp Leu Lys Met
1               5                   10                  15

Thr Ser Pro Thr Thr Glu Asp Thr Ala Thr Tyr Phe Cys Ala Arg
            20                  25                  30

<210> SEQ ID NO 8
<211> LENGTH: 7
<212> TYPE: PRT
<213> ORGANISM: Oryctolagus cuniculus

<400> SEQUENCE: 8

Gly Gly Gly Glu Phe Phe Ile
1               5

<210> SEQ ID NO 9
<211> LENGTH: 11
<212> TYPE: PRT
<213> ORGANISM: Artificial
<220> FEATURE:
<223> OTHER INFORMATION: Humanized Antibody Sequence

<400> SEQUENCE: 9

Trp Gly Pro Gly Thr Leu Val Thr Val Ser Ser
1               5                   10

<210> SEQ ID NO 10
<211> LENGTH: 330
<212> TYPE: PRT
<213> ORGANISM: Artificial
<220> FEATURE:
<223> OTHER INFORMATION: Humanized Antibody Sequence

<400> SEQUENCE: 10

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Ala
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

-continued

```
Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 11
<211> LENGTH: 1329
<212> TYPE: DNA
<213> ORGANISM: Artificial
<220> FEATURE:
<223> OTHER INFORMATION: Humanized Antibody Sequence

<400> SEQUENCE: 11

cagtcggtgg aggagtccgg gggtcgcctg gtcacgcctg ggacacccct gacactcacc     60

tgcaccgtct ctggattctc cctcagtagc gctgtaatga attgggtccg ccaggctcca    120

gggaaggggc tggaatggat cggaagtatt gttgctagtg gtaccacata ctacgcgagc    180

tgggcgaacg gccgattcac catctccaaa acctcgtcga ccacgatgga tctgaaaatg    240

accagtccga caaccgagga cacggccacc tatttctgtg ccagaggggg aggggaattt    300

ttcatctggg gcccggggac cctcgtcacc gtctcgagcg cctccaccaa gggcccatcg    360

gtcttccccc tggcaccctc ctccaagagc acctctgggg gcacagcggc cctgggctgc    420

ctggtcaagg actacttccc cgaaccggtg acggtgtcgt ggaactcagg cgccctgacc    480

agcggcgtgc acaccttccc ggctgtccta cagtcctcag gactctactc cctcagcagc    540

gtggtgaccg tgccctccag cagcttgggc acccagacct acatctgcaa cgtgaatcac    600

aagcccagca acaccaaggt ggacgcgaga gttgagccca aatcttgtga caaaactcac    660

acatgcccac cgtgcccagc acctgaactc ctggggggac cgtcagtctt cctcttcccc    720

ccaaaaccca aggacaccct catgatctcc cggacccctg aggtcacatg cgtggtggtg    780

gacgtgagcc acgaagaccc tgaggtcaag ttcaactggt acgtggacgg cgtggaggtg    840

cataatgcca agacaaagcc gcgggaggag cagtacgcca gcacgtaccg tgtggtcagc    900

gtcctcaccg tcctgcacca ggactggctg aatggcaagg agtacaagtg caaggtctcc    960

aacaaagccc tcccagcccc catcgagaaa accatctcca aagccaaagg gcagccccga   1020

gaaccacagg tgtacaccct gcccccatcc cgggaggaga tgaccaagaa ccaggtcagc   1080

ctgacctgcc tggtcaaagg cttctatccc agcgacatcg ccgtggagtg ggagagcaat   1140

gggcagccgg agaacaacta caagaccacg cctcccgtgc tggactccga cggctccttc   1200

ttcctctaca gcaagctcac cgtggacaag agcaggtggc agcaggggaa cgtcttctca   1260

tgctccgtga tgcatgaggc tctgcacaac cactacacgc agaagagcct ctccctgtct   1320

ccgggtaaa                                                           1329
```

<210> SEQ ID NO 12
<211> LENGTH: 339
<212> TYPE: DNA
<213> ORGANISM: Artificial
<220> FEATURE:
<223> OTHER INFORMATION: Humanized Antibody Sequence

<400> SEQUENCE: 12
cagtcggtgg aggagtccgg gggtcgcctg gtcacgcctg ggacacccct gacactcacc 60
tgcaccgtct ctggattctc cctcagtagc gctgtaatga attgggtccg ccaggctcca 120
gggaaggggc tggaatggat cggaagtatt gttgctagtg gtaccacata ctacgcgagc 180
tgggcgaacg gccgattcac catctccaaa acctcgtcga ccacgatgga tctgaaaatg 240
accagtccga caaccgagga cacggccacc tatttctgtg ccagaggggg aggggaattt 300
ttcatctggg gcccggggac cctcgtcacc gtctcgagc 339

<210> SEQ ID NO 13
<211> LENGTH: 87
<212> TYPE: DNA
<213> ORGANISM: Oryctolagus cuniculus

<400> SEQUENCE: 13
cagtcggtgg aggagtccgg gggtcgcctg gtcacgcctg ggacacccct gacactcacc 60
tgcaccgtct ctggattctc cctcagt 87

<210> SEQ ID NO 14
<211> LENGTH: 15
<212> TYPE: DNA
<213> ORGANISM: Oryctolagus cuniculus

<400> SEQUENCE: 14
agcgctgtaa tgaat 15

<210> SEQ ID NO 15
<211> LENGTH: 42
<212> TYPE: DNA
<213> ORGANISM: Oryctolagus cuniculus

<400> SEQUENCE: 15
tgggtccgcc aggctccagg gaaggggctg gaatggatcg ga 42

<210> SEQ ID NO 16
<211> LENGTH: 48
<212> TYPE: DNA
<213> ORGANISM: Oryctolagus cuniculus

<400> SEQUENCE: 16
agtattgttg ctagtggtac cacatactac gcgagctggg cgaacggc 48

<210> SEQ ID NO 17
<211> LENGTH: 93
<212> TYPE: DNA
<213> ORGANISM: Oryctolagus cuniculus

<400> SEQUENCE: 17
cgattcacca tctccaaaac ctcgtcgacc acgatggatc tgaaaatgac cagtccgaca 60
accgaggaca cggccaccta tttctgtgcc aga 93

<210> SEQ ID NO 18

-continued

<211> LENGTH: 21
<212> TYPE: DNA
<213> ORGANISM: Oryctolagus cuniculus

<400> SEQUENCE: 18
gggggagggg aatttttcat c 21

<210> SEQ ID NO 19
<211> LENGTH: 33
<212> TYPE: DNA
<213> ORGANISM: Artificial
<220> FEATURE:
<223> OTHER INFORMATION: Humanized Antibody Sequence

<400> SEQUENCE: 19
tggggcccgg ggaccctcgt caccgtctcg agc 33

<210> SEQ ID NO 20
<211> LENGTH: 990
<212> TYPE: DNA
<213> ORGANISM: Artificial
<220> FEATURE:
<223> OTHER INFORMATION: Humanized Antibody Sequence

<400> SEQUENCE: 20
gcctccacca agggcccatc ggtcttcccc ctggcaccct cctccaagag cacctctggg 60
ggcacagcgg ccctgggctg cctggtcaag gactacttcc ccgaaccggt gacggtgtcg 120
tggaactcag gcgccctgac cagcggcgtg cacaccttcc cggctgtcct acagtcctca 180
ggactctact ccctcagcag cgtggtgacc gtgccctcca gcagcttggg cacccagacc 240
tacatctgca acgtgaatca caagcccagc aacaccaagg tggacgcgag agttgagccc 300
aaatcttgtg acaaaactca cacatgccca ccgtgcccag cacctgaact cctgggggga 360
ccgtcagtct tcctcttccc cccaaaaccc aaggacaccc tcatgatctc ccggacccct 420
gaggtcacat gcgtggtggt ggacgtgagc cacgaagacc ctgaggtcaa gttcaactgg 480
tacgtggacg gcgtggaggt gcataatgcc aagacaaagc cgcgggagga gcagtacgcc 540
agcacgtacc gtgtggtcag cgtcctcacc gtcctgcacc aggactggct gaatggcaag 600
gagtacaagt gcaaggtctc caacaaagcc ctcccagccc ccatcgagaa aaccatctcc 660
aaagccaaag ggcagccccg agaaccacag gtgtacaccc tgcccccatc ccgggaggag 720
atgaccaaga accaggtcag cctgacctgc ctggtcaaag gcttctatcc cagcgacatc 780
gccgtggagt gggagagcaa tgggcagccg gagaacaact acaagaccac gcctcccgtg 840
ctggactccg acggctcctt cttcctctac agcaagctca ccgtggacaa gagcaggtgg 900
cagcagggga acgtcttctc atgctccgtg atgcatgagg ctctgcacaa ccactacacg 960
cagaagagcc tctccctgtc tccgggtaaa 990

<210> SEQ ID NO 21
<211> LENGTH: 216
<212> TYPE: PRT
<213> ORGANISM: Artificial
<220> FEATURE:
<223> OTHER INFORMATION: Humanized Antibody Sequence

<400> SEQUENCE: 21

Asp Pro Val Met Thr Gln Thr Pro Ser Ser Thr Ser Ala Ala Val Gly
1               5                   10                  15

Gly Thr Val Thr Ile Ser Cys Gln Ser Ser Glu Ser Val Tyr Ser Asn
            20                  25                  30

-continued

```
Tyr Leu Ser Trp Tyr Gln Gln Lys Pro Gly Gln Pro Pro Asn Phe Leu
        35                  40                  45

Ile Tyr Gln Ala Ser Asn Leu Ala Ser Gly Val Pro Ser Arg Phe Lys
    50                  55                  60

Gly Ser Gly Ser Gly Thr Gln Phe Thr Leu Thr Ile Thr Asp Leu Glu
65                  70                  75                  80

Cys Asp Asp Ala Ala Thr Tyr Tyr Cys Ala Gly Gly Tyr Ser Glu Asn
                85                  90                  95

Ile Val Gly Phe Gly Gly Gly Thr Glu Val Val Val Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215


<210> SEQ ID NO 22
<211> LENGTH: 110
<212> TYPE: PRT
<213> ORGANISM: Artificial
<220> FEATURE:
<223> OTHER INFORMATION: Humanized Antibody Sequence

<400> SEQUENCE: 22

Asp Pro Val Met Thr Gln Thr Pro Ser Ser Thr Ser Ala Ala Val Gly
1               5                   10                  15

Gly Thr Val Thr Ile Ser Cys Gln Ser Ser Glu Ser Val Tyr Ser Asn
            20                  25                  30

Tyr Leu Ser Trp Tyr Gln Gln Lys Pro Gly Gln Pro Pro Asn Phe Leu
        35                  40                  45

Ile Tyr Gln Ala Ser Asn Leu Ala Ser Gly Val Pro Ser Arg Phe Lys
    50                  55                  60

Gly Ser Gly Ser Gly Thr Gln Phe Thr Leu Thr Ile Thr Asp Leu Glu
65                  70                  75                  80

Cys Asp Asp Ala Ala Thr Tyr Tyr Cys Ala Gly Gly Tyr Ser Glu Asn
                85                  90                  95

Ile Val Gly Phe Gly Gly Gly Thr Glu Val Val Val Lys Arg
            100                 105                 110


<210> SEQ ID NO 23
<211> LENGTH: 23
<212> TYPE: PRT
<213> ORGANISM: Oryctolagus cuniculus

<400> SEQUENCE: 23

Asp Pro Val Met Thr Gln Thr Pro Ser Ser Thr Ser Ala Ala Val Gly
1               5                   10                  15
```

```
Gly Thr Val Thr Ile Ser Cys
            20


<210> SEQ ID NO 24
<211> LENGTH: 12
<212> TYPE: PRT
<213> ORGANISM: Oryctolagus cuniculus

<400> SEQUENCE: 24

Gln Ser Ser Glu Ser Val Tyr Ser Asn Tyr Leu Ser
1               5                   10


<210> SEQ ID NO 25
<211> LENGTH: 15
<212> TYPE: PRT
<213> ORGANISM: Oryctolagus cuniculus

<400> SEQUENCE: 25

Trp Tyr Gln Gln Lys Pro Gly Gln Pro Pro Asn Phe Leu Ile Tyr
1               5                   10                  15


<210> SEQ ID NO 26
<211> LENGTH: 7
<212> TYPE: PRT
<213> ORGANISM: Oryctolagus cuniculus

<400> SEQUENCE: 26

Gln Ala Ser Asn Leu Ala Ser
1               5


<210> SEQ ID NO 27
<211> LENGTH: 32
<212> TYPE: PRT
<213> ORGANISM: Oryctolagus cuniculus

<400> SEQUENCE: 27

Gly Val Pro Ser Arg Phe Lys Gly Ser Gly Ser Gly Thr Gln Phe Thr
1               5                   10                  15

Leu Thr Ile Thr Asp Leu Glu Cys Asp Asp Ala Ala Thr Tyr Tyr Cys
            20                  25                  30


<210> SEQ ID NO 28
<211> LENGTH: 10
<212> TYPE: PRT
<213> ORGANISM: Oryctolagus cuniculus

<400> SEQUENCE: 28

Ala Gly Gly Tyr Ser Glu Asn Ile Val Gly
1               5                   10


<210> SEQ ID NO 29
<211> LENGTH: 11
<212> TYPE: PRT
<213> ORGANISM: Artificial
<220> FEATURE:
<223> OTHER INFORMATION: Humanized Antibody Sequence

<400> SEQUENCE: 29

Phe Gly Gly Gly Thr Glu Val Val Val Lys Arg
1               5                   10


<210> SEQ ID NO 30
<211> LENGTH: 106
<212> TYPE: PRT
<213> ORGANISM: Artificial
```

<220> FEATURE:
<223> OTHER INFORMATION: Humanized Antibody Sequence

<400> SEQUENCE: 30

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 31
<211> LENGTH: 648
<212> TYPE: DNA
<213> ORGANISM: Artificial
<220> FEATURE:
<223> OTHER INFORMATION: Humanized Antibody Sequence

<400> SEQUENCE: 31
gaccctgtga tgacccagac tccatcttcc acgtctgcgg ctgtgggagg cacagtcacc 60
atcagttgcc agtccagtga gagtgtttat agtaactact tatcctggta tcagcagaaa 120
ccagggcagc ctcccaactt cctgatctac caggcatcca atttggcatc tggggtccca 180
tcgcggttca aaggcagtgg atctgggaca cagttcactc tcaccatcac cgacctggag 240
tgtgacgatg ccgccactta ttactgtgca ggcggttata gtgaaaacat tgttggtttc 300
ggcggaggga ccgaggtggt ggtcaaacgt acggtagcgg ccccatctgt cttcatcttc 360
ccgccatctg atgagcagtt gaaatctgga actgcctctg ttgtgtgcct gctgaataac 420
ttctatccca gagaggccaa agtacagtgg aaggtggata acgccctcca atcgggtaac 480
tcccaggaga gtgtcacaga gcaggacagc aaggacagca cctacagcct cagcagcacc 540
ctgacgctga gcaaagcaga ctacgagaaa cacaaagtct acgcctgcga agtcacccat 600
cagggcctga gctcgcccgt cacaaagagc ttcaacaggg gagagtgt 648

<210> SEQ ID NO 32
<211> LENGTH: 330
<212> TYPE: DNA
<213> ORGANISM: Artificial
<220> FEATURE:
<223> OTHER INFORMATION: Humanized Antibody Sequence

<400> SEQUENCE: 32
gaccctgtga tgacccagac tccatcttcc acgtctgcgg ctgtgggagg cacagtcacc 60
atcagttgcc agtccagtga gagtgtttat agtaactact tatcctggta tcagcagaaa 120
ccagggcagc ctcccaactt cctgatctac caggcatcca atttggcatc tggggtccca 180
tcgcggttca aaggcagtgg atctgggaca cagttcactc tcaccatcac cgacctggag 240
tgtgacgatg ccgccactta ttactgtgca ggcggttata gtgaaaacat tgttggtttc 300
ggcggaggga ccgaggtggt ggtcaaacgt 330

<210> SEQ ID NO 33
<211> LENGTH: 69
<212> TYPE: DNA
<213> ORGANISM: Oryctolagus cuniculus

<400> SEQUENCE: 33
gaccctgtga tgacccagac tccatcttcc acgtctgcgg ctgtgggagg cacagtcacc 60
atcagttgc 69

<210> SEQ ID NO 34
<211> LENGTH: 36
<212> TYPE: DNA
<213> ORGANISM: Oryctolagus cuniculus

<400> SEQUENCE: 34
cagtccagtg agagtgttta tagtaactac ttatcc 36

<210> SEQ ID NO 35
<211> LENGTH: 45
<212> TYPE: DNA
<213> ORGANISM: Oryctolagus cuniculus

<400> SEQUENCE: 35
tggtatcagc agaaaccagg gcagcctccc aacttcctga tctac 45

<210> SEQ ID NO 36
<211> LENGTH: 21
<212> TYPE: DNA
<213> ORGANISM: Oryctolagus cuniculus

<400> SEQUENCE: 36
caggcatcca atttggcatc t 21

<210> SEQ ID NO 37
<211> LENGTH: 96
<212> TYPE: DNA
<213> ORGANISM: Oryctolagus cuniculus

<400> SEQUENCE: 37
ggggtcccat cgcggttcaa aggcagtgga tctgggacac agttcactct caccatcacc 60
gacctggagt gtgacgatgc cgccacttat tactgt 96

<210> SEQ ID NO 38
<211> LENGTH: 30
<212> TYPE: DNA
<213> ORGANISM: Oryctolagus cuniculus

<400> SEQUENCE: 38
gcaggcggtt atagtgaaaa cattgttggt 30

<210> SEQ ID NO 39
<211> LENGTH: 33
<212> TYPE: DNA
<213> ORGANISM: Artificial
<220> FEATURE:
<223> OTHER INFORMATION: Humanized Antibody Sequence

<400> SEQUENCE: 39
ttcggcggag ggaccgaggt ggtggtcaaa cgt 33

<210> SEQ ID NO 40

<211> LENGTH: 318
<212> TYPE: DNA
<213> ORGANISM: Artificial
<220> FEATURE:
<223> OTHER INFORMATION: Humanized Antibody Sequence

<400> SEQUENCE: 40
acggtagcgg ccccatctgt cttcatcttc ccgccatctg atgagcagtt gaaatctgga 60
actgcctctg ttgtgtgcct gctgaataac ttctatccca gagaggccaa agtacagtgg 120
aaggtggata acgccctcca atcgggtaac tcccaggaga gtgtcacaga gcaggacagc 180
aaggacagca cctacagcct cagcagcacc ctgacgctga gcaaagcaga ctacgagaaa 240
cacaaagtct acgcctgcga agtcacccat cagggcctga gctcgcccgt cacaaagagc 300
ttcaacaggg gagagtgt 318

<210> SEQ ID NO 41
<211> LENGTH: 445
<212> TYPE: PRT
<213> ORGANISM: Artificial
<220> FEATURE:
<223> OTHER INFORMATION: Humanized Antibody Sequence

<400> SEQUENCE: 41

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Val Ser Ser Ala
20 25 30

Val Met Asn Trp Val Arg Gln Ala Pro Gly Lys Gly Leu Glu Trp Ile
35 40 45

Gly Ser Ile Val Ala Ser Gly Thr Thr Tyr Tyr Ala Ser Ser Ala Asn
50 55 60

Gly Arg Phe Thr Ile Ser Arg Asp Asn Ser Lys Asn Thr Leu Tyr Leu
65 70 75 80

Gln Met Asn Ser Leu Arg Ala Glu Asp Thr Ala Val Tyr Tyr Cys Ala
85 90 95

Arg Gly Gly Gly Glu Phe Phe Ile Trp Gly Gln Gly Thr Leu Val Thr
100 105 110

Val Ser Ser Ala Ser Thr Lys Gly Pro Ser Val Phe Pro Leu Ala Pro
115 120 125

Ser Ser Lys Ser Thr Ser Gly Gly Thr Ala Ala Leu Gly Cys Leu Val
130 135 140

Lys Asp Tyr Phe Pro Glu Pro Val Thr Val Ser Trp Asn Ser Gly Ala
145 150 155 160

Leu Thr Ser Gly Val His Thr Phe Pro Ala Val Leu Gln Ser Ser Gly
165 170 175

Leu Tyr Ser Leu Ser Ser Val Val Thr Val Pro Ser Ser Ser Leu Gly
180 185 190

Thr Gln Thr Tyr Ile Cys Asn Val Asn His Lys Pro Ser Asn Thr Lys
195 200 205

Val Asp Lys Lys Val Glu Pro Lys Ser Cys Asp Lys Thr His Thr Cys
210 215 220

Pro Pro Cys Pro Ala Pro Glu Leu Leu Gly Gly Pro Ser Val Phe Leu
225 230 235 240

Phe Pro Pro Lys Pro Lys Asp Thr Leu Met Ile Ser Arg Thr Pro Glu
245 250 255

Val Thr Cys Val Val Val Asp Val Ser His Glu Asp Pro Glu Val Lys 260 265 270

Phe Asn Trp Tyr Val Asp Gly Val Glu Val His Asn Ala Lys Thr Lys
275 280 285

Pro Arg Glu Glu Gln Tyr Ala Ser Thr Tyr Arg Val Val Ser Val Leu
290 295 300

Thr Val Leu His Gln Asp Trp Leu Asn Gly Lys Glu Tyr Lys Cys Lys
305 310 315 320

Val Ser Asn Lys Ala Leu Pro Ala Pro Ile Glu Lys Thr Ile Ser Lys
325 330 335

Ala Lys Gly Gln Pro Arg Glu Pro Gln Val Tyr Thr Leu Pro Pro Ser
340 345 350

Arg Glu Glu Met Thr Lys Asn Gln Val Ser Leu Thr Cys Leu Val Lys
355 360 365

Gly Phe Tyr Pro Ser Asp Ile Ala Val Glu Trp Glu Ser Asn Gly Gln
370 375 380

Pro Glu Asn Asn Tyr Lys Thr Thr Pro Pro Val Leu Asp Ser Asp Gly
385 390 395 400

Ser Phe Phe Leu Tyr Ser Lys Leu Thr Val Asp Lys Ser Arg Trp Gln
405 410 415

Gln Gly Asn Val Phe Ser Cys Ser Val Met His Glu Ala Leu His Asn
420 425 430

His Tyr Thr Gln Lys Ser Leu Ser Leu Ser Pro Gly Lys
435 440 445

<210> SEQ ID NO 42
<211> LENGTH: 115
<212> TYPE: PRT
<213> ORGANISM: Artificial
<220> FEATURE:
<223> OTHER INFORMATION: Humanized Antibody Sequence

<400> SEQUENCE: 42

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Val Ser Ser Ala
20 25 30

Val Met Asn Trp Val Arg Gln Ala Pro Gly Lys Gly Leu Glu Trp Ile
35 40 45

Gly Ser Ile Val Ala Ser Gly Thr Thr Tyr Tyr Ala Ser Ser Ala Asn
50 55 60

Gly Arg Phe Thr Ile Ser Arg Asp Asn Ser Lys Asn Thr Leu Tyr Leu
65 70 75 80

Gln Met Asn Ser Leu Arg Ala Glu Asp Thr Ala Val Tyr Tyr Cys Ala
85 90 95

Arg Gly Gly Gly Glu Phe Phe Ile Trp Gly Gln Gly Thr Leu Val Thr
100 105 110

Val Ser Ser
115

<210> SEQ ID NO 43
<211> LENGTH: 30
<212> TYPE: PRT
<213> ORGANISM: Artificial
<220> FEATURE:
<223> OTHER INFORMATION: Humanized Antibody Sequence

<400> SEQUENCE: 43

-continued

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser
            20                  25                  30


<210> SEQ ID NO 44
<211> LENGTH: 5
<212> TYPE: PRT
<213> ORGANISM: Oryctolagus cuniculus

<400> SEQUENCE: 44

Ser Ala Val Met Asn
1               5


<210> SEQ ID NO 45
<211> LENGTH: 14
<212> TYPE: PRT
<213> ORGANISM: Artificial
<220> FEATURE:
<223> OTHER INFORMATION: Humanized Antibody Sequence

<400> SEQUENCE: 45

Trp Val Arg Gln Ala Pro Gly Lys Gly Leu Glu Trp Ile Gly
1               5                   10


<210> SEQ ID NO 46
<211> LENGTH: 16
<212> TYPE: PRT
<213> ORGANISM: Artificial
<220> FEATURE:
<223> OTHER INFORMATION: Humanized Antibody Sequence

<400> SEQUENCE: 46

Ser Ile Val Ala Ser Gly Thr Thr Tyr Tyr Ala Ser Ser Ala Asn Gly
1               5                   10                  15


<210> SEQ ID NO 47
<211> LENGTH: 32
<212> TYPE: PRT
<213> ORGANISM: Artificial
<220> FEATURE:
<223> OTHER INFORMATION: Humanized Antibody Sequence

<400> SEQUENCE: 47

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30


<210> SEQ ID NO 48
<211> LENGTH: 7
<212> TYPE: PRT
<213> ORGANISM: Oryctolagus cuniculus

<400> SEQUENCE: 48

Gly Gly Gly Glu Phe Phe Ile
1               5


<210> SEQ ID NO 49
<211> LENGTH: 11
<212> TYPE: PRT
<213> ORGANISM: Artificial
<220> FEATURE:
<223> OTHER INFORMATION: Humanized Antibody Sequence

<400> SEQUENCE: 49
```

```
Trp Gly Gln Gly Thr Leu Val Thr Val Ser Ser
1               5                   10


<210> SEQ ID NO 50
<211> LENGTH: 330
<212> TYPE: PRT
<213> ORGANISM: Artificial
<220> FEATURE:
<223> OTHER INFORMATION: Humanized Antibody Sequence

<400> SEQUENCE: 50

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 51
```

<211> LENGTH: 1335
<212> TYPE: DNA
<213> ORGANISM: Artificial
<220> FEATURE:
<223> OTHER INFORMATION: Humanized Antibody Sequence

<400> SEQUENCE: 51
gaggtgcagc ttgtggagtc tgggggaggc ttggtccagc ctggggggtc cctgagactc 60
tcctgtgcag cctctggatt caccgtcagt agcgctgtaa tgaattgggt ccgtcaggct 120
ccagggaagg ggctggagtg gatcggaagt attgttgcta gtggtaccac atactacgct 180
agctctgcta acggccgatt caccatctcc agagacaatt ccaagaacac cctgtatctt 240
caaatgaaca gcctgagagc tgaggacact gctgtgtatt actgtgctag agggggaggg 300
gaatttttca tctggggcca agggaccctc gtcaccgtct cgagcgcctc caccaagggc 360
ccatcggtct tccccctggc accctcctcc aagagcacct ctgggggcac agcggccctg 420
ggctgcctgg tcaaggacta cttccccgaa ccggtgacgg tgtcgtggaa ctcaggcgcc 480
ctgaccagcg gcgtgcacac cttcccggct gtcctacagt cctcaggact ctactccctc 540
agcagcgtgg tgaccgtgcc ctccagcagc ttgggcaccc agacctacat ctgcaacgtg 600
aatcacaagc ccagcaacac caaggtggac aagaaagttg agcccaaatc ttgtgacaaa 660
actcacacat gcccaccgtg cccagcacct gaactcctgg ggggaccgtc agtcttcctc 720
ttccccccaa aacccaagga caccctcatg atctcccgga cccctgaggt cacatgcgtg 780
gtggtggacg tgagccacga agaccctgag gtcaagttca actggtacgt ggacggcgtg 840
gaggtgcata atgccaagac aaagccgcgg gaggagcagt acgccagcac gtaccgtgtg 900
gtcagcgtcc tcaccgtcct gcaccaggac tggctgaatg gcaaggagta caagtgcaag 960
gtctccaaca aagccctccc agcccccatc gagaaaacca tctccaaagc caaagggcag 1020
ccccgagaac cacaggtgta caccctgccc ccatcccggg aggagatgac caagaaccag 1080
gtcagcctga cctgcctggt caaaggcttc tatcccagcg acatcgccgt ggagtgggag 1140
agcaatgggc agccggagaa caactacaag accacgcctc ccgtgctgga ctccgacggc 1200
tccttcttcc tctacagcaa gctcaccgtg gacaagagca ggtggcagca ggggaacgtc 1260
ttctcatgct ccgtgatgca tgaggctctg cacaaccact acacgcagaa gagcctctcc 1320
ctgtctccgg gtaaa 1335

<210> SEQ ID NO 52
<211> LENGTH: 345
<212> TYPE: DNA
<213> ORGANISM: Artificial
<220> FEATURE:
<223> OTHER INFORMATION: Humanized Antibody Sequence

<400> SEQUENCE: 52
gaggtgcagc ttgtggagtc tgggggaggc ttggtccagc ctggggggtc cctgagactc 60
tcctgtgcag cctctggatt caccgtcagt agcgctgtaa tgaattgggt ccgtcaggct 120
ccagggaagg ggctggagtg gatcggaagt attgttgcta gtggtaccac atactacgct 180
agctctgcta acggccgatt caccatctcc agagacaatt ccaagaacac cctgtatctt 240
caaatgaaca gcctgagagc tgaggacact gctgtgtatt actgtgctag agggggaggg 300
gaatttttca tctggggcca agggaccctc gtcaccgtct cgagc 345

<210> SEQ ID NO 53
<211> LENGTH: 90

<212> TYPE: DNA
<213> ORGANISM: Artificial
<220> FEATURE:
<223> OTHER INFORMATION: Humanized Antibody Sequence

<400> SEQUENCE: 53
gaggtgcagc ttgtggagtc tgggggaggc ttggtccagc ctggggggtc cctgagactc 60
tcctgtgcag cctctggatt caccgtcagt 90

<210> SEQ ID NO 54
<211> LENGTH: 15
<212> TYPE: DNA
<213> ORGANISM: Oryctolagus cuniculus

<400> SEQUENCE: 54
agcgctgtaa tgaat 15

<210> SEQ ID NO 55
<211> LENGTH: 42
<212> TYPE: DNA
<213> ORGANISM: Artificial
<220> FEATURE:
<223> OTHER INFORMATION: Humanized Antibody Sequence

<400> SEQUENCE: 55
tgggtccgtc aggctccagg gaaggggctg gagtggatcg ga 42

<210> SEQ ID NO 56
<211> LENGTH: 48
<212> TYPE: DNA
<213> ORGANISM: Artificial
<220> FEATURE:
<223> OTHER INFORMATION: Humanized Antibody Sequence

<400> SEQUENCE: 56
agtattgttg ctagtggtac cacatactac gctagctctg ctaacggc 48

<210> SEQ ID NO 57
<211> LENGTH: 96
<212> TYPE: DNA
<213> ORGANISM: Artificial
<220> FEATURE:
<223> OTHER INFORMATION: Humanized Antibody Sequence

<400> SEQUENCE: 57
cgattcacca tctccagaga caattccaag aacaccctgt atcttcaaat gaacagcctg 60
agagctgagg acactgctgt gtattactgt gctaga 96

<210> SEQ ID NO 58
<211> LENGTH: 21
<212> TYPE: DNA
<213> ORGANISM: Oryctolagus cuniculus

<400> SEQUENCE: 58
gggggagggg aatttttcat c 21

<210> SEQ ID NO 59
<211> LENGTH: 33
<212> TYPE: DNA
<213> ORGANISM: Artificial
<220> FEATURE:
<223> OTHER INFORMATION: Humanized Antibody Sequence

<400> SEQUENCE: 59

-continued

```
tggggccaag ggaccctcgt caccgtctcg agc                                 33


<210> SEQ ID NO 60
<211> LENGTH: 990
<212> TYPE: DNA
<213> ORGANISM: Artificial
<220> FEATURE:
<223> OTHER INFORMATION: Humanized Antibody Sequence

<400> SEQUENCE: 60

gcctccacca agggcccatc ggtcttcccc ctggcaccct cctccaagag cacctctggg     60

ggcacagcgg ccctgggctg cctggtcaag gactacttcc ccgaaccggt gacggtgtcg    120

tggaactcag gcgccctgac cagcggcgtg cacaccttcc cggctgtcct acagtcctca    180

ggactctact ccctcagcag cgtggtgacc gtgccctcca gcagcttggg cacccagacc    240

tacatctgca acgtgaatca caagcccagc aacaccaagg tggacaagaa agttgagccc    300

aaatcttgtg acaaaactca cacatgccca ccgtgcccag cacctgaact cctgggggga    360

ccgtcagtct tcctcttccc cccaaaaccc aaggacaccc tcatgatctc ccggacccct    420

gaggtcacat gcgtggtggt ggacgtgagc cacgaagacc ctgaggtcaa gttcaactgg    480

tacgtggacg gcgtggaggt gcataatgcc aagacaaagc cgcgggagga gcagtacgcc    540

agcacgtacc gtgtggtcag cgtcctcacc gtcctgcacc aggactggct gaatggcaag    600

gagtacaagt gcaaggtctc caacaaagcc ctcccagccc ccatcgagaa aaccatctcc    660

aaagccaaag ggcagccccg agaaccacag gtgtacaccc tgcccccatc ccgggaggag    720

atgaccaaga accaggtcag cctgacctgc ctggtcaaag gcttctatcc cagcgacatc    780

gccgtggagt gggagagcaa tgggcagccg gagaacaact acaagaccac gcctcccgtg    840

ctggactccg acggctcctt cttcctctac agcaagctca ccgtggacaa gagcaggtgg    900

cagcagggga acgtcttctc atgctccgtg atgcatgagg ctctgcacaa ccactacacg    960

cagaagagcc tctccctgtc tccgggtaaa                                     990


<210> SEQ ID NO 61
<211> LENGTH: 216
<212> TYPE: PRT
<213> ORGANISM: Artificial
<220> FEATURE:
<223> OTHER INFORMATION: Humanized Antibody Sequence

<400> SEQUENCE: 61

Asp Ile Gln Met Thr Gln Ser Pro Ser Thr Leu Ser Ala Ser Val Gly
1               5                   10                  15

Asp Arg Val Thr Ile Thr Cys Gln Ser Ser Glu Ser Val Tyr Ser Asn
            20                  25                  30

Tyr Leu Ser Trp Tyr Gln Gln Lys Pro Gly Lys Ala Pro Lys Phe Leu
        35                  40                  45

Ile Tyr Gln Ala Ser Asn Leu Ala Ser Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Asp Asp Phe Ala Thr Tyr Tyr Cys Ala Gly Gly Tyr Ser Glu Asn
                85                  90                  95

Ile Val Gly Phe Gly Gly Gly Thr Lys Val Glu Ile Lys Arg Thr Val
            100                 105                 110

Ala Ala Pro Ser Val Phe Ile Phe Pro Pro Ser Asp Glu Gln Leu Lys
        115                 120                 125
```

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 62
<211> LENGTH: 110
<212> TYPE: PRT
<213> ORGANISM: Artificial
<220> FEATURE:
<223> OTHER INFORMATION: Humanized Antibody Sequence

<400> SEQUENCE: 62

Asp Ile Gln Met Thr Gln Ser Pro Ser Thr Leu Ser Ala Ser Val Gly
1               5                   10                  15

Asp Arg Val Thr Ile Thr Cys Gln Ser Ser Glu Ser Val Tyr Ser Asn
            20                  25                  30

Tyr Leu Ser Trp Tyr Gln Gln Lys Pro Gly Lys Ala Pro Lys Phe Leu
        35                  40                  45

Ile Tyr Gln Ala Ser Asn Leu Ala Ser Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Asp Asp Phe Ala Thr Tyr Tyr Cys Ala Gly Gly Tyr Ser Glu Asn
                85                  90                  95

Ile Val Gly Phe Gly Gly Gly Thr Lys Val Glu Ile Lys Arg
            100                 105                 110

<210> SEQ ID NO 63
<211> LENGTH: 23
<212> TYPE: PRT
<213> ORGANISM: Artificial
<220> FEATURE:
<223> OTHER INFORMATION: Humanized Antibody Sequence

<400> SEQUENCE: 63

Asp Ile Gln Met Thr Gln Ser Pro Ser Thr Leu Ser Ala Ser Val Gly
1               5                   10                  15

Asp Arg Val Thr Ile Thr Cys
            20

<210> SEQ ID NO 64
<211> LENGTH: 12
<212> TYPE: PRT
<213> ORGANISM: Oryctolagus cuniculus

<400> SEQUENCE: 64

Gln Ser Ser Glu Ser Val Tyr Ser Asn Tyr Leu Ser
1               5                   10

<210> SEQ ID NO 65

<211> LENGTH: 15
<212> TYPE: PRT
<213> ORGANISM: Artificial
<220> FEATURE:
<223> OTHER INFORMATION: Humanized Antibody Sequence

<400> SEQUENCE: 65

Trp Tyr Gln Gln Lys Pro Gly Lys Ala Pro Lys Phe Leu Ile Tyr
1 5 10 15

<210> SEQ ID NO 66
<211> LENGTH: 7
<212> TYPE: PRT
<213> ORGANISM: Oryctolagus cuniculus

<400> SEQUENCE: 66

Gln Ala Ser Asn Leu Ala Ser
1 5

<210> SEQ ID NO 67
<211> LENGTH: 32
<212> TYPE: PRT
<213> ORGANISM: Artificial
<220> FEATURE:
<223> OTHER INFORMATION: Humanized Antibody Sequence

<400> SEQUENCE: 67

Gly Val Pro Ser Arg Phe Ser Gly Ser Gly Ser Gly Thr Glu Phe Thr
1 5 10 15

Leu Thr Ile Ser Ser Leu Gln Pro Asp Asp Phe Ala Thr Tyr Tyr Cys
20 25 30

<210> SEQ ID NO 68
<211> LENGTH: 10
<212> TYPE: PRT
<213> ORGANISM: Oryctolagus cuniculus

<400> SEQUENCE: 68

Ala Gly Gly Tyr Ser Glu Asn Ile Val Gly
1 5 10

<210> SEQ ID NO 69
<211> LENGTH: 11
<212> TYPE: PRT
<213> ORGANISM: Artificial
<220> FEATURE:
<223> OTHER INFORMATION: Humanized Antibody Sequence

<400> SEQUENCE: 69

Phe Gly Gly Gly Thr Lys Val Glu Ile Lys Arg
1 5 10

<210> SEQ ID NO 70
<211> LENGTH: 106
<212> TYPE: PRT
<213> ORGANISM: Artificial
<220> FEATURE:
<223> OTHER INFORMATION: Humanized Antibody Sequence

<400> SEQUENCE: 70

Thr Val Ala Ala Pro Ser Val Phe Ile Phe Pro Pro Ser Asp Glu Gln
1 5 10 15

Leu Lys Ser Gly Thr Ala Ser Val Val Cys Leu Leu Asn Asn Phe Tyr
20 25 30

Pro Arg Glu Ala Lys Val Gln Trp Lys Val Asp Asn Ala Leu Gln Ser

```
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105
```

<210> SEQ ID NO 71
<211> LENGTH: 648
<212> TYPE: DNA
<213> ORGANISM: Artificial
<220> FEATURE:
<223> OTHER INFORMATION: Humanized Antibody Sequence

<400> SEQUENCE: 71

```
gacatccaga tgacccagtc tccttccacc ctgtctgcat ctgtaggaga cagagtcacc     60

atcacttgtc agtccagtga gagtgtttat agtaactact tatcctggta tcagcagaaa    120

ccaggaaaag cccctaagtt cctgatctat caggcatcca atttggcatc tggagtccca    180

tcaaggttca gcggcagtgg atctggaaca gaattcactc tcaccatcag cagcctgcag    240

cctgatgatt ttgcaactta ctactgtgca ggcggttata gtgaaaacat tgttggtttc    300

ggcggaggaa ccaaggtgga aatcaaacgt acggtagcgg ccccatctgt cttcatcttc    360

ccgccatctg atgagcagtt gaaatctgga actgcctctg ttgtgtgcct gctgaataac    420

ttctatccca gagaggccaa agtacagtgg aaggtggata acgccctcca atcgggtaac    480

tcccaggaga gtgtcacaga gcaggacagc aaggacagca cctacagcct cagcagcacc    540

ctgacgctga gcaaagcaga ctacgagaaa cacaaagtct acgcctgcga agtcacccat    600

cagggcctga gctcgcccgt cacaaagagc ttcaacaggg gagagtgt                 648
```

<210> SEQ ID NO 72
<211> LENGTH: 330
<212> TYPE: DNA
<213> ORGANISM: Artificial
<220> FEATURE:
<223> OTHER INFORMATION: Humanized Antibody Sequence

<400> SEQUENCE: 72

```
gacatccaga tgacccagtc tccttccacc ctgtctgcat ctgtaggaga cagagtcacc     60

atcacttgtc agtccagtga gagtgtttat agtaactact tatcctggta tcagcagaaa    120

ccaggaaaag cccctaagtt cctgatctat caggcatcca atttggcatc tggagtccca    180

tcaaggttca gcggcagtgg atctggaaca gaattcactc tcaccatcag cagcctgcag    240

cctgatgatt ttgcaactta ctactgtgca ggcggttata gtgaaaacat tgttggtttc    300

ggcggaggaa ccaaggtgga aatcaaacgt                                     330
```

<210> SEQ ID NO 73
<211> LENGTH: 69
<212> TYPE: DNA
<213> ORGANISM: Artificial
<220> FEATURE:
<223> OTHER INFORMATION: Humanized Antibody Sequence

<400> SEQUENCE: 73

```
gacatccaga tgacccagtc tccttccacc ctgtctgcat ctgtaggaga cagagtcacc     60
```

atcacttgt 69

<210> SEQ ID NO 74
<211> LENGTH: 36
<212> TYPE: DNA
<213> ORGANISM: Oryctolagus cuniculus

<400> SEQUENCE: 74
cagtccagtg agagtgttta tagtaactac ttatcc 36

<210> SEQ ID NO 75
<211> LENGTH: 45
<212> TYPE: DNA
<213> ORGANISM: Artificial
<220> FEATURE:
<223> OTHER INFORMATION: Humanized Antibody Sequence

<400> SEQUENCE: 75
tggtatcagc agaaaccagg aaaagcccct aagttcctga tctat 45

<210> SEQ ID NO 76
<211> LENGTH: 21
<212> TYPE: DNA
<213> ORGANISM: Oryctolagus cuniculus

<400> SEQUENCE: 76
caggcatcca atttggcatc t 21

<210> SEQ ID NO 77
<211> LENGTH: 96
<212> TYPE: DNA
<213> ORGANISM: Artificial
<220> FEATURE:
<223> OTHER INFORMATION: Humanized Antibody Sequence

<400> SEQUENCE: 77
ggagtcccat caaggttcag cggcagtgga tctggaacag aattcactct caccatcagc 60
agcctgcagc ctgatgattt tgcaacttac tactgt 96

<210> SEQ ID NO 78
<211> LENGTH: 30
<212> TYPE: DNA
<213> ORGANISM: Oryctolagus cuniculus

<400> SEQUENCE: 78
gcaggcggtt atagtgaaaa cattgttggt 30

<210> SEQ ID NO 79
<211> LENGTH: 33
<212> TYPE: DNA
<213> ORGANISM: Artificial
<220> FEATURE:
<223> OTHER INFORMATION: Humanized Antibody Sequence

<400> SEQUENCE: 79
ttcggcggag gaaccaaggt ggaaatcaaa cgt 33

<210> SEQ ID NO 80
<211> LENGTH: 318
<212> TYPE: DNA
<213> ORGANISM: Artificial
<220> FEATURE:
<223> OTHER INFORMATION: Humanized Antibody Sequence

<400> SEQUENCE: 80
acggtagcgg ccccatctgt cttcatcttc ccgccatctg atgagcagtt gaaatctgga 60
actgcctctg ttgtgtgcct gctgaataac ttctatccca gagaggccaa agtacagtgg 120
aaggtggata acgccctcca atcgggtaac tcccaggaga gtgtcacaga gcaggacagc 180
aaggacagca cctacagcct cagcagcacc ctgacgctga gcaaagcaga ctacgagaaa 240
cacaaagtct acgcctgcga agtcacccat cagggcctga gctcgcccgt cacaaagagc 300
ttcaacaggg gagagtgt 318

<210> SEQ ID NO 81
<211> LENGTH: 443
<212> TYPE: PRT
<213> ORGANISM: Artificial
<220> FEATURE:
<223> OTHER INFORMATION: Humanized Antibody Sequence

<400> SEQUENCE: 81

Gln Ser Val Glu Glu Ser Gly Gly Arg Leu Val Thr Pro Gly Thr Pro
1 5 10 15

Leu Thr Leu Thr Cys Thr Val Ser Gly Phe Ser Leu Ser Gly Ala Ala
20 25 30

Met Asn Trp Val Arg Gln Ala Pro Gly Lys Gly Leu Glu Trp Ile Gly
35 40 45

Val Ile Gly Asn Ser Gly Ser Thr Tyr Tyr Ala Ser Trp Ala Lys Gly
50 55 60

Arg Phe Thr Ile Ser Lys Thr Ser Ser Thr Thr Val Asp Leu Lys Met
65 70 75 80

Thr Ser Pro Thr Thr Glu Asp Thr Ala Thr Tyr Phe Cys Ala Arg Gly
85 90 95

Gly Gly Glu Phe Phe Ile Trp Gly Gln Gly Thr Leu Val Thr Val Ser
100 105 110

Ser Ala Ser Thr Lys Gly Pro Ser Val Phe Pro Leu Ala Pro Ser Ser
115 120 125

Lys Ser Thr Ser Gly Gly Thr Ala Ala Leu Gly Cys Leu Val Lys Asp
130 135 140

Tyr Phe Pro Glu Pro Val Thr Val Ser Trp Asn Ser Gly Ala Leu Thr
145 150 155 160

Ser Gly Val His Thr Phe Pro Ala Val Leu Gln Ser Ser Gly Leu Tyr
165 170 175

Ser Leu Ser Ser Val Val Thr Val Pro Ser Ser Ser Leu Gly Thr Gln
180 185 190

Thr Tyr Ile Cys Asn Val Asn His Lys Pro Ser Asn Thr Lys Val Asp
195 200 205

Ala Arg Val Glu Pro Lys Ser Cys Asp Lys Thr His Thr Cys Pro Pro
210 215 220

Cys Pro Ala Pro Glu Leu Leu Gly Gly Pro Ser Val Phe Leu Phe Pro
225 230 235 240

Pro Lys Pro Lys Asp Thr Leu Met Ile Ser Arg Thr Pro Glu Val Thr
245 250 255

Cys Val Val Val Asp Val Ser His Glu Asp Pro Glu Val Lys Phe Asn
260 265 270

Trp Tyr Val Asp Gly Val Glu Val His Asn Ala Lys Thr Lys Pro Arg
275 280 285

Glu Glu Gln Tyr Ala Ser Thr Tyr Arg Val Val Ser Val Leu Thr Val

```
    290                 295                 300

Leu His Gln Asp Trp Leu Asn Gly Lys Glu Tyr Lys Cys Lys Val Ser
305                 310                 315                 320

Asn Lys Ala Leu Pro Ala Pro Ile Glu Lys Thr Ile Ser Lys Ala Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
        435                 440


<210> SEQ ID NO 82
<211> LENGTH: 113
<212> TYPE: PRT
<213> ORGANISM: Artificial
<220> FEATURE:
<223> OTHER INFORMATION: Humanized Antibody Sequence

<400> SEQUENCE: 82

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Gly Ala Ala
            20                  25                  30

Met Asn Trp Val Arg Gln Ala Pro Gly Lys Gly Leu Glu Trp Ile Gly
        35                  40                  45

Val Ile Gly Asn Ser Gly Ser Thr Tyr Tyr Ala Ser Trp Ala Lys Gly
    50                  55                  60

Arg Phe Thr Ile Ser Lys Thr Ser Ser Thr Thr Val Asp Leu Lys Met
65                  70                  75                  80

Thr Ser Pro Thr Thr Glu Asp Thr Ala Thr Tyr Phe Cys Ala Arg Gly
                85                  90                  95

Gly Gly Glu Phe Phe Ile Trp Gly Gln Gly Thr Leu Val Thr Val Ser
            100                 105                 110

Ser


<210> SEQ ID NO 83
<211> LENGTH: 29
<212> TYPE: PRT
<213> ORGANISM: Oryctolagus cuniculus

<400> SEQUENCE: 83

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser
            20                  25


<210> SEQ ID NO 84
<211> LENGTH: 5
```

<212> TYPE: PRT
<213> ORGANISM: Oryctolagus cuniculus

<400> SEQUENCE: 84

Gly Ala Ala Met Asn
1               5

<210> SEQ ID NO 85
<211> LENGTH: 14
<212> TYPE: PRT
<213> ORGANISM: Oryctolagus cuniculus

<400> SEQUENCE: 85

Trp Val Arg Gln Ala Pro Gly Lys Gly Leu Glu Trp Ile Gly
1               5                   10

<210> SEQ ID NO 86
<211> LENGTH: 16
<212> TYPE: PRT
<213> ORGANISM: Oryctolagus cuniculus

<400> SEQUENCE: 86

Val Ile Gly Asn Ser Gly Ser Thr Tyr Tyr Ala Ser Trp Ala Lys Gly
1               5                   10                  15

<210> SEQ ID NO 87
<211> LENGTH: 31
<212> TYPE: PRT
<213> ORGANISM: Oryctolagus cuniculus

<400> SEQUENCE: 87

Arg Phe Thr Ile Ser Lys Thr Ser Ser Thr Thr Val Asp Leu Lys Met
1               5                   10                  15

Thr Ser Pro Thr Thr Glu Asp Thr Ala Thr Tyr Phe Cys Ala Arg
            20                  25                  30

<210> SEQ ID NO 88
<211> LENGTH: 7
<212> TYPE: PRT
<213> ORGANISM: Oryctolagus cuniculus

<400> SEQUENCE: 88

Gly Gly Gly Glu Phe Phe Ile
1               5

<210> SEQ ID NO 89
<211> LENGTH: 11
<212> TYPE: PRT
<213> ORGANISM: Artificial
<220> FEATURE:
<223> OTHER INFORMATION: Humanized Antibody Sequence

<400> SEQUENCE: 89

Trp Gly Gln Gly Thr Leu Val Thr Val Ser Ser
1               5                   10

<210> SEQ ID NO 90
<211> LENGTH: 330
<212> TYPE: PRT
<213> ORGANISM: Artificial
<220> FEATURE:
<223> OTHER INFORMATION: Humanized Antibody Sequence

<400> SEQUENCE: 90

Ala Ser Thr Lys Gly Pro Ser Val Phe Pro Leu Ala Pro Ser Ser Lys

-continued

```
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Ala
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 91
<211> LENGTH: 1329
<212> TYPE: DNA
<213> ORGANISM: Artificial
<220> FEATURE:
<223> OTHER INFORMATION: Humanized Antibody Sequence

<400> SEQUENCE: 91

```
cagtcggtgg aggagtccgg gggtcgcctg gtcacgcctg ggacacccct gacactcacc      60

tgcaccgtct ctggattctc cctcagtggc gctgcgatga actgggtccg ccaggctcca     120

gggaaggggc tggaatggat cggagttatt ggtaatagtg gtagcacata ctacgcgtcc     180

tgggcgaaag gccgattcac catctccaaa acctcgtcga ccacggtgga tctgaaaatg     240
```

accagtccga caaccgagga cacggccacc tatttctgtg ccagaggggg aggggaattt 300
ttcatctggg gccaagggac cctggtcacc gtctcgagcg cctccaccaa gggcccatcg 360
gtcttccccc tggcaccctc ctccaagagc acctctgggg gcacagcggc cctgggctgc 420
ctggtcaagg actacttccc cgaaccggtg acggtgtcgt ggaactcagg cgccctgacc 480
agcggcgtgc acaccttccc ggctgtccta cagtcctcag gactctactc cctcagcagc 540
gtggtgaccg tgccctccag cagcttgggc acccagacct acatctgcaa cgtgaatcac 600
aagcccagca acaccaaggt ggacgcgaga gttgagccca aatcttgtga caaaactcac 660
acatgcccac cgtgcccagc acctgaactc ctggggggac cgtcagtctt cctcttcccc 720
ccaaaaccca aggacaccct catgatctcc cggacccctg aggtcacatg cgtggtggtg 780
gacgtgagcc acgaagaccc tgaggtcaag ttcaactggt acgtggacgg cgtggaggtg 840
cataatgcca agacaaagcc gcgggaggag cagtacgcca gcacgtaccg tgtggtcagc 900
gtcctcaccg tcctgcacca ggactggctg aatggcaagg agtacaagtg caaggtctcc 960
aacaaagccc tcccagcccc catcgagaaa accatctcca aagccaaagg gcagccccga 1020
gaaccacagg tgtacaccct gcccccatcc cgggaggaga tgaccaagaa ccaggtcagc 1080
ctgacctgcc tggtcaaagg cttctatccc agcgacatcg ccgtggagtg ggagagcaat 1140
gggcagccgg agaacaacta caagaccacg cctcccgtgc tggactccga cggctccttc 1200
ttcctctaca gcaagctcac cgtggacaag agcaggtggc agcaggggaa cgtcttctca 1260
tgctccgtga tgcatgaggc tctgcacaac cactacacgc agaagagcct ctccctgtct 1320
ccgggtaaa 1329

<210> SEQ ID NO 92
<211> LENGTH: 339
<212> TYPE: DNA
<213> ORGANISM: Artificial
<220> FEATURE:
<223> OTHER INFORMATION: Humanized Antibody Sequence

<400> SEQUENCE: 92
cagtcggtgg aggagtccgg gggtcgcctg gtcacgcctg ggacacccct gacactcacc 60
tgcaccgtct ctggattctc cctcagtggc gctgcgatga actgggtccg ccaggctcca 120
gggaaggggc tggaatggat cggagttatt ggtaatagtg gtagcacata ctacgcgtcc 180
tgggcgaaag gccgattcac catctccaaa acctcgtcga ccacggtgga tctgaaaatg 240
accagtccga caaccgagga cacggccacc tatttctgtg ccagaggggg aggggaattt 300
ttcatctggg gccaagggac cctggtcacc gtctcgagc 339

<210> SEQ ID NO 93
<211> LENGTH: 87
<212> TYPE: DNA
<213> ORGANISM: Oryctolagus cuniculus

<400> SEQUENCE: 93
cagtcggtgg aggagtccgg gggtcgcctg gtcacgcctg ggacacccct gacactcacc 60
tgcaccgtct ctggattctc cctcagt 87

<210> SEQ ID NO 94
<211> LENGTH: 15
<212> TYPE: DNA
<213> ORGANISM: Oryctolagus cuniculus

<400> SEQUENCE: 94
ggcgctgcga tgaac 15

<210> SEQ ID NO 95
<211> LENGTH: 42
<212> TYPE: DNA
<213> ORGANISM: Oryctolagus cuniculus

<400> SEQUENCE: 95
tgggtccgcc aggctccagg gaaggggctg gaatggatcg ga 42

<210> SEQ ID NO 96
<211> LENGTH: 48
<212> TYPE: DNA
<213> ORGANISM: Oryctolagus cuniculus

<400> SEQUENCE: 96
gttattggta atagtggtag cacatactac gcgtcctggg cgaaaggc 48

<210> SEQ ID NO 97
<211> LENGTH: 93
<212> TYPE: DNA
<213> ORGANISM: Oryctolagus cuniculus

<400> SEQUENCE: 97
cgattcacca tctccaaaac ctcgtcgacc acggtggatc tgaaaatgac cagtccgaca 60
accgaggaca cggccaccta tttctgtgcc aga 93

<210> SEQ ID NO 98
<211> LENGTH: 21
<212> TYPE: DNA
<213> ORGANISM: Oryctolagus cuniculus

<400> SEQUENCE: 98
gggggagggg aatttttcat c 21

<210> SEQ ID NO 99
<211> LENGTH: 33
<212> TYPE: DNA
<213> ORGANISM: Artificial
<220> FEATURE:
<223> OTHER INFORMATION: Humanized Antibody Sequence

<400> SEQUENCE: 99
tggggccaag ggaccctggt caccgtctcg agc 33

<210> SEQ ID NO 100
<211> LENGTH: 990
<212> TYPE: DNA
<213> ORGANISM: Artificial
<220> FEATURE:
<223> OTHER INFORMATION: Humanized Antibody Sequence

<400> SEQUENCE: 100
gcctccacca agggcccatc ggtcttcccc ctggcaccct cctccaagag cacctctggg 60
ggcacagcgg ccctgggctg cctggtcaag gactacttcc ccgaaccggt gacggtgtcg 120
tggaactcag gcgccctgac cagcggcgtg cacaccttcc cggctgtcct acagtcctca 180
ggactctact ccctcagcag cgtggtgacc gtgccctcca gcagcttggg cacccagacc 240
tacatctgca acgtgaatca caagcccagc aacaccaagg tggacgcgag agttgagccc 300
aaatcttgtg acaaaactca cacatgccca ccgtgcccag cacctgaact cctgggggga 360

```
ccgtcagtct tcctcttccc cccaaaaccc aaggacaccc tcatgatctc ccggacccct    420

gaggtcacat gcgtggtggt ggacgtgagc cacgaagacc ctgaggtcaa gttcaactgg    480

tacgtggacg gcgtggaggt gcataatgcc aagacaaagc cgcgggagga gcagtacgcc    540

agcacgtacc gtgtggtcag cgtcctcacc gtcctgcacc aggactggct gaatggcaag    600

gagtacaagt gcaaggtctc caacaaagcc ctcccagccc ccatcgagaa aaccatctcc    660

aaagccaaag ggcagccccg agaaccacag gtgtacaccc tgcccccatc ccgggaggag    720

atgaccaaga accaggtcag cctgacctgc ctggtcaaag gcttctatcc cagcgacatc    780

gccgtggagt gggagagcaa tgggcagccg gagaacaact acaagaccac gcctcccgtg    840

ctggactccg acggctcctt cttcctctac agcaagctca ccgtggacaa gagcaggtgg    900

cagcagggga acgtcttctc atgctccgtg atgcatgagg ctctgcacaa ccactacacg    960

cagaagagcc tctccctgtc tccgggtaaa                                     990
```

```
<210> SEQ ID NO 101
<211> LENGTH: 217
<212> TYPE: PRT
<213> ORGANISM: Artificial
<220> FEATURE:
<223> OTHER INFORMATION: Humanized Antibody Sequence

<400> SEQUENCE: 101

Ala Gln Val Leu Thr Gln Thr Pro Ser Pro Val Ser Ala Ala Val Gly
1               5                   10                  15

Gly Thr Val Thr Ile Asn Cys Gln Ser Ser Glu Ser Val Tyr Lys Asn
            20                  25                  30

Asn Tyr Leu Ser Trp Tyr Gln Gln Lys Pro Gly Gln Pro Pro Lys Phe
        35                  40                  45

Leu Ile Tyr Gln Ala Ser Asn Leu Ala Asp Gly Val Pro Ser Arg Phe
    50                  55                  60

Lys Gly Ser Gly Ser Gly Thr Gln Phe Thr Leu Thr Ile Ser Asp Leu
65                  70                  75                  80

Glu Cys Asp Asp Ala Ala Thr Tyr Tyr Cys Ala Gly Gly Tyr Ser Thr
                85                  90                  95

Tyr Met Ser Gly Phe Gly Gly Gly Thr Glu Val Val Val Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215


<210> SEQ ID NO 102
<211> LENGTH: 111
<212> TYPE: PRT
```

<213> ORGANISM: Artificial
<220> FEATURE:
<223> OTHER INFORMATION: Humanized Antibody Sequence

<400> SEQUENCE: 102

```
Ala Gln Val Leu Thr Gln Thr Pro Ser Pro Val Ser Ala Ala Val Gly
1               5                   10                  15

Gly Thr Val Thr Ile Asn Cys Gln Ser Ser Glu Ser Val Tyr Lys Asn
            20                  25                  30

Asn Tyr Leu Ser Trp Tyr Gln Gln Lys Pro Gly Gln Pro Pro Lys Phe
        35                  40                  45

Leu Ile Tyr Gln Ala Ser Asn Leu Ala Asp Gly Val Pro Ser Arg Phe
    50                  55                  60

Lys Gly Ser Gly Ser Gly Thr Gln Phe Thr Leu Thr Ile Ser Asp Leu
65                  70                  75                  80

Glu Cys Asp Asp Ala Ala Thr Tyr Tyr Cys Ala Gly Gly Tyr Ser Thr
                85                  90                  95

Tyr Met Ser Gly Phe Gly Gly Gly Thr Glu Val Val Val Lys Arg
            100                 105                 110
```

<210> SEQ ID NO 103
<211> LENGTH: 23
<212> TYPE: PRT
<213> ORGANISM: Oryctolagus cuniculus

<400> SEQUENCE: 103

```
Ala Gln Val Leu Thr Gln Thr Pro Ser Pro Val Ser Ala Ala Val Gly
1               5                   10                  15

Gly Thr Val Thr Ile Asn Cys
            20
```

<210> SEQ ID NO 104
<211> LENGTH: 13
<212> TYPE: PRT
<213> ORGANISM: Oryctolagus cuniculus

<400> SEQUENCE: 104

```
Gln Ser Ser Glu Ser Val Tyr Lys Asn Asn Tyr Leu Ser
1               5                   10
```

<210> SEQ ID NO 105
<211> LENGTH: 15
<212> TYPE: PRT
<213> ORGANISM: Oryctolagus cuniculus

<400> SEQUENCE: 105

```
Trp Tyr Gln Gln Lys Pro Gly Gln Pro Pro Lys Phe Leu Ile Tyr
1               5                   10                  15
```

<210> SEQ ID NO 106
<211> LENGTH: 7
<212> TYPE: PRT
<213> ORGANISM: Oryctolagus cuniculus

<400> SEQUENCE: 106

```
Gln Ala Ser Asn Leu Ala Asp
1               5
```

<210> SEQ ID NO 107
<211> LENGTH: 32
<212> TYPE: PRT
<213> ORGANISM: Oryctolagus cuniculus

<400> SEQUENCE: 107

Gly Val Pro Ser Arg Phe Lys Gly Ser Gly Ser Gly Thr Gln Phe Thr
1 5 10 15

Leu Thr Ile Ser Asp Leu Glu Cys Asp Asp Ala Ala Thr Tyr Tyr Cys
20 25 30

<210> SEQ ID NO 108
<211> LENGTH: 10
<212> TYPE: PRT
<213> ORGANISM: Oryctolagus cuniculus

<400> SEQUENCE: 108

Ala Gly Gly Tyr Ser Thr Tyr Met Ser Gly
1 5 10

<210> SEQ ID NO 109
<211> LENGTH: 11
<212> TYPE: PRT
<213> ORGANISM: Artificial
<220> FEATURE:
<223> OTHER INFORMATION: Humanized Antibody Sequence

<400> SEQUENCE: 109

Phe Gly Gly Gly Thr Glu Val Val Val Lys Arg
1 5 10

<210> SEQ ID NO 110
<211> LENGTH: 106
<212> TYPE: PRT
<213> ORGANISM: Artificial
<220> FEATURE:
<223> OTHER INFORMATION: Humanized Antibody Sequence

<400> SEQUENCE: 110

Thr Val Ala Ala Pro Ser Val Phe Ile Phe Pro Pro Ser Asp Glu Gln
1 5 10 15

Leu Lys Ser Gly Thr Ala Ser Val Val Cys Leu Leu Asn Asn Phe Tyr
20 25 30

Pro Arg Glu Ala Lys Val Gln Trp Lys Val Asp Asn Ala Leu Gln Ser
35 40 45

Gly Asn Ser Gln Glu Ser Val Thr Glu Gln Asp Ser Lys Asp Ser Thr
50 55 60

Tyr Ser Leu Ser Ser Thr Leu Thr Leu Ser Lys Ala Asp Tyr Glu Lys
65 70 75 80

His Lys Val Tyr Ala Cys Glu Val Thr His Gln Gly Leu Ser Ser Pro
85 90 95

Val Thr Lys Ser Phe Asn Arg Gly Glu Cys
100 105

<210> SEQ ID NO 111
<211> LENGTH: 651
<212> TYPE: DNA
<213> ORGANISM: Artificial
<220> FEATURE:
<223> OTHER INFORMATION: Humanized Antibody Sequence

<400> SEQUENCE: 111
gcccaagtgc tgacccagac tccatcccca gtgtctgcag ctgtgggagg caccgtcacc 60
atcaattgcc agtccagtga gagtgtttat aagaacaact acttatcctg gtatcagcag 120
aaaccagggc agcctcccaa gttcctgatc taccaggcat ccaatttggc agatggggtc 180
ccatcgcggt tcaaaggcag tggatctggg acacagttca ctctcaccat cagcgacctg 240
gagtgtgacg atgccgccac ttattactgt gcaggcggtt atagtactta tatgtctggt 300
ttcggcggag ggaccgaggt ggtggtcaaa cgtacggtag cggccccatc tgtcttcatc 360
ttcccgccat ctgatgagca gttgaaatct ggaactgcct ctgttgtgtg cctgctgaat 420
aacttctatc ccagagaggc caaagtacag tggaaggtgg ataacgccct ccaatcgggt 480
aactcccagg agagtgtcac agagcaggac agcaaggaca gcacctacag cctcagcagc 540
accctgacgc tgagcaaagc agactacgag aaacacaaag tctacgcctg cgaagtcacc 600
catcagggcc tgagctcgcc cgtcacaaag agcttcaaca ggggagagtg t 651

<210> SEQ ID NO 112
<211> LENGTH: 333
<212> TYPE: DNA
<213> ORGANISM: Artificial
<220> FEATURE:
<223> OTHER INFORMATION: Humanized Antibody Sequence

<400> SEQUENCE: 112
gcccaagtgc tgacccagac tccatcccca gtgtctgcag ctgtgggagg caccgtcacc 60
atcaattgcc agtccagtga gagtgtttat aagaacaact acttatcctg gtatcagcag 120
aaaccagggc agcctcccaa gttcctgatc taccaggcat ccaatttggc agatggggtc 180
ccatcgcggt tcaaaggcag tggatctggg acacagttca ctctcaccat cagcgacctg 240
gagtgtgacg atgccgccac ttattactgt gcaggcggtt atagtactta tatgtctggt 300
ttcggcggag ggaccgaggt ggtggtcaaa cgt 333

<210> SEQ ID NO 113
<211> LENGTH: 69
<212> TYPE: DNA
<213> ORGANISM: Oryctolagus cuniculus

<400> SEQUENCE: 113
gcccaagtgc tgacccagac tccatcccca gtgtctgcag ctgtgggagg caccgtcacc 60
atcaattgc 69

<210> SEQ ID NO 114
<211> LENGTH: 39
<212> TYPE: DNA
<213> ORGANISM: Oryctolagus cuniculus

<400> SEQUENCE: 114
cagtccagtg agagtgttta taagaacaac tacttatcc 39

<210> SEQ ID NO 115
<211> LENGTH: 45
<212> TYPE: DNA
<213> ORGANISM: Oryctolagus cuniculus

<400> SEQUENCE: 115
tggtatcagc agaaaccagg gcagcctccc aagttcctga tctac 45

<210> SEQ ID NO 116
<211> LENGTH: 21
<212> TYPE: DNA
<213> ORGANISM: Oryctolagus cuniculus

<400> SEQUENCE: 116
caggcatcca atttggcaga t 21

<210> SEQ ID NO 117
<211> LENGTH: 96
<212> TYPE: DNA
<213> ORGANISM: Oryctolagus cuniculus

<400> SEQUENCE: 117
ggggtcccat cgcggttcaa aggcagtgga tctgggacac agttcactct caccatcagc 60
gacctggagt gtgacgatgc cgccacttat tactgt 96

<210> SEQ ID NO 118
<211> LENGTH: 30
<212> TYPE: DNA
<213> ORGANISM: Oryctolagus cuniculus

<400> SEQUENCE: 118
gcaggcggtt atagtactta tatgtctggt 30

<210> SEQ ID NO 119
<211> LENGTH: 33
<212> TYPE: DNA
<213> ORGANISM: Artificial
<220> FEATURE:
<223> OTHER INFORMATION: Humanized Antibody Sequence

<400> SEQUENCE: 119
ttcggcggag ggaccgaggt ggtggtcaaa cgt 33

<210> SEQ ID NO 120
<211> LENGTH: 318
<212> TYPE: DNA
<213> ORGANISM: Artificial
<220> FEATURE:
<223> OTHER INFORMATION: Humanized Antibody Sequence

<400> SEQUENCE: 120
acggtagcgg ccccatctgt cttcatcttc ccgccatctg atgagcagtt gaaatctgga 60
actgcctctg ttgtgtgcct gctgaataac ttctatccca gagaggccaa agtacagtgg 120
aaggtggata acgccctcca atcgggtaac tcccaggaga gtgtcacaga gcaggacagc 180
aaggacagca cctacagcct cagcagcacc ctgacgctga gcaaagcaga ctacgagaaa 240
cacaaagtct acgcctgcga agtcacccat cagggcctga gctcgcccgt cacaaagagc 300
ttcaacaggg gagagtgt 318

<210> SEQ ID NO 121
<211> LENGTH: 443
<212> TYPE: PRT
<213> ORGANISM: Artificial
<220> FEATURE:
<223> OTHER INFORMATION: Humanized Antibody Sequence

<400> SEQUENCE: 121

Gln Ser Val Glu Glu Ser Gly Gly Arg Leu Val Thr Pro Gly Thr Pro
1 5 10 15

Leu Thr Leu Thr Cys Thr Val Ser Gly Phe Ser Leu Ser Ser Ala Ala
20 25 30

Met Asn Trp Val Arg Gln Ala Pro Gly Lys Gly Leu Glu Trp Ile Gly
35 40 45

Ile Ile Asp Asn Thr Ala Gly Thr Tyr Tyr Ala Pro Trp Ala Lys Gly
50 55 60

```
Arg Phe Thr Ile Ser Lys Thr Ser Ser Thr Thr Val Asp Leu Lys Met
65                  70                  75                  80

Thr Ser Pro Thr Thr Glu Asp Thr Ala Thr Tyr Phe Cys Ala Arg Gly
                85                  90                  95

Gly Gly Glu Phe Phe Ile Trp Gly Pro Gly Thr Leu Val Thr Val Ser
            100                 105                 110

Ser Ala Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Lys Val Glu Pro Lys Ser Cys Asp Lys Thr His Thr Cys Pro Pro
    210                 215                 220

Cys Pro Ala Pro Glu Leu Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
        275                 280                 285

Glu Glu Gln Tyr Ala Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Ala Leu Pro Ala Pro Ile Glu Lys Thr Ile Ser Lys Ala Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
        435                 440
```

<210> SEQ ID NO 122
<211> LENGTH: 113
<212> TYPE: PRT
<213> ORGANISM: Artificial
<220> FEATURE:

<223> OTHER INFORMATION: Humanized Antibody Sequence

<400> SEQUENCE: 122

Gln Ser Val Glu Glu Ser Gly Gly Arg Leu Val Thr Pro Gly Thr Pro
1 5 10 15

Leu Thr Leu Thr Cys Thr Val Ser Gly Phe Ser Leu Ser Ser Ala Ala
20 25 30

Met Asn Trp Val Arg Gln Ala Pro Gly Lys Gly Leu Glu Trp Ile Gly
35 40 45

Ile Ile Asp Asn Thr Ala Gly Thr Tyr Tyr Ala Pro Trp Ala Lys Gly
50 55 60

Arg Phe Thr Ile Ser Lys Thr Ser Ser Thr Thr Val Asp Leu Lys Met
65 70 75 80

Thr Ser Pro Thr Thr Glu Asp Thr Ala Thr Tyr Phe Cys Ala Arg Gly
85 90 95

Gly Gly Glu Phe Phe Ile Trp Gly Pro Gly Thr Leu Val Thr Val Ser
100 105 110

Ser

<210> SEQ ID NO 123
<211> LENGTH: 29
<212> TYPE: PRT
<213> ORGANISM: Oryctolagus cuniculus

<400> SEQUENCE: 123

Gln Ser Val Glu Glu Ser Gly Gly Arg Leu Val Thr Pro Gly Thr Pro
1 5 10 15

Leu Thr Leu Thr Cys Thr Val Ser Gly Phe Ser Leu Ser
20 25

<210> SEQ ID NO 124
<211> LENGTH: 5
<212> TYPE: PRT
<213> ORGANISM: Oryctolagus cuniculus

<400> SEQUENCE: 124

Ser Ala Ala Met Asn
1 5

<210> SEQ ID NO 125
<211> LENGTH: 14
<212> TYPE: PRT
<213> ORGANISM: Oryctolagus cuniculus

<400> SEQUENCE: 125

Trp Val Arg Gln Ala Pro Gly Lys Gly Leu Glu Trp Ile Gly
1 5 10

<210> SEQ ID NO 126
<211> LENGTH: 16
<212> TYPE: PRT
<213> ORGANISM: Oryctolagus cuniculus

<400> SEQUENCE: 126

Ile Ile Asp Asn Thr Ala Gly Thr Tyr Tyr Ala Pro Trp Ala Lys Gly
1 5 10 15

<210> SEQ ID NO 127
<211> LENGTH: 31
<212> TYPE: PRT
<213> ORGANISM: Oryctolagus cuniculus

<400> SEQUENCE: 127

Arg Phe Thr Ile Ser Lys Thr Ser Ser Thr Thr Val Asp Leu Lys Met
1               5                   10                  15

Thr Ser Pro Thr Thr Glu Asp Thr Ala Thr Tyr Phe Cys Ala Arg
            20                  25                  30

<210> SEQ ID NO 128
<211> LENGTH: 7
<212> TYPE: PRT
<213> ORGANISM: Oryctolagus cuniculus

<400> SEQUENCE: 128

Gly Gly Gly Glu Phe Phe Ile
1               5

<210> SEQ ID NO 129
<211> LENGTH: 11
<212> TYPE: PRT
<213> ORGANISM: Artificial
<220> FEATURE:
<223> OTHER INFORMATION: Humanized Antibody Sequence

<400> SEQUENCE: 129

Trp Gly Pro Gly Thr Leu Val Thr Val Ser Ser
1               5                   10

<210> SEQ ID NO 130
<211> LENGTH: 330
<212> TYPE: PRT
<213> ORGANISM: Artificial
<220> FEATURE:
<223> OTHER INFORMATION: Humanized Antibody Sequence

<400> SEQUENCE: 130

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

-continued

```
His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 131
<211> LENGTH: 1329
<212> TYPE: DNA
<213> ORGANISM: Artificial
<220> FEATURE:
<223> OTHER INFORMATION: Humanized Antibody Sequence

<400> SEQUENCE: 131

```
cagtcggtgg aggagtccgg gggtcgcctg gtcacgcctg ggacacccct gacactcacc     60

tgcaccgtct ctggattctc cctcagtagc gctgcaatga actgggtccg ccaggctcca    120

gggaaggggc tggaatggat cggaattatt gataatactg ctggcacata ttacgcgccc    180

tgggcgaaag gccgattcac catctccaaa acctcgtcga ccacggtgga tctgaaaatg    240

accagtccga caaccgagga cacggccacc tatttctgtg ccagaggggg aggggaattt    300

ttcatctggg gcccgggcac cctcgtcacc gtctcgagcg cctccaccaa gggcccatcg    360

gtcttccccc tggcaccctc ctccaagagc acctctgggg gcacagcggc cctgggctgc    420

ctggtcaagg actacttccc cgaaccggtg acggtgtcgt ggaactcagg cgccctgacc    480

agcggcgtgc acaccttccc ggctgtccta cagtcctcag gactctactc cctcagcagc    540

gtggtgaccg tgccctccag cagcttgggc acccagacct acatctgcaa cgtgaatcac    600

aagcccagca acaccaaggt ggacaagaaa gttgagccca aatcttgtga caaaactcac    660

acatgcccac cgtgcccagc acctgaactc ctggggggac cgtcagtctt cctcttcccc    720

ccaaaaccca aggacaccct catgatctcc cggacccctg aggtcacatg cgtggtggtg    780

gacgtgagcc acgaagaccc tgaggtcaag ttcaactggt acgtggacgg cgtggaggtg    840

cataatgcca agacaaagcc gcgggaggag cagtacgcca gcacgtaccg tgtggtcagc    900

gtcctcaccg tcctgcacca ggactggctg aatggcaagg agtacaagtg caaggtctcc    960

aacaaagccc tcccagcccc catcgagaaa accatctcca aagccaaagg gcagccccga   1020

gaaccacagg tgtacaccct gcccccatcc cgggaggaga tgaccaagaa ccaggtcagc   1080

ctgacctgcc tggtcaaagg cttctatccc agcgacatcg ccgtggagtg ggagagcaat   1140

gggcagccgg agaacaacta caagaccacg cctcccgtgc tggactccga cggctccttc   1200

ttcctctaca gcaagctcac cgtggacaag agcaggtggc agcaggggaa cgtcttctca   1260
```

-continued

```
tgctccgtga tgcatgaggc tctgcacaac cactacacgc agaagagcct ctccctgtct   1320

ccgggtaaa                                                           1329


<210> SEQ ID NO 132
<211> LENGTH: 339
<212> TYPE: DNA
<213> ORGANISM: Artificial
<220> FEATURE:
<223> OTHER INFORMATION: Humanized Antibody Sequence

<400> SEQUENCE: 132

cagtcggtgg aggagtccgg gggtcgcctg gtcacgcctg ggacacccct gacactcacc     60

tgcaccgtct ctggattctc cctcagtagc gctgcaatga actgggtccg ccaggctcca    120

gggaaggggc tggaatggat cggaattatt gataatactg ctggcacata ttacgcgccc    180

tgggcgaaag gccgattcac catctccaaa acctcgtcga ccacggtgga tctgaaaatg    240

accagtccga caaccgagga cacggccacc tatttctgtg ccagaggggg aggggaattt    300

ttcatctggg gcccgggcac cctcgtcacc gtctcgagc                           339


<210> SEQ ID NO 133
<211> LENGTH: 87
<212> TYPE: DNA
<213> ORGANISM: Oryctolagus cuniculus

<400> SEQUENCE: 133

cagtcggtgg aggagtccgg gggtcgcctg gtcacgcctg ggacacccct gacactcacc     60

tgcaccgtct ctggattctc cctcagt                                         87


<210> SEQ ID NO 134
<211> LENGTH: 15
<212> TYPE: DNA
<213> ORGANISM: Oryctolagus cuniculus

<400> SEQUENCE: 134

agcgctgcaa tgaac                                                      15


<210> SEQ ID NO 135
<211> LENGTH: 42
<212> TYPE: DNA
<213> ORGANISM: Oryctolagus cuniculus

<400> SEQUENCE: 135

tgggtccgcc aggctccagg gaaggggctg gaatggatcg ga                        42


<210> SEQ ID NO 136
<211> LENGTH: 48
<212> TYPE: DNA
<213> ORGANISM: Oryctolagus cuniculus

<400> SEQUENCE: 136

attattgata atactgctgg cacatattac gcgccctggg cgaaaggc                  48


<210> SEQ ID NO 137
<211> LENGTH: 93
<212> TYPE: DNA
<213> ORGANISM: Oryctolagus cuniculus

<400> SEQUENCE: 137

cgattcacca tctccaaaac ctcgtcgacc acggtggatc tgaaaatgac cagtccgaca     60

accgaggaca cggccaccta tttctgtgcc aga                                  93
```

<210> SEQ ID NO 138
<211> LENGTH: 21
<212> TYPE: DNA
<213> ORGANISM: Oryctolagus cuniculus

<400> SEQUENCE: 138
gggggagggg aatttttcat c 21

<210> SEQ ID NO 139
<211> LENGTH: 33
<212> TYPE: DNA
<213> ORGANISM: Artificial
<220> FEATURE:
<223> OTHER INFORMATION: Humanized Antibody Sequence

<400> SEQUENCE: 139
tggggcccgg gcaccctcgt caccgtctcg agc 33

<210> SEQ ID NO 140
<211> LENGTH: 990
<212> TYPE: DNA
<213> ORGANISM: Artificial
<220> FEATURE:
<223> OTHER INFORMATION: Humanized Antibody Sequence

<400> SEQUENCE: 140
gcctccacca agggcccatc ggtcttcccc ctggcaccct cctccaagag cacctctggg 60
ggcacagcgg ccctgggctg cctggtcaag gactacttcc ccgaaccggt gacggtgtcg 120
tggaactcag gcgccctgac cagcggcgtg cacaccttcc cggctgtcct acagtcctca 180
ggactctact ccctcagcag cgtggtgacc gtgccctcca gcagcttggg cacccagacc 240
tacatctgca acgtgaatca caagcccagc aacaccaagg tggacaagaa agttgagccc 300
aaatcttgtg acaaaactca cacatgccca ccgtgcccag cacctgaact cctgggggga 360
ccgtcagtct tcctcttccc cccaaaaccc aaggacaccc tcatgatctc ccggacccct 420
gaggtcacat gcgtggtggt ggacgtgagc cacgaagacc ctgaggtcaa gttcaactgg 480
tacgtggacg gcgtggaggt gcataatgcc aagacaaagc cgcgggagga gcagtacgcc 540
agcacgtacc gtgtggtcag cgtcctcacc gtcctgcacc aggactggct gaatggcaag 600
gagtacaagt gcaaggtctc caacaaagcc ctcccagccc ccatcgagaa aaccatctcc 660
aaagccaaag ggcagccccg agaaccacag gtgtacaccc tgcccccatc ccgggaggag 720
atgaccaaga accaggtcag cctgacctgc ctggtcaaag gcttctatcc cagcgacatc 780
gccgtggagt gggagagcaa tgggcagccg gagaacaact acaagaccac gcctcccgtg 840
ctggactccg acggctcctt cttcctctac agcaagctca ccgtggacaa gagcaggtgg 900
cagcagggga acgtcttctc atgctccgtg atgcatgagg ctctgcacaa ccactacacg 960
cagaagagcc tctccctgtc tccgggtaaa 990

<210> SEQ ID NO 141
<211> LENGTH: 217
<212> TYPE: PRT
<213> ORGANISM: Artificial
<220> FEATURE:
<223> OTHER INFORMATION: Humanized Antibody Sequence

<400> SEQUENCE: 141

Ala Gln Val Leu Thr Gln Thr Pro Ser Ser Val Ser Ala Ala Val Gly
1 5 10 15

```
Gly Thr Val Thr Ile Asn Cys Gln Ser Ser Gln Ser Val His Asp Gly
            20                  25                  30

Ser Tyr Leu Ser Trp Tyr Gln Gln Lys Pro Gly Gln Pro Pro Asn Phe
        35                  40                  45

Leu Ile Tyr Gln Ala Ser Asn Leu Ala Ser Gly Val Pro Ser Arg Phe
    50                  55                  60

Lys Gly Ser Gly Ser Gly Thr Gln Phe Thr Leu Thr Ile Ser Asp Leu
65                  70                  75                  80

Glu Cys Asp Asp Ala Ala Thr Tyr Tyr Cys Ala Gly Gly Tyr Ser Ser
                85                  90                  95

Asn Ile Cys Gly Phe Gly Gly Gly Thr Glu Val Val Val Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215
```

<210> SEQ ID NO 142
<211> LENGTH: 111
<212> TYPE: PRT
<213> ORGANISM: Artificial
<220> FEATURE:
<223> OTHER INFORMATION: Humanized Antibody Sequence

<400> SEQUENCE: 142

```
Ala Gln Val Leu Thr Gln Thr Pro Ser Ser Val Ser Ala Ala Val Gly
1               5                   10                  15

Gly Thr Val Thr Ile Asn Cys Gln Ser Ser Gln Ser Val His Asp Gly
            20                  25                  30

Ser Tyr Leu Ser Trp Tyr Gln Gln Lys Pro Gly Gln Pro Pro Asn Phe
        35                  40                  45

Leu Ile Tyr Gln Ala Ser Asn Leu Ala Ser Gly Val Pro Ser Arg Phe
    50                  55                  60

Lys Gly Ser Gly Ser Gly Thr Gln Phe Thr Leu Thr Ile Ser Asp Leu
65                  70                  75                  80

Glu Cys Asp Asp Ala Ala Thr Tyr Tyr Cys Ala Gly Gly Tyr Ser Ser
                85                  90                  95

Asn Ile Cys Gly Phe Gly Gly Gly Thr Glu Val Val Val Lys Arg
            100                 105                 110
```

<210> SEQ ID NO 143
<211> LENGTH: 23
<212> TYPE: PRT
<213> ORGANISM: Oryctolagus cuniculus

<400> SEQUENCE: 143

-continued

Ala Gln Val Leu Thr Gln Thr Pro Ser Ser Val Ser Ala Ala Val Gly
1 5 10 15

Gly Thr Val Thr Ile Asn Cys
20

<210> SEQ ID NO 144
<211> LENGTH: 13
<212> TYPE: PRT
<213> ORGANISM: Oryctolagus cuniculus

<400> SEQUENCE: 144

Gln Ser Ser Gln Ser Val His Asp Gly Ser Tyr Leu Ser
1 5 10

<210> SEQ ID NO 145
<211> LENGTH: 15
<212> TYPE: PRT
<213> ORGANISM: Oryctolagus cuniculus

<400> SEQUENCE: 145

Trp Tyr Gln Gln Lys Pro Gly Gln Pro Pro Asn Phe Leu Ile Tyr
1 5 10 15

<210> SEQ ID NO 146
<211> LENGTH: 7
<212> TYPE: PRT
<213> ORGANISM: Oryctolagus cuniculus

<400> SEQUENCE: 146

Gln Ala Ser Asn Leu Ala Ser
1 5

<210> SEQ ID NO 147
<211> LENGTH: 32
<212> TYPE: PRT
<213> ORGANISM: Oryctolagus cuniculus

<400> SEQUENCE: 147

Gly Val Pro Ser Arg Phe Lys Gly Ser Gly Ser Gly Thr Gln Phe Thr
1 5 10 15

Leu Thr Ile Ser Asp Leu Glu Cys Asp Asp Ala Ala Thr Tyr Tyr Cys
20 25 30

<210> SEQ ID NO 148
<211> LENGTH: 10
<212> TYPE: PRT
<213> ORGANISM: Oryctolagus cuniculus

<400> SEQUENCE: 148

Ala Gly Gly Tyr Ser Ser Asn Ile Cys Gly
1 5 10

<210> SEQ ID NO 149
<211> LENGTH: 11
<212> TYPE: PRT
<213> ORGANISM: Artificial
<220> FEATURE:
<223> OTHER INFORMATION: Humanized Antibody Sequence

<400> SEQUENCE: 149

Phe Gly Gly Gly Thr Glu Val Val Val Lys Arg
1 5 10

<210> SEQ ID NO 150

<211> LENGTH: 106
<212> TYPE: PRT
<213> ORGANISM: Artificial
<220> FEATURE:
<223> OTHER INFORMATION: Humanized Antibody Sequence

<400> SEQUENCE: 150

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 151
<211> LENGTH: 651
<212> TYPE: DNA
<213> ORGANISM: Artificial
<220> FEATURE:
<223> OTHER INFORMATION: Humanized Antibody Sequence

<400> SEQUENCE: 151
gcgcaagtgc tgacccagac tccatcgtcc gtgtctgcag ctgtgggagg cacagtcacc 60
atcaattgcc agtccagtca gagtgttcat gatggcagct acttatcctg gtatcagcag 120
aaaccagggc agcctcccaa cttcctgatc taccaggcat ccaatttggc atctggggtc 180
ccatcgcggt tcaaaggcag tggatctggg acacagttca ctctcaccat cagcgacctg 240
gagtgtgacg atgccgccac ttattactgt gcaggcggtt atagtagtaa tatttgtggt 300
ttcggcggag ggaccgaggt ggtggtcaaa cgtacggtag cggccccatc tgtcttcatc 360
ttcccgccat ctgatgagca gttgaaatct ggaactgcct ctgttgtgtg cctgctgaat 420
aacttctatc ccagagaggc caaagtacag tggaaggtgg ataacgccct ccaatcgggt 480
aactcccagg agagtgtcac agagcaggac agcaaggaca gcacctacag cctcagcagc 540
accctgacgc tgagcaaagc agactacgag aaacacaaag tctacgcctg cgaagtcacc 600
catcagggcc tgagctcgcc cgtcacaaag agcttcaaca ggggagagtg t 651

<210> SEQ ID NO 152
<211> LENGTH: 333
<212> TYPE: DNA
<213> ORGANISM: Artificial
<220> FEATURE:
<223> OTHER INFORMATION: Humanized Antibody Sequence

<400> SEQUENCE: 152
gcgcaagtgc tgacccagac tccatcgtcc gtgtctgcag ctgtgggagg cacagtcacc 60
atcaattgcc agtccagtca gagtgttcat gatggcagct acttatcctg gtatcagcag 120
aaaccagggc agcctcccaa cttcctgatc taccaggcat ccaatttggc atctggggtc 180
ccatcgcggt tcaaaggcag tggatctggg acacagttca ctctcaccat cagcgacctg 240
gagtgtgacg atgccgccac ttattactgt gcaggcggtt atagtagtaa tatttgtggt 300
ttcggcggag ggaccgaggt ggtggtcaaa cgt 333

<210> SEQ ID NO 153
<211> LENGTH: 69
<212> TYPE: DNA
<213> ORGANISM: Oryctolagus cuniculus

<400> SEQUENCE: 153
gcgcaagtgc tgacccagac tccatcgtcc gtgtctgcag ctgtgggagg cacagtcacc 60
atcaattgc 69

<210> SEQ ID NO 154
<211> LENGTH: 39
<212> TYPE: DNA
<213> ORGANISM: Oryctolagus cuniculus

<400> SEQUENCE: 154
cagtccagtc agagtgttca tgatggcagc tacttatcc 39

<210> SEQ ID NO 155
<211> LENGTH: 45
<212> TYPE: DNA
<213> ORGANISM: Oryctolagus cuniculus

<400> SEQUENCE: 155
tggtatcagc agaaaccagg gcagcctccc aacttcctga tctac 45

<210> SEQ ID NO 156
<211> LENGTH: 21
<212> TYPE: DNA
<213> ORGANISM: Oryctolagus cuniculus

<400> SEQUENCE: 156
caggcatcca atttggcatc t 21

<210> SEQ ID NO 157
<211> LENGTH: 96
<212> TYPE: DNA
<213> ORGANISM: Oryctolagus cuniculus

<400> SEQUENCE: 157
ggggtcccat cgcggttcaa aggcagtgga tctgggacac agttcactct caccatcagc 60
gacctggagt gtgacgatgc cgccacttat tactgt 96

<210> SEQ ID NO 158
<211> LENGTH: 30
<212> TYPE: DNA
<213> ORGANISM: Oryctolagus cuniculus

<400> SEQUENCE: 158
gcaggcggtt atagtagtaa tatttgtggt 30

<210> SEQ ID NO 159
<211> LENGTH: 33
<212> TYPE: DNA
<213> ORGANISM: Artificial
<220> FEATURE:
<223> OTHER INFORMATION: Humanized Antibody Sequence

<400> SEQUENCE: 159
ttcggcggag ggaccgaggt ggtggtcaaa cgt 33

<210> SEQ ID NO 160
<211> LENGTH: 318
<212> TYPE: DNA
<213> ORGANISM: Artificial
<220> FEATURE:
<223> OTHER INFORMATION: Humanized Antibody Sequence

<400> SEQUENCE: 160
acggtagcgg ccccatctgt cttcatcttc ccgccatctg atgagcagtt gaaatctgga 60
actgcctctg ttgtgtgcct gctgaataac ttctatccca gagaggccaa agtacagtgg 120
aaggtggata acgccctcca atcgggtaac tcccaggaga gtgtcacaga gcaggacagc 180
aaggacagca cctacagcct cagcagcacc ctgacgctga gcaaagcaga ctacgagaaa 240
cacaaagtct acgcctgcga agtcacccat cagggcctga gctcgcccgt cacaaagagc 300
ttcaacaggg gagagtgt 318

<210> SEQ ID NO 161
<211> LENGTH: 443
<212> TYPE: PRT
<213> ORGANISM: Artificial
<220> FEATURE:
<223> OTHER INFORMATION: Humanized Antibody Sequence

<400> SEQUENCE: 161

Gln Ser Val Glu Ala Ser Gly Gly Arg Leu Val Thr Pro Gly Thr Pro
1               5                   10                  15

Leu Thr Leu Thr Cys Thr Val Ser Gly Phe Ser Leu Ser Ser Ala Ala
            20                  25                  30

Met Asn Trp Val Arg Gln Ala Pro Gly Lys Gly Leu Glu Trp Ile Gly
        35                  40                  45

Phe Ile Glu Tyr Ser Lys Asn Ile Val Tyr Ala Ser Trp Ala Lys Gly
    50                  55                  60

Arg Phe Thr Ile Ser Lys Val Ser Ser Thr Thr Val Asp Leu Lys Met
65                  70                  75                  80

Thr Ser Pro Thr Thr Glu Asp Thr Ala Thr Tyr Phe Cys Ala Arg Gly
                85                  90                  95

Gly Gly Glu Phe Phe Ile Trp Gly Gln Gly Thr Leu Val Thr Val Ser
            100                 105                 110

Ser Ala Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Lys Val Glu Pro Lys Ser Cys Asp Lys Thr His Thr Cys Pro Pro
    210                 215                 220

Cys Pro Ala Pro Glu Leu Leu Gly Gly Pro Ser Val Phe Leu Phe Pro
225                 230                 235                 240

Pro Lys Pro Lys Asp Thr Leu Met Ile Ser Arg Thr Pro Glu Val Thr

-continued

```
                245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
        275                 280                 285

Glu Glu Gln Tyr Ala Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Ala Leu Pro Ala Pro Ile Glu Lys Thr Ile Ser Lys Ala Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
        435                 440


<210> SEQ ID NO 162
<211> LENGTH: 113
<212> TYPE: PRT
<213> ORGANISM: Artificial
<220> FEATURE:
<223> OTHER INFORMATION: Humanized Antibody Sequence

<400> SEQUENCE: 162

Gln Ser Val Glu Ala Ser Gly Gly Arg Leu Val Thr Pro Gly Thr Pro
1               5                   10                  15

Leu Thr Leu Thr Cys Thr Val Ser Gly Phe Ser Leu Ser Ser Ala Ala
            20                  25                  30

Met Asn Trp Val Arg Gln Ala Pro Gly Lys Gly Leu Glu Trp Ile Gly
        35                  40                  45

Phe Ile Glu Tyr Ser Lys Asn Ile Val Tyr Ala Ser Trp Ala Lys Gly
    50                  55                  60

Arg Phe Thr Ile Ser Lys Val Ser Ser Thr Thr Val Asp Leu Lys Met
65                  70                  75                  80

Thr Ser Pro Thr Thr Glu Asp Thr Ala Thr Tyr Phe Cys Ala Arg Gly
                85                  90                  95

Gly Gly Glu Phe Phe Ile Trp Gly Gln Gly Thr Leu Val Thr Val Ser
            100                 105                 110

Ser


<210> SEQ ID NO 163
<211> LENGTH: 29
<212> TYPE: PRT
<213> ORGANISM: Oryctolagus cuniculus

<400> SEQUENCE: 163
```

-continued

```
Gln Ser Val Glu Ala Ser Gly Gly Arg Leu Val Thr Pro Gly Thr Pro
1               5                   10                  15

Leu Thr Leu Thr Cys Thr Val Ser Gly Phe Ser Leu Ser
            20                  25


<210> SEQ ID NO 164
<211> LENGTH: 5
<212> TYPE: PRT
<213> ORGANISM: Oryctolagus cuniculus

<400> SEQUENCE: 164

Ser Ala Ala Met Asn
1               5


<210> SEQ ID NO 165
<211> LENGTH: 14
<212> TYPE: PRT
<213> ORGANISM: Oryctolagus cuniculus

<400> SEQUENCE: 165

Trp Val Arg Gln Ala Pro Gly Lys Gly Leu Glu Trp Ile Gly
1               5                   10


<210> SEQ ID NO 166
<211> LENGTH: 16
<212> TYPE: PRT
<213> ORGANISM: Oryctolagus cuniculus

<400> SEQUENCE: 166

Phe Ile Glu Tyr Ser Lys Asn Ile Val Tyr Ala Ser Trp Ala Lys Gly
1               5                   10                  15


<210> SEQ ID NO 167
<211> LENGTH: 31
<212> TYPE: PRT
<213> ORGANISM: Oryctolagus cuniculus

<400> SEQUENCE: 167

Arg Phe Thr Ile Ser Lys Val Ser Ser Thr Thr Val Asp Leu Lys Met
1               5                   10                  15

Thr Ser Pro Thr Thr Glu Asp Thr Ala Thr Tyr Phe Cys Ala Arg
            20                  25                  30


<210> SEQ ID NO 168
<211> LENGTH: 7
<212> TYPE: PRT
<213> ORGANISM: Oryctolagus cuniculus

<400> SEQUENCE: 168

Gly Gly Gly Glu Phe Phe Ile
1               5


<210> SEQ ID NO 169
<211> LENGTH: 11
<212> TYPE: PRT
<213> ORGANISM: Artificial
<220> FEATURE:
<223> OTHER INFORMATION: Humanized Antibody Sequence

<400> SEQUENCE: 169

Trp Gly Gln Gly Thr Leu Val Thr Val Ser Ser
1               5                   10


<210> SEQ ID NO 170
```

<211> LENGTH: 330
<212> TYPE: PRT
<213> ORGANISM: Artificial
<220> FEATURE:
<223> OTHER INFORMATION: Humanized Antibody Sequence

<400> SEQUENCE: 170

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val Glu Pro Lys Ser Cys Asp Lys Thr His Thr Cys Pro Pro Cys
100 105 110

Pro Ala Pro Glu Leu Leu Gly Gly Pro Ser Val Phe Leu Phe Pro Pro
115 120 125

Lys Pro Lys Asp Thr Leu Met Ile Ser Arg Thr Pro Glu Val Thr Cys
130 135 140

Val Val Val Asp Val Ser His Glu Asp Pro Glu Val Lys Phe Asn Trp
145 150 155 160

Tyr Val Asp Gly Val Glu Val His Asn Ala Lys Thr Lys Pro Arg Glu
165 170 175

Glu Gln Tyr Ala Ser Thr Tyr Arg Val Val Ser Val Leu Thr Val Leu
180 185 190

His Gln Asp Trp Leu Asn Gly Lys Glu Tyr Lys Cys Lys Val Ser Asn
195 200 205

Lys Ala Leu Pro Ala Pro Ile Glu Lys Thr Ile Ser Lys Ala Lys Gly
210 215 220

Gln Pro Arg Glu Pro Gln Val Tyr Thr Leu Pro Pro Ser Arg Glu Glu
225 230 235 240

Met Thr Lys Asn Gln Val Ser Leu Thr Cys Leu Val Lys Gly Phe Tyr
245 250 255

Pro Ser Asp Ile Ala Val Glu Trp Glu Ser Asn Gly Gln Pro Glu Asn
260 265 270

Asn Tyr Lys Thr Thr Pro Pro Val Leu Asp Ser Asp Gly Ser Phe Phe
275 280 285

Leu Tyr Ser Lys Leu Thr Val Asp Lys Ser Arg Trp Gln Gln Gly Asn
290 295 300

Val Phe Ser Cys Ser Val Met His Glu Ala Leu His Asn His Tyr Thr
305 310 315 320

Gln Lys Ser Leu Ser Leu Ser Pro Gly Lys
325 330

<210> SEQ ID NO 171
<211> LENGTH: 1329
<212> TYPE: DNA
<213> ORGANISM: Artificial
<220> FEATURE:
<223> OTHER INFORMATION: Humanized Antibody Sequence

<400> SEQUENCE: 171
cagtcggtgg aggcgtccgg gggtcgcctg gtcacgcctg ggacacccct gacactcacc 60
tgcaccgtct ctggattctc cctcagtagc gctgcaatga actgggtccg ccaggctcca 120
gggaaggggc tggaatggat cggatttatt gagtatagta agaatatagt ttacgcgtcc 180
tgggcgaaag gccgattcac catctccaaa gtctcgtcga ccacggtgga tctgaaaatg 240
accagtccga caaccgagga cacggccacc tatttctgtg ccaggggggg aggggaattt 300
ttcatctggg gccaaggcac cctggtcacc gtctcgagcg cctccaccaa gggcccatcg 360
gtcttccccc tggcaccctc ctccaagagc acctctgggg gcacagcggc cctgggctgc 420
ctggtcaagg actacttccc cgaaccggtg acggtgtcgt ggaactcagg cgccctgacc 480
agcggcgtgc acaccttccc ggctgtccta cagtcctcag gactctactc cctcagcagc 540
gtggtgaccg tgccctccag cagcttgggc acccagacct acatctgcaa cgtgaatcac 600
aagcccagca acaccaaggt ggacaagaaa gttgagccca aatcttgtga caaaactcac 660
acatgcccac cgtgcccagc acctgaactc ctggggggac cgtcagtctt cctcttcccc 720
ccaaaaccca aggacaccct catgatctcc cggacccctg aggtcacatg cgtggtggtg 780
gacgtgagcc acgaagaccc tgaggtcaag ttcaactggt acgtggacgg cgtggaggtg 840
cataatgcca agacaaagcc gcgggaggag cagtacgcca gcacgtaccg tgtggtcagc 900
gtcctcaccg tcctgcacca ggactggctg aatggcaagg agtacaagtg caaggtctcc 960
aacaaagccc tcccagcccc catcgagaaa accatctcca aagccaaagg gcagccccga 1020
gaaccacagg tgtacaccct gcccccatcc cgggaggaga tgaccaagaa ccaggtcagc 1080
ctgacctgcc tggtcaaagg cttctatccc agcgacatcg ccgtggagtg ggagagcaat 1140
gggcagccgg agaacaacta caagaccacg cctcccgtgc tggactccga cggctccttc 1200
ttcctctaca gcaagctcac cgtggacaag agcaggtggc agcaggggaa cgtcttctca 1260
tgctccgtga tgcatgaggc tctgcacaac cactacacgc agaagagcct ctccctgtct 1320
ccgggtaaa 1329

<210> SEQ ID NO 172
<211> LENGTH: 339
<212> TYPE: DNA
<213> ORGANISM: Artificial
<220> FEATURE:
<223> OTHER INFORMATION: Humanized Antibody Sequence

<400> SEQUENCE: 172
cagtcggtgg aggcgtccgg gggtcgcctg gtcacgcctg ggacacccct gacactcacc 60
tgcaccgtct ctggattctc cctcagtagc gctgcaatga actgggtccg ccaggctcca 120
gggaaggggc tggaatggat cggatttatt gagtatagta agaatatagt ttacgcgtcc 180
tgggcgaaag gccgattcac catctccaaa gtctcgtcga ccacggtgga tctgaaaatg 240
accagtccga caaccgagga cacggccacc tatttctgtg ccaggggggg aggggaattt 300
ttcatctggg gccaaggcac cctggtcacc gtctcgagc 339

<210> SEQ ID NO 173
<211> LENGTH: 87
<212> TYPE: DNA
<213> ORGANISM: Oryctolagus cuniculus

<400> SEQUENCE: 173
cagtcggtgg aggcgtccgg gggtcgcctg gtcacgcctg ggacacccct gacactcacc 60
tgcaccgtct ctggattctc cctcagt 87

<210> SEQ ID NO 174
<211> LENGTH: 15
<212> TYPE: DNA
<213> ORGANISM: Oryctolagus cuniculus

<400> SEQUENCE: 174
agcgctgcaa tgaac 15

<210> SEQ ID NO 175
<211> LENGTH: 42
<212> TYPE: DNA
<213> ORGANISM: Oryctolagus cuniculus

<400> SEQUENCE: 175
tgggtccgcc aggctccagg gaaggggctg gaatggatcg ga 42

<210> SEQ ID NO 176
<211> LENGTH: 48
<212> TYPE: DNA
<213> ORGANISM: Oryctolagus cuniculus

<400> SEQUENCE: 176
tttattgagt atagtaagaa tatagtttac gcgtcctggg cgaaaggc 48

<210> SEQ ID NO 177
<211> LENGTH: 93
<212> TYPE: DNA
<213> ORGANISM: Oryctolagus cuniculus

<400> SEQUENCE: 177
cgattcacca tctccaaagt ctcgtcgacc acggtggatc tgaaaatgac cagtccgaca 60
accgaggaca cggccaccta tttctgtgcc agg 93

<210> SEQ ID NO 178
<211> LENGTH: 21
<212> TYPE: DNA
<213> ORGANISM: Oryctolagus cuniculus

<400> SEQUENCE: 178
gggggagggg aatttttcat c 21

<210> SEQ ID NO 179
<211> LENGTH: 33
<212> TYPE: DNA
<213> ORGANISM: Artificial
<220> FEATURE:
<223> OTHER INFORMATION: Humanized Antibody Sequence

<400> SEQUENCE: 179
tggggccaag gcaccctggt caccgtctcg agc 33

<210> SEQ ID NO 180
<211> LENGTH: 990
<212> TYPE: DNA
<213> ORGANISM: Artificial
<220> FEATURE:
<223> OTHER INFORMATION: Humanized Antibody Sequence

<400> SEQUENCE: 180
gcctccacca agggcccatc ggtcttcccc ctggcaccct cctccaagag cacctctggg 60

-continued

```
ggcacagcgg ccctgggctg cctggtcaag gactacttcc ccgaaccggt gacggtgtcg    120

tggaactcag gcgccctgac cagcggcgtg cacaccttcc cggctgtcct acagtcctca    180

ggactctact ccctcagcag cgtggtgacc gtgccctcca gcagcttggg cacccagacc    240

tacatctgca acgtgaatca caagcccagc aacaccaagg tggacaagaa agttgagccc    300

aaatcttgtg acaaaactca cacatgccca ccgtgcccag cacctgaact cctgggggga    360

ccgtcagtct tcctcttccc cccaaaaccc aaggacaccc tcatgatctc ccggacccct    420

gaggtcacat gcgtggtggt ggacgtgagc cacgaagacc ctgaggtcaa gttcaactgg    480

tacgtggacg gcgtggaggt gcataatgcc aagacaaagc cgcgggagga gcagtacgcc    540

agcacgtacc gtgtggtcag cgtcctcacc gtcctgcacc aggactggct gaatggcaag    600

gagtacaagt gcaaggtctc caacaaagcc ctcccagccc ccatcgagaa aaccatctcc    660

aaagccaaag ggcagccccg agaaccacag gtgtacaccc tgcccccatc ccgggaggag    720

atgaccaaga accaggtcag cctgacctgc ctggtcaaag gcttctatcc cagcgacatc    780

gccgtggagt gggagagcaa tgggcagccg gagaacaact acaagaccac gcctcccgtg    840

ctggactccg acggctcctt cttcctctac agcaagctca ccgtggacaa gagcaggtgg    900

cagcagggga acgtcttctc atgctccgtg atgcatgagg ctctgcacaa ccactacacg    960

cagaagagcc tctccctgtc tccgggtaaa                                     990


<210> SEQ ID NO 181
<211> LENGTH: 217
<212> TYPE: PRT
<213> ORGANISM: Artificial
<220> FEATURE:
<223> OTHER INFORMATION: Humanized Antibody Sequence

<400> SEQUENCE: 181

Ala Gln Val Leu Thr Gln Thr Pro Ser Ser Val Ser Ala Ala Val Gly
1               5                   10                  15

Gly Thr Val Thr Ile Asn Cys Gln Ser Ser Gln Ser Val Tyr Ser Asn
            20                  25                  30

Asn Arg Leu Ser Tyr Tyr Gln Gln Lys Pro Gly Gln Pro Pro Lys Leu
        35                  40                  45

Leu Ile Tyr Glu Ala Ser Ser Leu Ala Tyr Gly Val Pro Ser Arg Phe
    50                  55                  60

Lys Gly Ser Gly Ser Gly Thr Gln Phe Thr Leu Thr Ile Ser Asp Leu
65                  70                  75                  80

Glu Cys Asp Asp Ala Ala Thr Tyr Tyr Cys Ala Gly Ala Tyr Ser Asn
                85                  90                  95

Ser Ile Tyr Ser Phe Gly Gly Gly Thr Glu Val Val Val Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
```

-continued

```
        195                 200                 205

Thr Lys Ser Phe Asn Arg Gly Glu Cys
    210                 215
```

<210> SEQ ID NO 182
<211> LENGTH: 111
<212> TYPE: PRT
<213> ORGANISM: Artificial
<220> FEATURE:
<223> OTHER INFORMATION: Humanized Antibody Sequence

<400> SEQUENCE: 182

```
Ala Gln Val Leu Thr Gln Thr Pro Ser Ser Val Ser Ala Ala Val Gly
1               5                   10                  15

Gly Thr Val Thr Ile Asn Cys Gln Ser Ser Gln Ser Val Tyr Ser Asn
            20                  25                  30

Asn Arg Leu Ser Tyr Tyr Gln Gln Lys Pro Gly Gln Pro Pro Lys Leu
        35                  40                  45

Leu Ile Tyr Glu Ala Ser Ser Leu Ala Tyr Gly Val Pro Ser Arg Phe
    50                  55                  60

Lys Gly Ser Gly Ser Gly Thr Gln Phe Thr Leu Thr Ile Ser Asp Leu
65                  70                  75                  80

Glu Cys Asp Asp Ala Ala Thr Tyr Tyr Cys Ala Gly Ala Tyr Ser Asn
                85                  90                  95

Ser Ile Tyr Ser Phe Gly Gly Gly Thr Glu Val Val Val Lys Arg
            100                 105                 110
```

<210> SEQ ID NO 183
<211> LENGTH: 23
<212> TYPE: PRT
<213> ORGANISM: Oryctolagus cuniculus

<400> SEQUENCE: 183

```
Ala Gln Val Leu Thr Gln Thr Pro Ser Ser Val Ser Ala Ala Val Gly
1               5                   10                  15

Gly Thr Val Thr Ile Asn Cys
            20
```

<210> SEQ ID NO 184
<211> LENGTH: 13
<212> TYPE: PRT
<213> ORGANISM: Oryctolagus cuniculus

<400> SEQUENCE: 184

```
Gln Ser Ser Gln Ser Val Tyr Ser Asn Asn Arg Leu Ser
1               5                   10
```

<210> SEQ ID NO 185
<211> LENGTH: 15
<212> TYPE: PRT
<213> ORGANISM: Oryctolagus cuniculus

<400> SEQUENCE: 185

```
Tyr Tyr Gln Gln Lys Pro Gly Gln Pro Pro Lys Leu Leu Ile Tyr
1               5                   10                  15
```

<210> SEQ ID NO 186
<211> LENGTH: 7
<212> TYPE: PRT
<213> ORGANISM: Oryctolagus cuniculus

<400> SEQUENCE: 186

Glu Ala Ser Ser Leu Ala Tyr
1 5

<210> SEQ ID NO 187
<211> LENGTH: 32
<212> TYPE: PRT
<213> ORGANISM: Oryctolagus cuniculus

<400> SEQUENCE: 187

Gly Val Pro Ser Arg Phe Lys Gly Ser Gly Ser Gly Thr Gln Phe Thr
1 5 10 15

Leu Thr Ile Ser Asp Leu Glu Cys Asp Asp Ala Ala Thr Tyr Tyr Cys
20 25 30

<210> SEQ ID NO 188
<211> LENGTH: 10
<212> TYPE: PRT
<213> ORGANISM: Oryctolagus cuniculus

<400> SEQUENCE: 188

Ala Gly Ala Tyr Ser Asn Ser Ile Tyr Ser
1 5 10

<210> SEQ ID NO 189
<211> LENGTH: 11
<212> TYPE: PRT
<213> ORGANISM: Artificial
<220> FEATURE:
<223> OTHER INFORMATION: Humanized Antibody Sequence

<400> SEQUENCE: 189

Phe Gly Gly Gly Thr Glu Val Val Val Lys Arg
1 5 10

<210> SEQ ID NO 190
<211> LENGTH: 106
<212> TYPE: PRT
<213> ORGANISM: Artificial
<220> FEATURE:
<223> OTHER INFORMATION: Humanized Antibody Sequence

<400> SEQUENCE: 190

Thr Val Ala Ala Pro Ser Val Phe Ile Phe Pro Pro Ser Asp Glu Gln
1 5 10 15

Leu Lys Ser Gly Thr Ala Ser Val Val Cys Leu Leu Asn Asn Phe Tyr
20 25 30

Pro Arg Glu Ala Lys Val Gln Trp Lys Val Asp Asn Ala Leu Gln Ser
35 40 45

Gly Asn Ser Gln Glu Ser Val Thr Glu Gln Asp Ser Lys Asp Ser Thr
50 55 60

Tyr Ser Leu Ser Ser Thr Leu Thr Leu Ser Lys Ala Asp Tyr Glu Lys
65 70 75 80

His Lys Val Tyr Ala Cys Glu Val Thr His Gln Gly Leu Ser Ser Pro
85 90 95

Val Thr Lys Ser Phe Asn Arg Gly Glu Cys
100 105

<210> SEQ ID NO 191
<211> LENGTH: 651
<212> TYPE: DNA
<213> ORGANISM: Artificial
<220> FEATURE:

<223> OTHER INFORMATION: Humanized Antibody Sequence

<400> SEQUENCE: 191
gcgcaagtgc tgacccagac tccatcgtcc gtgtctgcag ctgtgggagg cacagtcacc 60
atcaattgcc agtccagtca gagtgtttat agtaacaacc ggttatcgta ctatcagcag 120
aaaccagggc agcctcccaa gctcctgatc tacgaagcat ccagtctggc atatggggtc 180
ccatcgcggt tcaaaggcag tggatctggg acacagttca ctctcaccat cagcgacctg 240
gagtgtgacg atgccgccac ttattactgt gcaggtgcct atagtaatag tatttatagt 300
ttcggcggag ggaccgaggt ggtggtcaaa cgtacggtag cggccccatc tgtcttcatc 360
ttcccgccat ctgatgagca gttgaaatct ggaactgcct ctgttgtgtg cctgctgaat 420
aacttctatc ccagagaggc caaagtacag tggaaggtgg ataacgccct ccaatcgggt 480
aactcccagg agagtgtcac agagcaggac agcaaggaca gcacctacag cctcagcagc 540
accctgacgc tgagcaaagc agactacgag aaacacaaag tctacgcctg cgaagtcacc 600
catcagggcc tgagctcgcc cgtcacaaag agcttcaaca ggggagagtg t 651

<210> SEQ ID NO 192
<211> LENGTH: 333
<212> TYPE: DNA
<213> ORGANISM: Artificial
<220> FEATURE:
<223> OTHER INFORMATION: Humanized Antibody Sequence

<400> SEQUENCE: 192
gcgcaagtgc tgacccagac tccatcgtcc gtgtctgcag ctgtgggagg cacagtcacc 60
atcaattgcc agtccagtca gagtgtttat agtaacaacc ggttatcgta ctatcagcag 120
aaaccagggc agcctcccaa gctcctgatc tacgaagcat ccagtctggc atatggggtc 180
ccatcgcggt tcaaaggcag tggatctggg acacagttca ctctcaccat cagcgacctg 240
gagtgtgacg atgccgccac ttattactgt gcaggtgcct atagtaatag tatttatagt 300
ttcggcggag ggaccgaggt ggtggtcaaa cgt 333

<210> SEQ ID NO 193
<211> LENGTH: 69
<212> TYPE: DNA
<213> ORGANISM: Oryctolagus cuniculus

<400> SEQUENCE: 193
gcgcaagtgc tgacccagac tccatcgtcc gtgtctgcag ctgtgggagg cacagtcacc 60
atcaattgc 69

<210> SEQ ID NO 194
<211> LENGTH: 39
<212> TYPE: DNA
<213> ORGANISM: Oryctolagus cuniculus

<400> SEQUENCE: 194
cagtccagtc agagtgttta tagtaacaac cggttatcg 39

<210> SEQ ID NO 195
<211> LENGTH: 45
<212> TYPE: DNA
<213> ORGANISM: Oryctolagus cuniculus

<400> SEQUENCE: 195
tactatcagc agaaaccagg gcagcctccc aagctcctga tctac 45

<210> SEQ ID NO 196
<211> LENGTH: 21
<212> TYPE: DNA
<213> ORGANISM: Oryctolagus cuniculus

<400> SEQUENCE: 196
gaagcatcca gtctggcata t 21

<210> SEQ ID NO 197
<211> LENGTH: 96
<212> TYPE: DNA
<213> ORGANISM: Oryctolagus cuniculus

<400> SEQUENCE: 197
ggggtcccat cgcggttcaa aggcagtgga tctgggacac agttcactct caccatcagc 60
gacctggagt gtgacgatgc cgccacttat tactgt 96

<210> SEQ ID NO 198
<211> LENGTH: 30
<212> TYPE: DNA
<213> ORGANISM: Oryctolagus cuniculus

<400> SEQUENCE: 198
gcaggtgcct atagtaatag tatttatagt 30

<210> SEQ ID NO 199
<211> LENGTH: 33
<212> TYPE: DNA
<213> ORGANISM: Artificial
<220> FEATURE:
<223> OTHER INFORMATION: Humanized Antibody Sequence

<400> SEQUENCE: 199
ttcggcggag ggaccgaggt ggtggtcaaa cgt 33

<210> SEQ ID NO 200
<211> LENGTH: 318
<212> TYPE: DNA
<213> ORGANISM: Artificial
<220> FEATURE:
<223> OTHER INFORMATION: Humanized Antibody Sequence

<400> SEQUENCE: 200
acggtagcgg ccccatctgt cttcatcttc ccgccatctg atgagcagtt gaaatctgga 60
actgcctctg ttgtgtgcct gctgaataac ttctatccca gagaggccaa agtacagtgg 120
aaggtggata acgccctcca atcgggtaac tcccaggaga gtgtcacaga gcaggacagc 180
aaggacagca cctacagcct cagcagcacc ctgacgctga gcaaagcaga ctacgagaaa 240
cacaaagtct acgcctgcga agtcacccat cagggcctga gctcgcccgt cacaaagagc 300
ttcaacaggg gagagtgt 318

<210> SEQ ID NO 201
<211> LENGTH: 443
<212> TYPE: PRT
<213> ORGANISM: Artificial
<220> FEATURE:
<223> OTHER INFORMATION: Humanized Antibody Sequence

<400> SEQUENCE: 201

Gln Ser Val Glu Ala Ser Gly Gly His Leu Val Thr Pro Gly Thr Pro
1 5 10 15

-continued

```
Leu Thr Leu Thr Cys Thr Val Ser Gly Phe Ser Leu Ser Ser Ala Ala
            20                  25                  30

Met Asn Trp Val Arg Gln Ala Pro Gly Lys Gly Leu Glu Trp Ile Gly
        35                  40                  45

Ser Val Asp Glu Arg Gln Asn Lys Tyr Tyr Ala Ser Trp Ala Lys Gly
    50                  55                  60

Arg Phe Thr Ile Ser Arg Thr Ser Ser Thr Thr Val Asn Leu Lys Met
65                  70                  75                  80

Thr Ser Pro Thr Thr Glu Asp Thr Ala Thr Tyr Phe Cys Ala Arg Gly
                85                  90                  95

Gly Gly Glu Phe Phe Ile Trp Gly Gln Gly Thr Leu Val Thr Val Ser
            100                 105                 110

Ser Ala Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Lys Val Glu Pro Lys Ser Cys Asp Lys Thr His Thr Cys Pro Pro
    210                 215                 220

Cys Pro Ala Pro Glu Leu Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
        275                 280                 285

Glu Glu Gln Tyr Ala Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Ala Leu Pro Ala Pro Ile Glu Lys Thr Ile Ser Lys Ala Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430
```

Thr Gln Lys Ser Leu Ser Leu Ser Pro Gly Lys
        435                 440

<210> SEQ ID NO 202
<211> LENGTH: 113
<212> TYPE: PRT
<213> ORGANISM: Artificial
<220> FEATURE:
<223> OTHER INFORMATION: Humanized Antibody Sequence

<400> SEQUENCE: 202

Gln Ser Val Glu Ala Ser Gly Gly His Leu Val Thr Pro Gly Thr Pro
1               5                   10                  15

Leu Thr Leu Thr Cys Thr Val Ser Gly Phe Ser Leu Ser Ser Ala Ala
            20                  25                  30

Met Asn Trp Val Arg Gln Ala Pro Gly Lys Gly Leu Glu Trp Ile Gly
        35                  40                  45

Ser Val Asp Glu Arg Gln Asn Lys Tyr Tyr Ala Ser Trp Ala Lys Gly
    50                  55                  60

Arg Phe Thr Ile Ser Arg Thr Ser Ser Thr Thr Val Asn Leu Lys Met
65                  70                  75                  80

Thr Ser Pro Thr Thr Glu Asp Thr Ala Thr Tyr Phe Cys Ala Arg Gly
                85                  90                  95

Gly Gly Glu Phe Phe Ile Trp Gly Gln Gly Thr Leu Val Thr Val Ser
            100                 105                 110

Ser

<210> SEQ ID NO 203
<211> LENGTH: 29
<212> TYPE: PRT
<213> ORGANISM: Oryctolagus cuniculus

<400> SEQUENCE: 203

Gln Ser Val Glu Ala Ser Gly Gly His Leu Val Thr Pro Gly Thr Pro
1               5                   10                  15

Leu Thr Leu Thr Cys Thr Val Ser Gly Phe Ser Leu Ser
            20                  25

<210> SEQ ID NO 204
<211> LENGTH: 5
<212> TYPE: PRT
<213> ORGANISM: Oryctolagus cuniculus

<400> SEQUENCE: 204

Ser Ala Ala Met Asn
1               5

<210> SEQ ID NO 205
<211> LENGTH: 14
<212> TYPE: PRT
<213> ORGANISM: Oryctolagus cuniculus

<400> SEQUENCE: 205

Trp Val Arg Gln Ala Pro Gly Lys Gly Leu Glu Trp Ile Gly
1               5                   10

<210> SEQ ID NO 206
<211> LENGTH: 16
<212> TYPE: PRT
<213> ORGANISM: Oryctolagus cuniculus

<400> SEQUENCE: 206

Ser Val Asp Glu Arg Gln Asn Lys Tyr Tyr Ala Ser Trp Ala Lys Gly
1 5 10 15

<210> SEQ ID NO 207
<211> LENGTH: 31
<212> TYPE: PRT
<213> ORGANISM: Oryctolagus cuniculus

<400> SEQUENCE: 207

Arg Phe Thr Ile Ser Arg Thr Ser Ser Thr Thr Val Asn Leu Lys Met
1 5 10 15

Thr Ser Pro Thr Thr Glu Asp Thr Ala Thr Tyr Phe Cys Ala Arg
20 25 30

<210> SEQ ID NO 208
<211> LENGTH: 7
<212> TYPE: PRT
<213> ORGANISM: Oryctolagus cuniculus

<400> SEQUENCE: 208

Gly Gly Gly Glu Phe Phe Ile
1 5

<210> SEQ ID NO 209
<211> LENGTH: 11
<212> TYPE: PRT
<213> ORGANISM: Artificial
<220> FEATURE:
<223> OTHER INFORMATION: Humanized Antibody Sequence

<400> SEQUENCE: 209

Trp Gly Gln Gly Thr Leu Val Thr Val Ser Ser
1 5 10

<210> SEQ ID NO 210
<211> LENGTH: 330
<212> TYPE: PRT
<213> ORGANISM: Artificial
<220> FEATURE:
<223> OTHER INFORMATION: Humanized Antibody Sequence

<400> SEQUENCE: 210

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val Glu Pro Lys Ser Cys Asp Lys Thr His Thr Cys Pro Pro Cys
100 105 110

Pro Ala Pro Glu Leu Leu Gly Gly Pro Ser Val Phe Leu Phe Pro Pro
115 120 125

Lys Pro Lys Asp Thr Leu Met Ile Ser Arg Thr Pro Glu Val Thr Cys
130 135 140

-continued

```
Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 211
<211> LENGTH: 1329
<212> TYPE: DNA
<213> ORGANISM: Artificial
<220> FEATURE:
<223> OTHER INFORMATION: Humanized Antibody Sequence

<400> SEQUENCE: 211

```
cagtcggtgg aggcgtccgg gggtcaccta gtcacgcctg ggacacccct gacactcacc     60

tgcaccgtct ctggattctc cctcagtagc gctgcaatga actgggtccg ccaggctcca    120

gggaaggggc tggaatggat cggatcggtt gatgagcgtc agaataaata ttacgcgtcc    180

tgggcgaaag gccgattcac catctccaga acctcgtcga ccacggtgaa tctgaaaatg    240

accagtccga caaccgagga cacggccacc tatttctgtg ccagaggggg aggggaattt    300

ttcatctggg gccagggcac cctcgtcacc gtctcgagcg cctccaccaa gggcccatcg    360

gtcttccccc tggcaccctc ctccaagagc acctctgggg gcacagcggc cctgggctgc    420

ctggtcaagg actacttccc cgaaccggtg acggtgtcgt ggaactcagg cgccctgacc    480

agcggcgtgc acaccttccc ggctgtccta cagtcctcag gactctactc cctcagcagc    540

gtggtgaccg tgccctccag cagcttgggc acccagacct acatctgcaa cgtgaatcac    600

aagcccagca acaccaaggt ggacaagaaa gttgagccca aatcttgtga caaaactcac    660

acatgcccac cgtgcccagc acctgaactc ctggggggac cgtcagtctt cctcttcccc    720

ccaaaaccca aggacaccct catgatctcc cggacccctg aggtcacatg cgtggtggtg    780

gacgtgagcc acgaagaccc tgaggtcaag ttcaactggt acgtggacgg cgtggaggtg    840

cataatgcca agacaaagcc gcgggaggag cagtacgcca gcacgtaccg tgtggtcagc    900

gtcctcaccg tcctgcacca ggactggctg aatggcaagg agtacaagtg caaggtctcc    960

aacaaagccc tcccagcccc catcgagaaa accatctcca aagccaaagg gcagccccga   1020
```

gaaccacagg tgtacaccct gcccccatcc cgggaggaga tgaccaagaa ccaggtcagc 1080
ctgacctgcc tggtcaaagg cttctatccc agcgacatcg ccgtggagtg ggagagcaat 1140
gggcagccgg agaacaacta caagaccacg cctcccgtgc tggactccga cggctccttc 1200
ttcctctaca gcaagctcac cgtggacaag agcaggtggc agcaggggaa cgtcttctca 1260
tgctccgtga tgcatgaggc tctgcacaac cactacacgc agaagagcct ctccctgtct 1320
ccgggtaaa 1329

<210> SEQ ID NO 212
<211> LENGTH: 339
<212> TYPE: DNA
<213> ORGANISM: Artificial
<220> FEATURE:
<223> OTHER INFORMATION: Humanized Antibody Sequence

<400> SEQUENCE: 212
cagtcggtgg aggcgtccgg gggtcaccta gtcacgcctg ggacacccct gacactcacc 60
tgcaccgtct ctggattctc cctcagtagc gctgcaatga actgggtccg ccaggctcca 120
gggaaggggc tggaatggat cggatcggtt gatgagcgtc agaataaata ttacgcgtcc 180
tgggcgaaag gccgattcac catctccaga acctcgtcga ccacggtgaa tctgaaaatg 240
accagtccga caaccgagga cacggccacc tatttctgtg ccagaggggg aggggaattt 300
ttcatctggg gccagggcac cctcgtcacc gtctcgagc 339

<210> SEQ ID NO 213
<211> LENGTH: 87
<212> TYPE: DNA
<213> ORGANISM: Oryctolagus cuniculus

<400> SEQUENCE: 213
cagtcggtgg aggcgtccgg gggtcaccta gtcacgcctg ggacacccct gacactcacc 60
tgcaccgtct ctggattctc cctcagt 87

<210> SEQ ID NO 214
<211> LENGTH: 15
<212> TYPE: DNA
<213> ORGANISM: Oryctolagus cuniculus

<400> SEQUENCE: 214
agcgctgcaa tgaac 15

<210> SEQ ID NO 215
<211> LENGTH: 42
<212> TYPE: DNA
<213> ORGANISM: Oryctolagus cuniculus

<400> SEQUENCE: 215
tgggtccgcc aggctccagg gaaggggctg gaatggatcg ga 42

<210> SEQ ID NO 216
<211> LENGTH: 48
<212> TYPE: DNA
<213> ORGANISM: Oryctolagus cuniculus

<400> SEQUENCE: 216
tcggttgatg agcgtcagaa taaatattac gcgtcctggg cgaaaggc 48

<210> SEQ ID NO 217

<211> LENGTH: 93
<212> TYPE: DNA
<213> ORGANISM: Oryctolagus cuniculus

<400> SEQUENCE: 217
cgattcacca tctccagaac ctcgtcgacc acggtgaatc tgaaaatgac cagtccgaca 60
accgaggaca cggccaccta tttctgtgcc aga 93

<210> SEQ ID NO 218
<211> LENGTH: 21
<212> TYPE: DNA
<213> ORGANISM: Oryctolagus cuniculus

<400> SEQUENCE: 218
gggggagggg aatttttcat c 21

<210> SEQ ID NO 219
<211> LENGTH: 33
<212> TYPE: DNA
<213> ORGANISM: Artificial
<220> FEATURE:
<223> OTHER INFORMATION: Humanized Antibody Sequence

<400> SEQUENCE: 219
tggggccagg gcaccctcgt caccgtctcg agc 33

<210> SEQ ID NO 220
<211> LENGTH: 990
<212> TYPE: DNA
<213> ORGANISM: Artificial
<220> FEATURE:
<223> OTHER INFORMATION: Humanized Antibody Sequence

<400> SEQUENCE: 220
gcctccacca agggcccatc ggtcttcccc ctggcaccct cctccaagag cacctctggg 60
ggcacagcgg ccctgggctg cctggtcaag gactacttcc ccgaaccggt gacggtgtcg 120
tggaactcag gcgccctgac cagcggcgtg cacaccttcc cggctgtcct acagtcctca 180
ggactctact ccctcagcag cgtggtgacc gtgccctcca gcagcttggg cacccagacc 240
tacatctgca acgtgaatca caagcccagc aacaccaagg tggacaagaa agttgagccc 300
aaatcttgtg acaaaactca cacatgccca ccgtgcccag cacctgaact cctgggggga 360
ccgtcagtct tcctcttccc cccaaaaccc aaggacaccc tcatgatctc ccggacccct 420
gaggtcacat gcgtggtggt ggacgtgagc cacgaagacc ctgaggtcaa gttcaactgg 480
tacgtggacg gcgtggaggt gcataatgcc aagacaaagc cgcgggagga gcagtacgcc 540
agcacgtacc gtgtggtcag cgtcctcacc gtcctgcacc aggactggct gaatggcaag 600
gagtacaagt gcaaggtctc caacaaagcc ctcccagccc ccatcgagaa aaccatctcc 660
aaagccaaag ggcagccccg agaaccacag gtgtacaccc tgcccccatc ccgggaggag 720
atgaccaaga accaggtcag cctgacctgc ctggtcaaag gcttctatcc cagcgacatc 780
gccgtggagt gggagagcaa tgggcagccg gagaacaact acaagaccac gcctcccgtg 840
ctggactccg acggctcctt cttcctctac agcaagctca ccgtggacaa gagcaggtgg 900
cagcagggga acgtcttctc atgctccgtg atgcatgagg ctctgcacaa ccactacacg 960
cagaagagcc tctccctgtc tccgggtaaa 990

<210> SEQ ID NO 221
<211> LENGTH: 217

<212> TYPE: PRT
<213> ORGANISM: Artificial
<220> FEATURE:
<223> OTHER INFORMATION: Humanized Antibody Sequence

<400> SEQUENCE: 221

```
Ala Gln Val Leu Thr Gln Thr Pro Ser Ser Val Ser Ala Ala Val Gly
1               5                   10                  15

Gly Thr Val Thr Ile Asn Cys Gln Ser Ser Gln Ser Val Tyr Ser Asn
            20                  25                  30

Asn Arg Leu Ser Trp Tyr Gln Gln Lys Pro Gly Gln Pro Pro Asn Leu
        35                  40                  45

Leu Ile Tyr Glu Ala Ser Ser Leu Ala Ser Gly Val Pro Ser Arg Phe
    50                  55                  60

Ser Gly Ser Gly Ser Gly Thr Gln Phe Thr Leu Thr Ile Ser Asp Leu
65                  70                  75                  80

Glu Cys Asp Asp Ala Ala Thr Tyr Tyr Cys Ala Gly Ala Tyr Asn Thr
                85                  90                  95

Gly Ile Tyr Gly Phe Gly Gly Gly Thr Glu Val Val Val Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215
```

<210> SEQ ID NO 222
<211> LENGTH: 111
<212> TYPE: PRT
<213> ORGANISM: Artificial
<220> FEATURE:
<223> OTHER INFORMATION: Humanized Antibody Sequence

<400> SEQUENCE: 222

```
Ala Gln Val Leu Thr Gln Thr Pro Ser Ser Val Ser Ala Ala Val Gly
1               5                   10                  15

Gly Thr Val Thr Ile Asn Cys Gln Ser Ser Gln Ser Val Tyr Ser Asn
            20                  25                  30

Asn Arg Leu Ser Trp Tyr Gln Gln Lys Pro Gly Gln Pro Pro Asn Leu
        35                  40                  45

Leu Ile Tyr Glu Ala Ser Ser Leu Ala Ser Gly Val Pro Ser Arg Phe
    50                  55                  60

Ser Gly Ser Gly Ser Gly Thr Gln Phe Thr Leu Thr Ile Ser Asp Leu
65                  70                  75                  80

Glu Cys Asp Asp Ala Ala Thr Tyr Tyr Cys Ala Gly Ala Tyr Asn Thr
                85                  90                  95

Gly Ile Tyr Gly Phe Gly Gly Gly Thr Glu Val Val Val Lys Arg
            100                 105                 110
```

<210> SEQ ID NO 223
<211> LENGTH: 23
<212> TYPE: PRT
<213> ORGANISM: Oryctolagus cuniculus

<400> SEQUENCE: 223

Ala Gln Val Leu Thr Gln Thr Pro Ser Ser Val Ser Ala Ala Val Gly
1 5 10 15

Gly Thr Val Thr Ile Asn Cys
20

<210> SEQ ID NO 224
<211> LENGTH: 13
<212> TYPE: PRT
<213> ORGANISM: Oryctolagus cuniculus

<400> SEQUENCE: 224

Gln Ser Ser Gln Ser Val Tyr Ser Asn Asn Arg Leu Ser
1 5 10

<210> SEQ ID NO 225
<211> LENGTH: 15
<212> TYPE: PRT
<213> ORGANISM: Oryctolagus cuniculus

<400> SEQUENCE: 225

Trp Tyr Gln Gln Lys Pro Gly Gln Pro Pro Asn Leu Leu Ile Tyr
1 5 10 15

<210> SEQ ID NO 226
<211> LENGTH: 7
<212> TYPE: PRT
<213> ORGANISM: Oryctolagus cuniculus

<400> SEQUENCE: 226

Glu Ala Ser Ser Leu Ala Ser
1 5

<210> SEQ ID NO 227
<211> LENGTH: 32
<212> TYPE: PRT
<213> ORGANISM: Oryctolagus cuniculus

<400> SEQUENCE: 227

Gly Val Pro Ser Arg Phe Ser Gly Ser Gly Ser Gly Thr Gln Phe Thr
1 5 10 15

Leu Thr Ile Ser Asp Leu Glu Cys Asp Asp Ala Ala Thr Tyr Tyr Cys
20 25 30

<210> SEQ ID NO 228
<211> LENGTH: 10
<212> TYPE: PRT
<213> ORGANISM: Oryctolagus cuniculus

<400> SEQUENCE: 228

Ala Gly Ala Tyr Asn Thr Gly Ile Tyr Gly
1 5 10

<210> SEQ ID NO 229
<211> LENGTH: 11
<212> TYPE: PRT
<213> ORGANISM: Artificial
<220> FEATURE:

<223> OTHER INFORMATION: Humanized Antibody Sequence

<400> SEQUENCE: 229

Phe Gly Gly Gly Thr Glu Val Val Val Lys Arg
1 5 10

<210> SEQ ID NO 230
<211> LENGTH: 106
<212> TYPE: PRT
<213> ORGANISM: Artificial
<220> FEATURE:
<223> OTHER INFORMATION: Humanized Antibody Sequence

<400> SEQUENCE: 230

Thr Val Ala Ala Pro Ser Val Phe Ile Phe Pro Pro Ser Asp Glu Gln
1 5 10 15

Leu Lys Ser Gly Thr Ala Ser Val Val Cys Leu Leu Asn Asn Phe Tyr
20 25 30

Pro Arg Glu Ala Lys Val Gln Trp Lys Val Asp Asn Ala Leu Gln Ser
35 40 45

Gly Asn Ser Gln Glu Ser Val Thr Glu Gln Asp Ser Lys Asp Ser Thr
50 55 60

Tyr Ser Leu Ser Ser Thr Leu Thr Leu Ser Lys Ala Asp Tyr Glu Lys
65 70 75 80

His Lys Val Tyr Ala Cys Glu Val Thr His Gln Gly Leu Ser Ser Pro
85 90 95

Val Thr Lys Ser Phe Asn Arg Gly Glu Cys
100 105

<210> SEQ ID NO 231
<211> LENGTH: 651
<212> TYPE: DNA
<213> ORGANISM: Artificial
<220> FEATURE:
<223> OTHER INFORMATION: Humanized Antibody Sequence

<400> SEQUENCE: 231
gcgcaagtgc tgacccagac tccatcgtcc gtgtctgcag ctgtgggagg cacagtcacc 60
atcaattgcc agtccagtca gagtgtttat agtaacaacc gcttatcctg gtatcagcag 120
aaaccagggc agcctcccaa tctcctgatc tacgaagcat ccagtctggc atctggggtc 180
ccatcgcggt tcagcggcag tggatctggg acacagttca ctctcaccat cagcgacctg 240
gagtgtgacg atgccgccac ttattactgt gcaggcgctt ataatactgg gatttatggt 300
ttcggcggag ggaccgaggt ggtggtcaaa cgtacggtag cggccccatc tgtcttcatc 360
ttcccgccat ctgatgagca gttgaaatct ggaactgcct ctgttgtgtg cctgctgaat 420
aacttctatc ccagagaggc caaagtacag tggaaggtgg ataacgccct ccaatcgggt 480
aactcccagg agagtgtcac agagcaggac agcaaggaca gcacctacag cctcagcagc 540
accctgacgc tgagcaaagc agactacgag aaacacaaag tctacgcctg cgaagtcacc 600
catcagggcc tgagctcgcc cgtcacaaag agcttcaaca ggggagagtg t 651

<210> SEQ ID NO 232
<211> LENGTH: 333
<212> TYPE: DNA
<213> ORGANISM: Artificial
<220> FEATURE:
<223> OTHER INFORMATION: Humanized Antibody Sequence

<400> SEQUENCE: 232
gcgcaagtgc tgacccagac tccatcgtcc gtgtctgcag ctgtgggagg cacagtcacc 60
atcaattgcc agtccagtca gagtgtttat agtaacaacc gcttatcctg gtatcagcag 120
aaaccagggc agcctcccaa tctcctgatc tacgaagcat ccagtctggc atctggggtc 180
ccatcgcggt tcagcggcag tggatctggg acacagttca ctctcaccat cagcgacctg 240
gagtgtgacg atgccgccac ttattactgt gcaggcgctt ataatactgg gatttatggt 300
ttcggcggag ggaccgaggt ggtggtcaaa cgt 333

<210> SEQ ID NO 233
<211> LENGTH: 69
<212> TYPE: DNA
<213> ORGANISM: Oryctolagus cuniculus

<400> SEQUENCE: 233
gcgcaagtgc tgacccagac tccatcgtcc gtgtctgcag ctgtgggagg cacagtcacc 60
atcaattgc 69

<210> SEQ ID NO 234
<211> LENGTH: 39
<212> TYPE: DNA
<213> ORGANISM: Oryctolagus cuniculus

<400> SEQUENCE: 234
cagtccagtc agagtgttta tagtaacaac cgcttatcc 39

<210> SEQ ID NO 235
<211> LENGTH: 45
<212> TYPE: DNA
<213> ORGANISM: Oryctolagus cuniculus

<400> SEQUENCE: 235
tggtatcagc agaaaccagg gcagcctccc aatctcctga tctac 45

<210> SEQ ID NO 236
<211> LENGTH: 21
<212> TYPE: DNA
<213> ORGANISM: Oryctolagus cuniculus

<400> SEQUENCE: 236
gaagcatcca gtctggcatc t 21

<210> SEQ ID NO 237
<211> LENGTH: 96
<212> TYPE: DNA
<213> ORGANISM: Oryctolagus cuniculus

<400> SEQUENCE: 237
ggggtcccat cgcggttcag cggcagtgga tctgggacac agttcactct caccatcagc 60
gacctggagt gtgacgatgc cgccacttat tactgt 96

<210> SEQ ID NO 238
<211> LENGTH: 30
<212> TYPE: DNA
<213> ORGANISM: Oryctolagus cuniculus

<400> SEQUENCE: 238
gcaggcgctt ataatactgg gatttatggt 30

<210> SEQ ID NO 239

<211> LENGTH: 33
<212> TYPE: DNA
<213> ORGANISM: Artificial
<220> FEATURE:
<223> OTHER INFORMATION: Humanized Antibody Sequence

<400> SEQUENCE: 239
ttcggcggag ggaccgaggt ggtggtcaaa cgt 33

<210> SEQ ID NO 240
<211> LENGTH: 318
<212> TYPE: DNA
<213> ORGANISM: Artificial
<220> FEATURE:
<223> OTHER INFORMATION: Humanized Antibody Sequence

<400> SEQUENCE: 240
acggtagcgg ccccatctgt cttcatcttc ccgccatctg atgagcagtt gaaatctgga 60
actgcctctg ttgtgtgcct gctgaataac ttctatccca gagaggccaa agtacagtgg 120
aaggtggata acgccctcca atcgggtaac tcccaggaga gtgtcacaga gcaggacagc 180
aaggacagca cctacagcct cagcagcacc ctgacgctga gcaaagcaga ctacgagaaa 240
cacaaagtct acgcctgcga agtcacccat cagggcctga gctcgcccgt cacaaagagc 300
ttcaacaggg gagagtgt 318

<210> SEQ ID NO 241
<211> LENGTH: 443
<212> TYPE: PRT
<213> ORGANISM: Artificial
<220> FEATURE:
<223> OTHER INFORMATION: Humanized Antibody Sequence

<400> SEQUENCE: 241

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Ala Ala
            20                  25                  30

Met Ser Trp Val Arg Gln Ala Pro Gly Lys Gly Leu Glu Trp Ile Gly
        35                  40                  45

Ile Ile Asp Asp Ser Gly Asn Thr Tyr Tyr Ala Ser Trp Ala Lys Ala
    50                  55                  60

Arg Phe Thr Ile Ser Lys Thr Ser Ser Thr Thr Val Asp Leu Lys Met
65                  70                  75                  80

Thr Ser Pro Thr Thr Glu Asp Thr Ala Thr Tyr Phe Cys Ala Arg Gly
                85                  90                  95

Gly Gly Glu Phe Phe Ile Trp Gly Pro Gly Thr Leu Val Thr Val Ser
            100                 105                 110

Ser Ala Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp

```
        195                 200                 205

Lys Lys Val Glu Pro Lys Ser Cys Asp Lys Thr His Thr Cys Pro Pro
    210                 215                 220

Cys Pro Ala Pro Glu Leu Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
        275                 280                 285

Glu Glu Gln Tyr Ala Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Ala Leu Pro Ala Pro Ile Glu Lys Thr Ile Ser Lys Ala Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
        435                 440


<210> SEQ ID NO 242
<211> LENGTH: 113
<212> TYPE: PRT
<213> ORGANISM: Artificial
<220> FEATURE:
<223> OTHER INFORMATION: Humanized Antibody Sequence

<400> SEQUENCE: 242

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Ala Ala
            20                  25                  30

Met Ser Trp Val Arg Gln Ala Pro Gly Lys Gly Leu Glu Trp Ile Gly
        35                  40                  45

Ile Ile Asp Asp Ser Gly Asn Thr Tyr Tyr Ala Ser Trp Ala Lys Ala
    50                  55                  60

Arg Phe Thr Ile Ser Lys Thr Ser Ser Thr Thr Val Asp Leu Lys Met
65                  70                  75                  80

Thr Ser Pro Thr Thr Glu Asp Thr Ala Thr Tyr Phe Cys Ala Arg Gly
                85                  90                  95

Gly Gly Glu Phe Phe Ile Trp Gly Pro Gly Thr Leu Val Thr Val Ser
            100                 105                 110

Ser
```

<210> SEQ ID NO 243
<211> LENGTH: 29
<212> TYPE: PRT
<213> ORGANISM: Oryctolagus cuniculus

<400> SEQUENCE: 243

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser
            20                  25

<210> SEQ ID NO 244
<211> LENGTH: 5
<212> TYPE: PRT
<213> ORGANISM: Oryctolagus cuniculus

<400> SEQUENCE: 244

Ser Ala Ala Met Ser
1               5

<210> SEQ ID NO 245
<211> LENGTH: 14
<212> TYPE: PRT
<213> ORGANISM: Oryctolagus cuniculus

<400> SEQUENCE: 245

Trp Val Arg Gln Ala Pro Gly Lys Gly Leu Glu Trp Ile Gly
1               5                   10

<210> SEQ ID NO 246
<211> LENGTH: 16
<212> TYPE: PRT
<213> ORGANISM: Oryctolagus cuniculus

<400> SEQUENCE: 246

Ile Ile Asp Asp Ser Gly Asn Thr Tyr Tyr Ala Ser Trp Ala Lys Ala
1               5                   10                  15

<210> SEQ ID NO 247
<211> LENGTH: 31
<212> TYPE: PRT
<213> ORGANISM: Oryctolagus cuniculus

<400> SEQUENCE: 247

Arg Phe Thr Ile Ser Lys Thr Ser Ser Thr Thr Val Asp Leu Lys Met
1               5                   10                  15

Thr Ser Pro Thr Thr Glu Asp Thr Ala Thr Tyr Phe Cys Ala Arg
            20                  25                  30

<210> SEQ ID NO 248
<211> LENGTH: 7
<212> TYPE: PRT
<213> ORGANISM: Oryctolagus cuniculus

<400> SEQUENCE: 248

Gly Gly Gly Glu Phe Phe Ile
1               5

<210> SEQ ID NO 249
<211> LENGTH: 11
<212> TYPE: PRT
<213> ORGANISM: Artificial
<220> FEATURE:

<223> OTHER INFORMATION: Humanized Antibody Sequence

<400> SEQUENCE: 249

Trp Gly Pro Gly Thr Leu Val Thr Val Ser Ser
1 5 10

<210> SEQ ID NO 250
<211> LENGTH: 330
<212> TYPE: PRT
<213> ORGANISM: Artificial
<220> FEATURE:
<223> OTHER INFORMATION: Humanized Antibody Sequence

<400> SEQUENCE: 250

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val Glu Pro Lys Ser Cys Asp Lys Thr His Thr Cys Pro Pro Cys
100 105 110

Pro Ala Pro Glu Leu Leu Gly Gly Pro Ser Val Phe Leu Phe Pro Pro
115 120 125

Lys Pro Lys Asp Thr Leu Met Ile Ser Arg Thr Pro Glu Val Thr Cys
130 135 140

Val Val Val Asp Val Ser His Glu Asp Pro Glu Val Lys Phe Asn Trp
145 150 155 160

Tyr Val Asp Gly Val Glu Val His Asn Ala Lys Thr Lys Pro Arg Glu
165 170 175

Glu Gln Tyr Ala Ser Thr Tyr Arg Val Val Ser Val Leu Thr Val Leu
180 185 190

His Gln Asp Trp Leu Asn Gly Lys Glu Tyr Lys Cys Lys Val Ser Asn
195 200 205

Lys Ala Leu Pro Ala Pro Ile Glu Lys Thr Ile Ser Lys Ala Lys Gly
210 215 220

Gln Pro Arg Glu Pro Gln Val Tyr Thr Leu Pro Pro Ser Arg Glu Glu
225 230 235 240

Met Thr Lys Asn Gln Val Ser Leu Thr Cys Leu Val Lys Gly Phe Tyr
245 250 255

Pro Ser Asp Ile Ala Val Glu Trp Glu Ser Asn Gly Gln Pro Glu Asn
260 265 270

Asn Tyr Lys Thr Thr Pro Pro Val Leu Asp Ser Asp Gly Ser Phe Phe
275 280 285

Leu Tyr Ser Lys Leu Thr Val Asp Lys Ser Arg Trp Gln Gln Gly Asn
290 295 300

Val Phe Ser Cys Ser Val Met His Glu Ala Leu His Asn His Tyr Thr
305 310 315 320

Gln Lys Ser Leu Ser Leu Ser Pro Gly Lys
325 330

<210> SEQ ID NO 251
<211> LENGTH: 1329
<212> TYPE: DNA
<213> ORGANISM: Artificial
<220> FEATURE:
<223> OTHER INFORMATION: Humanized Antibody Sequence

<400> SEQUENCE: 251
cagtcggtgg aggagtccgg gggtcgcctg gtcacgcctg ggacacccct gacactcacc 60
tgcaccgtct ctggattctc cctcagtagc gctgcaatga gctgggtccg ccaggctcca 120
gggaaggggc tggaatggat cggaattatt gatgatagtg gtaacacata ctacgcgtcc 180
tgggcgaaag cccgattcac catctccaaa acctcgtcga ccacggtgga tctgaaaatg 240
accagtccga caaccgagga cacggccacc tatttctgtg ccagaggggg aggggagttt 300
ttcatctggg gcccgggcac cctcgtcacc gtctcgagcg cctccaccaa gggcccatcg 360
gtcttccccc tggcaccctc ctccaagagc acctctgggg gcacagcggc cctgggctgc 420
ctggtcaagg actacttccc cgaaccggtg acggtgtcgt ggaactcagg cgccctgacc 480
agcggcgtgc acaccttccc ggctgtccta cagtcctcag gactctactc cctcagcagc 540
gtggtgaccg tgccctccag cagcttgggc acccagacct acatctgcaa cgtgaatcac 600
aagcccagca acaccaaggt ggacaagaaa gttgagccca aatcttgtga caaaactcac 660
acatgcccac cgtgcccagc acctgaactc ctggggggac cgtcagtctt cctcttcccc 720
ccaaaaccca aggacaccct catgatctcc cggacccctg aggtcacatg cgtggtggtg 780
gacgtgagcc acgaagaccc tgaggtcaag ttcaactggt acgtggacgg cgtggaggtg 840
cataatgcca agacaaagcc gcgggaggag cagtacgcca gcacgtaccg tgtggtcagc 900
gtcctcaccg tcctgcacca ggactggctg aatggcaagg agtacaagtg caaggtctcc 960
aacaaagccc tcccagcccc catcgagaaa accatctcca aagccaaagg gcagccccga 1020
gaaccacagg tgtacaccct gcccccatcc cgggaggaga tgaccaagaa ccaggtcagc 1080
ctgacctgcc tggtcaaagg cttctatccc agcgacatcg ccgtggagtg ggagagcaat 1140
gggcagccgg agaacaacta caagaccacg cctcccgtgc tggactccga cggctccttc 1200
ttcctctaca gcaagctcac cgtggacaag agcaggtggc agcaggggaa cgtcttctca 1260
tgctccgtga tgcatgaggc tctgcacaac cactacacgc agaagagcct ctccctgtct 1320
ccgggtaaa 1329

<210> SEQ ID NO 252
<211> LENGTH: 339
<212> TYPE: DNA
<213> ORGANISM: Artificial
<220> FEATURE:
<223> OTHER INFORMATION: Humanized Antibody Sequence

<400> SEQUENCE: 252
cagtcggtgg aggagtccgg gggtcgcctg gtcacgcctg ggacacccct gacactcacc 60
tgcaccgtct ctggattctc cctcagtagc gctgcaatga gctgggtccg ccaggctcca 120
gggaaggggc tggaatggat cggaattatt gatgatagtg gtaacacata ctacgcgtcc 180
tgggcgaaag cccgattcac catctccaaa acctcgtcga ccacggtgga tctgaaaatg 240
accagtccga caaccgagga cacggccacc tatttctgtg ccagaggggg aggggagttt 300
ttcatctggg gcccgggcac cctcgtcacc gtctcgagc 339

<210> SEQ ID NO 253
<211> LENGTH: 87
<212> TYPE: DNA
<213> ORGANISM: Oryctolagus cuniculus

<400> SEQUENCE: 253
cagtcggtgg aggagtccgg gggtcgcctg gtcacgcctg ggacacccct gacactcacc 60
tgcaccgtct ctggattctc cctcagt 87

<210> SEQ ID NO 254
<211> LENGTH: 15
<212> TYPE: DNA
<213> ORGANISM: Oryctolagus cuniculus

<400> SEQUENCE: 254
agcgctgcaa tgagc 15

<210> SEQ ID NO 255
<211> LENGTH: 42
<212> TYPE: DNA
<213> ORGANISM: Oryctolagus cuniculus

<400> SEQUENCE: 255
tgggtccgcc aggctccagg gaaggggctg gaatggatcg ga 42

<210> SEQ ID NO 256
<211> LENGTH: 48
<212> TYPE: DNA
<213> ORGANISM: Oryctolagus cuniculus

<400> SEQUENCE: 256
attattgatg atagtggtaa cacatactac gcgtcctggg cgaaagcc 48

<210> SEQ ID NO 257
<211> LENGTH: 93
<212> TYPE: DNA
<213> ORGANISM: Oryctolagus cuniculus

<400> SEQUENCE: 257
cgattcacca tctccaaaac ctcgtcgacc acggtggatc tgaaaatgac cagtccgaca 60
accgaggaca cggccaccta tttctgtgcc aga 93

<210> SEQ ID NO 258
<211> LENGTH: 21
<212> TYPE: DNA
<213> ORGANISM: Oryctolagus cuniculus

<400> SEQUENCE: 258
gggggagggg agtttttcat c 21

<210> SEQ ID NO 259
<211> LENGTH: 33
<212> TYPE: DNA
<213> ORGANISM: Artificial
<220> FEATURE:
<223> OTHER INFORMATION: Humanized Antibody Sequence

<400> SEQUENCE: 259
tggggcccgg gcaccctcgt caccgtctcg agc 33

<210> SEQ ID NO 260
<211> LENGTH: 990

<212> TYPE: DNA
<213> ORGANISM: Artificial
<220> FEATURE:
<223> OTHER INFORMATION: Humanized Antibody Sequence

<400> SEQUENCE: 260
gcctccacca agggcccatc ggtcttcccc ctggcaccct cctccaagag cacctctggg 60
ggcacagcgg ccctgggctg cctggtcaag gactacttcc ccgaaccggt gacggtgtcg 120
tggaactcag gcgccctgac cagcggcgtg cacaccttcc cggctgtcct acagtcctca 180
ggactctact ccctcagcag cgtggtgacc gtgccctcca gcagcttggg cacccagacc 240
tacatctgca acgtgaatca caagcccagc aacaccaagg tggacaagaa agttgagccc 300
aaatcttgtg acaaaactca cacatgccca ccgtgcccag cacctgaact cctgggggga 360
ccgtcagtct tcctcttccc cccaaaaccc aaggacaccc tcatgatctc ccggacccct 420
gaggtcacat gcgtggtggt ggacgtgagc cacgaagacc ctgaggtcaa gttcaactgg 480
tacgtggacg gcgtggaggt gcataatgcc aagacaaagc cgcgggagga gcagtacgcc 540
agcacgtacc gtgtggtcag cgtcctcacc gtcctgcacc aggactggct gaatggcaag 600
gagtacaagt gcaaggtctc caacaaagcc ctcccagccc ccatcgagaa aaccatctcc 660
aaagccaaag ggcagccccg agaaccacag gtgtacaccc tgcccccatc ccgggaggag 720
atgaccaaga accaggtcag cctgacctgc ctggtcaaag gcttctatcc cagcgacatc 780
gccgtggagt gggagagcaa tgggcagccg gagaacaact acaagaccac gcctcccgtg 840
ctggactccg acggctcctt cttcctctac agcaagctca ccgtggacaa gagcaggtgg 900
cagcagggga acgtcttctc atgctccgtg atgcatgagg ctctgcacaa ccactacacg 960
cagaagagcc tctccctgtc tccgggtaaa 990

<210> SEQ ID NO 261
<211> LENGTH: 217
<212> TYPE: PRT
<213> ORGANISM: Artificial
<220> FEATURE:
<223> OTHER INFORMATION: Humanized Antibody Sequence

<400> SEQUENCE: 261

Asp Pro Val Leu Thr Gln Thr Pro Ser Ser Val Ser Ala Ala Val Gly
1 5 10 15

Gly Thr Val Thr Ile Asn Cys Gln Ser Ser Gln Ser Val Tyr Asn Asn
20 25 30

Lys Trp Leu Ser Trp Tyr Gln Gln Lys Pro Gly Gln Ser Pro Lys Phe
35 40 45

Leu Ile Tyr Gln Ala Ser Asn Leu Ala Ser Gly Val Pro Ser Arg Phe
50 55 60

Lys Gly Ser Gly Ser Gly Thr Gln Phe Thr Leu Thr Ile Ser Asp Leu
65 70 75 80

Glu Cys Asp Asp Gly Ala Thr Tyr Tyr Cys Ala Gly Gly Tyr Arg Gly
85 90 95

Asn Val Cys Gly Phe Gly Gly Gly Thr Glu Val Val Val Lys Arg Thr
100 105 110

Val Ala Ala Pro Ser Val Phe Ile Phe Pro Pro Ser Asp Glu Gln Leu
115 120 125

Lys Ser Gly Thr Ala Ser Val Val Cys Leu Leu Asn Asn Phe Tyr Pro
130 135 140

Arg Glu Ala Lys Val Gln Trp Lys Val Asp Asn Ala Leu Gln Ser Gly 145 150 155 160

Asn Ser Gln Glu Ser Val Thr Glu Gln Asp Ser Lys Asp Ser Thr Tyr
165 170 175

Ser Leu Ser Ser Thr Leu Thr Leu Ser Lys Ala Asp Tyr Glu Lys His
180 185 190

Lys Val Tyr Ala Cys Glu Val Thr His Gln Gly Leu Ser Ser Pro Val
195 200 205

Thr Lys Ser Phe Asn Arg Gly Glu Cys
210 215

<210> SEQ ID NO 262
<211> LENGTH: 111
<212> TYPE: PRT
<213> ORGANISM: Artificial
<220> FEATURE:
<223> OTHER INFORMATION: Humanized Antibody Sequence

<400> SEQUENCE: 262

Asp Pro Val Leu Thr Gln Thr Pro Ser Ser Val Ser Ala Ala Val Gly
1 5 10 15

Gly Thr Val Thr Ile Asn Cys Gln Ser Ser Gln Ser Val Tyr Asn Asn
20 25 30

Lys Trp Leu Ser Trp Tyr Gln Gln Lys Pro Gly Gln Ser Pro Lys Phe
35 40 45

Leu Ile Tyr Gln Ala Ser Asn Leu Ala Ser Gly Val Pro Ser Arg Phe
50 55 60

Lys Gly Ser Gly Ser Gly Thr Gln Phe Thr Leu Thr Ile Ser Asp Leu
65 70 75 80

Glu Cys Asp Asp Gly Ala Thr Tyr Tyr Cys Ala Gly Gly Tyr Arg Gly
85 90 95

Asn Val Cys Gly Phe Gly Gly Gly Thr Glu Val Val Val Lys Arg
100 105 110

<210> SEQ ID NO 263
<211> LENGTH: 23
<212> TYPE: PRT
<213> ORGANISM: Oryctolagus cuniculus

<400> SEQUENCE: 263

Asp Pro Val Leu Thr Gln Thr Pro Ser Ser Val Ser Ala Ala Val Gly
1 5 10 15

Gly Thr Val Thr Ile Asn Cys
20

<210> SEQ ID NO 264
<211> LENGTH: 13
<212> TYPE: PRT
<213> ORGANISM: Oryctolagus cuniculus

<400> SEQUENCE: 264

Gln Ser Ser Gln Ser Val Tyr Asn Asn Lys Trp Leu Ser
1 5 10

<210> SEQ ID NO 265
<211> LENGTH: 15
<212> TYPE: PRT
<213> ORGANISM: Oryctolagus cuniculus

<400> SEQUENCE: 265

Trp Tyr Gln Gln Lys Pro Gly Gln Ser Pro Lys Phe Leu Ile Tyr

-continued 1               5                   10                  15

<210> SEQ ID NO 266
<211> LENGTH: 7
<212> TYPE: PRT
<213> ORGANISM: Oryctolagus cuniculus

<400> SEQUENCE: 266

Gln Ala Ser Asn Leu Ala Ser
1               5

<210> SEQ ID NO 267
<211> LENGTH: 32
<212> TYPE: PRT
<213> ORGANISM: Oryctolagus cuniculus

<400> SEQUENCE: 267

Gly Val Pro Ser Arg Phe Lys Gly Ser Gly Ser Gly Thr Gln Phe Thr
1               5                   10                  15

Leu Thr Ile Ser Asp Leu Glu Cys Asp Asp Gly Ala Thr Tyr Tyr Cys
            20                  25                  30

<210> SEQ ID NO 268
<211> LENGTH: 10
<212> TYPE: PRT
<213> ORGANISM: Oryctolagus cuniculus

<400> SEQUENCE: 268

Ala Gly Gly Tyr Arg Gly Asn Val Cys Gly
1               5                   10

<210> SEQ ID NO 269
<211> LENGTH: 11
<212> TYPE: PRT
<213> ORGANISM: Artificial
<220> FEATURE:
<223> OTHER INFORMATION: Humanized Antibody Sequence

<400> SEQUENCE: 269

Phe Gly Gly Gly Thr Glu Val Val Val Lys Arg
1               5                   10

<210> SEQ ID NO 270
<211> LENGTH: 106
<212> TYPE: PRT
<213> ORGANISM: Artificial
<220> FEATURE:
<223> OTHER INFORMATION: Humanized Antibody Sequence

<400> SEQUENCE: 270

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

```
Val Thr Lys Ser Phe Asn Arg Gly Glu Cys
            100                 105


<210> SEQ ID NO 271
<211> LENGTH: 651
<212> TYPE: DNA
<213> ORGANISM: Artificial
<220> FEATURE:
<223> OTHER INFORMATION: Humanized Antibody Sequence

<400> SEQUENCE: 271

gaccctgtgc tgacccagac tccatcgtcc gtgtctgcag ctgtgggagg cacagtcacc      60

atcaattgcc agtccagtca gagtgtttat aataacaagt ggttatcctg gtatcagcag     120

aaaccaggac agtctcccaa gttcctgatt taccaggcat ccaatttggc atctggggtc     180

ccatcgcggt tcaaaggcag tggatctggg acacagttca ctctcaccat cagcgacctg     240

gagtgtgacg atggcgccac ttattactgt gcaggcggct accgtggtaa tgtttgtggt     300

ttcggcggag ggaccgaggt ggtggtcaaa cgtacggtag cggccccatc tgtcttcatc     360

ttcccgccat ctgatgagca gttgaaatct ggaactgcct ctgttgtgtg cctgctgaat     420

aacttctatc ccagagaggc caaagtacag tggaaggtgg ataacgccct ccaatcgggt     480

aactcccagg agagtgtcac agagcaggac agcaaggaca gcacctacag cctcagcagc     540

accctgacgc tgagcaaagc agactacgag aaacacaaag tctacgcctg cgaagtcacc     600

catcagggcc tgagctcgcc cgtcacaaag agcttcaaca ggggagagtg t              651


<210> SEQ ID NO 272
<211> LENGTH: 333
<212> TYPE: DNA
<213> ORGANISM: Artificial
<220> FEATURE:
<223> OTHER INFORMATION: Humanized Antibody Sequence

<400> SEQUENCE: 272

gaccctgtgc tgacccagac tccatcgtcc gtgtctgcag ctgtgggagg cacagtcacc      60

atcaattgcc agtccagtca gagtgtttat aataacaagt ggttatcctg gtatcagcag     120

aaaccaggac agtctcccaa gttcctgatt taccaggcat ccaatttggc atctggggtc     180

ccatcgcggt tcaaaggcag tggatctggg acacagttca ctctcaccat cagcgacctg     240

gagtgtgacg atggcgccac ttattactgt gcaggcggct accgtggtaa tgtttgtggt     300

ttcggcggag ggaccgaggt ggtggtcaaa cgt                                  333


<210> SEQ ID NO 273
<211> LENGTH: 69
<212> TYPE: DNA
<213> ORGANISM: Oryctolagus cuniculus

<400> SEQUENCE: 273

gaccctgtgc tgacccagac tccatcgtcc gtgtctgcag ctgtgggagg cacagtcacc      60

atcaattgc                                                              69


<210> SEQ ID NO 274
<211> LENGTH: 39
<212> TYPE: DNA
<213> ORGANISM: Oryctolagus cuniculus

<400> SEQUENCE: 274

cagtccagtc agagtgttta taataacaag tggttatcc                             39
```

<210> SEQ ID NO 275
<211> LENGTH: 45
<212> TYPE: DNA
<213> ORGANISM: Oryctolagus cuniculus

<400> SEQUENCE: 275
tggtatcagc agaaaccagg acagtctccc aagttcctga tttac 45

<210> SEQ ID NO 276
<211> LENGTH: 21
<212> TYPE: DNA
<213> ORGANISM: Oryctolagus cuniculus

<400> SEQUENCE: 276
caggcatcca atttggcatc t 21

<210> SEQ ID NO 277
<211> LENGTH: 96
<212> TYPE: DNA
<213> ORGANISM: Oryctolagus cuniculus

<400> SEQUENCE: 277
ggggtcccat cgcggttcaa aggcagtgga tctgggacac agttcactct caccatcagc 60
gacctggagt gtgacgatgg cgccacttat tactgt 96

<210> SEQ ID NO 278
<211> LENGTH: 30
<212> TYPE: DNA
<213> ORGANISM: Oryctolagus cuniculus

<400> SEQUENCE: 278
gcaggcggct accgtggtaa tgtttgtggt 30

<210> SEQ ID NO 279
<211> LENGTH: 33
<212> TYPE: DNA
<213> ORGANISM: Artificial
<220> FEATURE:
<223> OTHER INFORMATION: Humanized Antibody Sequence

<400> SEQUENCE: 279
ttcggcggag ggaccgaggt ggtggtcaaa cgt 33

<210> SEQ ID NO 280
<211> LENGTH: 318
<212> TYPE: DNA
<213> ORGANISM: Artificial
<220> FEATURE:
<223> OTHER INFORMATION: Humanized Antibody Sequence

<400> SEQUENCE: 280
acggtagcgg ccccatctgt cttcatcttc ccgccatctg atgagcagtt gaaatctgga 60
actgcctctg ttgtgtgcct gctgaataac ttctatccca gagaggccaa agtacagtgg 120
aaggtggata acgccctcca atcgggtaac tcccaggaga gtgtcacaga gcaggacagc 180
aaggacagca cctacagcct cagcagcacc ctgacgctga gcaaagcaga ctacgagaaa 240
cacaaagtct acgcctgcga agtcacccat cagggcctga gctcgcccgt cacaaagagc 300
ttcaacaggg gagagtgt 318

<210> SEQ ID NO 281
<211> LENGTH: 443

<212> TYPE: PRT
<213> ORGANISM: Artificial
<220> FEATURE:
<223> OTHER INFORMATION: Humanized Antibody Sequence

<400> SEQUENCE: 281

```
Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Ala Ala
            20                  25                  30

Met Asn Trp Val Arg Gln Ala Pro Gly Lys Gly Leu Glu Trp Ile Gly
        35                  40                  45

Ile Phe Asp Pro Tyr Ser Ser Thr Tyr Tyr Ala Ser Trp Ala Lys Gly
    50                  55                  60

Arg Phe Thr Ile Ser Lys Thr Ser Ser Thr Thr Val Asp Leu Lys Met
65                  70                  75                  80

Thr Ser Pro Thr Thr Glu Asp Thr Ala Thr Tyr Phe Cys Ala Arg Gly
                85                  90                  95

Gly Gly Glu Phe Phe Ile Trp Gly Pro Gly Thr Leu Val Thr Val Ser
            100                 105                 110

Ser Ala Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Lys Val Glu Pro Lys Ser Cys Asp Lys Thr His Thr Cys Pro Pro
    210                 215                 220

Cys Pro Ala Pro Glu Leu Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
        275                 280                 285

Glu Glu Gln Tyr Ala Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Ala Leu Pro Ala Pro Ile Glu Lys Thr Ile Ser Lys Ala Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380
```

```
Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
        435                 440


<210> SEQ ID NO 282
<211> LENGTH: 113
<212> TYPE: PRT
<213> ORGANISM: Artificial
<220> FEATURE:
<223> OTHER INFORMATION: Humanized Antibody Sequence

<400> SEQUENCE: 282

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Ala Ala
            20                  25                  30

Met Asn Trp Val Arg Gln Ala Pro Gly Lys Gly Leu Glu Trp Ile Gly
        35                  40                  45

Ile Phe Asp Pro Tyr Ser Ser Thr Tyr Tyr Ala Ser Trp Ala Lys Gly
    50                  55                  60

Arg Phe Thr Ile Ser Lys Thr Ser Ser Thr Thr Val Asp Leu Lys Met
65                  70                  75                  80

Thr Ser Pro Thr Thr Glu Asp Thr Ala Thr Tyr Phe Cys Ala Arg Gly
                85                  90                  95

Gly Gly Glu Phe Phe Ile Trp Gly Pro Gly Thr Leu Val Thr Val Ser
            100                 105                 110

Ser


<210> SEQ ID NO 283
<211> LENGTH: 29
<212> TYPE: PRT
<213> ORGANISM: Oryctolagus cuniculus

<400> SEQUENCE: 283

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser
            20                  25


<210> SEQ ID NO 284
<211> LENGTH: 5
<212> TYPE: PRT
<213> ORGANISM: Oryctolagus cuniculus

<400> SEQUENCE: 284

Ser Ala Ala Met Asn
1               5


<210> SEQ ID NO 285
<211> LENGTH: 14
<212> TYPE: PRT
<213> ORGANISM: Oryctolagus cuniculus

<400> SEQUENCE: 285

Trp Val Arg Gln Ala Pro Gly Lys Gly Leu Glu Trp Ile Gly
```

1 5 10

<210> SEQ ID NO 286
<211> LENGTH: 16
<212> TYPE: PRT
<213> ORGANISM: Oryctolagus cuniculus

<400> SEQUENCE: 286

Ile Phe Asp Pro Tyr Ser Ser Thr Tyr Tyr Ala Ser Trp Ala Lys Gly
1 5 10 15

<210> SEQ ID NO 287
<211> LENGTH: 31
<212> TYPE: PRT
<213> ORGANISM: Oryctolagus cuniculus

<400> SEQUENCE: 287

Arg Phe Thr Ile Ser Lys Thr Ser Ser Thr Thr Val Asp Leu Lys Met
1 5 10 15

Thr Ser Pro Thr Thr Glu Asp Thr Ala Thr Tyr Phe Cys Ala Arg
20 25 30

<210> SEQ ID NO 288
<211> LENGTH: 7
<212> TYPE: PRT
<213> ORGANISM: Oryctolagus cuniculus

<400> SEQUENCE: 288

Gly Gly Gly Glu Phe Phe Ile
1 5

<210> SEQ ID NO 289
<211> LENGTH: 11
<212> TYPE: PRT
<213> ORGANISM: Artificial
<220> FEATURE:
<223> OTHER INFORMATION: Humanized Antibody Sequence

<400> SEQUENCE: 289

Trp Gly Pro Gly Thr Leu Val Thr Val Ser Ser
1 5 10

<210> SEQ ID NO 290
<211> LENGTH: 330
<212> TYPE: PRT
<213> ORGANISM: Artificial
<220> FEATURE:
<223> OTHER INFORMATION: Humanized Antibody Sequence

<400> SEQUENCE: 290

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

-continued

Lys Val Glu Pro Lys Ser Cys Asp Lys Thr His Thr Cys Pro Pro Cys
100 105 110

Pro Ala Pro Glu Leu Leu Gly Gly Pro Ser Val Phe Leu Phe Pro Pro
115 120 125

Lys Pro Lys Asp Thr Leu Met Ile Ser Arg Thr Pro Glu Val Thr Cys
130 135 140

Val Val Val Asp Val Ser His Glu Asp Pro Glu Val Lys Phe Asn Trp
145 150 155 160

Tyr Val Asp Gly Val Glu Val His Asn Ala Lys Thr Lys Pro Arg Glu
165 170 175

Glu Gln Tyr Ala Ser Thr Tyr Arg Val Val Ser Val Leu Thr Val Leu
180 185 190

His Gln Asp Trp Leu Asn Gly Lys Glu Tyr Lys Cys Lys Val Ser Asn
195 200 205

Lys Ala Leu Pro Ala Pro Ile Glu Lys Thr Ile Ser Lys Ala Lys Gly
210 215 220

Gln Pro Arg Glu Pro Gln Val Tyr Thr Leu Pro Pro Ser Arg Glu Glu
225 230 235 240

Met Thr Lys Asn Gln Val Ser Leu Thr Cys Leu Val Lys Gly Phe Tyr
245 250 255

Pro Ser Asp Ile Ala Val Glu Trp Glu Ser Asn Gly Gln Pro Glu Asn
260 265 270

Asn Tyr Lys Thr Thr Pro Pro Val Leu Asp Ser Asp Gly Ser Phe Phe
275 280 285

Leu Tyr Ser Lys Leu Thr Val Asp Lys Ser Arg Trp Gln Gln Gly Asn
290 295 300

Val Phe Ser Cys Ser Val Met His Glu Ala Leu His Asn His Tyr Thr
305 310 315 320

Gln Lys Ser Leu Ser Leu Ser Pro Gly Lys
325 330

<210> SEQ ID NO 291
<211> LENGTH: 1329
<212> TYPE: DNA
<213> ORGANISM: Artificial
<220> FEATURE:
<223> OTHER INFORMATION: Humanized Antibody Sequence

<400> SEQUENCE: 291
cagtcagtgg aggagtccgg gggtcgcctg gtcacgcctg ggacacccct aacactcacc 60
tgcaccgtct ctggattctc cctcagtagc gctgcaatga actgggtccg ccaggctcca 120
gggaaggggc tggaatggat cggtattttt gatccttata gtagtacata ctacgcgtcc 180
tgggcgaaag gccgattcac catctccaaa acctcgtcga ccacggtgga tctgaaaatg 240
accagtccga caaccgagga cacggccacc tatttctgtg ccagaggggg aggggaattt 300
ttcatctggg gcccaggcac cctcgtcacc gtctcgagcg cctccaccaa gggcccatcg 360
gtcttccccc tggcaccctc ctccaagagc acctctgggg gcacagcggc cctgggctgc 420
ctggtcaagg actacttccc cgaaccggtg acggtgtcgt ggaactcagg cgccctgacc 480
agcggcgtgc acaccttccc ggctgtccta cagtcctcag gactctactc cctcagcagc 540
gtggtgaccg tgccctccag cagcttgggc acccagacct acatctgcaa cgtgaatcac 600
aagcccagca acaccaaggt ggacaagaaa gttgagccca aatcttgtga caaaactcac 660
acatgcccac cgtgcccagc acctgaactc ctggggggac cgtcagtctt cctcttcccc 720
ccaaaaccca aggacaccct catgatctcc cggacccctg aggtcacatg cgtggtggtg 780
gacgtgagcc acgaagaccc tgaggtcaag ttcaactggt acgtggacgg cgtggaggtg 840
cataatgcca agacaaagcc gcgggaggag cagtacgcca gcacgtaccg tgtggtcagc 900
gtcctcaccg tcctgcacca ggactggctg aatggcaagg agtacaagtg caaggtctcc 960
aacaaagccc tcccagcccc catcgagaaa accatctcca aagccaaagg gcagccccga 1020
gaaccacagg tgtacaccct gcccccatcc cgggaggaga tgaccaagaa ccaggtcagc 1080
ctgacctgcc tggtcaaagg cttctatccc agcgacatcg ccgtggagtg ggagagcaat 1140
gggcagccgg agaacaacta caagaccacg cctcccgtgc tggactccga cggctccttc 1200
ttcctctaca gcaagctcac cgtggacaag agcaggtggc agcaggggaa cgtcttctca 1260
tgctccgtga tgcatgaggc tctgcacaac cactacacgc agaagagcct ctccctgtct 1320
ccgggtaaa 1329

<210> SEQ ID NO 292
<211> LENGTH: 339
<212> TYPE: DNA
<213> ORGANISM: Artificial
<220> FEATURE:
<223> OTHER INFORMATION: Humanized Antibody Sequence

<400> SEQUENCE: 292
cagtcagtgg aggagtccgg gggtcgcctg gtcacgcctg ggacacccct aacactcacc 60
tgcaccgtct ctggattctc cctcagtagc gctgcaatga actgggtccg ccaggctcca 120
gggaaggggc tggaatggat cggtattttt gatccttata gtagtacata ctacgcgtcc 180
tgggcgaaag gccgattcac catctccaaa acctcgtcga ccacggtgga tctgaaaatg 240
accagtccga caaccgagga cacggccacc tatttctgtg ccagaggggg aggggaattt 300
ttcatctggg gcccaggcac cctcgtcacc gtctcgagc 339

<210> SEQ ID NO 293
<211> LENGTH: 87
<212> TYPE: DNA
<213> ORGANISM: Oryctolagus cuniculus

<400> SEQUENCE: 293
cagtcagtgg aggagtccgg gggtcgcctg gtcacgcctg ggacacccct aacactcacc 60
tgcaccgtct ctggattctc cctcagt 87

<210> SEQ ID NO 294
<211> LENGTH: 15
<212> TYPE: DNA
<213> ORGANISM: Oryctolagus cuniculus

<400> SEQUENCE: 294
agcgctgcaa tgaac 15

<210> SEQ ID NO 295
<211> LENGTH: 42
<212> TYPE: DNA
<213> ORGANISM: Oryctolagus cuniculus

<400> SEQUENCE: 295
tgggtccgcc aggctccagg gaaggggctg gaatggatcg gt 42

<210> SEQ ID NO 296
<211> LENGTH: 48

<212> TYPE: DNA
<213> ORGANISM: Oryctolagus cuniculus

<400> SEQUENCE: 296
atttttgatc cttatagtag tacatactac gcgtcctggg cgaaaggc 48

<210> SEQ ID NO 297
<211> LENGTH: 93
<212> TYPE: DNA
<213> ORGANISM: Oryctolagus cuniculus

<400> SEQUENCE: 297
cgattcacca tctccaaaac ctcgtcgacc acggtggatc tgaaaatgac cagtccgaca 60
accgaggaca cggccaccta tttctgtgcc aga 93

<210> SEQ ID NO 298
<211> LENGTH: 21
<212> TYPE: DNA
<213> ORGANISM: Oryctolagus cuniculus

<400> SEQUENCE: 298
gggggagggg aatttttcat c 21

<210> SEQ ID NO 299
<211> LENGTH: 33
<212> TYPE: DNA
<213> ORGANISM: Artificial
<220> FEATURE:
<223> OTHER INFORMATION: Humanized Antibody Sequence

<400> SEQUENCE: 299
tggggcccag gcaccctcgt caccgtctcg agc 33

<210> SEQ ID NO 300
<211> LENGTH: 990
<212> TYPE: DNA
<213> ORGANISM: Artificial
<220> FEATURE:
<223> OTHER INFORMATION: Humanized Antibody Sequence

<400> SEQUENCE: 300
gcctccacca agggcccatc ggtcttcccc ctggcaccct cctccaagag cacctctggg 60
ggcacagcgg ccctgggctg cctggtcaag gactacttcc ccgaaccggt gacggtgtcg 120
tggaactcag gcgccctgac cagcggcgtg cacaccttcc cggctgtcct acagtcctca 180
ggactctact ccctcagcag cgtggtgacc gtgccctcca gcagcttggg cacccagacc 240
tacatctgca acgtgaatca caagcccagc aacaccaagg tggacaagaa agttgagccc 300
aaatcttgtg acaaaactca cacatgccca ccgtgcccag cacctgaact cctgggggga 360
ccgtcagtct tcctcttccc cccaaaaccc aaggacaccc tcatgatctc ccggacccct 420
gaggtcacat gcgtggtggt ggacgtgagc cacgaagacc ctgaggtcaa gttcaactgg 480
tacgtggacg gcgtggaggt gcataatgcc aagacaaagc cgcgggagga gcagtacgcc 540
agcacgtacc gtgtggtcag cgtcctcacc gtcctgcacc aggactggct gaatggcaag 600
gagtacaagt gcaaggtctc caacaaagcc ctcccagccc ccatcgagaa aaccatctcc 660
aaagccaaag ggcagccccg agaaccacag gtgtacaccc tgcccccatc ccgggaggag 720
atgaccaaga accaggtcag cctgacctgc ctggtcaaag gcttctatcc cagcgacatc 780
gccgtggagt gggagagcaa tgggcagccg gagaacaact acaagaccac gcctcccgtg 840
ctggactccg acggctcctt cttcctctac agcaagctca ccgtggacaa gagcaggtgg 900
cagcagggga acgtcttctc atgctccgtg atgcatgagg ctctgcacaa ccactacacg 960
cagaagagcc tctccctgtc tccgggtaaa 990

<210> SEQ ID NO 301
<211> LENGTH: 217
<212> TYPE: PRT
<213> ORGANISM: Artificial
<220> FEATURE:
<223> OTHER INFORMATION: Humanized Antibody Sequence

<400> SEQUENCE: 301

Ala Gln Val Leu Thr Gln Thr Pro Ser Ser Val Ser Ala Ala Val Gly
1 5 10 15

Gly Thr Val Thr Ile Asn Cys Gln Ser Ser Gln Ser Val Tyr Lys Asn
20 25 30

Lys Tyr Leu Ser Trp Tyr Gln Gln Lys Val Gly Gln Pro Pro Lys Phe
35 40 45

Leu Ile Tyr Gln Ala Ser Asn Leu Ala Ser Gly Val Pro Ser Arg Phe
50 55 60

Lys Gly Ser Gly Ser Gly Thr Gln Phe Thr Leu Thr Ile Ser Asp Leu
65 70 75 80

Glu Cys Asp Asp Ala Ala Thr Tyr Tyr Cys Ala Gly Gly Tyr Ser Gly
85 90 95

Asn Met Val Asp Phe Gly Gly Gly Thr Glu Val Val Val Lys Arg Thr
100 105 110

Val Ala Ala Pro Ser Val Phe Ile Phe Pro Pro Ser Asp Glu Gln Leu
115 120 125

Lys Ser Gly Thr Ala Ser Val Val Cys Leu Leu Asn Asn Phe Tyr Pro
130 135 140

Arg Glu Ala Lys Val Gln Trp Lys Val Asp Asn Ala Leu Gln Ser Gly
145 150 155 160

Asn Ser Gln Glu Ser Val Thr Glu Gln Asp Ser Lys Asp Ser Thr Tyr
165 170 175

Ser Leu Ser Ser Thr Leu Thr Leu Ser Lys Ala Asp Tyr Glu Lys His
180 185 190

Lys Val Tyr Ala Cys Glu Val Thr His Gln Gly Leu Ser Ser Pro Val
195 200 205

Thr Lys Ser Phe Asn Arg Gly Glu Cys
210 215

<210> SEQ ID NO 302
<211> LENGTH: 111
<212> TYPE: PRT
<213> ORGANISM: Artificial
<220> FEATURE:
<223> OTHER INFORMATION: Humanized Antibody Sequence

<400> SEQUENCE: 302

Ala Gln Val Leu Thr Gln Thr Pro Ser Ser Val Ser Ala Ala Val Gly
1 5 10 15

Gly Thr Val Thr Ile Asn Cys Gln Ser Ser Gln Ser Val Tyr Lys Asn
20 25 30

Lys Tyr Leu Ser Trp Tyr Gln Gln Lys Val Gly Gln Pro Pro Lys Phe
35 40 45

Leu Ile Tyr Gln Ala Ser Asn Leu Ala Ser Gly Val Pro Ser Arg Phe
50 55 60

Lys Gly Ser Gly Ser Gly Thr Gln Phe Thr Leu Thr Ile Ser Asp Leu
65 70 75 80

Glu Cys Asp Asp Ala Ala Thr Tyr Tyr Cys Ala Gly Gly Tyr Ser Gly
85 90 95

Asn Met Val Asp Phe Gly Gly Gly Thr Glu Val Val Val Lys Arg
100 105 110

<210> SEQ ID NO 303
<211> LENGTH: 23
<212> TYPE: PRT
<213> ORGANISM: Oryctolagus cuniculus

<400> SEQUENCE: 303

Ala Gln Val Leu Thr Gln Thr Pro Ser Ser Val Ser Ala Ala Val Gly
1 5 10 15

Gly Thr Val Thr Ile Asn Cys
20

<210> SEQ ID NO 304
<211> LENGTH: 13
<212> TYPE: PRT
<213> ORGANISM: Oryctolagus cuniculus

<400> SEQUENCE: 304

Gln Ser Ser Gln Ser Val Tyr Lys Asn Lys Tyr Leu Ser
1 5 10

<210> SEQ ID NO 305
<211> LENGTH: 15
<212> TYPE: PRT
<213> ORGANISM: Oryctolagus cuniculus

<400> SEQUENCE: 305

Trp Tyr Gln Gln Lys Val Gly Gln Pro Pro Lys Phe Leu Ile Tyr
1 5 10 15

<210> SEQ ID NO 306
<211> LENGTH: 7
<212> TYPE: PRT
<213> ORGANISM: Oryctolagus cuniculus

<400> SEQUENCE: 306

Gln Ala Ser Asn Leu Ala Ser
1 5

<210> SEQ ID NO 307
<211> LENGTH: 32
<212> TYPE: PRT
<213> ORGANISM: Oryctolagus cuniculus

<400> SEQUENCE: 307

Gly Val Pro Ser Arg Phe Lys Gly Ser Gly Ser Gly Thr Gln Phe Thr
1 5 10 15

Leu Thr Ile Ser Asp Leu Glu Cys Asp Asp Ala Ala Thr Tyr Tyr Cys
20 25 30

<210> SEQ ID NO 308
<211> LENGTH: 10
<212> TYPE: PRT
<213> ORGANISM: Oryctolagus cuniculus

<400> SEQUENCE: 308

Ala Gly Gly Tyr Ser Gly Asn Met Val Asp
1 5 10

<210> SEQ ID NO 309
<211> LENGTH: 11
<212> TYPE: PRT
<213> ORGANISM: Artificial
<220> FEATURE:
<223> OTHER INFORMATION: Humanized Antibody Sequence

<400> SEQUENCE: 309

Phe Gly Gly Gly Thr Glu Val Val Val Lys Arg
1 5 10

<210> SEQ ID NO 310
<211> LENGTH: 106
<212> TYPE: PRT
<213> ORGANISM: Artificial
<220> FEATURE:
<223> OTHER INFORMATION: Humanized Antibody Sequence

<400> SEQUENCE: 310

Thr Val Ala Ala Pro Ser Val Phe Ile Phe Pro Pro Ser Asp Glu Gln
1 5 10 15

Leu Lys Ser Gly Thr Ala Ser Val Val Cys Leu Leu Asn Asn Phe Tyr
20 25 30

Pro Arg Glu Ala Lys Val Gln Trp Lys Val Asp Asn Ala Leu Gln Ser
35 40 45

Gly Asn Ser Gln Glu Ser Val Thr Glu Gln Asp Ser Lys Asp Ser Thr
50 55 60

Tyr Ser Leu Ser Ser Thr Leu Thr Leu Ser Lys Ala Asp Tyr Glu Lys
65 70 75 80

His Lys Val Tyr Ala Cys Glu Val Thr His Gln Gly Leu Ser Ser Pro
85 90 95

Val Thr Lys Ser Phe Asn Arg Gly Glu Cys
100 105

<210> SEQ ID NO 311
<211> LENGTH: 651
<212> TYPE: DNA
<213> ORGANISM: Artificial
<220> FEATURE:
<223> OTHER INFORMATION: Humanized Antibody Sequence

<400> SEQUENCE: 311
gcccaagtgc tgacccagac tccatcgtcc gtgtctgcag ctgtgggagg cacagtcacc 60
atcaattgcc agtccagtca gagtgtttat aagaataagt acttatcctg gtatcagcag 120
aaagtagggc agcctcccaa gttcctgatc taccaggcat ccaatttggc atctggggtc 180
ccatcgcggt tcaaaggcag tggatctggg acacagttca ctctcaccat cagcgacctg 240
gagtgtgacg atgccgccac ttattactgt gcaggcggtt atagtggtaa tatggttgat 300
ttcggcggag ggaccgaggt ggtggtcaaa cgtacggtag cggccccatc tgtcttcatc 360
ttcccgccat ctgatgagca gttgaaatct ggaactgcct ctgttgtgtg cctgctgaat 420
aacttctatc ccagagaggc caaagtacag tggaaggtgg ataacgccct ccaatcgggt 480
aactcccagg agagtgtcac agagcaggac agcaaggaca gcacctacag cctcagcagc 540
accctgacgc tgagcaaagc agactacgag aaacacaaag tctacgcctg cgaagtcacc 600
catcagggcc tgagctcgcc cgtcacaaag agcttcaaca ggggagagtg t 651

<210> SEQ ID NO 312
<211> LENGTH: 333
<212> TYPE: DNA
<213> ORGANISM: Artificial
<220> FEATURE:
<223> OTHER INFORMATION: Humanized Antibody Sequence

<400> SEQUENCE: 312
gcccaagtgc tgacccagac tccatcgtcc gtgtctgcag ctgtgggagg cacagtcacc 60
atcaattgcc agtccagtca gagtgtttat aagaataagt acttatcctg gtatcagcag 120
aaagtagggc agcctcccaa gttcctgatc taccaggcat ccaatttggc atctggggtc 180
ccatcgcggt tcaaaggcag tggatctggg acacagttca ctctcaccat cagcgacctg 240
gagtgtgacg atgccgccac ttattactgt gcaggcggtt atagtggtaa tatggttgat 300
ttcggcggag ggaccgaggt ggtggtcaaa cgt 333

<210> SEQ ID NO 313
<211> LENGTH: 69
<212> TYPE: DNA
<213> ORGANISM: Oryctolagus cuniculus

<400> SEQUENCE: 313
gcccaagtgc tgacccagac tccatcgtcc gtgtctgcag ctgtgggagg cacagtcacc 60
atcaattgc 69

<210> SEQ ID NO 314
<211> LENGTH: 39
<212> TYPE: DNA
<213> ORGANISM: Oryctolagus cuniculus

<400> SEQUENCE: 314
cagtccagtc agagtgttta taagaataag tacttatcc 39

<210> SEQ ID NO 315
<211> LENGTH: 45
<212> TYPE: DNA
<213> ORGANISM: Oryctolagus cuniculus

<400> SEQUENCE: 315
tggtatcagc agaaagtagg gcagcctccc aagttcctga tctac 45

<210> SEQ ID NO 316
<211> LENGTH: 21
<212> TYPE: DNA
<213> ORGANISM: Oryctolagus cuniculus

<400> SEQUENCE: 316
caggcatcca atttggcatc t 21

<210> SEQ ID NO 317
<211> LENGTH: 96
<212> TYPE: DNA
<213> ORGANISM: Oryctolagus cuniculus

<400> SEQUENCE: 317
ggggtcccat cgcggttcaa aggcagtgga tctgggacac agttcactct caccatcagc 60
gacctggagt gtgacgatgc cgccacttat tactgt 96

<210> SEQ ID NO 318
<211> LENGTH: 30

<212> TYPE: DNA
<213> ORGANISM: Oryctolagus cuniculus

<400> SEQUENCE: 318
gcaggcggtt atagtggtaa tatggttgat 30

<210> SEQ ID NO 319
<211> LENGTH: 33
<212> TYPE: DNA
<213> ORGANISM: Artificial
<220> FEATURE:
<223> OTHER INFORMATION: Humanized Antibody Sequence

<400> SEQUENCE: 319
ttcggcggag ggaccgaggt ggtggtcaaa cgt 33

<210> SEQ ID NO 320
<211> LENGTH: 318
<212> TYPE: DNA
<213> ORGANISM: Artificial
<220> FEATURE:
<223> OTHER INFORMATION: Humanized Antibody Sequence

<400> SEQUENCE: 320
acggtagcgg ccccatctgt cttcatcttc ccgccatctg atgagcagtt gaaatctgga 60
actgcctctg ttgtgtgcct gctgaataac ttctatccca gagaggccaa agtacagtgg 120
aaggtggata acgccctcca atcgggtaac tcccaggaga gtgtcacaga gcaggacagc 180
aaggacagca cctacagcct cagcagcacc ctgacgctga gcaaagcaga ctacgagaaa 240
cacaaagtct acgcctgcga agtcacccat cagggcctga gctcgcccgt cacaaagagc 300
ttcaacaggg gagagtgt 318

<210> SEQ ID NO 321
<211> LENGTH: 443
<212> TYPE: PRT
<213> ORGANISM: Artificial
<220> FEATURE:
<223> OTHER INFORMATION: Humanized Antibody Sequence

<400> SEQUENCE: 321

Gln Ser Val Glu Glu Ser Gly Gly Arg Leu Val Thr Pro Gly Thr Pro
1 5 10 15

Leu Thr Leu Thr Cys Thr Val Ser Gly Phe Ser Leu Ser Ser Ala Ala
20 25 30

Leu Ser Trp Val Arg Gln Ala Pro Gly Lys Gly Leu Glu Trp Ile Gly
35 40 45

Ile Ile Asp Lys Gly Val Met Ser Tyr Tyr Ala Ser Trp Ala Lys Gly
50 55 60

Arg Phe Thr Ile Ser Lys Thr Ser Ser Thr Thr Val Asp Leu Lys Val
65 70 75 80

Thr Ser Pro Thr Thr Glu Asp Thr Ala Thr Tyr Phe Cys Ala Arg Gly
85 90 95

Gly Gly Glu Phe Phe Ile Trp Gly Gln Gly Thr Leu Val Thr Val Ser
100 105 110

Ser Ala Ser Thr Lys Gly Pro Ser Val Phe Pro Leu Ala Pro Ser Ser
115 120 125

Lys Ser Thr Ser Gly Gly Thr Ala Ala Leu Gly Cys Leu Val Lys Asp
130 135 140

Tyr Phe Pro Glu Pro Val Thr Val Ser Trp Asn Ser Gly Ala Leu Thr 145 150 155 160

Ser Gly Val His Thr Phe Pro Ala Val Leu Gln Ser Ser Gly Leu Tyr
165 170 175

Ser Leu Ser Ser Val Val Thr Val Pro Ser Ser Ser Leu Gly Thr Gln
180 185 190

Thr Tyr Ile Cys Asn Val Asn His Lys Pro Ser Asn Thr Lys Val Asp
195 200 205

Lys Lys Val Glu Pro Lys Ser Cys Asp Lys Thr His Thr Cys Pro Pro
210 215 220

Cys Pro Ala Pro Glu Leu Leu Gly Gly Pro Ser Val Phe Leu Phe Pro
225 230 235 240

Pro Lys Pro Lys Asp Thr Leu Met Ile Ser Arg Thr Pro Glu Val Thr
245 250 255

Cys Val Val Val Asp Val Ser His Glu Asp Pro Glu Val Lys Phe Asn
260 265 270

Trp Tyr Val Asp Gly Val Glu Val His Asn Ala Lys Thr Lys Pro Arg
275 280 285

Glu Glu Gln Tyr Ala Ser Thr Tyr Arg Val Val Ser Val Leu Thr Val
290 295 300

Leu His Gln Asp Trp Leu Asn Gly Lys Glu Tyr Lys Cys Lys Val Ser
305 310 315 320

Asn Lys Ala Leu Pro Ala Pro Ile Glu Lys Thr Ile Ser Lys Ala Lys
325 330 335

Gly Gln Pro Arg Glu Pro Gln Val Tyr Thr Leu Pro Pro Ser Arg Glu
340 345 350

Glu Met Thr Lys Asn Gln Val Ser Leu Thr Cys Leu Val Lys Gly Phe
355 360 365

Tyr Pro Ser Asp Ile Ala Val Glu Trp Glu Ser Asn Gly Gln Pro Glu
370 375 380

Asn Asn Tyr Lys Thr Thr Pro Pro Val Leu Asp Ser Asp Gly Ser Phe
385 390 395 400

Phe Leu Tyr Ser Lys Leu Thr Val Asp Lys Ser Arg Trp Gln Gln Gly
405 410 415

Asn Val Phe Ser Cys Ser Val Met His Glu Ala Leu His Asn His Tyr
420 425 430

Thr Gln Lys Ser Leu Ser Leu Ser Pro Gly Lys
435 440

<210> SEQ ID NO 322
<211> LENGTH: 113
<212> TYPE: PRT
<213> ORGANISM: Artificial
<220> FEATURE:
<223> OTHER INFORMATION: Humanized Antibody Sequence

<400> SEQUENCE: 322

Gln Ser Val Glu Glu Ser Gly Gly Arg Leu Val Thr Pro Gly Thr Pro
1 5 10 15

Leu Thr Leu Thr Cys Thr Val Ser Gly Phe Ser Leu Ser Ser Ala Ala
20 25 30

Leu Ser Trp Val Arg Gln Ala Pro Gly Lys Gly Leu Glu Trp Ile Gly
35 40 45

Ile Ile Asp Lys Gly Val Met Ser Tyr Tyr Ala Ser Trp Ala Lys Gly
50 55 60

Arg Phe Thr Ile Ser Lys Thr Ser Ser Thr Thr Val Asp Leu Lys Val

-continued 65 70 75 80

Thr Ser Pro Thr Thr Glu Asp Thr Ala Thr Tyr Phe Cys Ala Arg Gly
85 90 95

Gly Gly Glu Phe Phe Ile Trp Gly Gln Gly Thr Leu Val Thr Val Ser
100 105 110

Ser

<210> SEQ ID NO 323
<211> LENGTH: 29
<212> TYPE: PRT
<213> ORGANISM: Oryctolagus cuniculus

<400> SEQUENCE: 323

Gln Ser Val Glu Glu Ser Gly Gly Arg Leu Val Thr Pro Gly Thr Pro
1 5 10 15

Leu Thr Leu Thr Cys Thr Val Ser Gly Phe Ser Leu Ser
20 25

<210> SEQ ID NO 324
<211> LENGTH: 5
<212> TYPE: PRT
<213> ORGANISM: Oryctolagus cuniculus

<400> SEQUENCE: 324

Ser Ala Ala Leu Ser
1 5

<210> SEQ ID NO 325
<211> LENGTH: 14
<212> TYPE: PRT
<213> ORGANISM: Oryctolagus cuniculus

<400> SEQUENCE: 325

Trp Val Arg Gln Ala Pro Gly Lys Gly Leu Glu Trp Ile Gly
1 5 10

<210> SEQ ID NO 326
<211> LENGTH: 16
<212> TYPE: PRT
<213> ORGANISM: Oryctolagus cuniculus

<400> SEQUENCE: 326

Ile Ile Asp Lys Gly Val Met Ser Tyr Tyr Ala Ser Trp Ala Lys Gly
1 5 10 15

<210> SEQ ID NO 327
<211> LENGTH: 31
<212> TYPE: PRT
<213> ORGANISM: Oryctolagus cuniculus

<400> SEQUENCE: 327

Arg Phe Thr Ile Ser Lys Thr Ser Ser Thr Thr Val Asp Leu Lys Val
1 5 10 15

Thr Ser Pro Thr Thr Glu Asp Thr Ala Thr Tyr Phe Cys Ala Arg
20 25 30

<210> SEQ ID NO 328
<211> LENGTH: 7
<212> TYPE: PRT
<213> ORGANISM: Oryctolagus cuniculus

<400> SEQUENCE: 328

Gly Gly Gly Glu Phe Phe Ile
1 5

<210> SEQ ID NO 329
<211> LENGTH: 11
<212> TYPE: PRT
<213> ORGANISM: Artificial
<220> FEATURE:
<223> OTHER INFORMATION: Humanized Antibody Sequence

<400> SEQUENCE: 329

Trp Gly Gln Gly Thr Leu Val Thr Val Ser Ser
1 5 10

<210> SEQ ID NO 330
<211> LENGTH: 330
<212> TYPE: PRT
<213> ORGANISM: Artificial
<220> FEATURE:
<223> OTHER INFORMATION: Humanized Antibody Sequence

<400> SEQUENCE: 330

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val Glu Pro Lys Ser Cys Asp Lys Thr His Thr Cys Pro Pro Cys
100 105 110

Pro Ala Pro Glu Leu Leu Gly Gly Pro Ser Val Phe Leu Phe Pro Pro
115 120 125

Lys Pro Lys Asp Thr Leu Met Ile Ser Arg Thr Pro Glu Val Thr Cys
130 135 140

Val Val Val Asp Val Ser His Glu Asp Pro Glu Val Lys Phe Asn Trp
145 150 155 160

Tyr Val Asp Gly Val Glu Val His Asn Ala Lys Thr Lys Pro Arg Glu
165 170 175

Glu Gln Tyr Ala Ser Thr Tyr Arg Val Val Ser Val Leu Thr Val Leu
180 185 190

His Gln Asp Trp Leu Asn Gly Lys Glu Tyr Lys Cys Lys Val Ser Asn
195 200 205

Lys Ala Leu Pro Ala Pro Ile Glu Lys Thr Ile Ser Lys Ala Lys Gly
210 215 220

Gln Pro Arg Glu Pro Gln Val Tyr Thr Leu Pro Pro Ser Arg Glu Glu
225 230 235 240

Met Thr Lys Asn Gln Val Ser Leu Thr Cys Leu Val Lys Gly Phe Tyr
245 250 255

Pro Ser Asp Ile Ala Val Glu Trp Glu Ser Asn Gly Gln Pro Glu Asn
260 265 270

Asn Tyr Lys Thr Thr Pro Pro Val Leu Asp Ser Asp Gly Ser Phe Phe
275 280 285

-continued

```
Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 331
<211> LENGTH: 1329
<212> TYPE: DNA
<213> ORGANISM: Artificial
<220> FEATURE:
<223> OTHER INFORMATION: Humanized Antibody Sequence

<400> SEQUENCE: 331

cagtcggtgg aggagtccgg gggtcgcctg gtcacgcctg ggacacccct gacactcacc     60

tgcaccgtct ctggattctc cctcagtagc gctgcattga gctgggtccg ccaggctcca    120

gggaaggggc tggaatggat cggaattatt gataagggtg ttatgtctta ctacgcgtcc    180

tgggcgaaag gccgattcac catctccaaa acctcgtcga ccacggtgga tctaaaagtg    240

accagtccga caaccgagga cacggccacc tatttctgtg ccagaggggg gggggaattt    300

ttcatctggg gccagggcac cctcgtcacc gtctcgagcg cctccaccaa gggcccatcg    360

gtcttccccc tggcaccctc ctccaagagc acctctgggg gcacagcggc cctgggctgc    420

ctggtcaagg actacttccc cgaaccggtg acggtgtcgt ggaactcagg cgccctgacc    480

agcggcgtgc acaccttccc ggctgtccta cagtcctcag gactctactc cctcagcagc    540

gtggtgaccg tgccctccag cagcttgggc acccagacct acatctgcaa cgtgaatcac    600

aagcccagca acaccaaggt ggacaagaaa gttgagccca aatcttgtga caaaactcac    660

acatgcccac cgtgcccagc acctgaactc ctggggggac cgtcagtctt cctcttcccc    720

ccaaaaccca aggacaccct catgatctcc cggacccctg aggtcacatg cgtggtggtg    780

gacgtgagcc acgaagaccc tgaggtcaag ttcaactggt acgtggacgg cgtggaggtg    840

cataatgcca agacaaagcc gcgggaggag cagtacgcca gcacgtaccg tgtggtcagc    900

gtcctcaccg tcctgcacca ggactggctg aatggcaagg agtacaagtg caaggtctcc    960

aacaaagccc tcccagcccc catcgagaaa accatctcca aagccaaagg gcagccccga   1020

gaaccacagg tgtacaccct gcccccatcc cgggaggaga tgaccaagaa ccaggtcagc   1080

ctgacctgcc tggtcaaagg cttctatccc agcgacatcg ccgtggagtg ggagagcaat   1140

gggcagccgg agaacaacta caagaccacg cctcccgtgc tggactccga cggctccttc   1200

ttcctctaca gcaagctcac cgtggacaag agcaggtggc agcaggggaa cgtcttctca   1260

tgctccgtga tgcatgaggc tctgcacaac cactacacgc agaagagcct ctccctgtct   1320

ccgggtaaa                                                           1329


<210> SEQ ID NO 332
<211> LENGTH: 339
<212> TYPE: DNA
<213> ORGANISM: Artificial
<220> FEATURE:
<223> OTHER INFORMATION: Humanized Antibody Sequence

<400> SEQUENCE: 332

cagtcggtgg aggagtccgg gggtcgcctg gtcacgcctg ggacacccct gacactcacc     60

tgcaccgtct ctggattctc cctcagtagc gctgcattga gctgggtccg ccaggctcca    120
```

gggaaggggc tggaatggat cggaattatt gataagggtg ttatgtctta ctacgcgtcc 180
tgggcgaaag gccgattcac catctccaaa acctcgtcga ccacggtgga tctaaaagtg 240
accagtccga caaccgagga cacggccacc tatttctgtg ccagaggggg gggggaattt 300
ttcatctggg gccagggcac cctcgtcacc gtctcgagc 339

<210> SEQ ID NO 333
<211> LENGTH: 87
<212> TYPE: DNA
<213> ORGANISM: Oryctolagus cuniculus

<400> SEQUENCE: 333
cagtcggtgg aggagtccgg gggtcgcctg gtcacgcctg ggacacccct gacactcacc 60
tgcaccgtct ctggattctc cctcagt 87

<210> SEQ ID NO 334
<211> LENGTH: 15
<212> TYPE: DNA
<213> ORGANISM: Oryctolagus cuniculus

<400> SEQUENCE: 334
agcgctgcat tgagc 15

<210> SEQ ID NO 335
<211> LENGTH: 42
<212> TYPE: DNA
<213> ORGANISM: Oryctolagus cuniculus

<400> SEQUENCE: 335
tgggtccgcc aggctccagg gaaggggctg gaatggatcg ga 42

<210> SEQ ID NO 336
<211> LENGTH: 48
<212> TYPE: DNA
<213> ORGANISM: Oryctolagus cuniculus

<400> SEQUENCE: 336
attattgata agggtgttat gtcttactac gcgtcctggg cgaaaggc 48

<210> SEQ ID NO 337
<211> LENGTH: 93
<212> TYPE: DNA
<213> ORGANISM: Oryctolagus cuniculus

<400> SEQUENCE: 337
cgattcacca tctccaaaac ctcgtcgacc acggtggatc taaaagtgac cagtccgaca 60
accgaggaca cggccaccta tttctgtgcc aga 93

<210> SEQ ID NO 338
<211> LENGTH: 21
<212> TYPE: DNA
<213> ORGANISM: Oryctolagus cuniculus

<400> SEQUENCE: 338
gggggggggg aatttttcat c 21

<210> SEQ ID NO 339
<211> LENGTH: 33
<212> TYPE: DNA
<213> ORGANISM: Artificial
<220> FEATURE:

<223> OTHER INFORMATION: Humanized Antibody Sequence

<400> SEQUENCE: 339
tggggccagg gcaccctcgt caccgtctcg agc 33

<210> SEQ ID NO 340
<211> LENGTH: 990
<212> TYPE: DNA
<213> ORGANISM: Artificial
<220> FEATURE:
<223> OTHER INFORMATION: Humanized Antibody Sequence

<400> SEQUENCE: 340
gcctccacca agggcccatc ggtcttcccc ctggcaccct cctccaagag cacctctggg 60
ggcacagcgg ccctgggctg cctggtcaag gactacttcc ccgaaccggt gacggtgtcg 120
tggaactcag gcgccctgac cagcggcgtg cacaccttcc cggctgtcct acagtcctca 180
ggactctact ccctcagcag cgtggtgacc gtgccctcca gcagcttggg cacccagacc 240
tacatctgca acgtgaatca caagcccagc aacaccaagg tggacaagaa agttgagccc 300
aaatcttgtg acaaaactca cacatgccca ccgtgcccag cacctgaact cctgggggga 360
ccgtcagtct tcctcttccc cccaaaaccc aaggacaccc tcatgatctc ccggacccct 420
gaggtcacat gcgtggtggt ggacgtgagc cacgaagacc ctgaggtcaa gttcaactgg 480
tacgtggacg gcgtggaggt gcataatgcc aagacaaagc cgcgggagga gcagtacgcc 540
agcacgtacc gtgtggtcag cgtcctcacc gtcctgcacc aggactggct gaatggcaag 600
gagtacaagt gcaaggtctc caacaaagcc ctcccagccc ccatcgagaa aaccatctcc 660
aaagccaaag ggcagccccg agaaccacag gtgtacaccc tgcccccatc ccgggaggag 720
atgaccaaga accaggtcag cctgacctgc ctggtcaaag gcttctatcc cagcgacatc 780
gccgtggagt gggagagcaa tgggcagccg gagaacaact acaagaccac gcctcccgtg 840
ctggactccg acggctcctt cttcctctac agcaagctca ccgtggacaa gagcaggtgg 900
cagcagggga acgtcttctc atgctccgtg atgcatgagg ctctgcacaa ccactacacg 960
cagaagagcc tctccctgtc tccgggtaaa 990

<210> SEQ ID NO 341
<211> LENGTH: 217
<212> TYPE: PRT
<213> ORGANISM: Artificial
<220> FEATURE:
<223> OTHER INFORMATION: Humanized Antibody Sequence

<400> SEQUENCE: 341

Ala Gln Val Leu Thr Gln Thr Pro Ser Ser Val Ser Ala Ala Val Gly
1 5 10 15

Gly Thr Val Thr Ile Asn Cys Gln Ser Ser Lys Ser Val Tyr Asn Asn
20 25 30

Asn Trp Leu Ser Trp Tyr Gln Gln Lys Pro Gly Gln Pro Pro Lys Phe
35 40 45

Leu Ile Tyr Gln Ala Ser Asn Leu Ala Ser Gly Val Pro Ser Arg Phe
50 55 60

Lys Gly Ser Gly Ser Gly Thr Gln Phe Thr Leu Thr Ile Ser Asp Leu
65 70 75 80

Glu Cys Asp Asp Ala Ala Thr Tyr Tyr Cys Ala Gly Gly Tyr Ser Gly
85 90 95

Asn Ile Val Gly Phe Gly Gly Gly Thr Glu Val Val Val Lys Arg Thr

```
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215


<210> SEQ ID NO 342
<211> LENGTH: 111
<212> TYPE: PRT
<213> ORGANISM: Artificial
<220> FEATURE:
<223> OTHER INFORMATION: Humanized Antibody Sequence

<400> SEQUENCE: 342

Ala Gln Val Leu Thr Gln Thr Pro Ser Ser Val Ser Ala Ala Val Gly
1               5                   10                  15

Gly Thr Val Thr Ile Asn Cys Gln Ser Ser Lys Ser Val Tyr Asn Asn
            20                  25                  30

Asn Trp Leu Ser Trp Tyr Gln Gln Lys Pro Gly Gln Pro Pro Lys Phe
        35                  40                  45

Leu Ile Tyr Gln Ala Ser Asn Leu Ala Ser Gly Val Pro Ser Arg Phe
    50                  55                  60

Lys Gly Ser Gly Ser Gly Thr Gln Phe Thr Leu Thr Ile Ser Asp Leu
65                  70                  75                  80

Glu Cys Asp Asp Ala Ala Thr Tyr Tyr Cys Ala Gly Gly Tyr Ser Gly
                85                  90                  95

Asn Ile Val Gly Phe Gly Gly Gly Thr Glu Val Val Val Lys Arg
            100                 105                 110


<210> SEQ ID NO 343
<211> LENGTH: 23
<212> TYPE: PRT
<213> ORGANISM: Oryctolagus cuniculus

<400> SEQUENCE: 343

Ala Gln Val Leu Thr Gln Thr Pro Ser Ser Val Ser Ala Ala Val Gly
1               5                   10                  15

Gly Thr Val Thr Ile Asn Cys
            20


<210> SEQ ID NO 344
<211> LENGTH: 13
<212> TYPE: PRT
<213> ORGANISM: Oryctolagus cuniculus

<400> SEQUENCE: 344

Gln Ser Ser Lys Ser Val Tyr Asn Asn Asn Trp Leu Ser
1               5                   10
```

<210> SEQ ID NO 345
<211> LENGTH: 15
<212> TYPE: PRT
<213> ORGANISM: Oryctolagus cuniculus

<400> SEQUENCE: 345

Trp Tyr Gln Gln Lys Pro Gly Gln Pro Pro Lys Phe Leu Ile Tyr
1 5 10 15

<210> SEQ ID NO 346
<211> LENGTH: 7
<212> TYPE: PRT
<213> ORGANISM: Oryctolagus cuniculus

<400> SEQUENCE: 346

Gln Ala Ser Asn Leu Ala Ser
1 5

<210> SEQ ID NO 347
<211> LENGTH: 32
<212> TYPE: PRT
<213> ORGANISM: Oryctolagus cuniculus

<400> SEQUENCE: 347

Gly Val Pro Ser Arg Phe Lys Gly Ser Gly Ser Gly Thr Gln Phe Thr
1 5 10 15

Leu Thr Ile Ser Asp Leu Glu Cys Asp Asp Ala Ala Thr Tyr Tyr Cys
20 25 30

<210> SEQ ID NO 348
<211> LENGTH: 10
<212> TYPE: PRT
<213> ORGANISM: Oryctolagus cuniculus

<400> SEQUENCE: 348

Ala Gly Gly Tyr Ser Gly Asn Ile Val Gly
1 5 10

<210> SEQ ID NO 349
<211> LENGTH: 11
<212> TYPE: PRT
<213> ORGANISM: Artificial
<220> FEATURE:
<223> OTHER INFORMATION: Humanized Antibody Sequence

<400> SEQUENCE: 349

Phe Gly Gly Gly Thr Glu Val Val Val Lys Arg
1 5 10

<210> SEQ ID NO 350
<211> LENGTH: 106
<212> TYPE: PRT
<213> ORGANISM: Artificial
<220> FEATURE:
<223> OTHER INFORMATION: Humanized Antibody Sequence

<400> SEQUENCE: 350

Thr Val Ala Ala Pro Ser Val Phe Ile Phe Pro Pro Ser Asp Glu Gln
1 5 10 15

Leu Lys Ser Gly Thr Ala Ser Val Val Cys Leu Leu Asn Asn Phe Tyr
20 25 30

Pro Arg Glu Ala Lys Val Gln Trp Lys Val Asp Asn Ala Leu Gln Ser
35 40 45

-continued

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 351
<211> LENGTH: 651
<212> TYPE: DNA
<213> ORGANISM: Artificial
<220> FEATURE:
<223> OTHER INFORMATION: Humanized Antibody Sequence

<400> SEQUENCE: 351
gcgcaagtgc tgacccagac tccatcgtcc gtgtctgcag ctgtgggagg cacagtcacc 60
atcaattgcc agtccagtaa gagtgtttat aacaacaatt ggttatcctg gtatcaacag 120
aaaccagggc agcctcccaa gttcctgatc taccaggcat ccaatttggc atctggggtc 180
ccgtcgcggt tcaaaggcag tggatctggg acacagttca ctctcaccat cagcgacctc 240
gagtgtgacg atgccgccac ttattactgt gcaggcggtt atagtggtaa tattgttggt 300
ttcggcggag ggaccgaggt ggtggtcaaa cgtacggtag cggccccatc tgtcttcatc 360
ttcccgccat ctgatgagca gttgaaatct ggaactgcct ctgttgtgtg cctgctgaat 420
aacttctatc ccagagaggc caaagtacag tggaaggtgg ataacgccct ccaatcgggt 480
aactcccagg agagtgtcac agagcaggac agcaaggaca gcacctacag cctcagcagc 540
accctgacgc tgagcaaagc agactacgag aaacacaaag tctacgcctg cgaagtcacc 600
catcagggcc tgagctcgcc cgtcacaaag agcttcaaca ggggagagtg t 651

<210> SEQ ID NO 352
<211> LENGTH: 333
<212> TYPE: DNA
<213> ORGANISM: Artificial
<220> FEATURE:
<223> OTHER INFORMATION: Humanized Antibody Sequence

<400> SEQUENCE: 352
gcgcaagtgc tgacccagac tccatcgtcc gtgtctgcag ctgtgggagg cacagtcacc 60
atcaattgcc agtccagtaa gagtgtttat aacaacaatt ggttatcctg gtatcaacag 120
aaaccagggc agcctcccaa gttcctgatc taccaggcat ccaatttggc atctggggtc 180
ccgtcgcggt tcaaaggcag tggatctggg acacagttca ctctcaccat cagcgacctc 240
gagtgtgacg atgccgccac ttattactgt gcaggcggtt atagtggtaa tattgttggt 300
ttcggcggag ggaccgaggt ggtggtcaaa cgt 333

<210> SEQ ID NO 353
<211> LENGTH: 69
<212> TYPE: DNA
<213> ORGANISM: Oryctolagus cuniculus

<400> SEQUENCE: 353
gcgcaagtgc tgacccagac tccatcgtcc gtgtctgcag ctgtgggagg cacagtcacc 60
atcaattgc 69

<210> SEQ ID NO 354
<211> LENGTH: 39
<212> TYPE: DNA
<213> ORGANISM: Oryctolagus cuniculus

<400> SEQUENCE: 354
cagtccagta agagtgttta taacaacaat tggttatcc 39

<210> SEQ ID NO 355
<211> LENGTH: 45
<212> TYPE: DNA
<213> ORGANISM: Oryctolagus cuniculus

<400> SEQUENCE: 355
tggtatcaac agaaaccagg gcagcctccc aagttcctga tctac 45

<210> SEQ ID NO 356
<211> LENGTH: 21
<212> TYPE: DNA
<213> ORGANISM: Oryctolagus cuniculus

<400> SEQUENCE: 356
caggcatcca atttggcatc t 21

<210> SEQ ID NO 357
<211> LENGTH: 96
<212> TYPE: DNA
<213> ORGANISM: Oryctolagus cuniculus

<400> SEQUENCE: 357
ggggtcccgt cgcggttcaa aggcagtgga tctgggacac agttcactct caccatcagc 60
gacctcgagt gtgacgatgc cgccacttat tactgt 96

<210> SEQ ID NO 358
<211> LENGTH: 30
<212> TYPE: DNA
<213> ORGANISM: Oryctolagus cuniculus

<400> SEQUENCE: 358
gcaggcggtt atagtggtaa tattgttggt 30

<210> SEQ ID NO 359
<211> LENGTH: 33
<212> TYPE: DNA
<213> ORGANISM: Artificial
<220> FEATURE:
<223> OTHER INFORMATION: Humanized Antibody Sequence

<400> SEQUENCE: 359
ttcggcggag ggaccgaggt ggtggtcaaa cgt 33

<210> SEQ ID NO 360
<211> LENGTH: 318
<212> TYPE: DNA
<213> ORGANISM: Artificial
<220> FEATURE:
<223> OTHER INFORMATION: Humanized Antibody Sequence

<400> SEQUENCE: 360
acggtagcgg ccccatctgt cttcatcttc ccgccatctg atgagcagtt gaaatctgga 60
actgcctctg ttgtgtgcct gctgaataac ttctatccca gagaggccaa agtacagtgg 120
aaggtggata acgccctcca atcgggtaac tcccaggaga gtgtcacaga gcaggacagc 180
aaggacagca cctacagcct cagcagcacc ctgacgctga gcaaagcaga ctacgagaaa 240
cacaaagtct acgcctgcga agtcacccat cagggcctga gctcgcccgt cacaaagagc 300
ttcaacaggg gagagtgt 318

<210> SEQ ID NO 361
<211> LENGTH: 443
<212> TYPE: PRT
<213> ORGANISM: Artificial
<220> FEATURE:
<223> OTHER INFORMATION: Humanized Antibody Sequence

<400> SEQUENCE: 361

Gln Ser Val Glu Ala Ser Gly Gly Arg Leu Val Thr Pro Gly Thr Pro
1 5 10 15

Leu Thr Leu Thr Cys Thr Val Ser Gly Phe Ser Leu Ser Ser Ala Thr
20 25 30

Met Asn Trp Val Arg Gln Ala Pro Gly Lys Gly Leu Glu Trp Ile Gly
35 40 45

Leu Ile Gly Gly Asn Asp Glu Arg Tyr Tyr Ala Ser Trp Ala Lys Gly
50 55 60

Arg Phe Thr Ile Ser Lys Thr Ser Ser Thr Thr Val Asp Leu Lys Met
65 70 75 80

Thr Ser Pro Thr Thr Glu Asp Thr Ala Thr Tyr Phe Cys Ala Arg Gly
85 90 95

Gly Gly Glu Phe Phe Ile Trp Gly Pro Gly Thr Leu Val Thr Val Ser
100 105 110

Ser Ala Ser Thr Lys Gly Pro Ser Val Phe Pro Leu Ala Pro Ser Ser
115 120 125

Lys Ser Thr Ser Gly Gly Thr Ala Ala Leu Gly Cys Leu Val Lys Asp
130 135 140

Tyr Phe Pro Glu Pro Val Thr Val Ser Trp Asn Ser Gly Ala Leu Thr
145 150 155 160

Ser Gly Val His Thr Phe Pro Ala Val Leu Gln Ser Ser Gly Leu Tyr
165 170 175

Ser Leu Ser Ser Val Val Thr Val Pro Ser Ser Ser Leu Gly Thr Gln
180 185 190

Thr Tyr Ile Cys Asn Val Asn His Lys Pro Ser Asn Thr Lys Val Asp
195 200 205

Lys Lys Val Glu Pro Lys Ser Cys Asp Lys Thr His Thr Cys Pro Pro
210 215 220

Cys Pro Ala Pro Glu Leu Leu Gly Gly Pro Ser Val Phe Leu Phe Pro
225 230 235 240

Pro Lys Pro Lys Asp Thr Leu Met Ile Ser Arg Thr Pro Glu Val Thr
245 250 255

Cys Val Val Val Asp Val Ser His Glu Asp Pro Glu Val Lys Phe Asn
260 265 270

Trp Tyr Val Asp Gly Val Glu Val His Asn Ala Lys Thr Lys Pro Arg
275 280 285

Glu Glu Gln Tyr Ala Ser Thr Tyr Arg Val Val Ser Val Leu Thr Val
290 295 300

Leu His Gln Asp Trp Leu Asn Gly Lys Glu Tyr Lys Cys Lys Val Ser
305 310 315 320

Asn Lys Ala Leu Pro Ala Pro Ile Glu Lys Thr Ile Ser Lys Ala Lys
325 330 335

Gly Gln Pro Arg Glu Pro Gln Val Tyr Thr Leu Pro Pro Ser Arg Glu
340 345 350

Glu Met Thr Lys Asn Gln Val Ser Leu Thr Cys Leu Val Lys Gly Phe
355 360 365

Tyr Pro Ser Asp Ile Ala Val Glu Trp Glu Ser Asn Gly Gln Pro Glu
370 375 380

Asn Asn Tyr Lys Thr Thr Pro Pro Val Leu Asp Ser Asp Gly Ser Phe
385 390 395 400

Phe Leu Tyr Ser Lys Leu Thr Val Asp Lys Ser Arg Trp Gln Gln Gly
405 410 415

Asn Val Phe Ser Cys Ser Val Met His Glu Ala Leu His Asn His Tyr
420 425 430

Thr Gln Lys Ser Leu Ser Leu Ser Pro Gly Lys
435 440

<210> SEQ ID NO 362
<211> LENGTH: 113
<212> TYPE: PRT
<213> ORGANISM: Artificial
<220> FEATURE:
<223> OTHER INFORMATION: Humanized Antibody Sequence

<400> SEQUENCE: 362

Gln Ser Val Glu Ala Ser Gly Gly Arg Leu Val Thr Pro Gly Thr Pro
1 5 10 15

Leu Thr Leu Thr Cys Thr Val Ser Gly Phe Ser Leu Ser Ser Ala Thr
20 25 30

Met Asn Trp Val Arg Gln Ala Pro Gly Lys Gly Leu Glu Trp Ile Gly
35 40 45

Leu Ile Gly Gly Asn Asp Glu Arg Tyr Tyr Ala Ser Trp Ala Lys Gly
50 55 60

Arg Phe Thr Ile Ser Lys Thr Ser Ser Thr Thr Val Asp Leu Lys Met
65 70 75 80

Thr Ser Pro Thr Thr Glu Asp Thr Ala Thr Tyr Phe Cys Ala Arg Gly
85 90 95

Gly Gly Glu Phe Phe Ile Trp Gly Pro Gly Thr Leu Val Thr Val Ser
100 105 110

Ser

<210> SEQ ID NO 363
<211> LENGTH: 29
<212> TYPE: PRT
<213> ORGANISM: Oryctolagus cuniculus

<400> SEQUENCE: 363

Gln Ser Val Glu Ala Ser Gly Gly Arg Leu Val Thr Pro Gly Thr Pro
1 5 10 15

Leu Thr Leu Thr Cys Thr Val Ser Gly Phe Ser Leu Ser
20 25

<210> SEQ ID NO 364
<211> LENGTH: 5
<212> TYPE: PRT
<213> ORGANISM: Oryctolagus cuniculus

<400> SEQUENCE: 364

Ser Ala Thr Met Asn
1 5

<210> SEQ ID NO 365
<211> LENGTH: 14
<212> TYPE: PRT
<213> ORGANISM: Oryctolagus cuniculus

<400> SEQUENCE: 365

Trp Val Arg Gln Ala Pro Gly Lys Gly Leu Glu Trp Ile Gly
1 5 10

<210> SEQ ID NO 366
<211> LENGTH: 16
<212> TYPE: PRT
<213> ORGANISM: Oryctolagus cuniculus

<400> SEQUENCE: 366

Leu Ile Gly Gly Asn Asp Glu Arg Tyr Tyr Ala Ser Trp Ala Lys Gly
1 5 10 15

<210> SEQ ID NO 367
<211> LENGTH: 31
<212> TYPE: PRT
<213> ORGANISM: Oryctolagus cuniculus

<400> SEQUENCE: 367

Arg Phe Thr Ile Ser Lys Thr Ser Ser Thr Thr Val Asp Leu Lys Met
1 5 10 15

Thr Ser Pro Thr Thr Glu Asp Thr Ala Thr Tyr Phe Cys Ala Arg
20 25 30

<210> SEQ ID NO 368
<211> LENGTH: 7
<212> TYPE: PRT
<213> ORGANISM: Oryctolagus cuniculus

<400> SEQUENCE: 368

Gly Gly Gly Glu Phe Phe Ile
1 5

<210> SEQ ID NO 369
<211> LENGTH: 11
<212> TYPE: PRT
<213> ORGANISM: Artificial
<220> FEATURE:
<223> OTHER INFORMATION: Humanized Antibody Sequence

<400> SEQUENCE: 369

Trp Gly Pro Gly Thr Leu Val Thr Val Ser Ser
1 5 10

<210> SEQ ID NO 370
<211> LENGTH: 330
<212> TYPE: PRT
<213> ORGANISM: Artificial
<220> FEATURE:
<223> OTHER INFORMATION: Humanized Antibody Sequence

<400> SEQUENCE: 370

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

```
Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 371
<211> LENGTH: 1329
<212> TYPE: DNA
<213> ORGANISM: Artificial
<220> FEATURE:
<223> OTHER INFORMATION: Humanized Antibody Sequence

<400> SEQUENCE: 371

```
cagtcggtgg aggcgtccgg gggtcgcctg gtcacgcctg ggacacccct gacactcacc     60

tgcaccgtct ctggattctc cctcagtagc gctacaatga actgggtccg ccaggctcca    120

gggaaggggc tggaatggat cgggcttatt ggcggtaatg acgaaagata ctacgcgtcc    180

tgggcgaaag gccgattcac catctccaaa acctcgtcga ccacggtgga tctgaaaatg    240

accagtccga caaccgagga cacggccacc tatttctgtg ccagaggggg gggggaattt    300

ttcatctggg gcccgggcac cctggtcacc gtctcgagcg cctccaccaa gggcccatcg    360

gtcttccccc tggcaccctc ctccaagagc acctctgggg gcacagcggc cctgggctgc    420

ctggtcaagg actacttccc cgaaccggtg acggtgtcgt ggaactcagg cgccctgacc    480
```

```
agcggcgtgc acaccttccc ggctgtccta cagtcctcag gactctactc cctcagcagc    540

gtggtgaccg tgccctccag cagcttgggc acccagacct acatctgcaa cgtgaatcac    600

aagcccagca acaccaaggt ggacaagaaa gttgagccca aatcttgtga caaaactcac    660

acatgcccac cgtgcccagc acctgaactc ctggggggac cgtcagtctt cctcttcccc    720

ccaaaaccca aggacaccct catgatctcc cggacccctg aggtcacatg cgtggtggtg    780

gacgtgagcc acgaagaccc tgaggtcaag ttcaactggt acgtggacgg cgtggaggtg    840

cataatgcca agacaaagcc gcgggaggag cagtacgcca gcacgtaccg tgtggtcagc    900

gtcctcaccg tcctgcacca ggactggctg aatggcaagg agtacaagtg caaggtctcc    960

aacaaagccc tcccagcccc catcgagaaa accatctcca aagccaaagg gcagccccga   1020

gaaccacagg tgtacaccct gcccccatcc cgggaggaga tgaccaagaa ccaggtcagc   1080

ctgacctgcc tggtcaaagg cttctatccc agcgacatcg ccgtggagtg ggagagcaat   1140

gggcagccgg agaacaacta caagaccacg cctcccgtgc tggactccga cggctccttc   1200

ttcctctaca gcaagctcac cgtggacaag agcaggtggc agcaggggaa cgtcttctca   1260

tgctccgtga tgcatgaggc tctgcacaac cactacacgc agaagagcct ctccctgtct   1320

ccgggtaaa                                                           1329


<210> SEQ ID NO 372
<211> LENGTH: 339
<212> TYPE: DNA
<213> ORGANISM: Artificial
<220> FEATURE:
<223> OTHER INFORMATION: Humanized Antibody Sequence

<400> SEQUENCE: 372

cagtcggtgg aggcgtccgg gggtcgcctg gtcacgcctg ggacacccct gacactcacc     60

tgcaccgtct ctggattctc cctcagtagc gctacaatga actgggtccg ccaggctcca    120

gggaaggggc tggaatggat cgggcttatt ggcggtaatg acgaaagata ctacgcgtcc    180

tgggcgaaag gccgattcac catctccaaa acctcgtcga ccacggtgga tctgaaaatg    240

accagtccga caaccgagga cacggccacc tatttctgtg ccagaggggg gggggaattt    300

ttcatctggg gcccgggcac cctggtcacc gtctcgagc                           339


<210> SEQ ID NO 373
<211> LENGTH: 87
<212> TYPE: DNA
<213> ORGANISM: Oryctolagus cuniculus

<400> SEQUENCE: 373

cagtcggtgg aggcgtccgg gggtcgcctg gtcacgcctg ggacacccct gacactcacc     60

tgcaccgtct ctggattctc cctcagt                                         87


<210> SEQ ID NO 374
<211> LENGTH: 15
<212> TYPE: DNA
<213> ORGANISM: Oryctolagus cuniculus

<400> SEQUENCE: 374

agcgctacaa tgaac                                                      15


<210> SEQ ID NO 375
<211> LENGTH: 42
<212> TYPE: DNA
```

<213> ORGANISM: Oryctolagus cuniculus

<400> SEQUENCE: 375
tgggtccgcc aggctccagg gaaggggctg gaatggatcg gg 42

<210> SEQ ID NO 376
<211> LENGTH: 48
<212> TYPE: DNA
<213> ORGANISM: Oryctolagus cuniculus

<400> SEQUENCE: 376
cttattggcg gtaatgacga aagatactac gcgtcctggg cgaaaggc 48

<210> SEQ ID NO 377
<211> LENGTH: 93
<212> TYPE: DNA
<213> ORGANISM: Oryctolagus cuniculus

<400> SEQUENCE: 377
cgattcacca tctccaaaac ctcgtcgacc acggtggatc tgaaaatgac cagtccgaca 60
accgaggaca cggccaccta tttctgtgcc aga 93

<210> SEQ ID NO 378
<211> LENGTH: 21
<212> TYPE: DNA
<213> ORGANISM: Oryctolagus cuniculus

<400> SEQUENCE: 378
gggggggggg aatttttcat c 21

<210> SEQ ID NO 379
<211> LENGTH: 33
<212> TYPE: DNA
<213> ORGANISM: Artificial
<220> FEATURE:
<223> OTHER INFORMATION: Humanized Antibody Sequence

<400> SEQUENCE: 379
tggggcccgg gcaccctggt caccgtctcg agc 33

<210> SEQ ID NO 380
<211> LENGTH: 990
<212> TYPE: DNA
<213> ORGANISM: Artificial
<220> FEATURE:
<223> OTHER INFORMATION: Humanized Antibody Sequence

<400> SEQUENCE: 380
gcctccacca agggcccatc ggtcttcccc ctggcaccct cctccaagag cacctctggg 60
ggcacagcgg ccctgggctg cctggtcaag gactacttcc ccgaaccggt gacggtgtcg 120
tggaactcag gcgccctgac cagcggcgtg cacaccttcc cggctgtcct acagtcctca 180
ggactctact ccctcagcag cgtggtgacc gtgccctcca gcagcttggg cacccagacc 240
tacatctgca acgtgaatca caagcccagc aacaccaagg tggacaagaa agttgagccc 300
aaatcttgtg acaaaactca cacatgccca ccgtgcccag cacctgaact cctgggggga 360
ccgtcagtct tcctcttccc cccaaaaccc aaggacaccc tcatgatctc ccggacccct 420
gaggtcacat gcgtggtggt ggacgtgagc cacgaagacc ctgaggtcaa gttcaactgg 480
tacgtggacg gcgtggaggt gcataatgcc aagacaaagc cgcgggagga gcagtacgcc 540
agcacgtacc gtgtggtcag cgtcctcacc gtcctgcacc aggactggct gaatggcaag 600

```
gagtacaagt gcaaggtctc caacaaagcc ctcccagccc ccatcgagaa aaccatctcc    660

aaagccaaag ggcagccccg agaaccacag gtgtacaccc tgcccccatc ccgggaggag    720

atgaccaaga accaggtcag cctgacctgc ctggtcaaag gcttctatcc cagcgacatc    780

gccgtggagt gggagagcaa tgggcagccg gagaacaact acaagaccac gcctcccgtg    840

ctggactccg acggctcctt cttcctctac agcaagctca ccgtggacaa gagcaggtgg    900

cagcagggga acgtcttctc atgctccgtg atgcatgagg ctctgcacaa ccactacacg    960

cagaagagcc tctccctgtc tccgggtaaa                                      990
```

<210> SEQ ID NO 381
<211> LENGTH: 217
<212> TYPE: PRT
<213> ORGANISM: Artificial
<220> FEATURE:
<223> OTHER INFORMATION: Humanized Antibody Sequence

<400> SEQUENCE: 381

```
Ala Gln Val Leu Thr Gln Thr Pro Ser Ser Val Ser Ala Ala Val Gly
1               5                   10                  15

Gly Thr Val Thr Ile Asn Cys Gln Ser Ser Glu Ser Val Tyr Thr Asn
            20                  25                  30

Asp Arg Leu Ser Trp Tyr Gln Gln Lys Pro Gly Gln Pro Pro Lys Leu
        35                  40                  45

Leu Ile Tyr Glu Ala Ser Lys Leu Ala Ser Gly Val Pro Pro Arg Phe
    50                  55                  60

Ser Gly Ser Gly Ser Gly Thr Gln Phe Thr Leu Thr Ile Ser Asp Leu
65                  70                  75                  80

Glu Cys Asp Asp Ala Ala Thr Tyr Tyr Cys Ala Gly Ala Tyr Ser Thr
                85                  90                  95

Ser Ile His Gly Phe Gly Gly Gly Thr Glu Val Val Val Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215
```

<210> SEQ ID NO 382
<211> LENGTH: 111
<212> TYPE: PRT
<213> ORGANISM: Artificial
<220> FEATURE:
<223> OTHER INFORMATION: Humanized Antibody Sequence

<400> SEQUENCE: 382

```
Ala Gln Val Leu Thr Gln Thr Pro Ser Ser Val Ser Ala Ala Val Gly
1               5                   10                  15
```

```
Gly Thr Val Thr Ile Asn Cys Gln Ser Ser Glu Ser Val Tyr Thr Asn
            20                  25                  30

Asp Arg Leu Ser Trp Tyr Gln Gln Lys Pro Gly Gln Pro Pro Lys Leu
        35                  40                  45

Leu Ile Tyr Glu Ala Ser Lys Leu Ala Ser Gly Val Pro Pro Arg Phe
    50                  55                  60

Ser Gly Ser Gly Ser Gly Thr Gln Phe Thr Leu Thr Ile Ser Asp Leu
65                  70                  75                  80

Glu Cys Asp Asp Ala Ala Thr Tyr Tyr Cys Ala Gly Ala Tyr Ser Thr
                85                  90                  95

Ser Ile His Gly Phe Gly Gly Gly Thr Glu Val Val Val Lys Arg
            100                 105                 110


<210> SEQ ID NO 383
<211> LENGTH: 23
<212> TYPE: PRT
<213> ORGANISM: Oryctolagus cuniculus

<400> SEQUENCE: 383

Ala Gln Val Leu Thr Gln Thr Pro Ser Ser Val Ser Ala Ala Val Gly
1               5                   10                  15

Gly Thr Val Thr Ile Asn Cys
            20


<210> SEQ ID NO 384
<211> LENGTH: 13
<212> TYPE: PRT
<213> ORGANISM: Oryctolagus cuniculus

<400> SEQUENCE: 384

Gln Ser Ser Glu Ser Val Tyr Thr Asn Asp Arg Leu Ser
1               5                   10


<210> SEQ ID NO 385
<211> LENGTH: 15
<212> TYPE: PRT
<213> ORGANISM: Oryctolagus cuniculus

<400> SEQUENCE: 385

Trp Tyr Gln Gln Lys Pro Gly Gln Pro Pro Lys Leu Leu Ile Tyr
1               5                   10                  15


<210> SEQ ID NO 386
<211> LENGTH: 7
<212> TYPE: PRT
<213> ORGANISM: Oryctolagus cuniculus

<400> SEQUENCE: 386

Glu Ala Ser Lys Leu Ala Ser
1               5


<210> SEQ ID NO 387
<211> LENGTH: 32
<212> TYPE: PRT
<213> ORGANISM: Oryctolagus cuniculus

<400> SEQUENCE: 387

Gly Val Pro Pro Arg Phe Ser Gly Ser Gly Ser Gly Thr Gln Phe Thr
1               5                   10                  15

Leu Thr Ile Ser Asp Leu Glu Cys Asp Asp Ala Ala Thr Tyr Tyr Cys
            20                  25                  30
```

<210> SEQ ID NO 388
<211> LENGTH: 10
<212> TYPE: PRT
<213> ORGANISM: Oryctolagus cuniculus

<400> SEQUENCE: 388

Ala Gly Ala Tyr Ser Thr Ser Ile His Gly
1 5 10

<210> SEQ ID NO 389
<211> LENGTH: 11
<212> TYPE: PRT
<213> ORGANISM: Artificial
<220> FEATURE:
<223> OTHER INFORMATION: Humanized Antibody Sequence

<400> SEQUENCE: 389

Phe Gly Gly Gly Thr Glu Val Val Val Lys Arg
1 5 10

<210> SEQ ID NO 390
<211> LENGTH: 106
<212> TYPE: PRT
<213> ORGANISM: Artificial
<220> FEATURE:
<223> OTHER INFORMATION: Humanized Antibody Sequence

<400> SEQUENCE: 390

Thr Val Ala Ala Pro Ser Val Phe Ile Phe Pro Pro Ser Asp Glu Gln
1 5 10 15

Leu Lys Ser Gly Thr Ala Ser Val Val Cys Leu Leu Asn Asn Phe Tyr
20 25 30

Pro Arg Glu Ala Lys Val Gln Trp Lys Val Asp Asn Ala Leu Gln Ser
35 40 45

Gly Asn Ser Gln Glu Ser Val Thr Glu Gln Asp Ser Lys Asp Ser Thr
50 55 60

Tyr Ser Leu Ser Ser Thr Leu Thr Leu Ser Lys Ala Asp Tyr Glu Lys
65 70 75 80

His Lys Val Tyr Ala Cys Glu Val Thr His Gln Gly Leu Ser Ser Pro
85 90 95

Val Thr Lys Ser Phe Asn Arg Gly Glu Cys
100 105

<210> SEQ ID NO 391
<211> LENGTH: 651
<212> TYPE: DNA
<213> ORGANISM: Artificial
<220> FEATURE:
<223> OTHER INFORMATION: Humanized Antibody Sequence

<400> SEQUENCE: 391
gcgcaagtgc tgacccagac tccatcgtcc gtgtctgcag ctgtgggagg cacagtcacc 60
atcaattgcc agtccagtga gagtgtttat actaacgacc gcttatcctg gtatcagcag 120
aaaccagggc agcctcccaa gctcctgatc tacgaagcat ccaagctggc atctggggtc 180
ccaccgcggt tcagcggcag tggatctggg acacagttca ctctcaccat cagcgacctg 240
gagtgtgacg atgccgccac ttattactgt gcaggcgctt atagtactag tatccatggt 300
ttcggcggag ggaccgaggt ggtggtcaaa cgtacggtag cggccccatc tgtcttcatc 360
ttcccgccat ctgatgagca gttgaaatct ggaactgcct ctgttgtgtg cctgctgaat 420
aacttctatc ccagagaggc caaagtacag tggaaggtgg ataacgccct ccaatcgggt 480
aactcccagg agagtgtcac agagcaggac agcaaggaca gcacctacag cctcagcagc 540
accctgacgc tgagcaaagc agactacgag aaacacaaag tctacgcctg cgaagtcacc 600
catcagggcc tgagctcgcc cgtcacaaag agcttcaaca ggggagagtg t 651

<210> SEQ ID NO 392
<211> LENGTH: 333
<212> TYPE: DNA
<213> ORGANISM: Artificial
<220> FEATURE:
<223> OTHER INFORMATION: Humanized Antibody Sequence

<400> SEQUENCE: 392
gcgcaagtgc tgacccagac tccatcgtcc gtgtctgcag ctgtgggagg cacagtcacc 60
atcaattgcc agtccagtga gagtgtttat actaacgacc gcttatcctg gtatcagcag 120
aaaccagggc agcctcccaa gctcctgatc tacgaagcat ccaagctggc atctggggtc 180
ccaccgcggt tcagcggcag tggatctggg acacagttca ctctcaccat cagcgacctg 240
gagtgtgacg atgccgccac ttattactgt gcaggcgctt atagtactag tatccatggt 300
ttcggcggag ggaccgaggt ggtggtcaaa cgt 333

<210> SEQ ID NO 393
<211> LENGTH: 69
<212> TYPE: DNA
<213> ORGANISM: Oryctolagus cuniculus

<400> SEQUENCE: 393
gcgcaagtgc tgacccagac tccatcgtcc gtgtctgcag ctgtgggagg cacagtcacc 60
atcaattgc 69

<210> SEQ ID NO 394
<211> LENGTH: 39
<212> TYPE: DNA
<213> ORGANISM: Oryctolagus cuniculus

<400> SEQUENCE: 394
cagtccagtg agagtgttta tactaacgac cgcttatcc 39

<210> SEQ ID NO 395
<211> LENGTH: 45
<212> TYPE: DNA
<213> ORGANISM: Oryctolagus cuniculus

<400> SEQUENCE: 395
tggtatcagc agaaaccagg gcagcctccc aagctcctga tctac 45

<210> SEQ ID NO 396
<211> LENGTH: 21
<212> TYPE: DNA
<213> ORGANISM: Oryctolagus cuniculus

<400> SEQUENCE: 396
gaagcatcca agctggcatc t 21

<210> SEQ ID NO 397
<211> LENGTH: 96
<212> TYPE: DNA
<213> ORGANISM: Oryctolagus cuniculus

<400> SEQUENCE: 397
ggggtcccac cgcggttcag cggcagtgga tctgggacac agttcactct caccatcagc 60
gacctggagt gtgacgatgc cgccacttat tactgt 96

<210> SEQ ID NO 398
<211> LENGTH: 30
<212> TYPE: DNA
<213> ORGANISM: Oryctolagus cuniculus

<400> SEQUENCE: 398
gcaggcgctt atagtactag tatccatggt 30

<210> SEQ ID NO 399
<211> LENGTH: 33
<212> TYPE: DNA
<213> ORGANISM: Artificial
<220> FEATURE:
<223> OTHER INFORMATION: Humanized Antibody Sequence

<400> SEQUENCE: 399
ttcggcggag ggaccgaggt ggtggtcaaa cgt 33

<210> SEQ ID NO 400
<211> LENGTH: 318
<212> TYPE: DNA
<213> ORGANISM: Artificial
<220> FEATURE:
<223> OTHER INFORMATION: Humanized Antibody Sequence

<400> SEQUENCE: 400
acggtagcgg ccccatctgt cttcatcttc ccgccatctg atgagcagtt gaaatctgga 60
actgcctctg ttgtgtgcct gctgaataac ttctatccca gagaggccaa agtacagtgg 120
aaggtggata acgccctcca atcgggtaac tcccaggaga gtgtcacaga gcaggacagc 180
aaggacagca cctacagcct cagcagcacc ctgacgctga gcaaagcaga ctacgagaaa 240
cacaaagtct acgcctgcga agtcacccat cagggcctga gctcgcccgt cacaaagagc 300
ttcaacaggg gagagtgt 318

<210> SEQ ID NO 401

<400> SEQUENCE: 401

000

<210> SEQ ID NO 402

<400> SEQUENCE: 402

000

<210> SEQ ID NO 403

<400> SEQUENCE: 403

000

<210> SEQ ID NO 404

<400> SEQUENCE: 404

000

<210> SEQ ID NO 405

<400> SEQUENCE: 405

000

<210> SEQ ID NO 406

<400> SEQUENCE: 406

000

<210> SEQ ID NO 407

<400> SEQUENCE: 407

000

<210> SEQ ID NO 408

<400> SEQUENCE: 408

000

<210> SEQ ID NO 409

<400> SEQUENCE: 409

000

<210> SEQ ID NO 410

<400> SEQUENCE: 410

000

<210> SEQ ID NO 411

<400> SEQUENCE: 411

000

<210> SEQ ID NO 412

<400> SEQUENCE: 412

000

<210> SEQ ID NO 413

<400> SEQUENCE: 413

000

<210> SEQ ID NO 414

<400> SEQUENCE: 414

000

<210> SEQ ID NO 415

<400> SEQUENCE: 415

000

<210> SEQ ID NO 416

<400> SEQUENCE: 416

000

<210> SEQ ID NO 417

<400> SEQUENCE: 417

000

<210> SEQ ID NO 418

<400> SEQUENCE: 418

000

<210> SEQ ID NO 419

<400> SEQUENCE: 419

000

<210> SEQ ID NO 420

<400> SEQUENCE: 420

000

<210> SEQ ID NO 421

<400> SEQUENCE: 421

000

<210> SEQ ID NO 422

<400> SEQUENCE: 422

000

<210> SEQ ID NO 423

<400> SEQUENCE: 423

000

<210> SEQ ID NO 424

<400> SEQUENCE: 424

000

<210> SEQ ID NO 425

<400> SEQUENCE: 425

000

<210> SEQ ID NO 426

<400> SEQUENCE: 426

000

<210> SEQ ID NO 427

<400> SEQUENCE: 427

000

<210> SEQ ID NO 428

<400> SEQUENCE: 428

000

<210> SEQ ID NO 429

<400> SEQUENCE: 429

000

<210> SEQ ID NO 430

<400> SEQUENCE: 430

000

<210> SEQ ID NO 431

<400> SEQUENCE: 431

000

<210> SEQ ID NO 432

<400> SEQUENCE: 432

000

<210> SEQ ID NO 433

<400> SEQUENCE: 433

000

<210> SEQ ID NO 434

<400> SEQUENCE: 434

000

<210> SEQ ID NO 435

<400> SEQUENCE: 435

000

<210> SEQ ID NO 436

<400> SEQUENCE: 436

000

<210> SEQ ID NO 437

<400> SEQUENCE: 437

000

<210> SEQ ID NO 438

<400> SEQUENCE: 438

000

<210> SEQ ID NO 439

<400> SEQUENCE: 439

000

<210> SEQ ID NO 440

<400> SEQUENCE: 440

000

<210> SEQ ID NO 441

<400> SEQUENCE: 441

000

<210> SEQ ID NO 442

<400> SEQUENCE: 442

000

<210> SEQ ID NO 443

<400> SEQUENCE: 443

000

<210> SEQ ID NO 444

<400> SEQUENCE: 444

000

<210> SEQ ID NO 445

<400> SEQUENCE: 445

000

<210> SEQ ID NO 446

<400> SEQUENCE: 446

000

<210> SEQ ID NO 447

<400> SEQUENCE: 447

000

<210> SEQ ID NO 448

<400> SEQUENCE: 448

000

<210> SEQ ID NO 449

<400> SEQUENCE: 449

000

<210> SEQ ID NO 450

<400> SEQUENCE: 450

000

<210> SEQ ID NO 451

<400> SEQUENCE: 451

000

<210> SEQ ID NO 452

<400> SEQUENCE: 452

000

<210> SEQ ID NO 453

<400> SEQUENCE: 453

000

<210> SEQ ID NO 454

<400> SEQUENCE: 454

000

<210> SEQ ID NO 455

<400> SEQUENCE: 455

000

<210> SEQ ID NO 456

<400> SEQUENCE: 456

000

<210> SEQ ID NO 457

<400> SEQUENCE: 457

000

<210> SEQ ID NO 458

<400> SEQUENCE: 458

000

<210> SEQ ID NO 459

<400> SEQUENCE: 459

000

<210> SEQ ID NO 460

<400> SEQUENCE: 460

000

<210> SEQ ID NO 461

<400> SEQUENCE: 461

000

<210> SEQ ID NO 462

<400> SEQUENCE: 462

000

<210> SEQ ID NO 463

<400> SEQUENCE: 463

000

<210> SEQ ID NO 464

<400> SEQUENCE: 464

000

<210> SEQ ID NO 465

<400> SEQUENCE: 465

000

<210> SEQ ID NO 466

<400> SEQUENCE: 466

000

<210> SEQ ID NO 467

<400> SEQUENCE: 467

000

<210> SEQ ID NO 468

<400> SEQUENCE: 468

000

<210> SEQ ID NO 469

<400> SEQUENCE: 469

000

<210> SEQ ID NO 470

<400> SEQUENCE: 470

000

<210> SEQ ID NO 471

<400> SEQUENCE: 471

000

<210> SEQ ID NO 472

<400> SEQUENCE: 472

000

<210> SEQ ID NO 473

<400> SEQUENCE: 473

000

<210> SEQ ID NO 474

<400> SEQUENCE: 474

000

<210> SEQ ID NO 475

<400> SEQUENCE: 475

000

<210> SEQ ID NO 476

<400> SEQUENCE: 476

000

<210> SEQ ID NO 477

<400> SEQUENCE: 477

000

<210> SEQ ID NO 478

<400> SEQUENCE: 478

000

<210> SEQ ID NO 479

<400> SEQUENCE: 479

000

<210> SEQ ID NO 480

<400> SEQUENCE: 480

000

<210> SEQ ID NO 481
<211> LENGTH: 445
<212> TYPE: PRT
<213> ORGANISM: Artificial
<220> FEATURE:
<223> OTHER INFORMATION: Humanized Antibody Sequence

<400> SEQUENCE: 481

```
Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Tyr Ala
            20                  25                  30

Met Ile Trp Val Arg Gln Ala Pro Gly Lys Gly Leu Glu Trp Ile Gly
        35                  40                  45

Ile Ile Tyr Asp Asn Gly Asp Thr Tyr Tyr Ala Ser Trp Ala Lys Gly
    50                  55                  60
```

-continued

```
Arg Phe Thr Ile Ser Lys Thr Ser Thr Thr Val Tyr Leu Lys Ile Ala
65                  70                  75                  80

Ser Pro Thr Thr Glu Asp Thr Ala Thr Tyr Phe Cys Ala Arg Glu Pro
                85                  90                  95

Gly Ser Thr Thr Gln Asn Asp Leu Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Ala Arg Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Ala Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445


<210> SEQ ID NO 482
<211> LENGTH: 115
<212> TYPE: PRT
<213> ORGANISM: Artificial
<220> FEATURE:
<223> OTHER INFORMATION: Humanized Antibody Sequence
```

<400> SEQUENCE: 482

Gln Ser Val Glu Glu Ser Gly Gly Arg Leu Val Thr Pro Gly Thr Pro
1 5 10 15

Leu Thr Leu Thr Cys Thr Val Ser Gly Phe Ser Leu Ser Ser Tyr Ala
20 25 30

Met Ile Trp Val Arg Gln Ala Pro Gly Lys Gly Leu Glu Trp Ile Gly
35 40 45

Ile Ile Tyr Asp Asn Gly Asp Thr Tyr Tyr Ala Ser Trp Ala Lys Gly
50 55 60

Arg Phe Thr Ile Ser Lys Thr Ser Thr Thr Val Tyr Leu Lys Ile Ala
65 70 75 80

Ser Pro Thr Thr Glu Asp Thr Ala Thr Tyr Phe Cys Ala Arg Glu Pro
85 90 95

Gly Ser Thr Thr Gln Asn Asp Leu Trp Gly Gln Gly Thr Leu Val Thr
100 105 110

Val Ser Ser
115

<210> SEQ ID NO 483
<211> LENGTH: 29
<212> TYPE: PRT
<213> ORGANISM: Oryctolagus cuniculus

<400> SEQUENCE: 483

Gln Ser Val Glu Glu Ser Gly Gly Arg Leu Val Thr Pro Gly Thr Pro
1 5 10 15

Leu Thr Leu Thr Cys Thr Val Ser Gly Phe Ser Leu Ser
20 25

<210> SEQ ID NO 484
<211> LENGTH: 5
<212> TYPE: PRT
<213> ORGANISM: Oryctolagus cuniculus

<400> SEQUENCE: 484

Ser Tyr Ala Met Ile
1 5

<210> SEQ ID NO 485
<211> LENGTH: 14
<212> TYPE: PRT
<213> ORGANISM: Oryctolagus cuniculus

<400> SEQUENCE: 485

Trp Val Arg Gln Ala Pro Gly Lys Gly Leu Glu Trp Ile Gly
1 5 10

<210> SEQ ID NO 486
<211> LENGTH: 16
<212> TYPE: PRT
<213> ORGANISM: Oryctolagus cuniculus

<400> SEQUENCE: 486

Ile Ile Tyr Asp Asn Gly Asp Thr Tyr Tyr Ala Ser Trp Ala Lys Gly
1 5 10 15

<210> SEQ ID NO 487
<211> LENGTH: 30
<212> TYPE: PRT
<213> ORGANISM: Oryctolagus cuniculus

<400> SEQUENCE: 487

Arg Phe Thr Ile Ser Lys Thr Ser Thr Thr Val Tyr Leu Lys Ile Ala
1 5 10 15

Ser Pro Thr Thr Glu Asp Thr Ala Thr Tyr Phe Cys Ala Arg
20 25 30

<210> SEQ ID NO 488
<211> LENGTH: 10
<212> TYPE: PRT
<213> ORGANISM: Oryctolagus cuniculus

<400> SEQUENCE: 488

Glu Pro Gly Ser Thr Thr Gln Asn Asp Leu
1 5 10

<210> SEQ ID NO 489
<211> LENGTH: 11
<212> TYPE: PRT
<213> ORGANISM: Artificial
<220> FEATURE:
<223> OTHER INFORMATION: Humanized Antibody Sequence

<400> SEQUENCE: 489

Trp Gly Gln Gly Thr Leu Val Thr Val Ser Ser
1 5 10

<210> SEQ ID NO 490
<211> LENGTH: 330
<212> TYPE: PRT
<213> ORGANISM: Artificial
<220> FEATURE:
<223> OTHER INFORMATION: Humanized Antibody Sequence

<400> SEQUENCE: 490

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Ala
85 90 95

Arg Val Glu Pro Lys Ser Cys Asp Lys Thr His Thr Cys Pro Pro Cys
100 105 110

Pro Ala Pro Glu Leu Leu Gly Gly Pro Ser Val Phe Leu Phe Pro Pro
115 120 125

Lys Pro Lys Asp Thr Leu Met Ile Ser Arg Thr Pro Glu Val Thr Cys
130 135 140

Val Val Val Asp Val Ser His Glu Asp Pro Glu Val Lys Phe Asn Trp
145 150 155 160

Tyr Val Asp Gly Val Glu Val His Asn Ala Lys Thr Lys Pro Arg Glu
165 170 175

Glu Gln Tyr Ala Ser Thr Tyr Arg Val Val Ser Val Leu Thr Val Leu
180 185 190

-continued

```
His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 491
<211> LENGTH: 1335
<212> TYPE: DNA
<213> ORGANISM: Artificial
<220> FEATURE:
<223> OTHER INFORMATION: Humanized Antibody Sequence

<400> SEQUENCE: 491

cagtcggtgg aggagtccgg gggtcgcctg gtcacgcctg ggacacccct gacactcacc     60

tgcacagtct ctggattctc cctcagtagc tatgcgatga tctgggtccg ccaggctcca    120

gggaaggggc tggaatggat cggaatcatt tatgataatg gtgacacata ctacgcgagc    180

tgggcgaaag gccggttcac catctccaaa acctcgacca cggtgtatct gaagatcgcc    240

agtccgacaa ccgaggacac ggccacctac ttctgtgcca gagagcctgg tagtactact    300

cagaatgact tgtggggcca agggaccctg gtcaccgtct cgagcgcctc caccaagggc    360

ccatcggtct tccccctggc accctcctcc aagagcacct ctgggggcac agcggccctg    420

ggctgcctgg tcaaggacta cttccccgaa ccggtgacgg tgtcgtggaa ctcaggcgcc    480

ctgaccagcg gcgtgcacac cttcccggct gtcctacagt cctcaggact ctactccctc    540

agcagcgtgg tgaccgtgcc ctccagcagc ttgggcaccc agacctacat ctgcaacgtg    600

aatcacaagc ccagcaacac caaggtggac gcgagagttg agcccaaatc ttgtgacaaa    660

actcacacat gcccaccgtg cccagcacct gaactcctgg ggggaccgtc agtcttcctc    720

ttccccccaa aacccaagga caccctcatg atctcccgga cccctgaggt cacatgcgtg    780

gtggtggacg tgagccacga agaccctgag gtcaagttca actggtacgt ggacggcgtg    840

gaggtgcata atgccaagac aaagccgcgg gaggagcagt acgccagcac gtaccgtgtg    900

gtcagcgtcc tcaccgtcct gcaccaggac tggctgaatg gcaaggagta caagtgcaag    960

gtctccaaca aagccctccc agcccccatc gagaaaacca tctccaaagc caaagggcag   1020

ccccgagaac cacaggtgta caccctgccc ccatcccggg aggagatgac caagaaccag   1080

gtcagcctga cctgcctggt caaaggcttc tatcccagcg acatcgccgt ggagtgggag   1140

agcaatgggc agccggagaa caactacaag accacgcctc ccgtgctgga ctccgacggc   1200

tccttcttcc tctacagcaa gctcaccgtg gacaagagca ggtggcagca ggggaacgtc   1260
```

ttctcatgct ccgtgatgca tgaggctctg cacaaccact acacgcagaa gagcctctcc 1320
ctgtctccgg gtaaa 1335

<210> SEQ ID NO 492
<211> LENGTH: 345
<212> TYPE: DNA
<213> ORGANISM: Artificial
<220> FEATURE:
<223> OTHER INFORMATION: Humanized Antibody Sequence

<400> SEQUENCE: 492
cagtcggtgg aggagtccgg gggtcgcctg gtcacgcctg ggacacccct gacactcacc 60
tgcacagtct ctggattctc cctcagtagc tatgcgatga tctgggtccg ccaggctcca 120
gggaaggggc tggaatggat cggaatcatt tatgataatg gtgacacata ctacgcgagc 180
tgggcgaaag gccggttcac catctccaaa acctcgacca cggtgtatct gaagatcgcc 240
agtccgacaa ccgaggacac ggccacctac ttctgtgcca gagagcctgg tagtactact 300
cagaatgact tgtggggcca agggaccctg gtcaccgtct cgagc 345

<210> SEQ ID NO 493
<211> LENGTH: 87
<212> TYPE: DNA
<213> ORGANISM: Oryctolagus cuniculus

<400> SEQUENCE: 493
cagtcggtgg aggagtccgg gggtcgcctg gtcacgcctg ggacacccct gacactcacc 60
tgcacagtct ctggattctc cctcagt 87

<210> SEQ ID NO 494
<211> LENGTH: 15
<212> TYPE: DNA
<213> ORGANISM: Oryctolagus cuniculus

<400> SEQUENCE: 494
agctatgcga tgatc 15

<210> SEQ ID NO 495
<211> LENGTH: 42
<212> TYPE: DNA
<213> ORGANISM: Oryctolagus cuniculus

<400> SEQUENCE: 495
tgggtccgcc aggctccagg gaaggggctg gaatggatcg ga 42

<210> SEQ ID NO 496
<211> LENGTH: 48
<212> TYPE: DNA
<213> ORGANISM: Oryctolagus cuniculus

<400> SEQUENCE: 496
atcatttatg ataatggtga cacatactac gcgagctggg cgaaaggc 48

<210> SEQ ID NO 497
<211> LENGTH: 90
<212> TYPE: DNA
<213> ORGANISM: Oryctolagus cuniculus

<400> SEQUENCE: 497
cggttcacca tctccaaaac ctcgaccacg gtgtatctga agatcgccag tccgacaacc 60
gaggacacgg ccacctactt ctgtgccaga 90

<210> SEQ ID NO 498
<211> LENGTH: 30
<212> TYPE: DNA
<213> ORGANISM: Oryctolagus cuniculus

<400> SEQUENCE: 498
gagcctggta gtactactca gaatgacttg 30

<210> SEQ ID NO 499
<211> LENGTH: 33
<212> TYPE: DNA
<213> ORGANISM: Artificial
<220> FEATURE:
<223> OTHER INFORMATION: Humanized Antibody Sequence

<400> SEQUENCE: 499
tggggccaag ggaccctggt caccgtctcg agc 33

<210> SEQ ID NO 500
<211> LENGTH: 990
<212> TYPE: DNA
<213> ORGANISM: Artificial
<220> FEATURE:
<223> OTHER INFORMATION: Humanized Antibody Sequence

<400> SEQUENCE: 500
gcctccacca agggcccatc ggtcttcccc ctggcaccct cctccaagag cacctctggg 60
ggcacagcgg ccctgggctg cctggtcaag gactacttcc ccgaaccggt gacggtgtcg 120
tggaactcag gcgccctgac cagcggcgtg cacaccttcc cggctgtcct acagtcctca 180
ggactctact ccctcagcag cgtggtgacc gtgccctcca gcagcttggg cacccagacc 240
tacatctgca acgtgaatca caagcccagc aacaccaagg tggacgcgag agttgagccc 300
aaatcttgtg acaaaactca cacatgccca ccgtgcccag cacctgaact cctgggggga 360
ccgtcagtct tcctcttccc cccaaaaccc aaggacaccc tcatgatctc ccggacccct 420
gaggtcacat gcgtggtggt ggacgtgagc cacgaagacc ctgaggtcaa gttcaactgg 480
tacgtggacg gcgtggaggt gcataatgcc aagacaaagc cgcgggagga gcagtacgcc 540
agcacgtacc gtgtggtcag cgtcctcacc gtcctgcacc aggactggct gaatggcaag 600
gagtacaagt gcaaggtctc caacaaagcc ctcccagccc ccatcgagaa aaccatctcc 660
aaagccaaag ggcagccccg agaaccacag gtgtacaccc tgcccccatc ccgggaggag 720
atgaccaaga accaggtcag cctgacctgc ctggtcaaag gcttctatcc cagcgacatc 780
gccgtggagt gggagagcaa tgggcagccg gagaacaact acaagaccac gcctcccgtg 840
ctggactccg acggctcctt cttcctctac agcaagctca ccgtggacaa gagcaggtgg 900
cagcagggga acgtcttctc atgctccgtg atgcatgagg ctctgcacaa ccactacacg 960
cagaagagcc tctccctgtc tccgggtaaa 990

<210> SEQ ID NO 501
<211> LENGTH: 217
<212> TYPE: PRT
<213> ORGANISM: Artificial
<220> FEATURE:
<223> OTHER INFORMATION: Humanized Antibody Sequence

<400> SEQUENCE: 501

Asp Val Val Met Thr Gln Thr Pro Ala Ser Val Ser Glu Pro Val Gly
1 5 10 15

```
Gly Thr Val Thr Ile Lys Cys Gln Ala Ser Glu Asn Ile Tyr Asn Ser
            20                  25                  30

Leu Leu Trp Tyr Gln Gln Lys Pro Gly Gln Pro Pro Lys Leu Leu Ile
        35                  40                  45

Tyr Arg Ala Ser Thr Leu Ala Ser Gly Val Ser Ser Arg Phe Lys Gly
    50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Asn Tyr Tyr Asn Ile Trp Thr
                85                  90                  95

Asn Gly Ala Ala Phe Gly Gly Gly Thr Glu Val Val Val Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215
```

<210> SEQ ID NO 502
<211> LENGTH: 111
<212> TYPE: PRT
<213> ORGANISM: Artificial
<220> FEATURE:
<223> OTHER INFORMATION: Humanized Antibody Sequence

<400> SEQUENCE: 502

```
Asp Val Val Met Thr Gln Thr Pro Ala Ser Val Ser Glu Pro Val Gly
1               5                   10                  15

Gly Thr Val Thr Ile Lys Cys Gln Ala Ser Glu Asn Ile Tyr Asn Ser
            20                  25                  30

Leu Leu Trp Tyr Gln Gln Lys Pro Gly Gln Pro Pro Lys Leu Leu Ile
        35                  40                  45

Tyr Arg Ala Ser Thr Leu Ala Ser Gly Val Ser Ser Arg Phe Lys Gly
    50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Asn Tyr Tyr Asn Ile Trp Thr
                85                  90                  95

Asn Gly Ala Ala Phe Gly Gly Gly Thr Glu Val Val Val Lys Arg
            100                 105                 110
```

<210> SEQ ID NO 503
<211> LENGTH: 23
<212> TYPE: PRT
<213> ORGANISM: Oryctolagus cuniculus

<400> SEQUENCE: 503

```
Asp Val Val Met Thr Gln Thr Pro Ala Ser Val Ser Glu Pro Val Gly
1               5                   10                  15

Gly Thr Val Thr Ile Lys Cys
            20


<210> SEQ ID NO 504
<211> LENGTH: 11
<212> TYPE: PRT
<213> ORGANISM: Oryctolagus cuniculus

<400> SEQUENCE: 504

Gln Ala Ser Glu Asn Ile Tyr Asn Ser Leu Leu
1               5                   10


<210> SEQ ID NO 505
<211> LENGTH: 15
<212> TYPE: PRT
<213> ORGANISM: Oryctolagus cuniculus

<400> SEQUENCE: 505

Trp Tyr Gln Gln Lys Pro Gly Gln Pro Pro Lys Leu Leu Ile Tyr
1               5                   10                  15


<210> SEQ ID NO 506
<211> LENGTH: 7
<212> TYPE: PRT
<213> ORGANISM: Oryctolagus cuniculus

<400> SEQUENCE: 506

Arg Ala Ser Thr Leu Ala Ser
1               5


<210> SEQ ID NO 507
<211> LENGTH: 32
<212> TYPE: PRT
<213> ORGANISM: Oryctolagus cuniculus

<400> SEQUENCE: 507

Gly Val Ser Ser Arg Phe Lys Gly Ser Gly Ser Gly Thr Glu Phe Thr
1               5                   10                  15

Leu Thr Ile Ser Asp Leu Glu Cys Ala Asp Ala Ala Thr Tyr Tyr Cys
            20                  25                  30


<210> SEQ ID NO 508
<211> LENGTH: 12
<212> TYPE: PRT
<213> ORGANISM: Oryctolagus cuniculus

<400> SEQUENCE: 508

Gln Asn Tyr Tyr Asn Ile Trp Thr Asn Gly Ala Ala
1               5                   10


<210> SEQ ID NO 509
<211> LENGTH: 11
<212> TYPE: PRT
<213> ORGANISM: Artificial
<220> FEATURE:
<223> OTHER INFORMATION: Humanized Antibody Sequence

<400> SEQUENCE: 509

Phe Gly Gly Gly Thr Glu Val Val Val Lys Arg
1               5                   10


<210> SEQ ID NO 510
```

<211> LENGTH: 106
<212> TYPE: PRT
<213> ORGANISM: Artificial
<220> FEATURE:
<223> OTHER INFORMATION: Humanized Antibody Sequence

<400> SEQUENCE: 510

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 511
<211> LENGTH: 651
<212> TYPE: DNA
<213> ORGANISM: Artificial
<220> FEATURE:
<223> OTHER INFORMATION: Humanized Antibody Sequence

<400> SEQUENCE: 511
gatgttgtga tgacccagac tccagcctcc gtgtctgaac ctgtgggagg cacagtcacc 60
atcaagtgcc aggccagtga gaacatttac aactctttac tctggtatca gcagaaacca 120
gggcagcctc ccaagctcct gatctatagg gcatccactc tggcatctgg ggtctcatcg 180
cggttcaaag gcagtggatc tgggacagag ttcactctca ccatcagcga cctggagtgt 240
gccgatgctg ccacttacta ctgtcaaaac tattataata tatggactaa tggtgctgct 300
ttcggcggag ggaccgaggt ggtggtcaaa cgtacggtag cggccccatc tgtcttcatc 360
ttcccgccat ctgatgagca gttgaaatct ggaactgcct ctgttgtgtg cctgctgaat 420
aacttctatc ccagagaggc caaagtacag tggaaggtgg ataacgccct ccaatcgggt 480
aactcccagg agagtgtcac agagcaggac agcaaggaca gcacctacag cctcagcagc 540
accctgacgc tgagcaaagc agactacgag aaacacaaag tctacgcctg cgaagtcacc 600
catcagggcc tgagctcgcc cgtcacaaag agcttcaaca ggggagagtg t 651

<210> SEQ ID NO 512
<211> LENGTH: 333
<212> TYPE: DNA
<213> ORGANISM: Artificial
<220> FEATURE:
<223> OTHER INFORMATION: Humanized Antibody Sequence

<400> SEQUENCE: 512
gatgttgtga tgacccagac tccagcctcc gtgtctgaac ctgtgggagg cacagtcacc 60
atcaagtgcc aggccagtga gaacatttac aactctttac tctggtatca gcagaaacca 120
gggcagcctc ccaagctcct gatctatagg gcatccactc tggcatctgg ggtctcatcg 180
cggttcaaag gcagtggatc tgggacagag ttcactctca ccatcagcga cctggagtgt 240

-continued

```
gccgatgctg ccacttacta ctgtcaaaac tattataata tatggactaa tggtgctgct    300

ttcggcggag ggaccgaggt ggtggtcaaa cgt                                 333


<210> SEQ ID NO 513
<211> LENGTH: 69
<212> TYPE: DNA
<213> ORGANISM: Oryctolagus cuniculus

<400> SEQUENCE: 513

gatgttgtga tgacccagac tccagcctcc gtgtctgaac ctgtgggagg cacagtcacc     60

atcaagtgc                                                             69


<210> SEQ ID NO 514
<211> LENGTH: 33
<212> TYPE: DNA
<213> ORGANISM: Oryctolagus cuniculus

<400> SEQUENCE: 514

caggccagtg agaacattta caactcttta ctc                                  33


<210> SEQ ID NO 515
<211> LENGTH: 45
<212> TYPE: DNA
<213> ORGANISM: Oryctolagus cuniculus

<400> SEQUENCE: 515

tggtatcagc agaaaccagg gcagcctccc aagctcctga tctat                     45


<210> SEQ ID NO 516
<211> LENGTH: 21
<212> TYPE: DNA
<213> ORGANISM: Oryctolagus cuniculus

<400> SEQUENCE: 516

agggcatcca ctctggcatc t                                               21


<210> SEQ ID NO 517
<211> LENGTH: 96
<212> TYPE: DNA
<213> ORGANISM: Oryctolagus cuniculus

<400> SEQUENCE: 517

ggggtctcat cgcggttcaa aggcagtgga tctgggacag agttcactct caccatcagc     60

gacctggagt gtgccgatgc tgccacttac tactgt                               96


<210> SEQ ID NO 518
<211> LENGTH: 36
<212> TYPE: DNA
<213> ORGANISM: Oryctolagus cuniculus

<400> SEQUENCE: 518

caaaactatt ataatatatg gactaatggt gctgct                               36


<210> SEQ ID NO 519
<211> LENGTH: 33
<212> TYPE: DNA
<213> ORGANISM: Artificial
<220> FEATURE:
<223> OTHER INFORMATION: Humanized Antibody Sequence

<400> SEQUENCE: 519

ttcggcggag ggaccgaggt ggtggtcaaa cgt                                  33
```

<210> SEQ ID NO 520
<211> LENGTH: 318
<212> TYPE: DNA
<213> ORGANISM: Artificial
<220> FEATURE:
<223> OTHER INFORMATION: Humanized Antibody Sequence

<400> SEQUENCE: 520
acggtagcgg ccccatctgt cttcatcttc ccgccatctg atgagcagtt gaaatctgga 60
actgcctctg ttgtgtgcct gctgaataac ttctatccca gagaggccaa agtacagtgg 120
aaggtggata acgccctcca atcgggtaac tcccaggaga gtgtcacaga gcaggacagc 180
aaggacagca cctacagcct cagcagcacc ctgacgctga gcaaagcaga ctacgagaaa 240
cacaaagtct acgcctgcga agtcacccat cagggcctga gctcgcccgt cacaaagagc 300
ttcaacaggg gagagtgt 318

<210> SEQ ID NO 521
<211> LENGTH: 441
<212> TYPE: PRT
<213> ORGANISM: Artificial
<220> FEATURE:
<223> OTHER INFORMATION: Humanized Antibody Sequence

<400> SEQUENCE: 521

Gln Ser Val Glu Glu Ser Gly Gly Arg Leu Val Thr Pro Gly Thr Pro
1 5 10 15

Leu Thr Leu Thr Cys Thr Ala Ser Gly Ile Asp Leu Ser Gly Tyr Ala
20 25 30

Met Gly Trp Val Arg Gln Ala Pro Gly Lys Gly Leu Glu Trp Ile Gly
35 40 45

Asp Ile Ser Thr Tyr Gly Thr Thr Asp Tyr Ala Ser Trp Val Asn Gly
50 55 60

Arg Phe Thr Ile Ser Arg Thr Ser Thr Thr Val Thr Leu Lys Met Thr
65 70 75 80

Ser Leu Thr Thr Glu Asp Thr Ala Thr Tyr Phe Cys Ala Arg Asp Tyr
85 90 95

Trp Leu Ser Leu Trp Gly Pro Gly Thr Leu Val Thr Val Ser Ser Ala
100 105 110

Ser Thr Lys Gly Pro Ser Val Phe Pro Leu Ala Pro Ser Ser Lys Ser
115 120 125

Thr Ser Gly Gly Thr Ala Ala Leu Gly Cys Leu Val Lys Asp Tyr Phe
130 135 140

Pro Glu Pro Val Thr Val Ser Trp Asn Ser Gly Ala Leu Thr Ser Gly
145 150 155 160

Val His Thr Phe Pro Ala Val Leu Gln Ser Ser Gly Leu Tyr Ser Leu
165 170 175

Ser Ser Val Val Thr Val Pro Ser Ser Ser Leu Gly Thr Gln Thr Tyr
180 185 190

Ile Cys Asn Val Asn His Lys Pro Ser Asn Thr Lys Val Asp Ala Arg
195 200 205

Val Glu Pro Lys Ser Cys Asp Lys Thr His Thr Cys Pro Pro Cys Pro
210 215 220

Ala Pro Glu Leu Leu Gly Gly Pro Ser Val Phe Leu Phe Pro Pro Lys
225 230 235 240

Pro Lys Asp Thr Leu Met Ile Ser Arg Thr Pro Glu Val Thr Cys Val

```
                245                 250                 255

Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
        275                 280                 285

Gln Tyr Ala Ser Thr Tyr Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320

Ala Leu Pro Ala Pro Ile Glu Lys Thr Ile Ser Lys Ala Lys Gly Gln
                325                 330                 335

Pro Arg Glu Pro Gln Val Tyr Thr Leu Pro Pro Ser Arg Glu Glu Met
            340                 345                 350

Thr Lys Asn Gln Val Ser Leu Thr Cys Leu Val Lys Gly Phe Tyr Pro
        355                 360                 365

Ser Asp Ile Ala Val Glu Trp Glu Ser Asn Gly Gln Pro Glu Asn Asn
    370                 375                 380

Tyr Lys Thr Thr Pro Pro Val Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
            420                 425                 430

Lys Ser Leu Ser Leu Ser Pro Gly Lys
        435                 440


<210> SEQ ID NO 522
<211> LENGTH: 111
<212> TYPE: PRT
<213> ORGANISM: Artificial
<220> FEATURE:
<223> OTHER INFORMATION: Humanized Antibody Sequence

<400> SEQUENCE: 522

Gln Ser Val Glu Glu Ser Gly Gly Arg Leu Val Thr Pro Gly Thr Pro
1               5                   10                  15

Leu Thr Leu Thr Cys Thr Ala Ser Gly Ile Asp Leu Ser Gly Tyr Ala
            20                  25                  30

Met Gly Trp Val Arg Gln Ala Pro Gly Lys Gly Leu Glu Trp Ile Gly
        35                  40                  45

Asp Ile Ser Thr Tyr Gly Thr Thr Asp Tyr Ala Ser Trp Val Asn Gly
    50                  55                  60

Arg Phe Thr Ile Ser Arg Thr Ser Thr Thr Val Thr Leu Lys Met Thr
65                  70                  75                  80

Ser Leu Thr Thr Glu Asp Thr Ala Thr Tyr Phe Cys Ala Arg Asp Tyr
                85                  90                  95

Trp Leu Ser Leu Trp Gly Pro Gly Thr Leu Val Thr Val Ser Ser
            100                 105                 110


<210> SEQ ID NO 523
<211> LENGTH: 29
<212> TYPE: PRT
<213> ORGANISM: Oryctolagus cuniculus

<400> SEQUENCE: 523

Gln Ser Val Glu Glu Ser Gly Gly Arg Leu Val Thr Pro Gly Thr Pro
1               5                   10                  15
```

-continued

Leu Thr Leu Thr Cys Thr Ala Ser Gly Ile Asp Leu Ser
            20                  25

<210> SEQ ID NO 524
<211> LENGTH: 5
<212> TYPE: PRT
<213> ORGANISM: Oryctolagus cuniculus

<400> SEQUENCE: 524

Gly Tyr Ala Met Gly
1               5

<210> SEQ ID NO 525
<211> LENGTH: 14
<212> TYPE: PRT
<213> ORGANISM: Oryctolagus cuniculus

<400> SEQUENCE: 525

Trp Val Arg Gln Ala Pro Gly Lys Gly Leu Glu Trp Ile Gly
1               5                   10

<210> SEQ ID NO 526
<211> LENGTH: 16
<212> TYPE: PRT
<213> ORGANISM: Oryctolagus cuniculus

<400> SEQUENCE: 526

Asp Ile Ser Thr Tyr Gly Thr Thr Asp Tyr Ala Ser Trp Val Asn Gly
1               5                   10                  15

<210> SEQ ID NO 527
<211> LENGTH: 30
<212> TYPE: PRT
<213> ORGANISM: Oryctolagus cuniculus

<400> SEQUENCE: 527

Arg Phe Thr Ile Ser Arg Thr Ser Thr Thr Val Thr Leu Lys Met Thr
1               5                   10                  15

Ser Leu Thr Thr Glu Asp Thr Ala Thr Tyr Phe Cys Ala Arg
            20                  25                  30

<210> SEQ ID NO 528
<211> LENGTH: 6
<212> TYPE: PRT
<213> ORGANISM: Oryctolagus cuniculus

<400> SEQUENCE: 528

Asp Tyr Trp Leu Ser Leu
1               5

<210> SEQ ID NO 529
<211> LENGTH: 11
<212> TYPE: PRT
<213> ORGANISM: Artificial
<220> FEATURE:
<223> OTHER INFORMATION: Humanized Antibody Sequence

<400> SEQUENCE: 529

Trp Gly Pro Gly Thr Leu Val Thr Val Ser Ser
1               5                   10

<210> SEQ ID NO 530
<211> LENGTH: 330
<212> TYPE: PRT

<213> ORGANISM: Artificial
<220> FEATURE:
<223> OTHER INFORMATION: Humanized Antibody Sequence

<400> SEQUENCE: 530

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Ala
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 531
<211> LENGTH: 1323
<212> TYPE: DNA
<213> ORGANISM: Artificial
<220> FEATURE:
<223> OTHER INFORMATION: Humanized Antibody Sequence

<400> SEQUENCE: 531
cagtcggtgg aggagtccgg gggtcgcctg gtaacgcctg ggacacccct gacactcacc 60
tgcacagcct ctggaatcga cctcagtggc tatgcaatgg gctgggtccg ccaggctcca 120
gggaaggggc tggaatggat cggagacatt agtacctatg gtaccacaga ctacgcgagc 180
tgggtgaatg gccgattcac catctccaga acctcgacca cggtgactct gaaaatgacc 240
agtctgacaa ccgaggacac ggccacctat ttctgtgcca gagactattg gttgagcttg 300
tggggcccgg gcaccctcgt caccgtctcg agcgcctcca ccaagggccc atcggtcttc 360
cccctggcac cctcctccaa gagcacctct gggggcacag cggccctggg ctgcctggtc 420
aaggactact tccccgaacc ggtgacggtg tcgtggaact caggcgccct gaccagcggc 480
gtgcacacct tcccggctgt cctacagtcc tcaggactct actccctcag cagcgtggtg 540
accgtgccct ccagcagctt gggcacccag acctacatct gcaacgtgaa tcacaagccc 600
agcaacacca aggtggacgc gagagttgag cccaaatctt gtgacaaaac tcacacatgc 660
ccaccgtgcc cagcacctga actcctgggg ggaccgtcag tcttcctctt ccccccaaaa 720
cccaaggaca ccctcatgat ctcccggacc cctgaggtca catgcgtggt ggtggacgtg 780
agccacgaag accctgaggt caagttcaac tggtacgtgg acggcgtgga ggtgcataat 840
gccaagacaa agccgcggga ggagcagtac gccagcacgt accgtgtggt cagcgtcctc 900
accgtcctgc accaggactg gctgaatggc aaggagtaca agtgcaaggt ctccaacaaa 960
gccctcccag cccccatcga gaaaaccatc tccaaagcca aagggcagcc ccgagaacca 1020
caggtgtaca ccctgccccc atcccgggag gagatgacca agaaccaggt cagcctgacc 1080
tgcctggtca aaggcttcta tcccagcgac atcgccgtgg agtgggagag caatgggcag 1140
ccggagaaca actacaagac cacgcctccc gtgctggact ccgacggctc cttcttcctc 1200
tacagcaagc tcaccgtgga caagagcagg tggcagcagg ggaacgtctt ctcatgctcc 1260
gtgatgcatg aggctctgca caaccactac acgcagaaga gcctctccct gtctccgggt 1320
aaa 1323

<210> SEQ ID NO 532
<211> LENGTH: 333
<212> TYPE: DNA
<213> ORGANISM: Artificial
<220> FEATURE:
<223> OTHER INFORMATION: Humanized Antibody Sequence

<400> SEQUENCE: 532
cagtcggtgg aggagtccgg gggtcgcctg gtaacgcctg ggacacccct gacactcacc 60
tgcacagcct ctggaatcga cctcagtggc tatgcaatgg gctgggtccg ccaggctcca 120
gggaaggggc tggaatggat cggagacatt agtacctatg gtaccacaga ctacgcgagc 180
tgggtgaatg gccgattcac catctccaga acctcgacca cggtgactct gaaaatgacc 240
agtctgacaa ccgaggacac ggccacctat ttctgtgcca gagactattg gttgagcttg 300
tggggcccgg gcaccctcgt caccgtctcg agc 333

<210> SEQ ID NO 533
<211> LENGTH: 87
<212> TYPE: DNA
<213> ORGANISM: Oryctolagus cuniculus

<400> SEQUENCE: 533
cagtcggtgg aggagtccgg gggtcgcctg gtaacgcctg ggacacccct gacactcacc 60
tgcacagcct ctggaatcga cctcagt 87

<210> SEQ ID NO 534
<211> LENGTH: 15
<212> TYPE: DNA
<213> ORGANISM: Oryctolagus cuniculus

<400> SEQUENCE: 534
ggctatgcaa tgggc 15

<210> SEQ ID NO 535
<211> LENGTH: 42
<212> TYPE: DNA
<213> ORGANISM: Oryctolagus cuniculus

<400> SEQUENCE: 535
tgggtccgcc aggctccagg gaaggggctg gaatggatcg ga 42

<210> SEQ ID NO 536
<211> LENGTH: 48
<212> TYPE: DNA
<213> ORGANISM: Oryctolagus cuniculus

<400> SEQUENCE: 536
gacattagta cctatggtac cacagactac gcgagctggg tgaatggc 48

<210> SEQ ID NO 537
<211> LENGTH: 90
<212> TYPE: DNA
<213> ORGANISM: Oryctolagus cuniculus

<400> SEQUENCE: 537
cgattcacca tctccagaac ctcgaccacg gtgactctga aaatgaccag tctgacaacc 60
gaggacacgg ccacctattt ctgtgccaga 90

<210> SEQ ID NO 538
<211> LENGTH: 18
<212> TYPE: DNA
<213> ORGANISM: Oryctolagus cuniculus

<400> SEQUENCE: 538
gactattggt tgagcttg 18

<210> SEQ ID NO 539
<211> LENGTH: 33
<212> TYPE: DNA
<213> ORGANISM: Artificial
<220> FEATURE:
<223> OTHER INFORMATION: Humanized Antibody Sequence

<400> SEQUENCE: 539
tggggcccgg gcaccctcgt caccgtctcg agc 33

<210> SEQ ID NO 540
<211> LENGTH: 990
<212> TYPE: DNA
<213> ORGANISM: Artificial
<220> FEATURE:
<223> OTHER INFORMATION: Humanized Antibody Sequence

<400> SEQUENCE: 540
gcctccacca agggcccatc ggtcttcccc ctggcaccct cctccaagag cacctctggg 60
ggcacagcgg ccctgggctg cctggtcaag gactacttcc ccgaaccggt gacggtgtcg 120

-continued

```
tggaactcag gcgccctgac cagcggcgtg cacaccttcc cggctgtcct acagtcctca    180

ggactctact ccctcagcag cgtggtgacc gtgccctcca gcagcttggg cacccagacc    240

tacatctgca acgtgaatca caagcccagc aacaccaagg tggacgcgag agttgagccc    300

aaatcttgtg acaaaactca cacatgccca ccgtgcccag cacctgaact cctgggggga    360

ccgtcagtct tcctcttccc cccaaaaccc aaggacaccc tcatgatctc ccggacccct    420

gaggtcacat gcgtggtggt ggacgtgagc cacgaagacc ctgaggtcaa gttcaactgg    480

tacgtggacg gcgtggaggt gcataatgcc aagacaaagc cgcgggagga gcagtacgcc    540

agcacgtacc gtgtggtcag cgtcctcacc gtcctgcacc aggactggct gaatggcaag    600

gagtacaagt gcaaggtctc caacaaagcc ctcccagccc ccatcgagaa aaccatctcc    660

aaagccaaag ggcagccccg agaaccacag gtgtacaccc tgcccccatc ccgggaggag    720

atgaccaaga accaggtcag cctgacctgc ctggtcaaag gcttctatcc cagcgacatc    780

gccgtggagt gggagagcaa tgggcagccg gagaacaact acaagaccac gcctcccgtg    840

ctggactccg acggctcctt cttcctctac agcaagctca ccgtggacaa gagcaggtgg    900

cagcagggga acgtcttctc atgctccgtg atgcatgagg ctctgcacaa ccactacacg    960

cagaagagcc tctccctgtc tccgggtaaa                                     990
```

<210> SEQ ID NO 541
<211> LENGTH: 218
<212> TYPE: PRT
<213> ORGANISM: Artificial
<220> FEATURE:
<223> OTHER INFORMATION: Humanized Antibody Sequence

<400> SEQUENCE: 541

```
Ala Ala Val Leu Thr Gln Thr Pro Ser Pro Val Ser Ala Ala Val Gly
1               5                   10                  15

Gly Thr Val Thr Ile Lys Cys Gln Ser Ser Gln Ser Val Tyr Asp Asn
            20                  25                  30

Asn Ala Leu Ala Trp Tyr Gln Gln Lys Pro Gly Gln Pro Pro Lys Leu
        35                  40                  45

Leu Ile Tyr Ala Ala Ser Thr Leu Ala Ser Gly Val Pro Ser Arg Phe
    50                  55                  60

Lys Gly Ser Gly Ser Gly Thr Gln Phe Thr Leu Thr Ile Asn Gly Val
65                  70                  75                  80

Gln Cys Asp Asp Ala Ala Thr Tyr Tyr Cys Leu Gly Gly Tyr Asp Asp
                85                  90                  95

Pro Ala Asp Asn Ala Phe Gly Gly Gly Thr Glu Val Val Val Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205
```

```
Val Thr Lys Ser Phe Asn Arg Gly Glu Cys
    210                 215


<210> SEQ ID NO 542
<211> LENGTH: 112
<212> TYPE: PRT
<213> ORGANISM: Artificial
<220> FEATURE:
<223> OTHER INFORMATION: Humanized Antibody Sequence

<400> SEQUENCE: 542

Ala Ala Val Leu Thr Gln Thr Pro Ser Pro Val Ser Ala Ala Val Gly
1               5                   10                  15

Gly Thr Val Thr Ile Lys Cys Gln Ser Ser Gln Ser Val Tyr Asp Asn
            20                  25                  30

Asn Ala Leu Ala Trp Tyr Gln Gln Lys Pro Gly Gln Pro Pro Lys Leu
        35                  40                  45

Leu Ile Tyr Ala Ala Ser Thr Leu Ala Ser Gly Val Pro Ser Arg Phe
    50                  55                  60

Lys Gly Ser Gly Ser Gly Thr Gln Phe Thr Leu Thr Ile Asn Gly Val
65                  70                  75                  80

Gln Cys Asp Asp Ala Ala Thr Tyr Tyr Cys Leu Gly Gly Tyr Asp Asp
                85                  90                  95

Pro Ala Asp Asn Ala Phe Gly Gly Gly Thr Glu Val Val Val Lys Arg
            100                 105                 110


<210> SEQ ID NO 543
<211> LENGTH: 23
<212> TYPE: PRT
<213> ORGANISM: Oryctolagus cuniculus

<400> SEQUENCE: 543

Ala Ala Val Leu Thr Gln Thr Pro Ser Pro Val Ser Ala Ala Val Gly
1               5                   10                  15

Gly Thr Val Thr Ile Lys Cys
            20


<210> SEQ ID NO 544
<211> LENGTH: 13
<212> TYPE: PRT
<213> ORGANISM: Oryctolagus cuniculus

<400> SEQUENCE: 544

Gln Ser Ser Gln Ser Val Tyr Asp Asn Asn Ala Leu Ala
1               5                   10


<210> SEQ ID NO 545
<211> LENGTH: 15
<212> TYPE: PRT
<213> ORGANISM: Oryctolagus cuniculus

<400> SEQUENCE: 545

Trp Tyr Gln Gln Lys Pro Gly Gln Pro Pro Lys Leu Leu Ile Tyr
1               5                   10                  15


<210> SEQ ID NO 546
<211> LENGTH: 7
<212> TYPE: PRT
<213> ORGANISM: Oryctolagus cuniculus

<400> SEQUENCE: 546

Ala Ala Ser Thr Leu Ala Ser
```

1 5

<210> SEQ ID NO 547
<211> LENGTH: 32
<212> TYPE: PRT
<213> ORGANISM: Oryctolagus cuniculus

<400> SEQUENCE: 547

Gly Val Pro Ser Arg Phe Lys Gly Ser Gly Ser Gly Thr Gln Phe Thr
1 5 10 15

Leu Thr Ile Asn Gly Val Gln Cys Asp Asp Ala Ala Thr Tyr Tyr Cys
20 25 30

<210> SEQ ID NO 548
<211> LENGTH: 11
<212> TYPE: PRT
<213> ORGANISM: Oryctolagus cuniculus

<400> SEQUENCE: 548

Leu Gly Gly Tyr Asp Asp Pro Ala Asp Asn Ala
1 5 10

<210> SEQ ID NO 549
<211> LENGTH: 11
<212> TYPE: PRT
<213> ORGANISM: Artificial
<220> FEATURE:
<223> OTHER INFORMATION: Humanized Antibody Sequence

<400> SEQUENCE: 549

Phe Gly Gly Gly Thr Glu Val Val Val Lys Arg
1 5 10

<210> SEQ ID NO 550
<211> LENGTH: 106
<212> TYPE: PRT
<213> ORGANISM: Artificial
<220> FEATURE:
<223> OTHER INFORMATION: Humanized Antibody Sequence

<400> SEQUENCE: 550

Thr Val Ala Ala Pro Ser Val Phe Ile Phe Pro Pro Ser Asp Glu Gln
1 5 10 15

Leu Lys Ser Gly Thr Ala Ser Val Val Cys Leu Leu Asn Asn Phe Tyr
20 25 30

Pro Arg Glu Ala Lys Val Gln Trp Lys Val Asp Asn Ala Leu Gln Ser
35 40 45

Gly Asn Ser Gln Glu Ser Val Thr Glu Gln Asp Ser Lys Asp Ser Thr
50 55 60

Tyr Ser Leu Ser Ser Thr Leu Thr Leu Ser Lys Ala Asp Tyr Glu Lys
65 70 75 80

His Lys Val Tyr Ala Cys Glu Val Thr His Gln Gly Leu Ser Ser Pro
85 90 95

Val Thr Lys Ser Phe Asn Arg Gly Glu Cys
100 105

<210> SEQ ID NO 551
<211> LENGTH: 654
<212> TYPE: DNA
<213> ORGANISM: Artificial
<220> FEATURE:
<223> OTHER INFORMATION: Humanized Antibody Sequence

<400> SEQUENCE: 551
gcagccgtgc tgacccagac accatcgccc gtgtctgcag ctgtgggagg cacagtcacc 60
atcaagtgcc agtccagtca gagtgtttat gataacaatg ctttagcctg gtatcagcag 120
aaaccagggc agcctcccaa gctcctgatc tatgctgcat ccactctggc atctggggtc 180
ccatcgcggt tcaaaggcag tggatctggg acacagttca ctctcaccat caacggcgtg 240
cagtgtgacg atgctgccac ttactactgt ctaggcggtt atgatgatcc tgctgataat 300
gctttcggcg gagggaccga ggtggtggtc aaacgtacgg tagcggcccc atctgtcttc 360
atcttcccgc catctgatga gcagttgaaa tctggaactg cctctgttgt gtgcctgctg 420
aataacttct atcccagaga ggccaaagta cagtggaagg tggataacgc cctccaatcg 480
ggtaactccc aggagagtgt cacagagcag gacagcaagg acagcaccta cagcctcagc 540
agcaccctga cgctgagcaa agcagactac gagaaacaca aagtctacgc ctgcgaagtc 600
acccatcagg gcctgagctc gcccgtcaca aagagcttca acaggggaga gtgt 654

<210> SEQ ID NO 552
<211> LENGTH: 336
<212> TYPE: DNA
<213> ORGANISM: Artificial
<220> FEATURE:
<223> OTHER INFORMATION: Humanized Antibody Sequence

<400> SEQUENCE: 552
gcagccgtgc tgacccagac accatcgccc gtgtctgcag ctgtgggagg cacagtcacc 60
atcaagtgcc agtccagtca gagtgtttat gataacaatg ctttagcctg gtatcagcag 120
aaaccagggc agcctcccaa gctcctgatc tatgctgcat ccactctggc atctggggtc 180
ccatcgcggt tcaaaggcag tggatctggg acacagttca ctctcaccat caacggcgtg 240
cagtgtgacg atgctgccac ttactactgt ctaggcggtt atgatgatcc tgctgataat 300
gctttcggcg gagggaccga ggtggtggtc aaacgt 336

<210> SEQ ID NO 553
<211> LENGTH: 69
<212> TYPE: DNA
<213> ORGANISM: Oryctolagus cuniculus

<400> SEQUENCE: 553
gcagccgtgc tgacccagac accatcgccc gtgtctgcag ctgtgggagg cacagtcacc 60
atcaagtgc 69

<210> SEQ ID NO 554
<211> LENGTH: 39
<212> TYPE: DNA
<213> ORGANISM: Oryctolagus cuniculus

<400> SEQUENCE: 554
cagtccagtc agagtgttta tgataacaat gctttagcc 39

<210> SEQ ID NO 555
<211> LENGTH: 45
<212> TYPE: DNA
<213> ORGANISM: Oryctolagus cuniculus

<400> SEQUENCE: 555
tggtatcagc agaaaccagg gcagcctccc aagctcctga tctat 45

<210> SEQ ID NO 556
<211> LENGTH: 21
<212> TYPE: DNA
<213> ORGANISM: Oryctolagus cuniculus

<400> SEQUENCE: 556
gctgcatcca ctctggcatc t 21

<210> SEQ ID NO 557
<211> LENGTH: 96
<212> TYPE: DNA
<213> ORGANISM: Oryctolagus cuniculus

<400> SEQUENCE: 557
ggggtcccat cgcggttcaa aggcagtgga tctgggacac agttcactct caccatcaac 60
ggcgtgcagt gtgacgatgc tgccacttac tactgt 96

<210> SEQ ID NO 558
<211> LENGTH: 33
<212> TYPE: DNA
<213> ORGANISM: Oryctolagus cuniculus

<400> SEQUENCE: 558
ctaggcggtt atgatgatcc tgctgataat gct 33

<210> SEQ ID NO 559
<211> LENGTH: 33
<212> TYPE: DNA
<213> ORGANISM: Artificial
<220> FEATURE:
<223> OTHER INFORMATION: Humanized Antibody Sequence

<400> SEQUENCE: 559
ttcggcggag ggaccgaggt ggtggtcaaa cgt 33

<210> SEQ ID NO 560
<211> LENGTH: 318
<212> TYPE: DNA
<213> ORGANISM: Artificial
<220> FEATURE:
<223> OTHER INFORMATION: Humanized Antibody Sequence

<400> SEQUENCE: 560
acggtagcgg ccccatctgt cttcatcttc ccgccatctg atgagcagtt gaaatctgga 60
actgcctctg ttgtgtgcct gctgaataac ttctatccca gagaggccaa agtacagtgg 120
aaggtggata acgccctcca atcgggtaac tcccaggaga gtgtcacaga gcaggacagc 180
aaggacagca cctacagcct cagcagcacc ctgacgctga gcaaagcaga ctacgagaaa 240
cacaaagtct acgcctgcga agtcacccat cagggcctga gctcgcccgt cacaaagagc 300
ttcaacaggg gagagtgt 318

<210> SEQ ID NO 561
<211> LENGTH: 441
<212> TYPE: PRT
<213> ORGANISM: Artificial
<220> FEATURE:
<223> OTHER INFORMATION: Humanized Antibody Sequence

<400> SEQUENCE: 561

Gln Ser Val Glu Glu Ser Gly Gly Arg Leu Val Thr Pro Gly Thr Pro
1 5 10 15

Leu Thr Leu Thr Cys Thr Ala Ser Gly Phe Ser Leu Ser Arg Tyr Ala

-continued

```
            20                  25                  30

Met Gly Trp Val Arg Gln Ala Pro Gly Lys Gly Leu Glu Trp Ile Gly
        35                  40                  45

Asp Ile Ser Thr Tyr Gly Thr Thr Asp Tyr Ala Ser Trp Val Asn Gly
    50                  55                  60

Arg Phe Thr Ile Ser Arg Thr Ser Thr Thr Val Thr Leu Lys Met Thr
65                  70                  75                  80

Ser Leu Thr Thr Glu Asp Thr Ala Thr Tyr Phe Cys Ala Arg Asp Tyr
                85                  90                  95

Trp Leu Ser Leu Trp Gly Gln Gly Thr Leu Val Thr Val Ser Ser Ala
            100                 105                 110

Ser Thr Lys Gly Pro Ser Val Phe Pro Leu Ala Pro Ser Ser Lys Ser
        115                 120                 125

Thr Ser Gly Gly Thr Ala Ala Leu Gly Cys Leu Val Lys Asp Tyr Phe
    130                 135                 140

Pro Glu Pro Val Thr Val Ser Trp Asn Ser Gly Ala Leu Thr Ser Gly
145                 150                 155                 160

Val His Thr Phe Pro Ala Val Leu Gln Ser Ser Gly Leu Tyr Ser Leu
                165                 170                 175

Ser Ser Val Val Thr Val Pro Ser Ser Ser Leu Gly Thr Gln Thr Tyr
            180                 185                 190

Ile Cys Asn Val Asn His Lys Pro Ser Asn Thr Lys Val Asp Ala Arg
        195                 200                 205

Val Glu Pro Lys Ser Cys Asp Lys Thr His Thr Cys Pro Pro Cys Pro
    210                 215                 220

Ala Pro Glu Leu Leu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
        275                 280                 285

Gln Tyr Ala Ser Thr Tyr Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320

Ala Leu Pro Ala Pro Ile Glu Lys Thr Ile Ser Lys Ala Lys Gly Gln
                325                 330                 335

Pro Arg Glu Pro Gln Val Tyr Thr Leu Pro Pro Ser Arg Glu Glu Met
            340                 345                 350

Thr Lys Asn Gln Val Ser Leu Thr Cys Leu Val Lys Gly Phe Tyr Pro
        355                 360                 365

Ser Asp Ile Ala Val Glu Trp Glu Ser Asn Gly Gln Pro Glu Asn Asn
    370                 375                 380

Tyr Lys Thr Thr Pro Pro Val Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
            420                 425                 430

Lys Ser Leu Ser Leu Ser Pro Gly Lys
        435                 440
```

<210> SEQ ID NO 562
<211> LENGTH: 111
<212> TYPE: PRT
<213> ORGANISM: Artificial
<220> FEATURE:
<223> OTHER INFORMATION: Humanized Antibody Sequence

<400> SEQUENCE: 562

Gln Ser Val Glu Glu Ser Gly Gly Arg Leu Val Thr Pro Gly Thr Pro
1               5                   10                  15

Leu Thr Leu Thr Cys Thr Ala Ser Gly Phe Ser Leu Ser Arg Tyr Ala
            20                  25                  30

Met Gly Trp Val Arg Gln Ala Pro Gly Lys Gly Leu Glu Trp Ile Gly
        35                  40                  45

Asp Ile Ser Thr Tyr Gly Thr Thr Asp Tyr Ala Ser Trp Val Asn Gly
    50                  55                  60

Arg Phe Thr Ile Ser Arg Thr Ser Thr Thr Val Thr Leu Lys Met Thr
65                  70                  75                  80

Ser Leu Thr Thr Glu Asp Thr Ala Thr Tyr Phe Cys Ala Arg Asp Tyr
                85                  90                  95

Trp Leu Ser Leu Trp Gly Gln Gly Thr Leu Val Thr Val Ser Ser
            100                 105                 110

<210> SEQ ID NO 563
<211> LENGTH: 29
<212> TYPE: PRT
<213> ORGANISM: Oryctolagus cuniculus

<400> SEQUENCE: 563

Gln Ser Val Glu Glu Ser Gly Gly Arg Leu Val Thr Pro Gly Thr Pro
1               5                   10                  15

Leu Thr Leu Thr Cys Thr Ala Ser Gly Phe Ser Leu Ser
            20                  25

<210> SEQ ID NO 564
<211> LENGTH: 5
<212> TYPE: PRT
<213> ORGANISM: Oryctolagus cuniculus

<400> SEQUENCE: 564

Arg Tyr Ala Met Gly
1               5

<210> SEQ ID NO 565
<211> LENGTH: 14
<212> TYPE: PRT
<213> ORGANISM: Oryctolagus cuniculus

<400> SEQUENCE: 565

Trp Val Arg Gln Ala Pro Gly Lys Gly Leu Glu Trp Ile Gly
1               5                   10

<210> SEQ ID NO 566
<211> LENGTH: 16
<212> TYPE: PRT
<213> ORGANISM: Oryctolagus cuniculus

<400> SEQUENCE: 566

Asp Ile Ser Thr Tyr Gly Thr Thr Asp Tyr Ala Ser Trp Val Asn Gly
1               5                   10                  15

<210> SEQ ID NO 567
<211> LENGTH: 30
<212> TYPE: PRT
<213> ORGANISM: Oryctolagus cuniculus

<400> SEQUENCE: 567

Arg Phe Thr Ile Ser Arg Thr Ser Thr Thr Val Thr Leu Lys Met Thr
1               5                   10                  15

Ser Leu Thr Thr Glu Asp Thr Ala Thr Tyr Phe Cys Ala Arg
            20                  25                  30

<210> SEQ ID NO 568
<211> LENGTH: 6
<212> TYPE: PRT
<213> ORGANISM: Oryctolagus cuniculus

<400> SEQUENCE: 568

Asp Tyr Trp Leu Ser Leu
1               5

<210> SEQ ID NO 569
<211> LENGTH: 11
<212> TYPE: PRT
<213> ORGANISM: Artificial
<220> FEATURE:
<223> OTHER INFORMATION: Humanized Antibody Sequence

<400> SEQUENCE: 569

Trp Gly Gln Gly Thr Leu Val Thr Val Ser Ser
1               5                   10

<210> SEQ ID NO 570
<211> LENGTH: 330
<212> TYPE: PRT
<213> ORGANISM: Artificial
<220> FEATURE:
<223> OTHER INFORMATION: Humanized Antibody Sequence

<400> SEQUENCE: 570

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Ala
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu 165 170 175

Glu Gln Tyr Ala Ser Thr Tyr Arg Val Val Ser Val Leu Thr Val Leu
180 185 190

His Gln Asp Trp Leu Asn Gly Lys Glu Tyr Lys Cys Lys Val Ser Asn
195 200 205

Lys Ala Leu Pro Ala Pro Ile Glu Lys Thr Ile Ser Lys Ala Lys Gly
210 215 220

Gln Pro Arg Glu Pro Gln Val Tyr Thr Leu Pro Pro Ser Arg Glu Glu
225 230 235 240

Met Thr Lys Asn Gln Val Ser Leu Thr Cys Leu Val Lys Gly Phe Tyr
245 250 255

Pro Ser Asp Ile Ala Val Glu Trp Glu Ser Asn Gly Gln Pro Glu Asn
260 265 270

Asn Tyr Lys Thr Thr Pro Pro Val Leu Asp Ser Asp Gly Ser Phe Phe
275 280 285

Leu Tyr Ser Lys Leu Thr Val Asp Lys Ser Arg Trp Gln Gln Gly Asn
290 295 300

Val Phe Ser Cys Ser Val Met His Glu Ala Leu His Asn His Tyr Thr
305 310 315 320

Gln Lys Ser Leu Ser Leu Ser Pro Gly Lys
325 330

<210> SEQ ID NO 571
<211> LENGTH: 1323
<212> TYPE: DNA
<213> ORGANISM: Artificial
<220> FEATURE:
<223> OTHER INFORMATION: Humanized Antibody Sequence

<400> SEQUENCE: 571
cagtcggtgg aggagtctgg gggtcgcctg gtcacgcctg ggacacccct gacactcacc 60
tgcacagcct ctggattctc cctcagtaga tatgcaatgg gctgggtccg ccaggctcca 120
gggaaggggc tggaatggat cggagacatt agtacttatg gtaccacaga ctacgcgagc 180
tgggtgaatg gccgattcac catctccaga acctcgacca cggtgactct gaaaatgacc 240
agtctgacaa ccgaggacac ggccacctat ttctgtgcca gagactattg gttgagcttg 300
tggggccaag gcaccctcgt caccgtctcg agcgcctcca ccaagggccc atcggtcttc 360
cccctggcac cctcctccaa gagcacctct gggggcacag cggccctggg ctgcctggtc 420
aaggactact tccccgaacc ggtgacggtg tcgtggaact caggcgccct gaccagcggc 480
gtgcacacct tcccggctgt cctacagtcc tcaggactct actccctcag cagcgtggtg 540
accgtgccct ccagcagctt gggcacccag acctacatct gcaacgtgaa tcacaagccc 600
agcaacacca aggtggacgc gagagttgag cccaaatctt gtgacaaaac tcacacatgc 660
ccaccgtgcc cagcacctga actcctgggg ggaccgtcag tcttcctctt ccccccaaaa 720
cccaaggaca ccctcatgat ctcccggacc cctgaggtca catgcgtggt ggtggacgtg 780
agccacgaag accctgaggt caagttcaac tggtacgtgg acggcgtgga ggtgcataat 840
gccaagacaa agccgcggga ggagcagtac gccagcacgt accgtgtggt cagcgtcctc 900
accgtcctgc accaggactg gctgaatggc aaggagtaca agtgcaaggt ctccaacaaa 960
gccctcccag cccccatcga gaaaaccatc tccaaagcca aagggcagcc ccgagaacca 1020
caggtgtaca ccctgccccc atcccgggag gagatgacca agaaccaggt cagcctgacc 1080
tgcctggtca aggcttcta tcccagcgac atcgccgtgg agtgggagag caatgggcag 1140
ccggagaaca actacaagac cacgcctccc gtgctggact ccgacggctc cttcttcctc 1200
tacagcaagc tcaccgtgga caagagcagg tggcagcagg ggaacgtctt ctcatgctcc 1260
gtgatgcatg aggctctgca caaccactac acgcagaaga gcctctccct gtctccgggt 1320
aaa 1323

<210> SEQ ID NO 572
<211> LENGTH: 333
<212> TYPE: DNA
<213> ORGANISM: Artificial
<220> FEATURE:
<223> OTHER INFORMATION: Humanized Antibody Sequence

<400> SEQUENCE: 572
cagtcggtgg aggagtctgg gggtcgcctg gtcacgcctg ggacacccct gacactcacc 60
tgcacagcct ctggattctc cctcagtaga tatgcaatgg gctgggtccg ccaggctcca 120
gggaaggggc tggaatggat cggagacatt agtacttatg gtaccacaga ctacgcgagc 180
tgggtgaatg gccgattcac catctccaga acctcgacca cggtgactct gaaaatgacc 240
agtctgacaa ccgaggacac ggccacctat ttctgtgcca gagactattg gttgagcttg 300
tggggccaag gcaccctcgt caccgtctcg agc 333

<210> SEQ ID NO 573
<211> LENGTH: 87
<212> TYPE: DNA
<213> ORGANISM: Oryctolagus cuniculus

<400> SEQUENCE: 573
cagtcggtgg aggagtctgg gggtcgcctg gtcacgcctg ggacacccct gacactcacc 60
tgcacagcct ctggattctc cctcagt 87

<210> SEQ ID NO 574
<211> LENGTH: 15
<212> TYPE: DNA
<213> ORGANISM: Oryctolagus cuniculus

<400> SEQUENCE: 574
agatatgcaa tgggc 15

<210> SEQ ID NO 575
<211> LENGTH: 42
<212> TYPE: DNA
<213> ORGANISM: Oryctolagus cuniculus

<400> SEQUENCE: 575
tgggtccgcc aggctccagg gaaggggctg gaatggatcg ga 42

<210> SEQ ID NO 576
<211> LENGTH: 48
<212> TYPE: DNA
<213> ORGANISM: Oryctolagus cuniculus

<400> SEQUENCE: 576
gacattagta cttatggtac cacagactac gcgagctggg tgaatggc 48

<210> SEQ ID NO 577
<211> LENGTH: 90
<212> TYPE: DNA
<213> ORGANISM: Oryctolagus cuniculus

<400> SEQUENCE: 577
cgattcacca tctccagaac ctcgaccacg gtgactctga aaatgaccag tctgacaacc 60
gaggacacgg ccacctattt ctgtgccaga 90

<210> SEQ ID NO 578
<211> LENGTH: 18
<212> TYPE: DNA
<213> ORGANISM: Oryctolagus cuniculus

<400> SEQUENCE: 578
gactattggt tgagcttg 18

<210> SEQ ID NO 579
<211> LENGTH: 33
<212> TYPE: DNA
<213> ORGANISM: Artificial
<220> FEATURE:
<223> OTHER INFORMATION: Humanized Antibody Sequence

<400> SEQUENCE: 579
tggggccaag gcaccctcgt caccgtctcg agc 33

<210> SEQ ID NO 580
<211> LENGTH: 990
<212> TYPE: DNA
<213> ORGANISM: Artificial
<220> FEATURE:
<223> OTHER INFORMATION: Humanized Antibody Sequence

<400> SEQUENCE: 580
gcctccacca agggcccatc ggtcttcccc ctggcaccct cctccaagag cacctctggg 60
ggcacagcgg ccctgggctg cctggtcaag gactacttcc ccgaaccggt gacggtgtcg 120
tggaactcag gcgccctgac cagcggcgtg cacaccttcc cggctgtcct acagtcctca 180
ggactctact ccctcagcag cgtggtgacc gtgccctcca gcagcttggg cacccagacc 240
tacatctgca acgtgaatca caagcccagc aacaccaagg tggacgcgag agttgagccc 300
aaatcttgtg acaaaactca cacatgccca ccgtgcccag cacctgaact cctgggggga 360
ccgtcagtct tcctcttccc cccaaaaccc aaggacaccc tcatgatctc ccggacccct 420
gaggtcacat gcgtggtggt ggacgtgagc cacgaagacc ctgaggtcaa gttcaactgg 480
tacgtggacg gcgtggaggt gcataatgcc aagacaaagc cgcgggagga gcagtacgcc 540
agcacgtacc gtgtggtcag cgtcctcacc gtcctgcacc aggactggct gaatggcaag 600
gagtacaagt gcaaggtctc caacaaagcc ctcccagccc ccatcgagaa aaccatctcc 660
aaagccaaag ggcagccccg agaaccacag gtgtacaccc tgcccccatc ccgggaggag 720
atgaccaaga accaggtcag cctgacctgc ctggtcaaag gcttctatcc cagcgacatc 780
gccgtggagt gggagagcaa tgggcagccg gagaacaact acaagaccac gcctcccgtg 840
ctggactccg acggctcctt cttcctctac agcaagctca ccgtggacaa gagcaggtgg 900
cagcagggga acgtcttctc atgctccgtg atgcatgagg ctctgcacaa ccactacacg 960
cagaagagcc tctccctgtc tccgggtaaa 990

<210> SEQ ID NO 581
<211> LENGTH: 218
<212> TYPE: PRT
<213> ORGANISM: Artificial
<220> FEATURE:
<223> OTHER INFORMATION: Humanized Antibody Sequence

<400> SEQUENCE: 581

Ala Ala Val Leu Thr Gln Thr Pro Ser Pro Val Ser Ala Ala Val Gly
1 5 10 15

Gly Thr Val Thr Ile Lys Cys Gln Ser Ser Gln Ser Val Tyr Asp Asn
20 25 30

Asn Ala Leu Ala Trp Tyr Gln Gln Lys Pro Gly Gln Pro Pro Lys Leu
35 40 45

Leu Ile Tyr Ala Ala Ser Asn Leu Ala Ser Gly Val Pro Asp Arg Phe
50 55 60

Ser Gly Ser Gly Ser Gly Thr Gln Phe Thr Leu Thr Ile Ser Gly Val
65 70 75 80

Gln Cys Asp Asp Ala Ala Thr Tyr Tyr Cys Leu Gly Gly Tyr Asp Asp
85 90 95

Ala Ala Asp Asn Ala Phe Gly Gly Gly Thr Glu Val Val Val Lys Arg
100 105 110

Thr Val Ala Ala Pro Ser Val Phe Ile Phe Pro Pro Ser Asp Glu Gln
115 120 125

Leu Lys Ser Gly Thr Ala Ser Val Val Cys Leu Leu Asn Asn Phe Tyr
130 135 140

Pro Arg Glu Ala Lys Val Gln Trp Lys Val Asp Asn Ala Leu Gln Ser
145 150 155 160

Gly Asn Ser Gln Glu Ser Val Thr Glu Gln Asp Ser Lys Asp Ser Thr
165 170 175

Tyr Ser Leu Ser Ser Thr Leu Thr Leu Ser Lys Ala Asp Tyr Glu Lys
180 185 190

His Lys Val Tyr Ala Cys Glu Val Thr His Gln Gly Leu Ser Ser Pro
195 200 205

Val Thr Lys Ser Phe Asn Arg Gly Glu Cys
210 215

<210> SEQ ID NO 582
<211> LENGTH: 112
<212> TYPE: PRT
<213> ORGANISM: Artificial
<220> FEATURE:
<223> OTHER INFORMATION: Humanized Antibody Sequence

<400> SEQUENCE: 582

Ala Ala Val Leu Thr Gln Thr Pro Ser Pro Val Ser Ala Ala Val Gly
1 5 10 15

Gly Thr Val Thr Ile Lys Cys Gln Ser Ser Gln Ser Val Tyr Asp Asn
20 25 30

Asn Ala Leu Ala Trp Tyr Gln Gln Lys Pro Gly Gln Pro Pro Lys Leu
35 40 45

Leu Ile Tyr Ala Ala Ser Asn Leu Ala Ser Gly Val Pro Asp Arg Phe
50 55 60

Ser Gly Ser Gly Ser Gly Thr Gln Phe Thr Leu Thr Ile Ser Gly Val
65 70 75 80

Gln Cys Asp Asp Ala Ala Thr Tyr Tyr Cys Leu Gly Gly Tyr Asp Asp
85 90 95

Ala Ala Asp Asn Ala Phe Gly Gly Gly Thr Glu Val Val Val Lys Arg
100 105 110

<210> SEQ ID NO 583
<211> LENGTH: 23

<212> TYPE: PRT
<213> ORGANISM: Oryctolagus cuniculus

<400> SEQUENCE: 583

Ala Ala Val Leu Thr Gln Thr Pro Ser Pro Val Ser Ala Ala Val Gly
1 5 10 15

Gly Thr Val Thr Ile Lys Cys
20

<210> SEQ ID NO 584
<211> LENGTH: 13
<212> TYPE: PRT
<213> ORGANISM: Oryctolagus cuniculus

<400> SEQUENCE: 584

Gln Ser Ser Gln Ser Val Tyr Asp Asn Asn Ala Leu Ala
1 5 10

<210> SEQ ID NO 585
<211> LENGTH: 15
<212> TYPE: PRT
<213> ORGANISM: Oryctolagus cuniculus

<400> SEQUENCE: 585

Trp Tyr Gln Gln Lys Pro Gly Gln Pro Pro Lys Leu Leu Ile Tyr
1 5 10 15

<210> SEQ ID NO 586
<211> LENGTH: 7
<212> TYPE: PRT
<213> ORGANISM: Oryctolagus cuniculus

<400> SEQUENCE: 586

Ala Ala Ser Asn Leu Ala Ser
1 5

<210> SEQ ID NO 587
<211> LENGTH: 32
<212> TYPE: PRT
<213> ORGANISM: Oryctolagus cuniculus

<400> SEQUENCE: 587

Gly Val Pro Asp Arg Phe Ser Gly Ser Gly Ser Gly Thr Gln Phe Thr
1 5 10 15

Leu Thr Ile Ser Gly Val Gln Cys Asp Asp Ala Ala Thr Tyr Tyr Cys
20 25 30

<210> SEQ ID NO 588
<211> LENGTH: 11
<212> TYPE: PRT
<213> ORGANISM: Oryctolagus cuniculus

<400> SEQUENCE: 588

Leu Gly Gly Tyr Asp Asp Ala Ala Asp Asn Ala
1 5 10

<210> SEQ ID NO 589
<211> LENGTH: 11
<212> TYPE: PRT
<213> ORGANISM: Artificial
<220> FEATURE:
<223> OTHER INFORMATION: Humanized Antibody Sequence

<400> SEQUENCE: 589

Phe Gly Gly Gly Thr Glu Val Val Val Lys Arg
1 5 10

<210> SEQ ID NO 590
<211> LENGTH: 106
<212> TYPE: PRT
<213> ORGANISM: Artificial
<220> FEATURE:
<223> OTHER INFORMATION: Humanized Antibody Sequence

<400> SEQUENCE: 590

Thr Val Ala Ala Pro Ser Val Phe Ile Phe Pro Pro Ser Asp Glu Gln
1 5 10 15

Leu Lys Ser Gly Thr Ala Ser Val Val Cys Leu Leu Asn Asn Phe Tyr
20 25 30

Pro Arg Glu Ala Lys Val Gln Trp Lys Val Asp Asn Ala Leu Gln Ser
35 40 45

Gly Asn Ser Gln Glu Ser Val Thr Glu Gln Asp Ser Lys Asp Ser Thr
50 55 60

Tyr Ser Leu Ser Ser Thr Leu Thr Leu Ser Lys Ala Asp Tyr Glu Lys
65 70 75 80

His Lys Val Tyr Ala Cys Glu Val Thr His Gln Gly Leu Ser Ser Pro
85 90 95

Val Thr Lys Ser Phe Asn Arg Gly Glu Cys
100 105

<210> SEQ ID NO 591
<211> LENGTH: 654
<212> TYPE: DNA
<213> ORGANISM: Artificial
<220> FEATURE:
<223> OTHER INFORMATION: Humanized Antibody Sequence

<400> SEQUENCE: 591
gcagccgtgc tgacccagac accatcgccc gtgtctgcag ctgtgggagg cacagtcacc 60
atcaagtgcc agtccagtca gagtgtttat gataacaatg ctttagcctg gtatcagcag 120
aaaccaggac agcctcccaa gctcctgatc tatgctgcat ccaatctggc atctggggtc 180
ccagataggt tcagcggcag tggatctggg acacagttca ctctcaccat cagcggcgtg 240
cagtgtgacg atgctgccac ttactactgt ctaggcggtt atgatgatgc tgctgataat 300
gctttcggcg gagggaccga ggtggtggtc aaacgtacgg tagcggcccc atctgtcttc 360
atcttcccgc catctgatga gcagttgaaa tctggaactg cctctgttgt gtgcctgctg 420
aataacttct atcccagaga ggccaaagta cagtggaagg tggataacgc cctccaatcg 480
ggtaactccc aggagagtgt cacagagcag gacagcaagg acagcaccta cagcctcagc 540
agcaccctga cgctgagcaa agcagactac gagaaacaca aagtctacgc ctgcgaagtc 600
acccatcagg gcctgagctc gcccgtcaca aagagcttca acaggggaga gtgt 654

<210> SEQ ID NO 592
<211> LENGTH: 336
<212> TYPE: DNA
<213> ORGANISM: Artificial
<220> FEATURE:
<223> OTHER INFORMATION: Humanized Antibody Sequence

<400> SEQUENCE: 592
gcagccgtgc tgacccagac accatcgccc gtgtctgcag ctgtgggagg cacagtcacc 60
atcaagtgcc agtccagtca gagtgtttat gataacaatg ctttagcctg gtatcagcag 120

```
aaaccaggac agcctcccaa gctcctgatc tatgctgcat ccaatctggc atctggggtc    180

ccagataggt tcagcggcag tggatctggg acacagttca ctctcaccat cagcggcgtg    240

cagtgtgacg atgctgccac ttactactgt ctaggcggtt atgatgatgc tgctgataat    300

gctttcggcg gagggaccga ggtggtggtc aaacgt                              336


<210> SEQ ID NO 593
<211> LENGTH: 69
<212> TYPE: DNA
<213> ORGANISM: Oryctolagus cuniculus

<400> SEQUENCE: 593

gcagccgtgc tgacccagac accatcgccc gtgtctgcag ctgtgggagg cacagtcacc     60

atcaagtgc                                                             69


<210> SEQ ID NO 594
<211> LENGTH: 39
<212> TYPE: DNA
<213> ORGANISM: Oryctolagus cuniculus

<400> SEQUENCE: 594

cagtccagtc agagtgttta tgataacaat gctttagcc                            39


<210> SEQ ID NO 595
<211> LENGTH: 45
<212> TYPE: DNA
<213> ORGANISM: Oryctolagus cuniculus

<400> SEQUENCE: 595

tggtatcagc agaaaccagg acagcctccc aagctcctga tctat                     45


<210> SEQ ID NO 596
<211> LENGTH: 21
<212> TYPE: DNA
<213> ORGANISM: Oryctolagus cuniculus

<400> SEQUENCE: 596

gctgcatcca atctggcatc t                                               21


<210> SEQ ID NO 597
<211> LENGTH: 96
<212> TYPE: DNA
<213> ORGANISM: Oryctolagus cuniculus

<400> SEQUENCE: 597

ggggtcccag ataggttcag cggcagtgga tctgggacac agttcactct caccatcagc     60

ggcgtgcagt gtgacgatgc tgccacttac tactgt                               96


<210> SEQ ID NO 598
<211> LENGTH: 33
<212> TYPE: DNA
<213> ORGANISM: Oryctolagus cuniculus

<400> SEQUENCE: 598

ctaggcggtt atgatgatgc tgctgataat gct                                  33


<210> SEQ ID NO 599
<211> LENGTH: 33
<212> TYPE: DNA
<213> ORGANISM: Artificial
<220> FEATURE:
```

<223> OTHER INFORMATION: Humanized Antibody Sequence

<400> SEQUENCE: 599
ttcggcggag ggaccgaggt ggtggtcaaa cgt 33

<210> SEQ ID NO 600
<211> LENGTH: 318
<212> TYPE: DNA
<213> ORGANISM: Artificial
<220> FEATURE:
<223> OTHER INFORMATION: Humanized Antibody Sequence

<400> SEQUENCE: 600
acggtagcgg ccccatctgt cttcatcttc ccgccatctg atgagcagtt gaaatctgga 60
actgcctctg ttgtgtgcct gctgaataac ttctatccca gagaggccaa agtacagtgg 120
aaggtggata acgccctcca atcgggtaac tcccaggaga gtgtcacaga gcaggacagc 180
aaggacagca cctacagcct cagcagcacc ctgacgctga gcaaagcaga ctacgagaaa 240
cacaaagtct acgcctgcga agtcacccat cagggcctga gctcgcccgt cacaaagagc 300
ttcaacaggg gagagtgt 318

<210> SEQ ID NO 601
<211> LENGTH: 441
<212> TYPE: PRT
<213> ORGANISM: Artificial
<220> FEATURE:
<223> OTHER INFORMATION: Humanized Antibody Sequence

<400> SEQUENCE: 601

Gln Ser Val Glu Glu Ser Gly Gly Arg Leu Val Thr Pro Gly Thr Pro
1 5 10 15

Leu Thr Leu Thr Cys Thr Ala Ser Gly Phe Ser Leu Ser Ser Tyr Ala
20 25 30

Met Gly Trp Val Arg Gln Ala Pro Gly Lys Gly Leu Glu Trp Ile Gly
35 40 45

Asp Ile Ser Thr Tyr Gly Thr Thr Asp Tyr Ala Ser Trp Val Tyr Gly
50 55 60

Arg Phe Thr Ile Ser Arg Thr Ser Thr Thr Val Thr Leu Lys Met Thr
65 70 75 80

Ser Leu Thr Thr Glu Asp Thr Ala Thr Tyr Phe Cys Ala Arg Asp Tyr
85 90 95

Trp Leu Ser Leu Trp Gly Gln Gly Thr Leu Val Thr Val Ser Ser Ala
100 105 110

Ser Thr Lys Gly Pro Ser Val Phe Pro Leu Ala Pro Ser Ser Lys Ser
115 120 125

Thr Ser Gly Gly Thr Ala Ala Leu Gly Cys Leu Val Lys Asp Tyr Phe
130 135 140

Pro Glu Pro Val Thr Val Ser Trp Asn Ser Gly Ala Leu Thr Ser Gly
145 150 155 160

Val His Thr Phe Pro Ala Val Leu Gln Ser Ser Gly Leu Tyr Ser Leu
165 170 175

Ser Ser Val Val Thr Val Pro Ser Ser Ser Leu Gly Thr Gln Thr Tyr
180 185 190

Ile Cys Asn Val Asn His Lys Pro Ser Asn Thr Lys Val Asp Ala Arg
195 200 205

Val Glu Pro Lys Ser Cys Asp Lys Thr His Thr Cys Pro Pro Cys Pro
210 215 220

```
Ala Pro Glu Leu Leu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
        275                 280                 285

Gln Tyr Ala Ser Thr Tyr Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320

Ala Leu Pro Ala Pro Ile Glu Lys Thr Ile Ser Lys Ala Lys Gly Gln
                325                 330                 335

Pro Arg Glu Pro Gln Val Tyr Thr Leu Pro Pro Ser Arg Glu Glu Met
            340                 345                 350

Thr Lys Asn Gln Val Ser Leu Thr Cys Leu Val Lys Gly Phe Tyr Pro
        355                 360                 365

Ser Asp Ile Ala Val Glu Trp Glu Ser Asn Gly Gln Pro Glu Asn Asn
    370                 375                 380

Tyr Lys Thr Thr Pro Pro Val Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
            420                 425                 430

Lys Ser Leu Ser Leu Ser Pro Gly Lys
        435                 440


<210> SEQ ID NO 602
<211> LENGTH: 111
<212> TYPE: PRT
<213> ORGANISM: Artificial
<220> FEATURE:
<223> OTHER INFORMATION: Humanized Antibody Sequence

<400> SEQUENCE: 602

Gln Ser Val Glu Glu Ser Gly Gly Arg Leu Val Thr Pro Gly Thr Pro
1               5                   10                  15

Leu Thr Leu Thr Cys Thr Ala Ser Gly Phe Ser Leu Ser Ser Tyr Ala
            20                  25                  30

Met Gly Trp Val Arg Gln Ala Pro Gly Lys Gly Leu Glu Trp Ile Gly
        35                  40                  45

Asp Ile Ser Thr Tyr Gly Thr Thr Asp Tyr Ala Ser Trp Val Tyr Gly
    50                  55                  60

Arg Phe Thr Ile Ser Arg Thr Ser Thr Thr Val Thr Leu Lys Met Thr
65                  70                  75                  80

Ser Leu Thr Thr Glu Asp Thr Ala Thr Tyr Phe Cys Ala Arg Asp Tyr
                85                  90                  95

Trp Leu Ser Leu Trp Gly Gln Gly Thr Leu Val Thr Val Ser Ser
            100                 105                 110


<210> SEQ ID NO 603
<211> LENGTH: 29
<212> TYPE: PRT
<213> ORGANISM: Oryctolagus cuniculus
```

<400> SEQUENCE: 603

Gln Ser Val Glu Glu Ser Gly Gly Arg Leu Val Thr Pro Gly Thr Pro
1               5                   10                  15

Leu Thr Leu Thr Cys Thr Ala Ser Gly Phe Ser Leu Ser
            20                  25

<210> SEQ ID NO 604
<211> LENGTH: 5
<212> TYPE: PRT
<213> ORGANISM: Oryctolagus cuniculus

<400> SEQUENCE: 604

Ser Tyr Ala Met Gly
1               5

<210> SEQ ID NO 605
<211> LENGTH: 14
<212> TYPE: PRT
<213> ORGANISM: Oryctolagus cuniculus

<400> SEQUENCE: 605

Trp Val Arg Gln Ala Pro Gly Lys Gly Leu Glu Trp Ile Gly
1               5                   10

<210> SEQ ID NO 606
<211> LENGTH: 16
<212> TYPE: PRT
<213> ORGANISM: Oryctolagus cuniculus

<400> SEQUENCE: 606

Asp Ile Ser Thr Tyr Gly Thr Thr Asp Tyr Ala Ser Trp Val Tyr Gly
1               5                   10                  15

<210> SEQ ID NO 607
<211> LENGTH: 30
<212> TYPE: PRT
<213> ORGANISM: Oryctolagus cuniculus

<400> SEQUENCE: 607

Arg Phe Thr Ile Ser Arg Thr Ser Thr Thr Val Thr Leu Lys Met Thr
1               5                   10                  15

Ser Leu Thr Thr Glu Asp Thr Ala Thr Tyr Phe Cys Ala Arg
            20                  25                  30

<210> SEQ ID NO 608
<211> LENGTH: 6
<212> TYPE: PRT
<213> ORGANISM: Oryctolagus cuniculus

<400> SEQUENCE: 608

Asp Tyr Trp Leu Ser Leu
1               5

<210> SEQ ID NO 609
<211> LENGTH: 11
<212> TYPE: PRT
<213> ORGANISM: Artificial
<220> FEATURE:
<223> OTHER INFORMATION: Humanized Antibody Sequence

<400> SEQUENCE: 609

Trp Gly Gln Gly Thr Leu Val Thr Val Ser Ser
1               5                   10

<210> SEQ ID NO 610
<211> LENGTH: 330
<212> TYPE: PRT
<213> ORGANISM: Artificial
<220> FEATURE:
<223> OTHER INFORMATION: Humanized Antibody Sequence

<400> SEQUENCE: 610

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Ala
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 611
<211> LENGTH: 1323
<212> TYPE: DNA
<213> ORGANISM: Artificial
<220> FEATURE:
<223> OTHER INFORMATION: Humanized Antibody Sequence

<400> SEQUENCE: 611
cagtcggtgg aggagtccgg gggtcgcctg gtcacgcctg ggacacccct gacactcacc 60
tgcacagcct ctggattctc cctcagtagc tatgcaatgg gctgggtccg ccaggctcca 120
gggaaggggc tggaatggat cggagacatt agtacttatg gtaccacaga ctacgcgagc 180
tgggtgtatg gccgattcac catctccaga acctcgacca cggtgactct gaaaatgacc 240
agtctgacaa ccgaggacac ggccacctat ttctgtgcca gagactattg gttgagcttg 300
tggggccaag gcaccctggt caccgtctcg agcgcctcca ccaagggccc atcggtcttc 360
cccctggcac cctcctccaa gagcacctct gggggcacag cggccctggg ctgcctggtc 420
aaggactact tccccgaacc ggtgacggtg tcgtggaact caggcgccct gaccagcggc 480
gtgcacacct tcccggctgt cctacagtcc tcaggactct actccctcag cagcgtggtg 540
accgtgccct ccagcagctt gggcacccag acctacatct gcaacgtgaa tcacaagccc 600
agcaacacca aggtggacgc gagagttgag cccaaatctt gtgacaaaac tcacacatgc 660
ccaccgtgcc cagcacctga actcctgggg ggaccgtcag tcttcctctt ccccccaaaa 720
cccaaggaca ccctcatgat ctcccggacc cctgaggtca catgcgtggt ggtggacgtg 780
agccacgaag accctgaggt caagttcaac tggtacgtgg acggcgtgga ggtgcataat 840
gccaagacaa agccgcggga ggagcagtac gccagcacgt accgtgtggt cagcgtcctc 900
accgtcctgc accaggactg gctgaatggc aaggagtaca agtgcaaggt ctccaacaaa 960
gccctcccag cccccatcga gaaaaccatc tccaaagcca aagggcagcc ccgagaacca 1020
caggtgtaca ccctgccccc atcccgggag gagatgacca agaaccaggt cagcctgacc 1080
tgcctggtca aaggcttcta tcccagcgac atcgccgtgg agtgggagag caatgggcag 1140
ccggagaaca actacaagac cacgcctccc gtgctggact ccgacggctc cttcttcctc 1200
tacagcaagc tcaccgtgga caagagcagg tggcagcagg ggaacgtctt ctcatgctcc 1260
gtgatgcatg aggctctgca caaccactac acgcagaaga gcctctccct gtctccgggt 1320
aaa 1323

<210> SEQ ID NO 612
<211> LENGTH: 333
<212> TYPE: DNA
<213> ORGANISM: Artificial
<220> FEATURE:
<223> OTHER INFORMATION: Humanized Antibody Sequence

<400> SEQUENCE: 612
cagtcggtgg aggagtccgg gggtcgcctg gtcacgcctg ggacacccct gacactcacc 60
tgcacagcct ctggattctc cctcagtagc tatgcaatgg gctgggtccg ccaggctcca 120
gggaaggggc tggaatggat cggagacatt agtacttatg gtaccacaga ctacgcgagc 180
tgggtgtatg gccgattcac catctccaga acctcgacca cggtgactct gaaaatgacc 240
agtctgacaa ccgaggacac ggccacctat ttctgtgcca gagactattg gttgagcttg 300
tggggccaag gcaccctggt caccgtctcg agc 333

<210> SEQ ID NO 613
<211> LENGTH: 87
<212> TYPE: DNA
<213> ORGANISM: Oryctolagus cuniculus

<400> SEQUENCE: 613
cagtcggtgg aggagtccgg gggtcgcctg gtcacgcctg ggacacccct gacactcacc 60
tgcacagcct ctggattctc cctcagt 87

<210> SEQ ID NO 614
<211> LENGTH: 15
<212> TYPE: DNA
<213> ORGANISM: Oryctolagus cuniculus

<400> SEQUENCE: 614
agctatgcaa tgggc 15

<210> SEQ ID NO 615
<211> LENGTH: 42
<212> TYPE: DNA
<213> ORGANISM: Oryctolagus cuniculus

<400> SEQUENCE: 615
tgggtccgcc aggctccagg gaaggggctg gaatggatcg ga 42

<210> SEQ ID NO 616
<211> LENGTH: 48
<212> TYPE: DNA
<213> ORGANISM: Oryctolagus cuniculus

<400> SEQUENCE: 616
gacattagta cttatggtac cacagactac gcgagctggg tgtatggc 48

<210> SEQ ID NO 617
<211> LENGTH: 90
<212> TYPE: DNA
<213> ORGANISM: Oryctolagus cuniculus

<400> SEQUENCE: 617
cgattcacca tctccagaac ctcgaccacg gtgactctga aaatgaccag tctgacaacc 60
gaggacacgg ccacctattt ctgtgccaga 90

<210> SEQ ID NO 618
<211> LENGTH: 18
<212> TYPE: DNA
<213> ORGANISM: Oryctolagus cuniculus

<400> SEQUENCE: 618
gactattggt tgagcttg 18

<210> SEQ ID NO 619
<211> LENGTH: 33
<212> TYPE: DNA
<213> ORGANISM: Artificial
<220> FEATURE:
<223> OTHER INFORMATION: Humanized Antibody Sequence

<400> SEQUENCE: 619
tggggccaag gcaccctggt caccgtctcg agc 33

<210> SEQ ID NO 620
<211> LENGTH: 990
<212> TYPE: DNA
<213> ORGANISM: Artificial
<220> FEATURE:
<223> OTHER INFORMATION: Humanized Antibody Sequence

<400> SEQUENCE: 620

```
gcctccacca agggcccatc ggtcttcccc ctggcaccct cctccaagag cacctctggg     60

ggcacagcgg ccctgggctg cctggtcaag gactacttcc ccgaaccggt gacggtgtcg    120

tggaactcag gcgccctgac cagcggcgtg cacaccttcc cggctgtcct acagtcctca    180

ggactctact ccctcagcag cgtggtgacc gtgccctcca gcagcttggg cacccagacc    240

tacatctgca acgtgaatca caagcccagc aacaccaagg tggacgcgag agttgagccc    300

aaatcttgtg acaaaactca cacatgccca ccgtgcccag cacctgaact cctgggggga    360

ccgtcagtct tcctcttccc cccaaaaccc aaggacaccc tcatgatctc ccggacccct    420

gaggtcacat gcgtggtggt ggacgtgagc cacgaagacc ctgaggtcaa gttcaactgg    480

tacgtggacg gcgtggaggt gcataatgcc aagacaaagc cgcgggagga gcagtacgcc    540

agcacgtacc gtgtggtcag cgtcctcacc gtcctgcacc aggactggct gaatggcaag    600

gagtacaagt gcaaggtctc caacaaagcc ctcccagccc ccatcgagaa aaccatctcc    660

aaagccaaag ggcagccccg agaaccacag gtgtacaccc tgcccccatc ccgggaggag    720

atgaccaaga accaggtcag cctgacctgc ctggtcaaag gcttctatcc cagcgacatc    780

gccgtggagt gggagagcaa tgggcagccg gagaacaact acaagaccac gcctcccgtg    840

ctggactccg acggctcctt cttcctctac agcaagctca ccgtggacaa gagcaggtgg    900

cagcagggga acgtcttctc atgctccgtg atgcatgagg ctctgcacaa ccactacacg    960

cagaagagcc tctccctgtc tccgggtaaa                                     990
```

<210> SEQ ID NO 621
<211> LENGTH: 218
<212> TYPE: PRT
<213> ORGANISM: Artificial
<220> FEATURE:
<223> OTHER INFORMATION: Humanized Antibody Sequence

<400> SEQUENCE: 621

```
Ala Ala Val Leu Thr Gln Thr Pro Ser Pro Val Ser Ala Ala Val Gly
1               5                   10                  15

Gly Thr Val Thr Ile Lys Cys Gln Ser Ser Gln Ser Val Tyr Asp Asn
            20                  25                  30

Asn Ala Leu Ala Trp Tyr Gln Gln Lys Pro Gly Gln Pro Pro Lys Leu
        35                  40                  45

Leu Ile Tyr Ala Ala Ser Thr Leu Ala Ser Gly Val Pro Ser Arg Phe
    50                  55                  60

Ser Gly Ser Gly Ser Gly Thr Glu Phe Thr Leu Thr Ile Ser Gly Val
65                  70                  75                  80

Gln Cys Asp Asp Ala Ala Thr Tyr Tyr Cys Leu Gly Gly Tyr Tyr Asp
                85                  90                  95

Pro Ala Asp Asn Ala Phe Gly Gly Gly Thr Glu Val Val Val Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
```

180 185 190

His Lys Val Tyr Ala Cys Glu Val Thr His Gln Gly Leu Ser Ser Pro
195 200 205

Val Thr Lys Ser Phe Asn Arg Gly Glu Cys
210 215

<210> SEQ ID NO 622
<211> LENGTH: 112
<212> TYPE: PRT
<213> ORGANISM: Artificial
<220> FEATURE:
<223> OTHER INFORMATION: Humanized Antibody Sequence

<400> SEQUENCE: 622

Ala Ala Val Leu Thr Gln Thr Pro Ser Pro Val Ser Ala Ala Val Gly
1 5 10 15

Gly Thr Val Thr Ile Lys Cys Gln Ser Ser Gln Ser Val Tyr Asp Asn
20 25 30

Asn Ala Leu Ala Trp Tyr Gln Gln Lys Pro Gly Gln Pro Pro Lys Leu
35 40 45

Leu Ile Tyr Ala Ala Ser Thr Leu Ala Ser Gly Val Pro Ser Arg Phe
50 55 60

Ser Gly Ser Gly Ser Gly Thr Glu Phe Thr Leu Thr Ile Ser Gly Val
65 70 75 80

Gln Cys Asp Asp Ala Ala Thr Tyr Tyr Cys Leu Gly Gly Tyr Tyr Asp
85 90 95

Pro Ala Asp Asn Ala Phe Gly Gly Gly Thr Glu Val Val Val Lys Arg
100 105 110

<210> SEQ ID NO 623
<211> LENGTH: 23
<212> TYPE: PRT
<213> ORGANISM: Oryctolagus cuniculus

<400> SEQUENCE: 623

Ala Ala Val Leu Thr Gln Thr Pro Ser Pro Val Ser Ala Ala Val Gly
1 5 10 15

Gly Thr Val Thr Ile Lys Cys
20

<210> SEQ ID NO 624
<211> LENGTH: 13
<212> TYPE: PRT
<213> ORGANISM: Oryctolagus cuniculus

<400> SEQUENCE: 624

Gln Ser Ser Gln Ser Val Tyr Asp Asn Asn Ala Leu Ala
1 5 10

<210> SEQ ID NO 625
<211> LENGTH: 15
<212> TYPE: PRT
<213> ORGANISM: Oryctolagus cuniculus

<400> SEQUENCE: 625

Trp Tyr Gln Gln Lys Pro Gly Gln Pro Pro Lys Leu Leu Ile Tyr
1 5 10 15

<210> SEQ ID NO 626
<211> LENGTH: 7
<212> TYPE: PRT

<213> ORGANISM: Oryctolagus cuniculus

<400> SEQUENCE: 626

Ala Ala Ser Thr Leu Ala Ser
1 5

<210> SEQ ID NO 627
<211> LENGTH: 32
<212> TYPE: PRT
<213> ORGANISM: Oryctolagus cuniculus

<400> SEQUENCE: 627

Gly Val Pro Ser Arg Phe Ser Gly Ser Gly Ser Gly Thr Glu Phe Thr
1 5 10 15

Leu Thr Ile Ser Gly Val Gln Cys Asp Asp Ala Ala Thr Tyr Tyr Cys
20 25 30

<210> SEQ ID NO 628
<211> LENGTH: 11
<212> TYPE: PRT
<213> ORGANISM: Oryctolagus cuniculus

<400> SEQUENCE: 628

Leu Gly Gly Tyr Tyr Asp Pro Ala Asp Asn Ala
1 5 10

<210> SEQ ID NO 629
<211> LENGTH: 11
<212> TYPE: PRT
<213> ORGANISM: Artificial
<220> FEATURE:
<223> OTHER INFORMATION: Humanized Antibody Sequence

<400> SEQUENCE: 629

Phe Gly Gly Gly Thr Glu Val Val Val Lys Arg
1 5 10

<210> SEQ ID NO 630
<211> LENGTH: 106
<212> TYPE: PRT
<213> ORGANISM: Artificial
<220> FEATURE:
<223> OTHER INFORMATION: Humanized Antibody Sequence

<400> SEQUENCE: 630

Thr Val Ala Ala Pro Ser Val Phe Ile Phe Pro Pro Ser Asp Glu Gln
1 5 10 15

Leu Lys Ser Gly Thr Ala Ser Val Val Cys Leu Leu Asn Asn Phe Tyr
20 25 30

Pro Arg Glu Ala Lys Val Gln Trp Lys Val Asp Asn Ala Leu Gln Ser
35 40 45

Gly Asn Ser Gln Glu Ser Val Thr Glu Gln Asp Ser Lys Asp Ser Thr
50 55 60

Tyr Ser Leu Ser Ser Thr Leu Thr Leu Ser Lys Ala Asp Tyr Glu Lys
65 70 75 80

His Lys Val Tyr Ala Cys Glu Val Thr His Gln Gly Leu Ser Ser Pro
85 90 95

Val Thr Lys Ser Phe Asn Arg Gly Glu Cys
100 105

<210> SEQ ID NO 631
<211> LENGTH: 654

-continued

<212> TYPE: DNA
<213> ORGANISM: Artificial
<220> FEATURE:
<223> OTHER INFORMATION: Humanized Antibody Sequence

<400> SEQUENCE: 631
gcagccgtgc tgacccagac accatcgccc gtgtctgcag ctgtgggagg cacagtcacc 60
atcaagtgcc agtccagtca gagtgtttat gataacaatg ctttagcctg gtatcagcag 120
aaaccagggc agcctcccaa gctcctgatc tatgctgcat ccactctggc atctggggtc 180
ccatcgcggt tcagtggcag tggatctggg acagagttca ctctcaccat cagcggcgtg 240
cagtgtgacg atgctgccac ttactactgt ctaggcggtt attatgatcc tgctgataat 300
gctttcggcg gagggaccga ggtggtggtc aaacgtacgg tagcggcccc atctgtcttc 360
atcttcccgc catctgatga gcagttgaaa tctggaactg cctctgttgt gtgcctgctg 420
aataacttct atcccagaga ggccaaagta cagtggaagg tggataacgc cctccaatcg 480
ggtaactccc aggagagtgt cacagagcag gacagcaagg acagcaccta cagcctcagc 540
agcaccctga cgctgagcaa agcagactac gagaaacaca aagtctacgc ctgcgaagtc 600
acccatcagg gcctgagctc gcccgtcaca aagagcttca acaggggaga gtgt 654

<210> SEQ ID NO 632
<211> LENGTH: 336
<212> TYPE: DNA
<213> ORGANISM: Artificial
<220> FEATURE:
<223> OTHER INFORMATION: Humanized Antibody Sequence

<400> SEQUENCE: 632
gcagccgtgc tgacccagac accatcgccc gtgtctgcag ctgtgggagg cacagtcacc 60
atcaagtgcc agtccagtca gagtgtttat gataacaatg ctttagcctg gtatcagcag 120
aaaccagggc agcctcccaa gctcctgatc tatgctgcat ccactctggc atctggggtc 180
ccatcgcggt tcagtggcag tggatctggg acagagttca ctctcaccat cagcggcgtg 240
cagtgtgacg atgctgccac ttactactgt ctaggcggtt attatgatcc tgctgataat 300
gctttcggcg gagggaccga ggtggtggtc aaacgt 336

<210> SEQ ID NO 633
<211> LENGTH: 69
<212> TYPE: DNA
<213> ORGANISM: Oryctolagus cuniculus

<400> SEQUENCE: 633
gcagccgtgc tgacccagac accatcgccc gtgtctgcag ctgtgggagg cacagtcacc 60
atcaagtgc 69

<210> SEQ ID NO 634
<211> LENGTH: 39
<212> TYPE: DNA
<213> ORGANISM: Oryctolagus cuniculus

<400> SEQUENCE: 634
cagtccagtc agagtgttta tgataacaat gctttagcc 39

<210> SEQ ID NO 635
<211> LENGTH: 45
<212> TYPE: DNA
<213> ORGANISM: Oryctolagus cuniculus

<400> SEQUENCE: 635
tggtatcagc agaaaccagg gcagcctccc aagctcctga tctat 45

<210> SEQ ID NO 636
<211> LENGTH: 21
<212> TYPE: DNA
<213> ORGANISM: Oryctolagus cuniculus

<400> SEQUENCE: 636
gctgcatcca ctctggcatc t 21

<210> SEQ ID NO 637
<211> LENGTH: 96
<212> TYPE: DNA
<213> ORGANISM: Oryctolagus cuniculus

<400> SEQUENCE: 637
ggggtcccat cgcggttcag tggcagtgga tctgggacag agttcactct caccatcagc 60
ggcgtgcagt gtgacgatgc tgccacttac tactgt 96

<210> SEQ ID NO 638
<211> LENGTH: 33
<212> TYPE: DNA
<213> ORGANISM: Oryctolagus cuniculus

<400> SEQUENCE: 638
ctaggcggtt attatgatcc tgctgataat gct 33

<210> SEQ ID NO 639
<211> LENGTH: 33
<212> TYPE: DNA
<213> ORGANISM: Artificial
<220> FEATURE:
<223> OTHER INFORMATION: Humanized Antibody Sequence

<400> SEQUENCE: 639
ttcggcggag ggaccgaggt ggtggtcaaa cgt 33

<210> SEQ ID NO 640
<211> LENGTH: 318
<212> TYPE: DNA
<213> ORGANISM: Artificial
<220> FEATURE:
<223> OTHER INFORMATION: Humanized Antibody Sequence

<400> SEQUENCE: 640
acggtagcgg ccccatctgt cttcatcttc ccgccatctg atgagcagtt gaaatctgga 60
actgcctctg ttgtgtgcct gctgaataac ttctatccca gagaggccaa agtacagtgg 120
aaggtggata acgccctcca atcgggtaac tcccaggaga gtgtcacaga gcaggacagc 180
aaggacagca cctacagcct cagcagcacc ctgacgctga gcaaagcaga ctacgagaaa 240
cacaaagtct acgcctgcga agtcacccat cagggcctga gctcgcccgt cacaaagagc 300
ttcaacaggg gagagtgt 318

<210> SEQ ID NO 641
<211> LENGTH: 451
<212> TYPE: PRT
<213> ORGANISM: Artificial
<220> FEATURE:
<223> OTHER INFORMATION: Humanized Antibody Sequence

<400> SEQUENCE: 641

```
Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Tyr Asp
            20                  25                  30

Met Ser Trp Val Arg Gln Ala Pro Gly Lys Gly Leu Glu Tyr Ile Gly
        35                  40                  45

Ile Ile Asn Thr Asn Asp Asp Thr Trp Tyr Ala Ser Trp Val Lys Gly
    50                  55                  60

Arg Phe Thr Ile Ser Lys Thr Ser Ser Thr Thr Val Asp Leu Lys Met
65                  70                  75                  80

Thr Ser Leu Thr Thr Glu Asp Thr Ala Thr Tyr Phe Cys Ala Arg Ile
                85                  90                  95

Ser Asp Ala Tyr Val Phe Asp Tyr Ala Tyr Tyr Phe Thr Leu Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Ala Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Ala Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415
```

```
Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450


<210> SEQ ID NO 642
<211> LENGTH: 121
<212> TYPE: PRT
<213> ORGANISM: Artificial
<220> FEATURE:
<223> OTHER INFORMATION: Humanized Antibody Sequence

<400> SEQUENCE: 642

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Tyr Asp
            20                  25                  30

Met Ser Trp Val Arg Gln Ala Pro Gly Lys Gly Leu Glu Tyr Ile Gly
        35                  40                  45

Ile Ile Asn Thr Asn Asp Asp Thr Trp Tyr Ala Ser Trp Val Lys Gly
    50                  55                  60

Arg Phe Thr Ile Ser Lys Thr Ser Ser Thr Thr Val Asp Leu Lys Met
65                  70                  75                  80

Thr Ser Leu Thr Thr Glu Asp Thr Ala Thr Tyr Phe Cys Ala Arg Ile
                85                  90                  95

Ser Asp Ala Tyr Val Phe Asp Tyr Ala Tyr Tyr Phe Thr Leu Trp Gly
            100                 105                 110

Gln Gly Thr Leu Val Thr Val Ser Ser
        115                 120


<210> SEQ ID NO 643
<211> LENGTH: 29
<212> TYPE: PRT
<213> ORGANISM: Oryctolagus cuniculus

<400> SEQUENCE: 643

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser
            20                  25


<210> SEQ ID NO 644
<211> LENGTH: 5
<212> TYPE: PRT
<213> ORGANISM: Oryctolagus cuniculus

<400> SEQUENCE: 644

Ser Tyr Asp Met Ser
1               5


<210> SEQ ID NO 645
<211> LENGTH: 14
<212> TYPE: PRT
<213> ORGANISM: Oryctolagus cuniculus

<400> SEQUENCE: 645

Trp Val Arg Gln Ala Pro Gly Lys Gly Leu Glu Tyr Ile Gly
1               5                   10
```

<210> SEQ ID NO 646
<211> LENGTH: 16
<212> TYPE: PRT
<213> ORGANISM: Oryctolagus cuniculus

<400> SEQUENCE: 646

Ile Ile Asn Thr Asn Asp Asp Thr Trp Tyr Ala Ser Trp Val Lys Gly
1               5                   10                  15

<210> SEQ ID NO 647
<211> LENGTH: 31
<212> TYPE: PRT
<213> ORGANISM: Oryctolagus cuniculus

<400> SEQUENCE: 647

Arg Phe Thr Ile Ser Lys Thr Ser Ser Thr Thr Val Asp Leu Lys Met
1               5                   10                  15

Thr Ser Leu Thr Thr Glu Asp Thr Ala Thr Tyr Phe Cys Ala Arg
            20                  25                  30

<210> SEQ ID NO 648
<211> LENGTH: 15
<212> TYPE: PRT
<213> ORGANISM: Oryctolagus cuniculus

<400> SEQUENCE: 648

Ile Ser Asp Ala Tyr Val Phe Asp Tyr Ala Tyr Tyr Phe Thr Leu
1               5                   10                  15

<210> SEQ ID NO 649
<211> LENGTH: 11
<212> TYPE: PRT
<213> ORGANISM: Artificial
<220> FEATURE:
<223> OTHER INFORMATION: Humanized Antibody Sequence

<400> SEQUENCE: 649

Trp Gly Gln Gly Thr Leu Val Thr Val Ser Ser
1               5                   10

<210> SEQ ID NO 650
<211> LENGTH: 330
<212> TYPE: PRT
<213> ORGANISM: Artificial
<220> FEATURE:
<223> OTHER INFORMATION: Humanized Antibody Sequence

<400> SEQUENCE: 650

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Ala
                85                  90                  95

Arg Val Glu Pro Lys Ser Cys Asp Lys Thr His Thr Cys Pro Pro Cys
            100                 105                 110

```
Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

```
<210> SEQ ID NO 651
<211> LENGTH: 1353
<212> TYPE: DNA
<213> ORGANISM: Artificial
<220> FEATURE:
<223> OTHER INFORMATION: Humanized Antibody Sequence

<400> SEQUENCE: 651

cagtcggtgg aggagtccgg gggtcgcctg gtcacgcctg ggacacccct gacactcacc      60

tgcaccgtct ctggattctc cctcagcagc tacgacatga gctgggtccg ccaggctcca     120

ggaaaggggc tggaatacat cggcatcatt aatactaatg atgacacatg gtacgcgagc     180

tgggtgaaag gccgattcac catctccaaa acctcgtcga ccacggtgga tctgaaaatg     240

accagtctga caaccgagga cacggccacc tatttctgtg ccagaatatc cgatgcttat     300

gtttttgatt atgcgtatta ctttactttg tggggccagg ggaccctggt caccgtctcg     360

agcgcctcca ccaagggccc atcggtcttc cccctggcac cctcctccaa gagcacctct     420

gggggcacag cggccctggg ctgcctggtc aaggactact tccccgaacc ggtgacggtg     480

tcgtggaact caggcgccct gaccagcggc gtgcacacct tcccggctgt cctacagtcc     540

tcaggactct actccctcag cagcgtggtg accgtgccct ccagcagctt gggcacccag     600

acctacatct gcaacgtgaa tcacaagccc agcaacacca aggtggacgc gagagttgag     660

cccaaatctt gtgacaaaac tcacacatgc ccaccgtgcc cagcacctga actcctgggg     720

ggaccgtcag tcttcctctt ccccccaaaa cccaaggaca ccctcatgat ctcccggacc     780
```

cctgaggtca catgcgtggt ggtggacgtg agccacgaag accctgaggt caagttcaac 840
tggtacgtgg acggcgtgga ggtgcataat gccaagacaa agccgcggga ggagcagtac 900
gccagcacgt accgtgtggt cagcgtcctc accgtcctgc accaggactg gctgaatggc 960
aaggagtaca agtgcaaggt ctccaacaaa gccctcccag cccccatcga gaaaaccatc 1020
tccaaagcca aagggcagcc ccgagaacca caggtgtaca ccctgccccc atcccgggag 1080
gagatgacca agaaccaggt cagcctgacc tgcctggtca aaggcttcta tcccagcgac 1140
atcgccgtgg agtgggagag caatgggcag ccggagaaca actacaagac cacgcctccc 1200
gtgctggact ccgacggctc cttcttcctc tacagcaagc tcaccgtgga caagagcagg 1260
tggcagcagg ggaacgtctt ctcatgctcc gtgatgcatg aggctctgca caaccactac 1320
acgcagaaga gcctctccct gtctccgggt aaa 1353

<210> SEQ ID NO 652
<211> LENGTH: 363
<212> TYPE: DNA
<213> ORGANISM: Artificial
<220> FEATURE:
<223> OTHER INFORMATION: Humanized Antibody Sequence

<400> SEQUENCE: 652
cagtcggtgg aggagtccgg gggtcgcctg gtcacgcctg ggacacccct gacactcacc 60
tgcaccgtct ctggattctc cctcagcagc tacgacatga gctgggtccg ccaggctcca 120
ggaaaggggc tggaatacat cggcatcatt aatactaatg atgacacatg gtacgcgagc 180
tgggtgaaag gccgattcac catctccaaa acctcgtcga ccacggtgga tctgaaaatg 240
accagtctga caaccgagga cacggccacc tatttctgtg ccagaatatc cgatgcttat 300
gtttttgatt atgcgtatta ctttactttg tggggccagg ggaccctggt caccgtctcg 360
agc 363

<210> SEQ ID NO 653
<211> LENGTH: 87
<212> TYPE: DNA
<213> ORGANISM: Oryctolagus cuniculus

<400> SEQUENCE: 653
cagtcggtgg aggagtccgg gggtcgcctg gtcacgcctg ggacacccct gacactcacc 60
tgcaccgtct ctggattctc cctcagc 87

<210> SEQ ID NO 654
<211> LENGTH: 15
<212> TYPE: DNA
<213> ORGANISM: Oryctolagus cuniculus

<400> SEQUENCE: 654
agctacgaca tgagc 15

<210> SEQ ID NO 655
<211> LENGTH: 42
<212> TYPE: DNA
<213> ORGANISM: Oryctolagus cuniculus

<400> SEQUENCE: 655
tgggtccgcc aggctccagg aaaggggctg gaatacatcg gc 42

<210> SEQ ID NO 656
<211> LENGTH: 48

<212> TYPE: DNA
<213> ORGANISM: Oryctolagus cuniculus

<400> SEQUENCE: 656
atcattaata ctaatgatga cacatggtac gcgagctggg tgaaaggc 48

<210> SEQ ID NO 657
<211> LENGTH: 93
<212> TYPE: DNA
<213> ORGANISM: Oryctolagus cuniculus

<400> SEQUENCE: 657
cgattcacca tctccaaaac ctcgtcgacc acggtggatc tgaaaatgac cagtctgaca 60
accgaggaca cggccaccta tttctgtgcc aga 93

<210> SEQ ID NO 658
<211> LENGTH: 45
<212> TYPE: DNA
<213> ORGANISM: Oryctolagus cuniculus

<400> SEQUENCE: 658
atatccgatg cttatgtttt tgattatgcg tattacttta ctttg 45

<210> SEQ ID NO 659
<211> LENGTH: 33
<212> TYPE: DNA
<213> ORGANISM: Artificial
<220> FEATURE:
<223> OTHER INFORMATION: Humanized Antibody Sequence

<400> SEQUENCE: 659
tggggccagg ggaccctggt caccgtctcg agc 33

<210> SEQ ID NO 660
<211> LENGTH: 990
<212> TYPE: DNA
<213> ORGANISM: Artificial
<220> FEATURE:
<223> OTHER INFORMATION: Humanized Antibody Sequence

<400> SEQUENCE: 660
gcctccacca agggcccatc ggtcttcccc ctggcaccct cctccaagag cacctctggg 60
ggcacagcgg ccctgggctg cctggtcaag gactacttcc ccgaaccggt gacggtgtcg 120
tggaactcag gcgccctgac cagcggcgtg cacaccttcc cggctgtcct acagtcctca 180
ggactctact ccctcagcag cgtggtgacc gtgccctcca gcagcttggg cacccagacc 240
tacatctgca acgtgaatca caagcccagc aacaccaagg tggacgcgag agttgagccc 300
aaatcttgtg acaaaactca cacatgccca ccgtgcccag cacctgaact cctgggggga 360
ccgtcagtct tcctcttccc cccaaaaccc aaggacaccc tcatgatctc ccggacccct 420
gaggtcacat gcgtggtggt ggacgtgagc cacgaagacc ctgaggtcaa gttcaactgg 480
tacgtggacg gcgtggaggt gcataatgcc aagacaaagc cgcgggagga gcagtacgcc 540
agcacgtacc gtgtggtcag cgtcctcacc gtcctgcacc aggactggct gaatggcaag 600
gagtacaagt gcaaggtctc caacaaagcc ctcccagccc ccatcgagaa aaccatctcc 660
aaagccaaag ggcagccccg agaaccacag gtgtacaccc tgcccccatc ccgggaggag 720
atgaccaaga accaggtcag cctgacctgc ctggtcaaag gcttctatcc cagcgacatc 780
gccgtggagt gggagagcaa tgggcagccg gagaacaact acaagaccac gcctcccgtg 840

-continued

```
ctggactccg acggctcctt cttcctctac agcaagctca ccgtggacaa gagcaggtgg    900

cagcagggga acgtcttctc atgctccgtg atgcatgagg ctctgcacaa ccactacacg    960

cagaagagcc tctccctgtc tccgggtaaa                                     990
```

```
<210> SEQ ID NO 661
<211> LENGTH: 217
<212> TYPE: PRT
<213> ORGANISM: Artificial
<220> FEATURE:
<223> OTHER INFORMATION: Humanized Antibody Sequence

<400> SEQUENCE: 661

Ala Leu Val Met Thr Gln Thr Pro Ser Ser Val Ser Ala Ala Val Gly
1               5                   10                  15

Gly Thr Val Thr Ile Asn Cys Leu Ala Ser Gln Asn Ile Tyr Asn Ser
            20                  25                  30

Leu Ala Trp Tyr Gln Gln Lys Pro Gly Gln Pro Pro Lys Leu Leu Ile
        35                  40                  45

Tyr Arg Ala Ser Thr Leu Ala Ser Gly Val Ser Ser Arg Phe Lys Gly
    50                  55                  60

Ser Gly Ser Gly Thr Gln Phe Thr Leu Thr Ile Ser Gly Val Glu Cys
65                  70                  75                  80

Ala Asp Ala Ala Thr Tyr Tyr Cys Gln Gln Gly Ala Gly Ala Asp Asn
                85                  90                  95

Ile Gly Asn Pro Phe Gly Gly Gly Thr Glu Val Val Val Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215


<210> SEQ ID NO 662
<211> LENGTH: 111
<212> TYPE: PRT
<213> ORGANISM: Artificial
<220> FEATURE:
<223> OTHER INFORMATION: Humanized Antibody Sequence

<400> SEQUENCE: 662

Ala Leu Val Met Thr Gln Thr Pro Ser Ser Val Ser Ala Ala Val Gly
1               5                   10                  15

Gly Thr Val Thr Ile Asn Cys Leu Ala Ser Gln Asn Ile Tyr Asn Ser
            20                  25                  30

Leu Ala Trp Tyr Gln Gln Lys Pro Gly Gln Pro Pro Lys Leu Leu Ile
        35                  40                  45

Tyr Arg Ala Ser Thr Leu Ala Ser Gly Val Ser Ser Arg Phe Lys Gly
    50                  55                  60
```

Ser Gly Ser Gly Thr Gln Phe Thr Leu Thr Ile Ser Gly Val Glu Cys
65 70 75 80

Ala Asp Ala Ala Thr Tyr Tyr Cys Gln Gln Gly Ala Gly Ala Asp Asn
85 90 95

Ile Gly Asn Pro Phe Gly Gly Gly Thr Glu Val Val Val Lys Arg
100 105 110

<210> SEQ ID NO 663
<211> LENGTH: 23
<212> TYPE: PRT
<213> ORGANISM: Oryctolagus cuniculus

<400> SEQUENCE: 663

Ala Leu Val Met Thr Gln Thr Pro Ser Ser Val Ser Ala Ala Val Gly
1 5 10 15

Gly Thr Val Thr Ile Asn Cys
20

<210> SEQ ID NO 664
<211> LENGTH: 11
<212> TYPE: PRT
<213> ORGANISM: Oryctolagus cuniculus

<400> SEQUENCE: 664

Leu Ala Ser Gln Asn Ile Tyr Asn Ser Leu Ala
1 5 10

<210> SEQ ID NO 665
<211> LENGTH: 15
<212> TYPE: PRT
<213> ORGANISM: Oryctolagus cuniculus

<400> SEQUENCE: 665

Trp Tyr Gln Gln Lys Pro Gly Gln Pro Pro Lys Leu Leu Ile Tyr
1 5 10 15

<210> SEQ ID NO 666
<211> LENGTH: 7
<212> TYPE: PRT
<213> ORGANISM: Oryctolagus cuniculus

<400> SEQUENCE: 666

Arg Ala Ser Thr Leu Ala Ser
1 5

<210> SEQ ID NO 667
<211> LENGTH: 32
<212> TYPE: PRT
<213> ORGANISM: Oryctolagus cuniculus

<400> SEQUENCE: 667

Gly Val Ser Ser Arg Phe Lys Gly Ser Gly Ser Gly Thr Gln Phe Thr
1 5 10 15

Leu Thr Ile Ser Gly Val Glu Cys Ala Asp Ala Ala Thr Tyr Tyr Cys
20 25 30

<210> SEQ ID NO 668
<211> LENGTH: 12
<212> TYPE: PRT
<213> ORGANISM: Oryctolagus cuniculus

<400> SEQUENCE: 668

Gln Gln Gly Ala Gly Ala Asp Asn Ile Gly Asn Pro
1               5                   10

<210> SEQ ID NO 669
<211> LENGTH: 11
<212> TYPE: PRT
<213> ORGANISM: Artificial
<220> FEATURE:
<223> OTHER INFORMATION: Humanized Antibody Sequence

<400> SEQUENCE: 669

Phe Gly Gly Gly Thr Glu Val Val Val Lys Arg
1               5                   10

<210> SEQ ID NO 670
<211> LENGTH: 106
<212> TYPE: PRT
<213> ORGANISM: Artificial
<220> FEATURE:
<223> OTHER INFORMATION: Humanized Antibody Sequence

<400> SEQUENCE: 670

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 671
<211> LENGTH: 651
<212> TYPE: DNA
<213> ORGANISM: Artificial
<220> FEATURE:
<223> OTHER INFORMATION: Humanized Antibody Sequence

<400> SEQUENCE: 671
gcccttgtga tgacccagac tccatcctcc gtgtctgcag ctgtgggagg cacagtcacc      60
atcaattgcc tggccagtca gaacatttac aattctttag cctggtatca gcagaaacca    120
gggcagcctc ccaagctcct gatctacagg gcatccactc tggcatctgg ggtctcatcg    180
cggttcaaag gcagtggatc tgggacacag ttcactctca ccatcagcgg cgtggagtgt    240
gccgatgctg ccacttacta ctgtcaacag ggtgctggtg ctgataatat tggtaatcct    300
ttcggcggag ggaccgaggt ggtggtcaaa cgtacggtag cggccccatc tgtcttcatc    360
ttcccgccat ctgatgagca gttgaaatct ggaactgcct ctgttgtgtg cctgctgaat    420
aacttctatc ccagagaggc caaagtacag tggaaggtgg ataacgccct ccaatcgggt    480
aactcccagg agagtgtcac agagcaggac agcaaggaca gcacctacag cctcagcagc    540
accctgacgc tgagcaaagc agactacgag aaacacaaag tctacgcctg cgaagtcacc    600
catcagggcc tgagctcgcc cgtcacaaag agcttcaaca ggggagagtg t            651

<210> SEQ ID NO 672
<211> LENGTH: 333
<212> TYPE: DNA
<213> ORGANISM: Artificial
<220> FEATURE:
<223> OTHER INFORMATION: Humanized Antibody Sequence

<400> SEQUENCE: 672
gcccttgtga tgacccagac tccatcctcc gtgtctgcag ctgtgggagg cacagtcacc 60
atcaattgcc tggccagtca gaacatttac aattctttag cctggtatca gcagaaacca 120
gggcagcctc ccaagctcct gatctacagg gcatccactc tggcatctgg ggtctcatcg 180
cggttcaaag gcagtggatc tgggacacag ttcactctca ccatcagcgg cgtggagtgt 240
gccgatgctg ccacttacta ctgtcaacag ggtgctggtg ctgataatat tggtaatcct 300
ttcggcggag ggaccgaggt ggtggtcaaa cgt 333

<210> SEQ ID NO 673
<211> LENGTH: 69
<212> TYPE: DNA
<213> ORGANISM: Oryctolagus cuniculus

<400> SEQUENCE: 673
gcccttgtga tgacccagac tccatcctcc gtgtctgcag ctgtgggagg cacagtcacc 60
atcaattgc 69

<210> SEQ ID NO 674
<211> LENGTH: 33
<212> TYPE: DNA
<213> ORGANISM: Oryctolagus cuniculus

<400> SEQUENCE: 674
ctggccagtc agaacattta caattcttta gcc 33

<210> SEQ ID NO 675
<211> LENGTH: 45
<212> TYPE: DNA
<213> ORGANISM: Oryctolagus cuniculus

<400> SEQUENCE: 675
tggtatcagc agaaaccagg gcagcctccc aagctcctga tctac 45

<210> SEQ ID NO 676
<211> LENGTH: 21
<212> TYPE: DNA
<213> ORGANISM: Oryctolagus cuniculus

<400> SEQUENCE: 676
agggcatcca ctctggcatc t 21

<210> SEQ ID NO 677
<211> LENGTH: 96
<212> TYPE: DNA
<213> ORGANISM: Oryctolagus cuniculus

<400> SEQUENCE: 677
ggggtctcat cgcggttcaa aggcagtgga tctgggacac agttcactct caccatcagc 60
ggcgtggagt gtgccgatgc tgccacttac tactgt 96

<210> SEQ ID NO 678
<211> LENGTH: 36

<212> TYPE: DNA
<213> ORGANISM: Oryctolagus cuniculus

<400> SEQUENCE: 678
caacagggtg ctggtgctga taatattggt aatcct 36

<210> SEQ ID NO 679
<211> LENGTH: 33
<212> TYPE: DNA
<213> ORGANISM: Artificial
<220> FEATURE:
<223> OTHER INFORMATION: Humanized Antibody Sequence

<400> SEQUENCE: 679
ttcggcggag ggaccgaggt ggtggtcaaa cgt 33

<210> SEQ ID NO 680
<211> LENGTH: 318
<212> TYPE: DNA
<213> ORGANISM: Artificial
<220> FEATURE:
<223> OTHER INFORMATION: Humanized Antibody Sequence

<400> SEQUENCE: 680
acggtagcgg ccccatctgt cttcatcttc ccgccatctg atgagcagtt gaaatctgga 60
actgcctctg ttgtgtgcct gctgaataac ttctatccca gagaggccaa agtacagtgg 120
aaggtggata acgccctcca atcgggtaac tcccaggaga gtgtcacaga gcaggacagc 180
aaggacagca cctacagcct cagcagcacc ctgacgctga gcaaagcaga ctacgagaaa 240
cacaaagtct acgcctgcga agtcacccat cagggcctga gctcgcccgt cacaaagagc 300
ttcaacaggg gagagtgt 318

<210> SEQ ID NO 681
<211> LENGTH: 452
<212> TYPE: PRT
<213> ORGANISM: Artificial
<220> FEATURE:
<223> OTHER INFORMATION: Humanized Antibody Sequence

<400> SEQUENCE: 681

Gln Glu Gln Leu Val Glu Ser Gly Gly Gly Leu Val Gln Pro Glu Gly
1               5                   10                  15

Ser Leu Thr Leu Thr Cys Thr Ala Ser Gly Phe Ser Phe Ser Ser Ser
            20                  25                  30

Asp Tyr Met Cys Trp Val Arg Gln Ala Pro Gly Lys Gly Leu Glu Trp
        35                  40                  45

Ile Gly Cys Ile Asp Ala Gly Ser Ser Gly Asp Thr Tyr Phe Ala Ser
    50                  55                  60

Trp Ala Lys Gly Arg Phe Thr Ile Ser Lys Thr Ser Ser Thr Thr Val
65                  70                  75                  80

Thr Leu Gln Met Thr Ser Leu Thr Ala Ala Asp Thr Ala Thr Tyr Phe
                85                  90                  95

Cys Ala Arg His Leu Tyr Gly Ser Ile Thr Phe Ala Phe Gly Leu Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr 145 150 155 160

Val Ser Trp Asn Ser Gly Ala Leu Thr Ser Gly Val His Thr Phe Pro
165 170 175

Ala Val Leu Gln Ser Ser Gly Leu Tyr Ser Leu Ser Ser Val Val Thr
180 185 190

Val Pro Ser Ser Ser Leu Gly Thr Gln Thr Tyr Ile Cys Asn Val Asn
195 200 205

His Lys Pro Ser Asn Thr Lys Val Asp Ala Arg Val Glu Pro Lys Ser
210 215 220

Cys Asp Lys Thr His Thr Cys Pro Pro Cys Pro Ala Pro Glu Leu Leu
225 230 235 240

Gly Gly Pro Ser Val Phe Leu Phe Pro Pro Lys Pro Lys Asp Thr Leu
245 250 255

Met Ile Ser Arg Thr Pro Glu Val Thr Cys Val Val Val Asp Val Ser
260 265 270

His Glu Asp Pro Glu Val Lys Phe Asn Trp Tyr Val Asp Gly Val Glu
275 280 285

Val His Asn Ala Lys Thr Lys Pro Arg Glu Glu Gln Tyr Ala Ser Thr
290 295 300

Tyr Arg Val Val Ser Val Leu Thr Val Leu His Gln Asp Trp Leu Asn
305 310 315 320

Gly Lys Glu Tyr Lys Cys Lys Val Ser Asn Lys Ala Leu Pro Ala Pro
325 330 335

Ile Glu Lys Thr Ile Ser Lys Ala Lys Gly Gln Pro Arg Glu Pro Gln
340 345 350

Val Tyr Thr Leu Pro Pro Ser Arg Glu Glu Met Thr Lys Asn Gln Val
355 360 365

Ser Leu Thr Cys Leu Val Lys Gly Phe Tyr Pro Ser Asp Ile Ala Val
370 375 380

Glu Trp Glu Ser Asn Gly Gln Pro Glu Asn Asn Tyr Lys Thr Thr Pro
385 390 395 400

Pro Val Leu Asp Ser Asp Gly Ser Phe Phe Leu Tyr Ser Lys Leu Thr
405 410 415

Val Asp Lys Ser Arg Trp Gln Gln Gly Asn Val Phe Ser Cys Ser Val
420 425 430

Met His Glu Ala Leu His Asn His Tyr Thr Gln Lys Ser Leu Ser Leu
435 440 445

Ser Pro Gly Lys
450

<210> SEQ ID NO 682
<211> LENGTH: 122
<212> TYPE: PRT
<213> ORGANISM: Artificial
<220> FEATURE:
<223> OTHER INFORMATION: Humanized Antibody Sequence

<400> SEQUENCE: 682

Gln Glu Gln Leu Val Glu Ser Gly Gly Gly Leu Val Gln Pro Glu Gly
1 5 10 15

Ser Leu Thr Leu Thr Cys Thr Ala Ser Gly Phe Ser Phe Ser Ser Ser
20 25 30

Asp Tyr Met Cys Trp Val Arg Gln Ala Pro Gly Lys Gly Leu Glu Trp
35 40 45

Ile Gly Cys Ile Asp Ala Gly Ser Ser Gly Asp Thr Tyr Phe Ala Ser

-continued

```
    50                  55                  60

Trp Ala Lys Gly Arg Phe Thr Ile Ser Lys Thr Ser Ser Thr Thr Val
65                  70                  75                  80

Thr Leu Gln Met Thr Ser Leu Thr Ala Ala Asp Thr Ala Thr Tyr Phe
                85                  90                  95

Cys Ala Arg His Leu Tyr Gly Ser Ile Thr Phe Ala Phe Gly Leu Trp
            100                 105                 110

Gly Gln Gly Thr Leu Val Thr Val Ser Ser
        115                 120


<210> SEQ ID NO 683
<211> LENGTH: 30
<212> TYPE: PRT
<213> ORGANISM: Oryctolagus cuniculus

<400> SEQUENCE: 683

Gln Glu Gln Leu Val Glu Ser Gly Gly Gly Leu Val Gln Pro Glu Gly
1               5                   10                  15

Ser Leu Thr Leu Thr Cys Thr Ala Ser Gly Phe Ser Phe Ser
            20                  25                  30


<210> SEQ ID NO 684
<211> LENGTH: 6
<212> TYPE: PRT
<213> ORGANISM: Oryctolagus cuniculus

<400> SEQUENCE: 684

Ser Ser Asp Tyr Met Cys
1               5


<210> SEQ ID NO 685
<211> LENGTH: 14
<212> TYPE: PRT
<213> ORGANISM: Oryctolagus cuniculus

<400> SEQUENCE: 685

Trp Val Arg Gln Ala Pro Gly Lys Gly Leu Glu Trp Ile Gly
1               5                   10


<210> SEQ ID NO 686
<211> LENGTH: 18
<212> TYPE: PRT
<213> ORGANISM: Oryctolagus cuniculus

<400> SEQUENCE: 686

Cys Ile Asp Ala Gly Ser Ser Gly Asp Thr Tyr Phe Ala Ser Trp Ala
1               5                   10                  15

Lys Gly


<210> SEQ ID NO 687
<211> LENGTH: 31
<212> TYPE: PRT
<213> ORGANISM: Oryctolagus cuniculus

<400> SEQUENCE: 687

Arg Phe Thr Ile Ser Lys Thr Ser Ser Thr Thr Val Thr Leu Gln Met
1               5                   10                  15

Thr Ser Leu Thr Ala Ala Asp Thr Ala Thr Tyr Phe Cys Ala Arg
            20                  25                  30


<210> SEQ ID NO 688
```

<211> LENGTH: 12
<212> TYPE: PRT
<213> ORGANISM: Oryctolagus cuniculus

<400> SEQUENCE: 688

His Leu Tyr Gly Ser Ile Thr Phe Ala Phe Gly Leu
1 5 10

<210> SEQ ID NO 689
<211> LENGTH: 11
<212> TYPE: PRT
<213> ORGANISM: Artificial
<220> FEATURE:
<223> OTHER INFORMATION: Humanized Antibody Sequence

<400> SEQUENCE: 689

Trp Gly Gln Gly Thr Leu Val Thr Val Ser Ser
1 5 10

<210> SEQ ID NO 690
<211> LENGTH: 330
<212> TYPE: PRT
<213> ORGANISM: Artificial
<220> FEATURE:
<223> OTHER INFORMATION: Humanized Antibody Sequence

<400> SEQUENCE: 690

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Ala
85 90 95

Arg Val Glu Pro Lys Ser Cys Asp Lys Thr His Thr Cys Pro Pro Cys
100 105 110

Pro Ala Pro Glu Leu Leu Gly Gly Pro Ser Val Phe Leu Phe Pro Pro
115 120 125

Lys Pro Lys Asp Thr Leu Met Ile Ser Arg Thr Pro Glu Val Thr Cys
130 135 140

Val Val Val Asp Val Ser His Glu Asp Pro Glu Val Lys Phe Asn Trp
145 150 155 160

Tyr Val Asp Gly Val Glu Val His Asn Ala Lys Thr Lys Pro Arg Glu
165 170 175

Glu Gln Tyr Ala Ser Thr Tyr Arg Val Val Ser Val Leu Thr Val Leu
180 185 190

His Gln Asp Trp Leu Asn Gly Lys Glu Tyr Lys Cys Lys Val Ser Asn
195 200 205

Lys Ala Leu Pro Ala Pro Ile Glu Lys Thr Ile Ser Lys Ala Lys Gly
210 215 220

Gln Pro Arg Glu Pro Gln Val Tyr Thr Leu Pro Pro Ser Arg Glu Glu
225 230 235 240

Met Thr Lys Asn Gln Val Ser Leu Thr Cys Leu Val Lys Gly Phe Tyr
245 250 255

```
Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 691
<211> LENGTH: 1356
<212> TYPE: DNA
<213> ORGANISM: Artificial
<220> FEATURE:
<223> OTHER INFORMATION: Humanized Antibody Sequence

<400> SEQUENCE: 691

```
caggagcagc tggtggagtc cgggggaggc ctggtccagc ctgagggatc cctgacactc     60

acctgcacag cctctggatt ctccttcagt agcagcgact acatgtgctg ggtccgccag    120

gctccaggga aggggctgga gtggatcgga tgcattgatg ctggtagtag tggtgacact    180

tacttcgcga gctgggcgaa aggccgattc accatctcca aaacctcgtc gaccacggtg    240

actctgcaaa tgaccagtct gacagccgcg gacacggcca cctatttctg tgcgagacat    300

ctttatggta gtattacttt cgcctttggc ttgtggggcc agggcaccct ggtcaccgtc    360

tcgagcgcct ccaccaaggg cccatcggtc ttccccctgg caccctcctc caagagcacc    420

tctgggggca cagcggccct gggctgcctg gtcaaggact acttccccga accggtgacg    480

gtgtcgtgga actcaggcgc cctgaccagc ggcgtgcaca ccttcccggc tgtcctacag    540

tcctcaggac tctactccct cagcagcgtg gtgaccgtgc cctccagcag cttgggcacc    600

cagacctaca tctgcaacgt gaatcacaag cccagcaaca ccaaggtgga cgcgagagtt    660

gagcccaaat cttgtgacaa aactcacaca tgcccaccgt gcccagcacc tgaactcctg    720

gggggaccgt cagtcttcct cttcccccca aaacccaagg acaccctcat gatctcccgg    780

acccctgagg tcacatgcgt ggtggtggac gtgagccacg aagaccctga ggtcaagttc    840

aactggtacg tggacggcgt ggaggtgcat aatgccaaga caaagccgcg ggaggagcag    900

tacgccagca cgtaccgtgt ggtcagcgtc ctcaccgtcc tgcaccagga ctggctgaat    960

ggcaaggagt acaagtgcaa ggtctccaac aaagccctcc cagcccccat cgagaaaacc   1020

atctccaaag ccaaagggca gccccgagaa ccacaggtgt acaccctgcc cccatcccgg   1080

gaggagatga ccaagaacca ggtcagcctg acctgcctgg tcaaaggctt ctatcccagc   1140

gacatcgccg tggagtggga gagcaatggg cagccggaga acaactacaa gaccacgcct   1200

cccgtgctgg actccgacgg ctccttcttc ctctacagca agctcaccgt ggacaagagc   1260

aggtggcagc aggggaacgt cttctcatgc tccgtgatgc atgaggctct gcacaaccac   1320

tacacgcaga agagcctctc cctgtctccg ggtaaa                              1356
```

<210> SEQ ID NO 692
<211> LENGTH: 366
<212> TYPE: DNA
<213> ORGANISM: Artificial
<220> FEATURE:
<223> OTHER INFORMATION: Humanized Antibody Sequence

<400> SEQUENCE: 692
caggagcagc tggtggagtc cgggggaggc ctggtccagc ctgagggatc cctgacactc 60
acctgcacag cctctggatt ctccttcagt agcagcgact acatgtgctg ggtccgccag 120
gctccaggga aggggctgga gtggatcgga tgcattgatg ctggtagtag tggtgacact 180
tacttcgcga gctgggcgaa aggccgattc accatctcca aaacctcgtc gaccacggtg 240
actctgcaaa tgaccagtct gacagccgcg gacacggcca cctatttctg tgcgagacat 300
ctttatggta gtattacttt cgcctttggc ttgtggggcc agggcaccct ggtcaccgtc 360
tcgagc 366

<210> SEQ ID NO 693
<211> LENGTH: 90
<212> TYPE: DNA
<213> ORGANISM: Oryctolagus cuniculus

<400> SEQUENCE: 693
caggagcagc tggtggagtc cgggggaggc ctggtccagc ctgagggatc cctgacactc 60
acctgcacag cctctggatt ctccttcagt 90

<210> SEQ ID NO 694
<211> LENGTH: 18
<212> TYPE: DNA
<213> ORGANISM: Oryctolagus cuniculus

<400> SEQUENCE: 694
agcagcgact acatgtgc 18

<210> SEQ ID NO 695
<211> LENGTH: 42
<212> TYPE: DNA
<213> ORGANISM: Oryctolagus cuniculus

<400> SEQUENCE: 695
tgggtccgcc aggctccagg gaaggggctg gagtggatcg ga 42

<210> SEQ ID NO 696
<211> LENGTH: 54
<212> TYPE: DNA
<213> ORGANISM: Oryctolagus cuniculus

<400> SEQUENCE: 696
tgcattgatg ctggtagtag tggtgacact tacttcgcga gctgggcgaa aggc 54

<210> SEQ ID NO 697
<211> LENGTH: 93
<212> TYPE: DNA
<213> ORGANISM: Oryctolagus cuniculus

<400> SEQUENCE: 697
cgattcacca tctccaaaac ctcgtcgacc acggtgactc tgcaaatgac cagtctgaca 60
gccgcggaca cggccaccta tttctgtgcg aga 93

<210> SEQ ID NO 698
<211> LENGTH: 36
<212> TYPE: DNA
<213> ORGANISM: Oryctolagus cuniculus

<400> SEQUENCE: 698
catctttatg gtagtattac tttcgccttt ggcttg 36

<210> SEQ ID NO 699
<211> LENGTH: 33
<212> TYPE: DNA
<213> ORGANISM: Artificial
<220> FEATURE:
<223> OTHER INFORMATION: Humanized Antibody Sequence

<400> SEQUENCE: 699
tggggccagg gcaccctggt caccgtctcg agc 33

<210> SEQ ID NO 700
<211> LENGTH: 990
<212> TYPE: DNA
<213> ORGANISM: Artificial
<220> FEATURE:
<223> OTHER INFORMATION: Humanized Antibody Sequence

<400> SEQUENCE: 700
gcctccacca agggcccatc ggtcttcccc ctggcaccct cctccaagag cacctctggg 60
ggcacagcgg ccctgggctg cctggtcaag gactacttcc ccgaaccggt gacggtgtcg 120
tggaactcag gcgccctgac cagcggcgtg cacaccttcc cggctgtcct acagtcctca 180
ggactctact ccctcagcag cgtggtgacc gtgccctcca gcagcttggg cacccagacc 240
tacatctgca acgtgaatca caagcccagc aacaccaagg tggacgcgag agttgagccc 300
aaatcttgtg acaaaactca cacatgccca ccgtgcccag cacctgaact cctgggggga 360
ccgtcagtct tcctcttccc cccaaaaccc aaggacaccc tcatgatctc ccggacccct 420
gaggtcacat gcgtggtggt ggacgtgagc cacgaagacc ctgaggtcaa gttcaactgg 480
tacgtggacg gcgtggaggt gcataatgcc aagacaaagc cgcgggagga gcagtacgcc 540
agcacgtacc gtgtggtcag cgtcctcacc gtcctgcacc aggactggct gaatggcaag 600
gagtacaagt gcaaggtctc caacaaagcc ctcccagccc ccatcgagaa aaccatctcc 660
aaagccaaag ggcagccccg agaaccacag gtgtacaccc tgcccccatc ccgggaggag 720
atgaccaaga accaggtcag cctgacctgc ctggtcaaag gcttctatcc cagcgacatc 780
gccgtggagt gggagagcaa tgggcagccg gagaacaact acaagaccac gcctcccgtg 840
ctggactccg acggctcctt cttcctctac agcaagctca ccgtggacaa gagcaggtgg 900
cagcagggga acgtcttctc atgctccgtg atgcatgagg ctctgcacaa ccactacacg 960
cagaagagcc tctccctgtc tccgggtaaa 990

<210> SEQ ID NO 701
<211> LENGTH: 217
<212> TYPE: PRT
<213> ORGANISM: Artificial
<220> FEATURE:
<223> OTHER INFORMATION: Humanized Antibody Sequence

<400> SEQUENCE: 701

Ala Ala Val Leu Thr Gln Thr Pro Ser Pro Val Ser Ala Ala Val Gly
1 5 10 15

Gly Thr Val Thr Ile Asn Cys Gln Ala Ser Gln Ser Ile Gly Ser Asp
20 25 30

Leu Ala Trp Tyr Gln Gln Lys Pro Gly Gln Pro Pro Lys Leu Leu Ile
35 40 45

Tyr Asp Ala Ser Thr Leu Ala Ser Gly Val Pro Ser Arg Phe Ser Gly
50 55 60

```
Ser Gly Ser Gly Thr Gln Phe Thr Leu Thr Ile Ser Gly Val Gln Cys
65                  70                  75                  80

Asp Asp Ala Ala Thr Tyr Tyr Cys Gln Gly Thr Tyr Tyr Ser Ser Gly
                85                  90                  95

Trp Tyr Thr Ala Phe Gly Gly Gly Thr Glu Val Val Val Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215


<210> SEQ ID NO 702
<211> LENGTH: 111
<212> TYPE: PRT
<213> ORGANISM: Artificial
<220> FEATURE:
<223> OTHER INFORMATION: Humanized Antibody Sequence

<400> SEQUENCE: 702

Ala Ala Val Leu Thr Gln Thr Pro Ser Pro Val Ser Ala Ala Val Gly
1               5                   10                  15

Gly Thr Val Thr Ile Asn Cys Gln Ala Ser Gln Ser Ile Gly Ser Asp
            20                  25                  30

Leu Ala Trp Tyr Gln Gln Lys Pro Gly Gln Pro Pro Lys Leu Leu Ile
        35                  40                  45

Tyr Asp Ala Ser Thr Leu Ala Ser Gly Val Pro Ser Arg Phe Ser Gly
    50                  55                  60

Ser Gly Ser Gly Thr Gln Phe Thr Leu Thr Ile Ser Gly Val Gln Cys
65                  70                  75                  80

Asp Asp Ala Ala Thr Tyr Tyr Cys Gln Gly Thr Tyr Tyr Ser Ser Gly
                85                  90                  95

Trp Tyr Thr Ala Phe Gly Gly Gly Thr Glu Val Val Val Lys Arg
            100                 105                 110


<210> SEQ ID NO 703
<211> LENGTH: 23
<212> TYPE: PRT
<213> ORGANISM: Oryctolagus cuniculus

<400> SEQUENCE: 703

Ala Ala Val Leu Thr Gln Thr Pro Ser Pro Val Ser Ala Ala Val Gly
1               5                   10                  15

Gly Thr Val Thr Ile Asn Cys
            20


<210> SEQ ID NO 704
<211> LENGTH: 11
```

```
<212> TYPE: PRT
<213> ORGANISM: Oryctolagus cuniculus

<400> SEQUENCE: 704

Gln Ala Ser Gln Ser Ile Gly Ser Asp Leu Ala
1               5                   10


<210> SEQ ID NO 705
<211> LENGTH: 15
<212> TYPE: PRT
<213> ORGANISM: Oryctolagus cuniculus

<400> SEQUENCE: 705

Trp Tyr Gln Gln Lys Pro Gly Gln Pro Pro Lys Leu Leu Ile Tyr
1               5                   10                  15


<210> SEQ ID NO 706
<211> LENGTH: 7
<212> TYPE: PRT
<213> ORGANISM: Oryctolagus cuniculus

<400> SEQUENCE: 706

Asp Ala Ser Thr Leu Ala Ser
1               5


<210> SEQ ID NO 707
<211> LENGTH: 32
<212> TYPE: PRT
<213> ORGANISM: Oryctolagus cuniculus

<400> SEQUENCE: 707

Gly Val Pro Ser Arg Phe Ser Gly Ser Gly Ser Gly Thr Gln Phe Thr
1               5                   10                  15

Leu Thr Ile Ser Gly Val Gln Cys Asp Asp Ala Ala Thr Tyr Tyr Cys
            20                  25                  30


<210> SEQ ID NO 708
<211> LENGTH: 12
<212> TYPE: PRT
<213> ORGANISM: Oryctolagus cuniculus

<400> SEQUENCE: 708

Gln Gly Thr Tyr Tyr Ser Ser Gly Trp Tyr Thr Ala
1               5                   10


<210> SEQ ID NO 709
<211> LENGTH: 11
<212> TYPE: PRT
<213> ORGANISM: Artificial
<220> FEATURE:
<223> OTHER INFORMATION: Humanized Antibody Sequence

<400> SEQUENCE: 709

Phe Gly Gly Gly Thr Glu Val Val Val Lys Arg
1               5                   10


<210> SEQ ID NO 710
<211> LENGTH: 106
<212> TYPE: PRT
<213> ORGANISM: Artificial
<220> FEATURE:
<223> OTHER INFORMATION: Humanized Antibody Sequence

<400> SEQUENCE: 710

Thr Val Ala Ala Pro Ser Val Phe Ile Phe Pro Pro Ser Asp Glu Gln
```

-continued

```
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105
```

<210> SEQ ID NO 711
<211> LENGTH: 651
<212> TYPE: DNA
<213> ORGANISM: Artificial
<220> FEATURE:
<223> OTHER INFORMATION: Humanized Antibody Sequence

<400> SEQUENCE: 711

```
gcagccgtgc tgacccagac accatcgccc gtgtctgcag ctgtgggagg cacagtcacc     60

atcaattgcc aggccagtca gagcattggt agcgacttag cctggtatca gcagaaacca    120

gggcagcctc ccaagctcct gatctatgat gcatccactc tggcatctgg ggtcccatcg    180

cggttcagcg gcagtggatc tgggacacag ttcactctca ccatcagcgg cgtgcagtgt    240

gacgatgctg ccacttacta ctgtcaaggc acttattata gtagtggttg gtacactgct    300

ttcggcggag ggaccgaggt ggtggtcaaa cgtacggtag cggccccatc tgtcttcatc    360

ttcccgccat ctgatgagca gttgaaatct ggaactgcct ctgttgtgtg cctgctgaat    420

aacttctatc ccagagaggc caaagtacag tggaaggtgg ataacgccct ccaatcgggt    480

aactcccagg agagtgtcac agagcaggac agcaaggaca gcacctacag cctcagcagc    540

accctgacgc tgagcaaagc agactacgag aaacacaaag tctacgcctg cgaagtcacc    600

catcagggcc tgagctcgcc cgtcacaaag agcttcaaca ggggagagtg t             651
```

<210> SEQ ID NO 712
<211> LENGTH: 333
<212> TYPE: DNA
<213> ORGANISM: Artificial
<220> FEATURE:
<223> OTHER INFORMATION: Humanized Antibody Sequence

<400> SEQUENCE: 712

```
gcagccgtgc tgacccagac accatcgccc gtgtctgcag ctgtgggagg cacagtcacc     60

atcaattgcc aggccagtca gagcattggt agcgacttag cctggtatca gcagaaacca    120

gggcagcctc ccaagctcct gatctatgat gcatccactc tggcatctgg ggtcccatcg    180

cggttcagcg gcagtggatc tgggacacag ttcactctca ccatcagcgg cgtgcagtgt    240

gacgatgctg ccacttacta ctgtcaaggc acttattata gtagtggttg gtacactgct    300

ttcggcggag ggaccgaggt ggtggtcaaa cgt                                 333
```

<210> SEQ ID NO 713
<211> LENGTH: 69
<212> TYPE: DNA
<213> ORGANISM: Oryctolagus cuniculus

<400> SEQUENCE: 713
gcagccgtgc tgacccagac accatcgccc gtgtctgcag ctgtgggagg cacagtcacc 60
atcaattgc 69

<210> SEQ ID NO 714
<211> LENGTH: 33
<212> TYPE: DNA
<213> ORGANISM: Oryctolagus cuniculus

<400> SEQUENCE: 714
caggccagtc agagcattgg tagcgactta gcc 33

<210> SEQ ID NO 715
<211> LENGTH: 45
<212> TYPE: DNA
<213> ORGANISM: Oryctolagus cuniculus

<400> SEQUENCE: 715
tggtatcagc agaaaccagg gcagcctccc aagctcctga tctat 45

<210> SEQ ID NO 716
<211> LENGTH: 21
<212> TYPE: DNA
<213> ORGANISM: Oryctolagus cuniculus

<400> SEQUENCE: 716
gatgcatcca ctctggcatc t 21

<210> SEQ ID NO 717
<211> LENGTH: 96
<212> TYPE: DNA
<213> ORGANISM: Oryctolagus cuniculus

<400> SEQUENCE: 717
ggggtcccat cgcggttcag cggcagtgga tctgggacac agttcactct caccatcagc 60
ggcgtgcagt gtgacgatgc tgccacttac tactgt 96

<210> SEQ ID NO 718
<211> LENGTH: 36
<212> TYPE: DNA
<213> ORGANISM: Oryctolagus cuniculus

<400> SEQUENCE: 718
caaggcactt attatagtag tggttggtac actgct 36

<210> SEQ ID NO 719
<211> LENGTH: 33
<212> TYPE: DNA
<213> ORGANISM: Artificial
<220> FEATURE:
<223> OTHER INFORMATION: Humanized Antibody Sequence

<400> SEQUENCE: 719
ttcggcggag ggaccgaggt ggtggtcaaa cgt 33

<210> SEQ ID NO 720
<211> LENGTH: 318
<212> TYPE: DNA
<213> ORGANISM: Artificial
<220> FEATURE:
<223> OTHER INFORMATION: Humanized Antibody Sequence

<400> SEQUENCE: 720
acggtagcgg ccccatctgt cttcatcttc ccgccatctg atgagcagtt gaaatctgga 60
actgcctctg ttgtgtgcct gctgaataac ttctatccca gagaggccaa agtacagtgg 120
aaggtggata acgccctcca atcgggtaac tcccaggaga gtgtcacaga gcaggacagc 180
aaggacagca cctacagcct cagcagcacc ctgacgctga gcaaagcaga ctacgagaaa 240
cacaaagtct acgcctgcga agtcacccat cagggcctga gctcgcccgt cacaaagagc 300
ttcaacaggg gagagtgt 318

<210> SEQ ID NO 721
<211> LENGTH: 447
<212> TYPE: PRT
<213> ORGANISM: Artificial
<220> FEATURE:
<223> OTHER INFORMATION: Humanized Antibody Sequence

<400> SEQUENCE: 721

Gln Gln Leu Glu Gln Ser Gly Gly Gly Ala Glu Gly Gly Leu Val Lys
1 5 10 15

Pro Gly Gly Ser Leu Glu Leu Cys Cys Lys Ala Ser Gly Phe Ser Leu
20 25 30

Ser Ser Thr Tyr Trp Met Cys Trp Val Arg Gln Ala Pro Gly Lys Gly
35 40 45

Leu Glu Trp Ile Gly Cys Ile Tyr Thr Gly Ser Gly Ser Thr Asp Tyr
50 55 60

Ala Ser Trp Val Asn Gly Gln Phe Thr Leu Ser Arg Asp Ile Asp Gln
65 70 75 80

Ser Thr Gly Cys Leu Gln Leu Asn Ser Leu Thr Val Ala Asp Thr Ala
85 90 95

Met Tyr Tyr Cys Thr Lys Asn Phe Asp Leu Trp Gly Pro Gly Thr Leu
100 105 110

Val Thr Val Ser Ser Ala Ser Thr Lys Gly Pro Ser Val Phe Pro Leu
115 120 125

Ala Pro Ser Ser Lys Ser Thr Ser Gly Gly Thr Ala Ala Leu Gly Cys
130 135 140

Leu Val Lys Asp Tyr Phe Pro Glu Pro Val Thr Val Ser Trp Asn Ser
145 150 155 160

Gly Ala Leu Thr Ser Gly Val His Thr Phe Pro Ala Val Leu Gln Ser
165 170 175

Ser Gly Leu Tyr Ser Leu Ser Ser Val Val Thr Val Pro Ser Ser Ser
180 185 190

Leu Gly Thr Gln Thr Tyr Ile Cys Asn Val Asn His Lys Pro Ser Asn
195 200 205

Thr Lys Val Asp Ala Arg Val Glu Pro Lys Ser Cys Asp Lys Thr His
210 215 220

Thr Cys Pro Pro Cys Pro Ala Pro Glu Leu Leu Gly Gly Pro Ser Val
225 230 235 240

Phe Leu Phe Pro Pro Lys Pro Lys Asp Thr Leu Met Ile Ser Arg Thr
245 250 255

Pro Glu Val Thr Cys Val Val Val Asp Val Ser His Glu Asp Pro Glu
260 265 270

Val Lys Phe Asn Trp Tyr Val Asp Gly Val Glu Val His Asn Ala Lys
275 280 285

Thr Lys Pro Arg Glu Glu Gln Tyr Ala Ser Thr Tyr Arg Val Val Ser 290 295 300

Val Leu Thr Val Leu His Gln Asp Trp Leu Asn Gly Lys Glu Tyr Lys
305 310 315 320

Cys Lys Val Ser Asn Lys Ala Leu Pro Ala Pro Ile Glu Lys Thr Ile
325 330 335

Ser Lys Ala Lys Gly Gln Pro Arg Glu Pro Gln Val Tyr Thr Leu Pro
340 345 350

Pro Ser Arg Glu Glu Met Thr Lys Asn Gln Val Ser Leu Thr Cys Leu
355 360 365

Val Lys Gly Phe Tyr Pro Ser Asp Ile Ala Val Glu Trp Glu Ser Asn
370 375 380

Gly Gln Pro Glu Asn Asn Tyr Lys Thr Thr Pro Pro Val Leu Asp Ser
385 390 395 400

Asp Gly Ser Phe Phe Leu Tyr Ser Lys Leu Thr Val Asp Lys Ser Arg
405 410 415

Trp Gln Gln Gly Asn Val Phe Ser Cys Ser Val Met His Glu Ala Leu
420 425 430

His Asn His Tyr Thr Gln Lys Ser Leu Ser Leu Ser Pro Gly Lys
435 440 445

<210> SEQ ID NO 722
<211> LENGTH: 117
<212> TYPE: PRT
<213> ORGANISM: Artificial
<220> FEATURE:
<223> OTHER INFORMATION: Humanized Antibody Sequence

<400> SEQUENCE: 722

Gln Gln Leu Glu Gln Ser Gly Gly Gly Ala Glu Gly Gly Leu Val Lys
1 5 10 15

Pro Gly Gly Ser Leu Glu Leu Cys Cys Lys Ala Ser Gly Phe Ser Leu
20 25 30

Ser Ser Thr Tyr Trp Met Cys Trp Val Arg Gln Ala Pro Gly Lys Gly
35 40 45

Leu Glu Trp Ile Gly Cys Ile Tyr Thr Gly Ser Gly Ser Thr Asp Tyr
50 55 60

Ala Ser Trp Val Asn Gly Gln Phe Thr Leu Ser Arg Asp Ile Asp Gln
65 70 75 80

Ser Thr Gly Cys Leu Gln Leu Asn Ser Leu Thr Val Ala Asp Thr Ala
85 90 95

Met Tyr Tyr Cys Thr Lys Asn Phe Asp Leu Trp Gly Pro Gly Thr Leu
100 105 110

Val Thr Val Ser Ser
115

<210> SEQ ID NO 723
<211> LENGTH: 33
<212> TYPE: PRT
<213> ORGANISM: Oryctolagus cuniculus

<400> SEQUENCE: 723

Gln Gln Leu Glu Gln Ser Gly Gly Gly Ala Glu Gly Gly Leu Val Lys
1 5 10 15

Pro Gly Gly Ser Leu Glu Leu Cys Cys Lys Ala Ser Gly Phe Ser Leu
20 25 30

Ser

<210> SEQ ID NO 724
<211> LENGTH: 6
<212> TYPE: PRT
<213> ORGANISM: Oryctolagus cuniculus

<400> SEQUENCE: 724

Ser Thr Tyr Trp Met Cys
1               5

<210> SEQ ID NO 725
<211> LENGTH: 14
<212> TYPE: PRT
<213> ORGANISM: Oryctolagus cuniculus

<400> SEQUENCE: 725

Trp Val Arg Gln Ala Pro Gly Lys Gly Leu Glu Trp Ile Gly
1               5                   10

<210> SEQ ID NO 726
<211> LENGTH: 17
<212> TYPE: PRT
<213> ORGANISM: Oryctolagus cuniculus

<400> SEQUENCE: 726

Cys Ile Tyr Thr Gly Ser Gly Ser Thr Asp Tyr Ala Ser Trp Val Asn
1               5                   10                  15

Gly

<210> SEQ ID NO 727
<211> LENGTH: 32
<212> TYPE: PRT
<213> ORGANISM: Oryctolagus cuniculus

<400> SEQUENCE: 727

Gln Phe Thr Leu Ser Arg Asp Ile Asp Gln Ser Thr Gly Cys Leu Gln
1               5                   10                  15

Leu Asn Ser Leu Thr Val Ala Asp Thr Ala Met Tyr Tyr Cys Thr Lys
            20                  25                  30

<210> SEQ ID NO 728
<211> LENGTH: 4
<212> TYPE: PRT
<213> ORGANISM: Oryctolagus cuniculus

<400> SEQUENCE: 728

Asn Phe Asp Leu
1

<210> SEQ ID NO 729
<211> LENGTH: 11
<212> TYPE: PRT
<213> ORGANISM: Artificial
<220> FEATURE:
<223> OTHER INFORMATION: Humanized Antibody Sequence

<400> SEQUENCE: 729

Trp Gly Pro Gly Thr Leu Val Thr Val Ser Ser
1               5                   10

<210> SEQ ID NO 730
<211> LENGTH: 330
<212> TYPE: PRT
<213> ORGANISM: Artificial
<220> FEATURE:

<223> OTHER INFORMATION: Humanized Antibody Sequence

<400> SEQUENCE: 730

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Ala
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 731
<211> LENGTH: 1341
<212> TYPE: DNA
<213> ORGANISM: Artificial
<220> FEATURE:
<223> OTHER INFORMATION: Humanized Antibody Sequence

<400> SEQUENCE: 731

```
cagcagctgg agcagtccgg aggaggagcc gaaggaggcc tggtcaagcc tgggggatcc      60
```

```
ctggaactct gctgcaaggc ctctggattc tccctcagta gcacctactg gatgtgctgg    120

gtccgccagg ctccagggaa ggggctggag tggattggat gcatttatac tggtagtggt    180

agcacagact acgcgagctg ggtgaatggc caattcactc tctccagaga catcgaccag    240

agcacaggtt gcctacaact gaacagtctg acagtcgcgg acacggccat gtattactgt    300

acgaaaaatt ttgacttgtg gggcccgggc accctggtca ccgtctcgag cgcctccacc    360

aagggcccat cggtcttccc cctggcaccc tcctccaaga gcacctctgg gggcacagcg    420

gccctgggct gcctggtcaa ggactacttc cccgaaccgg tgacggtgtc gtggaactca    480

ggcgccctga ccagcggcgt gcacaccttc ccggctgtcc tacagtcctc aggactctac    540

tccctcagca gcgtggtgac cgtgccctcc agcagcttgg gcacccagac ctacatctgc    600

aacgtgaatc acaagcccag caacaccaag gtggacgcga gagttgagcc caaatcttgt    660

gacaaaactc acacatgccc accgtgccca gcacctgaac tcctgggggg accgtcagtc    720

ttcctcttcc ccccaaaacc caaggacacc ctcatgatct cccggacccc tgaggtcaca    780

tgcgtggtgg tggacgtgag ccacgaagac cctgaggtca agttcaactg gtacgtggac    840

ggcgtggagg tgcataatgc caagacaaag ccgcgggagg agcagtacgc cagcacgtac    900

cgtgtggtca gcgtcctcac cgtcctgcac caggactggc tgaatggcaa ggagtacaag    960

tgcaaggtct ccaacaaagc cctcccagcc cccatcgaga aaaccatctc caaagccaaa   1020

gggcagcccc gagaaccaca ggtgtacacc ctgcccccat cccgggagga gatgaccaag   1080

aaccaggtca gcctgacctg cctggtcaaa ggcttctatc ccagcgacat cgccgtggag   1140

tgggagagca atgggcagcc ggagaacaac tacaagacca cgcctcccgt gctggactcc   1200

gacggctcct tcttcctcta cagcaagctc accgtggaca agagcaggtg gcagcagggg   1260

aacgtcttct catgctccgt gatgcatgag gctctgcaca accactacac gcagaagagc   1320

ctctccctgt ctccgggtaa a                                             1341
```

<210> SEQ ID NO 732
<211> LENGTH: 351
<212> TYPE: DNA
<213> ORGANISM: Artificial
<220> FEATURE:
<223> OTHER INFORMATION: Humanized Antibody Sequence

<400> SEQUENCE: 732

```
cagcagctgg agcagtccgg aggaggagcc gaaggaggcc tggtcaagcc tgggggatcc     60

ctggaactct gctgcaaggc ctctggattc tccctcagta gcacctactg gatgtgctgg    120

gtccgccagg ctccagggaa ggggctggag tggattggat gcatttatac tggtagtggt    180

agcacagact acgcgagctg ggtgaatggc caattcactc tctccagaga catcgaccag    240

agcacaggtt gcctacaact gaacagtctg acagtcgcgg acacggccat gtattactgt    300

acgaaaaatt ttgacttgtg gggcccgggc accctggtca ccgtctcgag c             351
```

<210> SEQ ID NO 733
<211> LENGTH: 99
<212> TYPE: DNA
<213> ORGANISM: Oryctolagus cuniculus

<400> SEQUENCE: 733

```
cagcagctgg agcagtccgg aggaggagcc gaaggaggcc tggtcaagcc tgggggatcc     60

ctggaactct gctgcaaggc ctctggattc tccctcagt                            99
```

<210> SEQ ID NO 734
<211> LENGTH: 18
<212> TYPE: DNA
<213> ORGANISM: Oryctolagus cuniculus

<400> SEQUENCE: 734
agcacctact ggatgtgc 18

<210> SEQ ID NO 735
<211> LENGTH: 42
<212> TYPE: DNA
<213> ORGANISM: Oryctolagus cuniculus

<400> SEQUENCE: 735
tgggtccgcc aggctccagg gaaggggctg gagtggattg ga 42

<210> SEQ ID NO 736
<211> LENGTH: 51
<212> TYPE: DNA
<213> ORGANISM: Oryctolagus cuniculus

<400> SEQUENCE: 736
tgcatttata ctggtagtgg tagcacagac tacgcgagct gggtgaatgg c 51

<210> SEQ ID NO 737
<211> LENGTH: 96
<212> TYPE: DNA
<213> ORGANISM: Oryctolagus cuniculus

<400> SEQUENCE: 737
caattcactc tctccagaga catcgaccag agcacaggtt gcctacaact gaacagtctg 60
acagtcgcgg acacggccat gtattactgt acgaaa 96

<210> SEQ ID NO 738
<211> LENGTH: 12
<212> TYPE: DNA
<213> ORGANISM: Oryctolagus cuniculus

<400> SEQUENCE: 738
aattttgact tg 12

<210> SEQ ID NO 739
<211> LENGTH: 33
<212> TYPE: DNA
<213> ORGANISM: Artificial
<220> FEATURE:
<223> OTHER INFORMATION: Humanized Antibody Sequence

<400> SEQUENCE: 739
tggggcccgg gcaccctggt caccgtctcg agc 33

<210> SEQ ID NO 740
<211> LENGTH: 990
<212> TYPE: DNA
<213> ORGANISM: Artificial
<220> FEATURE:
<223> OTHER INFORMATION: Humanized Antibody Sequence

<400> SEQUENCE: 740
gcctccacca agggcccatc ggtcttcccc ctggcaccct cctccaagag cacctctggg 60
ggcacagcgg ccctgggctg cctggtcaag gactacttcc ccgaaccggt gacggtgtcg 120
tggaactcag gcgccctgac cagcggcgtg cacaccttcc cggctgtcct acagtcctca 180

```
ggactctact ccctcagcag cgtggtgacc gtgccctcca gcagcttggg cacccagacc    240

tacatctgca acgtgaatca caagcccagc aacaccaagg tggacgcgag agttgagccc    300

aaatcttgtg acaaaactca cacatgccca ccgtgcccag cacctgaact cctgggggga    360

ccgtcagtct tcctcttccc cccaaaaccc aaggacaccc tcatgatctc ccggacccct    420

gaggtcacat gcgtggtggt ggacgtgagc cacgaagacc ctgaggtcaa gttcaactgg    480

tacgtggacg gcgtggaggt gcataatgcc aagacaaagc cgcgggagga gcagtacgcc    540

agcacgtacc gtgtggtcag cgtcctcacc gtcctgcacc aggactggct gaatggcaag    600

gagtacaagt gcaaggtctc caacaaagcc ctcccagccc ccatcgagaa aaccatctcc    660

aaagccaaag ggcagccccg agaaccacag gtgtacaccc tgcccccatc ccgggaggag    720

atgaccaaga accaggtcag cctgacctgc ctggtcaaag gcttctatcc cagcgacatc    780

gccgtggagt gggagagcaa tgggcagccg gagaacaact acaagaccac gcctcccgtg    840

ctggactccg acggctcctt cttcctctac agcaagctca ccgtggacaa gagcaggtgg    900

cagcagggga acgtcttctc atgctccgtg atgcatgagg ctctgcacaa ccactacacg    960

cagaagagcc tctccctgtc tccgggtaaa                                      990
```

<210> SEQ ID NO 741
<211> LENGTH: 220
<212> TYPE: PRT
<213> ORGANISM: Artificial
<220> FEATURE:
<223> OTHER INFORMATION: Humanized Antibody Sequence

<400> SEQUENCE: 741

```
Ala Gln Val Leu Thr Gln Thr Pro Ser Ser Val Ser Ala Ala Val Gly
1               5                   10                  15

Gly Thr Val Thr Ile Asn Cys Gln Ser Ser Pro Ser Val Tyr Ser Asn
            20                  25                  30

Asn Tyr Leu Ser Trp Phe Gln Gln Lys Pro Gly Gln Pro Pro Lys Gly
        35                  40                  45

Leu Ile Ala Asp Ala Ser Thr Leu Ala Ser Gly Val Pro Ser Arg Phe
    50                  55                  60

Lys Gly Ser Gly Ser Gly Thr Gln Phe Thr Leu Thr Ile Ser Gly Val
65                  70                  75                  80

Gln Cys Asp Asp Ala Ala Ala Tyr Tyr Cys Leu Gly Tyr Tyr Asp Cys
                85                  90                  95

Gly Ser Thr Asp Cys His Ala Phe Gly Gly Gly Thr Glu Val Val Val
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 742
<211> LENGTH: 114
<212> TYPE: PRT
<213> ORGANISM: Artificial
<220> FEATURE:
<223> OTHER INFORMATION: Humanized Antibody Sequence

<400> SEQUENCE: 742

```
Ala Gln Val Leu Thr Gln Thr Pro Ser Ser Val Ser Ala Ala Val Gly
1               5                   10                  15

Gly Thr Val Thr Ile Asn Cys Gln Ser Ser Pro Ser Val Tyr Ser Asn
            20                  25                  30

Asn Tyr Leu Ser Trp Phe Gln Gln Lys Pro Gly Gln Pro Pro Lys Gly
        35                  40                  45

Leu Ile Ala Asp Ala Ser Thr Leu Ala Ser Gly Val Pro Ser Arg Phe
    50                  55                  60

Lys Gly Ser Gly Ser Gly Thr Gln Phe Thr Leu Thr Ile Ser Gly Val
65                  70                  75                  80

Gln Cys Asp Asp Ala Ala Ala Tyr Tyr Cys Leu Gly Tyr Tyr Asp Cys
                85                  90                  95

Gly Ser Thr Asp Cys His Ala Phe Gly Gly Gly Thr Glu Val Val Val
            100                 105                 110

Lys Arg
```

<210> SEQ ID NO 743
<211> LENGTH: 23
<212> TYPE: PRT
<213> ORGANISM: Oryctolagus cuniculus

<400> SEQUENCE: 743

```
Ala Gln Val Leu Thr Gln Thr Pro Ser Ser Val Ser Ala Ala Val Gly
1               5                   10                  15

Gly Thr Val Thr Ile Asn Cys
            20
```

<210> SEQ ID NO 744
<211> LENGTH: 13
<212> TYPE: PRT
<213> ORGANISM: Oryctolagus cuniculus

<400> SEQUENCE: 744

```
Gln Ser Ser Pro Ser Val Tyr Ser Asn Asn Tyr Leu Ser
1               5                   10
```

<210> SEQ ID NO 745
<211> LENGTH: 15
<212> TYPE: PRT
<213> ORGANISM: Oryctolagus cuniculus

<400> SEQUENCE: 745

```
Trp Phe Gln Gln Lys Pro Gly Gln Pro Pro Lys Gly Leu Ile Ala
1               5                   10                  15
```

<210> SEQ ID NO 746
<211> LENGTH: 7
<212> TYPE: PRT
<213> ORGANISM: Oryctolagus cuniculus

<400> SEQUENCE: 746

```
Asp Ala Ser Thr Leu Ala Ser
```

1 5

<210> SEQ ID NO 747
<211> LENGTH: 32
<212> TYPE: PRT
<213> ORGANISM: Oryctolagus cuniculus

<400> SEQUENCE: 747

Gly Val Pro Ser Arg Phe Lys Gly Ser Gly Ser Gly Thr Gln Phe Thr
1 5 10 15

Leu Thr Ile Ser Gly Val Gln Cys Asp Asp Ala Ala Ala Tyr Tyr Cys
20 25 30

<210> SEQ ID NO 748
<211> LENGTH: 13
<212> TYPE: PRT
<213> ORGANISM: Oryctolagus cuniculus

<400> SEQUENCE: 748

Leu Gly Tyr Tyr Asp Cys Gly Ser Thr Asp Cys His Ala
1 5 10

<210> SEQ ID NO 749
<211> LENGTH: 11
<212> TYPE: PRT
<213> ORGANISM: Artificial
<220> FEATURE:
<223> OTHER INFORMATION: Humanized Antibody Sequence

<400> SEQUENCE: 749

Phe Gly Gly Gly Thr Glu Val Val Val Lys Arg
1 5 10

<210> SEQ ID NO 750
<211> LENGTH: 106
<212> TYPE: PRT
<213> ORGANISM: Artificial
<220> FEATURE:
<223> OTHER INFORMATION: Humanized Antibody Sequence

<400> SEQUENCE: 750

Thr Val Ala Ala Pro Ser Val Phe Ile Phe Pro Pro Ser Asp Glu Gln
1 5 10 15

Leu Lys Ser Gly Thr Ala Ser Val Val Cys Leu Leu Asn Asn Phe Tyr
20 25 30

Pro Arg Glu Ala Lys Val Gln Trp Lys Val Asp Asn Ala Leu Gln Ser
35 40 45

Gly Asn Ser Gln Glu Ser Val Thr Glu Gln Asp Ser Lys Asp Ser Thr
50 55 60

Tyr Ser Leu Ser Ser Thr Leu Thr Leu Ser Lys Ala Asp Tyr Glu Lys
65 70 75 80

His Lys Val Tyr Ala Cys Glu Val Thr His Gln Gly Leu Ser Ser Pro
85 90 95

Val Thr Lys Ser Phe Asn Arg Gly Glu Cys
100 105

<210> SEQ ID NO 751
<211> LENGTH: 660
<212> TYPE: DNA
<213> ORGANISM: Artificial
<220> FEATURE:
<223> OTHER INFORMATION: Humanized Antibody Sequence

<400> SEQUENCE: 751
gcccaagtgc tgacccagac tccatcctcc gtgtctgcag ctgtgggagg cacagtcacc 60
atcaattgcc agtccagtcc gagtgtttat agtaacaact acttatcctg gtttcagcag 120
aaaccagggc agcctcccaa aggcctgatc gctgatgcat ccactctggc atctggggtc 180
ccatcgcggt tcaaaggcag tggatctggg acacagttca ctctcaccat cagcggcgtg 240
cagtgtgacg atgctgccgc ttactactgt ctaggctatt atgattgtgg tagtactgat 300
tgtcatgctt tcggcggagg gaccgaggtg gtggtcaaac gtacggtagc ggccccatct 360
gtcttcatct tcccgccatc tgatgagcag ttgaaatctg gaactgcctc tgttgtgtgc 420
ctgctgaata acttctatcc cagagaggcc aaagtacagt ggaaggtgga taacgccctc 480
caatcgggta actcccagga gagtgtcaca gagcaggaca gcaaggacag cacctacagc 540
ctcagcagca ccctgacgct gagcaaagca gactacgaga aacacaaagt ctacgcctgc 600
gaagtcaccc atcagggcct gagctcgccc gtcacaaaga gcttcaacag gggagagtgt 660

<210> SEQ ID NO 752
<211> LENGTH: 342
<212> TYPE: DNA
<213> ORGANISM: Artificial
<220> FEATURE:
<223> OTHER INFORMATION: Humanized Antibody Sequence

<400> SEQUENCE: 752
gcccaagtgc tgacccagac tccatcctcc gtgtctgcag ctgtgggagg cacagtcacc 60
atcaattgcc agtccagtcc gagtgtttat agtaacaact acttatcctg gtttcagcag 120
aaaccagggc agcctcccaa aggcctgatc gctgatgcat ccactctggc atctggggtc 180
ccatcgcggt tcaaaggcag tggatctggg acacagttca ctctcaccat cagcggcgtg 240
cagtgtgacg atgctgccgc ttactactgt ctaggctatt atgattgtgg tagtactgat 300
tgtcatgctt tcggcggagg gaccgaggtg gtggtcaaac gt 342

<210> SEQ ID NO 753
<211> LENGTH: 69
<212> TYPE: DNA
<213> ORGANISM: Oryctolagus cuniculus

<400> SEQUENCE: 753
gcccaagtgc tgacccagac tccatcctcc gtgtctgcag ctgtgggagg cacagtcacc 60
atcaattgc 69

<210> SEQ ID NO 754
<211> LENGTH: 39
<212> TYPE: DNA
<213> ORGANISM: Oryctolagus cuniculus

<400> SEQUENCE: 754
cagtccagtc cgagtgttta tagtaacaac tacttatcc 39

<210> SEQ ID NO 755
<211> LENGTH: 45
<212> TYPE: DNA
<213> ORGANISM: Oryctolagus cuniculus

<400> SEQUENCE: 755
tggtttcagc agaaaccagg gcagcctccc aaaggcctga tcgct 45

<210> SEQ ID NO 756
<211> LENGTH: 21
<212> TYPE: DNA
<213> ORGANISM: Oryctolagus cuniculus

<400> SEQUENCE: 756
gatgcatcca ctctggcatc t 21

<210> SEQ ID NO 757
<211> LENGTH: 96
<212> TYPE: DNA
<213> ORGANISM: Oryctolagus cuniculus

<400> SEQUENCE: 757
ggggtcccat cgcggttcaa aggcagtgga tctgggacac agttcactct caccatcagc 60
ggcgtgcagt gtgacgatgc tgccgcttac tactgt 96

<210> SEQ ID NO 758
<211> LENGTH: 39
<212> TYPE: DNA
<213> ORGANISM: Oryctolagus cuniculus

<400> SEQUENCE: 758
ctaggctatt atgattgtgg tagtactgat tgtcatgct 39

<210> SEQ ID NO 759
<211> LENGTH: 33
<212> TYPE: DNA
<213> ORGANISM: Artificial
<220> FEATURE:
<223> OTHER INFORMATION: Humanized Antibody Sequence

<400> SEQUENCE: 759
ttcggcggag ggaccgaggt ggtggtcaaa cgt 33

<210> SEQ ID NO 760
<211> LENGTH: 318
<212> TYPE: DNA
<213> ORGANISM: Artificial
<220> FEATURE:
<223> OTHER INFORMATION: Humanized Antibody Sequence

<400> SEQUENCE: 760
acggtagcgg ccccatctgt cttcatcttc ccgccatctg atgagcagtt gaaatctgga 60
actgcctctg ttgtgtgcct gctgaataac ttctatccca gagaggccaa agtacagtgg 120
aaggtggata acgccctcca atcgggtaac tcccaggaga gtgtcacaga gcaggacagc 180
aaggacagca cctacagcct cagcagcacc ctgacgctga gcaaagcaga ctacgagaaa 240
cacaaagtct acgcctgcga agtcacccat cagggcctga gctcgcccgt cacaaagagc 300
ttcaacaggg gagagtgt 318

<210> SEQ ID NO 761
<211> LENGTH: 447
<212> TYPE: PRT
<213> ORGANISM: Artificial
<220> FEATURE:
<223> OTHER INFORMATION: Humanized Antibody Sequence

<400> SEQUENCE: 761

Gln Gln Leu Glu Gln Ser Gly Gly Gly Ala Glu Gly Gly Leu Val Lys
1 5 10 15

Pro Gly Gly Ser Leu Glu Leu Cys Cys Lys Ala Ser Gly Phe Ser Leu

-continued

```
            20                  25                  30

Thr Thr Ser His Trp Met Cys Trp Val Arg Gln Ala Pro Gly Lys Gly
        35                  40                  45

Leu Asn Trp Ile Gly Cys Ile Ser Ala Gly Ser Gly Asp Ala Asp Tyr
    50                  55                  60

Ala Thr Trp Val Asp Ala Gln Phe Thr Leu Ser Arg Asp Ile Asp Gln
65                  70                  75                  80

Asn Thr Gly Cys Leu Gln Leu Asn Ser Leu Thr Pro Ala Asp Thr Ala
                85                  90                  95

Met Tyr Tyr Cys Thr Ile Asn Phe Glu Leu Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Ala Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Ala Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445
```

<210> SEQ ID NO 762
<211> LENGTH: 117
<212> TYPE: PRT
<213> ORGANISM: Artificial
<220> FEATURE:
<223> OTHER INFORMATION: Humanized Antibody Sequence

<400> SEQUENCE: 762

```
Gln Gln Leu Glu Gln Ser Gly Gly Gly Ala Glu Gly Gly Leu Val Lys
1               5                   10                  15

Pro Gly Gly Ser Leu Glu Leu Cys Cys Lys Ala Ser Gly Phe Ser Leu
            20                  25                  30

Thr Thr Ser His Trp Met Cys Trp Val Arg Gln Ala Pro Gly Lys Gly
        35                  40                  45

Leu Asn Trp Ile Gly Cys Ile Ser Ala Gly Ser Gly Asp Ala Asp Tyr
    50                  55                  60

Ala Thr Trp Val Asp Ala Gln Phe Thr Leu Ser Arg Asp Ile Asp Gln
65                  70                  75                  80

Asn Thr Gly Cys Leu Gln Leu Asn Ser Leu Thr Pro Ala Asp Thr Ala
                85                  90                  95

Met Tyr Tyr Cys Thr Ile Asn Phe Glu Leu Trp Gly Gln Gly Thr Leu
            100                 105                 110

Val Thr Val Ser Ser
        115
```

<210> SEQ ID NO 763
<211> LENGTH: 33
<212> TYPE: PRT
<213> ORGANISM: Oryctolagus cuniculus

<400> SEQUENCE: 763

```
Gln Gln Leu Glu Gln Ser Gly Gly Gly Ala Glu Gly Gly Leu Val Lys
1               5                   10                  15

Pro Gly Gly Ser Leu Glu Leu Cys Cys Lys Ala Ser Gly Phe Ser Leu
            20                  25                  30

Thr
```

<210> SEQ ID NO 764
<211> LENGTH: 6
<212> TYPE: PRT
<213> ORGANISM: Oryctolagus cuniculus

<400> SEQUENCE: 764

```
Thr Ser His Trp Met Cys
1               5
```

<210> SEQ ID NO 765
<211> LENGTH: 14
<212> TYPE: PRT
<213> ORGANISM: Oryctolagus cuniculus

<400> SEQUENCE: 765

```
Trp Val Arg Gln Ala Pro Gly Lys Gly Leu Asn Trp Ile Gly
1               5                   10
```

<210> SEQ ID NO 766
<211> LENGTH: 17
<212> TYPE: PRT
<213> ORGANISM: Oryctolagus cuniculus

<400> SEQUENCE: 766

```
Cys Ile Ser Ala Gly Ser Gly Asp Ala Asp Tyr Ala Thr Trp Val Asp
1               5                   10                  15

Ala
```

<210> SEQ ID NO 767
<211> LENGTH: 32
<212> TYPE: PRT
<213> ORGANISM: Oryctolagus cuniculus

<400> SEQUENCE: 767

```
Gln Phe Thr Leu Ser Arg Asp Ile Asp Gln Asn Thr Gly Cys Leu Gln
1               5                   10                  15

Leu Asn Ser Leu Thr Pro Ala Asp Thr Ala Met Tyr Tyr Cys Thr Ile
            20                  25                  30
```

<210> SEQ ID NO 768
<211> LENGTH: 4
<212> TYPE: PRT
<213> ORGANISM: Oryctolagus cuniculus

<400> SEQUENCE: 768

```
Asn Phe Glu Leu
1
```

<210> SEQ ID NO 769
<211> LENGTH: 11
<212> TYPE: PRT
<213> ORGANISM: Artificial
<220> FEATURE:
<223> OTHER INFORMATION: Humanized Antibody Sequence

<400> SEQUENCE: 769

```
Trp Gly Gln Gly Thr Leu Val Thr Val Ser Ser
1               5                   10
```

<210> SEQ ID NO 770
<211> LENGTH: 330
<212> TYPE: PRT
<213> ORGANISM: Artificial
<220> FEATURE:
<223> OTHER INFORMATION: Humanized Antibody Sequence

<400> SEQUENCE: 770

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Ala
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125
```

```
Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 771
<211> LENGTH: 1341
<212> TYPE: DNA
<213> ORGANISM: Artificial
<220> FEATURE:
<223> OTHER INFORMATION: Humanized Antibody Sequence

<400> SEQUENCE: 771

```
cagcagctgg agcagtccgg aggaggagcc gaaggaggcc tggtcaagcc tgggggatcc     60

ctggaactct gctgcaaagc ctctggattc tccctcacta cgagccactg gatgtgttgg    120

gtccgccagg ctccagggaa ggggctgaat tggattggat gcattagtgc cggtagtggt    180

gacgcagact acgcgacctg ggtggatgcc caattcactc tctccagaga catcgaccag    240

aacacaggtt gcctacaatt gaacagtctg acacccgcgg acacggccat gtattactgt    300

acgataaatt ttgagttgtg gggccaaggc accctggtca ccgtctcgag cgcctccacc    360

aagggcccat cggtcttccc cctggcaccc tcctccaaga gcacctctgg gggcacagcg    420

gccctgggct gcctggtcaa ggactacttc cccgaaccgg tgacggtgtc gtggaactca    480

ggcgccctga ccagcggcgt gcacaccttc ccggctgtcc tacagtcctc aggactctac    540

tccctcagca gcgtggtgac cgtgccctcc agcagcttgg gcacccagac ctacatctgc    600

aacgtgaatc acaagcccag caacaccaag gtggacgcga gagttgagcc caaatcttgt    660

gacaaaactc acacatgccc accgtgccca gcacctgaac tcctgggggg accgtcagtc    720

ttcctcttcc ccccaaaacc caaggacacc ctcatgatct cccggacccc tgaggtcaca    780

tgcgtggtgg tggacgtgag ccacgaagac cctgaggtca agttcaactg gtacgtggac    840

ggcgtggagg tgcataatgc caagacaaag ccgcgggagg agcagtacgc cagcacgtac    900
```

-continued cgtgtggtca gcgtcctcac cgtcctgcac caggactggc tgaatggcaa ggagtacaag 960
tgcaaggtct ccaacaaagc cctcccagcc cccatcgaga aaaccatctc caaagccaaa 1020
gggcagcccc gagaaccaca ggtgtacacc ctgcccccat cccgggagga gatgaccaag 1080
aaccaggtca gcctgacctg cctggtcaaa ggcttctatc ccagcgacat cgccgtggag 1140
tgggagagca atgggcagcc ggagaacaac tacaagacca cgcctcccgt gctggactcc 1200
gacggctcct tcttcctcta cagcaagctc accgtggaca agagcaggtg gcagcagggg 1260
aacgtcttct catgctccgt gatgcatgag gctctgcaca accactacac gcagaagagc 1320
ctctccctgt ctccgggtaa a 1341

<210> SEQ ID NO 772
<211> LENGTH: 351
<212> TYPE: DNA
<213> ORGANISM: Artificial
<220> FEATURE:
<223> OTHER INFORMATION: Humanized Antibody Sequence

<400> SEQUENCE: 772
cagcagctgg agcagtccgg aggaggagcc gaaggaggcc tggtcaagcc tgggggatcc 60
ctggaactct gctgcaaagc ctctggattc tccctcacta cgagccactg gatgtgttgg 120
gtccgccagg ctccagggaa ggggctgaat tggattggat gcattagtgc cggtagtggt 180
gacgcagact acgcgacctg ggtggatgcc caattcactc tctccagaga catcgaccag 240
aacacaggtt gcctacaatt gaacagtctg acacccgcgg acacggccat gtattactgt 300
acgataaatt ttgagttgtg gggccaaggc accctggtca ccgtctcgag c 351

<210> SEQ ID NO 773
<211> LENGTH: 99
<212> TYPE: DNA
<213> ORGANISM: Oryctolagus cuniculus

<400> SEQUENCE: 773
cagcagctgg agcagtccgg aggaggagcc gaaggaggcc tggtcaagcc tgggggatcc 60
ctggaactct gctgcaaagc ctctggattc tccctcact 99

<210> SEQ ID NO 774
<211> LENGTH: 18
<212> TYPE: DNA
<213> ORGANISM: Oryctolagus cuniculus

<400> SEQUENCE: 774
acgagccact ggatgtgt 18

<210> SEQ ID NO 775
<211> LENGTH: 42
<212> TYPE: DNA
<213> ORGANISM: Oryctolagus cuniculus

<400> SEQUENCE: 775
tgggtccgcc aggctccagg gaaggggctg aattggattg ga 42

<210> SEQ ID NO 776
<211> LENGTH: 51
<212> TYPE: DNA
<213> ORGANISM: Oryctolagus cuniculus

<400> SEQUENCE: 776
tgcattagtg ccggtagtgg tgacgcagac tacgcgacct gggtggatgc c 51

<210> SEQ ID NO 777
<211> LENGTH: 96
<212> TYPE: DNA
<213> ORGANISM: Oryctolagus cuniculus

<400> SEQUENCE: 777
caattcactc tctccagaga catcgaccag aacacaggtt gcctacaatt gaacagtctg 60
acacccgcgg acacggccat gtattactgt acgata 96

<210> SEQ ID NO 778
<211> LENGTH: 12
<212> TYPE: DNA
<213> ORGANISM: Oryctolagus cuniculus

<400> SEQUENCE: 778
aattttgagt tg 12

<210> SEQ ID NO 779
<211> LENGTH: 33
<212> TYPE: DNA
<213> ORGANISM: Artificial
<220> FEATURE:
<223> OTHER INFORMATION: Humanized Antibody Sequence

<400> SEQUENCE: 779
tggggccaag gcaccctggt caccgtctcg agc 33

<210> SEQ ID NO 780
<211> LENGTH: 990
<212> TYPE: DNA
<213> ORGANISM: Artificial
<220> FEATURE:
<223> OTHER INFORMATION: Humanized Antibody Sequence

<400> SEQUENCE: 780
gcctccacca agggcccatc ggtcttcccc ctggcaccct cctccaagag cacctctggg 60
ggcacagcgg ccctgggctg cctggtcaag gactacttcc ccgaaccggt gacggtgtcg 120
tggaactcag gcgccctgac cagcggcgtg cacaccttcc cggctgtcct acagtcctca 180
ggactctact ccctcagcag cgtggtgacc gtgccctcca gcagcttggg cacccagacc 240
tacatctgca acgtgaatca caagcccagc aacaccaagg tggacgcgag agttgagccc 300
aaatcttgtg acaaaactca cacatgccca ccgtgcccag cacctgaact cctgggggga 360
ccgtcagtct tcctcttccc cccaaaaccc aaggacaccc tcatgatctc ccggacccct 420
gaggtcacat gcgtggtggt ggacgtgagc cacgaagacc ctgaggtcaa gttcaactgg 480
tacgtggacg gcgtggaggt gcataatgcc aagacaaagc cgcgggagga gcagtacgcc 540
agcacgtacc gtgtggtcag cgtcctcacc gtcctgcacc aggactggct gaatggcaag 600
gagtacaagt gcaaggtctc caacaaagcc ctcccagccc ccatcgagaa aaccatctcc 660
aaagccaaag ggcagccccg agaaccacag gtgtacaccc tgcccccatc ccgggaggag 720
atgaccaaga accaggtcag cctgacctgc ctggtcaaag gcttctatcc cagcgacatc 780
gccgtggagt gggagagcaa tgggcagccg gagaacaact acaagaccac gcctcccgtg 840
ctggactccg acggctcctt cttcctctac agcaagctca ccgtggacaa gagcaggtgg 900
cagcagggga acgtcttctc atgctccgtg atgcatgagg ctctgcacaa ccactacacg 960
cagaagagcc tctccctgtc tccgggtaaa 990

<210> SEQ ID NO 781
<211> LENGTH: 219
<212> TYPE: PRT
<213> ORGANISM: Artificial
<220> FEATURE:
<223> OTHER INFORMATION: Humanized Antibody Sequence

<400> SEQUENCE: 781

Ala Gln Val Leu Thr Gln Thr Pro Ser Ser Val Ser Ala Ala Val Gly
1               5                   10                  15

Gly Thr Val Thr Ile Asn Cys Gln Ser Ser Pro Ser Val Tyr Ser Ser
            20                  25                  30

Tyr Leu Ser Trp Phe Gln Gln Lys Pro Gly Gln Pro Pro Lys Phe Leu
        35                  40                  45

Ile Tyr Glu Ala Ser Lys Leu Ala Ser Gly Val Pro Ser Arg Phe Ser
    50                  55                  60

Gly Ser Gly Ser Gly Thr Gln Phe Thr Leu Thr Ile Ser Gly Val Gln
65                  70                  75                  80

Cys Ser Asp Ala Ala Thr Tyr Tyr Cys Leu Gly Ala Tyr Asp Cys Gly
                85                  90                  95

Arg Thr Asp Cys His Ala Phe Gly Gly Gly Thr Glu Val Val Val Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 782
<211> LENGTH: 113
<212> TYPE: PRT
<213> ORGANISM: Artificial
<220> FEATURE:
<223> OTHER INFORMATION: Humanized Antibody Sequence

<400> SEQUENCE: 782

Ala Gln Val Leu Thr Gln Thr Pro Ser Ser Val Ser Ala Ala Val Gly
1               5                   10                  15

Gly Thr Val Thr Ile Asn Cys Gln Ser Ser Pro Ser Val Tyr Ser Ser
            20                  25                  30

Tyr Leu Ser Trp Phe Gln Gln Lys Pro Gly Gln Pro Pro Lys Phe Leu
        35                  40                  45

Ile Tyr Glu Ala Ser Lys Leu Ala Ser Gly Val Pro Ser Arg Phe Ser
    50                  55                  60

Gly Ser Gly Ser Gly Thr Gln Phe Thr Leu Thr Ile Ser Gly Val Gln
65                  70                  75                  80

Cys Ser Asp Ala Ala Thr Tyr Tyr Cys Leu Gly Ala Tyr Asp Cys Gly
                85                  90                  95

Arg Thr Asp Cys His Ala Phe Gly Gly Gly Thr Glu Val Val Val Lys
100 105 110

Arg

<210> SEQ ID NO 783
<211> LENGTH: 23
<212> TYPE: PRT
<213> ORGANISM: Oryctolagus cuniculus

<400> SEQUENCE: 783

Ala Gln Val Leu Thr Gln Thr Pro Ser Ser Val Ser Ala Ala Val Gly
1 5 10 15

Gly Thr Val Thr Ile Asn Cys
20

<210> SEQ ID NO 784
<211> LENGTH: 12
<212> TYPE: PRT
<213> ORGANISM: Oryctolagus cuniculus

<400> SEQUENCE: 784

Gln Ser Ser Pro Ser Val Tyr Ser Ser Tyr Leu Ser
1 5 10

<210> SEQ ID NO 785
<211> LENGTH: 15
<212> TYPE: PRT
<213> ORGANISM: Oryctolagus cuniculus

<400> SEQUENCE: 785

Trp Phe Gln Gln Lys Pro Gly Gln Pro Pro Lys Phe Leu Ile Tyr
1 5 10 15

<210> SEQ ID NO 786
<211> LENGTH: 7
<212> TYPE: PRT
<213> ORGANISM: Oryctolagus cuniculus

<400> SEQUENCE: 786

Glu Ala Ser Lys Leu Ala Ser
1 5

<210> SEQ ID NO 787
<211> LENGTH: 32
<212> TYPE: PRT
<213> ORGANISM: Oryctolagus cuniculus

<400> SEQUENCE: 787

Gly Val Pro Ser Arg Phe Ser Gly Ser Gly Ser Gly Thr Gln Phe Thr
1 5 10 15

Leu Thr Ile Ser Gly Val Gln Cys Ser Asp Ala Ala Thr Tyr Tyr Cys
20 25 30

<210> SEQ ID NO 788
<211> LENGTH: 13
<212> TYPE: PRT
<213> ORGANISM: Oryctolagus cuniculus

<400> SEQUENCE: 788

Leu Gly Ala Tyr Asp Cys Gly Arg Thr Asp Cys His Ala
1 5 10

<210> SEQ ID NO 789
<211> LENGTH: 11
<212> TYPE: PRT
<213> ORGANISM: Artificial
<220> FEATURE:
<223> OTHER INFORMATION: Humanized Antibody Sequence

<400> SEQUENCE: 789

Phe Gly Gly Gly Thr Glu Val Val Val Lys Arg
1               5                   10

<210> SEQ ID NO 790
<211> LENGTH: 106
<212> TYPE: PRT
<213> ORGANISM: Artificial
<220> FEATURE:
<223> OTHER INFORMATION: Humanized Antibody Sequence

<400> SEQUENCE: 790

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 791
<211> LENGTH: 657
<212> TYPE: DNA
<213> ORGANISM: Artificial
<220> FEATURE:
<223> OTHER INFORMATION: Humanized Antibody Sequence

<400> SEQUENCE: 791
gcccaagtgc tgacccagac tccatcctcc gtgtctgcag ctgtgggagg cacagtcacc 60
atcaattgcc agtccagtcc gagtgtttat agtagctact tatcctggtt tcagcagaaa 120
ccagggcagc ctcccaagtt cctgatctac gaagcatcca aactggcatc tggggtccca 180
tcgcggttca gcggcagtgg atctgggaca cagttcactc tcaccatcag cggcgtgcag 240
tgtagcgatg ctgccactta ctactgtctt ggcgcgtatg attgtggtcg tactgattgt 300
catgctttcg gcggagggac cgaggtggtg gtcaaacgta cggtagcggc cccatctgtc 360
ttcatcttcc cgccatctga tgagcagttg aaatctggaa ctgcctctgt tgtgtgcctg 420
ctgaataact tctatcccag agaggccaaa gtacagtgga aggtggataa cgccctccaa 480
tcgggtaact cccaggagag tgtcacagag caggacagca aggacagcac ctacagcctc 540
agcagcaccc tgacgctgag caaagcagac tacgagaaac acaaagtcta cgcctgcgaa 600
gtcacccatc agggcctgag ctcgcccgtc acaaagagct tcaacagggg agagtgt 657

<210> SEQ ID NO 792
<211> LENGTH: 339
<212> TYPE: DNA

<213> ORGANISM: Artificial
<220> FEATURE:
<223> OTHER INFORMATION: Humanized Antibody Sequence

<400> SEQUENCE: 792
gcccaagtgc tgacccagac tccatcctcc gtgtctgcag ctgtgggagg cacagtcacc 60
atcaattgcc agtccagtcc gagtgtttat agtagctact tatcctggtt tcagcagaaa 120
ccagggcagc ctcccaagtt cctgatctac gaagcatcca aactggcatc tggggtccca 180
tcgcggttca gcggcagtgg atctgggaca cagttcactc tcaccatcag cggcgtgcag 240
tgtagcgatg ctgccactta ctactgtctt ggcgcgtatg attgtggtcg tactgattgt 300
catgctttcg gcggagggac cgaggtggtg gtcaaacgt 339

<210> SEQ ID NO 793
<211> LENGTH: 69
<212> TYPE: DNA
<213> ORGANISM: Oryctolagus cuniculus

<400> SEQUENCE: 793
gcccaagtgc tgacccagac tccatcctcc gtgtctgcag ctgtgggagg cacagtcacc 60
atcaattgc 69

<210> SEQ ID NO 794
<211> LENGTH: 36
<212> TYPE: DNA
<213> ORGANISM: Oryctolagus cuniculus

<400> SEQUENCE: 794
cagtccagtc cgagtgttta tagtagctac ttatcc 36

<210> SEQ ID NO 795
<211> LENGTH: 45
<212> TYPE: DNA
<213> ORGANISM: Oryctolagus cuniculus

<400> SEQUENCE: 795
tggtttcagc agaaaccagg gcagcctccc aagttcctga tctac 45

<210> SEQ ID NO 796
<211> LENGTH: 21
<212> TYPE: DNA
<213> ORGANISM: Oryctolagus cuniculus

<400> SEQUENCE: 796
gaagcatcca aactggcatc t 21

<210> SEQ ID NO 797
<211> LENGTH: 96
<212> TYPE: DNA
<213> ORGANISM: Oryctolagus cuniculus

<400> SEQUENCE: 797
ggggtcccat cgcggttcag cggcagtgga tctgggacac agttcactct caccatcagc 60
ggcgtgcagt gtagcgatgc tgccacttac tactgt 96

<210> SEQ ID NO 798
<211> LENGTH: 39
<212> TYPE: DNA
<213> ORGANISM: Oryctolagus cuniculus

<400> SEQUENCE: 798
cttggcgcgt atgattgtgg tcgtactgat tgtcatgct 39

<210> SEQ ID NO 799
<211> LENGTH: 33
<212> TYPE: DNA
<213> ORGANISM: Artificial
<220> FEATURE:
<223> OTHER INFORMATION: Humanized Antibody Sequence

<400> SEQUENCE: 799
ttcggcggag ggaccgaggt ggtggtcaaa cgt 33

<210> SEQ ID NO 800
<211> LENGTH: 318
<212> TYPE: DNA
<213> ORGANISM: Artificial
<220> FEATURE:
<223> OTHER INFORMATION: Humanized Antibody Sequence

<400> SEQUENCE: 800
acggtagcgg ccccatctgt cttcatcttc ccgccatctg atgagcagtt gaaatctgga 60
actgcctctg ttgtgtgcct gctgaataac ttctatccca gagaggccaa agtacagtgg 120
aaggtggata acgccctcca atcgggtaac tcccaggaga gtgtcacaga gcaggacagc 180
aaggacagca cctacagcct cagcagcacc ctgacgctga gcaaagcaga ctacgagaaa 240
cacaaagtct acgcctgcga agtcacccat cagggcctga gctcgcccgt cacaaagagc 300
ttcaacaggg gagagtgt 318

<210> SEQ ID NO 801
<211> LENGTH: 447
<212> TYPE: PRT
<213> ORGANISM: Artificial
<220> FEATURE:
<223> OTHER INFORMATION: Humanized Antibody Sequence

<400> SEQUENCE: 801

Gln Gln Leu Glu Gln Ser Gly Gly Gly Ala Glu Gly Gly Leu Val Lys
1 5 10 15

Pro Gly Gly Ser Leu Lys Leu Ser Cys Lys Ala Ser Gly Phe Thr Ile
20 25 30

Ser Arg Asp Tyr Trp Ile Cys Trp Val Arg Gln Ala Pro Gly Lys Gly
35 40 45

Leu Glu Trp Ile Gly Cys Ile Ser Ala Gly Gly Gly Ser Thr Asp Tyr
50 55 60

Ala Asn Trp Val Asn Gly Arg Phe Thr Leu Ser Arg Asp Ile Asp Gln
65 70 75 80

Ser Thr Gly Cys Leu Gln Leu Asn Ser Leu Thr Asp Ala Asp Thr Ala
85 90 95

Met Tyr Tyr Cys Ala Gly Asn Leu Glu Ile Trp Gly Gln Gly Thr Leu
100 105 110

Val Thr Val Ser Ser Ala Ser Thr Lys Gly Pro Ser Val Phe Pro Leu
115 120 125

Ala Pro Ser Ser Lys Ser Thr Ser Gly Gly Thr Ala Ala Leu Gly Cys
130 135 140

Leu Val Lys Asp Tyr Phe Pro Glu Pro Val Thr Val Ser Trp Asn Ser
145 150 155 160

Gly Ala Leu Thr Ser Gly Val His Thr Phe Pro Ala Val Leu Gln Ser
165 170 175

```
Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Ala Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Ala Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445


<210> SEQ ID NO 802
<211> LENGTH: 117
<212> TYPE: PRT
<213> ORGANISM: Artificial
<220> FEATURE:
<223> OTHER INFORMATION: Humanized Antibody Sequence

<400> SEQUENCE: 802

Gln Gln Leu Glu Gln Ser Gly Gly Gly Ala Glu Gly Gly Leu Val Lys
1               5                   10                  15

Pro Gly Gly Ser Leu Lys Leu Ser Cys Lys Ala Ser Gly Phe Thr Ile
            20                  25                  30

Ser Arg Asp Tyr Trp Ile Cys Trp Val Arg Gln Ala Pro Gly Lys Gly
        35                  40                  45

Leu Glu Trp Ile Gly Cys Ile Ser Ala Gly Gly Gly Ser Thr Asp Tyr
    50                  55                  60

Ala Asn Trp Val Asn Gly Arg Phe Thr Leu Ser Arg Asp Ile Asp Gln
65                  70                  75                  80

Ser Thr Gly Cys Leu Gln Leu Asn Ser Leu Thr Asp Ala Asp Thr Ala
                85                  90                  95
```

```
Met Tyr Tyr Cys Ala Gly Asn Leu Glu Ile Trp Gly Gln Gly Thr Leu
            100                 105                 110

Val Thr Val Ser Ser
        115


<210> SEQ ID NO 803
<211> LENGTH: 33
<212> TYPE: PRT
<213> ORGANISM: Oryctolagus cuniculus

<400> SEQUENCE: 803

Gln Gln Leu Glu Gln Ser Gly Gly Gly Ala Glu Gly Gly Leu Val Lys
1               5                   10                  15

Pro Gly Gly Ser Leu Lys Leu Ser Cys Lys Ala Ser Gly Phe Thr Ile
            20                  25                  30

Ser


<210> SEQ ID NO 804
<211> LENGTH: 6
<212> TYPE: PRT
<213> ORGANISM: Oryctolagus cuniculus

<400> SEQUENCE: 804

Arg Asp Tyr Trp Ile Cys
1               5


<210> SEQ ID NO 805
<211> LENGTH: 14
<212> TYPE: PRT
<213> ORGANISM: Oryctolagus cuniculus

<400> SEQUENCE: 805

Trp Val Arg Gln Ala Pro Gly Lys Gly Leu Glu Trp Ile Gly
1               5                   10


<210> SEQ ID NO 806
<211> LENGTH: 17
<212> TYPE: PRT
<213> ORGANISM: Oryctolagus cuniculus

<400> SEQUENCE: 806

Cys Ile Ser Ala Gly Gly Gly Ser Thr Asp Tyr Ala Asn Trp Val Asn
1               5                   10                  15

Gly


<210> SEQ ID NO 807
<211> LENGTH: 32
<212> TYPE: PRT
<213> ORGANISM: Oryctolagus cuniculus

<400> SEQUENCE: 807

Arg Phe Thr Leu Ser Arg Asp Ile Asp Gln Ser Thr Gly Cys Leu Gln
1               5                   10                  15

Leu Asn Ser Leu Thr Asp Ala Asp Thr Ala Met Tyr Tyr Cys Ala Gly
            20                  25                  30


<210> SEQ ID NO 808
<211> LENGTH: 4
<212> TYPE: PRT
<213> ORGANISM: Oryctolagus cuniculus

<400> SEQUENCE: 808
```

Asn Leu Glu Ile
1

<210> SEQ ID NO 809
<211> LENGTH: 11
<212> TYPE: PRT
<213> ORGANISM: Artificial
<220> FEATURE:
<223> OTHER INFORMATION: Humanized Antibody Sequence

<400> SEQUENCE: 809

Trp Gly Gln Gly Thr Leu Val Thr Val Ser Ser
1 5 10

<210> SEQ ID NO 810
<211> LENGTH: 330
<212> TYPE: PRT
<213> ORGANISM: Artificial
<220> FEATURE:
<223> OTHER INFORMATION: Humanized Antibody Sequence

<400> SEQUENCE: 810

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Ala
85 90 95

Arg Val Glu Pro Lys Ser Cys Asp Lys Thr His Thr Cys Pro Pro Cys
100 105 110

Pro Ala Pro Glu Leu Leu Gly Gly Pro Ser Val Phe Leu Phe Pro Pro
115 120 125

Lys Pro Lys Asp Thr Leu Met Ile Ser Arg Thr Pro Glu Val Thr Cys
130 135 140

Val Val Val Asp Val Ser His Glu Asp Pro Glu Val Lys Phe Asn Trp
145 150 155 160

Tyr Val Asp Gly Val Glu Val His Asn Ala Lys Thr Lys Pro Arg Glu
165 170 175

Glu Gln Tyr Ala Ser Thr Tyr Arg Val Val Ser Val Leu Thr Val Leu
180 185 190

His Gln Asp Trp Leu Asn Gly Lys Glu Tyr Lys Cys Lys Val Ser Asn
195 200 205

Lys Ala Leu Pro Ala Pro Ile Glu Lys Thr Ile Ser Lys Ala Lys Gly
210 215 220

Gln Pro Arg Glu Pro Gln Val Tyr Thr Leu Pro Pro Ser Arg Glu Glu
225 230 235 240

Met Thr Lys Asn Gln Val Ser Leu Thr Cys Leu Val Lys Gly Phe Tyr
245 250 255

Pro Ser Asp Ile Ala Val Glu Trp Glu Ser Asn Gly Gln Pro Glu Asn
260 265 270

Asn Tyr Lys Thr Thr Pro Pro Val Leu Asp Ser Asp Gly Ser Phe Phe 275 280 285

Leu Tyr Ser Lys Leu Thr Val Asp Lys Ser Arg Trp Gln Gln Gly Asn
290 295 300

Val Phe Ser Cys Ser Val Met His Glu Ala Leu His Asn His Tyr Thr
305 310 315 320

Gln Lys Ser Leu Ser Leu Ser Pro Gly Lys
325 330

<210> SEQ ID NO 811
<211> LENGTH: 1341
<212> TYPE: DNA
<213> ORGANISM: Artificial
<220> FEATURE:
<223> OTHER INFORMATION: Humanized Antibody Sequence

<400> SEQUENCE: 811
cagcagctgg agcagtccgg aggaggagcc gaaggaggcc tggtcaagcc tgggggatcc 60
ctgaaactct cctgcaaagc ctctggattc accatcagta gggactactg gatatgttgg 120
gtccgccagg ctccagggaa ggggctggag tggattggat gcattagtgc tggtggtggt 180
agcacagact acgcgaactg ggtgaatggc cgattcactc tctccagaga catcgaccag 240
agcacaggtt gccttcaact gaacagtctg acagacgcgg acacggccat gtattactgt 300
gcgggaaatc tagagatctg gggccaaggg accctggtca ccgtctcgag cgcctccacc 360
aagggcccat cggtcttccc cctggcaccc tcctccaaga gcacctctgg gggcacagcg 420
gccctgggct gcctggtcaa ggactacttc cccgaaccgg tgacggtgtc gtggaactca 480
ggcgccctga ccagcggcgt gcacaccttc ccggctgtcc tacagtcctc aggactctac 540
tccctcagca gcgtggtgac cgtgccctcc agcagcttgg gcacccagac ctacatctgc 600
aacgtgaatc acaagcccag caacaccaag gtggacgcga gagttgagcc caaatcttgt 660
gacaaaactc acacatgccc accgtgccca gcacctgaac tcctgggggg accgtcagtc 720
ttcctcttcc ccccaaaacc caaggacacc ctcatgatct cccggacccc tgaggtcaca 780
tgcgtggtgg tggacgtgag ccacgaagac cctgaggtca agttcaactg gtacgtggac 840
ggcgtggagg tgcataatgc caagacaaag ccgcgggagg agcagtacgc cagcacgtac 900
cgtgtggtca gcgtcctcac cgtcctgcac caggactggc tgaatggcaa ggagtacaag 960
tgcaaggtct ccaacaaagc cctcccagcc cccatcgaga aaaccatctc caaagccaaa 1020
gggcagcccc gagaaccaca ggtgtacacc ctgcccccat cccgggagga gatgaccaag 1080
aaccaggtca gcctgacctg cctggtcaaa ggcttctatc ccagcgacat cgccgtggag 1140
tgggagagca atgggcagcc ggagaacaac tacaagacca cgcctcccgt gctggactcc 1200
gacggctcct tcttcctcta cagcaagctc accgtggaca agagcaggtg gcagcagggg 1260
aacgtcttct catgctccgt gatgcatgag gctctgcaca accactacac gcagaagagc 1320
ctctccctgt ctccgggtaa a 1341

<210> SEQ ID NO 812
<211> LENGTH: 351
<212> TYPE: DNA
<213> ORGANISM: Artificial
<220> FEATURE:
<223> OTHER INFORMATION: Humanized Antibody Sequence

<400> SEQUENCE: 812
cagcagctgg agcagtccgg aggaggagcc gaaggaggcc tggtcaagcc tgggggatcc 60
ctgaaactct cctgcaaagc ctctggattc accatcagta gggactactg gatatgttgg 120
gtccgccagg ctccagggaa ggggctggag tggattggat gcattagtgc tggtggtggt 180
agcacagact acgcgaactg ggtgaatggc cgattcactc tctccagaga catcgaccag 240
agcacaggtt gccttcaact gaacagtctg acagacgcgg acacggccat gtattactgt 300
gcgggaaatc tagagatctg gggccaaggg accctggtca ccgtctcgag c 351

<210> SEQ ID NO 813
<211> LENGTH: 99
<212> TYPE: DNA
<213> ORGANISM: Oryctolagus cuniculus

<400> SEQUENCE: 813
cagcagctgg agcagtccgg aggaggagcc gaaggaggcc tggtcaagcc tgggggatcc 60
ctgaaactct cctgcaaagc ctctggattc accatcagt 99

<210> SEQ ID NO 814
<211> LENGTH: 18
<212> TYPE: DNA
<213> ORGANISM: Oryctolagus cuniculus

<400> SEQUENCE: 814
agggactact ggatatgt 18

<210> SEQ ID NO 815
<211> LENGTH: 42
<212> TYPE: DNA
<213> ORGANISM: Oryctolagus cuniculus

<400> SEQUENCE: 815
tgggtccgcc aggctccagg gaaggggctg gagtggattg ga 42

<210> SEQ ID NO 816
<211> LENGTH: 51
<212> TYPE: DNA
<213> ORGANISM: Oryctolagus cuniculus

<400> SEQUENCE: 816
tgcattagtg ctggtggtgg tagcacagac tacgcgaact gggtgaatgg c 51

<210> SEQ ID NO 817
<211> LENGTH: 96
<212> TYPE: DNA
<213> ORGANISM: Oryctolagus cuniculus

<400> SEQUENCE: 817
cgattcactc tctccagaga catcgaccag agcacaggtt gccttcaact gaacagtctg 60
acagacgcgg acacggccat gtattactgt gcggga 96

<210> SEQ ID NO 818
<211> LENGTH: 12
<212> TYPE: DNA
<213> ORGANISM: Oryctolagus cuniculus

<400> SEQUENCE: 818
aatctagaga tc 12

<210> SEQ ID NO 819
<211> LENGTH: 33
<212> TYPE: DNA
<213> ORGANISM: Artificial

<220> FEATURE:
<223> OTHER INFORMATION: Humanized Antibody Sequence

<400> SEQUENCE: 819
tggggccaag ggaccctggt caccgtctcg agc 33

<210> SEQ ID NO 820
<211> LENGTH: 990
<212> TYPE: DNA
<213> ORGANISM: Artificial
<220> FEATURE:
<223> OTHER INFORMATION: Humanized Antibody Sequence

<400> SEQUENCE: 820
gcctccacca agggcccatc ggtcttcccc ctggcaccct cctccaagag cacctctggg 60
ggcacagcgg ccctgggctg cctggtcaag gactacttcc ccgaaccggt gacggtgtcg 120
tggaactcag gcgccctgac cagcggcgtg cacaccttcc cggctgtcct acagtcctca 180
ggactctact ccctcagcag cgtggtgacc gtgccctcca gcagcttggg cacccagacc 240
tacatctgca acgtgaatca caagcccagc aacaccaagg tggacgcgag agttgagccc 300
aaatcttgtg acaaaactca cacatgccca ccgtgcccag cacctgaact cctgggggga 360
ccgtcagtct tcctcttccc cccaaaaccc aaggacaccc tcatgatctc ccggacccct 420
gaggtcacat gcgtggtggt ggacgtgagc cacgaagacc ctgaggtcaa gttcaactgg 480
tacgtggacg gcgtggaggt gcataatgcc aagacaaagc cgcgggagga gcagtacgcc 540
agcacgtacc gtgtggtcag cgtcctcacc gtcctgcacc aggactggct gaatggcaag 600
gagtacaagt gcaaggtctc caacaaagcc ctcccagccc ccatcgagaa aaccatctcc 660
aaagccaaag ggcagccccg agaaccacag gtgtacaccc tgcccccatc ccgggaggag 720
atgaccaaga accaggtcag cctgacctgc ctggtcaaag gcttctatcc cagcgacatc 780
gccgtggagt gggagagcaa tgggcagccg gagaacaact acaagaccac gcctcccgtg 840
ctggactccg acggctcctt cttcctctac agcaagctca ccgtggacaa gagcaggtgg 900
cagcagggga acgtcttctc atgctccgtg atgcatgagg ctctgcacaa ccactacacg 960
cagaagagcc tctccctgtc tccgggtaaa 990

<210> SEQ ID NO 821
<211> LENGTH: 220
<212> TYPE: PRT
<213> ORGANISM: Artificial
<220> FEATURE:
<223> OTHER INFORMATION: Humanized Antibody Sequence

<400> SEQUENCE: 821

Ala Gln Val Leu Thr Gln Thr Pro Ser Ser Val Ser Ala Ala Val Gly
1               5                   10                  15

Gly Thr Val Thr Ile Asn Cys Gln Ser Ser Pro Ser Ile Tyr Ser Gly
            20                  25                  30

Ala Phe Leu Ser Trp Phe Gln Gln Lys Pro Gly Gln Pro Pro Lys Phe
        35                  40                  45

Leu Ile Tyr Glu Ala Ser Lys Leu Ala Ser Gly Val Pro Ser Arg Phe
    50                  55                  60

Ser Gly Ser Gly Ser Gly Thr Gln Phe Thr Leu Thr Ile Ser Asp Val
65                  70                  75                  80

Gln Cys Asp Asp Ala Ala Thr Tyr Tyr Cys Leu Gly Phe Tyr Asp Cys
                85                  90                  95

```
Ser Ser Val Asp Cys His Ala Phe Gly Gly Gly Thr Glu Val Val Val
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220


<210> SEQ ID NO 822
<211> LENGTH: 114
<212> TYPE: PRT
<213> ORGANISM: Artificial
<220> FEATURE:
<223> OTHER INFORMATION: Humanized Antibody Sequence

<400> SEQUENCE: 822

Ala Gln Val Leu Thr Gln Thr Pro Ser Ser Val Ser Ala Ala Val Gly
1               5                   10                  15

Gly Thr Val Thr Ile Asn Cys Gln Ser Ser Pro Ser Ile Tyr Ser Gly
            20                  25                  30

Ala Phe Leu Ser Trp Phe Gln Gln Lys Pro Gly Gln Pro Pro Lys Phe
        35                  40                  45

Leu Ile Tyr Glu Ala Ser Lys Leu Ala Ser Gly Val Pro Ser Arg Phe
    50                  55                  60

Ser Gly Ser Gly Ser Gly Thr Gln Phe Thr Leu Thr Ile Ser Asp Val
65                  70                  75                  80

Gln Cys Asp Asp Ala Ala Thr Tyr Tyr Cys Leu Gly Phe Tyr Asp Cys
                85                  90                  95

Ser Ser Val Asp Cys His Ala Phe Gly Gly Gly Thr Glu Val Val Val
            100                 105                 110

Lys Arg


<210> SEQ ID NO 823
<211> LENGTH: 23
<212> TYPE: PRT
<213> ORGANISM: Oryctolagus cuniculus

<400> SEQUENCE: 823

Ala Gln Val Leu Thr Gln Thr Pro Ser Ser Val Ser Ala Ala Val Gly
1               5                   10                  15

Gly Thr Val Thr Ile Asn Cys
            20


<210> SEQ ID NO 824
<211> LENGTH: 13
<212> TYPE: PRT
<213> ORGANISM: Oryctolagus cuniculus

<400> SEQUENCE: 824
```

Gln Ser Ser Pro Ser Ile Tyr Ser Gly Ala Phe Leu Ser
1 5 10

<210> SEQ ID NO 825
<211> LENGTH: 15
<212> TYPE: PRT
<213> ORGANISM: Oryctolagus cuniculus

<400> SEQUENCE: 825

Trp Phe Gln Gln Lys Pro Gly Gln Pro Pro Lys Phe Leu Ile Tyr
1 5 10 15

<210> SEQ ID NO 826
<211> LENGTH: 7
<212> TYPE: PRT
<213> ORGANISM: Oryctolagus cuniculus

<400> SEQUENCE: 826

Glu Ala Ser Lys Leu Ala Ser
1 5

<210> SEQ ID NO 827
<211> LENGTH: 32
<212> TYPE: PRT
<213> ORGANISM: Oryctolagus cuniculus

<400> SEQUENCE: 827

Gly Val Pro Ser Arg Phe Ser Gly Ser Gly Ser Gly Thr Gln Phe Thr
1 5 10 15

Leu Thr Ile Ser Asp Val Gln Cys Asp Asp Ala Ala Thr Tyr Tyr Cys
20 25 30

<210> SEQ ID NO 828
<211> LENGTH: 13
<212> TYPE: PRT
<213> ORGANISM: Oryctolagus cuniculus

<400> SEQUENCE: 828

Leu Gly Phe Tyr Asp Cys Ser Ser Val Asp Cys His Ala
1 5 10

<210> SEQ ID NO 829
<211> LENGTH: 11
<212> TYPE: PRT
<213> ORGANISM: Artificial
<220> FEATURE:
<223> OTHER INFORMATION: Humanized Antibody Sequence

<400> SEQUENCE: 829

Phe Gly Gly Gly Thr Glu Val Val Val Lys Arg
1 5 10

<210> SEQ ID NO 830
<211> LENGTH: 106
<212> TYPE: PRT
<213> ORGANISM: Artificial
<220> FEATURE:
<223> OTHER INFORMATION: Humanized Antibody Sequence

<400> SEQUENCE: 830

Thr Val Ala Ala Pro Ser Val Phe Ile Phe Pro Pro Ser Asp Glu Gln
1 5 10 15

Leu Lys Ser Gly Thr Ala Ser Val Val Cys Leu Leu Asn Asn Phe Tyr
20 25 30

-continued

```
Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105


<210> SEQ ID NO 831
<211> LENGTH: 660
<212> TYPE: DNA
<213> ORGANISM: Artificial
<220> FEATURE:
<223> OTHER INFORMATION: Humanized Antibody Sequence

<400> SEQUENCE: 831

gcccaagtgc tgacccagac tccatcctcc gtgtctgcag ctgtgggagg cacagtcacc      60

atcaattgcc agtccagtcc gagtatttat agtggcgcct ttttatcctg gtttcagcag     120

aaaccagggc agcctcccaa gttcctgatc tacgaagcct ccaaactggc atctggggtc     180

ccatcgcggt tcagtggcag tggatctggg acacagttca ctctcaccat cagcgacgta     240

cagtgtgacg atgctgccac ttactactgt ctaggctttt atgattgtag cagtgttgat     300

tgccatgctt tcggcggagg gaccgaggtg gtggtcaaac gtacggtagc ggccccatct     360

gtcttcatct tcccgccatc tgatgagcag ttgaaatctg gaactgcctc tgttgtgtgc     420

ctgctgaata acttctatcc cagagaggcc aaagtacagt ggaaggtgga taacgccctc     480

caatcgggta actcccagga gagtgtcaca gagcaggaca gcaaggacag cacctacagc     540

ctcagcagca ccctgacgct gagcaaagca gactacgaga aacacaaagt ctacgcctgc     600

gaagtcaccc atcagggcct gagctcgccc gtcacaaaga gcttcaacag gggagagtgt     660


<210> SEQ ID NO 832
<211> LENGTH: 342
<212> TYPE: DNA
<213> ORGANISM: Artificial
<220> FEATURE:
<223> OTHER INFORMATION: Humanized Antibody Sequence

<400> SEQUENCE: 832

gcccaagtgc tgacccagac tccatcctcc gtgtctgcag ctgtgggagg cacagtcacc      60

atcaattgcc agtccagtcc gagtatttat agtggcgcct ttttatcctg gtttcagcag     120

aaaccagggc agcctcccaa gttcctgatc tacgaagcct ccaaactggc atctggggtc     180

ccatcgcggt tcagtggcag tggatctggg acacagttca ctctcaccat cagcgacgta     240

cagtgtgacg atgctgccac ttactactgt ctaggctttt atgattgtag cagtgttgat     300

tgccatgctt tcggcggagg gaccgaggtg gtggtcaaac gt                        342


<210> SEQ ID NO 833
<211> LENGTH: 69
<212> TYPE: DNA
<213> ORGANISM: Oryctolagus cuniculus

<400> SEQUENCE: 833

gcccaagtgc tgacccagac tccatcctcc gtgtctgcag ctgtgggagg cacagtcacc      60
```

atcaattgc 69

<210> SEQ ID NO 834
<211> LENGTH: 39
<212> TYPE: DNA
<213> ORGANISM: Oryctolagus cuniculus

<400> SEQUENCE: 834
cagtccagtc cgagtattta tagtggcgcc tttttatcc 39

<210> SEQ ID NO 835
<211> LENGTH: 45
<212> TYPE: DNA
<213> ORGANISM: Oryctolagus cuniculus

<400> SEQUENCE: 835
tggtttcagc agaaaccagg gcagcctccc aagttcctga tctac 45

<210> SEQ ID NO 836
<211> LENGTH: 21
<212> TYPE: DNA
<213> ORGANISM: Oryctolagus cuniculus

<400> SEQUENCE: 836
gaagcctcca aactggcatc t 21

<210> SEQ ID NO 837
<211> LENGTH: 96
<212> TYPE: DNA
<213> ORGANISM: Oryctolagus cuniculus

<400> SEQUENCE: 837
ggggtcccat cgcggttcag tggcagtgga tctgggacac agttcactct caccatcagc 60
gacgtacagt gtgacgatgc tgccacttac tactgt 96

<210> SEQ ID NO 838
<211> LENGTH: 39
<212> TYPE: DNA
<213> ORGANISM: Oryctolagus cuniculus

<400> SEQUENCE: 838
ctaggctttt atgattgtag cagtgttgat tgccatgct 39

<210> SEQ ID NO 839
<211> LENGTH: 33
<212> TYPE: DNA
<213> ORGANISM: Artificial
<220> FEATURE:
<223> OTHER INFORMATION: Humanized Antibody Sequence

<400> SEQUENCE: 839
ttcggcggag ggaccgaggt ggtggtcaaa cgt 33

<210> SEQ ID NO 840
<211> LENGTH: 318
<212> TYPE: DNA
<213> ORGANISM: Artificial
<220> FEATURE:
<223> OTHER INFORMATION: Humanized Antibody Sequence

<400> SEQUENCE: 840
acggtagcgg ccccatctgt cttcatcttc ccgccatctg atgagcagtt gaaatctgga 60
actgcctctg ttgtgtgcct gctgaataac ttctatccca gagaggccaa agtacagtgg 120
aaggtggata acgccctcca atcgggtaac tcccaggaga gtgtcacaga gcaggacagc 180
aaggacagca cctacagcct cagcagcacc ctgacgctga gcaaagcaga ctacgagaaa 240
cacaaagtct acgcctgcga agtcacccat cagggcctga gctcgcccgt cacaaagagc 300
ttcaacaggg gagagtgt 318

<210> SEQ ID NO 841

<400> SEQUENCE: 841

000

<210> SEQ ID NO 842

<400> SEQUENCE: 842

000

<210> SEQ ID NO 843

<400> SEQUENCE: 843

000

<210> SEQ ID NO 844

<400> SEQUENCE: 844

000

<210> SEQ ID NO 845

<400> SEQUENCE: 845

000

<210> SEQ ID NO 846

<400> SEQUENCE: 846

000

<210> SEQ ID NO 847

<400> SEQUENCE: 847

000

<210> SEQ ID NO 848

<400> SEQUENCE: 848

000

<210> SEQ ID NO 849

<400> SEQUENCE: 849

000

<210> SEQ ID NO 850

<400> SEQUENCE: 850

000

<210> SEQ ID NO 851

<400> SEQUENCE: 851

000

<210> SEQ ID NO 852

<400> SEQUENCE: 852

000

<210> SEQ ID NO 853

<400> SEQUENCE: 853

000

<210> SEQ ID NO 854

<400> SEQUENCE: 854

000

<210> SEQ ID NO 855

<400> SEQUENCE: 855

000

<210> SEQ ID NO 856

<400> SEQUENCE: 856

000

<210> SEQ ID NO 857

<400> SEQUENCE: 857

000

<210> SEQ ID NO 858

<400> SEQUENCE: 858

000

<210> SEQ ID NO 859

<400> SEQUENCE: 859

000

<210> SEQ ID NO 860

<400> SEQUENCE: 860

000

<210> SEQ ID NO 861

<400> SEQUENCE: 861

000

<210> SEQ ID NO 862

<400> SEQUENCE: 862

000

<210> SEQ ID NO 863

<400> SEQUENCE: 863

000

<210> SEQ ID NO 864

<400> SEQUENCE: 864

000

<210> SEQ ID NO 865

<400> SEQUENCE: 865

000

<210> SEQ ID NO 866

<400> SEQUENCE: 866

000

<210> SEQ ID NO 867

<400> SEQUENCE: 867

000

<210> SEQ ID NO 868

<400> SEQUENCE: 868

000

<210> SEQ ID NO 869

<400> SEQUENCE: 869

000

<210> SEQ ID NO 870

<400> SEQUENCE: 870

000

<210> SEQ ID NO 871

<400> SEQUENCE: 871

000

<210> SEQ ID NO 872

<400> SEQUENCE: 872

000

<210> SEQ ID NO 873

<400> SEQUENCE: 873

000

<210> SEQ ID NO 874
<400> SEQUENCE: 874
000

<210> SEQ ID NO 875
<400> SEQUENCE: 875
000

<210> SEQ ID NO 876
<400> SEQUENCE: 876
000

<210> SEQ ID NO 877
<400> SEQUENCE: 877
000

<210> SEQ ID NO 878
<400> SEQUENCE: 878
000

<210> SEQ ID NO 879
<400> SEQUENCE: 879
000

<210> SEQ ID NO 880
<400> SEQUENCE: 880
000

<210> SEQ ID NO 881
<400> SEQUENCE: 881
000

<210> SEQ ID NO 882
<400> SEQUENCE: 882
000

<210> SEQ ID NO 883
<400> SEQUENCE: 883
000

<210> SEQ ID NO 884
<400> SEQUENCE: 884
000

<210> SEQ ID NO 885

<400> SEQUENCE: 885

000

<210> SEQ ID NO 886

<400> SEQUENCE: 886

000

<210> SEQ ID NO 887

<400> SEQUENCE: 887

000

<210> SEQ ID NO 888

<400> SEQUENCE: 888

000

<210> SEQ ID NO 889

<400> SEQUENCE: 889

000

<210> SEQ ID NO 890

<400> SEQUENCE: 890

000

<210> SEQ ID NO 891

<400> SEQUENCE: 891

000

<210> SEQ ID NO 892

<400> SEQUENCE: 892

000

<210> SEQ ID NO 893

<400> SEQUENCE: 893

000

<210> SEQ ID NO 894

<400> SEQUENCE: 894

000

<210> SEQ ID NO 895

<400> SEQUENCE: 895

000

<210> SEQ ID NO 896

<400> SEQUENCE: 896

000

<210> SEQ ID NO 897

<400> SEQUENCE: 897

000

<210> SEQ ID NO 898

<400> SEQUENCE: 898

000

<210> SEQ ID NO 899

<400> SEQUENCE: 899

000

<210> SEQ ID NO 900

<400> SEQUENCE: 900

000

<210> SEQ ID NO 901

<400> SEQUENCE: 901

000

<210> SEQ ID NO 902

<400> SEQUENCE: 902

000

<210> SEQ ID NO 903

<400> SEQUENCE: 903

000

<210> SEQ ID NO 904

<400> SEQUENCE: 904

000

<210> SEQ ID NO 905

<400> SEQUENCE: 905

000

<210> SEQ ID NO 906

<400> SEQUENCE: 906

000

<210> SEQ ID NO 907

<400> SEQUENCE: 907

000

<210> SEQ ID NO 908

<400> SEQUENCE: 908

000

<210> SEQ ID NO 909

<400> SEQUENCE: 909

000

<210> SEQ ID NO 910

<400> SEQUENCE: 910

000

<210> SEQ ID NO 911

<400> SEQUENCE: 911

000

<210> SEQ ID NO 912

<400> SEQUENCE: 912

000

<210> SEQ ID NO 913

<400> SEQUENCE: 913

000

<210> SEQ ID NO 914

<400> SEQUENCE: 914

000

<210> SEQ ID NO 915

<400> SEQUENCE: 915

000

<210> SEQ ID NO 916

<400> SEQUENCE: 916

000

<210> SEQ ID NO 917

<400> SEQUENCE: 917

000

<210> SEQ ID NO 918

<400> SEQUENCE: 918

000

<210> SEQ ID NO 919
<400> SEQUENCE: 919
000

<210> SEQ ID NO 920
<400> SEQUENCE: 920
000

<210> SEQ ID NO 921
<400> SEQUENCE: 921
000

<210> SEQ ID NO 922
<400> SEQUENCE: 922
000

<210> SEQ ID NO 923
<400> SEQUENCE: 923
000

<210> SEQ ID NO 924
<400> SEQUENCE: 924
000

<210> SEQ ID NO 925
<400> SEQUENCE: 925
000

<210> SEQ ID NO 926
<400> SEQUENCE: 926
000

<210> SEQ ID NO 927
<400> SEQUENCE: 927
000

<210> SEQ ID NO 928
<400> SEQUENCE: 928
000

<210> SEQ ID NO 929
<400> SEQUENCE: 929
000

<210> SEQ ID NO 930

<400> SEQUENCE: 930

000

<210> SEQ ID NO 931

<400> SEQUENCE: 931

000

<210> SEQ ID NO 932

<400> SEQUENCE: 932

000

<210> SEQ ID NO 933

<400> SEQUENCE: 933

000

<210> SEQ ID NO 934

<400> SEQUENCE: 934

000

<210> SEQ ID NO 935

<400> SEQUENCE: 935

000

<210> SEQ ID NO 936

<400> SEQUENCE: 936

000

<210> SEQ ID NO 937

<400> SEQUENCE: 937

000

<210> SEQ ID NO 938

<400> SEQUENCE: 938

000

<210> SEQ ID NO 939

<400> SEQUENCE: 939

000

<210> SEQ ID NO 940

<400> SEQUENCE: 940

000

<210> SEQ ID NO 941

<400> SEQUENCE: 941

000

<210> SEQ ID NO 942

<400> SEQUENCE: 942

000

<210> SEQ ID NO 943

<400> SEQUENCE: 943

000

<210> SEQ ID NO 944

<400> SEQUENCE: 944

000

<210> SEQ ID NO 945

<400> SEQUENCE: 945

000

<210> SEQ ID NO 946

<400> SEQUENCE: 946

000

<210> SEQ ID NO 947

<400> SEQUENCE: 947

000

<210> SEQ ID NO 948

<400> SEQUENCE: 948

000

<210> SEQ ID NO 949

<400> SEQUENCE: 949

000

<210> SEQ ID NO 950

<400> SEQUENCE: 950

000

<210> SEQ ID NO 951

<400> SEQUENCE: 951

000

<210> SEQ ID NO 952

<400> SEQUENCE: 952

000

<210> SEQ ID NO 953
<400> SEQUENCE: 953
000

<210> SEQ ID NO 954
<400> SEQUENCE: 954
000

<210> SEQ ID NO 955
<400> SEQUENCE: 955
000

<210> SEQ ID NO 956
<400> SEQUENCE: 956
000

<210> SEQ ID NO 957
<400> SEQUENCE: 957
000

<210> SEQ ID NO 958
<400> SEQUENCE: 958
000

<210> SEQ ID NO 959
<400> SEQUENCE: 959
000

<210> SEQ ID NO 960
<400> SEQUENCE: 960
000

<210> SEQ ID NO 961
<400> SEQUENCE: 961
000

<210> SEQ ID NO 962
<400> SEQUENCE: 962
000

<210> SEQ ID NO 963
<400> SEQUENCE: 963
000

<210> SEQ ID NO 964

<400> SEQUENCE: 964

000

<210> SEQ ID NO 965

<400> SEQUENCE: 965

000

<210> SEQ ID NO 966

<400> SEQUENCE: 966

000

<210> SEQ ID NO 967

<400> SEQUENCE: 967

000

<210> SEQ ID NO 968

<400> SEQUENCE: 968

000

<210> SEQ ID NO 969

<400> SEQUENCE: 969

000

<210> SEQ ID NO 970

<400> SEQUENCE: 970

000

<210> SEQ ID NO 971

<400> SEQUENCE: 971

000

<210> SEQ ID NO 972

<400> SEQUENCE: 972

000

<210> SEQ ID NO 973

<400> SEQUENCE: 973

000

<210> SEQ ID NO 974

<400> SEQUENCE: 974

000

<210> SEQ ID NO 975

<400> SEQUENCE: 975

000

<210> SEQ ID NO 976

<400> SEQUENCE: 976

000

<210> SEQ ID NO 977

<400> SEQUENCE: 977

000

<210> SEQ ID NO 978

<400> SEQUENCE: 978

000

<210> SEQ ID NO 979

<400> SEQUENCE: 979

000

<210> SEQ ID NO 980

<400> SEQUENCE: 980

000

<210> SEQ ID NO 981

<400> SEQUENCE: 981

000

<210> SEQ ID NO 982

<400> SEQUENCE: 982

000

<210> SEQ ID NO 983

<400> SEQUENCE: 983

000

<210> SEQ ID NO 984

<400> SEQUENCE: 984

000

<210> SEQ ID NO 985

<400> SEQUENCE: 985

000

<210> SEQ ID NO 986

<400> SEQUENCE: 986

000

<210> SEQ ID NO 987

<400> SEQUENCE: 987

000

<210> SEQ ID NO 988

<400> SEQUENCE: 988

000

<210> SEQ ID NO 989

<400> SEQUENCE: 989

000

<210> SEQ ID NO 990

<400> SEQUENCE: 990

000

<210> SEQ ID NO 991

<400> SEQUENCE: 991

000

<210> SEQ ID NO 992

<400> SEQUENCE: 992

000

<210> SEQ ID NO 993

<400> SEQUENCE: 993

000

<210> SEQ ID NO 994

<400> SEQUENCE: 994

000

<210> SEQ ID NO 995

<400> SEQUENCE: 995

000

<210> SEQ ID NO 996

<400> SEQUENCE: 996

000

<210> SEQ ID NO 997

<400> SEQUENCE: 997

000

<210> SEQ ID NO 998

<400> SEQUENCE: 998

000

<210> SEQ ID NO 999

<400> SEQUENCE: 999

000

<210> SEQ ID NO 1000

<400> SEQUENCE: 1000

000

<210> SEQ ID NO 1001

<400> SEQUENCE: 1001

000

<210> SEQ ID NO 1002

<400> SEQUENCE: 1002

000

<210> SEQ ID NO 1003

<400> SEQUENCE: 1003

000

<210> SEQ ID NO 1004

<400> SEQUENCE: 1004

000

<210> SEQ ID NO 1005

<400> SEQUENCE: 1005

000

<210> SEQ ID NO 1006

<400> SEQUENCE: 1006

000

<210> SEQ ID NO 1007

<400> SEQUENCE: 1007

000

<210> SEQ ID NO 1008

<400> SEQUENCE: 1008

000

-continued

<210> SEQ ID NO 1009

<400> SEQUENCE: 1009

000

<210> SEQ ID NO 1010

<400> SEQUENCE: 1010

000

<210> SEQ ID NO 1011

<400> SEQUENCE: 1011

000

<210> SEQ ID NO 1012

<400> SEQUENCE: 1012

000

<210> SEQ ID NO 1013

<400> SEQUENCE: 1013

000

<210> SEQ ID NO 1014

<400> SEQUENCE: 1014

000

<210> SEQ ID NO 1015

<400> SEQUENCE: 1015

000

<210> SEQ ID NO 1016

<400> SEQUENCE: 1016

000

<210> SEQ ID NO 1017

<400> SEQUENCE: 1017

000

<210> SEQ ID NO 1018

<400> SEQUENCE: 1018

000

<210> SEQ ID NO 1019

<400> SEQUENCE: 1019

000

<210> SEQ ID NO 1020

<400> SEQUENCE: 1020

000

<210> SEQ ID NO 1021

<400> SEQUENCE: 1021

000

<210> SEQ ID NO 1022

<400> SEQUENCE: 1022

000

<210> SEQ ID NO 1023

<400> SEQUENCE: 1023

000

<210> SEQ ID NO 1024

<400> SEQUENCE: 1024

000

<210> SEQ ID NO 1025

<400> SEQUENCE: 1025

000

<210> SEQ ID NO 1026

<400> SEQUENCE: 1026

000

<210> SEQ ID NO 1027

<400> SEQUENCE: 1027

000

<210> SEQ ID NO 1028

<400> SEQUENCE: 1028

000

<210> SEQ ID NO 1029

<400> SEQUENCE: 1029

000

<210> SEQ ID NO 1030

<400> SEQUENCE: 1030

000

<210> SEQ ID NO 1031

<400> SEQUENCE: 1031

000

<210> SEQ ID NO 1032

<400> SEQUENCE: 1032

000

<210> SEQ ID NO 1033

<400> SEQUENCE: 1033

000

<210> SEQ ID NO 1034

<400> SEQUENCE: 1034

000

<210> SEQ ID NO 1035

<400> SEQUENCE: 1035

000

<210> SEQ ID NO 1036

<400> SEQUENCE: 1036

000

<210> SEQ ID NO 1037

<400> SEQUENCE: 1037

000

<210> SEQ ID NO 1038

<400> SEQUENCE: 1038

000

<210> SEQ ID NO 1039

<400> SEQUENCE: 1039

000

<210> SEQ ID NO 1040

<400> SEQUENCE: 1040

000

<210> SEQ ID NO 1041

<400> SEQUENCE: 1041

000

<210> SEQ ID NO 1042

<400> SEQUENCE: 1042

000

<210> SEQ ID NO 1043
<400> SEQUENCE: 1043
000

<210> SEQ ID NO 1044
<400> SEQUENCE: 1044
000

<210> SEQ ID NO 1045
<400> SEQUENCE: 1045
000

<210> SEQ ID NO 1046
<400> SEQUENCE: 1046
000

<210> SEQ ID NO 1047
<400> SEQUENCE: 1047
000

<210> SEQ ID NO 1048
<400> SEQUENCE: 1048
000

<210> SEQ ID NO 1049
<400> SEQUENCE: 1049
000

<210> SEQ ID NO 1050
<400> SEQUENCE: 1050
000

<210> SEQ ID NO 1051
<400> SEQUENCE: 1051
000

<210> SEQ ID NO 1052
<400> SEQUENCE: 1052
000

<210> SEQ ID NO 1053
<400> SEQUENCE: 1053
000

<210> SEQ ID NO 1054

<400> SEQUENCE: 1054

000

<210> SEQ ID NO 1055

<400> SEQUENCE: 1055

000

<210> SEQ ID NO 1056

<400> SEQUENCE: 1056

000

<210> SEQ ID NO 1057

<400> SEQUENCE: 1057

000

<210> SEQ ID NO 1058

<400> SEQUENCE: 1058

000

<210> SEQ ID NO 1059

<400> SEQUENCE: 1059

000

<210> SEQ ID NO 1060

<400> SEQUENCE: 1060

000

<210> SEQ ID NO 1061

<400> SEQUENCE: 1061

000

<210> SEQ ID NO 1062

<400> SEQUENCE: 1062

000

<210> SEQ ID NO 1063

<400> SEQUENCE: 1063

000

<210> SEQ ID NO 1064

<400> SEQUENCE: 1064

000

<210> SEQ ID NO 1065

<400> SEQUENCE: 1065

000

<210> SEQ ID NO 1066

<400> SEQUENCE: 1066

000

<210> SEQ ID NO 1067

<400> SEQUENCE: 1067

000

<210> SEQ ID NO 1068

<400> SEQUENCE: 1068

000

<210> SEQ ID NO 1069

<400> SEQUENCE: 1069

000

<210> SEQ ID NO 1070

<400> SEQUENCE: 1070

000

<210> SEQ ID NO 1071

<400> SEQUENCE: 1071

000

<210> SEQ ID NO 1072

<400> SEQUENCE: 1072

000

<210> SEQ ID NO 1073

<400> SEQUENCE: 1073

000

<210> SEQ ID NO 1074

<400> SEQUENCE: 1074

000

<210> SEQ ID NO 1075

<400> SEQUENCE: 1075

000

<210> SEQ ID NO 1076

<400> SEQUENCE: 1076

000

<210> SEQ ID NO 1077

<400> SEQUENCE: 1077

000

<210> SEQ ID NO 1078

<400> SEQUENCE: 1078

000

<210> SEQ ID NO 1079

<400> SEQUENCE: 1079

000

<210> SEQ ID NO 1080

<400> SEQUENCE: 1080

000

<210> SEQ ID NO 1081

<400> SEQUENCE: 1081

000

<210> SEQ ID NO 1082

<400> SEQUENCE: 1082

000

<210> SEQ ID NO 1083

<400> SEQUENCE: 1083

000

<210> SEQ ID NO 1084

<400> SEQUENCE: 1084

000

<210> SEQ ID NO 1085

<400> SEQUENCE: 1085

000

<210> SEQ ID NO 1086

<400> SEQUENCE: 1086

000

<210> SEQ ID NO 1087

<400> SEQUENCE: 1087

000

<210> SEQ ID NO 1088

<400> SEQUENCE: 1088

000

<210> SEQ ID NO 1089

<400> SEQUENCE: 1089

000

<210> SEQ ID NO 1090

<400> SEQUENCE: 1090

000

<210> SEQ ID NO 1091

<400> SEQUENCE: 1091

000

<210> SEQ ID NO 1092

<400> SEQUENCE: 1092

000

<210> SEQ ID NO 1093

<400> SEQUENCE: 1093

000

<210> SEQ ID NO 1094

<400> SEQUENCE: 1094

000

<210> SEQ ID NO 1095

<400> SEQUENCE: 1095

000

<210> SEQ ID NO 1096

<400> SEQUENCE: 1096

000

<210> SEQ ID NO 1097

<400> SEQUENCE: 1097

000

<210> SEQ ID NO 1098

<400> SEQUENCE: 1098

000

<210> SEQ ID NO 1099

<400> SEQUENCE: 1099

000

<210> SEQ ID NO 1100

<400> SEQUENCE: 1100

000

<210> SEQ ID NO 1101

<400> SEQUENCE: 1101

000

<210> SEQ ID NO 1102

<400> SEQUENCE: 1102

000

<210> SEQ ID NO 1103

<400> SEQUENCE: 1103

000

<210> SEQ ID NO 1104

<400> SEQUENCE: 1104

000

<210> SEQ ID NO 1105

<400> SEQUENCE: 1105

000

<210> SEQ ID NO 1106

<400> SEQUENCE: 1106

000

<210> SEQ ID NO 1107

<400> SEQUENCE: 1107

000

<210> SEQ ID NO 1108

<400> SEQUENCE: 1108

000

<210> SEQ ID NO 1109

<400> SEQUENCE: 1109

000

<210> SEQ ID NO 1110

<400> SEQUENCE: 1110

000

<210> SEQ ID NO 1111
<400> SEQUENCE: 1111
000

<210> SEQ ID NO 1112
<400> SEQUENCE: 1112
000

<210> SEQ ID NO 1113
<400> SEQUENCE: 1113
000

<210> SEQ ID NO 1114
<400> SEQUENCE: 1114
000

<210> SEQ ID NO 1115
<400> SEQUENCE: 1115
000

<210> SEQ ID NO 1116
<400> SEQUENCE: 1116
000

<210> SEQ ID NO 1117
<400> SEQUENCE: 1117
000

<210> SEQ ID NO 1118
<400> SEQUENCE: 1118
000

<210> SEQ ID NO 1119
<400> SEQUENCE: 1119
000

<210> SEQ ID NO 1120
<400> SEQUENCE: 1120
000

<210> SEQ ID NO 1121
<400> SEQUENCE: 1121
000

<210> SEQ ID NO 1122

<400> SEQUENCE: 1122

000

<210> SEQ ID NO 1123

<400> SEQUENCE: 1123

000

<210> SEQ ID NO 1124

<400> SEQUENCE: 1124

000

<210> SEQ ID NO 1125

<400> SEQUENCE: 1125

000

<210> SEQ ID NO 1126

<400> SEQUENCE: 1126

000

<210> SEQ ID NO 1127

<400> SEQUENCE: 1127

000

<210> SEQ ID NO 1128

<400> SEQUENCE: 1128

000

<210> SEQ ID NO 1129

<400> SEQUENCE: 1129

000

<210> SEQ ID NO 1130

<400> SEQUENCE: 1130

000

<210> SEQ ID NO 1131

<400> SEQUENCE: 1131

000

<210> SEQ ID NO 1132

<400> SEQUENCE: 1132

000

<210> SEQ ID NO 1133

<400> SEQUENCE: 1133

000

<210> SEQ ID NO 1134

<400> SEQUENCE: 1134

000

<210> SEQ ID NO 1135

<400> SEQUENCE: 1135

000

<210> SEQ ID NO 1136

<400> SEQUENCE: 1136

000

<210> SEQ ID NO 1137

<400> SEQUENCE: 1137

000

<210> SEQ ID NO 1138

<400> SEQUENCE: 1138

000

<210> SEQ ID NO 1139

<400> SEQUENCE: 1139

000

<210> SEQ ID NO 1140

<400> SEQUENCE: 1140

000

<210> SEQ ID NO 1141

<400> SEQUENCE: 1141

000

<210> SEQ ID NO 1142

<400> SEQUENCE: 1142

000

<210> SEQ ID NO 1143

<400> SEQUENCE: 1143

000

<210> SEQ ID NO 1144

<400> SEQUENCE: 1144

000

<210> SEQ ID NO 1145

<400> SEQUENCE: 1145

000

<210> SEQ ID NO 1146

<400> SEQUENCE: 1146

000

<210> SEQ ID NO 1147

<400> SEQUENCE: 1147

000

<210> SEQ ID NO 1148

<400> SEQUENCE: 1148

000

<210> SEQ ID NO 1149

<400> SEQUENCE: 1149

000

<210> SEQ ID NO 1150

<400> SEQUENCE: 1150

000

<210> SEQ ID NO 1151

<400> SEQUENCE: 1151

000

<210> SEQ ID NO 1152

<400> SEQUENCE: 1152

000

<210> SEQ ID NO 1153

<400> SEQUENCE: 1153

000

<210> SEQ ID NO 1154

<400> SEQUENCE: 1154

000

<210> SEQ ID NO 1155

<400> SEQUENCE: 1155

000

<210> SEQ ID NO 1156

<400> SEQUENCE: 1156

000

<210> SEQ ID NO 1157

<400> SEQUENCE: 1157

000

<210> SEQ ID NO 1158

<400> SEQUENCE: 1158

000

<210> SEQ ID NO 1159

<400> SEQUENCE: 1159

000

<210> SEQ ID NO 1160

<400> SEQUENCE: 1160

000

<210> SEQ ID NO 1161

<400> SEQUENCE: 1161

000

<210> SEQ ID NO 1162

<400> SEQUENCE: 1162

000

<210> SEQ ID NO 1163

<400> SEQUENCE: 1163

000

<210> SEQ ID NO 1164

<400> SEQUENCE: 1164

000

<210> SEQ ID NO 1165

<400> SEQUENCE: 1165

000

<210> SEQ ID NO 1166

<400> SEQUENCE: 1166

000

<210> SEQ ID NO 1167

<400> SEQUENCE: 1167

000

<210> SEQ ID NO 1168

<400> SEQUENCE: 1168

000

<210> SEQ ID NO 1169

<400> SEQUENCE: 1169

000

<210> SEQ ID NO 1170

<400> SEQUENCE: 1170

000

<210> SEQ ID NO 1171

<400> SEQUENCE: 1171

000

<210> SEQ ID NO 1172

<400> SEQUENCE: 1172

000

<210> SEQ ID NO 1173

<400> SEQUENCE: 1173

000

<210> SEQ ID NO 1174

<400> SEQUENCE: 1174

000

<210> SEQ ID NO 1175

<400> SEQUENCE: 1175

000

<210> SEQ ID NO 1176

<400> SEQUENCE: 1176

000

<210> SEQ ID NO 1177

<400> SEQUENCE: 1177

000

<210> SEQ ID NO 1178

<400> SEQUENCE: 1178

000

<210> SEQ ID NO 1179

<400> SEQUENCE: 1179

000

<210> SEQ ID NO 1180

<400> SEQUENCE: 1180

000

<210> SEQ ID NO 1181

<400> SEQUENCE: 1181

000

<210> SEQ ID NO 1182

<400> SEQUENCE: 1182

000

<210> SEQ ID NO 1183

<400> SEQUENCE: 1183

000

<210> SEQ ID NO 1184

<400> SEQUENCE: 1184

000

<210> SEQ ID NO 1185

<400> SEQUENCE: 1185

000

<210> SEQ ID NO 1186

<400> SEQUENCE: 1186

000

<210> SEQ ID NO 1187

<400> SEQUENCE: 1187

000

<210> SEQ ID NO 1188

<400> SEQUENCE: 1188

000

<210> SEQ ID NO 1189

<400> SEQUENCE: 1189

000

<210> SEQ ID NO 1190

<400> SEQUENCE: 1190

000

<210> SEQ ID NO 1191

<400> SEQUENCE: 1191

000

<210> SEQ ID NO 1192

<400> SEQUENCE: 1192

000

<210> SEQ ID NO 1193

<400> SEQUENCE: 1193

000

<210> SEQ ID NO 1194

<400> SEQUENCE: 1194

000

<210> SEQ ID NO 1195

<400> SEQUENCE: 1195

000

<210> SEQ ID NO 1196

<400> SEQUENCE: 1196

000

<210> SEQ ID NO 1197

<400> SEQUENCE: 1197

000

<210> SEQ ID NO 1198

<400> SEQUENCE: 1198

000

<210> SEQ ID NO 1199

<400> SEQUENCE: 1199

000

<210> SEQ ID NO 1200

<400> SEQUENCE: 1200

000

<210> SEQ ID NO 1201

<400> SEQUENCE: 1201

000

<210> SEQ ID NO 1202

<400> SEQUENCE: 1202

000

<210> SEQ ID NO 1203

<400> SEQUENCE: 1203

000

<210> SEQ ID NO 1204

<400> SEQUENCE: 1204

000

<210> SEQ ID NO 1205

<400> SEQUENCE: 1205

000

<210> SEQ ID NO 1206

<400> SEQUENCE: 1206

000

<210> SEQ ID NO 1207

<400> SEQUENCE: 1207

000

<210> SEQ ID NO 1208

<400> SEQUENCE: 1208

000

<210> SEQ ID NO 1209

<400> SEQUENCE: 1209

000

<210> SEQ ID NO 1210

<400> SEQUENCE: 1210

000

<210> SEQ ID NO 1211

<400> SEQUENCE: 1211

000

<210> SEQ ID NO 1212

<400> SEQUENCE: 1212

000

<210> SEQ ID NO 1213

<400> SEQUENCE: 1213

000

<210> SEQ ID NO 1214

<400> SEQUENCE: 1214

000

<210> SEQ ID NO 1215

<400> SEQUENCE: 1215

000

<210> SEQ ID NO 1216

<400> SEQUENCE: 1216

000

<210> SEQ ID NO 1217

<400> SEQUENCE: 1217

000

<210> SEQ ID NO 1218

<400> SEQUENCE: 1218

000

<210> SEQ ID NO 1219

<400> SEQUENCE: 1219

000

<210> SEQ ID NO 1220

<400> SEQUENCE: 1220

000

<210> SEQ ID NO 1221

<400> SEQUENCE: 1221

000

<210> SEQ ID NO 1222

<400> SEQUENCE: 1222

000

<210> SEQ ID NO 1223

<400> SEQUENCE: 1223

000

<210> SEQ ID NO 1224

<400> SEQUENCE: 1224

000

<210> SEQ ID NO 1225

<400> SEQUENCE: 1225

000

<210> SEQ ID NO 1226

<400> SEQUENCE: 1226

000

<210> SEQ ID NO 1227

<400> SEQUENCE: 1227

000

<210> SEQ ID NO 1228

<400> SEQUENCE: 1228

000

<210> SEQ ID NO 1229

<400> SEQUENCE: 1229

000

<210> SEQ ID NO 1230

<400> SEQUENCE: 1230

000

<210> SEQ ID NO 1231

<400> SEQUENCE: 1231

000

<210> SEQ ID NO 1232

<400> SEQUENCE: 1232

000

<210> SEQ ID NO 1233

<400> SEQUENCE: 1233

000

<210> SEQ ID NO 1234

<400> SEQUENCE: 1234

000

<210> SEQ ID NO 1235

<400> SEQUENCE: 1235

000

<210> SEQ ID NO 1236

<400> SEQUENCE: 1236

000

<210> SEQ ID NO 1237

<400> SEQUENCE: 1237

000

<210> SEQ ID NO 1238

<400> SEQUENCE: 1238

000

<210> SEQ ID NO 1239

<400> SEQUENCE: 1239

000

<210> SEQ ID NO 1240

<400> SEQUENCE: 1240

000

<210> SEQ ID NO 1241
<211> LENGTH: 38
<212> TYPE: PRT
<213> ORGANISM: Homo sapiens
<220> FEATURE:
<221> NAME/KEY: MOD_RES
<222> LOCATION: (38)..(38)
<223> OTHER INFORMATION: AMIDATION

<400> SEQUENCE: 1241

```
His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu Gly Lys Arg Tyr Lys
            20                  25                  30

Gln Arg Val Lys Asn Lys
        35
```

<210> SEQ ID NO 1242
<211> LENGTH: 27
<212> TYPE: PRT
<213> ORGANISM: Homo sapiens
<220> FEATURE:
<221> NAME/KEY: MOD_RES
<222> LOCATION: (27)..(27)
<223> OTHER INFORMATION: AMIDATION

<400> SEQUENCE: 1242

```
His Ser Asp Gly Ile Phe Thr Asp Ser Tyr Ser Arg Tyr Arg Lys Gln
1               5                   10                  15
```

```
Met Ala Val Lys Lys Tyr Leu Ala Ala Val Leu
            20                  25


<210> SEQ ID NO 1243
<211> LENGTH: 28
<212> TYPE: PRT
<213> ORGANISM: Homo sapiens
<220> FEATURE:
<221> NAME/KEY: MOD_RES
<222> LOCATION: (28)..(28)
<223> OTHER INFORMATION: AMIDATION

<400> SEQUENCE: 1243

His Ser Asp Ala Val Phe Thr Asp Asn Tyr Thr Arg Leu Arg Lys Gln
1               5                   10                  15

Met Ala Val Lys Lys Tyr Leu Asn Ser Ile Leu Asn
            20                  25


<210> SEQ ID NO 1244
<211> LENGTH: 330
<212> TYPE: PRT
<213> ORGANISM: Artificial
<220> FEATURE:
<223> OTHER INFORMATION: Humanized antibody sequence

<400> SEQUENCE: 1244

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255
```

-continued

Pro Ser Asp Ile Ala Val Glu Trp Glu Ser Asn Gly Gln Pro Glu Asn
260 265 270

Asn Tyr Lys Thr Thr Pro Pro Val Leu Asp Ser Asp Gly Ser Phe Phe
275 280 285

Leu Tyr Ser Lys Leu Thr Val Asp Lys Ser Arg Trp Gln Gln Gly Asn
290 295 300

Val Phe Ser Cys Ser Val Met His Glu Ala Leu His Asn His Tyr Thr
305 310 315 320

Gln Lys Ser Leu Ser Leu Ser Pro Gly Lys
325 330

<210> SEQ ID NO 1245
<211> LENGTH: 330
<212> TYPE: PRT
<213> ORGANISM: Artificial
<220> FEATURE:
<223> OTHER INFORMATION: Humanized antibody sequence

<400> SEQUENCE: 1245

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Ala
85 90 95

Arg Val Glu Pro Lys Ser Cys Asp Lys Thr His Thr Cys Pro Pro Cys
100 105 110

Pro Ala Pro Glu Leu Leu Gly Gly Pro Ser Val Phe Leu Phe Pro Pro
115 120 125

Lys Pro Lys Asp Thr Leu Met Ile Ser Arg Thr Pro Glu Val Thr Cys
130 135 140

Val Val Val Asp Val Ser His Glu Asp Pro Glu Val Lys Phe Asn Trp
145 150 155 160

Tyr Val Asp Gly Val Glu Val His Asn Ala Lys Thr Lys Pro Arg Glu
165 170 175

Glu Gln Tyr Ala Ser Thr Tyr Arg Val Val Ser Val Leu Thr Val Leu
180 185 190

His Gln Asp Trp Leu Asn Gly Lys Glu Tyr Lys Cys Lys Val Ser Asn
195 200 205

Lys Ala Leu Pro Ala Pro Ile Glu Lys Thr Ile Ser Lys Ala Lys Gly
210 215 220

Gln Pro Arg Glu Pro Gln Val Tyr Thr Leu Pro Pro Ser Arg Glu Glu
225 230 235 240

Met Thr Lys Asn Gln Val Ser Leu Thr Cys Leu Val Lys Gly Phe Tyr
245 250 255

Pro Ser Asp Ile Ala Val Glu Trp Glu Ser Asn Gly Gln Pro Glu Asn
260 265 270

Asn Tyr Lys Thr Thr Pro Pro Val Leu Asp Ser Asp Gly Ser Phe Phe
275 280 285

```
Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 1246
<211> LENGTH: 330
<212> TYPE: PRT
<213> ORGANISM: Artificial
<220> FEATURE:
<223> OTHER INFORMATION: Humanized antibody sequence

<400> SEQUENCE: 1246

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320
```

-continued

```
Gln Lys Ser Leu Ser Leu Ser Pro Gly Lys
            325                 330
```

SCREENING METHOD FOR IDENTIFYING ANTI-PACAP ANTIBODIES OR ANTIBODY FRAGMENTS SUITABLE FOR USE IN TREATING OR PREVENTING PACAP-ASSOCIATED PHOTOPHOBIA OR LIGHT AVERSION

CROSS-REFERENCE TO RELATED APPLICATIONS

This application is a divisional of U.S. application Ser. No. 15/130,215, filed Apr. 15, 2016, which claims the benefit of U.S. Provisional Application Ser. No. 62/148,550, filed Apr. 16, 2015, U.S. Provisional Application Ser. No. 62/148,557, filed Apr. 16, 2015, U.S. Provisional Application Ser. No. 62/148,562, filed Apr. 16, 2015, U.S. Provisional Application Ser. No. 62/148,596, filed Apr. 16, 2015, U.S. Provisional Application Ser. No. 62/148,643, filed Apr. 16, 2015, U.S. Provisional Application Ser. No. 62/148,583, filed Apr. 16, 2015, U.S. Provisional Application Ser. No. 62/148,640, filed Apr. 16, 2015, each and all of which is hereby incorporated by reference in its entirety.

SEQUENCE DISCLOSURE

This application includes as part of its disclosure an electronic sequence listing text file named "11432570006401.txt", having a size of 479,667 bytes and created on Nov. 20, 2020, which is hereby incorporated by reference in its entirety.

FIELD OF THE INVENTION

This invention generally pertains to in vivo screening assays for identification of agents able to treat or prevent photophobia, as well as antibodies and antigen binding fragments thereof, preferably humanized, chimerized, and human antibodies and antigen binding fragments thereof, and compositions containing such antibodies and antigen binding fragments thereof, wherein such antibodies and antigen binding fragments thereof specifically bind to Pituitary Adenylate Cyclase-Activating Polypeptide ("P ACAP") and therapeutic and diagnostic uses for the antibodies, antigen binding fragments, and compositions thereof.

BACKGROUND

Pituitary Adenylate Cyclase-Activating Polypeptide ("PACAP") is a member of the secretin/vasoactive intestinal peptide ("VIP")/growth hormone-releasing hormone ("GHRH") family. PACAP is a multifunctional vasodilatory peptide that exists in two α-amidated active forms, one with 38 amino acids (PACAP38; SEQ ID NO: 1241) and the other with 27 amino acids (PACAP27; SEQ ID NO: 1242). Both peptides have the same N-terminal 27 amino acids and are synthesized from the same precursor protein, prepro-PACAP (See, Moody et al., *Curr. Opin. Endocrinol. Diabetes Obes.,* 18(1): 61-67, 2011). PACAP38 is the more prevalent active form, representing up to 90% of PACAP forms in mammalian tissues (See, Kaiser and Russo, *Neuropeptides,* 47:451-461, 2013). The sequence of PACAP38 is identical in all mammals and differs from the avian and amphibian orthologs by only one amino acid (See, Vaudry et al., *Pharmacol. Rev.,* 52:269-324, 2000). The secretin/VIP/GHRH family includes mammalian peptide histidine methioneamide ("PHM"), secretin, glucagon, glucagon-like peptide-1 ("GLP1"), glucagon-like peptide-2 ("GLP2"), glucose-dependent-insulinotrophic-polypeptide ("GIP"), and growth-hormone-releasing-factor ("GRF"). PACAP27 has 68% sequence identity to VIP at the amino acid level (See, Vaudry et al. 2000).

PACAP is widely distributed in the brain and peripheral organs, e.g., the endocrine system, gonads, sympathetic neurons, respiratory system, gastrointestinal tract, cardiovascular system, and urogenital tracts (See, Schytz et al., *Neurotherapeutics,* 7:191-196, 2010). In particular, PACAP is expressed throughout the nervous system, including a presence in the trigeminovascular system, trigeminal ganglia, spinal cord, hypothalamus, and pituitary. PACAP has roles in neurodevelopment, neuroprotection, neuromodulation, neurogenic inflammation, and nociception with multiple actions (See, Kaiser and Russo (2013)).

Consistent with its widespread distribution, PACAP exerts pleiotropic effects including modulation of neurotransmitter release, vasodilation, bronchodilation, and activation of intestinal motility, increase of insulin and histamine secretion, as well as stimulation of cell proliferation and/or differentiation. PACAP has been shown to act as a hormone, a neurohormone, a neurotransmitter, and a trophic factor in a number of tissues (See, Vaudry et al., *Pharmacological Rev.,* 52(2):269-324, 2000).

The biological effects of PACAP are mediated via three different G-protein coupled receptors: PAC1-R, vasoactive intestinal peptide receptor type 1 ("VPAC1-R"), and vasoactive intestinal peptide receptor type 2 ("VPAC2-R"). These receptors are expressed in diverse tissues. PAC1-R is particularly abundant in the nervous system (e.g., olfactory bulb, thalamus, hypothalamus, cerebellum, and spinal dorsal horn), pituitary, and adrenal glands. By contrast, VPAC1-R and VPAC2-R are expressed mainly in the lung, liver, and testis, although they have been detected in other tissues as well. VPAC1-R expression has been detected in the nervous system (e.g., cerebral cortex and hippocampus), smooth muscle cells of lung, liver, intestine, megakaryocytes, and platelets. VPAC1-R associates with receptor-associated membrane protein ("RAMP", specifically RAMP2) (See, Christopoulos et al., *J. Biol. Chem.,* 278:3293-3297, 2002). VPAC2-R expression profile includes the nervous (e.g., thalamus, hippocampus, brain stem, and dorsal root ganglia ("DRG")), cardiovascular system, gastrointestinal system, pancreas, and reproductive systems (See, Usdin et al., *Endocrin.,* 135:2662-2680, 1994; Sheward et al., *Neurosci.,* 67:409-418, 1995).

PAC1-R is selective for PACAP38 and PACAP27. In particular, PAC1-R binds to PACAP with 100-1000-fold greater affinity than VIP, i.e., $K_D$~0.5 nM for PACAP27/PACAP38 vs. $K_D$~500 nM for VIP. Conversely, VPAC1-R and VPAC2-R have equal affinities for PACAP and VIP ($K_D$~1 nM) (See Schytz et al. (2010)).

Upon activation, these receptors are all capable of causing downstream production of cyclic adenosine monophosphate ("cAMP"), and/or activation of phospholipase C ("PLC"), and/or modulation of phospholipase D ("PLD"). In particular, PAC1-R is coupled to dual signal transduction pathways acting through cAMP and $Ca^{2+}$, whereas VPAC1-R and VPAC2-R are coupled principally to adenylyl cyclase. PAC1-R is coupled to $G_s$ protein, which activates adenylyl cyclase to form cAMP that in turn activates protein kinase A. PAC1-R also couples to Gq and thereby activates PLC, which produces inositol phosphate, which increases cytosolic calcium release from intra-cellular calcium stores. There is some evidence for a role of PAC1-R in PLD activation (See McCulloch et al., *Ann. N. Y. Acad. Sci.,* 921:175-185, 2000). Another PACAP signaling pathway results in the elevation of intra-cellular sodium levels via activation of nonselective cation channels (See Roy et al., *American Journal of Physiology*: Regulatory, *Integrative and Comparative Physiology,* 304(12):R1070-R1084, 2013).

PACAP is hypothesized to play a role in a multitude of diseases and disorders, including but not limited to migraine, headache, and pain, though such a role for PACAP has not been clinically demonstrated. Migraines are believed to have a neurovascular component. Migraines affect approximately 10% of the adult population in the U.S. and are typically accompanied by intense headaches. Approximately 20-30% of migraine sufferers experience aura, comprising focal neurological phenomena that precede and/or accompany the event. A role for PACAP in migraine has been suggested by several observations: (1) plasma levels of PACAP are elevated during migraine attacks (ictal), as compared to interictal levels, in humans (see, Tuka et al., *Cephalalgia,* 33(13):1085-1095, 2013); (2) an infusion of PACAP38 triggered headaches in healthy subjects, and headaches followed by migraine-like attacks in migraineurs (see, Schytz et al., *Brain,* 132:16-25 2009; and Amin et al., *Brain,* 137:779-794, 2014, respectively); (3) PACAP-induced vasodilation may play a role in neurogenic inflammation (see, Kaiser and Russo, *Neuropeptides,* 47:451-461, 2013); and (4) PACAP-induced migraines are associated with photophobia, phonophobia, nausea, and respond to triptans (see, Amin et al., *Brain,* 32:140-149 2012). PACAP has also been shown to induce vasodilation, photophobia, as well as mast cell degranulation and neuronal activation (See, Markovics et al., *Neurobiology of Disease,* 45:633-644 2012; Baun et al., *Cephalalgia,* 32(4):337-345, 2012; Chan et al., *Pharmacology & Therapeutics,* 129:332-351, 2011).

One effective treatment for migraines is the administration of triptans, which are a family of tryptamine-based drugs, including sumatriptan and rizatriptan. Members of this family have an affinity for multiple serotonin receptors, including 5-$HT_{1B}$, 5-$HT_{1D}$, and 5-$HT_{1F}$. Members of this family of drugs selectively constrict cerebral vessels, but also cause vasoconstrictive effects on coronary vessels (See Durham, *New Eng. J. Med.,* 350 (11):1073-75, 2004). There is a theoretical risk of coronary spasm in patients with established heart disease following administration, and cardiac events after taking triptans in rare instances may occur. Accordingly, they are contraindicated for some patients with coronary vascular disease.

Similarly, pain may often be addressed through the administration of certain narcotics or non-steroidal anti-inflammatory drugs ("NSAIDs"). However, the administration of these treatments often has negative consequences. NSAIDs have the potential to cause kidney failure, intestinal bleeding, and liver dysfunction. Narcotics have the potential to cause nausea, vomiting, impaired mental functioning, and addiction. Therefore, it is desirable to identify alternative treatments for pain in order to avoid certain of these negative consequences.

PACAP may also be involved in diseases and disorders other than migraine, headache, and pain. For example, PACAP may correlate to or even play a causal role in anxiety disorders (WO 2012/106407); thrombocytopenia (WO 2004/062684); and inflammatory skin diseases (WO 2010/007175). PACAP and PAC1-R polymorphisms are associated with post-traumatic stress syndrome ("PTSD") in females, major depressive disorder, and generalized anxiety disorder, suggesting a role for PACAP in these conditions. Further, supporting a role for PACAP in thrombocytopenia, trisomy 18 patients have excess PACAP and exhibit defective megakaryocyte maturation (See, Schytz et al. 2010; and Moody et al., *Curr. Opin. Endocrinol. Diabetes Obes.,* 18(1):61-67, 2011).

Also, PACAP and other neuropeptides, such as Calcitonin Gene-Related Peptide ("CGRP"), substance P, neurokinin A, bradykinin, and endothelin-1, are expressed in the lower urinary tract ("LUT") (see, Arms and Vizzard, *Handbook Exp. Pharmacol.,* 202:395-423 2011) and reportedly may play a role in LUT dysfunction and urinary tract disorders such as urinary tract infection ("UTI"), abnormal voiding, urinary urgency, nocturia, urinary incontinence, overactive bladder, and the pain associated with such conditions.

PACAP and PACAP receptors have also been suggested to modulate inflammatory and neuropathic pain and have been implicated in both pronociception and antinociception (See, Davis-Taber et al., *J. Pain,* 9(5):449-56 2008). PACAP has also been reported to be required for spinal desensitization and the induction of neuropathic pain (See, Mabuchi et al., *J. Neurosci.,* 24(33):7283-91, 2004). Additionally, morphine withdrawal behavior is reportedly modified in PACAP-receptor deficient mice further suggesting the role of PACAP in morphine withdrawal anxiolytic response (See, Martin et al., *Mol. Brain Res.,* 110(1):109-18 2003).

BRIEF SUMMARY OF THE INVENTION

In one aspect, the present invention in general relates to a method of screening for an antibody or antigen binding fragment that may be suitable for use in treating or preventing Pituitary Adenylate Cyclase-Activating Peptide (PACAP)-associated photophobia or light aversion, or precluding the onset of PACAP-associated photophobia or light aversion, in a subject in need thereof, which may comprise:

(i) providing at least one first test subject and at least one second test subject;

(ii) administering PACAP to the at least one first test subject and the at least one second test subject;

(iii) further administering to the at least one first test subject one or more anti-PACAP antibodies, anti-Pituitary Adenylate Cyclase Activating Polypeptide type 1 Receptor (PAC1-R) antibodies, anti-vasoactive intestinal peptide receptor type 1 (VPAC1-R) antibodies, or anti-vasoactive intestinal peptide receptor type 2 (VPAC2-R) antibodies, or an antigen binding fragment of any of the foregoing;

(iv) comparing the response of the at least one first test subject and at least one second test subject to light; and (v) based on this comparison, identifying one or more antibodies or antigen binding fragments thereof that yield a decreased light aversion or decreased photophobia in the at least one first test subject as compared with the at least one second test subject, thereby identifying an antibody or antigen binding fragment suitable for use in treating or preventing PACAP-associated photophobia or light aversion, or precluding the onset of PACAP-associated photophobia or light aversion in a subject in need thereof.

In certain embodiments, the invention embraces a method of administering one or more antibodies or antigen binding fragments may comprise administering at least one anti-PACAP antibody or antigen binding fragment thereof. In another embodiment, the invention relates to a method of administering one or more antibodies or antigen binding fragments that may comprise administering at least one anti-PAC1-R antibody or antigen binding fragment thereof. The invention may also generally pertain to a method wherein the efficacy of the one or more antibodies or antigen binding fragments for inhibiting PACAP-associated photophobia or light aversion, or precluding the onset of PACAP-associated photophobia or light aversion, may be confirmed in a human subject. Moreover, another aspect of the invention relates to a method wherein at least one first test subject and at least one second test subject may be different subjects.

Furthermore, the invention generally embraces a method of screening for an antibody or antigen binding fragment thereof that may be suitable for use in treating or preventing Pituitary Adenylate Cyclase-Activating Peptide (PACAP)-associated photophobia or light aversion, or precluding the onset of PACAP-associated photophobia or light aversion, in a subject in need thereof, which may comprise:

(i) providing at least one first test subject and at least one second test subject;

(ii) administering to the at least one first test subject one or more anti-PACAP antibodies, anti-Pituitary Adenylate Cyclase Activating Polypeptide type 1 Receptor (PAC1-R) antibodies, anti-vasoactive intestinal peptide receptor type 1 (VPAC1-R) antibodies, or anti-vasoactive intestinal peptide receptor type 2 (VPAC2-R) antibodies, preferably at least one anti-PACAP antibody and/or at least one anti-PAC1-R antibody, or an antigen binding fragment of any of the foregoing;

(iii) administering PACAP to the at least one first test subject and the at least one second test subject;

(iv) comparing the response of the at least one first test subject and at least one second test subject to light; and (v) based on this comparison, identifying antibodies or antigen binding fragments that yield decreased photophobia or decreased light aversion in the at least one first test subject as compared with the at least one second test subject, identifying an antibody or antigen binding fragment suitable for use in treating or preventing PACAP-associated photophobia or light aversion, or identifying an antibody or antigen binding fragment suitable for precluding the onset of PACAP-associated photophobia or light aversion, in a subject in need thereof.

Moreover, the invention relates to a method wherein administering one or more antibody or antigen binding fragments may comprise administering one or more anti-PACAP antibodies or antigen binding fragments thereof. Furthermore, one aspect of the invention generally pertains to a method wherein administering the one or more antibody or antigen binding fragments may comprise administering one or more anti-PAC1-R antibodies or antigen binding fragments thereof. In another embodiment, the invention embraces a method wherein the efficacy of one or more antibodies or antigen binding fragments for inhibiting PACAP-associated photophobia or light aversion, or precluding the onset of PACAP-associated photophobia or light aversion, may be confirmed in a human subject. Additionally, the invention relates to a method wherein the at least one first test subject and/or the at least one second test subject of any of the methods disclosed herein may be a mammal, e.g., wherein the at least one first test subject and/or at least one second test subject may be a mouse, monkey, rabbit, human, rat, guinea pig, dog, or hamster. Furthermore, said monkey may be a macaque, marmoset, tamarin, spider monkey, owl money, vervet monkey, squirrel monkey, or baboon. Additionally, the invention generally relates to a method wherein the at least one first test subject of any of the methods disclosed herein or at least one second test subject of any of the methods disclosed herein may be a mouse, e.g., a CD1 mouse. The invention also embraces any of the methods disclosed herein wherein the identified antibody or antigen binding fragment thereof may specifically bind PACAP.

In an additional embodiment, the invention relates to a method that may comprise adapting the identified antibody or antigen binding fragment for use in treating a subject who may suffer from one or more of migraine, hemiplegic migraines, cluster headaches, migrainous neuralgia, chronic headaches, tension headaches, secondary headaches due to an underlying structural problem in the head or neck, cranial neuralgia, sinus headaches, allergy-induced headaches, headache, or other migraine condition. Additionally, said subject of any of the methods disclosed herein may have an ocular disorder associated with photophobia that may be selected from one or more of achromatopsia, aniridia, photophobia caused by an anticholinergic drug, aphakia (absence of the lens of the eye), buphthalmos (abnormally narrow angle between the cornea and iris), cataracts, cone dystrophy, congenital abnormalities of the eye, viral conjunctivitis ("pink eye"), corneal abrasion, corneal dystrophy, corneal ulcer, disruption of the corneal epithelium, ectopia lentis, endophthalmitis, eye trauma caused by disease, injury, or infection such as chalazion, episcleritis, glaucoma, keratoconus, or optic nerve hypoplasia, hydrophthalmos, or congenital glaucoma Iritis, optic neuritis, pigment dispersion syndrome, pupillary dilation (naturally or chemically induced), retinal detachment, scarring of the cornea or sclera, and uveitis. Also, said subject of any of the methods disclosed herein may have a nervous-system-related or neurological condition associated with photophobia selected from one or more of autism spectrum disorders, chiari malformation, dyslexia, encephalitis including myalgic encephalomyelitis (chronic fatigue syndrome), meningitis, subarachnoid hemorrhage, tumor of the posterior cranial fossa, ankylosing spondylitis, albinism, ariboflavinosis, benzodiazepines (long term use of or withdrawal from benzodiazepines), chemotherapy, chikungunya infection, cystinosis, Ehlers-Danlos syndrome, hangover, influenza infection, infectious mononucleosis, magnesium deficiency, mercury poisoning, migraine, rabies, and tyrosinemia type II (Richner-Hanhart syndrome). Furthermore, said subject of any of the methods disclosed herein may have a photophobia associated disorder that may be selected from one or more of migraine (with or without aura), iritis, uveitis, meningitis, depression, bipolar disorder, cluster headache or another trigeminal autonomic cephalalgia or blepharospasm, depression, post-traumatic stress syndrome (PTSD) traumatic brain injury, and agoraphobia. In a further embodiment, the invention relates to a method wherein the at least one first subject and/or at least one second subject may suffer from migraine headaches. Yet another embodiment of the invention relates to a method wherein the one or more antibodies or antigen binding fragments thereof may be for use in combination with another active agent for treating migraine. Also, the invention generally pertains to a method wherein the identified antibody or antigen binding fragment thereof may be for use as a monotherapy. For example, said antibody or antigen binding fragment thereof may be for use in combination with another active agent effective for treating migraine, wherein antibody and active agent may be for joint or separate administration. Also, said antibody or fragment thereof may be for use in treating subjects suffering from migraines, in combination with one or more of an analgesic, a triptan, a topiramate, a dihydroergotamine, and an opioid.

The invention also embraces any of the methods disclosed herein wherein anti-PACAP antibodies or antigen binding fragments thereof identified in the disclosed methods, comprise human, humanized, or chimerized anti-PACAP antibodies or antigen binding fragments thereof, which comprise (a) a variable heavy chain comprising a CDR1 sequence consisting of SEQ ID NO: 4; a CDR2 sequence consisting of SEQ ID NO: 6; and a CDR3 sequence consisting of SEQ ID NO: 8; and/or (b) a variable light chain comprising a CDR1 sequence consisting of SEQ ID NO: 24; a CDR2 sequence consisting of SEQ ID NO: 26; and a CDR3 sequence consisting of SEQ ID NO: 28. Alternatively, the selected anti-PACAP antibodies or antigen binding fragments may comprise (a) a variable heavy chain comprising an amino acid sequence with at least 80, 85, 90, 95, 96, 97, 98, or 99% sequence identity to SEQ ID NO: 2 and/or (b) a variable light chain comprising an amino acid sequence with at least 80, 85, 90, 95, 96, 97, 98, or 99% sequence identity to SEQ ID NO: 22. In another specific embodiment, the selected anti-PACAP antibodies and antigen binding fragments thereof may comprise (a) a variable heavy chain having the amino acid sequence of SEQ ID NO: 2, and/or (b) a variable light chain having the amino acid sequence of SEQ ID NO:22. In another embodiment, the selected anti-PACAP antibodies or antigen binding fragments comprise (a) a heavy chain having the amino acid sequence of SEQ ID NO: 1, and/or (b) a light chain having the amino acid sequence of SEQ ID NO: 21.

The invention also embraces any of the methods disclosed herein wherein anti-PACAP antibodies and antigen binding fragments thereof identified by the disclosed methods, preferably human, humanized, or chimerized anti-PACAP antibodies and antigen binding fragments, comprise (a) a variable heavy chain comprising a CDR1 sequence consisting of SEQ ID NO: 44; a CDR2 sequence consisting of SEQ ID NO: 46; and a CDR3 sequence consisting of SEQ ID NO: 48; and/or (b) a variable light chain comprising a CDR1 sequence consisting of SEQ ID NO: 64; a CDR2 sequence consisting of SEQ ID NO: 66; and a CDR3 sequence consisting of SEQ ID NO: 68. More specifically, the selected anti-PACAP antibodies or antigen binding fragments thereof comprise (a) a variable heavy chain comprising an amino acid sequence with at least 80, 85, 90, 95, 96, 97, 98, or 99% sequence identity to SEQ ID NO: 42, and/or (b) a variable light chain comprising an amino acid sequence with at least 80, 85, 90, 95, 96, 97, 98, or 99% sequence identity to SEQ ID NO: 62. In another specific embodiment, the selected anti-PACAP antibodies or antigen binding fragments thereof comprise (a) a variable heavy chain having the amino acid sequence of SEQ ID NO: 42, and/or (b) a variable light chain having the amino acid sequence of SEQ ID NO: 62. More specifically, selected anti-PACAP antibodies and antigen binding fragments thereof may comprise (a) a heavy chain having the amino acid sequence of SEQ ID NO: 41, and/or (b) a light chain having the amino acid sequence of SEQ ID NO: 61.

The invention also embraces any of the methods disclosed herein wherein anti-PACAP antibodies and antigen binding fragments thereof identified by the disclosed methods, preferably human, humanized, or chimerized anti-PACAP antibodies and antigen binding fragments, may comprise (a) a variable heavy chain comprising a CDR1 sequence consisting of SEQ ID NO: 84; a CDR2 sequence consisting of SEQ ID NO:86; and a CDR3 sequence consisting of SEQ ID NO: 88; and/or (b) a variable light chain comprising a CDR1 sequence consisting of SEQ ID NO: 104; a CDR2 sequence consisting of SEQ ID NO: 106; and a CDR3 sequence consisting of SEQ ID NO: 108. In a further specific embodiment, the selected anti-PACAP antibodies or antigen binding fragments comprise (a) a variable heavy chain comprising an amino acid sequence with at least 80, 85, 90, 95, 96, 97, 98, or 99% sequence identity to SEQ ID NO: 82, and/or (b) a variable light chain comprising an amino acid sequence with at least 80, 85, 90, 95, 96, 97, 98, or 99% sequence identity to SEQ ID NO: 102. In another embodiment, the selected anti-PACAP antibodies or antigen binding fragments comprise (a) a variable heavy chain having the amino acid sequence of SEQ ID NO: 82, and/or (b) a variable light chain having the amino acid sequence of SEQ ID NO: 102. In another specific embodiment, the selected anti-PACAP antibodies and antigen binding fragments thereof may comprise (a) a heavy chain having the amino acid sequence of SEQ ID NO: 81, and/or (b) a light chain having the amino acid sequence of SEQ ID NO: 101.

The invention also embraces any of the methods disclosed herein wherein anti-PACAP antibodies and antigen binding fragments thereof identified by the disclosed methods, preferably human, humanized, or chimerized anti-PACAP antibodies or antigen binding fragments, may comprise (a) a variable heavy chain comprising a CDR1 sequence consisting of SEQ ID NO: 124; a CDR2 sequence consisting of SEQ ID NO: 126; and a CDR3 sequence consisting of SEQ ID NO: 128; and/or (b) a variable light chain comprising a CDR1 sequence consisting of SEQ ID NO: 144; a CDR2 sequence consisting of SEQ ID NO:146; and a CDR3 sequence consisting of SEQ ID NO: 148. In a further specific embodiment, the selected anti-PACAP antibodies or antigen binding fragments may comprise (a) a variable heavy chain comprising an amino acid sequence with at least 80, 85, 90, 95, 96, 97, 98, or 99% sequence identity to SEQ ID NO: 122 and/or (b) a variable light chain comprising an amino acid sequence with at least 80, 85, 90, 95, 96, 97, 98, or 99% sequence identity to SEQ ID NO: 142. In another specific embodiment, selected anti-PACAP antibodies and antigen binding fragments thereof may comprise (a) a variable heavy chain having the amino acid sequence of SEQ ID NO: 122, and/or (b) a variable light chain having the amino acid sequence of SEQ ID NO: 142. In another specific embodiment, selected anti-PACAP antibodies and antigen binding fragments thereof may comprise (a) a heavy chain having the amino acid sequence of SEQ ID NO: 121, and/or (b) a light chain having the amino acid sequence of SEQ ID NO: 141.

The invention also embraces any of the methods disclosed herein wherein anti-PACAP antibodies and antigen binding fragments identified by the disclosed methods, preferably human, humanized, or chimerized anti-PACAP antibodies and antigen binding fragments thereof, may comprise (a) a variable heavy chain comprising a CDR1 sequence consisting of SEQ ID NO: 164; a CDR2 sequence consisting of SEQ ID NO: 166; and a CDR3 sequence consisting of SEQ ID NO: 168; and/or (b) a variable light chain comprising a CDR1 sequence consisting of SEQ ID NO: 184; a CDR2 sequence consisting of SEQ ID NO: 186; and a CDR3 sequence consisting of SEQ ID NO: 188. In a further specific embodiment, selected anti-PACAP antibodies and antigen binding fragments thereof may comprise (a) a variable heavy chain comprising an amino acid sequence with at least 80, 85, 90, 95, 96, 97, 98, or 99% sequence identity to SEQ ID NO: 162, and/or (b) a variable light chain comprising an amino acid sequence with at least 80, 85, 90, 95, 96, 97, 98, or 99% sequence identity to SEQ ID NO: 182. In another specific embodiment, selected anti-PACAP antibodies and antigen binding fragments thereof may comprise (a) a variable heavy chain having the amino acid sequence of SEQ ID NO: 162, and/or (b) a variable light chain having the amino acid sequence of SEQ ID NO: 182. In a further specific embodiment, selected anti-PACAP antibodies or antigen binding fragments thereof may comprise (a) a heavy chain having the amino acid sequence of SEQ ID NO: 161, and/or (b) a light chain having the amino acid sequence of SEQ ID NO: 181.

The invention also embraces any of the methods disclosed herein wherein anti-PACAP antibodies and antigen binding fragments thereof identified by the disclosed methods, preferably human, humanized, or chimerized anti-PACAP antibodies and antigen binding fragments thereof, may comprise (a) a variable heavy chain comprising a CDR1 sequence consisting of SEQ ID NO: 204; a CDR2 sequence consisting of SEQ ID NO: 206; and a CDR3 sequence consisting of SEQ ID NO: 208; and/or (b) a variable light chain comprising a CDR1 sequence consisting of SEQ ID NO: 224; a CDR2 sequence consisting of SEQ ID NO: 226; and a CDR3 sequence consisting of SEQ ID NO: 228. In a further specific embodiment, selected anti-PACAP antibodies and antigen binding fragments thereof may comprise (a) a variable heavy chain comprising an amino acid sequence with at least 80, 85, 90, 95, 96, 97, 98, or 99% sequence identity to SEQ ID NO: 202, and/or (b) a variable light chain comprising an amino acid sequence with at least 80, 85, 90, 95, 96, 97, 98, or 99% sequence identity to SEQ ID NO: 222. In another specific embodiment, selected anti-PACAP antibodies and antigen binding fragments thereof may comprise (a) a variable heavy chain having the amino acid sequence of SEQ ID NO: 202, and/or (b) a variable light chain having the amino acid sequence of SEQ ID NO: 222. In another specific embodiment, selected anti-PACAP antibodies and antigen binding fragments thereof may comprise (a) a heavy chain having the amino acid sequence of SEQ ID NO: 201, and/or (b) a light chain having the amino acid sequence of SEQ ID NO: 221.

The invention also embraces any of the methods disclosed herein wherein anti-PACAP antibodies and antigen binding fragments thereof selected by the disclosed methods, preferably human, humanized, or chimerized anti-PACAP antibodies and antigen binding fragments thereof, may comprise (a) a variable heavy chain comprising a CDR1 sequence consisting of SEQ ID NO: 244; a CDR2 sequence consisting of SEQ ID NO: 246; and a CDR3 sequence consisting of SEQ ID NO: 248; and/or (b) a variable light chain comprising a CDR1 sequence consisting of SEQ ID NO: 264; a CDR2 sequence consisting of SEQ ID NO: 266; and a CDR3 sequence consisting of SEQ ID NO: 268. In a further specific embodiment, selected anti-PACAP antibodies and antigen binding fragments thereof may comprise (a) a variable heavy chain comprising an amino acid sequence with at least 80, 85, 90, 95, 96, 97, 98, or 99% sequence identity to SEQ ID NO: 242, and/or (b) a variable light chain comprising an amino acid sequence with at least 80, 85, 90, 95, 96, 97, 98, or 99% sequence identity to SEQ ID NO: 262. In another specific embodiment, selected anti-PACAP antibodies and antigen binding fragments thereof may comprise (a) a variable heavy chain having the amino acid sequence of SEQ ID NO: 242, and/or (b) a variable light chain having the amino acid sequence of SEQ ID NO: 262. In another specific embodiment, the selected anti-PACAP antibodies and antigen binding fragments thereof may comprise (a) a heavy chain having the amino acid sequence of SEQ ID NO: 241, and/or (b) a light chain having the amino acid sequence of SEQ ID NO: 261.

The invention also embraces any of the methods disclosed herein wherein anti-PACAP antibodies and antigen binding fragments thereof identified by the disclosed methods, preferably human, humanized, or chimerized anti-PACAP antibodies and antigen binding fragments thereof, may comprising (a) a variable heavy chain comprising a CDR1 sequence consisting of SEQ ID NO: 284; a CDR2 sequence consisting of SEQ ID NO: 286; and a CDR3 sequence consisting of SEQ ID NO: 288; and/or (b) a variable light chain comprising a CDR1 sequence consisting of SEQ ID NO: 304; a CDR2 sequence consisting of SEQ ID NO: 306; and a CDR3 sequence consisting of SEQ ID NO: 308. In a further specific embodiment, selected anti-PACAP antibodies and antigen binding fragments thereof may comprise a variable heavy chain comprising an amino acid sequence with at least 80, 85, 90, 95, 96, 97, 98, or 99% sequence identity to SEQ ID NO: 282, and/or a variable light chain comprising an amino acid sequence with at least 80, 85, 90, 95, 96, 97, 98, or 99% sequence identity to SEQ ID NO: 302. In another specific embodiment, selected anti-PACAP antibodies and antigen binding fragments thereof may comprise (a) a variable heavy chain having the amino acid sequence of SEQ ID NO: 282, and/or (b) a variable light chain having the amino acid sequence of SEQ ID NO: 302. In another specific embodiment, selected anti-PACAP antibodies and antigen binding fragments thereof may comprise (a) a heavy chain having the amino acid sequence of SEQ ID NO: 281, and/or (b) a light chain having the amino acid sequence of SEQ ID NO: 301.

The invention also embraces any of the methods disclosed herein wherein anti-PACAP antibodies and antigen binding fragments thereof identified by the disclosed methods, preferably human, humanized, or chimerized anti-PACAP antibodies and antigen binding fragments thereof, may comprise (a) a variable heavy chain comprising a CDR1 sequence consisting of SEQ ID NO: 324; a CDR2 sequence consisting of SEQ ID NO: 326; and a CDR3 sequence consisting of SEQ ID NO: 328; and/or (b) a variable light chain comprising a CDR1 sequence consisting of SEQ ID NO: 344; a CDR2 sequence consisting of SEQ ID NO: 346; and a CDR3 sequence consisting of SEQ ID NO: 348. In a further specific embodiment, selected anti-PACAP antibodies and antigen binding fragments thereof may comprise a variable heavy chain comprising an amino acid sequence with at least 80, 85, 90, 95, 96, 97, 98, or 99% sequence identity to SEQ ID NO: 322, and/or a variable light chain comprising an amino acid sequence with at least 80, 85, 90, 95, 96, 97, 98, or 99% sequence identity to SEQ ID NO: 342. In another specific embodiment, selected anti-PACAP antibodies and antigen binding fragments thereof may comprise (a) a variable heavy chain having the amino acid sequence of SEQ ID NO: 322, and/or (b) a variable light chain having the amino acid sequence of SEQ ID NO: 342. In another specific embodiment, the selected anti-PACAP antibodies and antigen binding fragments thereof may comprise (a) a heavy chain having the amino acid sequence of SEQ ID NO: 321, and/or (b) a light chain having the amino acid sequence of SEQ ID NO: 341.

The invention also embraces any of the methods disclosed herein wherein anti-PACAP antibodies and antigen binding fragments thereof identified by the disclosed methods, preferably human, humanized, or chimerized anti-PACAP antibodies and antigen binding fragments thereof, may comprise (a) a variable heavy chain comprising a CDR1 sequence consisting of SEQ ID NO: 364; a CDR2 sequence consisting of SEQ ID NO: 366; and a CDR3 sequence consisting of SEQ ID NO: 368; and/or (b) a variable light chain comprising a CDR1 sequence consisting of SEQ ID NO: 384; a CDR2 sequence consisting of SEQ ID NO: 386; and a CDR3 sequence consisting of SEQ ID NO: 388. In a further specific embodiment, selected anti-PACAP antibodies and antigen binding fragments thereof may comprise a variable heavy chain comprising an amino acid sequence with at least 80, 85, 90, 95, 96, 97, 98, or 99% sequence identity to SEQ ID NO: 362, and/or a variable light chain comprising an amino acid sequence with at least 80, 85, 90, 95, 96, 97, 98, or 99% sequence identity to SEQ ID NO: 382. In another specific embodiment, selected anti-PACAP antibodies and antigen binding fragments thereof may comprise (a) a variable heavy chain having the amino acid sequence of SEQ ID NO: 362, and/or (b) a variable light chain having the amino acid sequence of SEQ ID NO: 382. In another specific embodiment, selected anti-PACAP antibodies and antigen binding fragments thereof may comprise (a) a heavy chain having the amino acid sequence of SEQ ID NO: 361, and/or (b) a light chain having the amino acid sequence of SEQ ID NO: 381.

The invention also embraces any of the methods disclosed herein wherein anti-PACAP antibodies and antigen binding fragments thereof identified by the disclosed methods, preferably human, humanized, or chimerized anti-PACAP antibodies and antigen binding fragments thereof, may comprise (a) a variable heavy chain comprising a CDR1 sequence consisting of SEQ ID NO: 484; a CDR2 sequence consisting of SEQ ID NO: 486; and a CDR3 sequence consisting of SEQ ID NO: 488; and/or (b) a variable light chain comprising a CDR1 sequence consisting of SEQ ID NO: 504; a CDR2 sequence consisting of SEQ ID NO: 506; and a CDR3 sequence consisting of SEQ ID NO: 508. In a further specific embodiment, selected anti-PACAP antibodies and antigen binding fragments thereof may comprise a variable heavy chain comprising an amino acid sequence with at least 80, 85, 90, 95, 96, 97, 98, or 99% sequence identity to SEQ ID NO: 482, and/or a variable light chain comprising an amino acid sequence with at least 80, 85, 90, 95, 96, 97, 98, or 99% sequence identity to SEQ ID NO: 502. In another specific embodiment, selected anti-PACAP antibodies and antigen binding fragments thereof may comprise (a) a variable heavy chain having the amino acid sequence of SEQ ID NO: 482, and/or (b) a variable light chain having the amino acid sequence of SEQ ID NO: 502. In a specific embodiment, selected anti-PACAP antibodies and antigen binding fragments thereof may comprise (a) a heavy chain having the amino acid sequence of SEQ ID NO: 481, and/or (b) a light chain having the amino acid sequence of SEQ ID NO: 501.

The invention also embraces any of the methods disclosed herein wherein anti-PACAP antibodies and antigen binding fragments thereof identified by the disclosed methods, preferably human, humanized, or chimerized anti-PACAP antibodies and antigen binding fragments thereof, may comprise (a) a variable heavy chain comprising a CDR1 sequence consisting of SEQ ID NO: 524; a CDR2 sequence consisting of SEQ ID NO: 526; and a CDR3 sequence consisting of SEQ ID NO: 528; and/or (b) a variable light chain comprising a CDR1 sequence consisting of SEQ ID NO: 544; a CDR2 sequence consisting of SEQ ID NO: 546; and a CDR3 sequence consisting of SEQ ID NO: 548. In a further specific embodiment, selected anti-PACAP antibodies and antigen binding fragments thereof may comprise a variable heavy chain comprising an amino acid sequence with at least 80, 85, 90, 95, 96, 97, 98, or 99% sequence identity to SEQ ID NO: 522, and/or a variable light chain comprising an amino acid sequence with at least 80, 85, 90, 95, 96, 97, 98, or 99% sequence identity to SEQ ID NO: 542. In another specific embodiment, selected anti-PACAP antibodies and antigen binding fragments thereof may comprise (a) a variable heavy chain having the amino acid sequence of SEQ ID NO: 522, and/or (b) a variable light chain having the amino acid sequence of SEQ ID NO: 542. In a further specific embodiment, selected anti-PACAP antibodies and antigen binding fragments thereof may comprise (a) a heavy chain having the amino acid sequence of SEQ ID NO: 521, and/or (b) a light chain having the amino acid sequence of SEQ ID NO: 541.

The invention also embraces any of the methods disclosed herein wherein anti-PACAP antibodies and antigen binding fragments thereof identified by the disclosed methods, preferably human, humanized, or chimerized anti-PACAP antibodies and antigen binding fragments thereof, may comprise (a) a variable heavy chain comprising a CDR1 sequence consisting of SEQ ID NO: 564; a CDR2 sequence consisting of SEQ ID NO: 566; and a CDR3 sequence consisting of SEQ ID NO: 568; and/or (b) a variable light chain comprising a CDR1 sequence consisting of SEQ ID NO: 584; a CDR2 sequence consisting of SEQ ID NO: 586; and a CDR3 sequence consisting of SEQ ID NO: 588. In a further specific embodiment, selected anti-PACAP antibodies and antigen binding fragments thereof may comprise a variable heavy chain comprising an amino acid sequence with at least 80, 85, 90, 95, 96, 97, 98, or 99% sequence identity to SEQ ID NO: 562, and/or a variable light chain comprising an amino acid sequence with at least 80, 85, 90, 95, 96, 97, 98, or 99% sequence identity to SEQ ID NO: 582. In another specific embodiment, selected anti-PACAP antibodies and antigen binding fragments thereof may comprise (a) a variable heavy chain having the amino acid sequence of SEQ ID NO: 562, and/or (b) a variable light chain having the amino acid sequence of SEQ ID NO: 582. In a further specific embodiment, selected anti-PACAP antibodies and antigen binding fragments thereof may comprise (a) a heavy chain having the amino acid sequence of SEQ ID NO: 561, and/or (b) a light chain having the amino acid sequence of SEQ ID NO: 581.

The invention also embraces any of the methods disclosed herein wherein anti-PACAP antibodies and antigen binding fragments thereof identified by the disclosed methods, preferably human, humanized, or chimerized anti-PACAP antibodies and antigen binding fragments thereof, may comprise (a) a variable heavy chain comprising a CDR1 sequence consisting of SEQ ID NO: 604; a CDR2 sequence consisting of SEQ ID NO: 606; and a CDR3 sequence consisting of SEQ ID NO: 608; and/or (b) a variable light chain comprising a CDR1 sequence consisting of SEQ ID NO: 624; a CDR2 sequence consisting of SEQ ID NO: 626; and a CDR3 sequence consisting of SEQ ID NO: 628. In a further specific embodiment, selected anti-PACAP antibodies and antigen binding fragments thereof may comprise a variable heavy chain comprising an amino acid sequence with at least 80, 85, 90, 95, 96, 97, 98, or 99% sequence identity to SEQ ID NO: 602, and/or a variable light chain comprising an amino acid sequence with at least 80, 85, 90, 95, 96, 97, 98, or 99% sequence identity to SEQ ID NO: 622. In a further specific embodiment, selected anti-PACAP antibodies and antigen binding fragments thereof may comprise (a) a variable heavy chain having the amino acid sequence of SEQ ID NO: 602, and/or (b) a variable light chain having the amino acid sequence of SEQ ID NO: 622. In another specific embodiment, selected anti-PACAP antibodies and antigen binding fragments thereof may comprise (a) a heavy chain having the amino acid sequence of SEQ ID NO: 601, and/or (b) a light chain having the amino acid sequence of SEQ ID NO: 621.

The invention also embraces any of the methods disclosed herein wherein anti-PACAP antibodies and antigen binding fragments thereof identified by the disclosed methods, preferably human, humanized, or chimerized anti-PACAP antibodies and antigen binding fragments thereof, may comprise (a) a variable heavy chain comprising a CDR1 sequence consisting of SEQ ID NO: 644; a CDR2 sequence consisting of SEQ ID NO: 646; and a CDR3 sequence consisting of SEQ ID NO: 648; and/or (b) a variable light chain comprising a CDR1 sequence consisting of SEQ ID NO: 664; a CDR2 sequence consisting of SEQ ID NO: 666; and a CDR3 sequence consisting of SEQ ID NO: 668. In a further specific embodiment, selected anti-PACAP antibodies and antigen binding fragments thereof may comprise a variable heavy chain comprising an amino acid sequence with at least 80, 85, 90, 95, 96, 97, 98, or 99% sequence identity to SEQ ID NO: 642, and/or a variable light chain comprising an amino acid sequence with at least 80, 85, 90, 95, 96, 97, 98, or 99% sequence identity to SEQ ID NO: 662. In another specific embodiment, selected anti-PACAP antibodies and antigen binding fragments thereof may comprise (a) a variable heavy chain having the amino acid sequence of SEQ ID NO: 642, and/or (b) a variable light chain having the amino acid sequence of SEQ ID NO: 662. In another specific embodiment, selected anti-PACAP antibodies and antigen binding fragments thereof may comprise (a) a heavy chain having the amino acid sequence of SEQ ID NO: 641, and/or (b) a light chain having the amino acid sequence of SEQ ID NO: 661.

The invention also embraces any of the methods disclosed herein wherein anti-PACAP antibodies and antigen binding fragments thereof identified by the disclosed methods, preferably human, humanized, or chimerized anti-PACAP antibodies and antigen binding fragments thereof, may comprise (a) a variable heavy chain comprising a CDR1 sequence consisting of SEQ ID NO: 684; a CDR2 sequence consisting of SEQ ID NO: 686; and a CDR3 sequence consisting of SEQ ID NO: 688; and/or (b) a variable light chain comprising a CDR1 sequence consisting of SEQ ID NO: 704; a CDR2 sequence consisting of SEQ ID NO: 706; and a CDR3 sequence consisting of SEQ ID NO: 708. In a further specific embodiment, selected anti-PACAP antibodies and antigen binding fragments thereof may comprise a variable heavy chain comprising an amino acid sequence with at least 80, 85, 90, 95, 96, 97, 98, or 99% sequence identity to SEQ ID NO: 682, and/or a variable light chain comprising an amino acid sequence with at least 80, 85, 90, 95, 96, 97, 98, or 99% sequence identity to SEQ ID NO: 702. In another specific embodiment, selected anti-PACAP antibodies and antigen binding fragments thereof may comprise (a) a variable heavy chain having the amino acid sequence of SEQ ID NO: 682, and/or (b) a variable light chain having the amino acid sequence of SEQ ID NO: 702. In another specific embodiment, selected anti-PACAP antibodies and antigen binding fragments may comprise (a) a heavy chain having the amino acid sequence of SEQ ID NO: 681, and/or (b) a light chain having the amino acid sequence of SEQ ID NO: 701.

The invention also embraces any of the methods disclosed herein wherein anti-PACAP antibodies and antigen binding fragments thereof identified by the disclosed methods, preferably human, humanized, or chimerized anti-PACAP antibodies and antigen binding fragments thereof, may comprise (a) a variable heavy chain comprising a CDR1 sequence consisting of SEQ ID NO: 724; a CDR2 sequence consisting of SEQ ID NO: 726; and a CDR3 sequence consisting of SEQ ID NO: 728; and/or (b) a variable light chain comprising a CDR1 sequence consisting of SEQ ID NO: 744; a CDR2 sequence consisting of SEQ ID NO: 746; and a CDR3 sequence consisting of SEQ ID NO: 748. In a further specific embodiment, selected anti-PACAP antibodies and antigen binding fragments thereof may comprise a variable heavy chain comprising an amino acid sequence with at least 80, 85, 90, 95, 96, 97, 98, or 99% sequence identity to SEQ ID NO: 722, and/or a variable light chain comprising an amino acid sequence with at least 80, 85, 90, 95, 96, 97, 98, or 99% sequence identity to SEQ ID NO: 742. In another specific embodiment, selected anti-PACAP antibodies and antigen binding fragments thereof may comprise (a) a variable heavy chain having the amino acid sequence of SEQ ID NO: 722, and/or (b) a variable light chain having the amino acid sequence of SEQ ID NO: 742. In a further specific embodiment, the selected anti-PACAP antibodies and antigen binding fragments thereof may comprise (a) a heavy chain having the amino acid sequence of SEQ ID NO: 721, and/or (b) a light chain having the amino acid sequence of SEQ ID NO: 741.

The invention also embraces any of the methods disclosed herein wherein anti-PACAP antibodies and antigen binding fragments thereof identified by the disclosed methods, preferably human, humanized, or chimerized anti-PACAP antibodies and antigen binding fragments thereof, may comprise (a) a variable heavy chain comprising a CDR1 sequence consisting of SEQ ID NO: 764; a CDR2 sequence consisting of SEQ ID NO: 766; and a CDR3 sequence consisting of SEQ ID NO: 768; and/or (b) a variable light chain comprising a CDR1 sequence consisting of SEQ ID NO: 784; a CDR2 sequence consisting of SEQ ID NO: 786; and a CDR3 sequence consisting of SEQ ID NO: 788. In a further specific embodiment, selected anti-PACAP antibodies and antigen binding fragments thereof may comprise a variable heavy chain comprising an amino acid sequence with at least 80, 85, 90, 95, 96, 97, 98, or 99% sequence identity to SEQ ID NO: 762, and/or a variable light chain comprising an amino acid sequence with at least 80, 85, 90, 95, 96, 97, 98, or 99% sequence identity to SEQ ID NO: 782. In another specific embodiment, selected anti-PACAP antibodies and antigen binding fragments thereof may comprise (a) a variable heavy chain having the amino acid sequence of SEQ ID NO: 762, and/or (b) a variable light chain having the amino acid sequence of SEQ ID NO: 782. In another specific embodiment, selected anti-PACAP antibodies and antigen binding fragments thereof may comprise (a) a heavy chain having the amino acid sequence of SEQ ID NO: 761, and/or (b) a light chain having the amino acid sequence of SEQ ID NO: 781.

The invention also embraces any of the methods disclosed herein wherein anti-PACAP antibodies and antigen binding fragments thereof identified by the disclosed methods, preferably human, humanized, or chimerized anti-PACAP antibodies and antigen binding fragments thereof, may comprise (a) a variable heavy chain comprising a CDR1 sequence consisting of SEQ ID NO: 804; a CDR2 sequence consisting of SEQ ID NO: 806; and a CDR3 sequence consisting of SEQ ID NO: 808; and/or (b) a variable light chain comprising a CDR1 sequence consisting of SEQ ID NO: 824; a CDR2 sequence consisting of SEQ ID NO: 826; and a CDR3 sequence consisting of SEQ ID NO: 828. In a further specific embodiment, selected anti-PACAP antibodies and antigen binding fragments thereof may comprise a variable heavy chain comprising an amino acid sequence with at least 80, 85, 90, 95, 96, 97, 98, or 99% sequence identity to SEQ ID NO: 802, and/or a variable light chain comprising an amino acid sequence with at least 80, 85, 90, 95, 96, 97, 98, or 99% sequence identity to SEQ ID NO: 822. In a further embodiment, selected anti-PACAP antibodies and antigen binding fragments thereof may comprise (a) a variable heavy chain having the amino acid sequence of SEQ ID NO: 802, and/or (b) a variable light chain having the amino acid sequence of SEQ ID NO: 822. In another specific embodiment, selected anti-PACAP antibodies and antigen binding fragments thereof may comprise (a) a heavy chain having the amino acid sequence of SEQ ID NO: 801, and/or (b) a light chain having the amino acid sequence of SEQ ID NO: 821.

Additionally, another aspect of the invention generally relates to any of the methods disclosed herein wherein the anti-PACAP antibody or fragment thereof may comprise: a light chain and/or a heavy chain, which has a framework (FR) region and one or more Complementary Determining Region(s) (CDR), and wherein one or more of the FR or CDR residues in the light chain and/or heavy chain may be substituted with another amino acid residue. Also, the invention pertains to any of the methods disclosed herein wherein the antibody or fragment thereof may be a humanized antibody or fragment thereof; and/or wherein the antibody or fragment thereof may be a chimeric antibody or fragment thereof; and/or wherein the antibody or fragment thereof may comprise a single chain antibody or fragment thereof. Said chimeric antibody or fragment thereof according to the invention may comprise a human Fc, e.g., wherein the human Fc may be derived from IgG1, IgG2, IgG3, or IgG4.

Furthermore, the invention generally pertains to any of the methods disclosed herein wherein anti-PACAP antibodies or fragments thereof may comprise a polypeptide sequence that may have at least 90% or greater homology to two of the polypeptide sequences of the invention. Additionally, the invention relates to any of the methods disclosed herein wherein the anti-PACAP antibody or fragment thereof may comprise a polypeptide sequence having at least 95% or greater homology to any one of the polypeptide sequences of the invention.

Moreover, another aspect of the invention embraces any of the methods disclosed herein wherein the anti-PACAP antibody or fragment thereof may bind to PACAP with a binding affinity (KD) of less than or equal to $5\times10^{-5}$ M, $10^{-5}$ M, $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $10^{-9}$M, $5\times10^{-19}$ M, $10^{-19}$ M, $5\times10^{-11}$ M, $10^{-11}$ M, $5\times10^{-12}$ M, $10^{-12}$ M, $5\times10^{-13}$ M, or $10^{-13}$ M, as determined by ELISA, bio-layer interferometry ("BLI"), KinExA® (kinetic exclusion assay), or surface plasmon resonance at 25° C. or 37° C. Furthermore, the invention embraces a method wherein the anti-PACAP antibody or fragment thereof may bind to PACAP with a KD that may be less than about 100 nM, less than about 40 nM, less than about 1 nM, less than about 100 pM, less than about 50 pM, or less than about 25 pM, and/or wherein the anti-PACAP antibody or fragment thereof may bind to PACAP with a KD that may be between about 10 pM and about 100 pM.

Another embodiment of the invention relates to any of the methods disclosed herein wherein the antibody or fragment thereof may be entirely non-glycosylated, or may lack N-glycosylation, or may contain only mannose residues. An additional embodiment of the invention pertains to any of the methods disclosed herein wherein the antibody or fragment thereof may contain an Fc region that may be modified to alter effector function, half-life, proteolysis, and/or glycosylation. The invention additionally embraces any of the methods disclosed herein wherein the anti-PACAP antibody or fragment thereof may specifically bind to circulating soluble PACAP molecules in vivo. An additional embodiment of the invention encompasses any of the methods disclosed herein wherein the anti-PACAP antibody or fragment thereof may specifically bind to PACAP27 and/or PACAP38.

In yet another embodiment, the invention embraces any of the methods disclosed herein wherein the affinity of said anti-PACAP antibody or fragment thereof for PACAP may be at least 10-fold, 30-fold, 100-fold, 300-fold, 1000-fold, 3000-fold, 10000-fold, 30000-fold, 100000-fold, 300000-fold, 1000000-fold, 3000000-fold, 10000000-fold, 30000000-fold or more stronger than the affinity of said anti-PACAP antibody and antigen binding fragment to VIP. Also, the invention pertains to any of the methods disclosed herein wherein the anti-PACAP antibody or fragment thereof may (a) inhibit or neutralize at least one biological effect elicited by PACAP; (b) neutralize or inhibit PACAP activation of at least one of PAC1-R, VPAC1-R and/or VPAC2-R; (c) neutralize or inhibit PACAP activation of each of PAC1-R, VPAC1-R and VPAC2-R; (d) neutralize or inhibit PACAP activation of PAC1-R; (e) inhibits PACAP binding to at least one of PAC1-R, VPAC1-R and/or VPAC2-R; (f) inhibits PACAP binding to each of PAC1-R, VPAC1-R and/or VPAC2-R; (g) inhibits PACAP binding to PAC1-R; and/or (h) inhibits PACAP-induced cAMP production. Additionally, the invention encompasses any of the methods disclosed herein wherein the anti-PACAP antibody or fragment thereof may inhibit the association of PACAP with one or more PACAP receptors including PAC-1R, VPAC1-R, and/or VPAC2-R.

An additional embodiment of the invention embraces any of the methods disclosed herein wherein the antibody or fragment thereof may be administered intramuscularly, subcutaneously, intravenously, rectally, by infusion, orally, transdermally, or by inhalation. Also, the invention relates to any of the methods disclosed herein wherein the antibody or fragment thereof may be administered intravenously. Also, the invention encompasses any of the methods disclosed herein wherein the antibody or fragment thereof may be administered with an additional therapeutic agent or regimen selected from anti-histamines, anti-inflammatory agents, and antibiotics. Also, another embodiment of the invention pertains to any of the methods disclosed herein wherein the antibody or fragment thereof may be directly or indirectly attached to a detectable label or therapeutic agent. The invention further relates to any of the methods disclosed herein wherein the antibody or fragment thereof may further comprise an effector moiety. Said effector moiety may be a detectable moiety or a functional moiety, e.g., wherein said detectable moiety may be a fluorescent dye, an enzyme, a substrate, a bioluminescent material, a radioactive material, or a chemiluminescent material, or said functional moiety may be streptavidin, avidin, biotin, a cytotoxin, a cytotoxic agent, or a radioactive material.

Another aspect of the invention generally relates to a method of assessing the potential in vivo efficacy of a candidate anti-Pituitary Adenylate Cyclase-Activating Peptide (PACAP) antibody, an anti-Pituitary Adenylate Cyclase Activating Polypeptide type 1 Receptor (PAC1-R) antibody, and antigen binding fragment thereof for treating PACAP-associated photophobia or light aversion, that may comprise determining whether the antibody or fragment thereof may inhibit or diminish light aversion behavior in a rodent administered PACAP, as compared to a rodent administered PACAP in the presence of one or more of the candidate anti-PACAP, anti-PAC1-R antibody or fragment thereof. For example, said method of assessment may be used to assess whether the antibody or fragment thereof may be effective for treatment of a neurological condition characterized by increased PACAP levels, and/or said method of assessment may be used to assess whether the antibody or fragment thereof may be effective for treatment of migraine, menstrual migraine, or chronic migraine. Additionally, said method of assessment may be used to assess whether the antibody or fragment thereof may be effective for treatment of migraines (with or without aura), weight loss, cancer or tumors, angiogenesis associated with cancer or tumor growth, angiogenesis associated with cancer or tumor survival, hemiplegic migraines, cluster headaches, migrainous neuralgia, chronic headaches, tension headaches, general headaches, headache-free migraine, abdominal migraine, hot flashes, chronic paroxysomal hemicrania, secondary headaches caused by an underlying structural problem in the head or neck, cranial neuralgia, sinus headaches, allergy-induced headaches or allergy-induced migraines, pain, inflammatory pain, post-operative incision pain, complex regional pain syndrome, cancer pain, primary or metastatic bone cancer pain, fracture pain, osteoporotic fracture pain, pain resulting from burn, osteoporosis, gout joint pain, pain associated with sickle cell crises, nociceptive pain, hepatocellular carcinoma, breast cancer, liver cirrhosis, neurogenic pain, neuropathic pain, trigeminal neuralgia, post-herpetic neuralgia, phantom limb pain, fibromyalgia, menstrual pain, ovarialgia, reflex sympathetic dystrophy, neurogenic pain, osteoarthritis or rheumatoid arthritis pain, lower back pain, diabetic neuropathy, sciatica, visceral pain associated with gastro-esophageal reflux, dyspepsia, irritable bowel syndrome, inflammatory bowel disease, Crohn's disease, ileitis, ulcerative colitis, renal colic, dysmenorrhea, cystitis, menstrual period, labor, menopause, prostatitis, or pancreatitis.

An additional embodiment of the invention relates to any of the methods disclosed herein wherein any of said methods may further comprise administering an additional active agent selected from a beta-blocker, flunarizine, valproic acid, topiramate, amitriptyline, venlafaxine, gabapentin, naproxen, butterbur root, vitamin B2, and/or magnesium. Also, said additional active agent may be selected from agonists, antagonists, and modulators of TNF-α, IL-2, IL-4, IL-6, IL-10, IL-12, IL-13, IL-18, IFN-α, IFN-γ, BAFF, CXCL13, IP-10, VEGF, EPO, EGF, HRG, Hepatocyte growth Factor (HGF), hepcidin, antibodies reactive against any of the foregoing, and antibodies reactive against any of their receptors. Yet another embodiment of the invention embraces any of the methods disclosed herein wherein any of said methods may further comprise administering analgesics, anti-histamines, antipyretics, anti-inflammatories, antibiotics, antivirals, and/or anti-cytokine agents.

An additional embodiment of the invention relates to any of the methods disclosed herein wherein any of said methods may further comprise administering an active agent that may be selected from one or more of the following: 2-arylpropionic acids, aceclofenac, acemetacin, acetylsalicylic acid, alclofenac, alminoprofen, amoxiprin, ampyrone, arylalkanoic acids, azapropazone, benorylate/benorilate, benoxaprofen, bromfenac, carprofen, celecoxib, choline magnesium salicylate, clofezone, COX-2 inhibitors, dexibuprofen, dexketoprofen, diclofenac, diflunisal, droxicam, ethenzamide, etodolac, etoricoxib, faislamine, fenamic acids, fenbufen, fenoprofen, flufenamic acid, flunoxaprofen, flurbiprofen, ibuprofen, ibuproxam, indomethacin, indoprofen, kebuzone, ketoprofen, ketorolac, lornoxicam, loxoprofen, lumiracoxib, magnesium salicylate, meclofenamic acid, mefenamic acid, meloxicam, metamizole, methyl salicylate, mofebutazone, nabumetone, naproxen, N-arylanthranilic acids, Nerve Growth Factor (NGF), oxametacin, oxaprozin, oxicams, oxyphenbutazone, oxytocin, parecoxib, phenazone, phenylbutazone, phenylbutazone, piroxicam, pirprofen, profens, proglumetacin, pyrazolidine derivatives, rofecoxib, salicyl salicylate, salicylamide, salicylates, substance P, sulfinpyrazone, sulindac, suprofen, tenoxicam, tiaprofenic acid, tolfenamic acid, tolmetin, and valdecoxib.

Additionally, the invention relates to any of the methods disclosed herein wherein any of said methods may further comprise administering an anti-histamine active agent that may be selected from one or more of the following: acrivastine, astemizole, azatadine, azelastine, betatastine, brompheniramine, buclizine, cetirizine, cetirizine analogues, chlorpheniramine, clemastine, CS 560, cyproheptadine, desloratadine, dexchlorpheniramine, ebastine, epinastine, fexofenadine, HSR 609, hydroxyzine, levocabastine, loratidine, methscopolamine, mizolastine, norastemizole, phenindamine, promethazine, pyrilamine, terfenadine, and tranilast. Moreover, the invention encompasses any of the methods disclosed herein where any of said methods may further comprise administering an antibiotic active agent that may be selected from one or more of the following: amikacin, aminoglycosides, amoxicillin, ampicillin, ansamycins, arsphenamine, azithromycin, azlocillin, aztreonam, bacitracin, carbacephem, carbapenems, carbenicillin, cefaclor, cefadroxil, cefalexin, cefalothin, cefalotin, cefamandole, cefazolin, cefdinir, cefditoren, cefepime, cefixime, cefoperazone, cefotaxime, cefoxitin, cefpodoxime, cefprozil, ceftazidime, ceftibuten, ceftizoxime, ceftobiprole, ceftriaxone, cefuroxime, cephalosporins, chloramphenicol, cilastatin, ciprofloxacin, clarithromycin, clindamycin, cloxacillin, colistin, co-trimoxazole, dalfopristin, demeclocycline, dicloxacillin, dirithromycin, doripenem, doxycycline, enoxacin, ertapenem, erythromycin, ethambutol, flucloxacillin, fosfomycin, furazolidone, fusidic acid, gatifloxacin, geldanamycin, gentamicin, glycopeptides, herbimycin, imipenem, isoniazid, kanamycin, levofloxacin, lincomycin, linezolid, lomefloxacin, loracarbef, macrolides, mafenide, meropenem, methicillin, metronidazole, mezlocillin, minocycline, monobactams, moxifloxacin, mupirocin, nafcillin, neomycin, netilmicin, nitrofurantoin, norfloxacin, ofloxacin, oxacillin, oxytetracycline, paromomycin, penicillin, penicillins, piperacillin, platensimycin, polymyxin B, polypeptides, prontosil, pyrazinamide, quinolones, quinupristin, rifampicin, rifampin, roxithromycin, spectinomycin, streptomycin, sulfacetamide, sulfamethizole, sulfanilamide, sulfasalazine, sulfisoxazole, sulfonamides, teicoplanin, telithromycin, tetracycline, tetracyclines, ticarcillin, tinidazole, tobramycin, trimethoprim, trimethoprim-sulfamethoxazole, troleandomycin, trovafloxacin, and vancomycin.

Also, the invention relates to any of the methods disclosed herein wherein any of said methods may further comprise administering an active agent that may be selected from: aldosterone, beclomethasone, betamethasone, corticosteroids, cortisol, cortisone acetate, deoxycorticosterone acetate, dexamethasone, fludrocortisone acetate, glucocorticoids, hydrocortisone, methylprednisolone, prednisolone, prednisone, steroids, and triamcinolone, and combinations thereof. An additional embodiment of the invention pertains to any of the methods disclosed herein wherein any of said methods may further comprise administering an active agent that ma be selected from: ibuprofen, naproxen, sumatriptan, paracetamol/acetaminophen, caffeine, a triptan, a corticosteroid, an anti-mimetic, and combinations thereof.

Another aspect of the invention generally encompasses a method of screening for antibodies or antigen binding fragments that may decrease or inhibit light-induced pain signaling through intrinsically photosensitive retinal ganglion cells ("ipRGCs"), that may comprise:

(i) providing at least one first test subject and at least one second test subject;
(ii) administering PACAP to the first test subject and the second test subject;
(iii) administering to the first test subject one or more of anti-Pituitary Adenylate Cyclase-Activating Peptide (PACAP) antibodies, anti-Pituitary Adenylate Cyclase Activating Polypeptide type 1 Receptor (PAC1-R) antibodies, anti-vasoactive intestinal peptide receptor type 1 (VPAC1-R) antibodies, or anti-vasoactive intestinal peptide receptor type 2 (VPAC2-R) antibodies, preferably an anti-PACAP antibody or anti-PAC1-R antibody, or an antigen binding fragment of any of the foregoing;
(iv) comparing the response of the at least one first test subject and at least one second test subject to light; and
(v) based on this comparison identifying one or more antibodies that decrease or inhibit light-induced pain signaling through intrinsically photosensitive retinal ganglion cells ("ipRGCs").

An additional embodiment of the invention relates to a method of screening for a test substance that may treat or prevent photophobia or light aversion in a subject in need thereof by decreasing or inhibiting light-induced pain signaling through intrinsically photosensitive retinal ganglion cells ("ipRGCs"), that may comprise:

(i) providing at least one first test subject and at least one second test subject;
(ii) administering PACAP to the first test subject and the second test subject;
(iii) administering to the first test subject one or more of anti-Pituitary Adenylate Cyclase-Activating Peptide (PACAP) antibodies, anti-Pituitary Adenylate Cyclase Activating Polypeptide type 1 Receptor (PAC1-R) antibodies, anti-vasoactive intestinal peptide receptor type 1 (VPAC1-R) antibodies, or anti-vasoactive intestinal peptide receptor type 2 (VPAC2-R) antibodies, preferably an anti-PACAP antibody or anti-PAC1-R antibody, or an antigen binding fragment of any of the foregoing;
(iv) comparing the response of the at least one first test subject and at least one second test subject to light; and
(v) based on this comparison, identifying one or more antibodies or antigen binding fragments thereof that may be useful for treating or preventing light-induced pain signaling through ipRGCs.

An aspect of the present invention in general relates to anti-PACAP antibodies and antigen binding fragments thereof, preferably human, humanized, or chimerized anti-human PACAP antibodies or antibody fragments thereof that may antagonize, inhibit, neutralize or block at least one biological effect associated with human PACAP.

Moreover, the invention pertains to anti-PACAP antibodies and antigen binding fragments thereof that may include human, humanized or chimerized anti-PACAP antibodies or antibody fragments thereof that specifically compete for binding to human PACAP with an antibody selected from the group consisting of Ab1, Ab2, Ab13, Ab14, Ab15, Ab16, Ab17, Ab18, Ab19, Ab1.H, Ab5, Ab7, Ab11, Ab12, Ab4, Ab3, Ab6, Ab8, and Ab9, or an antigen-binding fragment thereof.

Additionally, the anti-PACAP antibodies and antigen binding fragments of the invention may include human, humanized or chimerized anti-PACAP antibodies or antibody fragments that may specifically bind to at least one linear or conformational epitope bound by an anti-PACAP antibody selected from the group consisting of Ab1, Ab2, Ab13, Ab14, Ab15, Ab16, Ab17, Ab18, Ab19, Ab1.H, Ab5, Ab7, Ab11, Ab12, Ab4, Ab3, Ab6, Ab8, and Ab9 or an antigen-binding fragment thereof. The epitope may be identified by alanine scanning, e.g., as disclosed in Example 12, or another art-recognized method. Also, in another embodiment, the anti-PACAP antibodies and antigen binding fragments thereof of the invention may include human, humanized or chimerized anti-PACAP antibodies or antibody fragments thereof which may bind to the identical epitopes as any one of Ab1, Ab2, Ab13, Ab14, Ab15, Ab16, Ab17, Ab18, Ab19, Ab1.H, Ab5, Ab7, Ab11, Ab12, Ab4, Ab3, Ab6, Ab8, and Ab9 or an antigen-binding fragment thereof. The epitope may be identified by alanine scanning, e.g., as disclosed in Example 12, or another art-recognized method.

In a further embodiment of the invention, the anti-PACAP antibodies or antigen binding fragments thereof of the invention may include human, humanized or chimerized anti-PACAP antibodies or antibody fragments which may specifically bind to an epitope on human PACAP or a fragment or variant thereof containing the corresponding amino acid residues wherein said epitope includes one or more of the following:

i. at least one of residues 7, 10, 13, and 14 of a human PACAP;
ii. at least one of residues 5, 6, 8, 10, and 13 of a human PACAP;
iii. at least one of residues 6, 8, 9, 10, and 13 of a human PACAP;
iv. at least one of residues 5, 6, 8, 9, 10, and 13 of a human PACAP;
v. at least one of residues 7, 10, 12, 13, 14, and 17 of a human PACAP;
vi. at least one of residues 5, 6, 8, 9, 10, 12, and 13 of a human PACAP;
vii. at least one of residues 5, 6, 8, 9, 10, 13, and 14 of a human PACAP;
viii. at least one of residues 6, 8, 10, 11, 13, 14, and 18 of a human PACAP;
ix. at least one of residues 8, 9, 10, 13, 14, 17, and 18 of a human PACAP;
x. at least one of residues 3, 4, 5, 6, 7, 10, 13, and 14 of a human PACAP;
xi. at least one of residues 5, 6, 8, 9, 10, 12, 13, and 14 of a human PACAP;
xii. at least one of residues 5, 6, 9, 10, 12, 13, 14, and 17 of a human PACAP;
xiii. at least one of residues 6, 8, 10, 11, 13, 14, 18, and 22 of a human PACAP;
xiv. at least one of residues 8, 9, 10, 11, 12, 13, 14, 17, and 21 of a human PACAP;
xv. at least one of residues 4, 5, 6, 8, 9, 10, 12, 13, 14, and 17 of a human PACAP;
xvi. at least two of the residues of any one of (i)-(xv);
xvii. at least three of the residues of any one of (i)-(xv);
xviii. at least four of the residues of any one of (i)-(xv);
xix. at least five of the residues of any one of (ii)-(xv);
xx. at least six of the residues of any one of (iv)-(xv);
xxi. at least seven of the residues of any one of (vi)-(xv);
xxii. at least eight of the residues of any one of (x)-(xv);
xxiii. at least nine of the residues of (xiv) or (xv); and
xxiv. all ten residues of (xv);

In a specific embodiment of the invention, anti-PACAP antibodies or antigen binding fragments thereof of the invention may include human, humanized or chimerized anti-PACAP antibodies or antibody fragments which specifically bind to an epitope on human PACAP, or a fragment or variant thereof that may contain the corresponding amino acid residues that may include residues 8 and/or 14 of human PACAP. Also, in another embodiment of the invention, the anti-PACAP antibodies or antigen binding fragments thereof may include a human, humanized or chimerized anti-PACAP antibodies or antibody fragments thereof, which specifically bind to an epitope on human PACAP (or a fragment or variant thereof containing the corresponding amino acid residues that may be present in human wild-type PACAP38) but not human wild-type human PACAP27. The epitope may be identified by alanine scanning, e.g., as disclosed in Example 12 or another art-recognized method.

In an additional embodiment of the invention, anti-PACAP antibodies or antigen binding fragments thereof of the invention may include human, humanized or chimerized anti-PACAP antibodies or antibody fragments thereof which may specifically bind to an epitope on human PACAP or a fragment or variant thereof that contain the corresponding amino acid residues, wherein said epitope may consist of the residues of any one of (i)-(xv) as described above. The epitope may be identified by alanine scanning, e.g., as disclosed in Example 12, or another art-recognized method.

Another aspect of the invention also embraces anti-PACAP antibodies or antigen binding fragments thereof that may include human, humanized or chimerized anti-PACAP antibodies or antibody fragment which specifically bind to an epitope on human PACAP (or a fragment or variant thereof that may contain the corresponding amino acid residues) that may be present in human wild-type PACAP38 and in human wild-type human PACAP27.

Additionally, the anti-PACAP antibodies or antigen binding fragments thereof may include human, humanized or chimerized anti-PACAP antibodies or antibody fragments thereof, which may specifically bind to human wild-type human PACAP38 but which may not bind or appreciably bind to human wild-type human PACAP27. The invention may also embody anti-PACAP antibodies or antigen binding fragments thereof that may include human, humanized or chimerized anti-PACAP antibodies or antibody fragments thereof which may specifically interact with residues 28 and 31 of human PACAP38. In another embodiment of the invention, the anti-PACAP antibodies and antigen binding fragments thereof of the invention may include human, humanized or chimerized anti-PACAP antibodies or antibody fragments thereof which may have a $K_D$ for human PACAP38 which may be at least 10, 100, 1000, 10,000 or 100,000 fold lower (stronger) than the $K_D$ of said antibody or antibody fragment to human PACAP27.

In another embodiment, the anti-PACAP antibodies and antigen binding fragments thereof of the invention may include human, humanized or chimerized anti-PACAP antibodies or antibody fragments thereof which do not bind to or do not appreciably bind to human Vasoactive Intestinal Peptide ("VIP"). Said anti-PACAP antibodies or antibody fragments thereof may have a KD for human PACAP which may be at least 10, 100, 1000, 10,000 or 100,000 fold lower (stronger) than the KD of said antibody or antibody fragment to human VIP.

In embodiments of the invention, a human, humanized or chimerized anti-PACAP antibody or antibody fragment as disclosed herein, may inhibit or may neutralize at least one biological effect elicited by human PACAP.

In another embodiment, the anti-PACAP antibodies and antigen binding fragments thereof of the invention may include human, humanized or chimerized anti-PACAP antibodies or antibody fragments thereof that may comprise one or more of the following properties: (a) inhibit, block or prevent PACAP activation of at least one of PAC1 receptor ("PAC1-R"), vasoactive intestinal peptide receptor type 1 ("VPAC1-R"), and/or vasoactive intestinal peptide receptor type 2 ("VPAC2-R"); (b) inhibit, block or prevent PACAP activation of each of PAC1-R, VPAC1-R, and VPAC2-R; (c) inhibit, block or prevent PACAP activation of PAC1-R; (d) are capable of inhibiting PACAP binding to at least one of PAC1-R, VPAC1-R, and/or VPAC2-R; (e) are capable of inhibiting PACAP binding to each of PAC1-R, VPAC1-R, and/or VPAC2-R; (f) may be capable of inhibiting PACAP binding to PAC1-R-expressing cells; (g) are capable of inhibiting PACAP binding to VPAC1-R-expressing cells; (h) are capable of inhibiting PACAP binding to VPAC2-R-expressing cells; (i) do inhibit PACAP binding to the cell surface, e.g. via a glycosaminoglycan ("GAG"); (j) do not inhibit PACAP-mediated binding of such antibody to the cell surface, e.g., via a GAG; (k) do inhibit PACAP-mediated binding of such antibody to the cell surface, e.g., via a glycosaminoglycan ("GAG"); (1) inhibit, block or prevent PACAP-induced cAMP production; and/or (m) when administered to a subject reduce PACAP-induced vasodilation, photophobia, mast cell degranulation and/or neuronal activation.

The invention may also pertain to anti-PACAP antibodies and antigen binding fragments thereof that may be preferably human, humanized or chimerized anti-PACAP antibodies or antibody fragments which may be substantially non-immunogenic in human subjects. The invention may also relate to anti-PACAP antibodies and antigen binding fragments thereof that may be preferably human, humanized or chimerized anti-PACAP antibodies or antibody fragments, which may be suitable for treating a human subject having an acute, episodic or chronic condition associated with increased vasodilation, photophobia, mast cell degranulation and/or neuronal activation.

The invention may also embody anti-PACAP antibodies and antigen binding fragments thereof that may be preferably human, humanized or chimerized anti-PACAP antibodies or antibody fragments that may comprise at least 2 complementarity determining regions ("CDRs") of an anti-PACAP antibody that may be selected from Ab1, Ab2, Ab13, Ab14, Ab15, Ab16, Ab17, Ab18, Ab19, Ab1.H, Ab5, Ab7, Ab11, Ab12, Ab4, Ab3, Ab6, Ab8, or Ab9, preferably including the $V_H$ CDR3 and/or the $V_L$ CDR3. Another additional embodiment of the invention may include anti-PACAP antibodies and antigen binding fragments thereof that may be preferably human, humanized or chimerized anti-PACAP antibodies or antibody fragments that may comprise at least 3, at least 4, at least 5, or all 6 CDRS of an anti-PACAP antibody selected from Ab1, Ab2, Ab13, Ab14, Ab15, Ab16, Ab17, Ab18, Ab19, Ab1.H, Ab5, Ab7, Ab11, Ab12, Ab4, Ab3, Ab6, Ab8, or Ab9. In instances where all 6 CDRs may not be present, preferably at least the $V_H$ CDR3 and the $V_L$ CDR3 may be present.

In another embodiment of the invention, anti-PACAP antibodies and antigen binding fragments thereof, preferably human, humanized or chimerized anti-PACAP antibodies or antibody fragments thereof, may comprise a sequence variant of any of the antibodies or antibody fragments of the invention that may contain one or more modifications that may putatively alter binding affinity or immunogenicity.

In a specific embodiment, anti-PACAP antibodies and antigen binding fragments thereof according to the invention, comprise human, humanized, or chimerized anti-PACAP antibodies or antigen binding fragments thereof, which comprise (a) a variable heavy chain comprising a CDR1 sequence consisting of SEQ ID NO: 4; a CDR2 sequence consisting of SEQ ID NO: 6; and a CDR3 sequence consisting of SEQ ID NO: 8; and/or (b) a variable light chain comprising a CDR1 sequence consisting of SEQ ID NO: 24; a CDR2 sequence consisting of SEQ ID NO: 26; and a CDR3 sequence consisting of SEQ ID NO: 28. Alternatively, the anti-PACAP antibodies and antigen binding fragments thereof may comprise (a) a variable heavy chain comprising an amino acid sequence with at least 80, 85, 90, 95, 96, 97, 98, or 99% sequence identity to SEQ ID NO: 2, and/or (b) a variable light chain comprising an amino acid sequence with at least 80, 85, 90, 95, 96, 97, 98, or 99% sequence identity to SEQ ID NO: 22. In a more specific embodiment, the anti-PACAP antibodies and antigen binding fragments thereof may comprise (a) a variable heavy chain having the amino acid sequence of SEQ ID NO: 2, and/or (b) a variable light chain having the amino acid sequence of SEQ ID NO: 22. More specifically, the anti-PACAP antibodies and antigen binding fragments thereof can comprise (a) a heavy chain having the amino acid sequence of SEQ ID NO: 1, and/or (b) a light chain having the amino acid sequence of SEQ ID NO: 21.

In another specific embodiment, the anti-PACAP antibodies and antigen binding fragments thereof according to the invention, preferably human, humanized, or chimerized anti-PACAP antibodies and antigen binding fragments thereof, comprise (a) a variable heavy chain comprising a CDR1 sequence consisting of SEQ ID NO: 44; a CDR2 sequence consisting of SEQ ID NO: 46; and a CDR3 sequence consisting of SEQ ID NO: 48; and/or (b) a variable light chain comprising a CDR1 sequence consisting of SEQ ID NO: 64; a CDR2 sequence consisting of SEQ ID NO: 66; and a CDR3 sequence consisting of SEQ ID NO: 68. More specifically, the anti-PACAP antibodies and antigen binding fragments thereof comprise (a) a variable heavy chain comprising an amino acid sequence with at least 80, 85, 90, 95, 96, 97, 98, or 99% sequence identity to SEQ ID NO: 42, and/or (b) a variable light chain comprising an amino acid sequence with at least 80, 85, 90, 95, 96, 97, 98, or 99% sequence identity to SEQ ID NO: 62. In another specific embodiment, the anti-PACAP antibodies and antigen binding fragments thereof comprise (a) a variable heavy chain having the amino acid sequence of SEQ ID NO: 42, and/or (b) a variable light chain having the amino acid sequence of SEQ ID NO: 62. More specifically, the anti-PACAP antibodies and antigen binding fragments thereof may comprise (a) a heavy chain having the amino acid sequence of SEQ ID NO: 41, and/or (b) a light chain having the amino acid sequence of SEQ ID NO: 61.

In another specific embodiment, anti-PACAP antibodies and antigen binding fragments thereof according to the invention, preferably human, humanized, or chimerized anti-PACAP antibodies and antigen binding fragments thereof, may comprise (a) a variable heavy chain comprising a CDR1 sequence consisting of SEQ ID NO: 84; a CDR2 sequence consisting of SEQ ID NO: 86; and a CDR3 sequence consisting of SEQ ID NO: 88; and/or (b) a variable light chain comprising a CDR1 sequence consisting of SEQ ID NO: 104; a CDR2 sequence consisting of SEQ ID NO: 106; and a CDR3 sequence consisting of SEQ ID NO: 108. Alternatively, the anti-PACAP antibodies and antigen binding fragments thereof can comprise (a) a variable heavy chain comprising an amino acid sequence with at least 80, 85, 90, 95, 96, 97, 98, or 99% sequence identity to SEQ ID NO: 82, and/or (b) a variable light chain comprising an amino acid sequence with at least 80, 85, 90, 95, 96, 97, 98, or 99% sequence identity to SEQ ID NO: 102. In another specific embodiment, the anti-PACAP antibodies and antigen binding fragments thereof may comprise (a) a variable heavy chain having the amino acid sequence of SEQ ID NO: 82, and/or (b) a variable light chain having the amino acid sequence of SEQ ID NO: 102. More specifically, the anti-PACAP antibodies and antigen binding fragments thereof can comprise (a) a heavy chain having the amino acid sequence of SEQ ID NO: 81, and/or (b) a light chain having the amino acid sequence of SEQ ID NO: 101.

In another specific embodiment, the anti-PACAP antibodies and antigen binding fragments thereof according to the invention, preferably human, humanized, or chimerized anti-PACAP antibodies and antigen binding fragments thereof, may comprise (a) a variable heavy chain comprising a CDR1 sequence consisting of SEQ ID NO: 124; a CDR2 sequence consisting of SEQ ID NO: 126; and a CDR3 sequence consisting of SEQ ID NO: 128; and/or (b) a variable light chain comprising a CDR1 sequence consisting of SEQ ID NO: 144; a CDR2 sequence consisting of SEQ ID NO: 146; and a CDR3 sequence consisting of SEQ ID NO: 148. Alternatively, the anti-PACAP antibodies and antigen binding fragments thereof may comprise (a) a variable heavy chain comprising an amino acid sequence with at least 80, 85, 90, 95, 96, 97, 98, or 99% sequence identity to SEQ ID NO: 122 and/or (b) a variable light chain comprising an amino acid sequence with at least 80, 85, 90, 95, 96, 97, 98, or 99% sequence identity to SEQ ID NO: 142. In another embodiment, the anti-PACAP antibodies and antigen binding fragments thereof may comprise (a) a variable heavy chain having the amino acid sequence of SEQ ID NO: 122, and/or (b) a variable light chain having the amino acid sequence of SEQ ID NO: 142. More specifically, the anti-PACAP antibodies and antigen binding fragments thereof can comprise (a) a heavy chain having the amino acid sequence of SEQ ID NO: 121, and/or (b) a light chain having the amino acid sequence of SEQ ID NO: 141.

In another specific embodiment, the anti-PACAP antibodies and antigen binding fragments thereof according to the invention, preferably human, humanized, or chimerized anti-PACAP antibodies and antigen binding fragments thereof, may comprise (a) a variable heavy chain comprising a CDR1 sequence consisting of SEQ ID NO: 164; a CDR2 sequence consisting of SEQ ID NO: 166; and a CDR3 sequence consisting of SEQ ID NO: 168; and/or (b) a variable light chain comprising a CDR1 sequence consisting of SEQ ID NO: 184; a CDR2 sequence consisting of SEQ ID NO: 186; and a CDR3 sequence consisting of SEQ ID NO: 188. Alternatively, the anti-PACAP antibodies and antigen binding fragments thereof can comprise (a) a variable heavy chain comprising an amino acid sequence with at least 80, 85, 90, 95, 96, 97, 98, or 99% sequence identity to SEQ ID NO: 162, and/or (b) a variable light chain comprising an amino acid sequence with at least 80, 85, 90, 95, 96, 97, 98, or 99% sequence identity to SEQ ID NO: 182. In another embodiment, the anti-PACAP antibodies and antigen binding fragments thereof comprise (a) a variable heavy chain having the amino acid sequence of SEQ ID NO: 162, and/or (b) a variable light chain having the amino acid sequence of SEQ ID NO: 182. More specifically, the anti-PACAP antibodies and antigen binding fragments thereof can comprise (a) a heavy chain having the amino acid sequence of SEQ ID NO: 161, and/or (b) a light chain having the amino acid sequence of SEQ ID NO: 181.

In another specific embodiment, the anti-PACAP antibodies and antigen binding fragments thereof according to the invention, are preferably human, humanized, or chimerized anti-PACAP antibodies and antigen binding fragments thereof, and comprise (a) a variable heavy chain comprising a CDR1 sequence consisting of SEQ ID NO: 204; a CDR2 sequence consisting of SEQ ID NO: 206; and a CDR3 sequence consisting of SEQ ID NO: 208; and/or (b) a variable light chain comprising a CDR1 sequence consisting of SEQ ID NO: 224; a CDR2 sequence consisting of SEQ ID NO: 226; and a CDR3 sequence consisting of SEQ ID NO: 228. Alternatively, the anti-PACAP antibodies and antigen binding fragments thereof can comprise (a) a variable heavy chain comprising an amino acid sequence with at least 80, 85, 90, 95, 96, 97, 98, or 99% sequence identity to SEQ ID NO: 202 and/or (b) a variable light chain comprising an amino acid sequence with at least 80, 85, 90, 95, 96, 97, 98, or 99% sequence identity to SEQ ID NO: 222. In another embodiment, the anti-PACAP antibodies and antigen binding fragments thereof comprise (a) a variable heavy chain having the amino acid sequence of SEQ ID NO: 202, and/or (b) a variable light chain having the amino acid sequence of SEQ ID NO: 222. More specifically, the anti-PACAP antibodies and antigen binding fragments thereof can comprise (a) a heavy chain having the amino acid sequence of SEQ ID NO: 201, and/or (b) a light chain having the amino acid sequence of SEQ ID NO: 221.

In another specific embodiment, the anti-PACAP antibodies and antigen binding fragments thereof according to the invention, are preferably human, humanized, or chimerized anti-PACAP antibodies and antigen binding fragments thereof, and comprise (a) a variable heavy chain comprising a CDR1 sequence consisting of SEQ ID NO: 244; a CDR2 sequence consisting of SEQ ID NO: 246; and a CDR3 sequence consisting of SEQ ID NO: 248; and/or (b) a variable light chain comprising a CDR1 sequence consisting of SEQ ID NO: 264; a CDR2 sequence consisting of SEQ ID NO: 266; and a CDR3 sequence consisting of SEQ ID NO: 268. Alternatively, the anti-PACAP antibodies and antigen binding fragments thereof can comprise (a) a variable heavy chain comprising an amino acid sequence with at least 80, 85, 90, 95, 96, 97, 98, or 99% sequence identity to SEQ ID NO: 242 and/or (b) a variable light chain comprising an amino acid sequence with at least 80, 85, 90, 95, 96, 97, 98, or 99% sequence identity to SEQ ID NO: 262. In another embodiment, the anti-PACAP antibodies and antigen binding fragments thereof comprise (a) a variable heavy chain having the amino acid sequence of SEQ ID NO: 242, and/or (b) a variable light chain having the amino acid sequence of SEQ ID NO: 262. More specifically, the anti-PACAP antibodies and antigen binding fragments thereof can comprise (a) a heavy chain having the amino acid sequence of SEQ ID NO: 241, and/or (b) a light chain having the amino acid sequence of SEQ ID NO: 261.

In another specific embodiment, the anti-PACAP antibodies and antigen binding fragments thereof according to the invention, are preferably human, humanized, or chimerized anti-PACAP antibodies and antigen binding fragments thereof, and comprise (a) a variable heavy chain comprising a CDR1 sequence consisting of SEQ ID NO: 284; a CDR2 sequence consisting of SEQ ID NO: 286; and a CDR3 sequence consisting of SEQ ID NO: 288; and/or (b) a variable light chain comprising a CDR1 sequence consisting of SEQ ID NO: 304; a CDR2 sequence consisting of SEQ ID NO: 306; and a CDR3 sequence consisting of SEQ ID NO: 308. Alternatively, the anti-PACAP antibodies and antigen binding fragments thereof can comprise a variable heavy chain comprising an amino acid sequence with at least 80, 85, 90, 95, 96, 97, 98, or 99% sequence identity to SEQ ID NO: 282, and/or a variable light chain comprising an amino acid sequence with at least 80, 85, 90, 95, 96, 97, 98, or 99% sequence identity to SEQ ID NO: 302. In another embodiment, the anti-PACAP antibodies and antigen binding fragments thereof comprise (a) a variable heavy chain having the amino acid sequence of SEQ ID NO: 282, and/or (b) a variable light chain having the amino acid sequence of SEQ ID NO: 302. More specifically, the anti-PACAP antibodies and antigen binding fragments thereof can comprise (a) a heavy chain having the amino acid sequence of SEQ ID NO: 281, and/or (b) a light chain having the amino acid sequence of SEQ ID NO: 301.

In another specific embodiment, the anti-PACAP antibodies and antigen binding fragments thereof according to the invention, are preferably human, humanized, or chimerized anti-PACAP antibodies and antigen binding fragments thereof, and comprise (a) a variable heavy chain comprising a CDR1 sequence consisting of SEQ ID NO: 324; a CDR2 sequence consisting of SEQ ID NO: 326; and a CDR3 sequence consisting of SEQ ID NO: 328; and/or (b) a variable light chain comprising a CDR1 sequence consisting of SEQ ID NO: 344; a CDR2 sequence consisting of SEQ ID NO: 346; and a CDR3 sequence consisting of SEQ ID NO: 348. Alternatively, the anti-PACAP antibodies and antigen binding fragments thereof can comprise a variable heavy chain comprising an amino acid sequence with at least 80, 85, 90, 95, 96, 97, 98, or 99% sequence identity to SEQ ID NO: 322, and/or a variable light chain comprising an amino acid sequence with at least 80, 85, 90, 95, 96, 97, 98, or 99% sequence identity to SEQ ID NO: 342. In another embodiment, the anti-PACAP antibodies and antigen binding fragments thereof comprise (a) a variable heavy chain having the amino acid sequence of SEQ ID NO: 322, and/or (b) a variable light chain having the amino acid sequence of SEQ ID NO: 342. More specifically, the anti-PACAP antibodies and antigen binding fragments thereof can comprise (a) a heavy chain having the amino acid sequence of SEQ ID NO: 321, and/or (b) a light chain having the amino acid sequence of SEQ ID NO: 341.

In another specific embodiment, the anti-PACAP antibodies and antigen binding fragments thereof according to the invention, are preferably human, humanized, or chimerized anti-PACAP antibodies and antigen binding fragments thereof, and comprise (a) a variable heavy chain comprising a CDR1 sequence consisting of SEQ ID NO: 364; a CDR2 sequence consisting of SEQ ID NO: 366; and a CDR3 sequence consisting of SEQ ID NO: 368; and/or (b) a variable light chain comprising a CDR1 sequence consisting of SEQ ID NO: 384; a CDR2 sequence consisting of SEQ ID NO: 386; and a CDR3 sequence consisting of SEQ ID NO: 388. Alternatively, the anti-PACAP antibodies and antigen binding fragments thereof can comprise a variable heavy chain comprising an amino acid sequence with at least 80, 85, 90, 95, 96, 97, 98, or 99% sequence identity to SEQ ID NO: 362, and/or a variable light chain comprising an amino acid sequence with at least 80, 85, 90, 95, 96, 97, 98, or 99% sequence identity to SEQ ID NO: 382. In another embodiment, the anti-PACAP antibodies and antigen binding fragments thereof comprise (a) a variable heavy chain having the amino acid sequence of SEQ ID NO: 362, and/or (b) a variable light chain having the amino acid sequence of SEQ ID NO: 382. More specifically, the anti-PACAP antibodies and antigen binding fragments thereof can comprise (a) a heavy chain having the amino acid sequence of SEQ ID NO: 361, and/or (b) a light chain having the amino acid sequence of SEQ ID NO: 381.

In another specific embodiment, the anti-PACAP antibodies and antigen binding fragments thereof according to the invention, are preferably human, humanized, or chimerized anti-PACAP antibodies and antigen binding fragments thereof, and comprise (a) a variable heavy chain comprising a CDR1 sequence consisting of SEQ ID NO: 484; a CDR2 sequence consisting of SEQ ID NO: 486; and a CDR3 sequence consisting of SEQ ID NO: 488; and/or (b) a variable light chain comprising a CDR1 sequence consisting of SEQ ID NO: 504; a CDR2 sequence consisting of SEQ ID NO: 506; and a CDR3 sequence consisting of SEQ ID NO: 508. Alternatively, the anti-PACAP antibodies and antigen binding fragments thereof can comprise a variable heavy chain comprising an amino acid sequence with at least 80, 85, 90, 95, 96, 97, 98, or 99% sequence identity to SEQ ID NO: 482, and/or a variable light chain comprising an amino acid sequence with at least 80, 85, 90, 95, 96, 97, 98, or 99% sequence identity to SEQ ID NO: 502. In another embodiment, the anti-PACAP antibodies and antigen binding fragments thereof comprise (a) a variable heavy chain having the amino acid sequence of SEQ ID NO: 482, and/or (b) a variable light chain having the amino acid sequence of SEQ ID NO: 502. More specifically, the anti-PACAP antibodies and antigen binding fragments thereof can comprise (a) a heavy chain having the amino acid sequence of SEQ ID NO: 481, and/or (b) a light chain having the amino acid sequence of SEQ ID NO: 501.

In another specific embodiment, the anti-PACAP antibodies and antigen binding fragments thereof according to the invention, are preferably human, humanized, or chimerized anti-PACAP antibodies and antigen binding fragments thereof, and comprise (a) a variable heavy chain comprising a CDR1 sequence consisting of SEQ ID NO: 524; a CDR2 sequence consisting of SEQ ID NO: 526; and a CDR3 sequence consisting of SEQ ID NO: 528; and/or (b) a variable light chain comprising a CDR1 sequence consisting of SEQ ID NO: 544; a CDR2 sequence consisting of SEQ ID NO: 546; and a CDR3 sequence consisting of SEQ ID NO: 548. Alternatively, the anti-PACAP antibodies and antigen binding fragments thereof can comprise a variable heavy chain comprising an amino acid sequence with at least 80, 85, 90, 95, 96, 97, 98, or 99% sequence identity to SEQ ID NO: 522, and/or a variable light chain comprising an amino acid sequence with at least 80, 85, 90, 95, 96, 97, 98, or 99% sequence identity to SEQ ID NO: 542. In another embodiment, the anti-PACAP antibodies and antigen binding fragments thereof comprise (a) a variable heavy chain having the amino acid sequence of SEQ ID NO: 522, and/or (b) a variable light chain having the amino acid sequence of SEQ ID NO: 542. More specifically, the anti-PACAP antibodies and antigen binding fragments thereof can comprise (a) a heavy chain having the amino acid sequence of SEQ ID NO: 521, and/or (b) a light chain having the amino acid sequence of SEQ ID NO: 541.

In another specific embodiment, the anti-PACAP antibodies and antigen binding fragments thereof according to the invention, are preferably human, humanized, or chimerized anti-PACAP antibodies and antigen binding fragments thereof, and comprise (a) a variable heavy chain comprising a CDR1 sequence consisting of SEQ ID NO: 564; a CDR2 sequence consisting of SEQ ID NO: 566; and a CDR3 sequence consisting of SEQ ID NO: 568; and/or (b) a variable light chain comprising a CDR1 sequence consisting of SEQ ID NO: 584; a CDR2 sequence consisting of SEQ ID NO: 586; and a CDR3 sequence consisting of SEQ ID NO: 588. Alternatively, the anti-PACAP antibodies and antigen binding fragments thereof can comprise a variable heavy chain comprising an amino acid sequence with at least 80, 85, 90, 95, 96, 97, 98, or 99% sequence identity to SEQ ID NO: 562, and/or a variable light chain comprising an amino acid sequence with at least 80, 85, 90, 95, 96, 97, 98, or 99% sequence identity to SEQ ID NO: 582. In another embodiment, the anti-PACAP antibodies and antigen binding fragments thereof comprise (a) a variable heavy chain having the amino acid sequence of SEQ ID NO: 562, and/or (b) a variable light chain having the amino acid sequence of SEQ ID NO: 582. More specifically, the anti-PACAP antibodies and antigen binding fragments thereof can comprise (a) a heavy chain having the amino acid sequence of SEQ ID NO: 561, and/or (b) a light chain having the amino acid sequence of SEQ ID NO: 581.

In another specific embodiment, the anti-PACAP antibodies and antigen binding fragments thereof according to the invention, are preferably human, humanized, or chimerized anti-PACAP antibodies and antigen binding fragments thereof, and comprise (a) a variable heavy chain comprising a CDR1 sequence consisting of SEQ ID NO: 604; a CDR2 sequence consisting of SEQ ID NO: 606; and a CDR3 sequence consisting of SEQ ID NO: 608; and/or (b) a variable light chain comprising a CDR1 sequence consisting of SEQ ID NO: 624; a CDR2 sequence consisting of SEQ ID NO: 626; and a CDR3 sequence consisting of SEQ ID NO: 628. Alternatively, the anti-PACAP antibodies and antigen binding fragments thereof can comprise a variable heavy chain comprising an amino acid sequence with at least 80, 85, 90, 95, 96, 97, 98, or 99% sequence identity to SEQ ID NO: 602, and/or a variable light chain comprising an amino acid sequence with at least 80, 85, 90, 95, 96, 97, 98, or 99% sequence identity to SEQ ID NO: 622. In another embodiment, the anti-PACAP antibodies and antigen binding fragments thereof comprise (a) a variable heavy chain having the amino acid sequence of SEQ ID NO: 602, and/or (b) a variable light chain having the amino acid sequence of SEQ ID NO: 622. More specifically, the anti-PACAP antibodies and antigen binding fragments thereof can comprise (a) a heavy chain having the amino acid sequence of SEQ ID NO: 601, and/or (b) a light chain having the amino acid sequence of SEQ ID NO: 621.

In another specific embodiment, the anti-PACAP antibodies and antigen binding fragments thereof according to the invention, are preferably human, humanized, or chimerized anti-PACAP antibodies and antigen binding fragments thereof, and comprise (a) a variable heavy chain comprising a CDR1 sequence consisting of SEQ ID NO: 644; a CDR2 sequence consisting of SEQ ID NO: 646; and a CDR3 sequence consisting of SEQ ID NO: 648; and/or (b) a variable light chain comprising a CDR1 sequence consisting of SEQ ID NO: 664; a CDR2 sequence consisting of SEQ ID NO: 666; and a CDR3 sequence consisting of SEQ ID NO: 668. Alternatively, the anti-PACAP antibodies and antigen binding fragments thereof can comprise a variable heavy chain comprising an amino acid sequence with at least 80, 85, 90, 95, 96, 97, 98, or 99% sequence identity to SEQ ID NO: 642, and/or a variable light chain comprising an amino acid sequence with at least 80, 85, 90, 95, 96, 97, 98, or 99% sequence identity to SEQ ID NO: 662. In another embodiment, the anti-PACAP antibodies and antigen binding fragments thereof comprise (a) a variable heavy chain having the amino acid sequence of SEQ ID NO: 642, and/or (b) a variable light chain having the amino acid sequence of SEQ ID NO: 662. More specifically, the anti-PACAP antibodies and antigen binding fragments thereof can comprise (a) a heavy chain having the amino acid sequence of SEQ ID NO: 641, and/or (b) a light chain having the amino acid sequence of SEQ ID NO: 661.

In another specific embodiment, the anti-PACAP antibodies and antigen binding fragments thereof according to the invention, are preferably human, humanized, or chimerized anti-PACAP antibodies and antigen binding fragments thereof, and comprise (a) a variable heavy chain comprising a CDR1 sequence consisting of SEQ ID NO: 684; a CDR2 sequence consisting of SEQ ID NO: 686; and a CDR3 sequence consisting of SEQ ID NO: 688; and/or (b) a variable light chain comprising a CDR1 sequence consisting of SEQ ID NO: 704; a CDR2 sequence consisting of SEQ ID NO: 706; and a CDR3 sequence consisting of SEQ ID NO: 708. Alternatively, the anti-PACAP antibodies and antigen binding fragments thereof can comprise a variable heavy chain comprising an amino acid sequence with at least 80, 85, 90, 95, 96, 97, 98, or 99% sequence identity to SEQ ID NO: 682, and/or a variable light chain comprising an amino acid sequence with at least 80, 85, 90, 95, 96, 97, 98, or 99% sequence identity to SEQ ID NO: 702. In another embodiment, the anti-PACAP antibodies and antigen binding fragments thereof comprise (a) a variable heavy chain having the amino acid sequence of SEQ ID NO: 682, and/or (b) a variable light chain having the amino acid sequence of SEQ ID NO: 702. More specifically, the anti-PACAP antibodies and antigen binding fragments thereof can comprise (a) a heavy chain having the amino acid sequence of SEQ ID NO: 681, and/or (b) a light chain having the amino acid sequence of SEQ ID NO: 701.

In another specific embodiment, the anti-PACAP antibodies and antigen binding fragments thereof according to the invention, are preferably human, humanized, or chimerized anti-PACAP antibodies and antigen binding fragments thereof, and comprise (a) a variable heavy chain comprising a CDR1 sequence consisting of SEQ ID NO: 724; a CDR2 sequence consisting of SEQ ID NO: 726; and a CDR3 sequence consisting of SEQ ID NO: 728; and/or (b) a variable light chain comprising a CDR1 sequence consisting of SEQ ID NO: 744; a CDR2 sequence consisting of SEQ ID NO: 746; and a CDR3 sequence consisting of SEQ ID NO: 748. Alternatively, the anti-PACAP antibodies and antigen binding fragments thereof can comprise a variable heavy chain comprising an amino acid sequence with at least 80, 85, 90, 95, 96, 97, 98, or 99% sequence identity to SEQ ID NO: 722, and/or a variable light chain comprising an amino acid sequence with at least 80, 85, 90, 95, 96, 97, 98, or 99% sequence identity to SEQ ID NO: 742. In another embodiment, the anti-PACAP antibodies and antigen binding fragments thereof comprise (a) a variable heavy chain having the amino acid sequence of SEQ ID NO: 722, and/or (b) a variable light chain having the amino acid sequence of SEQ ID NO: 742. More specifically, the anti-PACAP antibodies and antigen binding fragments thereof can comprise (a) a heavy chain having the amino acid sequence of SEQ ID NO: 721, and/or (b) a light chain having the amino acid sequence of SEQ ID NO: 741.

In another specific embodiment, the anti-PACAP antibodies and antigen binding fragments thereof according to the invention, are preferably human, humanized, or chimerized anti-PACAP antibodies and antigen binding fragments thereof, and comprise (a) a variable heavy chain comprising a CDR1 sequence consisting of SEQ ID NO: 764; a CDR2 sequence consisting of SEQ ID NO: 766; and a CDR3 sequence consisting of SEQ ID NO: 768; and/or (b) a variable light chain comprising a CDR1 sequence consisting of SEQ ID NO: 784; a CDR2 sequence consisting of SEQ ID NO: 786; and a CDR3 sequence consisting of SEQ ID NO: 788. Alternatively, the anti-PACAP antibodies and antigen binding fragments thereof fragment can comprise a variable heavy chain comprising an amino acid sequence with at least 80, 85, 90, 95, 96, 97, 98, or 99% sequence identity to SEQ ID NO: 762, and/or a variable light chain comprising an amino acid sequence with at least 80, 85, 90, 95, 96, 97, 98, or 99% sequence identity to SEQ ID NO: 782. In another embodiment, the anti-PACAP antibodies and antigen binding fragments thereof comprise (a) a variable heavy chain having the amino acid sequence of SEQ ID NO: 762, and/or (b) a variable light chain having the amino acid sequence of SEQ ID NO: 782. More specifically, the anti-PACAP antibodies and antigen binding fragments thereof can comprise (a) a heavy chain having the amino acid sequence of SEQ ID NO: 761, and/or (b) a light chain having the amino acid sequence of SEQ ID NO: 781.

In another specific embodiment, the anti-PACAP antibodies and antigen binding fragments thereof according to the invention, are preferably human, humanized, or chimerized anti-PACAP antibodies and antigen binding fragments thereof, and comprise (a) a variable heavy chain comprising a CDR1 sequence consisting of SEQ ID NO: 804; a CDR2 sequence consisting of SEQ ID NO: 806; and a CDR3 sequence consisting of SEQ ID NO: 808; and/or (b) a variable light chain comprising a CDR1 sequence consisting of SEQ ID NO: 824; a CDR2 sequence consisting of SEQ ID NO: 826; and a CDR3 sequence consisting of SEQ ID NO: 828. Alternatively, the anti-PACAP antibodies and antigen binding fragments thereof can comprise a variable heavy chain comprising an amino acid sequence with at least 80, 85, 90, 95, 96, 97, 98, or 99% sequence identity to SEQ ID NO: 802, and/or a variable light chain comprising an amino acid sequence with at least 80, 85, 90, 95, 96, 97, 98, or 99% sequence identity to SEQ ID NO: 822. In another embodiment, the anti-PACAP antibodies and antigen binding fragments thereof comprise (a) a variable heavy chain having the amino acid sequence of SEQ ID NO: 802, and/or (b) a variable light chain having the amino acid sequence of SEQ ID NO: 822. More specifically, the anti-PACAP antibodies and antigen binding fragments thereof can comprise (a) a heavy chain having the amino acid sequence of SEQ ID NO: 801, and/or (b) a light chain having the amino acid sequence of SEQ ID NO: 821.

Additionally, the anti-PACAP antibodies and antigen binding fragments of the invention may include human, humanized or chimerized anti-PACAP antibodies or antibody fragments wherein the antibodies or antibody fragments may be selected from the group consisting of scFvs, camelbodies, nanobodies, Immunoglobulin New Antigen Receptor ("IgNAR"), fragment antigen binding ("Fab") fragments, Fab' fragments, MetMab like antibodies, monovalent antibody fragments, and $F(ab')_2$ fragments. In another embodiment, the anti-PACAP antibodies and antigen binding fragments of the invention, preferably human, humanized or chimerized anti-PACAP antibodies or antibody fragments, may substantially or entirely lack N-glycosylation and/or O-glycosylation. Also, the invention embraces an embodiment of the invention wherein the anti-PACAP antibodies and antigen binding fragments of the invention, preferably human, humanized or chimerized anti-PACAP antibodies or antibody fragments, may comprise a human constant domain, e.g. that of an IgG1, IgG2, IgG3, or IgG4 antibody or fragment thereof.

An additional embodiment of the invention relates to anti-PACAP antibodies and antigen binding fragments, preferably human, humanized or chimerized anti-PACAP antibodies or antibody fragments, wherein said antibodies or antibody fragments may comprise an Fc region that may have been modified to alter at least one of effector function, half-life, proteolysis, or glycosylation, e.g., wherein the Fc region may contain one or more mutations that may alter or eliminate N- and/or O-glycosylation.

In yet another embodiment of the invention, anti-PACAP antibodies and antigen binding fragments, preferably human, humanized or chimerized anti-PACAP antibodies or antibody fragments, may bind to PACAP with a binding affinity (KD) of less than or equal to $5\times10^{-5}$ M, $10^{-5}$ M, $5\times10^{-6}$ M, $10^{-6}$ M, $5\times10^{-7}$ M, $10^{-7}$ M, $5\times10^{-8}$ M, $10^{-8}$M, $5\times10^{-9}$ M, $10^{-9}$ M, $5\times10^{-19}$ M, $10^{-19}$ M, $5\times10^{-11}$ M, $10^{-11}$ M, $5\times10^{-12}$ M, $10^{-12}$ M, $5\times10^{-13}$ M, or $10^{-13}$ M, e.g., as may be determined by ELISA, bio-layer interferometry ("BLI"), KinExA® (kinetic exclusion assay) or by use of surface plasmon resonance at 25° or 37° C. Also, another embodiment of the invention pertains to anti-PACAP antibodies and antigen binding fragments, preferably human, humanized or chimerized anti-PACAP antibodies or antibody fragments, wherein said antibodies or antibody fragments may bind to PACAP with a binding affinity (KD) of less than or equal to $5\times10^{-19}$ M, $10^{-19}$ M, $5\times10^{-11}$ M, $10^{-11}$ M, $5\times10^{-12}$ M, or $10^{-12}$ M. Additionally, the anti-PACAP antibodies and antigen binding fragments, preferably human, humanized or chimerized anti-PACAP antibodies or antibody fragments, of the invention may include anti-PACAP antibodies or antibody fragments which bind to PACAP with an off-rate ($k_{off}$) of less than or equal to $5\times10^{-4}$ $s^{-1}$, $10^{-4}$ $s^{-1}$, $5\times10^{-5}$ $s^{-1}$, or 10-5 $s^{-1}$.

Another embodiment of the invention relates to anti-PACAP antibodies and antigen binding fragments, preferably human, humanized or chimerized anti-PACAP antibodies or antibody fragments, wherein said antibodies and antibody fragments may be directly or indirectly attached to a detectable label or therapeutic agent. An additional embodiment of the invention pertains to anti-PACAP antibodies and antigen binding fragments, preferably human, humanized or chimerized anti-PACAP antibodies or antibody fragments that when administered to a subject may inhibit or may neutralize at least one biological effect elicited by PACAP. The anti-PACAP antibodies and antigen binding fragments, preferably human, humanized or chimerized anti-PACAP antibodies or antibody fragments, of the invention may neutralize or may inhibit PACAP activation of at least one of PAC1-R, VPAC1-R, or VPAC2-R; may neutralize or may inhibit PACAP activation of each of PAC1-R, VPAC1-R, and VPAC2-R; may neutralize or may inhibit PACAP activation of PAC1-R; may be capable of inhibiting or preventing PACAP binding to at least one of PAC1-R, VPAC1-R, or VPAC2-R; may be capable of inhibiting or preventing PACAP binding to each of PAC1-R, VPAC1-R, and VPAC2-R; may be capable of inhibiting or preventing PACAP binding to PAC1-R-expressing cells, VPAC1-R-expressing cells, and/or VPAC2-R-expressing cells; may inhibit or block PACAP-induced cAMP production; may, when administered to a subject, may reduce PACAP-induced vasodilation, photophobia, mast cell degranulation and/or neuronal activation.

In yet another embodiment of the invention, anti-PACAP antibodies and antigen binding fragments, preferably human, humanized or chimerized anti-PACAP antibodies or antibody fragments, may bind to PACAP with a $K_D$ that may be less than about 100 nM; with a $K_D$ that may be less than about 40 nM; with a $K_D$ that may be less than about 100 pM; with a $K_D$ that may be less than about 50 pM; with a $K_D$ that may be less than about 25 pM; or with a $K_D$ that may be between about 10 pM and about 100 pM. The invention also embraces anti-PACAP antibodies and antigen binding fragments, preferably human, humanized or chimerized anti-PACAP antibodies or antibody fragments, that may have stronger binding affinity for PACAP as compared to VIP and/or that may not bind to VIP, e.g., wherein said antibodies or antibody fragments thereof may have an affinity to PACAP that may be at least 10-fold, 30-fold, 100-fold, 300-fold, 1000-fold, 3000-fold, 10000-fold, 30000-fold, 100000-fold, 300000-fold, 1000000-fold, 3000000-fold, 10000000-fold, 30000000-fold or more stronger than the affinity of said antibody or antibody fragment to VIP.

In another embodiment, the invention pertains to anti-PACAP antibodies and antigen binding fragments, preferably human, humanized or chimerized anti-PACAP antibodies or antibody fragments, that may be attached to at least one effector moiety, e.g., wherein said effector moiety may comprise a chemical linker. In another embodiment, the invention pertains to anti-PACAP antibodies and antigen binding fragments, preferably human, humanized or chimerized anti-PACAP antibodies or antibody fragments, that may be attached to one or more detectable moieties, e.g., wherein said detectable moieties may comprise a fluorescent dye, enzyme, substrate, bioluminescent material, radioactive material, chemiluminescent moiety, and/or mixtures thereof. Also, the anti-PACAP antibodies and antigen binding fragments of the invention, preferably human, humanized or chimerized anti-PACAP antibodies or antibody fragments, may be attached to one or more functional moieties.

Another embodiment of the invention relates to anti-idiotypic antibodies that may be produced against anti-PACAP antibodies or antibody fragments, wherein said anti-idiotypic antibodies optionally may neutralize one or more biological effects of the anti-PACAP antibody to which it may bind. This embodiment of the invention may also relate to a method of using said anti-idiotypic antibody to monitor the in vivo levels of said anti-PACAP antibody or antibody fragment in a subject or to neutralize the in vivo effects of said anti-PACAP antibody in a subject.

In yet another embodiment, the invention pertains to a composition that may be suitable for therapeutic, prophylactic, or a diagnostic use, whereby the composition may comprise a therapeutically, prophylactically or diagnostically effective amount of at least one anti-PACAP antibody or antibody fragment or anti-idiotypic antibody, e.g., wherein the composition may be suitable for administration via injection, topical, oral, inhalation or transdermal; may be suitable for subcutaneous, intravenous, intramuscular, topical, oral, inhalatory, intranasal, intrabuccal, vaginal, anal, transdermal, intraperitoneal, or intrathecal administration; and/or wherein the composition may be suitable for subcutaneous intravenous or intramuscular administration. The invention also embraces an embodiment of the invention wherein said composition of at least one anti-PACAP antibody or antibody fragment or anti-idiotypic antibody may be lyophilized; and/or wherein said composition may comprise a pharmaceutically acceptable diluent, carrier, solubilizer, emulsifier, preservative, or mixture thereof. Said composition of the invention may further comprise at least one other active agent, e.g., wherein the other active agent may be selected from the group consisting of a chemotherapeutic, an analgesic, an anti-inflammatory, an immunosuppressant, a cytokine, an antiproliferative, an antiemetic and/or a cytotoxin. Said composition may also be lyophilized, stabilized, and/or may be formulated for administration by injection.

A further embodiment of the invention embraces an isolated nucleic acid sequence or nucleic acid sequences that may encode an anti-PACAP antibody or antibody fragment or anti-idiotypic antibody, and wherein said isolated nucleic acid sequence or nucleic acid sequences may be contained within a vector or vectors. Additionally, in an embodiment of the invention, a host cell may comprise said isolated nucleic acid sequence or sequences, wherein said host cell may be a mammalian, bacterial, fungal, yeast, avian, amphibian, plant or insect cell; and/or said host cell may be a filamentous fungus or a yeast. Wherein said host cell may be a yeast cell, the yeast may be selected from the following genera: *Arxiozyma; Ascobotryozyma; Citeromyces; Debaryomyces; Dekkera; Eremothecium; Issatchenkia; Kazachstania; Kluyveromyces; Kodamaea; Lodderomyces; Pachysolen; Pichia; Saccharomyces; Saturnispora; Tetrapisispora; Torulaspora; Williopsis*; and *Zygosaccharomyces*; or the yeast may be genus *Pichia*. In an embodiment of the invention, the yeast host cell may be selected from *Pichia pastoris, Pichia methanolica* and *Hansenula polymorpha* (*Pichia angusta*).

The invention also relates to a method of expressing an anti-PACAP antibody or antibody fragment that may comprise culturing any of but not limited to the host cells disclosed herein under conditions that may provide for expression of said antibody or antibody fragment. Additionally, the invention pertains to said method wherein the host cell may be a yeast cell or CHO cell that may stably express and may secrete said antibody or antibody fragment. For example, said yeast cell may be a polyploid yeast that may be made by a method that may comprise: (i) introducing at least one expression vector containing one or more heterologous polynucleotides encoding said antibody operably linked to a promoter and a signal sequence into a haploid yeast cell; (ii) producing by mating or spheroplast fusion a polyploid yeast from said first and/or second haploid yeast cell; (iii) selecting polyploid yeast cells that stably express said antibody; and (iv) producing stable polyploid yeast cultures from said polyploid yeast cells that stably express said antibody into the culture medium; and said polyploid yeast may be of the genus *Pichia*. Additionally in another embodiment, the invention embraces a method of expressing an anti-PACAP antibody or antibody fragment that may comprise culturing a host cell wherein said host cell may be a mammalian cell, e.g., a CHO cell.

Additionally, the invention pertains to a method that may block, inhibit, block or neutralize one or more biological effects associated with PACAP in a subject that may comprise administering to said subject a therapeutically or prophylactically effective amount of a human, humanized or chimerized anti-PACAP antibody or antibody fragment that may antagonize, inhibit, neutralize or block at least one biological effect associated with human PACAP. Another aspect of the invention relates to a method that may block, inhibit, or neutralize one or more biological effects associated with PACAP in a subject that may comprise administering to a subject a therapeutically or prophylactically effective amount of a human, humanized or chimerized anti-PACAP antibody or antibody fragment that may antagonize, inhibit, neutralize or block at least one biological effect associated with human PACAP and that may not substantially interact with (bind) VIP.

Another aspect of the invention generally relates to a method that may block, inhibit, or neutralize one or more biological effects, e.g., vasomotor effects, associated with PACAP in a subject that may comprise administering to a subject a therapeutically or prophylactically effective amount of a human, humanized or chimerized anti-PACAP antibody or antibody fragment that may comprise one or more of the following: inhibits, blocks or neutralizes at least one biological effect elicited by PACAP; neutralizes or inhibits PACAP activation of at least one of PAC1-R, VPAC1-R, and/or VPAC2-R; inhibits, blocks or neutralizes PACAP activation of each of PAC1-R, VPAC1-R, and VPAC2-R; neutralizes or inhibits PACAP activation of PAC1-R; inhibits PACAP binding to at least one of PAC1-R, VPAC1-R, and/or VPAC2-R; inhibits PACAP binding to each of PAC1-R, VPAC1-R, and/or VPAC2-R; inhibits PACAP binding to PAC1-R-expressing cells; inhibits PACAP binding to VPAC1-R and/or VPAC2-R-expressing cells; does not inhibit PACAP-mediated binding of such antibody to the cell surface, e.g., via a glycosaminoglycan ("GAG"); inhibits PACAP binding to the cell surface, e.g. via a glycosaminoglycan ("GAG"); inhibits PACAP-induced cAMP production; and/or, when administered to a subject, reduces PACAP-induced vasodilation, photophobia, mast cell degranulation and/or neuronal activation.

Another embodiment of the invention relates to a method that may block, inhibit, or neutralize vasodilation, e.g., vasodilation of the dural arteries, which may be associated with or may be elicited by PACAP in a subject that may comprise administering to a subject a therapeutically or prophylactically effective amount of a human, humanized or chimerized anti-PACAP antibody or antibody fragment that may block, inhibit, or neutralize vasodilation associated with, or elicited by PACAP.

Yet another embodiment of the invention pertains to a method that may treat or prevent the onset, frequency, severity or duration of headache or migraine, e.g., wherein said headache or migraine may be selected from migraine with aura, migraine without aura, hemiplegic migraine, cluster headache, migrainous neuralgia, chronic headache, chronic migraine, medication overuse headache, and tension headache, in a subject that may comprise administering to a subject in need thereof an effective amount of a human, humanized or chimerized anti-human PACAP antibody or antibody fragment that may elicit one or more of the following effects: inhibits or neutralizes at least one biological effect elicited by PACAP; neutralizes or inhibits PACAP activation of at least one of PAC1-R, VPAC1-R, and/or VPAC2-R; neutralizes or inhibits PACAP activation of each of PAC1-R, VPAC1-R, and VPAC2-R; neutralizes or inhibits PACAP activation of PAC1-R; inhibits PACAP binding to at least one of PAC1-R, VPAC1-R, and/or VPAC2-R; inhibits PACAP binding to each of PAC1-R, VPAC1-R, and/or VPAC2-R; inhibits PACAP binding to PAC1-R-expressing cells; inhibits PACAP binding to VPAC1-R and/or VPAC2-R-expressing cells; does not inhibit PACAP-mediated binding of such antibody to the cell surface, e.g., via a GAG; inhibits PACAP binding to the cell surface, e.g. via a glycosaminoglycan ("GAG"); inhibits PACAP-induced cyclic adenosine monophosphate ("cAMP") production; and/or, when administered to a subject, reduces PACAP-induced vasodilation, photophobia, mast cell degranulation and/or neuronal activation.

Another embodiment of the invention relates to a method of treating a human subject that may have an acute, episodic or chronic condition that may be associated with at least one of increased vasodilation, photophobia, mast cell degranulation and neuronal activation or a combination of said conditions that may comprise administering to a subject in need thereof an effective amount of an antagonistic human, humanized or chimerized anti-human PACAP antibody or antibody fragment.

The invention also pertains to any of the methods disclosed herein that may be effected by the administration of a therapeutically or prophylactically effective amount of at least one human, humanized or chimerized anti-PACAP antibody or antibody fragment; and/or wherein said anti-PACAP antibody may be a human antibody or antibody fragment; and/or wherein said anti-PACAP antibody may be a humanized antibody or antibody fragment; and/or wherein said anti-PACAP antibody may be a chimeric antibody or antibody fragment.

Another embodiment of the invention also relates to a method wherein an anti-PACAP antibody or antibody fragment of the invention may bind to PACAP27 and/or PACAP38 and may block PACAP27 and/or PACAP38 binding to PAC1-R, VPAC1-R, and/or VPAC2-R. Another embodiment of the invention pertains to a method wherein said anti-PACAP antibody or antibody fragment may bind to PACAP27 and/or PACAP38 and may block PACAP27 and/or PACAP38 binding to each of PAC1-R, VPAC1-R, and VPAC2-R. Yet another embodiment of the invention relates to a method wherein said anti-PACAP antibody or antibody fragment may bind to PACAP27 and/or PACAP38 and may block PACAP27 and/or PACAP38 binding to PAC1-R-expressing cells. Additionally, said anti-PACAP antibody or antibody fragment of the invention may have an affinity to PACAP that may be at least 10-fold, 30-fold, 100-fold, 300-fold, 1000-fold, 3000-fold, 10000-fold, 30000-fold, 100000-fold, 300000-fold, 1000000-fold, 3000000-fold, 10000000-fold, 30000000-fold or more stronger than the affinity of said antibody or antibody fragment to VIP.

The invention embraces a method that may block, inhibit, block or neutralize one or more biological effects associated with PACAP in a subject that may comprise administering to said subject a therapeutically or prophylactically effective amount of a human, humanized or chimerized anti-PACAP antibody or antibody fragment that may antagonize, inhibit, neutralize or blocks at least one biological effect associated with human PACAP, and wherein said subject may have a condition selected from the group consisting of migraine with aura, migraine without aura, hemiplegic migraines, cluster headaches, migrainous neuralgia, chronic headaches, tension headaches, general headaches, hot flush, photophobia, chronic paroxysmal hemicrania, secondary headaches due to an underlying structural problem in the head, secondary headaches due to an underlying structural problem in the neck, cranial neuralgia, sinus headaches, headache associated with sinusitis, allergy-induced headaches, allergy-induced migraines, trigeminal neuralgia, post-herpetic neuralgia, phantom limb pain, fibromyalgia, reflex sympathetic dystrophy, pain, chronic pain, inflammatory pain, post-operative incision pain, post-surgical pain, trauma-related pain, lower back pain, eye pain, tooth pain, complex regional pain syndrome, cancer pain, primary or metastatic bone cancer pain, fracture pain, osteoporotic fracture pain, pain resulting from burn, gout joint pain, pain associated with sickle cell crises, pain associated with temporomandibular disorders, cirrhosis, hepatitis, neurogenic pain, neuropathic pain, nociceptic pain, visceral pain, menstrual pain, ovarialgia, osteoarthritis pain, rheumatoid arthritis pain, diabetic neuropathy, sciatica, dyspepsia, irritable bowel syndrome, inflammatory bowel disease, Crohn's disease, ileitis, ulcerative colitis, renal colic, dysmenorrhea, cystitis, interstitial cystitis, menstrual period, labor, menopause, pancreatitis, schizophrenia, depression, post-traumatic stress disorder ("PTSD"), anxiety disorders, autoimmune diabetes, Sjögren's syndrome, multiple sclerosis, overactive bladder, bronchial hyperreactivity, asthma, stroke, bronchitis, bronchodilation, emphysema, chronic obstructive pulmonary disease ("COPD"), inflammatory dermatitis, adenocarcinoma in glandular tissue, blastoma in embryonic tissue of organs, carcinoma in epithelial tissue, leukemia in tissues that form blood cells, lymphoma in lymphatic tissue, myeloma in bone marrow, sarcoma in connective or supportive tissue, adrenal cancer, AIDS-related lymphoma, anemia, bladder cancer, bone cancer, brain cancer, breast cancer, carcinoid tumors, cervical cancer, chemotherapy, colon cancer, cytopenia, endometrial cancer, esophageal cancer, gastric cancer, head cancer, neck cancer, hepatobiliary cancer, kidney cancer, leukemia, liver cancer, lung cancer, lymphoma, Hodgkin's disease, non-Hodgkin's, nervous system tumors, oral cancer, ovarian cancer, pancreatic cancer, prostate cancer, rectal cancer, skin cancer, stomach cancer, testicular cancer, thyroid cancer, urethral cancer, cancer of bone marrow, multiple myeloma, tumors that metastasize to the bone, tumors infiltrating the nerve and hollow viscus, tumors near neural structures, acne vulgaris, atopic dermatitis, urticaria, keloids, hypertrophic scars and rosacea, endothelial dysfunction, Raynaud's syndrome, coronary heart disease ("CHD"), coronary artery disease ("CAD"), heart failure, peripheral arterial disease ("PAD"), diabetes, pulmonary hypertension ("PH"), connective tissue disorder, allergic dermatitis, psoriasis, pruritus, neurogenic cutaneous redness, erythema, sarcoidosis, shock, sepsis, opiate withdrawal syndrome, morphine tolerance, and epilepsy. Additionally, said subject may have a condition selected from the group consisting of migraine, headache and a pain associated disease or condition, wherein said headache or migraine may selected from the group consisting of migraine with aura, migraine without aura, hemiplegic migraine, cluster headache, migrainous neuralgia, chronic headache, chronic migraine, medication overuse headache, and tension headache. Also, said subject may have a ocular disorder associated with photophobia that may be selected from the group consisting of achromatopsia, aniridia, photophobia caused by an anticholinergic drug, aphakia, buphthalmos, cataracts, cone dystrophy, congenital abnormalities of the eye, viral conjunctivitis, corneal abrasion, corneal dystrophy, corneal ulcer, disruption of the corneal epithelium, ectopia lentis, endophthalmitis, eye trauma caused by disease, eye trauma caused by injury, eye trauma caused by infection, chalazion, episcleritis, glaucoma, keratoconus, optic nerve hypoplasia, hydrophthalmos, congenital glaucoma iritis, optic neuritis, pigment dispersion syndrome, pupillary dilation, retinal detachment, scarring of the cornea, sclera and uveitis. Further, said subject may have a nervous system-related or neurological condition associated with photophobia that may be selected from the group consisting of autism spectrum disorders, Chiari malformation, dyslexia, encephalitis, meningitis, subarachnoid hemorrhage, tumor of the posterior cranial fossa, ankylosing spondylitis, albinism, ariboflavinosis, benzodiazepines, chemotherapy, chikungunya, cystinosis, Ehlers-Danlos syndrome, hangover, influenza, infectious mononucleosis, magnesium deficiency, mercury poisoning, migraine, rabies, and tyrosinemia type II. Additionally, said subject may have a photophobia associated disorder that may be selected from the group consisting of migraine with aura, migraine without aura, iritis, uveitis, meningitis, depression, bipolar disorder, cluster headache or anther trigeminal autonomic cephalalgia ("TAC") or blepharospasm, depression, agoraphobia and bipolar disorder.

The invention also embraces any of the methods disclosed herein wherein the method relates to an antibody or antibody fragment that may be a human, humanized, or chimerized anti-PACAP antibody or antibody fragment; and/or wherein the antibody or antibody fragment may a human, humanized, or chimerized anti-PACAP antibody or antibody fragment; and/or wherein the antibody or antibody fragment may be an anti-PACAP antibody or antibody fragment that may comprise the same CDRs as an anti-PACAP antibody that may be selected from Ab1, Ab2, Ab13, Ab14, Ab15, Ab16, Ab17, Ab18, Ab19, Ab1.H, Ab5, Ab7, Ab11, Ab12, Ab4, Ab3, Ab6, Ab8, or Ab9.

The invention also embraces any of the methods disclosed herein wherein the anti-PACAP antibodies and antigen binding fragments thereof according to the invention comprise human, humanized, or chimerized anti-PACAP antibodies or antigen binding fragments thereof, which comprise (a) a variable heavy chain comprising a CDR1 sequence consisting of SEQ ID NO: 4; a CDR2 sequence consisting of SEQ ID NO: 6; and a CDR3 sequence consisting of SEQ ID NO: 8; and/or (b) a variable light chain comprising a CDR1 sequence consisting of SEQ ID NO: 24; a CDR2 sequence consisting of SEQ ID NO: 26; and a CDR3 sequence consisting of SEQ ID NO: 28. Alternatively, the anti-PACAP antibodies and antigen binding fragments thereof may comprise (a) a variable heavy chain comprising an amino acid sequence with at least 80, 85, 90, 95, 96, 97, 98, or 99% sequence identity to SEQ ID NO: 2, and/or (b) a variable light chain comprising an amino acid sequence with at least 80, 85, 90, 95, 96, 97, 98, or 99% sequence identity to SEQ ID NO: 22. In a more specific embodiment, the anti-PACAP antibodies and antigen binding fragments thereof may comprise (a) a variable heavy chain having the amino acid sequence of SEQ ID NO: 2, and/or (b) a variable light chain having the amino acid sequence of SEQ ID NO: 22. More specifically, the anti-PACAP antibodies and antigen binding fragments thereof can comprise (a) a heavy chain having the amino acid sequence of SEQ ID NO: 1, and/or (b) a light chain having the amino acid sequence of SEQ ID NO: 21.

The invention also embraces any of the methods disclosed herein wherein the anti-PACAP antibodies and antigen binding fragments thereof according to the invention, preferably human, humanized, or chimerized anti-PACAP antibodies and antigen binding fragments thereof, comprise (a) a variable heavy chain comprising a CDR1 sequence consisting of SEQ ID NO: 44; a CDR2 sequence consisting of SEQ ID NO: 46; and a CDR3 sequence consisting of SEQ ID NO: 48; and/or (b) a variable light chain comprising a CDR1 sequence consisting of SEQ ID NO: 64; a CDR2 sequence consisting of SEQ ID NO: 66; and a CDR3 sequence consisting of SEQ ID NO: 68. More specifically, the anti-PACAP antibodies and antigen binding fragments thereof comprise (a) a variable heavy chain comprising an amino acid sequence with at least 80, 85, 90, 95, 96, 97, 98, or 99% sequence identity to SEQ ID NO: 42, and/or (b) a variable light chain comprising an amino acid sequence with at least 80, 85, 90, 95, 96, 97, 98, or 99% sequence identity to SEQ ID NO: 62. In another specific embodiment, the anti-PACAP antibodies and antigen binding fragments thereof comprise (a) a variable heavy chain having the amino acid sequence of SEQ ID NO: 42, and/or (b) a variable light chain having the amino acid sequence of SEQ ID NO: 62. More specifically, the anti-PACAP antibodies and antigen binding fragments thereof may comprise (a) a heavy chain having the amino acid sequence of SEQ ID NO: 41, and/or (b) a light chain having the amino acid sequence of SEQ ID NO: 61.

The invention also embraces any of the methods disclosed herein wherein the anti-PACAP antibodies and antigen binding fragments thereof according to the invention, preferably human, humanized, or chimerized anti-PACAP antibodies and antigen binding fragments thereof, may comprise (a) a variable heavy chain comprising a CDR1 sequence consisting of SEQ ID NO: 84; a CDR2 sequence consisting of SEQ ID NO: 86; and a CDR3 sequence consisting of SEQ ID NO: 88; and/or (b) a variable light chain comprising a CDR1 sequence consisting of SEQ ID NO: 104; a CDR2 sequence consisting of SEQ ID NO: 106; and a CDR3 sequence consisting of SEQ ID NO: 108. Alternatively, the anti-PACAP antibodies and antigen binding fragments thereof can comprise (a) a variable heavy chain comprising an amino acid sequence with at least 80, 85, 90, 95, 96, 97, 98, or 99% sequence identity to SEQ ID NO: 82, and/or (b) a variable light chain comprising an amino acid sequence with at least 80, 85, 90, 95, 96, 97, 98, or 99% sequence identity to SEQ ID NO: 102. In another specific embodiment, the anti-PACAP antibodies and antigen binding fragments thereof may comprise (a) a variable heavy chain having the amino acid sequence of SEQ ID NO: 82, and/or (b) a variable light chain having the amino acid sequence of SEQ ID NO: 102. More specifically, the anti-PACAP antibodies and antigen binding fragments thereof can comprise (a) a heavy chain having the amino acid sequence of SEQ ID NO: 81, and/or (b) a light chain having the amino acid sequence of SEQ ID NO: 101.

The invention also embraces any of the methods disclosed herein wherein the anti-PACAP antibodies and antigen binding fragments thereof according to the invention, preferably human, humanized, or chimerized anti-PACAP antibodies and antigen binding fragments thereof, may comprise (a) a variable heavy chain comprising a CDR1 sequence consisting of SEQ ID NO: 124; a CDR2 sequence consisting of SEQ ID NO: 126; and a CDR3 sequence consisting of SEQ ID NO: 128; and/or (b) a variable light chain comprising a CDR1 sequence consisting of SEQ ID NO: 144; a CDR2 sequence consisting of SEQ ID NO: 146; and a CDR3 sequence consisting of SEQ ID NO: 148. Alternatively, the anti-PACAP antibodies and antigen binding fragments thereof may comprise (a) a variable heavy chain comprising an amino acid sequence with at least 80, 85, 90, 95, 96, 97, 98, or 99% sequence identity to SEQ ID NO: 122 and/or (b) a variable light chain comprising an amino acid sequence with at least 80, 85, 90, 95, 96, 97, 98, or 99% sequence identity to SEQ ID NO: 142. In another embodiment, the anti-PACAP antibodies and antigen binding fragments thereof may comprise (a) a variable heavy chain having the amino acid sequence of SEQ ID NO: 122, and/or (b) a variable light chain having the amino acid sequence of SEQ ID NO: 142. More specifically, the anti-PACAP antibodies and antigen binding fragments thereof can comprise (a) a heavy chain having the amino acid sequence of SEQ ID NO: 121, and/or (b) a light chain having the amino acid sequence of SEQ ID NO: 141.

The invention also embraces any of the methods disclosed herein wherein the anti-PACAP antibodies and antigen binding fragments thereof according to the invention, preferably human, humanized, or chimerized anti-PACAP antibodies and antigen binding fragments thereof, may comprise (a) a variable heavy chain comprising a CDR1 sequence consisting of SEQ ID NO: 164; a CDR2 sequence consisting of SEQ ID NO: 166; and a CDR3 sequence consisting of SEQ ID NO: 168; and/or (b) a variable light chain comprising a CDR1 sequence consisting of SEQ ID NO: 184; a CDR2 sequence consisting of SEQ ID NO: 186; and a CDR3 sequence consisting of SEQ ID NO: 188. Alternatively, the anti-PACAP antibodies and antigen binding fragments thereof can comprise (a) a variable heavy chain comprising an amino acid sequence with at least 80, 85, 90, 95, 96, 97, 98, or 99% sequence identity to SEQ ID NO: 162, and/or (b) a variable light chain comprising an amino acid sequence with at least 80, 85, 90, 95, 96, 97, 98, or 99% sequence identity to SEQ ID NO: 182. In another embodiment, the anti-PACAP antibodies and antigen binding fragments thereof comprise (a) a variable heavy chain having the amino acid sequence of SEQ ID NO: 162, and/or (b) a variable light chain having the amino acid sequence of SEQ ID NO: 182. More specifically, the anti-PACAP antibodies and antigen binding fragments thereof can comprise (a) a heavy chain having the amino acid sequence of SEQ ID NO: 161, and/or (b) a light chain having the amino acid sequence of SEQ ID NO: 181.

The invention also embraces any of the methods disclosed herein wherein the anti-PACAP antibodies and antigen binding fragments thereof according to the invention, are preferably human, humanized, or chimerized anti-PACAP antibodies and antigen binding fragments thereof, and comprise (a) a variable heavy chain comprising a CDR1 sequence consisting of SEQ ID NO: 204; a CDR2 sequence consisting of SEQ ID NO: 206; and a CDR3 sequence consisting of SEQ ID NO: 208; and/or (b) a variable light chain comprising a CDR1 sequence consisting of SEQ ID NO: 224; a CDR2 sequence consisting of SEQ ID NO: 226; and a CDR3 sequence consisting of SEQ ID NO: 228. Alternatively, the anti-PACAP antibodies and antigen binding fragments thereof can comprise (a) a variable heavy chain comprising an amino acid sequence with at least 80, 85, 90, 95, 96, 97, 98, or 99% sequence identity to SEQ ID NO: 202 and/or (b) a variable light chain comprising an amino acid sequence with at least 80, 85, 90, 95, 96, 97, 98, or 99% sequence identity to SEQ ID NO: 222. In another embodiment, the anti-PACAP antibodies and antigen binding fragments thereof comprise (a) a variable heavy chain having the amino acid sequence of SEQ ID NO: 202, and/or (b) a variable light chain having the amino acid sequence of SEQ ID NO: 222. More specifically, the anti-PACAP antibodies and antigen binding fragments thereof can comprise (a) a heavy chain having the amino acid sequence of SEQ ID NO: 201, and/or (b) a light chain having the amino acid sequence of SEQ ID NO: 221.

The invention also embraces any of the methods disclosed herein wherein the anti-PACAP antibodies and antigen binding fragments thereof according to the invention, are preferably human, humanized, or chimerized anti-PACAP antibodies and antigen binding fragments thereof, and comprise (a) a variable heavy chain comprising a CDR1 sequence consisting of SEQ ID NO: 244; a CDR2 sequence consisting of SEQ ID NO: 246; and a CDR3 sequence consisting of SEQ ID NO: 248; and/or (b) a variable light chain comprising a CDR1 sequence consisting of SEQ ID NO: 264; a CDR2 sequence consisting of SEQ ID NO: 266; and a CDR3 sequence consisting of SEQ ID NO: 268. Alternatively, the anti-PACAP antibodies and antigen binding fragments thereof can comprise (a) a variable heavy chain comprising an amino acid sequence with at least 80, 85, 90, 95, 96, 97, 98, or 99% sequence identity to SEQ ID NO: 242 and/or (b) a variable light chain comprising an amino acid sequence with at least 80, 85, 90, 95, 96, 97, 98, or 99% sequence identity to SEQ ID NO: 262. In another embodiment, the anti-PACAP antibodies and antigen binding fragments thereof comprise (a) a variable heavy chain having the amino acid sequence of SEQ ID NO: 242, and/or (b) a variable light chain having the amino acid sequence of SEQ ID NO: 262. More specifically, the anti-PACAP antibodies and antigen binding fragments thereof can comprise (a) a heavy chain having the amino acid sequence of SEQ ID NO: 241, and/or (b) a light chain having the amino acid sequence of SEQ ID NO: 261.

The invention also embraces any of the methods disclosed herein wherein the anti-PACAP antibodies and antigen binding fragments thereof according to the invention, are preferably human, humanized, or chimerized anti-PACAP antibodies and antigen binding fragments thereof, and comprise (a) a variable heavy chain comprising a CDR1 sequence consisting of SEQ ID NO: 284; a CDR2 sequence consisting of SEQ ID NO: 286; and a CDR3 sequence consisting of SEQ ID NO: 288; and/or (b) a variable light chain comprising a CDR1 sequence consisting of SEQ ID NO: 304; a CDR2 sequence consisting of SEQ ID NO: 306; and a CDR3 sequence consisting of SEQ ID NO: 308. Alternatively, the anti-PACAP antibodies and antigen binding fragments thereof can comprise a variable heavy chain comprising an amino acid sequence with at least 80, 85, 90, 95, 96, 97, 98, or 99% sequence identity to SEQ ID NO: 282, and/or a variable light chain comprising an amino acid sequence with at least 80, 85, 90, 95, 96, 97, 98, or 99% sequence identity to SEQ ID NO: 302. In another embodiment, the anti-PACAP antibodies and antigen binding fragments thereof comprise (a) a variable heavy chain having the amino acid sequence of SEQ ID NO: 282, and/or (b) a variable light chain having the amino acid sequence of SEQ ID NO: 302. More specifically, the anti-PACAP antibodies and antigen binding fragments thereof can comprise (a) a heavy chain having the amino acid sequence of SEQ ID NO: 281, and/or (b) a light chain having the amino acid sequence of SEQ ID NO: 301.

The invention also embraces any of the methods disclosed herein wherein the anti-PACAP antibodies and antigen binding fragments thereof according to the invention, are preferably human, humanized, or chimerized anti-PACAP antibodies and antigen binding fragments thereof, and comprise (a) a variable heavy chain comprising a CDR1 sequence consisting of SEQ ID NO: 324; a CDR2 sequence consisting of SEQ ID NO: 326; and a CDR3 sequence consisting of SEQ ID NO: 328; and/or (b) a variable light chain comprising a CDR1 sequence consisting of SEQ ID NO: 344; a CDR2 sequence consisting of SEQ ID NO: 346; and a CDR3 sequence consisting of SEQ ID NO: 348. Alternatively, the anti-PACAP antibodies and antigen binding fragments thereof can comprise a variable heavy chain comprising an amino acid sequence with at least 80, 85, 90, 95, 96, 97, 98, or 99% sequence identity to SEQ ID NO: 322, and/or a variable light chain comprising an amino acid sequence with at least 80, 85, 90, 95, 96, 97, 98, or 99% sequence identity to SEQ ID NO: 342. In another embodiment, the anti-PACAP antibodies and antigen binding fragments thereof comprise (a) a variable heavy chain having the amino acid sequence of SEQ ID NO: 322, and/or (b) a variable light chain having the amino acid sequence of SEQ ID NO: 342. More specifically, the anti-PACAP antibodies and antigen binding fragments thereof can comprise (a) a heavy chain having the amino acid sequence of SEQ ID NO: 321, and/or (b) a light chain having the amino acid sequence of SEQ ID NO: 341.

The invention also embraces any of the methods disclosed herein wherein the anti-PACAP antibodies and antigen binding fragments thereof according to the invention, are preferably human, humanized, or chimerized anti-PACAP antibodies and antigen binding fragments thereof, and comprise (a) a variable heavy chain comprising a CDR1 sequence consisting of SEQ ID NO: 364; a CDR2 sequence consisting of SEQ ID NO: 366; and a CDR3 sequence consisting of SEQ ID NO: 368; and/or (b) a variable light chain comprising a CDR1 sequence consisting of SEQ ID NO: 384; a CDR2 sequence consisting of SEQ ID NO: 386; and a CDR3 sequence consisting of SEQ ID NO: 388. Alternatively, the anti-PACAP antibodies and antigen binding fragments thereof can comprise a variable heavy chain comprising an amino acid sequence with at least 80, 85, 90, 95, 96, 97, 98, or 99% sequence identity to SEQ ID NO: 362, and/or a variable light chain comprising an amino acid sequence with at least 80, 85, 90, 95, 96, 97, 98, or 99% sequence identity to SEQ ID NO: 382. In another embodiment, the anti-PACAP antibodies and antigen binding fragments thereof comprise (a) a variable heavy chain having the amino acid sequence of SEQ ID NO: 362, and/or (b) a variable light chain having the amino acid sequence of SEQ ID NO: 382. More specifically, the anti-PACAP antibodies and antigen binding fragments thereof can comprise (a) a heavy chain having the amino acid sequence of SEQ ID NO: 361, and/or (b) a light chain having the amino acid sequence of SEQ ID NO: 381.

The invention also embraces any of the methods disclosed herein wherein the anti-PACAP antibodies and antigen binding fragments thereof according to the invention, are preferably human, humanized, or chimerized anti-PACAP antibodies and antigen binding fragments thereof, and comprise (a) a variable heavy chain comprising a CDR1 sequence consisting of SEQ ID NO: 484; a CDR2 sequence consisting of SEQ ID NO: 486; and a CDR3 sequence consisting of SEQ ID NO: 488; and/or (b) a variable light chain comprising a CDR1 sequence consisting of SEQ ID NO: 504; a CDR2 sequence consisting of SEQ ID NO: 506; and a CDR3 sequence consisting of SEQ ID NO: 508. Alternatively, the anti-PACAP antibodies and antigen binding fragments thereof can comprise a variable heavy chain comprising an amino acid sequence with at least 80, 85, 90, 95, 96, 97, 98, or 99% sequence identity to SEQ ID NO: 482, and/or a variable light chain comprising an amino acid sequence with at least 80, 85, 90, 95, 96, 97, 98, or 99% sequence identity to SEQ ID NO: 502. In another embodiment, the anti-PACAP antibodies and antigen binding fragments thereof comprise (a) a variable heavy chain having the amino acid sequence of SEQ ID NO: 482, and/or (b) a variable light chain having the amino acid sequence of SEQ ID NO: 502. More specifically, the anti-PACAP antibodies and antigen binding fragments thereof can comprise (a) a heavy chain having the amino acid sequence of SEQ ID NO: 481, and/or (b) a light chain having the amino acid sequence of SEQ ID NO: 501.

The invention also embraces any of the methods disclosed herein wherein the anti-PACAP antibodies and antigen binding fragments thereof according to the invention, are preferably human, humanized, or chimerized anti-PACAP antibodies and antigen binding fragments thereof, and comprise (a) a variable heavy chain comprising a CDR1 sequence consisting of SEQ ID NO: 524; a CDR2 sequence consisting of SEQ ID NO: 526; and a CDR3 sequence consisting of SEQ ID NO: 528; and/or (b) a variable light chain comprising a CDR1 sequence consisting of SEQ ID NO: 544; a CDR2 sequence consisting of SEQ ID NO: 546; and a CDR3 sequence consisting of SEQ ID NO: 548. Alternatively, the anti-PACAP antibodies and antigen binding fragments thereof can comprise a variable heavy chain comprising an amino acid sequence with at least 80, 85, 90, 95, 96, 97, 98, or 99% sequence identity to SEQ ID NO: 522, and/or a variable light chain comprising an amino acid sequence with at least 80, 85, 90, 95, 96, 97, 98, or 99% sequence identity to SEQ ID NO: 542. In another embodiment, the anti-PACAP antibodies and antigen binding fragments thereof comprise (a) a variable heavy chain having the amino acid sequence of SEQ ID NO: 522, and/or (b) a variable light chain having the amino acid sequence of SEQ ID NO: 542. More specifically, the anti-PACAP antibodies and antigen binding fragments thereof can comprise (a) a heavy chain having the amino acid sequence of SEQ ID NO: 521, and/or (b) a light chain having the amino acid sequence of SEQ ID NO: 541.

The invention also embraces any of the methods disclosed herein wherein the anti-PACAP antibodies and antigen binding fragments thereof according to the invention, are preferably human, humanized, or chimerized anti-PACAP antibodies and antigen binding fragments thereof, and comprise (a) a variable heavy chain comprising a CDR1 sequence consisting of SEQ ID NO: 564; a CDR2 sequence consisting of SEQ ID NO: 566; and a CDR3 sequence consisting of SEQ ID NO: 568; and/or (b) a variable light chain comprising a CDR1 sequence consisting of SEQ ID NO: 584; a CDR2 sequence consisting of SEQ ID NO: 586; and a CDR3 sequence consisting of SEQ ID NO: 588. Alternatively, the anti-PACAP antibodies and antigen binding fragments thereof can comprise a variable heavy chain comprising an amino acid sequence with at least 80, 85, 90, 95, 96, 97, 98, or 99% sequence identity to SEQ ID NO: 562, and/or a variable light chain comprising an amino acid sequence with at least 80, 85, 90, 95, 96, 97, 98, or 99% sequence identity to SEQ ID NO: 582. In another embodiment, the anti-PACAP antibodies and antigen binding fragments thereof comprise (a) a variable heavy chain having the amino acid sequence of SEQ ID NO: 562, and/or (b) a variable light chain having the amino acid sequence of SEQ ID NO: 582. More specifically, the anti-PACAP antibodies and antigen binding fragments thereof can comprise (a) a heavy chain having the amino acid sequence of SEQ ID NO: 561, and/or (b) a light chain having the amino acid sequence of SEQ ID NO: 581.

The invention also embraces any of the methods disclosed herein wherein the anti-PACAP antibodies and antigen binding fragments thereof according to the invention, are preferably human, humanized, or chimerized anti-PACAP antibodies and antigen binding fragments thereof, and comprise (a) a variable heavy chain comprising a CDR1 sequence consisting of SEQ ID NO: 604; a CDR2 sequence consisting of SEQ ID NO: 606; and a CDR3 sequence consisting of SEQ ID NO: 608; and/or (b) a variable light chain comprising a CDR1 sequence consisting of SEQ ID NO: 624; a CDR2 sequence consisting of SEQ ID NO: 626; and a CDR3 sequence consisting of SEQ ID NO: 628. Alternatively, the anti-PACAP antibodies and antigen binding fragments thereof can comprise a variable heavy chain comprising an amino acid sequence with at least 80, 85, 90, 95, 96, 97, 98, or 99% sequence identity to SEQ ID NO: 602, and/or a variable light chain comprising an amino acid sequence with at least 80, 85, 90, 95, 96, 97, 98, or 99% sequence identity to SEQ ID NO: 622. In another embodiment, the anti-PACAP antibodies and antigen binding fragments thereof comprise (a) a variable heavy chain having the amino acid sequence of SEQ ID NO: 602, and/or (b) a variable light chain having the amino acid sequence of SEQ ID NO: 622. More specifically, the anti-PACAP antibodies and antigen binding fragments thereof can comprise (a) a heavy chain having the amino acid sequence of SEQ ID NO: 601, and/or (b) a light chain having the amino acid sequence of SEQ ID NO: 621.

The invention also embraces any of the methods disclosed herein wherein the anti-PACAP antibodies and antigen binding fragments thereof according to the invention, are preferably human, humanized, or chimerized anti-PACAP antibodies and antigen binding fragments thereof, and comprise (a) a variable heavy chain comprising a CDR1 sequence consisting of SEQ ID NO: 644; a CDR2 sequence consisting of SEQ ID NO: 646; and a CDR3 sequence consisting of SEQ ID NO: 648; and/or (b) a variable light chain comprising a CDR1 sequence consisting of SEQ ID NO: 664; a CDR2 sequence consisting of SEQ ID NO: 666; and a CDR3 sequence consisting of SEQ ID NO: 668. Alternatively, the anti-PACAP antibodies and antigen binding fragments thereof can comprise a variable heavy chain comprising an amino acid sequence with at least 80, 85, 90, 95, 96, 97, 98, or 99% sequence identity to SEQ ID NO: 642, and/or a variable light chain comprising an amino acid sequence with at least 80, 85, 90, 95, 96, 97, 98, or 99% sequence identity to SEQ ID NO: 662. In another embodiment, the anti-PACAP antibodies and antigen binding fragments thereof comprise (a) a variable heavy chain having the amino acid sequence of SEQ ID NO: 642, and/or (b) a variable light chain having the amino acid sequence of SEQ ID NO: 662. More specifically, the anti-PACAP antibodies and antigen binding fragments thereof can comprise (a) a heavy chain having the amino acid sequence of SEQ ID NO: 641, and/or (b) a light chain having the amino acid sequence of SEQ ID NO: 661.

The invention also embraces any of the methods disclosed herein wherein the anti-PACAP antibodies and antigen binding fragments thereof according to the invention, are preferably human, humanized, or chimerized anti-PACAP antibodies and antigen binding fragments thereof, and comprise (a) a variable heavy chain comprising a CDR1 sequence consisting of SEQ ID NO: 684; a CDR2 sequence consisting of SEQ ID NO: 686; and a CDR3 sequence consisting of SEQ ID NO: 688; and/or (b) a variable light chain comprising a CDR1 sequence consisting of SEQ ID NO: 704; a CDR2 sequence consisting of SEQ ID NO: 706; and a CDR3 sequence consisting of SEQ ID NO: 708. Alternatively, the anti-PACAP antibodies and antigen binding fragments thereof can comprise a variable heavy chain comprising an amino acid sequence with at least 80, 85, 90, 95, 96, 97, 98, or 99% sequence identity to SEQ ID NO: 682, and/or a variable light chain comprising an amino acid sequence with at least 80, 85, 90, 95, 96, 97, 98, or 99% sequence identity to SEQ ID NO: 702. In another embodiment, the anti-PACAP antibodies and antigen binding fragments thereof comprise (a) a variable heavy chain having the amino acid sequence of SEQ ID NO: 682, and/or (b) a variable light chain having the amino acid sequence of SEQ ID NO: 702. More specifically, the anti-PACAP antibodies and antigen binding fragments thereof can comprise (a) a heavy chain having the amino acid sequence of SEQ ID NO: 681, and/or (b) a light chain having the amino acid sequence of SEQ ID NO: 701.

The invention also embraces any of the methods disclosed herein wherein the anti-PACAP antibodies and antigen binding fragments thereof according to the invention, are preferably human, humanized, or chimerized anti-PACAP antibodies and antigen binding fragments thereof, and comprise (a) a variable heavy chain comprising a CDR1 sequence consisting of SEQ ID NO: 724; a CDR2 sequence consisting of SEQ ID NO: 726; and a CDR3 sequence consisting of SEQ ID NO: 728; and/or (b) a variable light chain comprising a CDR1 sequence consisting of SEQ ID NO: 744; a CDR2 sequence consisting of SEQ ID NO: 746; and a CDR3 sequence consisting of SEQ ID NO: 748. Alternatively, the anti-PACAP antibodies and antigen binding fragments thereof can comprise a variable heavy chain comprising an amino acid sequence with at least 80, 85, 90, 95, 96, 97, 98, or 99% sequence identity to SEQ ID NO: 722, and/or a variable light chain comprising an amino acid sequence with at least 80, 85, 90, 95, 96, 97, 98, or 99% sequence identity to SEQ ID NO: 742. In another embodiment, the anti-PACAP antibodies and antigen binding fragments thereof comprise (a) a variable heavy chain having the amino acid sequence of SEQ ID NO: 722, and/or (b) a variable light chain having the amino acid sequence of SEQ ID NO: 742. More specifically, the anti-PACAP antibodies and antigen binding fragments thereof can comprise (a) a heavy chain having the amino acid sequence of SEQ ID NO: 721, and/or (b) a light chain having the amino acid sequence of SEQ ID NO: 741.

The invention also embraces any of the methods disclosed herein wherein the anti-PACAP antibodies and antigen binding fragments thereof according to the invention, are preferably human, humanized, or chimerized anti-PACAP antibodies and antigen binding fragments thereof, and comprise (a) a variable heavy chain comprising a CDR1 sequence consisting of SEQ ID NO: 764; a CDR2 sequence consisting of SEQ ID NO: 766; and a CDR3 sequence consisting of SEQ ID NO: 768; and/or (b) a variable light chain comprising a CDR1 sequence consisting of SEQ ID NO: 784; a CDR2 sequence consisting of SEQ ID NO: 786; and a CDR3 sequence consisting of SEQ ID NO: 788. Alternatively, the anti-PACAP antibodies and antigen binding fragments thereof fragment can comprise a variable heavy chain comprising an amino acid sequence with at least 80, 85, 90, 95, 96, 97, 98, or 99% sequence identity to SEQ ID NO: 762, and/or a variable light chain comprising an amino acid sequence with at least 80, 85, 90, 95, 96, 97, 98, or 99% sequence identity to SEQ ID NO: 782. In another embodiment, the anti-PACAP antibodies and antigen binding fragments thereof comprise (a) a variable heavy chain having the amino acid sequence of SEQ ID NO: 762, and/or (b) a variable light chain having the amino acid sequence of SEQ ID NO: 782. More specifically, the anti-PACAP antibodies and antigen binding fragments thereof can comprise (a) a heavy chain having the amino acid sequence of SEQ ID NO: 761, and/or (b) a light chain having the amino acid sequence of SEQ ID NO: 781.

The invention also embraces any of the methods disclosed herein wherein the anti-PACAP antibodies and antigen binding fragments thereof according to the invention, are preferably human, humanized, or chimerized anti-PACAP antibodies and antigen binding fragments thereof, and comprise (a) a variable heavy chain comprising a CDR1 sequence consisting of SEQ ID NO: 804; a CDR2 sequence consisting of SEQ ID NO: 806; and a CDR3 sequence consisting of SEQ ID NO: 808; and/or (b) a variable light chain comprising a CDR1 sequence consisting of SEQ ID NO: 824; a CDR2 sequence consisting of SEQ ID NO: 826; and a CDR3 sequence consisting of SEQ ID NO: 828. Alternatively, the anti-PACAP antibodies and antigen binding fragments thereof can comprise a variable heavy chain comprising an amino acid sequence with at least 80, 85, 90, 95, 96, 97, 98, or 99% sequence identity to SEQ ID NO: 802, and/or a variable light chain comprising an amino acid sequence with at least 80, 85, 90, 95, 96, 97, 98, or 99% sequence identity to SEQ ID NO: 822. In another embodiment, the anti-PACAP antibodies and antigen binding fragments thereof comprise (a) a variable heavy chain having the amino acid sequence of SEQ ID NO: 802, and/or (b) a variable light chain having the amino acid sequence of SEQ ID NO: 822. More specifically, the anti-PACAP antibodies and antigen binding fragments thereof can comprise (a) a heavy chain having the amino acid sequence of SEQ ID NO: 801, and/or (b) a light chain having the amino acid sequence of SEQ ID NO: 821.

The invention also relates to any of the methods disclosed herein wherein the anti-PACAP antibodies or antibody fragments may be selected from the group consisting of scFvs, camelbodies, nanobodies, Immunoglobulin New Antigen Receptor ("IgNAR"), fragment antigen binding ("Fab")

fragments, Fab' fragments, MetMab like antibodies, monovalent antibody fragments, and $F(ab')_2$ fragments. Additionally, the invention relates to any of the methods disclosed herein wherein the anti-PACAP antibody or antibody fragment may substantially or entirely lack N-glycosylation and/or O-glycosylation. Also, the invention pertains to any of the methods disclosed herein wherein the anti-PACAP antibody or antibody fragment may comprise a human constant domain, e.g., that of an IgG1, IgG2, IgG3, or IgG4 antibody.

Another aspect of the invention pertains to any of the methods disclosed herein wherein the anti-PACAP antibody or antibody fragment may comprise an Fc region that may have been modified to alter at least one of effector function, half-life, proteolysis, or glycosylation, e.g., the Fc region may contain one or more mutations that alters or eliminates N- and/or O-glycosylation.

A further aspect of the invention relates to any of the methods disclosed herein wherein the anti-PACAP antibody or antibody fragment may bind to PACAP with a binding affinity ($K_D$) of less than or equal to $5\times10^{-5}$ M, $10^{-5}$ M, $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, or $10^{-13}$ M. Also, said anti-PACAP antibody or antibody fragment of any of the methods disclosed herein may bind to PACAP with a binding affinity ($K_D$) of less than or equal to $5\times10^{-10}$ M, $10^{-10}$ M, $5\times10^{-11}$ M, $10^{-11}$ M, $5\times10^{-12}$ M, or $10^{-12}$ M. Another embodiment of the invention pertains any of the methods disclosed herein wherein the anti-PACAP antibody or antibody fragment may bind to PACAP with an off-rate ($k_{off}$) of less than or equal to $5\times10^{-4}$ $s^{-1}$, $10^{-4}$ $s^{-1}$, $5\times10^{-5}$ $s^{-1}$, or $10^{-5}$ $s^{-1}$.

Moreover, the invention embraces any of the methods disclosed herein wherein the anti-PACAP antibody or antibody fragment may be directly or indirectly attached to a detectable label or therapeutic agent. Also, the invention relates to any of the methods disclosed herein wherein the anti-PACAP antibody or antibody fragment may bind to PACAP with a KD that may be less than about 100 nM, less than about 40 nM, less than about 1 nM, less than about 100 pM, less than about 50 pM, or less than about 25 pM. Also, the invention embraces any of the methods disclosed herein wherein the anti-PACAP antibody or antibody fragment may bind to PACAP with a KD that may be between about 10 pM and about 100 pM. The invention further pertains to any of the methods disclosed herein wherein the method may further comprise administering separately or co-administering another agent, e.g., wherein the other agent may be selected from a chemotherapeutic, an analgesic, an anti-inflammatory, an immunosuppressant, a cytokine, an antiproliferative, an antiemetic or a cytotoxin. Also, the invention embraces any of the methods disclosed herein wherein the other therapeutic agent may be an analgesic, and said analgesic may be a non-steroidal anti-inflammatory drug ("NSAID"), an opioid analgesic, another antibody or a non-antibody biologic, and further wherein said other antibody may be an anti-NGF antibody or antibody fragment; and/or may be an anti-Calcitonin Gene-Related Peptide ("CGRP") antibody or antibody fragment and/or an anti-CGRP receptor antibody or antibody fragment. The invention also pertains to any of the methods disclosed herein wherein said NSAID may be a cyclooxygenase 1 and/or cyclooxygenase 2 inhibitor; and/or wherein said NSAID may be selected from the group consisting of (1) propionic acid derivatives including ibuprofen, naproxen, naprosyn, diclofenac, and ketoprofen; (2) acetic acid derivatives including tolmetin and sulindac; (3) fenamic acid derivatives including mefenamic acid and meclofenamic acid; (4) biphenylcarboxylic acid derivatives including diflunisal and flufenisal; and (5) oxicams including piroxim, sudoxicam, and isoxicam. The invention further relates to any of the methods disclosed herein wherein said opioid analgesic may be selected from the group consisting of codeine, dihydrocodeine, diacetylmorphine, hydrocodone, hydromorphone, levorphanol, oxymorphone, alfentanil, buprenorphine, butorphanol, fentanyl, sufentanil, meperidine, methadone, nalbuphine, propoxyphene, pentazocine, and pharmaceutically acceptable salts thereof; and/or wherein the opioid analgesic may be morphine or a morphine derivative or pharmaceutically acceptable salt thereof; and/or wherein the combined administration of the opioid analgesic and the anti-PACAP antibody or antigen binding fragment may increase the analgesic effect as compared to either the opioid analgesic or the anti-PACAP antibody or antigen binding fragment administered alone.

Furthermore, the invention relates to any of the methods disclosed herein wherein a subject of any of the methods disclosed herein may have previously received an anti-CGRP antibody or antibody fragment and/or an anti-CGRP receptor antibody or antibody fragment; and/or wherein said subject may be a migraineur who may have not adequately responded to anti-CGRP antibody and/or an anti-CGRP receptor antibody or antibody fragment treatment; and/or wherein said subject may have previously received at least one anti-CGRP antibody or antibody fragment and/or an anti-CGRP receptor antibody or antibody fragment administration that may have elicited an immune response to the anti-CGRP antibody or antibody fragment and/or the anti-CGRP receptor antibody or antibody fragment.

Moreover, the invention embraces any of the methods disclosed herein wherein the antibody or antigen binding fragment thereof of the invention may ameliorate or treat one or more conditions associated with PACAP expression in a subject in need thereof, said condition may be selected from the group consisting of: migraine with aura, migraine without aura, hemiplegic migraines, cluster headaches, migrainous neuralgia, chronic headaches, tension headaches, general headaches, hot flush, photophobia, chronic paroxysmal hemicrania, secondary headaches due to an underlying structural problem in the head, secondary headaches due to an underlying structural problem in the neck, cranial neuralgia, sinus headaches, headache associated with sinusitis, allergy-induced headaches, allergy-induced migraines, trigeminal neuralgia, post-herpetic neuralgia, phantom limb pain, fibromyalgia, reflex sympathetic dystrophy, pain, chronic pain, inflammatory pain, post-operative incision pain, post-surgical pain, trauma-related pain, lower back pain, eye pain, tooth pain, complex regional pain syndrome, cancer pain, primary or metastatic bone cancer pain, fracture pain, osteoporotic fracture pain, pain resulting from burn, gout joint pain, pain associated with sickle cell crises, pain associated with temporomandibular disorders, cirrhosis, hepatitis, neurogenic pain, neuropathic pain, nociceptic pain, visceral pain, menstrual pain, ovarialgia, osteoarthritis pain, rheumatoid arthritis pain, diabetic neuropathy, sciatica, dyspepsia, irritable bowel syndrome, inflammatory bowel disease, Crohn's disease, ileitis, ulcerative colitis, renal colic, dysmenorrhea, cystitis, interstitial cystitis, menstrual period, labor, menopause, pancreatitis, schizophrenia, depression, post-traumatic stress disorder, anxiety disorders, autoimmune diabetes, Sjögren's syndrome, multiple sclerosis, overactive bladder, bronchial hyperreactivity, asthma, stroke, bronchitis, bronchodilation, emphysema, chronic obstructive pulmonary disease ("COPD"), inflammatory dermatitis, adenocarcinoma in glandular tissue, blastoma in embryonic tissue of organs, carcinoma in epithelial tissue, leukemia in tissues that form blood cells, lymphoma in lymphatic tissue, myeloma in bone marrow, sarcoma in connective or supportive tissue, adrenal cancer, AIDS-related lymphoma, anemia, bladder cancer, bone cancer, brain cancer, breast cancer, carcinoid tumors, cervical cancer, chemotherapy, colon cancer, cytopenia, endometrial cancer, esophageal cancer, gastric cancer, head cancer, neck cancer, hepatobiliary cancer, kidney cancer, leukemia, liver cancer, lung cancer, lymphoma, Hodgkin's disease, non-Hodgkin's, nervous system tumors, oral cancer, ovarian cancer, pancreatic cancer, prostate cancer, rectal cancer, skin cancer, stomach cancer, testicular cancer, thyroid cancer, urethral cancer, cancer of bone marrow, multiple myeloma, tumors that metastasize to the bone, tumors infiltrating the nerve and hollow viscus, tumors near neural structures, acne vulgaris, atopic dermatitis, urticaria, keloids, hypertrophic scars and rosacea, endothelial dysfunction, Raynaud's syndrome, coronary heart disease ("CHD"), coronary artery disease ("CAD"), heart failure, peripheral arterial disease ("PAD"), diabetes, pulmonary hypertension ("PH"), connective tissue disorder, allergic dermatitis, psoriasis, pruritus, neurogenic cutaneous redness, erythema, sarcoidosis, shock, sepsis, opiate withdrawal syndrome, morphine tolerance, and epilepsy.

In another embodiment of the invention, an anti-PACAP antibody or antibody fragment or a method as disclosed herein may inhibit the effects of PACAP on vasodilation; and/or may inhibit the effects of PACAP on cAMP production; and/or may inhibit the effects of PACAP on PLC resulting in reduced Ca++ and PLD levels; and/or may inhibit the effects of PACAP on adenylate cyclase activity; and/or may inhibit the effects of PACAP on its binding to any or all of PAC1-R, VPAC1-R or VPAC2-R; and/or may inhibit the effects of PACAP on neurodevelopment; may inhibit the effects of PACAP on neuroprotection; and/or may inhibit the effects of PACAP on neuromodulation; and/or may inhibit the effects of PACAP on neurogenic inflammation; and/or may inhibit the effects of PACAP on nociception; and/or may modulate the interaction of PACAP with binding the cell surface, e.g. via at least one GAG, e.g., wherein at least one said GAG may comprise one or more of heparin, chondroitin, keratin, and hyaluronic acid, and further wherein said antibody or antibody fragment or method may block or inhibit receptor-independent cellular uptake of PACAP3 8 and/or PACAP27 and/or may inhibit or may block GAG-dependent uptake of PACAP38 and/or PACAP27 by cells.

A further embodiment of the invention relates to method of therapy or prophylaxis that may comprise the administration of an anti-PACAP antibody or antibody fragment of the invention. Additionally, the invention pertains to a composition that may be used in human therapy that may contain an anti-PACAP antibody or antibody fragment of the invention. Said composition may contain another active agent, e.g., wherein the other agent may selected from a chemotherapeutic, an analgesic, an anti-inflammatory, an immunosuppressant, a cytokine, an antiproliferative, an anti-emetic or a cytotoxin. Wherein said other agent may be an analgesic, said analgesic may be a NSAID, an opioid analgesic, another antibody or a non-antibody biologic. When said other agent may be an analgesic that may be another antibody, the other antibody may be an anti-NGF antibody or antibody fragment, and/or the other antibody may be an anti-Calcitonin Gene-Related Peptide ("CGRP") antibody or antibody fragment and/or an anti-CGRP receptor antibody or antibody fragment. Wherein said other agent may be a NSAID, said NSAID may be a cyclooxygenase 1 and/or cyclooxygenase 2 inhibitor; and/or said NSAID may be selected from the group consisting of (1) propionic acid derivatives including ibuprofen, naproxen, naprosyn, diclofenac, and ketoprofen; (2) acetic acid derivatives including tolmetin and sulindac; (3) fenamic acid derivatives including mefenamic acid and meclofenamic acid; (4) biphenylcarboxylic acid derivatives including diflunisal and flufenisal; and (5) oxicams including piroxim, sudoxicam, and isoxicam. Wherein said other agent may be an opioid analgesic, said opioid analgesic may be selected from the group consisting of codeine, dihydrocodeine, diacetylmorphine, hydrocodone, hydromorphone, levorphanol, oxymorphone, alfentanil, buprenorphine, butorphanol, fentanyl, sufentanil, meperidine, methadone, nalbuphine, propoxyphene, pentazocine, and pharmaceutically acceptable salts thereof; and/or said opioid analgesic may be morphine or a morphine derivative or pharmaceutically acceptable salt thereof; and/or said opioid analgesic and an anti-PACAP antibody or antigen binding fragment according to the invention may increase the analgesic effect as compared to either the opioid analgesic or the anti-PACAP antibody or antigen binding fragment administered alone.

In another embodiment of the invention, an anti-PACAP antibody or fragment or composition according to the invention, wherein the anti-PACAP antibody or fragment and another active agent may be combined therewith or may be administered in combination, may elicit a synergistic or additive effect on the treatment or prevention of a PACAP associated effect, e.g., migraine or on pain. Another embodiment of the invention additionally embraces an anti-PACAP antibody or fragment or composition according the invention that may be used in therapy or diagnosis, e.g., migraine treatment or prophylaxis. A further embodiment of the invention relates to an anti-PACAP antibody or fragment or composition according to the invention that may be used for treating one or more of hot flush, migraine with or without aura, hemiplegic migraine, cluster headache, migrainous neuralgia, chronic headache, chronic migraine, medication overuse headache or tension headache.

Another embodiment of the invention pertains an anti-PACAP antibody or fragment or composition according to the invention that may be used for ameliorating, controlling, reducing incidence of, or delaying the development or progression of headache, e.g., migraine with or without aura, hemiplegic migraine, cluster headache, migrainous neuralgia, chronic headache, chronic migraine, medication overuse headache or tension headache. In an embodiment of the invention, the use may be for a subject who may have previously received or may be receiving an anti-CGRP antibody or antibody fragment and/or an anti-CGRP receptor antibody or antibody fragment, and further wherein said subject may be a migraineur who may not have adequately responded to anti-CGRP antibody or antibody fragment and/or anti-CGRP receptor antibody or antibody fragment treatment; and/or wherein said subject may have previously received at least one anti-CGRP antibody or antibody fragment and/or anti-CGRP receptor antibody or antibody fragment administration that may have elicited an immune response to the anti-CGRP antibody or antibody fragment and/or anti-CGRP receptor antibody or antibody fragment.

BRIEF DESCRIPTION OF THE SEVERAL VIEWS OF THE DRAWING

FIG. 1A-1B provides the polypeptide sequences of the heavy chain variable region for antibodies Ab1, Ab1.H, Ab2, Ab13, Ab14, Ab15, Ab16, Ab17, Ab18, Ab19, Ab5, Ab7, Ab11, Ab12, Ab4, Ab3, Ab6, Ab8, and Ab9 (SEQ ID NOs: 2; 42; 82; 122; 162; 202; 242; 282; 322; 362; 482; 522; 562; 602; 642; 682; 722; 762; and 802, respectively) aligned by their FRs and CDRs.

FIG. 2A-2B provides the polypeptide sequences of the light chain variable region for antibodies Ab1, Ab1.H, Ab2, Ab13, Ab14, Ab15, Ab16, Ab17, Ab18, Ab19, Ab5, Ab7, Ab11, Ab12, Ab4, Ab3, Ab6, Ab8, and Ab9 (SEQ ID NOs: 22; 62; 102; 142; 182; 222; 262; 302; 342; 382; 502; 542; 582; 622; 662; 702; 742; 782; and 822, respectively) aligned by their FRs, and CDRs.

FIG. 3A-3F provides the polynucleotide sequences encoding the heavy chain variable region for antibodies Ab1, Ab1.H, Ab2, Ab13, Ab14, Ab15, Ab16, Ab17, Ab18, Ab19, Ab5, Ab7, Ab11, Ab12, Ab4, Ab3, Ab6, Ab8, and Ab9 (SEQ ID NOs: 12; 52; 92; 132; 172; 212; 252; 292; 332; 372; 492; 532; 572; 612; 652; 692; 732; 772; and 812, respectively) aligned by their FRs, and CDRs.

FIG. 4A-4E provides the polynucleotide sequences encoding the light chain variable region for antibodies Ab1, Ab1.H, Ab2, Ab13, Ab14, Ab15, Ab16, Ab17, Ab18, Ab19, Ab5, Ab7, Ab11, Ab12, Ab4, Ab3, Ab6, Ab8, and Ab9 (SEQ ID NOs: 32; 72; 112; 152; 192; 232; 272; 312; 352; 392; 512; 552; 592; 632; 672; 712; 752; 792; and 832, respectively) aligned by their FRs, and CDRs.

FIG. 5 provides the polypeptide sequence coordinates for certain antibody heavy chain protein sequence features including the variable region and complementarity determining regions (CDRs) of the heavy chain for antibodies Ab1, Ab1.H, Ab2, Ab3, Ab4, Ab5, Ab6, Ab7, Ab8, Ab9, Ab11, Ab12, Ab13, Ab14, Ab15, Ab16, Ab17, Ab18, and Ab19.

FIG. 6 provides the polypeptide sequence coordinates for certain antibody heavy chain protein sequence features including the constant region and framework regions (FR) of the heavy chain for antibodies Ab1, Ab1.H, Ab2, Ab3, Ab4, Ab5, Ab6, Ab7, Ab8, Ab9, Ab11, Ab12, Ab13, Ab14, Ab15, Ab16, Ab17, Ab18, and Ab19.

FIG. 7 provides the polypeptide sequence coordinates for certain antibody light chain protein sequence features including the variable region and complementarity determining regions (CDRs) of the light chain for antibodies Ab1, Ab1.H, Ab2, Ab3, Ab4, Ab5, Ab6, Ab7, Ab8, Ab9, Ab11, Ab12, Ab13, Ab14, Ab15, Ab16, Ab17, Ab18, and Ab19.

FIG. 8 provides the polypeptide sequence coordinates for certain antibody light chain protein sequence features including the constant region and framework regions (FR) of the light chain for antibodies Ab1, Ab1.H, Ab2, Ab3, Ab4, Ab5, Ab6, Ab7, Ab8, Ab9, Ab11, Ab12, Ab13, Ab14, Ab15, Ab16, Ab17, Ab18, and Ab19.

FIG. 9 provides the polynucleotide sequence coordinates for certain antibody heavy chain DNA sequence features including the variable region and complementarity determining regions (CDRs) of the heavy chain for antibodies Ab1, Ab1.H, Ab2, Ab3, Ab4, Ab5, Ab6, Ab7, Ab8, Ab9, Ab11, Ab12, Ab13, Ab14, Ab15, Ab16, Ab17, Ab18, and Ab19.

FIG. 10 provides the polynucleotide sequence coordinates for certain antibody heavy chain DNA sequence features including the constant region and framework regions (FR) of the heavy chain for antibodies Ab1, Ab1.H, Ab2, Ab3, Ab4, Ab5, Ab6, Ab7, Ab8, Ab9, Ab11, Ab12, Ab13, Ab14, Ab15, Ab16, Ab17, Ab18, and Ab19.

FIG. 11 provides the polynucleotide sequence coordinates for certain antibody light chain DNA sequence features including the variable region and complementarity determining regions (CDRs) of the light chain for antibodies Ab1, Ab1.H, Ab2, Ab3, Ab4, Ab5, Ab6, Ab7, Ab8, Ab9, Ab11, Ab12, Ab13, Ab14, Ab15, Ab16, Ab17, Ab18, and Ab19.

FIG. 12 provides the polynucleotide sequence coordinates for certain antibody light chain DNA sequence features including the constant region and framework regions (FR) of the light chain for antibodies Ab1, Ab1.H, Ab2, Ab3, Ab4, Ab5, Ab6, Ab7, Ab8, Ab9, Ab11, Ab12, Ab13, Ab14, Ab15, Ab16, Ab17, Ab18, and Ab19.

DETAILED DESCRIPTION

Definitions

Figure 13:
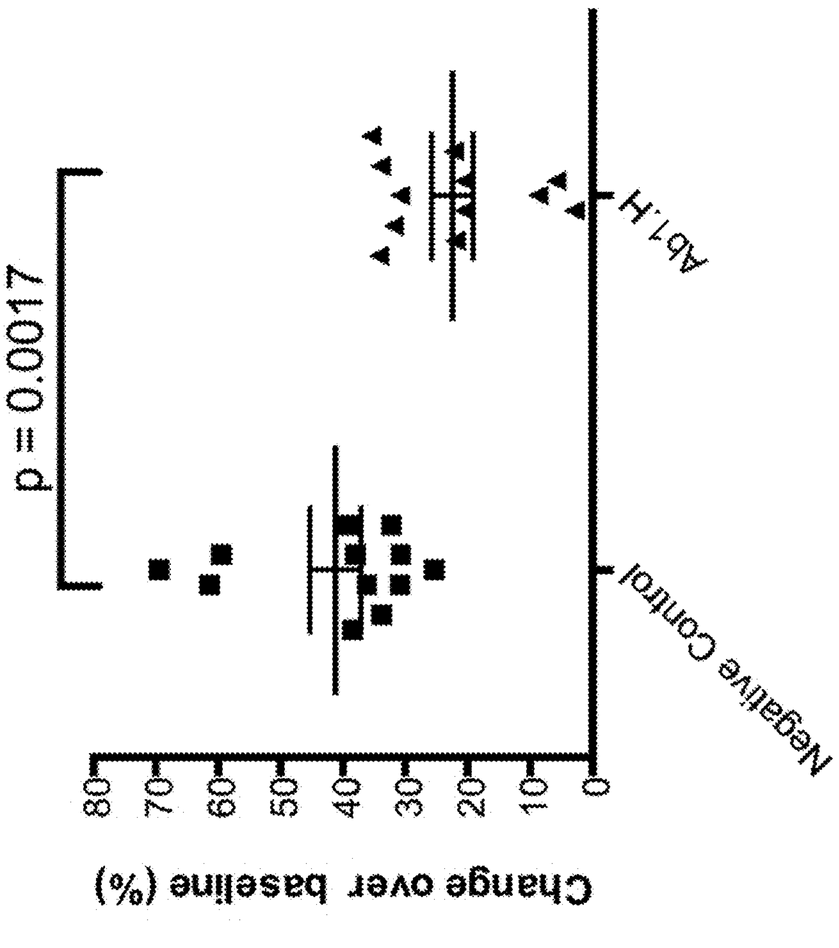
FIG. 13 provides representative data showing a reduction in vasodilation obtained by administering Ab1.H following PACAP38 administration in a rabbit model, relative to a vehicle control, obtained following the protocol in Example 7 infra.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention, which will be limited only by the appended claims. As used herein the singular forms "a", "and", and "the" include plural referents unless the context clearly dictates otherwise. Thus, for example, reference to "a cell" includes a plurality of such cells and reference to "the protein" includes reference to one or more proteins and equivalents thereof known to those skilled in the art, and so forth. All technical and scientific terms used herein have the same meaning as commonly understood to one of ordinary skill in the art to which this invention belongs unless clearly indicated otherwise.

Pituitary Adenylate Cyclase Activating Polypeptide (PACAP): As used herein, unless stated otherwise PACAP includes any mammalian form of PACAP, and in particular encompasses the following *Homo sapiens* PACAP27 and *Homo sapiens* PACAP38 amino acid sequences:

PACAP38:

HSDGIFTDSYSRYRKQMAVKKY-LAAVLGKRYKQRVKNK (SEQ ID NO: 1241), wherein the C-terminal lysine is amidated; but also any mutants, splice variants, isoforms, orthologs, homologs, and variants of this sequence.

PACAP27:

HSDGIFTDSYSRYRKQMAVKKYLAAVL (SEQ ID NO: 1242), wherein the C-terminal leucine is amidated; but also any mutants, splice variants, isoforms, orthologs, homologs, and variants of this sequence.

"Photophobia" herein refers to a symptom of abnormal intolerance to visual perception of light, sometimes additionally defined by abnormal or irrational fear of light, or by presence of actual physical photosensitivity of the eyes. In the present invention photophobia includes in particular light aversion associated with migraine, cluster headaches and other neurological causes of light aversive behavior that can trigger a migraine or cluster headache. Patients/subjects can develop photophobia as a result of several different medical conditions, related to the eye or the nervous system. Photophobia can be caused by an increased response to light starting at any step in the visual system such as: (i) too much light entering the eye, (ii) too much light can enter the eye if it is damaged, such as with corneal abrasion and retinal damage, or if a pupil(s) is unable to normally constrict (seen with damage to the oculomotor nerve), (iii) overstimulation of the photoreceptors in the retina, (iv) excessive electric impulses to the optic nerve, and (v) excessive response in the central nervous system.

"Effective treatment or prevention of photophobia" herein refers to inhibiting light aversive behavior or photophobia or inhibiting the onset of light aversive behavior or photophobia in a subject in need thereof, e.g., a subject having an active migraine attack or cluster headache or a subject prone to migraine or cluster headaches, or one of the other photophobia-associated disorders identified herein after administration of an effective amount of an anti-PACAP antibody or antigen binding fragment thereof according to the invention. The treatment may be effected as a monotherapy or in association with another active agent such as topiramate or dihydroergotamine by way of example.

The term "migraine" refers to a complex and disabling neurological disorder that may progress during four stages: prodrome, aura, headache, and postdrome. A migraine is defined by the International Headache Society as a headache that lasts for 4-72 hours and is characterized by at least two of the following: unilateral localization, pulsating quality, moderate to severe pain intensity; and aggravation by movement such as walking. In addition, the headache must be accompanied by at least one of the following: nausea and/or vomiting, photophobia, or phonophobia. A migraine may also be accompanied by aura, which typically precedes the deadline during the premonition or prodrome phase, and often results in visual changes, e.g., a scintillating scotoma that moves across the visual field. The prodrome may also be accompanied by other symptoms, e.g., fatigue, gastrointestinal issues, and mood changes. A migraineur is often incapacitated for extended periods of time. The postdrome is the final phase and occurs after the attack, during which time the migraineur may feel exhausted or mildly euphoric.

The term "headache" refers to pain in any region of the head. Headaches may occur on one or both sides of the head, be isolated to a certain location, radiate across the head from one point, or have a vise-like quality. A headache may be a sharp pain, throbbing sensation or dull ache. Headaches may appear gradually or suddenly, and they may last less than an hour or for several days.

The term "pain associated disease or condition" refers to any disease or condition defined, in whole or in part, by acute and/or chronic pain. Pain is generally defined as an unpleasant sensory and emotional experience associated with actual or potential tissue damage, or described in terms of such damage. Pain may be classified as neurogenic, neuropathic, inflammatory, or nociceptic.

The term "opioid analgesic" herein refers to all drugs, natural or synthetic, with morphine-like actions. The synthetic and semi-synthetic opioid analgesics are derivatives of five chemical classes of compound: phenanthrenes; phenylheptylamines; phenylpiperidines; morphinans; and benzomorphans, all of which are within the scope of the term. Exemplary opioid analgesics include codeine, dihydrocodeine, diacetylmorphine, hydrocodone, hydromorphone, levorphanol, oxymorphone, alfentanil, buprenorphine, butorphanol, fentanyl, sufentanil, meperidine, methadone, nalbuphine, propoxyphene, and pentazocine, or pharmaceutically acceptable salts thereof.

The term "NSAID" refers to a non-steroidal anti-inflammatory compound. NSAIDs are categorized by virtue of their ability to inhibit cyclooxygenase. Cyclooxygenase 1 and cyclooxygenase 2 are two major isoforms of cyclooxygenase and most standard NSAIDs are mixed inhibitors of the two isoforms. Most standard NSAIDs fall within one of the following five structural categories: (1) propionic acid derivatives, such as ibuprofen, naproxen, naprosyn, diclofenac, and ketoprofen; (2) acetic acid derivatives, such as tolmetin and sulindac; (3) fenamic acid derivatives, such as mefenamic acid and meclofenamic acid; (4) biphenylcarboxylic acid derivatives, such as diflunisal and flufenisal; and (5) oxicams, such as piroxim, sudoxicam, and isoxicam. Another class of NSAID has been described that selectively inhibit cyclooxygenase 2. COX-2 inhibitors have been described, e.g., in U.S. Pat. Nos. 5,616,601; 5,604,260; 5,593,994; 5,550,142; 5,536,752; 5,521,213; 5,475,995; 5,639,780; 5,604,253; 5,552,422; 5,510,368; 5,436,265; 5,409,944; and 5,130,311, all of which are hereby incorporated by reference. Certain exemplary COX-2 inhibitors include celecoxib (SC-58635), DUP-697, flosulide (CGP-28238), meloxicam, 6-methoxy-2 naphthylacetic acid (6-MNA), rofecoxib, MK-966, nabumetone (prodrug for 6-MNA), nimesulide, NS-398, SC-5766, SC-58215, T-614; or combinations thereof.

As used herein, "treatment" is an approach for obtaining beneficial or desired clinical results. For purposes of this invention, beneficial or desired clinical results include, but are not limited to, one or more of the following: improvement in any aspect of PACAP-related conditions such as migraine or headache. For example in the context of headache or migraine treatment this includes lessening severity, alleviation of pain intensity, and other associated symptoms, reducing frequency of recurrence, increasing the quality of life of those suffering from the headache, and decreasing dose of other medications required to treat the headache. For migraine, other associated symptoms include, but are not limited to, nausea, vomiting, and sensitivity to light, sound, and/or movement. For cluster headache, other associated symptoms include, but are not limited to swelling under or around the eyes, excessive tears, red eye, rhinorrhea or nasal congestion, and red flushed face.

"Reducing incidence" or "prophylaxis" or "prevention" means any of reducing severity for a particular disease, condition, symptom, or disorder (the terms disease, condition, and disorder are used interchangeably throughout the application). Reduction in severity includes reducing drugs and/or therapies generally used for the condition by, for example, reducing the need for, amount of, and/or exposure to drugs or therapies. Reduction in severity also includes reducing the duration, and/or frequency of the particular condition, symptom, or disorder (including, for example, delaying or increasing time to next episodic attack in an individual).

"Ameliorating" headache or one or more symptoms of headache or migraine or other PACAP-related condition means a lessening or improvement of one or more symptoms of the condition, e.g., headache or migraine as compared to not administering an anti-PACAP antagonist antibody. "Ameliorating" also includes shortening or reduction in duration of a symptom.

As used herein, "controlling headache" or "controlling migraine" or "controlling" another PACAP-related condition refers to maintaining or reducing severity or duration of one or more symptoms of the condition, e.g., headache or migraine or frequency of headache or migraine attacks in an individual (as compared to the level before treatment). For example, the duration or severity of head pain, or frequency of attacks is reduced by at least about any of 10%, 20%, 30%, 40%, 50%, 60%, 70%, 80%, 90%, or 100% in the individual as compared to the level before treatment. The reduction in the duration or severity of head pain, or frequency of attacks can last for any length of time, e.g., 2 weeks, 4 weeks (1 month), 8 weeks (2 months), 16 weeks (3 months), 4 months, 5 months, 6 months, 9 months, 12 months, etc.

As used therein, "delaying" the development of a PACAP-related condition such as migraine or headache means to defer, hinder, slow, retard, stabilize, and/or postpone progression of the condition or disease. This delay can be of varying lengths of time, depending on the history of the condition or disease and/or individuals being treated. As is evident to one skilled in the art, a sufficient or significant delay can, in effect, encompass prevention, in that the individual does not develop headache (e.g., migraine). A method that "delays" development of the symptom is a method that reduces probability of developing the symptom in a given time frame and/or reduces extent of the symptoms in a given time frame, when compared to not using the method. Such comparisons are typically based on clinical studies, using a statistically significant number of subjects.

"Development" or "progression" of a PACAP-related condition such as migraine or headache, preferably a condition associated with photophobia or light aversion, means initial manifestations and/or ensuing progression of the disorder or symptom or side effect of such disorder such as photophobia or light aversion. Development of headache or migraine can be detectable and assessed using standard clinical techniques as well known in the art. However, development also refers to progression that may be undetectable. For purpose of this invention, development, or progression refers to the biological course of the symptoms. "Development" includes occurrence, recurrence, and onset.

As used herein "onset" or "occurrence" of a condition such as headache or migraine includes initial onset and/or recurrence.

As used herein, an "effective dosage" or "effective amount" of drug, compound, or pharmaceutical composition is an amount sufficient to effect beneficial or desired results, e.g., an amount sufficient to treat or ameliorate or prevent PACAP associate photophobia or light aversion. For prophylactic use, beneficial or desired results include results such as eliminating or reducing the risk, lessening the severity, or delaying the outset of the disease, including biochemical, histological, and/or behavioral symptoms of the disease, its complications and intermediate pathological phenotypes presenting during development of the disease. For therapeutic use, beneficial or desired results include clinical results such as reducing pain intensity, duration, or frequency of headache attack, and decreasing one or more symptoms resulting from headache (biochemical, histological, and/or behavioral), including its complications and intermediate pathological phenotypes presenting during development of the disease, increasing the quality of life of those suffering from the disease, decreasing the dose of other medications required to treat the disease, enhancing effect of another medication, and/or delaying the progression of the disease of patients. For instance, clinical results include reducing the sensation of photophobia, light aversion, or avoidance and sensitivity to light. An effective dosage can be administered in one or more administrations. For purposes of this invention, an effective dosage of drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

A "suitable host cell" or "host cell" generally includes any cell wherein the subject anti-PACAP antibodies and antigen binding fragments thereof can be produced recombinantly using techniques and materials readily available. For example, the anti-PACAP antibodies and antigen binding fragments thereof of the present invention can be produced in genetically engineered host cells according to conventional techniques. Suitable host cells are those cell types that can be transformed or transfected with exogenous DNA and grown in culture, and include bacteria, fungal cells (e.g., yeast), and cultured higher eukaryotic cells (including cultured cells of multicellular organisms), particularly cultured mammalian cells, e.g., human or non-human mammalian cells. In an exemplary embodiment these antibodies may be expressed in CHO cells. Techniques for manipulating cloned DNA molecules and introducing exogenous DNA into a variety of host cells are disclosed by Sambrook et al., *Molecular Cloning: A Laboratory Manual,* 2nd ed., Cold Spring Harbor, N.Y.: Cold Spring Harbor Laboratory Press (1989), and *Current Protocols in Molecular Biology*, Ausubel et al., editors, New York, N.Y.: Green and Wiley and Sons (1993).

In some exemplary embodiments the antibodies may be expressed in mating competent yeast, e.g., any haploid, diploid or tetraploid yeast that can be grown in culture. Yeast useful in fermentation expression methods may exist in a haploid, diploid, or other polyploid form. The cells of a given ploidy may, under appropriate conditions, proliferate for an indefinite number of generations in that form. Diploid cells can also sporulate to form haploid cells. Sequential mating can result in tetraploid strains through further mating or fusion of diploid strains. The present invention contemplates the use of haploid yeast, as well as diploid or other polyploid yeast cells produced, for example, by mating or spheroplast fusion. By way of example, such yeast may include members of the Saccharomycetaceae family, which includes the genera *Arxiozyma; Ascobotryozyma; Citeromyces; Debaryomyces; Dekkera; Eremothecium; Issatchenkia; Kazachstania; Kluyveromyces; Kodamaea; Lodderomyces; Pachysolen; Pichia; Saccharomyces; Saturnispora; Tetrapisispora; Torulaspora; Williopsis*; and *Zygosaccharomyces*. Other types of yeast potentially useful in the invention include *Yarrowia; Rhodosporidium; Candida; Hansenula; Filobasium; Sporidiobolus; Bullera; Leucosporidium* and *Filobasidella*.

In a preferred exemplary embodiment of the invention, the mating competent yeast used for antibody expression may comprise a member of the genus *Pichia*. In a further preferred exemplary embodiment of the invention, the mating competent yeast of the genus *Pichia* is one of the following species: *Pichia pastoris, Pichia methanolica*, and *Hansenula polymorpha* (*Pichia angusta*). In a particularly preferred embodiment of the invention, the mating competent yeast of the genus *Pichia* is the species *Pichia pastoris*.

A "selectable marker" herein refers to a gene or gene fragment that confers a growth phenotype (physical growth characteristic) on a cell receiving that gene as, for example through a transformation event. The selectable marker allows that cell to survive and grow in a selective growth medium under conditions in which cells that do not receive that selectable marker gene cannot grow. Selectable marker genes generally fall into several types, including positive selectable marker genes such as a gene that confers on a cell resistance to an antibiotic or other drug, temperature when two temperature sensitive ("ts") mutants are crossed or a is mutant is transformed; negative selectable marker genes such as a biosynthetic gene that confers on a cell the ability to grow in a medium without a specific nutrient needed by all cells that do not have that biosynthetic gene, or a mutagenized biosynthetic gene that confers on a cell inability to grow by cells that do not have the wild type gene; and the like. Suitable markers include but are not limited to: ZEO; G418; LYS3; MET1; MET3a; ADE1; ADE3; URA3; and the like.

An "expression vector" herein refers to DNA vectors containing elements that facilitate manipulation for the expression of a foreign protein within the target host cell, e.g., a bacterial, insect, yeast, plant, amphibian, reptile, avian, or mammalian cell, and most typically a yeast or mammalian cell, e.g., a CHO cell. Conveniently, manipulation of sequences and production of DNA for transformation is first performed in a bacterial host, e.g. *E. coli*, and usually vectors will include sequences to facilitate such manipulations, including a bacterial origin of replication and appropriate bacterial selection marker. Selection markers encode proteins necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, (b) complement auxotrophic deficiencies, or (c) supply critical nutrients not available from complex media. Exemplary vectors and methods for transformation of yeast are described, for example, in Burke, D., Dawson, D., & Stearns, T., *Methods in yeast genetics: a Cold Spring Harbor Laboratory course manual*, Plainview, N.Y.: Cold Spring Harbor Laboratory Press (2000). Expression vectors for use in the methods of the invention may include yeast or mammalian specific sequences, including a selectable auxotrophic or drug marker for identifying transformed host strains. A drug marker may further be used to amplify copy number of the vector in a yeast host cell.

The polypeptide coding sequence of interest is operably linked to transcriptional and translational regulatory sequences that provide for expression of the polypeptide in the desired host cells, e.g., yeast or mammalian cells. These vector components may include, but are not limited to, one or more of the following: an enhancer element, a promoter, and a transcription termination sequence. Sequences for the secretion of the polypeptide may also be included, e.g. a signal sequence, and the like. An origin of replication, e.g., a yeast origin of replication, is optional, as expression vectors are often integrated into the host cell genome. In one embodiment of the invention, the polypeptide of interest is operably linked, or fused, to sequences providing for optimized secretion of the polypeptide from yeast diploid cells.

Nucleic acids are "operably linked" when placed into a functional relationship with another nucleic acid sequence. For example, DNA for a signal sequence is operably linked to DNA for a polypeptide if it is expressed as a preprotein that participates in the secretion of the polypeptide; a promoter or enhancer is operably linked to a coding sequence if it affects the transcription of the sequence. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites or alternatively via a PCR/recombination method familiar to those skilled in the art (GATEWAY® Technology; Invitrogen, Carlsbad California). If such sites do not exist, the synthetic oligonucleotide adapters or linkers are used in accordance with conventional practice.

Promoters are untranslated sequences located upstream (5') to the start codon of a structural gene (generally within about 100 to 1000 bp) that control the transcription and translation of particular nucleic acid sequences to which they are operably linked. Such promoters fall into several classes: inducible, constitutive, and repressible promoters (that increase levels of transcription in response to absence of a repressor). Inducible promoters may initiate increased levels of transcription from DNA under their control in response to some change in culture conditions, e.g., the presence or absence of a nutrient or a change in temperature.

The promoter fragment may also serve as the site for homologous recombination and integration of the expression vector into the same site in the host cell, e.g., yeast cell, genome; alternatively, a selectable marker may be used as the site for homologous recombination. *Pichia* transformation is described in Cregg et al., *Mol. Cell. Biol.,* 5:3376-3385 (1985). Suitable promoters for use in different eukaryotic and prokaryotic cells are well known and commercially available.

The polypeptides of interest may be produced recombinantly not only directly, but also as a fusion polypeptide with a heterologous polypeptide, e.g. a signal sequence or other polypeptide having a specific cleavage site at the N-terminus of the mature protein or polypeptide. In general, the signal sequence may be a component of the vector, or it may be a part of the polypeptide coding sequence that is inserted into the vector. The heterologous signal sequence selected preferably is one that is recognized and processed through one of the standard pathways available within the host cell, e.g., a mammalian cell, an insect cell, or a yeast cell. Additionally, these signal peptide sequences may be engineered to provide for enhanced secretion in expression systems. Secretion signals of interest also include mammalian and yeast signal sequences, which may be heterologous to the protein being secreted, or may be a native sequence for the protein being secreted. Signal sequences include pre-peptide sequences, and in some instances may include propeptide sequences. Many such signal sequences are known in the art, including the signal sequences found on immunoglobulin chains, e.g., K28 preprotoxin sequence, PHA-E, FACE, human MCP-1, human serum albumin signal sequences, human Ig heavy chain, human Ig light chain, and the like. For example, see Hashimoto et. al., *Protein Eng.,* 11(2):75 (1998); and Kobayashi et. al., *Therapeutic Apheresis,* 2(4): 257 (1998)).

Transcription may be increased by inserting a transcriptional activator sequence into the vector. These activators are cis-acting elements of DNA, usually about from 10 to 300 bp, which act on a promoter to increase its transcription. Transcriptional enhancers are relatively orientation and position independent, having been found 5' and 3' to the transcription unit, within an intron, as well as within the coding sequence itself. The enhancer may be spliced into the expression vector at a position 5' or 3' to the coding sequence, but is preferably located at a site 5' from the promoter.

Expression vectors used in eukaryotic host cells may also contain sequences necessary for the termination of transcription and for stabilizing the mRNA. Such sequences are commonly available from 3' to the translation termination codon, in untranslated regions of eukaryotic or viral DNAs or cDNAs. These regions contain nucleotide segments transcribed as polyadenylated fragments in the untranslated portion of the mRNA.

Construction of suitable vectors containing one or more of the above-listed components employs standard ligation techniques or PCR/recombination methods. Isolated plasmids or DNA fragments are cleaved, tailored, and re-ligated in the form desired to generate the plasmids required or via recombination methods. For analysis to confirm correct sequences in plasmids constructed, the ligation mixtures are used to transform host cells, and successful transformants selected by antibiotic resistance (e.g. ampicillin or Zeocin) where appropriate. Plasmids from the transformants are prepared, analyzed by restriction endonuclease digestion, and/or sequenced.

As an alternative to restriction and ligation of fragments, recombination methods based on specific attachment ("att") sites and recombination enzymes may be used to insert DNA sequences into a vector. Such methods are described, for example, by Landy, *Ann. Rev. Biochem.,* 58:913-949 (1989); and are known to those of skill in the art. Such methods utilize intermolecular DNA recombination that is mediated by a mixture of lambda and *E. coli*-encoded recombination proteins. Recombination occurs between att sites on the interacting DNA molecules. For a description of att sites see Weisberg and Landy, *Site-Specific Recombination in Phage Lambda*, in *Lambda II*, p. 211-250, Cold Spring Harbor, NY: Cold Spring Harbor Press (1983). The DNA segments flanking the recombination sites are switched, such that after recombination, the att sites are hybrid sequences comprised of sequences donated by each parental vector. The recombination can occur between DNAs of any topology.

Att sites may be introduced into a sequence of interest by ligating the sequence of interest into an appropriate vector; generating a PCR product containing att B sites through the use of specific primers; generating a cDNA library cloned into an appropriate vector containing att sites; and the like.

Folding, as used herein, refers to the three-dimensional structure of polypeptides and proteins, where interactions between amino acid residues act to stabilize the structure. While non-covalent interactions are important in determining structure, usually the proteins of interest will have intra- and/or intermolecular covalent disulfide bonds formed by two cysteine residues. For naturally occurring proteins and polypeptides or derivatives and variants thereof, the proper folding is typically the arrangement that results in optimal biological activity, and can conveniently be monitored by assays for activity, e.g. ligand binding, enzymatic activity, etc.

In some instances, for example where the desired product is of synthetic origin, assays based on biological activity will be less meaningful. The proper folding of such molecules may be determined on the basis of physical properties, energetic considerations, modeling studies, and the like.

The expression host may be further modified by the introduction of sequences encoding one or more enzymes that enhance folding and disulfide bond formation, i.e. foldases, chaperonins, etc. Such sequences may be constitutively or inducibly expressed in the yeast host cell, using vectors, markers, etc. as known in the art. Preferably the sequences, including transcriptional regulatory elements sufficient for the desired pattern of expression, are stably integrated in the yeast genome through a targeted methodology.

For example, the eukaryotic protein disulfide isomerase ("PDI") is not only an efficient catalyst of protein cysteine oxidation and disulfide bond isomerization, but also exhibits chaperone activity. Co-expression of PDI can facilitate the production of active proteins having multiple disulfide bonds. Also of interest is the expression of immunoglobulin heavy chain binding protein ("BIP"); cyclophilin; and the like. In one embodiment of the invention, each of the haploid parental strains expresses a distinct folding enzyme, e.g. one strain may express BIP, and the other strain may express PDI or combinations thereof.

Cultured mammalian cells are also preferred exemplary hosts for production of the disclosed anti-PACAP antibodies and antigen binding fragments thereof. As mentioned CHO cells are particularly suitable for expression of antibodies. Many procedures are known in the art for manufacturing monoclonal antibodies in mammalian cells. (See, Galfre, G. and Milstein, C., *Methods Enzym.,* 73:3-46, 1981; Basalp et al., *Turk. J. Biol.,* 24:189-196, 2000; Wurm, F. M., *Nat. Biotechnol.,* 22:1393-1398, 2004; and Li et al., *mAbs,* 2(5): 466-477, 2010). As mentioned in further detail infra, common host cell lines employed in mammalian monoclonal antibody manufacturing schemes include, but are not limited to, human embryonic retinoblast cell line PER.C6® (Crucell N.V., Leiden, The Netherlands), NS0 murine myeloma cells (Medical Research Council, London, UK), CV1 monkey kidney cell line, 293 human embryonic kidney cell line, BHK baby hamster kidney cell line, VERO African green monkey kidney cell line, human cervical carcinoma cell line HELA, MDCK canine kidney cells, BRL buffalo rat liver cells, W138 human lung cells, HepG2 human liver cells, MMT mouse mammary tumor cells, TRI cells, MRCS cells, Fs4 cells, myeloma or lymphoma cells, or Chinese Hamster (*Cricetulus griseus*) Ovary (CHO) cells, and the like. Many different subclones or sub-cell lines of CHO cells known in the art that are useful and optimized for production of recombinant monoclonal antibodies, such as the DP12 (CHO K1 dhfr-) cell line, NS0 cells are a non-Ig secreting, non-light chain-synthesizing subclone of NS-1 cells that are resistant to azaguanine. Other Chinese Hamster and CHO cells are commercially available (from ATCC, etc.), including CHO-DXB11 (CHO-DUKX), CHO-pro3, CHO-DG44, CHO 1-15, CHO DP-12, Lec2, M1WT3, Lec8, pgsA-745, and the like, all of which are genetically altered to optimize the cell line for various parameters. Monoclonal antibodies are commonly manufactured using a batch fed method whereby the monoclonal antibody chains are expressed in a mammalian cell line and secreted into the tissue culture medium in a bioreactor. Medium (or feed) is continuously supplied to the bioreactor to maximize recombinant protein expression. Recombinant monoclonal antibody is then purified from the collected media. In some circumstances, additional steps are needed to reassemble the antibodies through reduction of disulfide bonds, etc. Such production methods can be scaled to be as large as 10,000 L in a single batch or more. It is now routine to obtain as much as 20 pg/cell/day through the use of such cell lines and methodologies, providing titers as high as 10 g/L or more, amounting to 15 to 100 kg from bioreactors of 10 kL to 25 kL. (Li et al., 2010). Various details of this production methodology, including cloning of the polynucleotides encoding the antibodies into expression vectors, transfecting cells with these expression vectors, selecting for transfected cells, and expressing and purifying the recombinant monoclonal antibodies from these cells are provided below.

For recombinant production of an anti-PACAP antibody or antigen binding fragment in mammalian cells, nucleic acids encoding the antibody or fragment thereof are generally inserted into a replicable vector for further cloning (amplification of the DNA) or for expression. DNA encoding the antibody is readily isolated or synthesized using conventional procedures (e.g., by using oligonucleotide probes that are capable of binding specifically to DNAs encoding the heavy and light chains of the antibody). The vector components generally include, but are not limited to, one or more of the following: a signal sequence, an origin of replication, one or more marker genes, an enhancer element, a promoter, and a transcription termination sequence. Selection of promoters, terminators, selectable markers, vectors, and other elements is a matter of routine design within the level of ordinary skill in the art. Many such elements are known in the art and are available through commercial suppliers.

The antibodies of this invention may be produced recombinantly not only directly, but also as a fusion polypeptide with a heterologous polypeptide, which is preferably a signal sequence or other polypeptide having a specific cleavage site at the N-terminus of the mature protein or polypeptide. The homologous or heterologous signal sequence selected preferably is one that is recognized and processed (i.e., cleaved by a signal peptidase) by the host cell. In mammalian cell expression, mammalian signal sequences as well as viral secretory leaders, for example, the herpes simplex gD signal, are available.

Such expression vectors and cloning vectors will generally contain a nucleic acid sequence that enables the vector to replicate in one or more selected host cells. Typically, in cloning vectors this sequence is one that enables the vector to replicate independently of the host chromosomal DNA, and includes origins of replication or autonomously replicating sequences. Such sequences are well known for a variety of bacteria, yeast, and viruses, e.g., the origin of replication from the plasmid pBR322 is suitable for most Gram-negative bacteria, the 2mu plasmid origin is suitable for yeast, and various viral origins (Simian Virus 40 ("SV40"), polyoma, adenovirus, vesicular stomatitis virus ("VSV"), or bovine papillomavirus ("BPV") are useful for cloning vectors in mammalian cells. Generally, the origin of replication component is not needed for mammalian expression vectors (the SV40 origin may typically be used only because it contains the early promoter).

These vectors will also typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

One example of a selection scheme utilizes a drug to arrest growth of a host cell. Drug selection is generally used to select for cultured mammalian cells into which foreign DNA has been inserted. Such cells are commonly referred to as "transfectants". Cells that have been cultured in the presence of the selective agent and are able to pass the gene of interest to their progeny are referred to as "stable transfectants." Examples of such dominant selection use the drugs neomycin, mycophenolic acid, and hygromycin. An exemplary selectable marker is a gene encoding resistance to the antibiotic neomycin. Selection is carried out in the presence of a neomycin-type drug, such as G-418 or the like. Those cells that are successfully transformed with a heterologous gene produce a protein conferring drug resistance and thus survive the selection regimen.

Selection systems can also be used to increase the expression level of the gene of interest, a process referred to as "amplification." Amplification of transfectants typically occurs by culturing the cells in the presence of a low level of the selective agent and then increasing the amount of selective agent to select for cells that produce high levels of the products of the introduced genes. Exemplary suitable selectable markers for mammalian cells are those that enable the identification of cells competent to take up the antibody nucleic acid, such as dihydrofolate reductase ("DHFR"), thymidine kinase, metallothionein-I and -II, preferably primate metallothionein genes, adenosine deaminase, ornithine decarboxylase, etc.

For example, an amplifiable selectable marker for mammalian cells is dihydrofolate reductase, which confers resistance to methotrexate. Other drug resistance genes (e.g. hygromycin resistance, multi-drug resistance, puromycin acetyltransferase) can also be used. Cells transformed with the DHFR selection gene are first identified by culturing all of the transformants in a culture medium that contains methotrexate ("MTX"), a competitive antagonist of DHFR. An appropriate host cell when wild-type DHFR is employed is the Chinese hamster ovary ("CHO") cell line deficient in DHFR activity.

Alternatively, host cells (particularly wild-type hosts that contain endogenous DHFR) transformed or co-transformed with DNA sequences encoding antibody, wild-type DHFR protein, and another selectable marker such as aminoglycoside 3'-phosphotransferase ("APH") can be selected by cell growth in medium containing a selection agent for the selectable marker such as an aminoglycosidic antibiotic, e.g., kanamycin, neomycin, or G-418. See U.S. Pat. No. 4,965,199.

These vectors may comprise an enhancer sequence that facilitates transcription of a DNA encoding the antibody. Many enhancer sequences are known from mammalian genes (for example, globin, elastase, albumin, alpha-fetoprotein, and insulin). A frequently used enhancer is one derived from a eukaryotic cell virus. Examples thereof include the SV40 enhancer on the late side of the replication origin (bp 100-270), the cytomegalovirus early promoter enhancer, the polyoma enhancer on the late side of the replication origin, and adenovirus enhancers (See, Yaniv, *Nature,* 297:17-18, 1982, on enhancing elements for activation of eukaryotic promoters). The enhancer may be spliced into the vector at a position 5' or 3' to the antibody-encoding sequence, but is preferably located at a site 5' from the promoter.

Expression and cloning vectors will also generally comprise a promoter that is recognized by the host organism and is operably linked to the antibody nucleic acid. Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Antibody transcription from vectors in mammalian host cells is controlled, for example, by promoters obtained from the genomes of viruses such as polyoma virus, fowlpox virus, adenovirus (such as Adenovirus 2), BPV, avian sarcoma virus, cytomegalovirus, a retrovirus, hepatitis-B virus, and most preferably SV40, from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the BPV as a vector is disclosed in U.S. Pat. No. 4,419,446. A modification of this system is described in U.S. Pat. No. 4,601,978. See also Reyes et al., *Nature,* 297:598-601 (1982) on expression of human beta-interferon cDNA in mouse cells under the control of a thymidine kinase promoter from herpes simplex virus. Alternatively, the rous sarcoma virus long terminal repeat can be used as the promoter.

Strong transcription promoters can be used, such as promoters from SV40, cytomegalovirus, or myeloproliferative sarcoma virus. See, e.g., U.S. Pat. No. 4,956,288 and U.S. Patent Publication No. 20030103986. Other suitable promoters include those from metallothionein genes (U.S. Pat. Nos. 4,579,821 and 4,601,978) and the adenovirus major late promoter. Expression vectors for use in mammalian cells include pZP-1, pZP-9, and pZMP21, which have been deposited with the American Type Culture Collection, 10801 University Blvd., Manassas, VA USA under accession numbers 98669, 98668, and PTA-5266, respectively, and derivatives of these vectors.

Expression vectors used in eukaryotic host cells (yeast, fungus, insect, plant, animal, human, or a nucleated cell from other multicellular organism) will also generally contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding the antibody. One useful transcription termination component is the bovine growth hormone polyadenylation region. See WO 94/11026 and the expression vector disclosed therein.

Suitable host cells for cloning or expressing the subject antibodies include prokaryote, yeast, or higher eukaryote cells described above. However, interest has been greatest in vertebrate cells, and propagation of vertebrate cells in culture has become a routine procedure. Examples of useful mammalian host cell lines are monkey kidney CV1 line transformed by SV40 (COS-1 (ATCC No. CRL 1650); and COS-7, ATCC CRL 1651); human embryonic kidney line (293 or 293 cells subcloned for growth in suspension culture, (ATCC No. CRL 1573; Graham et al., *J. Gen. Virol.,* 36:59-72 (1977)); baby hamster kidney cells (BHK, ATCC CCL 10, ATCC No. CRL 1632; BHK 570, ATCC No. CRL 10314); CHO cells (CHO-K1, ATCC No. CCL 61; CHO-DG44, Urlaub et al., *Proc. Natl. Acad. Sci. USA,* 77:4216-4220 (1980)); mouse sertoli cells (TM4*, Mather, Biol. Reprod.,* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.,* 383:44-68 (1982)); MRC 5 cells; FS4 cells; and a human hepatoma line (Hep G2). Additional suitable cell lines are known in the art and available from public depositories such as the American Type Culture Collection, Manassas, VA.

Host cells are transformed with the above-described expression or cloning vectors for antibody production and cultured in conventional nutrient media modified as appropriate for inducing promoters, selecting transformants, or amplifying the genes encoding the desired sequences as discussed supra.

The mammalian host cells used to produce the antibody of this invention may be cultured in a variety of media. Commercially available media such as Ham's F10 (Sigma-Aldrich Corporation, St. Louis, MO), Minimal Essential Medium (("MEM" (Sigma-Aldrich Corporation, St. Louis, MO), Roswell Park Memorial Institute-1640 medium ("RPMI-1640", Sigma-Aldrich Corporation, St. Louis, MO), and Dulbecco's Modified Eagle's Medium (("DMEM" Sigma-Aldrich Corporation, St. Louis, MO) are suitable for culturing the host cells. In addition, any of the media described in Ham et al., Meth. Enz., 58:44 (1979), Barnes et al., Anal. Biochem., 102:255 (1980), U.S. Pat. Nos. 4,767,704; 4,657,866; 4,927,762; 4,560,655; or 5,122,469; WO 90/03430; WO 87/00195; or U.S. Pat. Reexam No. 30,985 can be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as Gentamycin drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan. Methods of development and optimization of media and culture conditions are known in the art (See, Gronemeyer et al., Bioengineering, 1(4):188-212, 2014).

After culture conditions are optimized and a preferred cell line clone is selected, these cells are cultured (either adherent cells or suspension cultures) most typically in a batch-fed process in a bioreactor (many models are commercially available) that involves continuously feeding the cell culture with medium and feed, optimized for the particular cell line chosen and selected for this purpose. (See, Butler, M., *Appl. Microbiol. Biotechnol.,* 68:283-291, 2005; and Kelley, B., mAb, 1(5):443-452, 2009). Perfusion systems are also available in which media and feed are continuously supplied to the culture while the same volume of media is being withdrawn from the bioreactor. (Wurm, 2004). Synthetic media, also commercially available, are available for growing cells in a batch-fed culture, avoiding the possibility of contamination from outside sources, such as with the use of animal components, such as bovine serum albumin, etc. However, animal-component-free hydrolysates are commercially available to help boost cell density, culture viability and productivity. (Li et al., 2010). Many studies have been performed in an effort to optimize cell culture media, including careful attention to head space available in roller bottles, redox potentials during growth and expression phases, presence of reducing agents to maintain disulfide bonds during production, etc. (See, for instance, Hutterer et al., mAbs, 5(4):608-613, 2013; and Mullan et al., *BMC Proceed.,* 5(Suppl 8):P110, 2011). Various methodologies have been developed to address the possibility of harmful oxidation during recombinant monoclonal antibody production. (See, for example, U.S. Pat. No. 8,574,869). Cultured cells may be grown by feeding nutrients continuously or as separately administered amounts. Often various process parameters such as cell concentration, pH, temperature, $CO_2$, $dO_2$, osmolality, amount of metabolites such as glucose, lactate, glutamine and glutamate, and the like, are monitored by the use of probes during the cell growth either on-line by direct connection to calibrated analyzers or off-line by intervention of operators. The culturing step also typically involves ensuring that the cells growing in culture maintain the transfected recombinant genes by any means known in the art for cell selection.

Following fermentation, i.e., upon reaching maximum cell growth and recombinant protein expression, the culturing step is typically followed by a harvesting step, whereby the cells are separated from the medium and a harvested cell culture media is thereby obtained. (See, Liu et al., mAbs, 2(5):480-499, 2010). Typically various purification steps, involving column chromatography and the like, follow culturing to separate the recombinant monoclonal antibody from cell components and cell culture media components. The exact purification steps needed for this phase of the production of recombinant monoclonal antibodies depends on the site of expression of the proteins, i.e., in the cytosol of the cells themselves, or the more commonly preferred route of protein excreted into the cell culture medium. Various cell components may be separated using techniques known in the art such as differential centrifugation techniques, gravity-based cell settling, and/or size exclusion chromatograph/filtration techniques that can include tangential flow micro-filtration or depth filtration. (See, Pollock et al., *Biotechnol. Bioeng.,* 110:206-219, 2013, and Liu et al., 2010). Centrifugation of cell components may be achieved on a large scale by use of continuous disk stack centrifuges followed by clarification using depth and membrane filters. (See, Kelley, 2009). Most often, after clarification, the recombinant protein is further purified by Protein A chromatography due to the high affinity of Protein A for the Fc domain of antibodies, and typically occurs using a low pH/acidification elution step (typically the acidification step is combined with a precautionary virus inactivation step). Flocculation and/or precipitation steps using acidic or cationic polyelectrolytes may also be employed to separate animal cells in suspension cultures from soluble proteins. (Liu et al., 2010). Lastly, anion- and cation-exchange chromatography, hydrophobic interaction chromatograph ("HIC"), hydrophobic charge induction chromatograph (HCIC), hydroxyapatite chromatography using ceramic hydroxyapatite $(Ca_5(PO_4)_3OH)_2$, and combinations of these techniques are typically used to polish the solution of recombinant monoclonal antibody. Final formulation and concentration of the desired monoclonal antibody may be achieved by use of ultracentrifugation techniques. Purification yields are typically 70 to 80%. (Kelley, 2009).

The terms "desired protein" or "desired antibody" are used interchangeably and refer generally to a parent antibody specific to a target, i.e., PACAP or a chimeric or humanized antibody or a binding portion thereof derived therefrom as described herein. The term "antibody" is intended to include any polypeptide chain-containing molecular structure with a specific shape that fits to and recognizes an epitope, where one or more non-covalent binding interactions stabilize the complex between the molecular structure and the epitope. The archetypal antibody molecule is the immunoglobulin, and all types of immunoglobulins, IgG, IgM, IgA, IgE, IgD, etc., from all sources, e.g. human, rodent, rabbit, cow, sheep, pig, dog, other mammals, chicken, other avians, etc., are considered to be "antibodies." A preferred source for producing antibodies useful as starting material according to the invention is rabbits. Examples thereof include chimeric antibodies, human antibodies and other non-human mammalian antibodies, humanized antibodies, single chain antibodies (such as scFvs), camelbodies, nanobodies, IgNAR (single-chain antibodies which may be derived from sharks, for example), small-modular immunopharmaceuticals ("SMIPs"), and antibody fragments such as Fabs, Fab', $F(ab')_2$, and the like (See Streltsov et al., *Protein Sci.,* 14(11):2901-9 (2005); Greenberg et al., *Nature,* 374(6518):168-73 (1995); Nuttall et al., *Mol. Immunol.,* 38(4):313-26 (2001); Hamers-Casterman et al., *Nature,* 363(6428):446-8 (1993); Gill et al., *Curr. Opin. Biotechnol.*, (6):653-8 (2006)).

For example, antibodies or antigen binding fragments thereof may be produced by genetic engineering. In this technique, as with other methods, antibody-producing cells are sensitized to the desired antigen or immunogen. The messenger RNA isolated from antibody producing cells is used as a template to make cDNA using PCR amplification. A library of vectors, each containing one heavy chain gene and one light chain gene retaining the initial antigen specificity, is produced by insertion of appropriate sections of the amplified immunoglobulin cDNA into the expression vectors. A combinatorial library is constructed by combining the heavy chain gene library with the light chain gene library. This results in a library of clones that co-express a heavy and light chain (resembling the Fab fragment or antigen binding fragment of an antibody molecule). The vectors that carry these genes are co-transfected into a host cell. When antibody gene synthesis is induced in the transfected host, the heavy and light chain proteins self-assemble to produce active antibodies that can be detected by screening with the antigen or immunogen.

Antibody coding sequences of interest include those encoded by native sequences, as well as nucleic acids that, by virtue of the degeneracy of the genetic code, are not identical in sequence to the disclosed nucleic acids, and variants thereof. Variant polypeptides can include amino acid ("aa") substitutions, additions, or deletions. The amino acid substitutions can be conservative amino acid substitutions or substitutions to eliminate non-essential amino acids, such as to alter a glycosylation site, or to minimize misfolding by substitution or deletion of one or more cysteine residues that are not necessary for function. Variants can be designed so as to retain or have enhanced biological activity of a particular region of the protein (e.g., a functional domain, catalytic amino acid residues, etc.). Variants also include fragments of the polypeptides disclosed herein, particularly biologically active fragments and/or fragments corresponding to functional domains. Techniques for in vitro mutagenesis of cloned genes are known. Also included in the subject invention are polypeptides that have been modified using ordinary molecular biological techniques so as to improve their resistance to proteolytic degradation or to optimize solubility properties or to render them more suitable as a therapeutic agent.

Chimeric antibodies may be made by recombinant means by combining the $V_L$ and $V_H$ regions, obtained from antibody producing cells of one species with the constant light and heavy chain regions from another. Typically chimeric antibodies utilize rodent or rabbit variable regions and human constant regions, in order to produce an antibody with predominantly human domains. The production of such chimeric antibodies is well known in the art, and may be achieved by standard means (as described, e.g., in U.S. Pat. No. 5,624,659, incorporated herein by reference in its entirety). It is further contemplated that the human constant regions of chimeric antibodies of the invention may be selected from IgG1, IgG2, IgG3, and IgG4 constant regions.

Humanized antibodies are engineered to contain even more human-like immunoglobulin domains, and incorporate only the complementarity determining regions of the animal-derived antibody. This is accomplished by carefully examining the sequence of the hyper-variable loops of the variable regions of the monoclonal antibody and fitting them to the structure of the human antibody chains. Although facially complex, the process is straightforward in practice. See, e.g., U.S. Pat. No. 6,187,287, incorporated fully herein by reference.

In addition to entire immunoglobulins (or their recombinant counterparts), immunoglobulin fragments comprising the epitope binding site (e.g., Fab', $F(ab')_2$, or other fragments) may be synthesized. "Fragment" or minimal immunoglobulins may be designed utilizing recombinant immunoglobulin techniques. For instance "Fv" immunoglobulins for use in the present invention may be produced by synthesizing a fused variable light chain region and a variable heavy chain region. Combinations of antibodies are also of interest, e.g. diabodies, which comprise two distinct Fv specificities. In another embodiment of the invention, small molecule immunopharmaceuticals ("SMIPs"), camelbodies, nanobodies, and IgNAR are encompassed by immunoglobulin fragments.

Immunoglobulins and fragments thereof may be modified post-translationally, e.g. to add effector moieties such as chemical linkers, detectable moieties, such as fluorescent dyes, enzymes, toxins, substrates, bioluminescent materials, radioactive materials, chemiluminescent moieties, and the like, or specific binding moieties, such as streptavidin, avidin, or biotin, and the like may be utilized in the methods and compositions of the present invention. Examples of additional effector molecules are provided infra.

A polynucleotide sequence "corresponds" to a polypeptide sequence if translation of the polynucleotide sequence in accordance with the genetic code yields the polypeptide sequence (i.e., the polynucleotide sequence "encodes" the polypeptide sequence), one polynucleotide sequence "corresponds" to another polynucleotide sequence if the two sequences encode the same polypeptide sequence.

A "heterologous" region or domain of a DNA construct is an identifiable segment of DNA within a larger DNA molecule that is not found in association with the larger molecule in nature. Thus, when the heterologous region encodes a mammalian gene, the DNA flanking the gene usually does not flank the mammalian genomic DNA in the genome of the source organism. Another example of a heterologous region is a construct where the coding sequence itself is not found in nature (e.g., a cDNA where the genomic coding sequence contains introns or synthetic sequences having codons different than the native gene). Allelic variations or naturally-occurring mutational events do not give rise to a heterologous region of DNA as defined herein.

A "coding sequence" is an in-frame sequence of codons that correspond to or encode a protein or peptide sequence. Two coding sequences correspond to each other if the sequences or their complementary sequences encode the same amino acid sequences. A coding sequence in association with appropriate regulatory sequences may be transcribed and translated into a polypeptide. A polyadenylation signal and transcription termination sequence will usually be located 3' to the coding sequence. A "promoter sequence" is a DNA regulatory region capable of initiating transcription of a downstream (3' direction) coding sequence, and typically contain additional sites for binding of regulatory molecules, e.g., transcription factors, that affect the transcription of the coding sequence. A coding sequence is "under the control" of the promoter sequence or "operatively linked" to the promoter when RNA polymerase binds the promoter sequence in a cell and transcribes the coding sequence into mRNA, which is then in turn translated into the protein encoded by the coding sequence.

The general structure of antibodies in vertebrates now is well understood. See Edelman, G. M., *Ann. N.Y. Acad. Sci.,* 190:5 (1971). Antibodies consist of two identical light polypeptide chains of molecular weight approximately 23,000 daltons (the "light chain"), and two identical heavy chains of molecular weight 53,000-70,000 (the "heavy chain"). The four chains are joined by disulfide bonds in a "Y" configuration wherein the light chains bracket the heavy chains starting at the mouth of the "Y" configuration. The "branch" portion of the "Y" configuration is designated the $F_{ab}$ region; the stem portion of the "Y" configuration is designated the $F_C$ region. The amino acid sequence orientation runs from the N-terminal end at the top of the "Y" configuration to the C-terminal end at the bottom of each chain. The N-terminal end possesses the variable region having specificity for the antigen that elicited it, and is approximately 100 amino acids in length, there being slight variations between light and heavy chain and from antibody to antibody.

The variable region is linked in each chain to a constant region that extends the remaining length of the chain and that within a particular class of antibody does not vary with the specificity of the antibody (i.e., the antigen eliciting it).

There are five known major classes of constant regions that determine the class of the immunoglobulin molecule (IgG, IgM, IgA, IgD, and IgE corresponding to γ, μ, α, δ, and ε (gamma, mu, alpha, delta, or epsilon) heavy chain constant regions). The constant region or class determines subsequent effector function of the antibody, including activation of complement (see Kabat, E. A., *Structural Concepts in Immunology and Immunochemistry,* 2nd Ed., p. 413-436, New York, NY: Holt, Rinehart, Winston (1976)), and other cellular responses (see Andrews et al., *Clinical Immunology*, pp. 1-18, W. B. Sanders, Philadelphia, PA (1980); Kohl et al., *Immunology,* 48:187 (1983)); while the variable region determines the antigen with which it will react. Light chains are classified as either κ (kappa) or λ (lambda). Each heavy chain class can be prepared with either kappa or lambda light chain. The light and heavy chains are covalently bonded to each other, and the "tail" portions of the two heavy chains are bonded to each other by covalent disulfide linkages when the immunoglobulins are generated either by hybridomas or by B-cells.

The expression "variable region" or "VR" refers to the domains within each pair of light and heavy chains in an antibody that are involved directly in binding the antibody to the antigen. Each heavy chain has at one end a variable domain ($V_H$) followed by a number of constant domains. Each light chain has a variable domain ($V_L$) at one end and a constant domain at its other end; the constant domain of the light chain is aligned with the first constant domain of the heavy chain, and the light chain variable domain is aligned with the variable domain of the heavy chain.

The expressions "complementarity determining region," "hypervariable region," or "CDR" refer to one or more of the hyper-variable or complementarity determining regions ("CDRs") found in the variable regions of light or heavy chains of an antibody (See Kabat et al., *Sequences of Proteins of Immunological Interest,* $4^{th}$ ed., Bethesda, MD: U.S. Dept. of Health and Human Services, Public Health Service, National Institutes of Health (1987)). These expressions include the hypervariable regions as defined by Kabat et al., (*Sequences of Proteins of Immunological Interest*, NIH Publication No. 91-3242, Bethesda, MD: U.S. Dept. of Health and Human Services, National Institutes of Health (1983)) or the hypervariable loops in 3-dimensional structures of antibodies (Chothia and Lesk, *J. Mol. Biol.,* 196: 901-917 (1987)). The CDRs in each chain are held in close proximity by framework regions ("FRs") and, with the CDRs from the other chain, contribute to the formation of the antigen binding site. Within the CDRs there are select amino acids that have been described as the selectivity determining regions ("SDRs") that represent the critical contact residues used by the CDR in the antibody-antigen interaction (see Kashmiri et al., *Methods,* 36(1):25-34 (2005)).

An "epitope" or "binding site" is an area or region on an antigen to which an antigen-binding peptide (such as an antibody) specifically binds. A protein epitope may comprise amino acid residues directly involved in the binding (also called immunodominant component of the epitope) and other amino acid residues, which are not directly involved in the binding, such as amino acid residues that are effectively blocked by the specifically antigen binding peptide (in other words, the amino acid residue is within the "footprint" of the specifically antigen binding peptide). The term epitope herein includes both types of amino acid binding sites in any particular region of PACAP, i.e., PACAP38 and PACAP27, that specifically binds to an anti-PACAP antibody. PACAP may comprise a number of different epitopes, which may include, without limitation, (1) linear peptide antigenic determinants, (2) conformational antigenic determinants that consist of one or more non-contiguous amino acids located near each other in a mature PACAP conformation; and (3) post-translational antigenic determinants that consist, either in whole or part, of molecular structures covalently attached to a PACAP protein such as carbohydrate groups. In particular, the term "epitope" includes the specific residues in a protein or peptide, e.g., PACAP, which are involved in the binding of an antibody to such protein or peptide as determined by known and accepted methods such as alanine scanning techniques. Such methods are exemplified herein.

The phrase that an antibody (e.g., first antibody) binds "substantially" or "at least partially" the same epitope as another antibody (e.g., second antibody) means that the epitope binding site for the first antibody comprises at least 10%, 20%, 30%, 40%, 50%, 60%, 70%, 80%, 90%, or more of the amino acid residues on the antigen that constitutes the epitope binding site of the second antibody. Also, that a first antibody binds substantially or partially the same or overlapping epitope as a second antibody means that the first and second antibodies compete in binding to the antigen, as described above. Thus, the term "binds to substantially the same epitope or determinant as" a monoclonal antibody means that an antibody "competes" with the antibody.

The phrase "binds to the same or overlapping epitope or determinant as" an antibody of interest means that an antibody "competes" with said antibody of interest for at least one, (e.g., at least 2, at least 3, at least 4, at least 5) or all residues on PACAP to which said antibody of interest specifically binds. The identification of one or more antibodies that bind(s) to substantially or essentially the same epitope as the monoclonal antibodies described herein can be readily determined using alanine scanning. Additionally, any one of variety of immunological screening assays in which antibody competition can be assessed. A number of such assays are routinely practiced and well known in the art (see, e.g., U.S. Pat. No. 5,660,827, issued Aug. 26, 1997, which is specifically incorporated herein by reference). It will be understood that actually determining the epitope to which an antibody described herein binds is not in any way required to identify an antibody that binds to the same or substantially the same or overlapping epitope as the monoclonal antibody described herein.

For example, where the test antibodies to be examined are obtained from different source animals, or are even of a different Ig isotype, a simple competition assay may be employed in which the control antibody is mixed with the test antibody and then applied to a sample containing PACAP. Protocols based upon ELISAs, radioimmunoassays, Western blotting, and the use of BIACORE® (GE Healthcare Life Sciences, Marlborough, MA) analysis are suitable for use in such simple competition studies.

In certain embodiments, the control anti-PACAP antibody is pre-mixed with varying amounts of the test antibody (e.g., in ratios of about 1:1, 1:2, 1:10, or about 1:100) for a period of time prior to applying to the PACAP38 or PACAP27 antigen sample. In other embodiments, the control and varying amounts of test antibody can simply be added separately and admixed during exposure to the PACAP38 or PACAP27 antigen sample. As long as bound antibodies can be distinguished from free antibodies (e.g., by using separation or washing techniques to eliminate unbound antibodies) and control antibody from the test antibody (e.g., by using species specific or isotype specific secondary antibodies or by specifically labeling the control antibody with a detectable label) it can be determined if the test antibody reduces the binding of the control antibody to the PACAP38 or PACAP27 antigens, indicating that the test antibody recognizes substantially the same epitope as the control anti-PACAP antibody. The binding of the (labeled) control antibody in the presence of a completely irrelevant antibody (that does not bind PACAP) can serve as the control high value. The control low value can be obtained by incubating the labeled control antibody with the same but unlabeled control antibody, where competition would occur and reduce binding of the labeled antibody. In a test assay, a significant reduction in labeled antibody reactivity in the presence of a test antibody is indicative of a test antibody that recognizes substantially the same epitope, i.e., one that competes with the labeled control antibody. For example, any test antibody that reduces the binding of the control antibody to PACAP38 or PACAP27 by at least about 50%, such as at least about 60%, or more preferably at least about 70% (e.g., about 65-100%), at any ratio of test antibody between about 1:1 or 1:10 and about 1:100 is considered to be an antibody that binds to substantially the same or overlapping epitope or determinant as the control antibody.

Preferably, such test antibody will reduce the binding of the control antibody to PACAP38 or PACAP27 antigen preferably at least about 50%, at least about 60%, at least about 80%, or at least about 90% (e.g., about 95%) of the binding of the control antibody observed in the absence of the test antibody.

A simple competition assay in which a test antibody is applied at saturating concentration to a surface onto which PACAP38 or PACAP27 is immobilized also may be advantageously employed. The surface in the simple competition assay is preferably a BIACORE® (GE Healthcare Life Sciences, Marlborough, MA) chip (or other media suitable for surface plasmon resonance ("SPR") analysis). The binding of a control antibody that binds PACAP38 or PACAP27 to the PACAP-coated surface is measured. This binding to the PACAP38- or PACAP27-containing surface of the control antibody alone is compared with the binding of the control antibody in the presence of a test antibody. A significant reduction in binding to the PACAP38- or PACAP27-containing surface by the control antibody in the presence of a test antibody indicates that the test antibody recognizes substantially the same epitope as the control antibody such that the test antibody "competes" with the control antibody. Any test antibody that reduces the binding of control antibody by at least about 20% or more, at least about 40%, at least about 50%, at least about 70%, or more, can be considered to be an antibody that binds to substantially the same epitope or determinant as the control antibody. Preferably, such test antibody will reduce the binding of the control antibody to PACAP38 or PACAP27 by at least about 50% (e.g., at least about 60%, at least about 70%, or more). It will be appreciated that the order of control and test antibodies can be reversed; i.e. the control antibody can be first bound to the surface and then the test antibody is brought into contact with the surface thereafter in a competition assay. Preferably, the "sandwich-style" binding assay exemplified in Example 9 infra is used. Alternatively, the antibody having greater affinity for PACAP38 or PACAP27 antigen is bound to the PACAP38- or PACAP27-containing surface first, as it will be expected that the decrease in binding seen for the second antibody (assuming the antibodies are competing) will be of greater magnitude. Further examples of such assays are provided in e.g., Saunal and Regenmortel, *J. Immunol. Methods,* 183:33-41 (1995), the disclosure of which is incorporated herein by reference.

In addition, whether an antibody binds the same or overlapping epitope(s) on PACAP as another antibody or the epitope bound by a test antibody may in particular be determined using a Western-blot based assay. In this assay a library of peptides corresponding to the antigen bound by the antibody, the PACAP protein, is made, that comprise overlapping portions of the protein, typically 10-25, 10-20, or 10-15 amino acids long. These different overlapping amino acid peptides encompassing the PACAP sequence are synthesized and covalently bound to a PEPSPOTS™ nitrocellulose membrane (JPT Peptide Technologies, Berlin, Germany). Blots are then prepared and probed according to the manufacturer's recommendations.

Essentially, the immunoblot assay then detects by fluorometric means what peptides in the library bind to the test antibody and thereby can identify what residues on the antigen, i.e., PACAP, interact with the test antibody. (See U.S. Pat. No. 7,935,340, incorporated by reference herein).

Various epitope mapping techniques are known in the art. By way of example, X-ray co-crystallography of the antigen and antibody; NMR; SPR (e.g., at 25° or 37° C.); array-based oligo-peptide scanning (or "pepscan analysis"); site-directed mutagenesis (e.g., alanine scanning); mutagenesis mapping; hydrogen-deuterium exchange; phage display; and limited proteolysis are all epitope mapping techniques that are well known in the art (See, e.g., *Epitope Mapping Protocols: Second Edition, Methods in Molecular Biology*, editors Mike Schutkowski and Ulrich Reineke, 2nd Ed., New York, NY: Humana Press (2009), and Epitope Mapping Protocols, Methods in Molecular Biology, editor Glenn Morris, 1st Ed., New York, NY: Humana Press (1996), both of which are herein incorporated by referenced in their entirety).

The identification of one or more antibodies that bind(s) to substantially or essentially the same epitope as the monoclonal antibodies described herein, e.g., Ab1, Ab2, Ab3, Ab4, Ab5, Ab6, Ab7, Ab8, Ab9, Ab11, Ab12, Ab13, Ab14, Ab15, Ab16, Ab17, Ab18, Ab19, or Ab1.H, can be readily determined using any one of variety of immunological screening assays in which antibody competition can be assessed. A number of such assays are routinely practiced and well known in the art (see, e.g., U.S. Pat. No. 5,660,827, issued Aug. 26, 1997, which is incorporated herein by reference). It will be understood that determining the epitope to which an antibody described herein binds is not in any way required to identify an antibody that binds to the same or substantially the same epitope as the monoclonal antibody described herein.

For example, where the test antibodies to be examined are obtained from different source animals, or are even of a different Ig isotype, a simple competition assay may be employed in which the control antibody (one of Ab1, Ab2, Ab3, Ab4, Ab5, Ab6, Ab7, Ab8, Ab9, Ab11, Ab12, Ab13, Ab14, Ab15, Ab16, Ab17, Ab18, Ab19, or Ab1.H, for example) is mixed with the test antibody and then applied to a sample containing either or both PACAP38 and PACAP27, each of which is known to be bound by Ab1, Ab2, Ab3, Ab4, Ab5, Ab6, Ab7, Ab8, Ab9, Ab11, Ab12, Ab13, Ab14, Ab15, Ab16, Ab17, Ab18, Ab19, Ab1.H. Protocols based upon ELISAs, radioimmunoassays, Western blotting, and BIACORE® (GE Healthcare Life Sciences, Marlborough, MA) analysis (as described in the Examples section herein) are suitable for use in such simple competition studies.

In certain embodiments, the method comprises pre-mixing the control antibody with varying amounts of the test antibody (e.g., in ratios of about 1:1, 1:2, 1:10, or about 1:100) for a period of time prior to applying to the PACAP antigen sample. In other embodiments, the control and varying amounts of test antibody can be added separately and admixed during exposure to the PACAP antigen sample. As long as bound antibodies can be distinguished from free antibodies (e.g., by using separation or washing techniques to eliminate unbound antibodies) and control antibody from the test antibody (e.g., by using species specific or isotype specific secondary antibodies or by specifically labelling the control antibody with a detectable label), the method can be used to determine that the test antibody reduces the binding of the control antibody to the PACAP antigen, indicating that the test antibody recognizes substantially the same epitope as the control antibody (e.g., Ab1, Ab2, Ab3, Ab4, Ab5, Ab6, Ab7, Ab8, Ab9, Ab11, Ab12, Ab13, Ab14, Ab15, Ab16, Ab17, Ab18, Ab19, or Ab1.H). The binding of the (labeled) control antibody in the presence of a completely irrelevant antibody (that does not bind PACAP) can serve as the control high value. The control low value can be obtained by incubating the labeled control antibody with the same but unlabeled control antibody, where competition would occur and reduce binding of the labeled antibody. In a test assay, a significant reduction in labeled antibody reactivity in the presence of a test antibody is indicative of a test antibody that recognizes substantially the same epitope, i.e., one that competes with the labeled control antibody. For example, any test antibody that reduces the binding of Ab1, Ab2, Ab3, Ab4, Ab5, Ab6, Ab7, Ab8, Ab9, Ab11, Ab12, Ab13, Ab14, Ab15, Ab16, Ab17, Ab18, Ab19, or Ab1.H to both of PACAP38 and PACAP27 antigens by at least about 50%, such as at least about 60%, or more preferably at least about 70% (e.g., about 65-100%), at any ratio of control Ab1, Ab2, Ab3, Ab4, Ab5, Ab6, Ab7, Ab8, Ab9, Ab11, Ab12, Ab13, Ab14, Ab15, Ab16, Ab17, Ab18, Ab19, or Ab1.H:test antibody or Ab1, Ab2, Ab3, Ab4, Ab5, Ab6, Ab7, Ab8, Ab9, Ab11, Ab12, Ab13, Ab14, Ab15, Ab16, Ab17, Ab18, Ab19, or Ab1.H:test antibody between about 1:1 or 1:10 and about 1:100 is considered to be an antibody that binds to substantially the same epitope or determinant as Ab1, Ab2, Ab3, Ab4, Ab5, Ab6, Ab7, Ab8, Ab9, Ab11, Ab12, Ab13, Ab14, Ab15, Ab16, Ab17, Ab18, Ab19, or Ab1.H, respectively. Preferably, such test antibody will reduce the binding of Ab1, Ab2, Ab3, Ab4, Ab5, Ab6, Ab7, Ab8, Ab9, Ab11, Ab12, Ab13, Ab14, Ab15, Ab16, Ab17, Ab18, Ab19, or Ab1.H to at least one, preferably each, of the PACAP38 and PACAP27 antigens preferably at least about 50%, at least about 60%, at least about 80% or at least about 90% (e.g., about 95%) of the binding of Ab1, Ab2, Ab3, Ab4, Ab5, Ab6, Ab7, Ab8, Ab9, Ab11, Ab12, Ab13, Ab14, Ab15, Ab16, Ab17, Ab18, Ab19, or Ab1.H observed in the absence of the test antibody. These methods can be adapted to identify and/or evaluate antibodies that compete with other control antibodies.

A simple competition assay in which a test antibody is applied at saturating concentration to a surface onto which either PACAP38 or PACAP27, or both, are immobilized also may be advantageously employed. The surface in the simple competition assay is preferably of a media suitable for OCTET® and/or PROTEON®. The binding of a control antibody (e.g., Ab1, Ab2, Ab3, Ab4, Ab5, Ab6, Ab7, Ab8, Ab9, Ab11, Ab12, Ab13, Ab14, Ab15, Ab16, Ab17, Ab18, Ab19, or Ab1.H) to the PACAP-coated surface is measured. This binding to the PACAP-containing surface of the control antibody alone is compared with the binding of the control antibody in the presence of a test antibody. A significant reduction in binding to the PACAP-containing surface by the control antibody in the presence of a test antibody indicates that the test antibody recognizes substantially the same epitope as the control antibody such that the test antibody "competes" with the control antibody. Any test antibody that reduces the binding of control antibody (such as Ab1, Ab2, Ab3, Ab4, Ab5, Ab6, Ab7, Ab8, Ab9, Ab11, Ab12, Ab13, Ab14, Ab15, Ab16, Ab17, Ab18, Ab19, or Ab1.H) to both of PACAP38 and PACAP27 antigens by at least about 20% or more, at least about 40%, at least about 50%, at least about 70%, or more, can be considered to be an antibody that binds to substantially the same epitope or determinant as the control antibody (e.g., Ab1, Ab2, Ab3, Ab4, Ab5, Ab6, Ab7, Ab8, Ab9, Ab11, Ab12, Ab13, Ab14, Ab15, Ab16, Ab17, Ab18, Ab19, or Ab1.H). Preferably, such test antibody will reduce the binding of the control antibody (e.g., Ab1, Ab2, Ab3, Ab4, Ab5, Ab6, Ab7, Ab8, Ab9, Ab11, Ab12, Ab13, Ab14, Ab15, Ab16, Ab17, Ab18, Ab19, or Ab1.H) to the PACAP antigen by at least about 50% (e.g., at least about 60%, at least about 70%, or more). It will be appreciated that the order of control and test antibodies can be reversed; i.e. the control antibody can be first bound to the surface and then the test antibody is brought into contact with the surface thereafter in a competition assay. Preferably, the antibody having higher affinity for PACAP38 and PACAP27 is bound to the PACAP-containing surface first, as it will be expected that the decrease in binding seen for the second antibody (assuming the antibodies are competing) will be of greater magnitude. Further examples of such assays are provided in, e.g., Saunal and Regenmortel, *J. Immunol. Methods,* 183: 33-41 (1989), the disclosure of which is incorporated herein by reference.

Determination of whether an antibody, antigen binding fragment thereof, or antibody derivative binds within one of the epitope regions defined above can be carried out in ways known to the person skilled in the art. In another example of such mapping/characterization methods, an epitope region for an anti-PACAP antibody may be determined by epitope "footprinting" using chemical modification of the exposed amines/carboxyls in the PACAP38 and PACAP27 protein. One specific example of such a foot-printing technique is the use of hydrogen-deuterium exchange detected by mass spectrometry ("HXMS"), wherein a hydrogen/deuterium exchange of receptor and ligand protein amide protons, binding, and back exchange occurs, wherein the backbone amide groups participating in protein binding are protected from back exchange and therefore will remain deuterated. Relevant regions can be identified at this point by peptic proteolysis, fast microbore high-performance liquid chromatography separation, and/or electrospray ionization mass spectrometry (See, e.g., Ehring H., *Analytical Biochemistry,* 267(2):252-259 (1999) and Engen, J. R. & Smith, D. L., *Anal. Chem.,* 73:256A-265A (2001)). Another example of a suitable epitope identification technique is nuclear magnetic resonance epitope mapping ("NMR"), where typically the position of the signals in two-dimensional NMR spectres of the free antigen and the antigen complexed with the antigen binding peptide, such as an antibody, are compared. The antigen typically is selectively isotopically labeled with $^{15}$N so that only signals corresponding to the antigen and no signals from the antigen binding peptide are seen in the NMR-spectrum. Antigen signals originating from amino acids involved in the interaction with the antigen binding peptide typically will shift position in the spectres of the complex compared to the spectres of the free antigen, and the amino acids involved in the binding can be identified that way, See, e.g., *Ernst Schering Res. Found. Workshop*, (44): 149-67 (2004); Huang et al., *J. Mol. Biol.,* 281(1):61-67 (1998); and Saito and Patterson, *Methods,* 9(3):516-24 (1996)). Epitope mapping/characterization also can be performed using mass spectrometry ("MS") methods (See, e.g., Downard, *J. Mass Spectrom.,* 35(4):493-503 (2000) and Kiselar and Downard, *Anal. Chem.,* 71(9):1792-801 (1999)).

Protease digestion techniques also can be useful in the context of epitope mapping and identification. Antigenic determinant-relevant regions/sequences can be determined by protease digestion, e.g. by using trypsin in a ratio of about 1:50 to PACAP38 or PACAP27 overnight ("o/n") digestion at 37° C. and pH 7-8, followed by mass spectrometry ("MS") analysis for peptide identification. The peptides protected from trypsin cleavage by the anti-PACAP antibody can subsequently be identified by comparison of samples subjected to trypsin digestion and samples incubated with antibody and then subjected to digestion by e.g. trypsin (thereby revealing a footprint for the antibody). Other enzymes like chymotrypsin or pepsin can be used in similar epitope characterization methods. Moreover, enzymatic digestion can provide a quick method for analyzing whether a potential antigenic determinant sequence is within a region of PACAP in the context of a PACAP-binding polypeptide. If the polypeptide is not surface exposed, it is most likely not relevant in terms of immunogenicity/antigenicity (See, e.g., Manca, *Ann.* 1*st. Super. Sanità,* 27(1):15-9 (1991) for a discussion of similar techniques).

Site-directed mutagenesis is another technique useful for characterization of a binding epitope. For example, in "alanine-scanning" site-directed mutagenesis (also known as alanine scanning, alanine scanning mutagenesis, alanine scanning mutations, combinatorial alanine scanning, or creation of alanine point mutations, for example), each residue within a protein segment is replaced with an alanine residue (or another residue such as valine where alanine is present in the wild-type sequence) through such methodologies as direct peptide or protein synthesis, site-directed mutagenesis, the GENEART™ Mutagenesis Service (Thermo Fisher Scientific, Waltham, MA U.S.A.) or shotgun mutagenesis, for example. A series of single point mutants of the molecule is thereby generated using this technique; the number of mutants generated is equivalent to the number of residues in the molecule, each residue being replaced, one at a time, by a single alanine residue. Alanine is generally used to replace native (wild-type) residues because of its non-bulky, chemically inert, methyl functional group that can mimic the secondary structure preferences that many other amino acids may possess. Subsequently, the effects replacing a native residue with an alanine has on binding affinity of an alanine scanning mutant and its binding partner can be measured using such methods as, but not limited to, SPR binding experiments. If a mutation leads to a significant reduction in binding affinity, it is most likely that the mutated residue is involved in binding. Monoclonal antibodies specific for structural epitopes (i.e., antibodies that do not bind the unfolded protein) can be used as a positive control for binding affinity experiments to verify that the alanine-replacement does not influence the overall tertiary structure of the protein (as changes to the overall fold of the protein may indirectly affect binding and thereby produce a false positive result). See, e.g., Clackson and Wells, *Science,* 267:383-386 (1995); Weiss et al., *Proc. Natl. Acad. Sci. USA,* 97(16):8950-8954 (2000); and Wells, *Proc. Natl. Acad. Sci. USA,* 93:1-6 (1996). In Example 12 alanine scanning methods are used to identify the specific epitope or residues of PACAP which specifically interact with the anti-PACAP antibodies disclosed herein.

Electron microscopy can also be used for epitope "footprinting". For example, Wang et al., *Nature,* 355:275-278 (1992) used coordinated application of cryoelectron microscopy, three-dimensional image reconstruction, and X-ray crystallography to determine the physical footprint of a Fab-fragment on the capsid surface of native cowpea mosaic virus.

Other forms of "label-free" assay for epitope evaluation include SPR (sold commercially as the BIACORE® system, GE Healthcare Life Sciences, Marlborough, MA) and reflectometric interference spectroscopy ("RifS") (See, e.g., Fagerstam et al., *Journal of Molecular Recognition,* 3:208-14 (1990); Nice et al., *J. Chromatogr.,* 646:159-168 (1993); Leipert et al., *Angew. Chem. Int. Ed.,* 37:3308-3311 (1998); Kroger et al., *Biosensors and Bioelectronics,* 17:937-944 (2002)).

The expressions "framework region" or "FR" refer to one or more of the framework regions within the variable regions of the light and heavy chains of an antibody (See Kabat et al., *Sequences of Proteins of Immunological Interest,* $4^{th}$ edition, Bethesda, MD: U.S. Dept. of Health and Human Services, Public Health Service, National Institutes of Health (1987)). These expressions include those amino acid sequence regions interposed between the CDRs within the variable regions of the light and heavy chains of an antibody.

The term "Fc region" is used to define a C-terminal region of an immunoglobulin heavy chain. The "Fc region" may be a native sequence Fc region or a variant Fc region. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The numbering of the residues in the Fc region is that of the EU index as in Kabat. Kabat et al., *Sequences of Proteins of Immunological Interest,* 5th edition, Bethesda, MD: U.S. Dept. of Health and Human Services, Public Health Service, *National Institutes of Health* (1991). The Fc region of an immunoglobulin generally comprises two constant domains, CH2 and CH3.

The terms "Fc receptor" and "FcR" describe a receptor that binds to the Fc region of an antibody. The preferred FcR is a native sequence human FcR. Moreover, a preferred FcR is one that binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. FcRs are reviewed in Ravetch and Kinet, *Ann. Rev. Immunol.,* 9:457-92 (1991); Capel et al., *Immunomethods,* 4:25-34 (1994); and de Haas et al., *J. Lab. Clin. Med.,* 126:330-41 (1995). "FcR" also includes the neonatal receptor, FcRn, which is responsible for the transfer of maternal IgGs to the fetus (Guyer et al., *J. Immunol.,* 117:587 (1976); and Kim et al., *J. Immunol.,* 24:249 (1994)), and which primarily functions to modulate and/or extend the half-life of antibodies in circulation. To the extent that the disclosed anti-PACAP antibodies are aglycosylated, as a result of the expression system and/or sequence, the subject antibodies are expected to bind FcRn receptors, but not to bind (or to minimally bind) Fcγ receptors.

A "functional Fc region" possesses at least one effector function of a native sequence Fc region. Exemplary "effector functions" include C1q binding; complement dependent cytotoxicity ("CDC"); Fc receptor binding; antibody-dependent cell-mediated cytotoxicity ("ADCC"); phagocytosis; down-regulation of cell surface receptors (e.g. B cell receptor ("BCR")), etc. Such effector functions generally require the Fc region to be combined with a binding domain (e.g. an antibody variable domain) and can be assessed using various assays known in the art for evaluating such antibody effector functions.

A "native sequence Fc region" comprises an amino acid sequence identical to the amino acid sequence of an Fc region found in nature. A "variant Fc region" comprises an amino acid sequence that differs from that of a native sequence Fc region by virtue of at least one amino acid modification, yet retains at least one effector function of the native sequence Fc region. Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. The variant Fc region herein will preferably possess at least about 80% sequence identity with a native sequence Fc region and/or with an Fc region of a parent polypeptide, and most preferably at least about 90% sequence identity therewith, more preferably at least about 95%, at least about 96%, at least about 97%, at least about 98%, or at least about 99% sequence identity therewith. Anti-PACAP Antibodies and Binding Fragments Thereof Having Binding Affinity for PACAP PACAP is a multifunctional vasodilatory peptide with expression throughout the central nervous system ("CNS") and periphery. PACAP is a member of the secretin/VIP/GRH family. PACAP exists in two α-amidated active forms, PACAP38 (SEQ ID NO: 1241) and PACAP27 (SEQ ID NO: 1242). Herein, the term "PACAP" includes either or both of PACAP38 and PACAP27 unless expressly indicated otherwise. PACAP is highly conserved between species.

In humans, PACAP is derived from a 176 amino acid precursor protein (preproPACAP) and the gene is located on chromosome 18p11, with PACAP38 encoded for by exon 5 (Vaudry et al., *Pharmacol. Rev.,* 61:283-357 (2009)). PreproPACAP contains an N-terminal 24 amino acid signal protein, a 29 amino acid PACAP-related peptide and PACAP in the C-terminal domain. The precursor is metabolized by prohormone convertase enzymes into biologically active PACAP38 and PACAP27.

VIP (SEQ ID NO: 1243) belongs to the same protein family as PACAP and shares high homology with PACAP, i.e., VIP and PACAP27 have 68% sequence homology at the amino acid level, as well as similar overall secondary structure, i.e. long alpha-helical structures at the C-terminus.

PACAP's actions are mediated via three different G-protein coupled receptors: PAC1-R, VPAC1-R, and VPAC2-R. VPAC1-R can associate with all of the receptor-associated membrane proteins ("RAMPs", Kaiser & Russo, *Neuropeptides* 47: 451-461 (2013)). PAC1-R is selective for PACAP, whereas VPAC1-R and VPAC2-R bind to both VIP and PACAP with high affinity. PAC1-R binds to PACAP with 100-1000-fold higher affinity than VIP, i.e., $K_D$~0.5 nM for PACAP27/PACAP38 vs. $K_D$~500 nM for VIP. Conversely, VPAC1-R and VPAC2-R have equal affinities for PACAP and VIP ($K_D$~1 nM) (See Schytz et al. (2010)). All three receptors are widely expressed in both peripheral tissues and in the CNS, with PAC1-R predominantly expressed in the CNS, most abundantly in the olfactory bulb, thalamus, hypothalamus, the dentate gyrus of the hippocampus and in granule cells of the cerebellum (Hashimoto et al., *J. Comp. Neurol.,* 371:567-577 (1996); Shioda et al., *Neurosci. Res.,* 28:345-354 (1997)).

Activation of the PAC1-R, VPAC1-R, and/or VPAC2-R results in increased adenylate cyclase activity and, thus, increased cAMP production. However, PACAP receptors can also mediate their effects through PLC, leading to increased $Ca^{2+}$ levels, and PLD.

PACAP has a wide range of biological effects, including a role in neurodevelopment, neuroprotection, neuromodulation, neurogenic inflammation, and nociception. PACAP is also reported to interact with glycosaminoglycans ("GAGs"). GAGs are long, unbranched polysaccharides composed of repeating disaccharide units, such as heparin, chondroitin, keratin, and hyaluronic acid. It has been shown that the cellular uptake of PACAP is dependent on the expression of GAG proteins and that PACAP bound to sulfated GAGs. Particularly, it was determined that PACAP38 binding to GAGs was capable of inducing receptor-independent cellular uptake of PACAP38. This study further demonstrated that a random coil-to-α-helix transition in PACAP38 was essential for GAG-dependent uptake of PACAP38, as a mutant PACAP38 that could not undergo the structural transition was not internalized by GAG-containing cell lines as efficiently as the wild-type form of PACAP38 (Neree et al., *FEBS Lett.,* 588(24):4590-4596, 2014). In a follow up study, it was determined that PACAP's ability to cluster GAGs, i.e., heparin, was directly related to its ability to function as a cell penetrating peptide ("CPP"). It is hypothesized that this activity is attributable to the heparin-binding, or Cardin-Weintraub, motif found in secretin/glucagon/GHRH family members, such as PACAP (Neree et al., *Int. J. Mol. Sci.,* 16:27391-27400, 2015). Interestingly, Neree et al. (2015) presented data demonstrating that PACAP38 was able to cluster sulfated GAGs in vitro. These data suggested that the observed clustering effect is important for the GAG-mediated cellular uptake of PACAP38, as other peptides, such as glucagon, displayed higher binding affinities for sulfated GAGs (heparin) but are not internalized by cells as efficiently as PACAP38. Further, it is reported that in in vitro studies in which cells are exposed to PACAP, cartilage formation is increased, including cartilage matrix that is rich in sulphated GAG proteins, consistent with its putative protective role expressed during various cellular stress responses (Juhász et al., *PLoS ONE,* 9(3):e91541, 2014). Using cell types that lack PACAP-specific receptors on their plasma membranes, such as CHO-K1 cells, Doan et al. presented data demonstrating the ability of such cells to engage in receptor-independent cellular uptake of various forms of fluorescently-labeled PACAP38 and PACAP27 (Doan et al., *Biochem. Biophys. Acta,* 1823:940-949, 2012).

The present invention provides exemplary antibodies or antigen binding fragments thereof that bind PACAP, including human PACAP. Other antibodies or antigen binding fragments thereof that bind PACAP, including those having different CDRs, and epitopic specificity may be obtained using the disclosure of the present specification, and using methods that are generally known in the art. Such antibodies and antigen binding fragments thereof antagonize the biological effects of PACAP in vivo and therefore are useful in treating or preventing PACAP-related conditions including, for example, headache, migraine, pain, photophobia, hot flush, PTSD, and anxiety disorders. In preferred embodiments, the antibody or antigen binding fragment thereof according to the invention comprises one or more CDRs, a $V_L$ chain and/or $V_H$ chain of the anti-PACAP antibodies and antigen binding fragments thereof described herein.

In some embodiments, an anti-PACAP antibody or antigen binding fragment thereof according to the invention will interfere with, block, reduce, or modulate the interaction between PACAP and its receptor(s) (e.g., PAC1-R, VPAC1-

R, and VPAC2-R). In some instances an anti-PACAP antibody or antigen binding fragment thereof according to the invention is "neutralizing", e.g., it totally prevents the specific interaction of PACAP with PAC1-R, VPAC1-R, and/or VPAC2-R. In some embodiments, the antibody or antigen binding fragment thereof neutralizes PACAP, e.g., by remaining bound to PACAP in a location and/or manner that prevents PACAP from specifically binding to PAC1-R, VPAC1-R, and/or VPAC2-R.

In some embodiments, the antibody or antigen binding fragment thereof according to the invention is capable of inhibiting PACAP-mediated activity (including binding to PAC1-R-expressing cells). In some embodiments, the antibody or antigen binding fragment thereof according to the invention are humanized, such as humanized rabbit antibodies to PACAP.

As mentioned, the anti-PACAP antibodies or antigen binding fragments thereof according to the invention have a variety of uses. For example, the subject antibodies and fragments can be useful in therapeutic applications, as well as diagnostically in binding assays. The subject anti-PACAP antibodies or antigen binding fragments thereof are useful for affinity purification of PACAP, in particular human PACAP or its ligands and in screening assays to identify other antagonists of PACAP activity. Some of the antibodies or antigen binding fragments thereof are useful for inhibiting binding of PACAP to PAC1-R, VPAC1-R, and/or VPAC2-R, or inhibiting PACAP-mediated activities and/or biological effects.

As used herein, the term "one or more biological effects associated with PACAP refers to any biological effect mediated, induced, or otherwise attributable to PACAP, e.g., binding properties, functional properties, and other properties of biological significance. Non-limiting exemplary biological effects of PACAP include PACAP binding to PAC1-R, VPAC1-R, GAGs, and/or VPAC2-R; PACAP activating PAC1-R, VPAC1-R, and/or VPAC2-R-mediated signaling; PACAP-mediated increase in cAMP production; PACAP-mediated increase in PLC activity; PACAP-mediated increase in PLD activity; PACAP-mediated increase in $Ca^{2+}$ levels; and PACAP-mediated vasodilation, photophobia, mast cell degranulation, and/or neuronal activation. The subject anti-PACAP antibodies are capable of inhibiting one, a combination of, or all of these exemplary PACAP biological activities. For example, the anti-PACAP antibodies and antigen binding fragments thereof provided herein are capable of inhibiting PACAP-induced vasodilation (see Example 7 and Example 8).

The antibody or antigen binding fragment thereof according to the invention can be used in a variety of therapeutic applications. For example, in some embodiments the anti-PACAP antibody or antigen binding fragment thereof are useful for treating conditions associated with PACAP, such as, but not limited to, migraine (with or without aura), hemiplegic migraines, cluster headaches, migrainous neuralgia, chronic headaches, tension headaches, general headaches, hot flush, photophobia, chronic paroxysmal hemicrania, secondary headaches due to an underlying structural problem in the head or neck, cranial neuralgia, sinus headaches (e.g., headache associated with sinusitis), allergy-induced headaches or migraines, pain, chronic pain, neuroinflammatory or inflammatory pain, post-operative incision pain, post-surgical pain, trauma-related pain, eye pain, tooth pain, complex regional pain syndrome, cancer pain (e.g., primary or metastatic bone cancer pain), fracture pain, osteoporotic fracture pain, pain resulting from burn, gout joint pain, pain associated with sickle cell crises, pain associated with temporomandibular disorders, cirrhosis, hepatitis, neurogenic pain, neuropathic pain, nociceptic pain, visceral pain, trigeminal neuralgia, post-herpetic neuralgia, phantom limb pain, fibromyalgia, menstrual pain, ovarialgia, reflex sympathetic dystrophy, osteoarthritis or rheumatoid arthritis pain, lower back pain, diabetic neuropathy, sciatica, dyspepsia, irritable bowel syndrome, inflammatory bowel disease, Crohn's disease, ileitis, ulcerative colitis, renal colic, dysmenorrhea, cystitis, interstitial cystitis, menstrual period, labor, menopause, pancreatitis, schizophrenia, depression, PTSD, anxiety disorders, diabetes, autoimmune diabetes, endothelial dysfunction, ischemia, Raynaud's syndrome, coronary heart disease ("CHD"), coronary artery disease ("CAD"), heart failure, peripheral arterial disease ("PAD"), pulmonary hypertension ("PH"), connective tissue disorders, stroke, Sjögren's syndrome, multiple sclerosis, bronchial hyperreactivity, asthma, bronchitis, bronchodilation, emphysema, chronic obstructive pulmonary disease ("COPD"), inflammatory dermatitis, adenocarcinoma in glandular tissue, blastoma in embryonic tissue of organs, carcinoma in epithelial tissue, leukemia in tissues that form blood cells, lymphoma in lymphatic tissue, myeloma in bone marrow, sarcoma in connective or supportive tissue, adrenal cancer, AIDS-related lymphoma, anemia, bladder cancer, bone cancer, brain cancer, breast cancer, carcinoid tumors, cervical cancer, chemotherapy, colon cancer, cytopenia, endometrial cancer, esophageal cancer, gastric cancer, head cancer, neck cancer, hepatobiliary cancer, kidney cancer, leukemia, liver cancer, lung cancer, lymphoma, Hodgkin's disease, non-Hodgkin's, nervous system tumors, oral cancer, ovarian cancer, pancreatic cancer, prostate cancer, rectal cancer, skin cancer, stomach cancer, testicular cancer, thyroid cancer, urethral cancer, cancer of bone marrow, multiple myeloma, tumors that metastasize to the bone, tumors infiltrating the nerve and hollow viscus, tumors near neural structures, acne vulgaris, atopic dermatitis, urticaria, keloids, hypertrophic scars and rosacea, allergic dermatitis, psoriasis, pruritus, neurogenic cutaneous redness, erythema, weight loss, anorexia, sarcoidosis, shock, sepsis, opiate withdrawal syndrome, morphine tolerance, epilepsy, LUT disorders such as urinary tract infection, abnormal voiding, urinary urgency, nocturia, urinary incontinence, overactive bladder, and for preventing or alleviating the pain associated with such LUT conditions.

Specific examples of visceral pain, i.e., pain associated with the viscera, or the internal organs of the body include pain that affects organs such as e.g., the heart, lungs, reproductive organs, bladder, ureters, the digestive organs, liver, pancreas, spleen, and kidneys. Conditions associated therewith include by way of example pancreatitis, labor, abdominal surgery associated with ileus, cystitis, menstrual period, or dysmenorrhea. Likewise, kidney pain, epigastric pain, pleural pain, and painful biliary colic, appendicitis pain may all be considered to be visceral pain. Substernal pain or pressure from early myocardial infarction is also visceral. Diseases of the stomach, duodenum or colon can cause visceral pain. Commonly encountered gastrointestinal ("GI") disorders that cause visceral pain include functional bowel disorder ("FBD") and inflammatory bowel disease ("IBD"). Such GI disorders may further include gastroesophageal reflux, dyspepsia, irritable bowel syndrome ("IBS") and functional abdominal pain syndrome ("FAPS"), and, with respect to IBD, Crohn's disease, ileitis, and ulcerative colitis.

The subject anti-PACAP antibodies and antigen binding fragments thereof may be used alone or in association with other active agents or drugs, including other biologics, to treat any subject in which blocking, inhibiting, or neutralizing the in vivo effect of PACAP or blocking or inhibiting the interaction of PACAP and its receptors, PAC1-R, VPAC1-R, and VPAC2-R, is therapeutically desirable.

Exemplary anti-PACAP antibodies and antigen binding fragments thereof according to the invention, and the specific CDRs thereof are identified in this section. For convenience, each exemplified antibody or antigen binding fragment thereof, and corresponding sequences are separately identified by a specific nomenclature, i.e., Ab1, Ab1.H, Ab2, Ab3, Ab4, Ab5, Ab6, Ab7, Ab8, Ab9, Ab11, Ab12, Ab13, Ab14, Ab15, Ab16, Ab17, Ab18, and Ab19, The anti-PACAP antibodies and antigen binding fragments thereof comprising the invention have binding affinity for PACAP, wherein the binding affinity comprises anti-PACAP antibodies or antigen binding fragments thereof specifically binding to PACAP38 and PACAP27, but not binding VIP, and/or antibodies or antigen binding fragments thereof specifically binding to PACAP38, but not binding to PACAP27 or VIP, and/or antibodies or antigen binding fragments thereof specifically binding to a linear and/or conformational epitope within PACAP38 and/or PACAP27. More specifically, the epitopes of PACAP38 and/or PACAP27 to which antagonistic anti-PACAP antibodies or antigen binding fragments thereof according to the invention bind will include those which are identified in Example 12 or residues thereof (as determined by use of alanine scanning) and/or other epitopic identification methods.

Anti-PACAP Antibody Polypeptides and Polynucleotides Encoding the Polypeptides Antibody Ab1.H In one embodiment, the invention includes the use or administration of antibodies and antigen binding fragments having binding specificity to PACAP that possess a heavy chain sequence comprising the sequence of SEQ ID NO: 41 which consists of the heavy chain variable region of SEQ ID NO: 42 linked to the heavy chain constant region of SEQ ID NO: 50.

In one embodiment, the invention includes the use or administration of antibodies and antigen binding fragments having binding specificity to PACAP that contain a variable heavy chain sequence comprising the sequence set forth below:

(SEQ ID NO: 42)
EVQLVESGGGLVQPGGSLRLSCAASGFTVSSAVMNWVRQAPGKGLEWIGS

IVASGTTYYASSANGRFTISRDNSKNTLYLQMNSLRAEDTAVYYCARGGG

EFFIWGQGTLVTVSS.

In another embodiment, the invention includes the use of antibodies and antigen binding fragments thereof having binding specificity to PACAP that possess the same epitopic specificity as Ab1.H, and which contain a constant heavy chain sequence comprising the polypeptide of SEQ ID NO: 1244, 1245, or 1246, or comprising the sequence set forth below:

(SEQ ID NO: 50)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYASTYRVVSVLTVLHQDWLNGK

-continued

EYKCKVSNKALPAPIEKTISKAKGQPREPQVYTLPPSREEMTKNQVSLTC

LVKGFYPSDIAVEWESNGQPENNYKTTPPVLDSDGSFFLYSKLTVDKSRW

QQGNVFSCSVMHEALHNHYTQKSLSLSPGK.

In another embodiment, the invention includes the use or administration of antibodies and antigen binding fragments having binding specificity to PACAP that contain a light chain sequence comprising the sequence of SEQ ID NO: 61 which consists of the light chain variable region of SEQ ID NO: 62 linked to the light chain constant region of SEQ ID NO: 70.

In another embodiment, the invention includes the use or administration of antibodies and antigen binding fragments having binding specificity to PACAP that contain a variable light chain sequence comprising the sequence set forth below:

(SEQ ID NO: 62)
DIQMTQSPSTLSASVGDRVTITCQSSESVYSNYLSWYQQKPGKAPKFLIY

QASNLASGVPSRFSGSGSGTEFTLTISSLQPDDFATYYCAGGYSENIVGF

GGGTKVEIKR.

In another embodiment, the invention includes the use or administration of antibodies and antigen binding fragments thereof having binding specificity to PACAP that bind the same epitope as Ab1.H, and which contain a constant light chain sequence comprising the sequence set forth below:

(SEQ ID NO: 70)
TVAAPSVFIFPPSDEQLKSGTASVVCLLNNFYPREAKVQWKVDNALQSGN

SQESVTEQDSKDSTYSLSSTLTLSKADYEKHKVYACEVTHQGLSSPVTKS

FNRGEC.

In another embodiment, the invention includes the use or administration of antibodies and antigen binding fragments thereof having binding specificity to PACAP and that contain one, two, or three of the polypeptide sequences of SEQ ID NO: 44; SEQ ID NO: 46; and SEQ ID NO: 48, which correspond to the CDRs, or hypervariable regions, of the heavy chain sequence of SEQ ID NO: 41, or which contain the variable heavy chain sequence of SEQ ID NO: 42, and/or which further contain one, two, or three of the polypeptide sequences of SEQ ID NO: 64; SEQ ID NO: 66; and SEQ ID NO: 68, which correspond to the CDRs, or hypervariable regions, of the light chain sequence of SEQ ID NO: 61, or which contain the variable light chain sequence of SEQ ID NO: 62, or antibodies or antigen binding fragments thereof containing combinations of sequences, which are at least 80%, 85%, 90%, 95%, 96%, 97%, 98%, or 99% identical thereto. In another embodiment of the invention, the anti-PACAP antibodies or antigen binding fragments thereof comprise, or alternatively consist of, combinations of one or more of the exemplified variable heavy chain and variable light chain sequences, or the heavy chain and light chain sequences set forth above, or sequences that are at least 90% or 95% identical thereto.

The invention further contemplates the use or administration of anti-PACAP antibodies and antigen binding fragments thereof comprising one, two, three, or four of the polypeptide sequences of SEQ ID NO: 43; SEQ ID NO: 45; SEQ ID NO: 47; and SEQ ID NO: 49, which correspond to the FRs, or constant regions, of the heavy chain sequence of SEQ ID NO: 41, or the variable heavy chain sequence of SEQ ID NO: 42, and/or one, two, three, or four of the polypeptide sequences of SEQ ID NO: 63; SEQ ID NO: 65; SEQ ID NO: 67; and SEQ ID NO: 69, which correspond to the FRs of the light chain sequence of SEQ ID NO: 61, or the variable light chain sequence of SEQ ID NO: 62, or combinations of these polypeptide sequences, or sequences which are at least 80%, 90%, 95%, 96%, 97%, 98% or 99% identical therewith.

In another embodiment of the invention, the antibodies and antigen binding fragments thereof useful in the disclosed methods comprise, or alternatively consist of, combinations of one or more of the FRs, CDRs, the variable heavy chain and variable light chain sequences, and the heavy chain and light chain sequences set forth above, including all of them, or sequences which are at least 90% or 95% identical thereto.

In another embodiment of the invention, the anti-PACAP antibodies and antigen binding fragments useful in the disclosed methods comprise, or alternatively consist of, the polypeptide sequence of SEQ ID NO: 41, or SEQ ID NO: 42, or polypeptides that are at least 90% or 95% identical thereto. In another embodiment of the invention, the antibodies and antigen binding fragments thereof useful in the disclosed methods comprise, or alternatively consist of, the polypeptide sequence of SEQ ID NO: 61, or SEQ ID NO: 62, or polypeptides that are at least 90% or 95% identical thereto.

In a further embodiment of the invention, the antibodies and antigen binding fragments thereof useful in the disclosed methods have binding specificity to PACAP and comprise, or alternatively consist of, one, two, or three of the polypeptide sequences of SEQ ID NO: 44; SEQ ID NO: 46; and SEQ ID NO: 48, which correspond to the CDRs, or hypervariable regions, of the heavy chain sequence of SEQ ID NO: 41, or the variable heavy chain sequence of SEQ ID NO: 42, or sequences that are at least 90%, or 95% identical thereto.

In a further embodiment of the invention, the antibodies and antigen binding fragments useful in the disclosed methods have binding specificity to PACAP and comprise, or alternatively consist of, one, two, or three of the polypeptide sequences of SEQ ID NO: 64; SEQ ID NO: 66; and SEQ ID NO: 68 which correspond to the CDRs, or hypervariable regions, of the light chain sequence of SEQ ID NO: 61, or the variable light chain sequence of SEQ ID NO: 62, or sequences that are at least 90%, or 95% identical thereto.

In a further embodiment of the invention, the antibodies and antigen binding fragments thereof useful in the disclosed methods have binding specificity to PACAP and comprise, or alternatively consist of, one, two, three, or four of the polypeptide sequences of SEQ ID NO: 43; SEQ ID NO: 45; SEQ ID NO: 47; and SEQ ID NO: 49, which correspond to the FRs, or constant regions, of the heavy chain sequence of SEQ ID NO: 41, or the variable heavy chain sequence of SEQ ID NO: 42, or sequences that are at least 90% or 95% identical thereto.

In a further embodiment of the invention, the antibodies and antigen binding fragments thereof useful in the disclosed methods have binding specificity to PACAP and comprise, or alternatively consist of, one, two, three, or four of the polypeptide sequences of SEQ ID NO: 63; SEQ ID NO: 65; SEQ ID NO: 67; and SEQ ID NO: 69, which correspond to the FRs or constant regions, of the light chain sequence of SEQ ID NO: 61, or the variable light chain sequence of SEQ ID NO: 62, or sequences that are at least 90% or 95% identical thereto.

The invention also contemplates the use or administration of anti-PACAP antibodies and antigen binding fragments thereof that include one or more of the antigen binding fragments described herein. In one embodiment of the invention, antibodies and antigen binding fragments thereof useful in the disclosed methods have binding specificity to PACAP and comprise, or alternatively consist of, one, two, three or more, including all of the following antigen binding fragments: the variable heavy chain region of SEQ ID NO: 42; the variable light chain region of SEQ ID NO: 62; the CDRs (SEQ ID NO: 44; SEQ ID NO: 46; and SEQ ID NO: 48) of the variable heavy chain region of SEQ ID NO: 42; and the CDRs (SEQ ID NO: 64; SEQ ID NO: 66; and SEQ ID NO: 68) of the variable light chain region of SEQ ID NO: 62, or sequences that are at least 90% or 95% identical thereto.

The invention also contemplates the use or administration of anti-PACAP antibodies and antigen binding fragments thereof that include one or more of the antigen binding fragments described herein. In one embodiment of the invention, antigen binding fragments of the antibodies useful in the disclosed methods have binding specificity to PACAP and comprise, or alternatively consist of, one, two, three or more, including all of the following antigen binding fragments: the variable heavy chain region of SEQ ID NO: 42; the variable light chain region of SEQ ID NO: 62; the FRs (SEQ ID NO: 43; SEQ ID NO: 45; SEQ ID NO: 47; and SEQ ID NO: 49) of the variable heavy chain region of SEQ ID NO: 42; and the FRs (SEQ ID NO: 63; SEQ ID NO: 65; SEQ ID NO: 67; and SEQ ID NO: 69) of the variable light chain region of SEQ ID NO: 62.

In another embodiment of the invention, the anti-PACAP antibody useful in the disclosed methods is Ab1.H, comprising, or alternatively consisting of, SEQ ID NO: 41 and SEQ ID NO: 61, or SEQ ID NO: 42 and SEQ ID NO: 62, or an antibody or antigen binding fragment comprising the CDRs of Ab1.H and having at least one of the biological activities set forth herein, or is an anti-PACAP antibody that competes with Ab1.H in binding PACAP, for instance an antibody containing sequences that are at least 90%, 95%, 96%, 97%, 98%, or 99% identical to that of Ab1.H, or an antibody that binds to the same or overlapping epitope(s) on PACAP as Ab1.H.

In a further embodiment of the invention, anti-PACAP antigen binding fragments useful in the disclosed methods comprise, or alternatively consist of, Fab (fragment antigen binding) fragments having binding specificity for PACAP. With respect to antibody Ab1.H, the Fab fragment preferably includes the variable heavy chain sequence of SEQ ID NO: 42 and the variable light chain sequence of SEQ ID NO: 62, or sequences that are at least 90%, 95%, 96%, 97%, 98%, or 99% identical thereto. This embodiment of the invention further includes the use of Fabs containing additions, deletions, and variants of SEQ ID NO: 42 and/or SEQ ID NO: 62, which retain the binding specificity for PACAP.

In one embodiment of the invention described herein, anti-PACAP Fab fragments useful in the disclosed methods can be produced by enzymatic digestion (e.g., papain) of Ab1.H. In another embodiment of the invention, anti-PACAP antibodies such as Ab1.H or Fab fragments thereof useful in the disclosed methods can be produced via expression in mammalian cells such as CHO, NSO, or HEK 293 cells, fungal, insect, or microbial systems such as yeast cells (for example haploid or diploid yeast such as haploid or diploid *Pichia*) and other yeast strains. Suitable *Pichia* species include, but are not limited to, *Pichia pastoris*.

In an additional embodiment, the invention is further directed to the use or administration of polynucleotides encoding antibody polypeptides having binding specificity to PACAP, or PACAP receptors, including the heavy and/or light chains of Ab1.H as well as fragments, variants, combinations of one or more of the FRs, CDRs, the variable heavy chain and variable light chain sequences, and the heavy chain and light chain sequences set forth above, including all of them, or sequences that are at least 90% or 95% identical thereto.

In another embodiment, the invention contemplates an isolated anti-PACAP antibody comprising a $V_H$ polypeptide sequence of SEQ ID NO: 42, or a variant thereof; and further comprising a $V_L$ polypeptide sequence of SEQ ID NO: 62, or a variant thereof, wherein one or more of the framework region residues ("FR residues") and/or CDR residues in said $V_H$ or $V_L$ polypeptide has been substituted with another amino acid residue resulting in an anti-PACAP antibody that specifically binds PACAP. The invention also includes humanized and chimeric forms of these antibodies. The chimeric and humanized antibodies may include an Fc derived from IgG1, IgG2, IgG3, or IgG4 constant regions.

In one embodiment of the invention, the chimeric or humanized antibodies or fragments or $V_H$ or $V_L$ polypeptides originate or are derived from one or more rabbit antibodies, e.g., a rabbit antibody isolated from a clonal rabbit B cell population.

In some aspects, the invention provides a vector comprising a nucleic acid molecule encoding an anti-PACAP antibody or fragment thereof as disclosed herein. In some embodiments, the invention provides a host cell comprising a nucleic acid molecule encoding an anti-PACAP antibody or fragment thereof as disclosed herein.

In some aspects, the invention provides an isolated antibody or antigen binding fragment thereof that competes for binding to PACAP with an antibody or antigen binding fragment thereof disclosed herein.

In some aspects, the invention provides a nucleic acid molecule encoding an antibody or antigen binding fragment thereof as disclosed herein.

In some aspects, the invention provides a pharmaceutical or diagnostic composition comprising at least one antibody or antigen binding fragment thereof as disclosed herein.

In some aspects, the invention provides a method for treating or preventing a condition associated with elevated PACAP levels in a subject, comprising administering to a subject in need thereof an effective amount of at least one isolated antibody or antigen binding fragment thereof as disclosed herein.

In some aspects, the invention provides a method of inhibiting binding of PACAP to PAC1-R, VPAC1-R, and/or VPAC2-R in a subject comprising administering an effective amount of at least one antibody or antigen binding fragment thereof as disclosed herein.

In some aspects, the invention provides an antibody or antigen binding fragment thereof that selectively binds to PACAP, wherein the antibody or antigen binding fragment thereof binds to PACAP with a $K_D$ of less than or equal to $5\times10^{-5}$ M, $10^{-5}$ M, $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $10^{-12}$ M, $5\times10^{-11}$ M, $10^{-11}$ M, $5\times10^{-12}$ M, $5\times10^{-13}$ M, or $10^{-13}$ M; preferably, with a $K_D$ of less than or equal to $5\times10^{-10}$ M, $10^{-10}$ M, $5\times10^{-11}$ M, $10^{-11}$ M, $5\times10^{-12}$ M, or $10^{-12}$ M; more preferably, with a $K_D$ that is less than about 100 pM, less than about 50 pM, less than about 40 pM, less than about 25 pM, less than about 1 pM, between about 10 pM and about 100 pM, between about 1 pM and about 100 pM, or between about 1 pM and about 10 pM. Preferably, the anti-PACAP antibody or antigen binding fragment thereof has no cross-reactivity or minimal cross-reactivity with VIP.

The inventive antibodies and antigen binding fragments thereof may be modified post-translationally to add effector moieties such as chemical linkers, detectable moieties such as for example fluorescent dyes, enzymes, substrates, bioluminescent materials, radioactive materials, and chemiluminescent moieties, or functional moieties such as for example streptavidin, avidin, biotin, a cytotoxin, a cytotoxic agent, and radioactive materials.

Antibodies and antigen binding fragments thereof may also be chemically modified to provide additional advantages such as increased solubility, stability and circulating time (in vivo half-life) of the polypeptide, or decreased immunogenicity (See U.S. Pat. No. 4,179,337). The chemical moieties for derivatization may be selected from water soluble polymers such as polyethylene glycol, ethylene glycol/propylene glycol copolymers, carboxymethylcellulose, dextran, polyvinyl alcohol, and the like. The antibodies and fragments thereof may be modified at random positions within the molecule, or at predetermined positions within the molecule and may include one, two, three, or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog). For example, the polyethylene glycol may have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 50,000, 55,000, 60,000, 65,000, 70,000, 75,000, 80,000, 85,000, 90,000, 95,000, or 100,000 kDa. Branched polyethylene glycols are described, for example, in U.S. Pat. No. 5,643,575; Morpurgo et al., *Appl. Biochem. Biotechnol.,* 56:59-72 (1996); Vorobjev et al., *Nucleosides and Nucleotides,* 18:2745-2750 (1999); and Caliceti et al., *Bioconjug. Chem.,* 10:638-646 (1999), the disclosures of each of which are incorporated herein by reference.

There are a number of attachment methods available to those skilled in the art (See e.g., EP 0 401 384, herein incorporated by reference, disclosing a method of coupling PEG to G-CSF; and Malik et al., *Exp. Hematol.,* 20:1028-1035 (1992) (reporting pegylation of GM-CSF using tresyl chloride)). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

As suggested above, polyethylene glycol may be attached to proteins via linkage to any of a number of amino acid residues. For example, polyethylene glycol can be linked to polypeptides via covalent bonds to lysine, histidine, aspartic acid, glutamic acid, or cysteine residues. One or more reaction chemistries may be employed to attach polyethylene glycol to specific amino acid residues (e.g., lysine, histidine, aspartic acid, glutamic acid, or cysteine) or to more than one type of amino acid residue (e.g., lysine, histidine, aspartic acid, glutamic acid, cysteine and combinations thereof).

Alternatively, antibodies or antigen binding fragments thereof may have increased in vivo half-lives via fusion with albumin (including but not limited to recombinant human serum albumin or fragments or variants thereof (See, e.g., U.S. Pat. No. 5,876,969, EP 0 413 622, and U.S. Pat. No. 5,766,883, herein incorporated by reference in their entirety)), or other circulating blood proteins such as transferrin or ferritin. In a preferred embodiment, polypeptides and/or antibodies of the present invention (including fragments or variants thereof) are fused with the mature form of human serum albumin (i.e., amino acids 1-585 of human serum albumin as shown in FIGS. 1 and 2 of EP 0 322 094) which is herein incorporated by reference in its entirety. Polynucleotides encoding fusion proteins of the invention are also encompassed by the invention.

Regarding detectable moieties, further exemplary enzymes include, but are not limited to, horseradish peroxidase, acetylcholinesterase, alkaline phosphatase, beta-galactosidase, and luciferase. Further exemplary fluorescent materials include, but are not limited to, rhodamine, fluorescein, fluorescein isothiocyanate, umbelliferone, dichlorotriazinylamine, phycoerythrin, and dansyl chloride. Further exemplary chemiluminescent moieties include, but are not limited to, luminol. Further exemplary bioluminescent materials include, but are not limited to, luciferin and aequorin. Further exemplary radioactive materials include, but are not limited to, Iodine 125 ($^{125}I$) Carbon 14 ($^{14}C$), Sulfur 35 ($^{35}S$), Tritium ($^{3}H$) and Phosphorus 32 ($^{32}P$).

Methods are known in the art for conjugating an antibody or antigen binding fragment thereof to a detectable moiety and the like, such as for example those methods described by Hunter et al., *Nature,* 144:945 (1962); David et al., *Biochemistry,* 13:1014 (1974); Pain et al., *J. Immunol. Meth.,* 40:219 (1981); and Nygren, *J., Histochem. and Cytochem.,* 30:407 (1982).

Embodiments described herein further include variants and equivalents that are substantially homologous to the antibodies, antibody fragments, diabodies, SMIPs, camelbodies, nanobodies, IgNAR, polypeptides, variable regions, and CDRs set forth herein. These may contain, e.g., conservative substitution mutations, (i.e., the substitution of one or more amino acids by similar amino acids). For example, conservative substitution refers to the substitution of an amino acid with another within the same general class, e.g., one acidic amino acid with another acidic amino acid, one basic amino acid with another basic amino acid, or one neutral amino acid by another neutral amino acid. What is intended by a conservative amino acid substitution is well known in the art.

In another embodiment, the invention contemplates polypeptide sequences having at least 90% or greater sequence homology to any one or more of the polypeptide sequences of antigen binding fragments, variable regions and CDRs set forth herein. More preferably, the invention contemplates polypeptide sequences having at least 95% or greater sequence homology, even more preferably at least 98% or greater sequence homology, and still more preferably at least 99% or greater sequence homology to any one or more of the polypeptide sequences of antigen binding fragments, variable regions, and CDRs set forth herein.

Methods for determining homology between nucleic acid and amino acid sequences are well known to those of ordinary skill in the art.

In another embodiment, the invention further contemplates the above-recited polypeptide homologs of the antigen binding fragments, variable regions and CDRs set forth herein further having anti-PACAP activity. Non-limiting examples of anti-PACAP activity are set forth herein, e.g., ability to inhibit PACAP binding to PAC1-R, VPAC1-R, and/or VPAC2-R, thereby resulting in the reduced production of cAMP.

In another embodiment, the invention further contemplates the generation and use of antibodies that bind any of the foregoing sequences, including, but not limited to, anti-idiotypic antibodies. In an exemplary embodiment, such an anti-idiotypic antibody could be administered to a subject who has received an anti-PACAP antibody to modulate, reduce, or neutralize, the effect of the anti-PACAP antibody. Such antibodies could also be useful for treatment of an autoimmune disease characterized by the presence of anti-PACAP antibodies. A further exemplary use of such antibodies, e.g., anti-idiotypic antibodies, is for detection of the anti-PACAP antibodies of the present invention, for example to monitor the levels of the anti-PACAP antibodies present in a subject's blood or other bodily fluids. For example, in one embodiment, the invention provides a method of using the anti-idiotypic antibody to monitor the in vivo levels of said anti-PACAP antibody or antigen binding fragment thereof in a subject or to neutralize said anti-PACAP antibody in a subject being administered said anti-PACAP antibody or antigen binding fragment thereof.

The present invention also contemplates anti-PACAP antibodies comprising any of the polypeptide or polynucleotide sequences described herein substituted for any of the other polynucleotide sequences described herein. For example, without limitation thereto, the present invention contemplates antibodies comprising the combination of any of the variable light chain and variable heavy chain sequences described herein, and further contemplates antibodies resulting from substitution of any of the CDR sequences described herein for any of the other CDR sequences described herein.

Exemplary Polynucleotides Encoding Anti-PACAP Antibody Polypeptides

The invention is further directed to polynucleotides encoding antibody polypeptides having binding specificity to PACAP.

Antibody Ab1.H

In one embodiment, the invention is further directed to the use of polynucleotides encoding antibody polypeptides having binding specificity to PACAP. In one embodiment of the invention, polynucleotides comprise, or alternatively consist of, the polynucleotide sequence of SEQ ID NO: 51 which encodes the heavy chain sequence of SEQ ID NO: 41 and which consists of the heavy chain variable region coding sequence of SEQ ID NO: 52 and the heavy chain constant region coding sequence of SEQ ID NO: 60.

In another embodiment of the invention, the polynucleotides comprise, or alternatively consist of, the following polynucleotide sequence encoding the variable heavy chain polypeptide sequence of SEQ ID NO: 42:

(SEQ ID NO: 52)
gaggtgcagcttgtggagtctgggggaggcttggtccagcctggggggtc cctgagactctcctgtgcagcctctggattcaccgtcagtagcgctgtaa tgaattgggtccgtcaggctccagggaaggggctggagtggatcggaagt attgttgctagtggtaccacatactacgctagctctgctaacggccgatt caccatctccagagacaattccaagaacaccctgtatcttcaaatgaaca gcctgagagctgaggacactgctgtgtattactgtgctagagggggaggg gaatttttcatctggggccaagggaccctcgtcaccgtctcgagc.

In another embodiment of the invention, polynucleotides comprise, or alternatively consist of, the following polynucleotide sequence encoding the constant heavy chain polypeptide sequence of SEQ ID NO: 50:

(SEQ ID NO: 60)
gcctccaccaagggcccatcggtcttccccctggcaccctcctccaagag cacctctgggggcacagcggccctgggctgcctggtcaaggactacttcc ccgaaccggtgacggtgtcgtggaactcaggcgccctgaccagcggcgtg cacaccttcccggctgtcctacagtcctcaggactctactccctcagcag cgtggtgaccgtgccctccagcagcttgggcacccagacctacatctgca acgtgaatcacaagcccagcaacaccaaggtggacaagaaagttgagccc aaatcttgtgacaaaactcacacatgcccaccgtgcccagcacctgaact cctggggggaccgtcagtcttcctcttccccccaaaacccaaggacaccc tcatgatctcccggacccctgaggtcacatgcgtggtggtggacgtgagc cacgaagaccctgaggtcaagttcaactggtacgtggacggcgtggaggt gcataatgccaagacaaagccgcgggaggagcagtacgccagcacgtacc gtgtggtcagcgtcctcaccgtcctgcaccaggactggctgaatggcaag gagtacaagtgcaaggtctccaacaaagccctcccagcccccatcgagaa aaccatctccaaagccaaagggcagccccgagaaccacaggtgtacaccc tgcccccatcccgggaggagatgaccaagaaccaggtcagcctgacctgc ctggtcaaaggcttctatcccagcgacatcgccgtggagtgggagagcaa tgggcagccggagaacaactacaagaccacgcctcccgtgctggactccg acggctccttcttcctctacagcaagctcaccgtggacaagagcaggtgg cagcaggggaacgtcttctcatgctccgtgatgcatgaggctctgcacaa ccactacacgcagaagagcctctccctgtctccgggtaaa.

In another embodiment of the invention, polynucleotides comprise, or alternatively consist of, the polynucleotide sequence of SEQ ID NO: 71 which encodes the light chain polypeptide sequence of SEQ ID NO: 61 and which consists of the light chain variable region coding sequence of SEQ ID NO: 72 and the light chain constant region coding sequence of SEQ ID NO: 80.

In another embodiment of the invention, polynucleotides comprise, or alternatively consist of, the following polynucleotide sequence encoding the variable light chain polypeptide sequence of SEQ ID NO: 62:

(SEQ ID NO: 72)
gacatccagatgacccagtctccttccaccctgtctgcatctgtaggaga cagagtcaccatcacttgtcagtccagtgagagtgtttatagtaactact tatcctggtatcagcagaaaccaggaaaagcccctaagttcctgatctat caggcatccaatttggcatctggagtcccatcaaggttcagcggcagtgg atctggaacagaattcactctcaccatcagcagcctgcagcctgatgatt ttgcaacttactactgtgcaggcggttatagtgaaaacattgttggtttc ggcggaggaaccaaggtggaaatcaaacgt.

In another embodiment of the invention, polynucleotides comprise, or alternatively consist of, the following polynucleotide sequence encoding the constant light chain polypeptide sequence of SEQ ID NO: 70:

(SEQ ID NO: 80)
acggtagcggccccatctgtcttcatcttcccgccatctgatgagcagtt gaaatctggaactgcctctgttgtgtgcctgctgaataacttctatccca gagaggccaaagtacagtggaaggtggataacgccctccaatcgggtaac tcccaggagagtgtcacagagcaggacagcaaggacagcacctacagcct cagcagcaccctgacgctgagcaaagcagactacgagaaacacaaagtct acgcctgcgaagtcacccatcagggcctgagctcgcccgtcacaaagagc ttcaacaggggagagtgt.

In a further embodiment of the invention, polynucleotides encoding antigen binding fragments having binding specificity to PACAP comprise, or alternatively consist of, one or more of the polynucleotide sequences of SEQ ID NO: 54; SEQ ID NO: 56; and SEQ ID NO: 58, which correspond to polynucleotides encoding the CDRs, or hypervariable regions, of the heavy chain sequence of SEQ ID NO: 41, or the variable heavy chain sequence of SEQ ID NO: 42, and/or one or more of the polynucleotide sequences of SEQ ID NO: 74; SEQ ID NO: 76 and SEQ ID NO: 78, which correspond to the CDRs, or hypervariable regions, of the light chain sequence of SEQ ID NO: 61, or the variable light chain sequence of SEQ ID NO: 62, or combinations of these polynucleotide sequences. In another embodiment of the invention, the polynucleotides encoding the antibodies and antigen binding fragments thereof comprise, or alternatively consist of, combinations of polynucleotides encoding one or more of the CDRs, the variable heavy chain and variable light chain sequences, and the heavy chain and light chain sequences set forth above, including all of them.

In a further embodiment of the invention, polynucleotides encoding antigen binding fragments having binding specificity to PACAP comprise, or alternatively consist of, one or more of the polynucleotide sequences of SEQ ID NO: 53; SEQ ID NO: 55; SEQ ID NO: 57; and SEQ ID NO: 59, which correspond to polynucleotides encoding the FRs, or constant regions, of the heavy chain sequence of SEQ ID NO: 41, or the variable heavy chain sequence of SEQ ID NO: 42, and/or one or more of the polynucleotide sequences of SEQ ID NO: 73; SEQ ID NO: 75; SEQ ID NO: 77; and SEQ ID NO: 79, which correspond to the FRs, or constant regions, of the light chain sequence of SEQ ID NO: 61, or the variable light chain sequence of SEQ ID NO: 62, or combinations of these polynucleotide sequences. In another embodiment of the invention, the polynucleotides encoding the antibodies and antigen binding fragments thereof comprise, or alternatively consist of, combinations of one or more of the FRs, the variable heavy chain and variable light chain sequences, and the heavy chain and light chain sequences set forth above, including all of them.

The invention also contemplates the use of polynucleotide sequences including one or more of the polynucleotide sequences encoding antigen binding fragments described herein. In one embodiment of the invention, polynucleotides encoding antigen binding fragments having binding specificity to PACAP comprise, or alternatively consist of, one, two, three or more, including all of the following polynucleotides encoding antigen binding fragments: the polynucleotide SEQ ID NO: 51 encoding the heavy chain sequence of SEQ ID NO: 41; the polynucleotide SEQ ID NO: 52 encoding the variable heavy chain sequence of SEQ ID NO: 42; the polynucleotide SEQ ID NO: 71 encoding the light chain sequence of SEQ ID NO: 61; the polynucleotide SEQ ID NO: 72 encoding the variable light chain sequence of SEQ ID NO: 62; polynucleotides encoding the CDRs (SEQ ID NO: 54; SEQ ID NO: 56; and SEQ ID NO: 58) of the heavy chain sequence of SEQ ID NO: 41 or the variable heavy chain sequence of SEQ ID NO: 42; polynucleotides encoding the CDRs (SEQ ID NO: 74; SEQ ID NO: 76; and SEQ ID NO: 78) of the light chain sequence of SEQ ID NO: 61, or the variable light chain sequence of SEQ ID NO: 62; polynucleotides encoding the FRs (SEQ ID NO: 53; SEQ ID NO: 55; SEQ ID NO: 57; and SEQ ID NO: 59) of the heavy chain sequence of SEQ ID NO: 41, or the variable heavy chain sequence of SEQ ID NO: 42; and polynucleotides encoding the FRs (SEQ ID NO: 73; SEQ ID NO: 75; SEQ ID NO: 77; and SEQ ID NO: 79) of the light chain sequence of SEQ ID NO: 61, or the variable light chain sequence of SEQ ID NO: 62.

In a preferred embodiment of the invention, polynucleotides comprise, or alternatively consist of, polynucleotides encoding Fab fragments having binding specificity for PACAP. With respect to antibody Ab1.H, the polynucleotides encoding the full length Ab1.H antibody comprise, or alternatively consist of, the polynucleotide SEQ ID NO: 51 encoding the heavy chain sequence of SEQ ID NO: 41, and the polynucleotide SEQ ID NO: 71 encoding the light chain sequence of SEQ ID NO: 61.

Another embodiment of the invention contemplates these polynucleotides incorporated into an expression vector for expression in mammalian cells such as CHO, NSO, HEK-293 cells, or in fungal, insect, or microbial systems such as yeast cells such as the yeast *Pichia*. Suitable *Pichia* species include, but are not limited to, *Pichia pastoris*. In one embodiment of the invention described herein, Fab fragments can be produced by enzymatic digestion (e.g., papain) of Ab1.H following expression of the full-length polynucleotides in a suitable host. In another embodiment of the invention, anti-PACAP antibodies such as Ab1.H or Fab fragments thereof can be produced via expression of Ab1.H polynucleotides in mammalian cells such as CHO, NSO, or HEK 293 cells, fungal, insect, or microbial systems such as yeast cells (for example diploid yeast such as diploid *Pichia*) and other yeast strains. Suitable *Pichia* species include, but are not limited to, *Pichia pastoris*.

Host cells and vectors comprising said polynucleotides are also contemplated.

The invention further contemplates vectors comprising the polynucleotide sequences encoding the variable heavy and light chain polypeptide sequences, as well as the individual CDRs (hypervariable regions), as set forth herein, as well as host cells comprising said vector sequences. In embodiments of the invention, the host cells are mammalian cells, such as CHO cells. In embodiments of the invention, the host cells are yeast cells, such as yeast cells of the genus *Pichia*.

B-Cell Screening and Isolation

In one embodiment, the present invention contemplates the preparation and isolation of a clonal population of antigen-specific B-cells that may be used for isolating at least one PACAP antigen-specific cell, which can be used to produce a monoclonal antibody against PACAP, which is specific to a desired PACAP antigen, or a nucleic acid sequence corresponding to such an antibody. Methods of preparing and isolating said clonal population of antigen-specific B-cells are taught, for example, in U.S. Patent Publication No. US2007/0269868 to Carvalho-Jensen et al., the disclosure of which is herein incorporated by reference in its entirety. Methods of preparing and isolating said clonal population of antigen-specific B-cells are also taught herein in the examples. Methods of "enriching" a cell population by size or density are known in the art. See, e.g., U.S. Pat. No. 5,627,052. These steps can be used in addition to enriching the cell population by antigen-specificity.

Methods of Humanizing Antibodies

In another embodiment, the present invention contemplates methods for humanizing antibody heavy and light chains. Methods for humanizing antibody heavy and light chains that may be applied to anti-PACAP antibodies are taught, for example, in U.S. Patent Publication No. US2009/0022659 to Olson et al., and in U.S. Pat. No. 7,935,340 to Garcia-Martinez et al., the disclosures of each of which are herein incorporated by reference in their entireties.

Methods of Producing Antibodies and Fragments Thereof

In another embodiment, the present invention contemplates methods for producing anti-PACAP antibodies and fragments thereof. Methods for producing anti-PACAP antibodies and fragments thereof secreted from polyploidal, preferably diploid or tetraploid strains of mating competent yeast are taught, for example, in U.S. Patent Publication No. US2009/0022659 to Olson et al., and in U.S. Pat. No. 7,935,340 to Garcia-Martinez et al., the disclosures of each of which are herein incorporated by reference in their entireties.

Other methods of producing antibodies are well known to those of ordinary skill in the art. For example, methods of producing chimeric antibodies are now well known in the art (See, for example, U.S. Pat. No. 4,816,567 to Cabilly et al.; Morrison et al., *Proc. Natl. Acad. Sci. U.S.A.,* 81:8651-55 (1984); Neuberger et al., *Nature,* 314:268-270 (1985); Boulianne, G. L. et al., *Nature,* 312:643-46 (1984), the disclosures of each of which are herein incorporated by reference in their entireties).

Likewise, other methods of producing humanized antibodies are now well known in the art (See, for example, U.S. Pat. Nos. 5,530,101, 5,585,089, 5,693,762, and 6,180,370 to Queen et al; U.S. Pat. Nos. 5,225,539 and 6,548,640 to Winter; U.S. Pat. Nos. 6,054,297, 6,407,213 and 6,639,055 to Carter et al; U.S. Pat. No. 6,632,927 to Adair; Jones, P. T. et al., *Nature,* 321:522-525 (1986); Reichmann, L. et al., *Nature,* 332:323-327 (1988); Verhoeyen, M. et al., *Science,* 239:1534-36 (1988), the disclosures of each of which are herein incorporated by reference in their entireties).

Antibody polypeptides of the invention having PACAP binding specificity may also be produced by constructing, using conventional techniques well known to those of ordinary skill in the art, an expression vector containing a promoter (optionally as a component of a eukaryotic or prokaryotic operon) and a DNA sequence encoding an antibody heavy chain in which the DNA sequence encoding the CDRs required for antibody specificity is derived from a non-human cell source, preferably a rabbit B-cell source, while the DNA sequence encoding the remaining parts of the antibody chain is derived from a human cell source.

A second expression vector is produced using the same conventional means well known to those of ordinary skill in the art, said expression vector containing a promoter (optionally as a component of a eukaryotic or prokaryotic operon) and a DNA sequence encoding an antibody light chain in which the DNA sequence encoding the CDRs required for antibody specificity is derived from a non-human cell source, preferably a rabbit B-cell source, while the DNA sequence encoding the remaining parts of the antibody chain is derived from a human cell source.

The expression vectors are transfected into a host cell by convention techniques well known to those of ordinary skill in the art to produce a transfected host cell, said transfected host cell cultured by conventional techniques well known to those of ordinary skill in the art to produce said antibody polypeptides.

The host cell may be co-transfected with the two expression vectors described above, the first expression vector containing DNA encoding a promoter (optionally as a component of a eukaryotic or prokaryotic operon) and a light chain-derived polypeptide and the second vector containing DNA encoding a promoter (optionally as a component of a eukaryotic or prokaryotic operon) and a heavy chain-derived polypeptide. The two vectors contain different selectable markers, but preferably achieve substantially equal expression of the heavy and light chain polypeptides. Alternatively, a single vector may be used, the vector including DNA encoding both the heavy and light chain polypeptides. The coding sequences for the heavy and light chains may comprise cDNA, genomic DNA, or both.

The host cells used to express the antibody polypeptides may be either a bacterial cell such as *E. coli*, or a eukaryotic cell such as *P. pastoris*. In one embodiment of the invention, a mammalian cell of a well-defined type for this purpose, such as a myeloma cell, a CHO cell line, a NSO cell line, or a HEK293 cell line may be used.

The general methods by which the vectors may be constructed, transfection methods required to produce the host cell and culturing methods required to produce the antibody polypeptides from said host cells all include conventional techniques. Although preferably the cell line used to produce the antibody is a mammalian cell line, any other suitable cell line, such as a bacterial cell line such as an *E. coli*-derived bacterial strain, or a yeast cell line, may alternatively be used.

Similarly, once produced the antibody polypeptides may be purified according to standard procedures in the art, such as for example cross-flow filtration, ammonium sulphate precipitation, affinity column chromatography, hydrophobic interaction chromatography ("HIC"), and the like.

The antibody polypeptides described herein may also be used for the design and synthesis of either peptide or non-peptide mimetics that would be useful for the same therapeutic applications as the antibody polypeptides of the invention (See, for example, Saragobi et al., *Science,* 253: 792-795 (1991), the contents of which are herein incorporated by reference in its entirety).

Screening Assays

The invention also includes screening assays designed to assist in the identification and/or selection of antibodies and antigen binding fragments thereof having binding specificity for PACAP or a PACAP receptor, such as PAC1-R, useful in the disclosed methods for treating, ameliorating, or preventing diseases and disorders associated with PACAP, such as photophobia or light aversion, in subjects exhibiting symptoms of a PACAP associated disease or disorder, particularly conditions associated with PACAP-associated photophobia or light aversion, which are identified herein. Exemplary screening methods are useful for identifying or selecting polypeptides having activities that ameliorate, inhibit, reduce, treat, prevent, relieve, or otherwise diminish the effects of photophobia and/or light aversion or conditions associated with photophobia.

In some embodiments, the antibody or fragment thereof disclosed herein is used as a diagnostic tool. The antibody can be used to assay the amount of PACAP present in a sample and/or subject, for instance a subject being treated for PACAP-associated photophobia or a subject having already been treated for PACAP-associated photophobia. In some embodiments, the diagnostic antibody is not a neutralizing antibody. In some embodiments, the diagnostic antibody binds to a different epitope than the neutralizing antibody binds to. In some embodiments, the two antibodies do not compete with one another.

In some embodiments, the anti-PACAP, or anti-PACAP receptor, antibodies or antigen binding fragments thereof are used or provided in an assay kit and/or for use in a method for the detection of PACAP in mammalian tissues, or cells in order to screen/diagnose for a disease or disorder associated with changes in levels of PACAP, or changes in light aversion or PACAP-associated photophobia. The kit comprises an antibody that binds PACAP and means for indicating the binding of the antibody with PACAP, if present, and optionally PACAP protein levels. Various means for indicating the presence of an antibody can be used. For example, fluorophores, other molecular probes, or enzymes can be linked to the antibody and the presence of the antibody can be observed in a variety of ways. The method for screening for such disorders can involve the use of the kit, or simply the use of one of the disclosed antibodies, and the determination of whether the antibody binds to PACAP in a sample. As will be appreciated by one of skill in the art, high or elevated levels of PACAP will result in larger amounts of the antibody binding to PACAP in the sample. Thus, degree of antibody binding can be used to determine how much PACAP is in a sample. Subjects or samples with an amount of PACAP that is greater than a predetermined amount (e.g., an amount or range that a person without a PACAP-related disorder would have, such as a "normal" amount, or an amount typically present in a cohort of individuals who exhibit no PACAP-associated photophobia or light aversion) can be characterized as having a PACAP-mediated disorder, e.g., migraine, headache, pain, photophobia, light aversion, or other condition.

The present invention further provides for a kit for detecting binding of an anti-PACAP, or anti-PACAP receptor, antibody of the invention to PACAP, or PACAP receptor, respectively. In particular, the kit may be used to detect the presence of PACAP specifically reactive with an anti-PACAP antibody of the invention, or an immunoreactive fragment thereof. The kit may also include an antibody bound to a substrate, a secondary antibody reactive with the antigen, and a reagent for detecting a reaction of the secondary antibody with the antigen. Such a kit may be an ELISA kit and may comprise the substrate, primary, and secondary antibodies when appropriate, and any other necessary reagents, such as detectable moieties, enzyme substrates, and color reagents, for example, as described herein. The diagnostic kit may also be in the form of an immunoblot kit. The diagnostic kit may also be in the form of a chemiluminescent kit (see, for example, Meso Scale Discovery, Gaithersburg, MD). The diagnostic kit may also be a lanthanide-based detection kit (PerkinElmer, San Jose, CA).

A skilled clinician would understand that a biological sample includes, but is not limited to, sera, plasma, urine, saliva, mucous, pleural fluid, synovial fluid and spinal fluid.

Methods of Ameliorating or Reducing Symptoms of, or Treating, or Preventing, Diseases and Disorders Associated with PACAP In another embodiment of the invention, anti-PACAP antibodies described herein, or antigen binding fragments thereof, are useful for ameliorating or reducing the symptoms of, or treating, or preventing, diseases and disorders associated with PACAP. Non-limiting examples of such symptoms or diseases may be photophobia, light aversion or avoidance, and sensitivity to light. Anti-PACAP antibodies described herein, or antigen binding fragments thereof, as well as combinations, can also be administered in a therapeutically effective amount to patients in need of treatment of diseases and disorders associated with PACAP in the form of a pharmaceutical composition as described in greater detail below.

In another embodiment of the invention, anti-PACAP antibodies described herein, or antigen binding fragments thereof, are useful (either alone or in combination with another agent) for ameliorating or reducing the symptoms of, or treating, or preventing a disease or condition associated with PACAP, such as photophobia, light aversion or avoidance and sensitivity to light.

In another embodiment of the invention, anti-PACAP antibodies described herein, or antigen binding fragments thereof, with or without a second agent, are useful for ameliorating or reducing the symptoms of, or treating, or preventing, the following non-limiting listing of diseases and disorders: migraine (with or without aura), hemiplegic migraines, cluster headaches, migrainous neuralgia, chronic headaches, tension headaches, general headaches, hot flush, photophobia, chronic paroxysmal hemicrania, secondary headaches due to an underlying structural problem in the head or neck, cranial neuralgia, sinus headaches (e.g., headache associated with sinusitis), allergy-induced headaches or migraines, pain, chronic pain, neuroinflammatory or inflammatory pain, post-operative incision pain, post-surgical pain, trauma-related pain, eye pain, tooth pain, complex regional pain syndrome, cancer pain (e.g., primary or metastatic bone cancer pain), fracture pain, osteoporotic fracture pain, pain resulting from burn, gout joint pain, pain associated with sickle cell crises, pain associated with temporomandibular disorders, cirrhosis, hepatitis, neurogenic pain, neuropathic pain, nociceptic pain, visceral pain, trigeminal neuralgia, post-herpetic neuralgia, phantom limb pain, fibromyalgia, menstrual pain, ovarialgia, reflex sympathetic dystrophy, osteoarthritis or rheumatoid arthritis pain, lower back pain, diabetic neuropathy, sciatica, dyspepsia, irritable bowel syndrome, inflammatory bowel disease, Crohn's disease, ileitis, ulcerative colitis, renal colic, dysmenorrhea, cystitis, interstitial cystitis, menstrual period, labor, menopause, pancreatitis, schizophrenia, depression, post-traumatic stress disorder, anxiety disorders, diabetes, autoimmune diabetes, endothelial dysfunction, ischemia, Raynaud's syndrome, coronary heart disease ("CHD"), coronary artery disease ("CAD"), heart failure, peripheral arterial disease ("PAD"), pulmonary hypertension ("PH"), connective tissue disorders, stroke, Sjögren's syndrome, multiple sclerosis, bronchial hyperreactivity, asthma, bronchitis, bronchodilation, emphysema, chronic obstructive pulmonary disease ("COPD"), inflammatory dermatitis, adenocarcinoma in glandular tissue, blastoma in embryonic tissue of organs, carcinoma in epithelial tissue, leukemia in tissues that form blood cells, lymphoma in lymphatic tissue, myeloma in bone marrow, sarcoma in connective or supportive tissue, adrenal cancer, AIDS-related lymphoma, anemia, bladder cancer, bone cancer, brain cancer, breast cancer, carcinoid tumors, cervical cancer, chemotherapy, colon cancer, cytopenia, endometrial cancer, esophageal cancer, gastric cancer, head cancer, neck cancer, hepatobiliary cancer, kidney cancer, leukemia, liver cancer, lung cancer, lymphoma, Hodgkin's disease, non-Hodgkin's, nervous system tumors, oral cancer, ovarian cancer, pancreatic cancer, prostate cancer, rectal cancer, skin cancer, stomach cancer, testicular cancer, thyroid cancer, urethral cancer, cancer of bone marrow, multiple myeloma, tumors that metastasize to the bone, tumors infiltrating the nerve and hollow viscus, tumors near neural structures. Further preferably the cancer pain comprises visceral pain, preferably visceral pain which arises from pancreatic cancer and/or metastases in the abdomen. Further preferably the cancer pain comprises somatic pain, preferably somatic pain due to one or more of metastasis in the bone, postsurgical pain, sarcomas cancer of the connective tissue, cancer of bone tissue, cancer of blood-forming cells of the bone marrow, multiple myeloma, leukemia, primary or secondary bone cancer, acne vulgaris, atopic dermatitis, urticaria, keloids, hypertrophic scars and rosacea, allergic dermatitis, psoriasis, pruritus, neurogenic cutaneous redness, erythema, weight loss, anorexia, sarcoidosis, shock, sepsis, opiate withdrawal syndrome, morphine tolerance, epilepsy, lower urinary tract ("LUT") disorders such as urinary tract infection, abnormal voiding, urinary urgency, nocturia, urinary incontinence, overactive bladder and for preventing or alleviating the pain associated with such LUT conditions. Preferably, the subject anti-PACAP antibodies and antigen binding fragments described herein are useful for ameliorating or reducing the symptoms of, treating, or preventing migraine, headache and a pain associated disease or condition.

In particular, the subject anti-PACAP antibodies and antigen binding fragments can also be useful for ameliorating or reducing the symptoms of, treating, or preventing photophobia, occurring with a headache and/or migraine as well as occurring independent of a headache and/or a migraine.

Migraineurs typically develop worsening pain and migraine symptoms when exposed to light, a phenomenon known as photophobia. Photophobia is also common in ocular disorders, such as iritis and uveitis, and intracranial disorders, such as meningitis. In the classic visual pathway, light activates rods and cones in the retina, which activate retinal ganglion cells that project via the optic nerve, to the lateral geniculate nucleus, superior colliculus, and then the visual cortex. This pathway includes image-forming and non-image-forming data. A new pathway (non-image-forming information) allows maintenance of normal circadian rhythms via the suprachiasmatic nucleus and is regulated by intrinsically photosensitive retinal ganglion cells (ipRGCs). These ipRGCs are independent of the rods and cones and contain melanopsin, a photopigment.

Noseda, R. et al., *Nat. Neurosci.,* 13:239-245 (2010) studied blind individuals who had migraine and correlated these findings with rat models involving tracing of ipRGC projections to areas in perception of pain from the dura. Of the blind patients with migraine, 6 had no light perception due to severe optic nerve damage or bilateral enucleation. These subjects experienced abnormal sleep patterns and poor pupillary light responses. Their migraines did not worsen with light exposure. In contrast, 14 blind subjects who were able to detect light despite minimal perception of images had normal sleep patterns and a normal pupillary light reflex. Despite widespread rod and cone degeneration, these patients had worsening migraine symptoms with light exposure during migraine attacks, suggesting that ipRGCs, and not rods and cones, are important in photophobia.

These retinal projections of non-image-forming brain areas project to the contralateral dorsocaudal region of the posterior thalamus, as demonstrated by anterograde tracing in the rat. ipRGC input to this area modulates dura-sensitive pain neurons, which also project to this region. Thalamic neurons, dually sensitive to dural pain and light input, project widely to multiple cortical regions, including the primary somatosensory cortex, the primary and secondary motor cortices, the parietal association cortex, and the primary and secondary visual cortices. These cortical projections may help explain other common migraine symptoms, in addition to photophobia, such as motor weakness or incoordination, visual disturbances, and poor concentration.

Photophobia also accompanies other less frequent but likewise disabling conditions, such as cluster headache and other trigeminal autonomic cephalalgias and blepharospasm. The mechanisms underlying photophobia involve the trigeminal system. Photophobia in blind patients suggests contributions from a nonvisual pathway. In addition, trigeminal autonomic cephalalgias, a less common group of primary headache disorders, are characterized by unilateral trigeminal-mediated pain frequently associated with ipsilateral photophobia.

Common causes of photophobia include migraine headaches, cataracts, or severe ophthalmologic diseases such as uveitis or corneal abrasion. A more extensive list of disorders associated with photophobia includes eye related causes such as achromatopsia, aniridia, anticholinergic drugs may cause photophobia by paralyzing the iris sphincter muscle, aphakia (absence of the lens of the eye), buphthalmos (abnormally narrow angle between the cornea and iris), cataracts, cone dystrophy, congenital abnormalities of the eye, viral conjunctivitis ("pink eye"), corneal abrasion, corneal dystrophy, corneal ulcer, disruption of the corneal epithelium, such as that caused by a corneal foreign body or keratitis, ectopia lentis, endophthalmitis, eye trauma caused by disease, injury, or infection such as chalazion, episcleritis, glaucoma, keratoconus, or optic nerve hypoplasia, hydrophthalmos, or congenital glaucoma iritis, optic neuritis, pigment dispersion syndrome, pupillary dilation (naturally or chemically induced), retinal detachment, scarring of the cornea or sclera and uveitis.

In addition, photophobia has nervous-system-related or neurological causes including: autism spectrum disorders, Chiari malformation, dyslexia, encephalitis including myalgic encephalomyelitis aka chronic fatigue syndrome, meningitis, subarachnoid hemorrhage, tumor of the posterior cranial fossa, as well as other causes such as ankylosing spondylitis, albinism, ariboflavinosis, benzodiazepines (long term use of or withdrawal from benzodiazepines), chemotherapy, chikungunya, cystinosis, Ehlers-Danlos syndrome, hangover, influenza, infectious mononucleosis, magnesium deficiency, mercury poisoning, migraine, rabies, and tyrosinemia type II, also known as "Richner-Hanhart syndrome".

Additionally, it is known that photophobia is elevated in depression, bipolar disorder and agoraphobia.

The subject anti-PACAP antibodies and antigen binding fragments described herein can be effective for treating or preventing photophobia in any of these conditions, preferably, in a subject with post-traumatic stress disorder ("PTSD") or in a subject with traumatic brain injury.

Headaches may be classified by cause, as discussed below.

Primary Headaches.

A primary headache is caused by problems with or overactivity of pain-sensitive structures in the head. A primary headache is generally not considered to be a symptom of an underlying disease. Instead, chemical activity in the brain, the nerves or blood vessels of the head outside the skull, or muscles of the head and neck, or some combination of these factors, may play a role in primary headaches. Some people may carry genes that make them more likely to develop such headaches. Exemplary common primary headaches include, but are not limited to, cluster headache; tension headache (or tension-type headache); and trigeminal autonomic cephalalgia ("TAC"), including paroxysmal hemicrania. There are other headache patterns that may be considered types of primary headache, e.g., chronic daily headaches, cough headaches, exercise headaches, and sex headaches. These headaches are less common and have distinct features, such as an unusual duration or pain associated with a certain activity. Although these headaches are generally considered primary, each of them could be a symptom of an underlying disease. Additionally, some primary headaches can be triggered by lifestyle factors, including: alcohol; certain foods (e.g., processed meats that contain nitrates); changes in sleep or lack of sleep; poor posture; skipped meals; and stress.

Secondary Headaches.

A secondary headache is a symptom of a disease that can activate the pain-sensitive nerves of the head. Any number of conditions, which can vary greatly in severity, may cause secondary headaches. Exemplary sources of secondary headaches include, but are not limited to, acute sinusitis; arterial tears (carotid or vertebral dissections); venous thrombosis in the brain; brain aneurysm; brain arteriovenous malformation; carbon monoxide poisoning; Chiari malformation; concussion; dehydration; dental problems; ear infection (middle ear); encephalitis; giant cell arteritis; glaucoma; hangovers; influenza (flu); intracranial hematoma; medications to treat other disorders; meningitis; monosodium glutamate ("MSG"); overuse of pain medication; panic attacks; post-concussion syndrome; pressure from tight-fitting headgear, e.g., helmet or goggles; pseudotumor cerebri; toxoplasmosis; and trigeminal neuralgia. Specific types of secondary headaches include, but are not limited to, external compression headaches (a result of pressure-causing headgear); ice cream headaches (commonly called "brain freeze"); rebound headaches (caused by overuse of pain medication); sinus headaches (caused by inflammation and congestion in sinus cavities); spinal headaches (caused by low levels of cerebrospinal fluid, possibly the result of trauma, spinal tap or spinal anesthesia); and thunderclap headaches (a group of disorders that involves sudden, severe headaches).

Exemplary, non-limiting pain associated diseases and disorders that can be treated and/or prevented by the administration of the anti-PACAP antibodies of the present invention include, pain resulting from any condition associated with neurogenic, neuropathic, inflammatory, or nociceptic pain. Preferably, the pain-associated disorder will be associated with increased PACAP at the pain site.

In certain embodiments, the pain associated disorder to be treated is cancer pain arising from malignancy or from cancer selected from one or more of: adenocarcinoma in glandular tissue, blastoma in embryonic tissue of organs, carcinoma in epithelial tissue, leukemia in tissues that form blood cells, lymphoma in lymphatic tissue, myeloma in bone marrow, sarcoma in connective or supportive tissue, adrenal cancer, AIDS-related lymphoma, anemia, bladder cancer, bone cancer, brain cancer, breast cancer, carcinoid tumors, cervical cancer, chemotherapy, colon cancer, cytopenia, endometrial cancer, esophageal cancer, gastric cancer, head cancer, neck cancer, hepatobiliary cancer, kidney cancer, leukemia, liver cancer, lung cancer, lymphoma, Hodgkin's disease, non-Hodgkin's, nervous system tumors, oral cancer, ovarian cancer, pancreatic cancer, prostate cancer, rectal cancer, skin cancer, stomach cancer, testicular cancer, thyroid cancer, urethral cancer, cancer of bone marrow, multiple myeloma, tumors that metastasize to the bone, tumors infiltrating the nerve and hollow viscus, tumors near neural structures. Further preferably the cancer pain comprises visceral pain, preferably visceral pain which arises from pancreatic cancer and/or metastases in the abdomen. Further preferably the cancer pain comprises somatic pain, preferably somatic pain due to one or more of metastasis in the bone, postsurgical pain, sarcomas cancer of the connective tissue, cancer of bone tissue, cancer of blood-forming cells of the bone marrow, multiple myeloma, leukemia, primary or secondary bone cancer.

In other embodiments, the pain associated condition to be treated is associated with neuropathic pain and included, by way of example, trigeminal neuralgia, post-herpetic neuralgia, phantom limb pain, fibromyalgia, and reflex sympathetic dystrophy are preferably treated.

Further exemplary pain associated diseases or conditions, include but are not limited to, general pain, chronic pain, inflammatory pain, post-operative incision pain, post-surgical pain, trauma-related pain, lower back pain, eye pain, tooth pain, complex regional pain syndrome, cancer pain (e.g., primary or metastatic bone cancer pain), fracture pain, osteoporotic fracture pain, pain resulting from burn, gout joint pain, pain associated with sickle cell crises, pain associated with temporomandibular disorders, cirrhosis, hepatitis, neurogenic pain, neuropathic pain, nociceptic pain, visceral pain, trigeminal neuralgia, post-herpetic neuralgia, phantom limb pain, fibromyalgia, menstrual pain, ovarialgia, reflex sympathetic dystrophy, osteoarthritis or rheumatoid arthritis pain, lower back pain, diabetic neuropathy, sciatica, dyspepsia, irritable bowel syndrome, inflammatory bowel disease, Crohn's disease, ileitis, ulcerative colitis, renal colic, dysmenorrhea, cystitis, interstitial cystitis, menstrual period, labor, menopause, pancreatitis, schizophrenia, depression, post-traumatic stress disorder, anxiety disorders, diabetes, autoimmune diabetes, endothelial dysfunction, ischemia, Raynaud's syndrome, coronary heart disease ("CHD"), coronary artery disease ("CAD"), heart failure, peripheral arterial disease ("PAD"), pulmonary hypertension ("PH"), connective tissue disorders, stroke, Sjögren's syndrome, multiple sclerosis, overactive bladder, bronchial hyperreactivity, asthma, bronchitis, bronchodilation, emphysema, chronic obstructive pulmonary disease ("COPD"), inflammatory dermatitis, acne vulgaris, atopic dermatitis, urticaria, keloids, hypertrophic scars and rosacea, allergic dermatitis, psoriasis, pruritus, neurogenic cutaneous redness, erythema, sarcoidosis, shock, sepsis, and opiate withdrawal syndrome.

Thus, the present invention includes methods of treating, preventing, and/or ameliorating any disease or disorder associated with PACAP activity or PACAP upregulation (including any of the above mentioned exemplary pain associated diseases, disorders and conditions) through use of the antibodies and antigen binding fragments of the invention.

Also, the subject PACAP antibodies and antigen binding fragments may be used alone or in conjunction with other active agents, e.g., opioids and non-opioid analgesics such as NSAIDs to elicit analgesia or to potentiate the efficacy of another analgesic.

The subject antibodies potentially may be combined with any opioid analgesic or NSAID or other analgesic, potentially another antibody or another biologic such as, e.g., an anti-NGF or anti-CGRP or anti-CGRP-R antibody or antibody fragment or NGF, CGRP or CGRP-R polypeptide fragment or conjugate, in order to increase or enhance pain management. This may allow for such analgesic compounds to be administered for longer duration or at reduced dosages thereby potentially alleviating adverse side effects associated therewith.

Of particular interest is the co-administration of the subject anti-PACAP antibodies and antibody fragments with an anti-CGRP antibody (e.g., ALD403) or an anti-CGRP-R antibody or antibody fragment and, moreover, the use of the subject anti-PACAP antibodies and antibody fragments to treat subjects that previously received an anti-CGRP or anti-CGRP-R antibody or antibody fragment. For example, the previously treated subject (who previously received at least one anti-CGRP or anti-CGRP-R antibody or antibody fragment administration) may be a migraineur who did not adequately respond to anti-CGRP or anti-CGRP-R antibody treatment ("poor responder") and/or has elicited an immune response to the anti-CGRP or anti-CGRP-R antibody or antibody fragment.

Likewise, the co-administration of the subject anti-PACAP antibodies and antigen binding fragments with BOTOX® (Botulinum toxin) is also of particular interest, e.g., in treating a migraineur. In some instances, the migraineur may not have adequately responded to previous treatments ("poor responder") and/or has elicited an immune response to the previous treatment.

In some embodiments, aspirin and/or acetaminophen may be taken in conjunction with the subject anti-PACAP antibody or antigen binding fragment. Aspirin is another type of non-steroidal anti-inflammatory compound.

The subject to which the pharmaceutical formulation is administered can be, e.g., any human or non-human animal that is in need of such treatment, prevention and/or amelioration, or who would otherwise benefit from the inhibition or attenuation of PACAP-mediated activity. For example, the subject can be an individual that is diagnosed with, or who is deemed to be at risk of being afflicted by any of the aforementioned diseases or disorders. The present invention further includes the use of any of the pharmaceutical formulations disclosed herein in the manufacture of a medicament for the treatment, prevention and/or amelioration of any disease or disorder associated with PACAP activity (including any of the above mentioned exemplary diseases, disorders and conditions).

Administration

In one embodiment of the invention, the anti-PACAP antibodies described herein, or PACAP binding fragments thereof, as well as combinations of said antibodies or antigen binding fragments thereof, are administered to a subject at a concentration of between 0.1 mg/ml and about any one of 0.5, 1, 5, 10, 15 20, 25, 30, 35, 40, 45, 50, 55, 60, 65, 70, 75, 80, 85, 90, 95, 100, 110, 120, 130, 140, 150, 160, 170, 180, 190, or 200 mg/ml, +/−10% error.

In another embodiment of the invention, the anti-PACAP antibodies and fragments thereof described herein are administered to a subject at a dose of between about 0.01 and 100.0 or 200.0 mg/kg of body weight of the recipient subject. In certain embodiments, depending on the type and severity of the PACAP-related disease, about 1 μg/kg to 50 mg/kg (e.g., 0.1-20 mg/kg) of antibody is an initial candidate dosage for administration to the patient, whether, for example, by one or more separate administrations, or by continuous infusion. In another embodiment, about 1 μg/kg to 15 mg/kg (e.g., 0.1 mg/kg-10 mg/kg) of antibody is an initial candidate dosage for administration to the patient. A typical daily dosage might range from about 1 μg/kg to 100 mg/kg or more, depending on several factors, e.g., the particular mammal being treated, the clinical condition of the individual patient, the cause of the disorder, the site of delivery of the agent, the method of administration, the scheduling of administration, and other factors known to medical practitioners. However, other dosage regimens may be useful.

For example, in addition to the relative dosages (mg/kg) discussed herein, the subject anti-PACAP antibodies and antigen binding fragments thereof can be administered to a subject at an absolute dose (mg). Accordingly, in one embodiment of the invention, the anti-PACAP antibodies and antigen binding fragments thereof described herein are administered to a subject at a dose of between about 1 microgram and about 1000 milligrams regardless of the route of administration.

In a preferred embodiment of the invention, the anti-PACAP antibodies described herein, or anti-PACAP antigen binding fragments thereof, as well as combinations of said antibodies or antigen binding fragments thereof, are administered to a recipient subject with a frequency of once every twenty-six weeks or less, such as once every sixteen weeks or less, once every eight weeks or less, once every four weeks or less, once every two weeks or less, once every week or less, or once daily or less.

According to preferred embodiments, the antibody containing medicament or pharmaceutical composition is peripherally administered to a subject via a route selected from one or more of: orally, sublingually, buccally, topically, rectally, via inhalation, transdermally, subcutaneously, intravenously, intra-arterially, or intramuscularly, via intracardiac administration, intraosseously, intradermally, intraperitoneally, transmucosally, vaginally, intravitreally, epicutaneously, intra-articularly, peri-articularly, or locally.

Fab fragments may be administered every two weeks or less, every week or less, once daily or less, multiple times per day, and/or every few hours. In one embodiment of the invention, a patient receives Fab fragments of 0.1 mg/kg to 40 mg/kg per day given in divided doses of 1 to 6 times a day, or in a continuous perfusion form, effective to obtain desired results.

It is to be understood that the concentration of the antibody or Fab administered to a given patient may be greater or lower than the exemplary administration concentrations set forth above.

A person of skill in the art would be able to determine an effective dosage and frequency of administration through routine experimentation, for example guided by the disclosure herein and the teachings in, *Goodman & Gilman's The Pharmacological Basis of Therapeutics*, Brunton, L. L. et al. editors, $11^{th}$ edition, New York, New York: McGraw-Hill (2006); Howland, R. D. et al., *Pharmacology, Volume* 864, *Lippincott's illustrated reviews*., Philadelphia, PA: Lippincott Williams & Wilkins (2006); and Golan, D. E., *Principles of pharmacology: the pathophysiologic basis of drug therapy*, Philadelphia, PA: Lippincott Williams & Wilkins (2007).

In another embodiment of the invention, the anti-PACAP antibodies described herein, or PACAP binding fragments thereof, as well as combinations of said antibodies or antigen binding fragments thereof, are administered to a subject in a pharmaceutical formulation. In a preferred embodiment, the subject is a human.

A "pharmaceutical composition" or "medicament" refers to a chemical or biological composition suitable for administration to a subject, preferably a mammal, more preferably a human. Such compositions may be specifically formulated for administration via one or more of a number of routes, including but not limited to buccal, epicutaneous, epidural, inhalation, intraarterial, intracardial, intracerebroventricular, intradermal, intramuscular, intranasal, intraocular, intraperitoneal, intraspinal, intrathecal, intravenous, oral, parenteral, rectally via an enema or suppository, subcutaneous, subdermal, sublingual, transdermal, and transmucosal. In addition, administration can occur by means of injection, powder, liquid, gel, drops, or other means of administration.

In one embodiment of the invention, the anti-PACAP antibodies described herein, or PACAP binding fragments thereof, as well as combinations of said antibodies or antigen binding fragments thereof, may be optionally administered in combination with one or more active agents. Such active agents include analgesic, anti-histamine, antipyretic, anti-inflammatory, antibiotic, antiviral, and anti-cytokine agents. Active agents include agonists, antagonists, and modulators of TNF-α, IL-2, IL-4, IL-6, IL-10, IL-12, IL-13, IL-18, IFN-α, IFN-γ, BAFF, CXCL13, IP-10, VEGF, EPO, EGF, HRG, Hepatocyte Growth Factor ("HGF"), Hepcidin, NGF, CGRP including antibodies reactive against any of the foregoing, and antibodies reactive against any of their receptors. Active agents also include but are not limited to 2-arylpropionic acids, aceclofenac, acemetacin, acetylsalicylic acid (aspirin), alclofenac, alminoprofen, amoxiprin, ampyrone, arylalkanoic acids, azapropazone, benorylate/benorilate, benoxaprofen, bromfenac, carprofen, celecoxib, choline magnesium salicylate, clofezone, COX-2 inhibitors, dexibuprofen, dexketoprofen, diclofenac, diflunisal, droxicam, ethenzamide, etodolac, etoricoxib, faislamine, fenamic acids, fenbufen, fenoprofen, flufenamic acid, flunoxaprofen, flurbiprofen, ibuprofen, ibuproxam, indomethacin, indoprofen, kebuzone, ketoprofen, ketorolac, lornoxicam, loxoprofen, lumiracoxib, magnesium salicylate, meclofenamic acid, mefenamic acid, meloxicam, metamizole, methyl salicylate, mofebutazone, nabumetone, naproxen, N-arylanthranilic acids, NGF, oxametacin, oxaprozin, oxicams, oxyphenbutazone, oxytocin, parecoxib, phenazone, phenylbutazone, phenylbutazone, piroxicam, pirprofen, profens, proglumetacin, pyrazolidine derivatives, rofecoxib, salicyl salicylate, salicylamide, salicylates, substance P, sulfinpyrazone, sulindac, suprofen, tenoxicam, tiaprofenic acid, tolfenamic acid, tolmetin, and valdecoxib. For instance, the selected anti-PACAP antibodies, or PACAP-binding fragments thereof, as well as combinations of these antibodies or antigen binding fragments, can be optionally administered in combination with oxytocin, for instance administered in a nasal formulation, for intranasal delivery.

An anti-histamine can be any compound that opposes the action of histamine or its release from cells (e.g., mast cells). Anti-histamines include but are not limited to acrivastine, astemizole, azatadine, azelastine, betatastine, brompheniramine, buclizine, cetirizine, cetirizine analogues, chlorpheniramine, clemastine, CS 560, cyproheptadine, desloratadine, dexchlorpheniramine, ebastine, epinastine, fexofenadine, HSR 609, hydroxyzine, levocabastine, loratadine, methscopolamine, mizolastine, norastemizole, phenindamine, promethazine, pyrilamine, terfenadine, and tranilast.

Antibiotics include but are not limited to amikacin, aminoglycosides, amoxicillin, ampicillin, ansamycins, arsphenamine, azithromycin, azlocillin, aztreonam, bacitracin, carbacephem, carbapenems, carbenicillin, cefaclor, cefadroxil, cefalexin, cefalothin, cefalotin, cefamandole, cefazolin, cefdinir, cefditoren, cefepime, cefixime, cefoperazone, cefotaxime, cefoxitin, cefpodoxime, cefprozil, ceftazidime, ceftibuten, ceftizoxime, ceftobiprole, ceftriaxone, cefuroxime, cephalosporins, chloramphenicol, cilastatin, ciprofloxacin, clarithromycin, clindamycin, cloxacillin, colistin, co-trimoxazole, dalfopristin, demeclocycline, dicloxacillin, dirithromycin, doripenem, doxycycline, enoxacin, ertapenem, erythromycin, ethambutol, flucloxacillin, fosfomycin, furazolidone, fusidic acid, gatifloxacin, geldanamycin, gentamicin, glycopeptides, herbimycin, imipenem, isoniazid, kanamycin, levofloxacin, lincomycin, linezolid, lomefloxacin, loracarbef, macrolides, mafenide, meropenem, methicillin, metronidazole, mezlocillin, minocycline, monobactams, moxifloxacin, mupirocin, nafcillin, neomycin, netilmicin, nitrofurantoin, norfloxacin, ofloxacin, oxacillin, oxytetracycline, paromomycin, penicillin, penicillins, piperacillin, platensimycin, polymyxin B, polypeptides, prontosil, pyrazinamide, quinolones, quinupristin, rifampicin, rifampin, roxithromycin, spectinomycin, streptomycin, sulfacetamide, sulfamethizole, sulfanilamide, sulfasalazine, sulfisoxazole, sulfonamides, teicoplanin, telithromycin, tetracycline, tetracyclines, ticarcillin, tinidazole, tobramycin, trimethoprim, trimethoprim-sulfamethoxazole, troleandomycin, trovafloxacin, and vancomycin.

Active agents also include aldosterone, beclomethasone, betamethasone, corticosteroids, cortisol, cortisone acetate, deoxycorticosterone acetate, dexamethasone, fludrocortisone acetate, glucocorticoids, hydrocortisone, methylprednisolone, prednisolone, prednisone, steroids, and triamcinolone. Any suitable combination of these active agents is also contemplated.

A "pharmaceutical excipient" or a "pharmaceutically acceptable excipient" is a carrier, usually a liquid, in which an active therapeutic agent is formulated. In one embodiment of the invention, the active therapeutic agent is a humanized antibody described herein, or one or more fragments thereof. The excipient generally does not provide any pharmacological activity to the formulation, though it may provide chemical and/or biological stability, and release characteristics. Exemplary formulations can be found, for example, in *Remington's Pharmaceutical Sciences*, Gennaro, A. editor, $19^{th}$ edition, Philadelphia, PA: Williams and Wilkins (1995), which is incorporated by reference.

As used herein "pharmaceutically acceptable carrier" or "excipient" includes any and all solvents, dispersion media, coatings, antibacterial and antifungal agents, isotonic, and absorption delaying agents that are physiologically compatible. In one embodiment, the carrier is suitable for parenteral administration. Alternatively, the carrier can be suitable for intravenous, intraperitoneal, intramuscular, or sublingual administration. Pharmaceutically acceptable carriers include sterile aqueous solutions or dispersions and sterile powders for the extemporaneous preparation of sterile injectable solutions or dispersions. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

Pharmaceutical compositions typically must be sterile and stable under the conditions of manufacture and storage. The invention contemplates that the pharmaceutical composition is present in lyophilized form. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol), and suitable mixtures thereof. The invention further contemplates the inclusion of a stabilizer in the pharmaceutical composition. The proper fluidity can be maintained, for example, by the maintenance of the required particle size in the case of dispersion and by the use of surfactants.

In many cases, it will be preferable to include isotonic agents, for example, sugars, polyalcohols such as mannitol and sorbitol, or sodium chloride in the composition. Absorption of the injectable compositions can be prolonged by including an agent that delays absorption, for example, monostearate salts and gelatin. Moreover, the alkaline polypeptide can be formulated in a time-release formulation, for example in a composition that includes a slow release polymer. The active compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid, polylactic and polyglycolic copolymers ("PLG"). Many methods for the preparation of such formulations are known to those skilled in the art.

For each of the recited embodiments, the compounds can be administered by a variety of dosage forms. Any biologically acceptable dosage form known to persons of ordinary skill in the art, and combinations thereof, are contemplated. Examples of such dosage forms include, without limitation, reconstitutable powders, elixirs, liquids, solutions, suspensions, emulsions, powders, granules, particles, microparticles, dispersible granules, cachets, inhalants, aerosol inhalants, patches, particle inhalants, implants, depot implants, injectables (including subcutaneous, intramuscular, intravenous, and intradermal), infusions, and combinations thereof.

The above description of various illustrated embodiments of the invention is not intended to be exhaustive or to limit the invention to the precise form disclosed. While specific embodiments of, and examples for, the invention are described herein for illustrative purposes, various equivalent modifications are possible within the scope of the invention, as those skilled in the relevant art will recognize. The teachings provided herein of the invention can be applied to other purposes, other than the examples described above.

These and other changes can be made to the invention in light of the above detailed description. In general, in the following claims, the terms used should not be construed to limit the invention to the specific embodiments disclosed in the specification and the claims. Accordingly, the invention is not limited by the disclosure, but instead the scope of the invention is to be determined entirely by the following claims.

The invention may be practiced in ways other than those particularly described in the foregoing description and examples. Numerous modifications and variations of the invention are possible in light of the above teachings and, therefore, are within the scope of the appended claims.

Certain teachings related to methods for obtaining a clonal population of antigen-specific B-cells were disclosed in U.S. Patent Publication No. US2013/0316353, the disclosure of which is herein incorporated by reference in its entirety.

Certain teachings related to humanization of rabbit-derived monoclonal antibodies and preferred sequence modifications to maintain antigen-binding affinity were disclosed in International Publication No. WO 2008/144757, entitled Novel Rabbit Antibody Humanization Methods and Humanized Rabbit Antibodies, filed May 21, 2008, the disclosure of which is herein incorporated by reference in its entirety.

Certain teachings related to producing antibodies or fragments thereof using mating competent yeast and corresponding methods were disclosed in U.S. Patent Publication No. US2006/0270045, the disclosure of which is herein incorporated by reference in its entirety.

Certain teachings related to producing antibodies or fragments thereof in *Pichia* and preferred methods for obtaining and purifying antibodies are also disclosed in U.S. Patent Publication Nos. 2014/0288272; 2014/0287952; 2013/0055888; and 2012/0277408, the disclosures of each of which are herein incorporated by reference in their entirety.

Certain teachings related to producing antibodies or fragments thereof in CHO cells and exemplary methods for obtaining and purifying antibodies are also disclosed in U.S. Pat. and Publication Nos. 7,932,087; 2009/0285795; 9,090,672; and 2010/0221781; the disclosures of each of which are herein incorporated by reference in their entirety.

Certain anti-PACAP antibody polynucleotides and polypeptides are disclosed in the sequence listing accompanying this patent application filing, and the disclosure of said sequence listing is herein incorporated by reference in its entirety.

The entire disclosure of each document cited (including patents, patent applications, journal articles, abstracts, manuals, books, or other disclosures) in the Background of the Invention, Detailed Description, and Examples is herein incorporated by reference in their entireties.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.), but some experimental errors and deviations should be allowed for. Unless otherwise indicated, parts are parts by weight, molecular weight is average molecular weight, temperature is in degrees centigrade; and pressure is at or near atmospheric.

EXAMPLES

Example 1: Preparation of Antibodies that Selectively Bind PACAP

By using an antibody selection protocol substantially as described herein, a panel of antibodies specific to PACAP38 and PACAP27, and a panel of antibodies specific to PACAP38 only, were produced.

Immunization Strategy

Rabbits were immunized with PACAP38 (American Peptide, Vista, CA) (SEQ ID NO: 1241). Peptides were prepared for immunization as follows. A 0.15 ml volume of 10 mg/ml keyhole limpet hemocyanin ("KLH") dissolved in Dulbecco's phosphate buffered saline ("DPBS") supplemented to 1M NaCl was combined with 1.0 ml of 1 mg/ml peptide (dissolved in deionized water). Then 1.0 ml of 40 mM carbodiimide was added prior to a 12-hour incubation at room temperature with gentle mixing. Excess carbodiimide and unconjugated peptide were removed by dialysis to DPBS prior to sterile filtration. Next unconjugated peptide equal to the initial mass of KLH was added prior to preparation for injection into rabbits. Alternatively, equal masses of sterile KLH and peptide were mixed without carbodiimide chemistry.

Immunizations were performed by diluting 200 μg of antigen to 0.5 ml with DPBS and mixing with an equal volume of complete Freund's adjuvant for subcutaneous 1 ml injection at Day 1.

Boost injections of 100 μg were performed with incomplete Freund's adjuvant at Days 21 and 42.

Antibody Selection Functional Titer Assessment

To identify antibodies that neutralize PACAP38 (SEQ ID NO: 1241) induced signaling via PAC1-R, polyclonal antibody solutions were first purified via Protein A and dialyzed into a neutral buffer. Briefly, antibody solutions were incubated with PACAP38 (SEQ ID NO: 1241) at 4× the final concentration (100 pM) for 1 hr. While the antibody/antigen complexes were incubated, PAC1-R expressing PC-12 cells (Japanese Collection of Research Bioresources Cell Bank) were washed and re-suspended at $2\times10^6$ cells per ml in cell culture media. Cells (10 μl) and antigen/antibody complex (40 μl) were transferred to a homogenous time resolved fluorescence ("HTRF") plate and shaken at room temperature for 30 min. Following the incubation, 20 μl of (1:20 diluted) $Eu^{3+}$ cryptate-labeled mAb anti-cAMP and 20 μl of (1:20 diluted) d2-labeled cAMP in lysis buffer were added, and the plate was incubated for 1 hr while shaking. Following incubation, plates were read (excitation 330 nm, emission 620/665 nm), and a ratio of 620:665 signal was determined.

Tissue Harvesting

Once acceptable titers were established, the rabbit(s) were sacrificed. Spleen, lymph nodes, and whole blood were harvested and processed as follows:

Spleen and lymph nodes were processed into a single cell suspension by disassociating the tissue and pushing through sterile wire mesh at 70 μm (Thermo Fisher Scientific, Waltham, MA) with a plunger of a 20 cc syringe. Cells were collected in phosphate buffered saline ("PBS"). Cells were then washed twice by centrifugation. After the last wash, cell density was determined by trypan blue. Cells were centrifuged at 1500 RPM for 10 minutes; the supernatant was then discarded. Cells were resuspended in the appropriate volume of 10% dimethyl sulfoxide ("DMSO", Sigma-Aldrich Co., St. Louis, MO) in fetal bovine serum ("FBS" HYCLONE™, GE Healthcare Life Sciences, Marlborough, MA) and dispensed at 1 ml/vial. Vials were stored at −70° C. in a slow freezing chamber for 24 hours and stored in liquid nitrogen.

Peripheral blood mononuclear cells ("PBMCs") were isolated by mixing whole blood with equal parts of PBS. 35 ml of the whole blood mixture was carefully layered onto 8 ml of LYMPHOLYTE® Rabbit (Cedarlane Laboratories, Burlington, Ontario) into a 45 ml conical tube (Corning, Corning, NY) and centrifuged for 30 minutes at 2500 RPM at room temperature without brakes. After centrifugation, the PBMC layers were carefully removed using a glass Pasteur pipette (VWR International, Radnor, PA), combined, and placed into a clean 50 ml vial. Cells were washed twice with PBS by centrifugation at 1500 RPM for 10 minutes at room temperature, and cell density was determined by trypan blue staining. After the last wash, cells were resuspended in an appropriate volume of 10% DMSO/FBS medium and frozen as described above.

B-Cell Selection, Enrichment, and Culture Conditions

On the day of setting up B-cell culture, PBMC, splenocyte, or lymph node vials were thawed for use. Vials were removed from liquid nitrogen tank and placed in a 37° C. water bath until thawed. Contents of vials were transferred into 15 ml conical centrifuge tube (Corning, Inc., Corning, NY) and 10 ml of modified RPMI was slowly added to the tube. Cells were centrifuged for 5 minutes at 2000 RPM, and the supernatant was discarded. Cells were resuspended in 10 ml of fresh media. Cell density and viability was determined by trypan blue.

For positive selection of anti-PACAP38 producing B-cells, biotinylated PACAP38 (SEQ ID NO: 1241) was pre-loaded onto the streptavidin beads as follows. 75 μl of streptavidin beads (Miltenyi Biotec, Auburn, CA) were mixed with N-terminally biotinylated PACAP38 (10 μg/ml final concentration) and 300 μl of PBS supplemented with 0.5% biotin free bovine serum albumin ("BSA") and 2 mM EDTA ("PBF"). This mixture was incubated at 4° C. for 30 minutes, and unbound biotinylated PACAP38 (AnaSpec, Fremont, CA) was removed using a MACS® separation column (Miltenyi Biotec, Auburn, CA) with a 1 ml rinse to remove unbound material. The bound material was plunged out by detachment from the magnet and used to resuspend cells from above in 100 μl per $1\times10^7$ cells. The mixture was then incubated at 4° C. for 30 minutes and washed once with 10 ml of PBF. After washing, the cells were resuspended in 500 μl of PBF and set aside. A MACS® MS column (Miltenyi Biotec, Auburn, CA) was pre-rinsed with 500 μl of PBF on a magnetic stand (Miltenyi Biotec, Auburn, CA). Cell suspension was applied to the column through a pre-filter, and unbound fraction was collected. The column was washed with 2.5 ml of PBF buffer. The column was removed from the magnet stand and placed onto a clean, sterile 1.5 ml EPPENDORF™ tube. 1 ml of PBF buffer was added to the top of the column, and positive selected cells were collected. The yield and viability of positive cell fraction was determined by trypan blue staining. Positive selection yielded an average of 1% of the starting cell concentration.

A pilot cell screen was established to provide information on seeding levels for the culture. Plates were seeded at 5, 10, 25, 50, 100, or 200 enriched B-cells/well. In addition, each well contained 25-50K cells/well of irradiated EL-4.B5 cells (5,000 Rads) and an appropriate level of activated rabbit T-cell supernatant (See U.S. Patent Application Publication No. 20070269868) (ranging from 1-5% depending on preparation) in high glucose modified RPMI medium at a final volume of 250 μl/well. Cultures were incubated for 5 to 7 days at 37° C. in 4% $CO_2$.

B-Cell Culture Screening by Antigen-Recognition (ELISA)

To identify wells producing anti-PACAP38 antibodies, B-cell supernatants were tested by antigen-recognition (ELISA). Briefly, NEUTRAVIDIN™-coated plates (Thermo Fisher Scientific, Waltham, MA), were coated with either N-term or C-term biotinylated PACAP38 (AnaSpec Inc., Fremont, CA) (50 μl per well; 1 μg/ml) diluted in ELISA buffer (0.5% fish skin gelatin in PBS pH 7.4) either for approximately 1 hour at room temperature or alternatively overnight at 4° C. The plates were then further blocked with ELISA buffer for one hour at room temperature and washed using PBS with 0.05% Tween 20 ("wash buffer"). B-cell supernatant samples (50 μl) were transferred onto the wells and incubated for one hour at room temperature. After this incubation, the plate was washed with wash buffer. For development, an anti-rabbit specific Fc-Horse Radish Peroxidase ("Fc-HRP") (1:5000 dilution in ELISA buffer) was added onto the wells and incubated for 45 minutes at room temperature. After a 3× wash step with wash solution, the plate was developed using 3,3',5,5'-Tetramethylbenzidine ("TMB") substrate for two minutes at room temperature, and the reaction was quenched using 0.5M HCl. The well absorbance was read at 450 nm.

To identify wells producing anti-PACAP38 antibodies that do not recognize VIP (SEQ ID NO: 1243), supernatant from wells positive for PACAP38 binding by ELISA were tested by ELISA for binding to VIP. Briefly, biotinylated VIP (AnaSpec Inc., Fremont, CA) was bound onto NEUTRAVIDIN™ coated plates (50 μg per well, 1 μg/μl each peptide). B-cell supernatant samples (50 μl) were tested without prior dilution. Recognition in this assay may indicate cross reactivity with a closely related peptide, VIP.

Identification of Functional Activity in B-Cell Supernatants Using One or More Assays To identify wells producing anti-PACAP38 antibodies that block signaling of PACAP38 via PAC1-R, supernatant from positive wells for PACAP38 binding by ELISA were tested in a cAMP HTRF assay (Cisbio US, Bedford, MA). Supernatants (78 μl) were pre-incubated with 2 μl 5 nM PACAP38 (American Peptide Company, Sunnyvale, CA) for 1 hour at 37° C. During the incubation, PC-12 cells were prepared as described for titer assessment. Cells (10 μl) and antigen/antibody complex (40 μl) were transferred to an HTRF plate and shaken at room temperature for 30 minutes. Following the incubation, 20 μl of (1:20 diluted) $Eu^{3+}$ cryptate-labeled mAb anti-cAMP and 20 μl of (1:20 diluted) d2-labeled cAMP in lysis buffer were added, and the plate was incubated for 1 hour while shaking. Following incubation plates were read (excitation 330 nm, emission 620/665 nm), and a ratio of 620:665 signal was determined.

Isolation of Antigen-Specific B-Cells

Antigen-specific B-cells were isolated (for general methods see co-owned publication no. WO 2014/146074, which is hereby incorporated by reference in its entirety). Plates containing wells of interest were removed from −70° C., and the cells from each well were recovered using five washes of 200 μl of medium (10% RPMI complete, 55 μM β-mercaptoethanol ("BME")) per well. The recovered cells were pelleted by centrifugation and the supernatant was carefully removed. Cells from each well were then re-suspended in 100 μl of medium and transferred to a 96 well plate. Cells were incubated for 90 minutes at 37° C. Following incubation, cells were pelleted by centrifugation, stained with a fluorescein isothiocyanate-labeled ("FITC-labeled") anti-rabbit IgG (final concentration 6.25 μg/ml) (Creative Diagnostics, Shirley, NY), and washed with up to 2 ml fluorescence-activated cell sorting buffer ("FACS buffer") (Dulbecco's PBS w/2% FBS) and re-suspended in 250 μl of FACS buffer.

Control wells from the same culture sets that were similar in composition to pooled wells of interest were thawed and stained alongside target wells. These samples were initially run on FACS (BD INFLUX™, Becton, Dickinson and Company, Franklin Lakes, NJ), and gates were established for IgG, viability, and physical parameters (Forward scatter ("FSC")/side scatter ("SSC")) that differentiate B-cells from the murine EL4 cells. Once gates were established, the sample of interest was run, and IgG positive, viable cells that were of a consistent physical (FSC/SSC) population were sorted individually into wells of a 96 well plate pre-loaded with RT-PCR master mix. Upwards of 8 cells per well were sorted. Sorted plates were removed from the sorter and transferred directly to thermocyclers for PCR.

Amplification and Sequence Determination of Antibody Sequences from FACS-Sorted B-Cells Antibody sequences were recovered using a combined RT-PCR based method from a single cell sorted B-cell. Primers containing restriction enzymes were designed to anneal in conserved and constant regions of the target immunoglobulin genes (heavy and light), such as rabbit immunoglobulin sequences, and a two-step nested PCR recovery was used to amplify the antibody sequence. Amplicons from each well were sequenced and analyzed. Representative antibodies from the resulting sequence clusters were selected for recombinant protein expression. The original heavy and light variable regions amplified from rabbit cells were cloned into human heavy and light chain constant region expression vectors via restriction enzyme digestion and ligation, and via Gibson method. Vectors containing subcloned DNA fragments were amplified and purified. The sequences of the subcloned heavy and light chains were verified prior to expression.

Recombinant Production of Monoclonal Antibody of Desired Antigen Specificity and/or Functional Properties To determine antigen specificity and functional properties of recovered antibodies from specific B-cells, the heavy and light chain plasmids were co-transfected to generate rabbit/human chimeric antibodies for testing. Briefly, heavy and light chimeric plasmids were transiently transfected into HEK-293 cells. Transfections were allowed to incubate for 5-7 days, and upon harvest, cells were pelleted by centrifugation. Supernatants were submitted for purification via Protein A. Resulting purified chimeric antibodies were then evaluated in a variety of assays to confirm specificity and potency.

Using the above-described methods, numerous functional (antagonistic) antibodies that bind PACAP38 and PACAP27, or that bind PACAP38 only, but which do not, or do not appreciably, bind to VIP were identified. Polypeptide and exemplary coding sequences of exemplary antagonistic anti-PACAP antibodies are contained in the included biological sequence listing.

The full-length antibodies Ab1, Ab1.H, Ab2, Ab13, Ab14, Ab15, Ab16, Ab17, Ab18, Ab19, Ab5, Ab7, Ab11, Ab12, Ab4, Ab3, Ab6, Ab8, and Ab9 used in these examples were expressed as the heavy chain polypeptides having the sequences of SEQ ID NOS: 1; 41; 81; 121; 161; 201; 241; 281; 321; 361; 481; 521; 561; 601; 641; 681; 721; 761; and 801, respectively, and the light chain polypeptides of SEQ ID NOS: 21; 61; 101; 141; 181; 221; 261; 301; 341; 381; 501; 541; 581; 621; 661; 701; 741; 781; 821, respectively. The heavy chain polypeptides of antibodies Ab1, Ab1.H, Ab2, Ab13, Ab14, Ab15, Ab16, Ab17, Ab18, Ab19, Ab5, Ab7, Ab11, Ab12, Ab4, Ab3, Ab6, Ab8, and Ab9 were expressed from the polynucleotides of SEQ ID NOS: 11; 51; 91; 131; 171; 211; 251; 291; 331; 371; 491; 531; 571; 611; 651; 691; 731; 771; 811, respectively. The light chain polypeptides of antibodies Ab1, Ab1.H, Ab2, Ab13, Ab14, Ab15, Ab16, Ab17, Ab18, Ab19, Ab5, Ab7, Ab11, Ab12, Ab4, Ab3, Ab6, Ab8, and Ab9 were expressed from the polynucleotides of SEQ ID NOS: 31; 71; 111; 151; 191; 231; 271; 311; 351 391; 511; 551; 591; 631; 671; 711; 751; 791; and 831, respectively. Additional features of said antibodies are identified by SEQ ID NOS in FIGS. 1-12.

Antigen Binding Specificity of Antibodies by Competitive HTRF Binding Assay

The binding and functional properties of exemplary anti-PACAP38 and anti-PACAP27 antibodies produced according to the invention are further described below.

To identify antibodies that preferentially bind PACAP38 (SEQ ID NO: 1241) and PACAP27 (SEQ ID NO: 1242), but do not bind VIP (SEQ ID NO: 1243), or to identify antibodies that specifically bind PACAP38, but do not bind appreciably PACAP27, or do not appreciably bind VIP, etc., a competition HTRF binding assay was performed.

In parallel, 10 μl of an antibody dilution series (highest final concentration of 100 nM) were incubated with 10 μl of N-terminal or C-terminal biotinylated PACAP38 (35 nM final) alone, or in combination with either PACAP27 (350 nM final) or VIP (350 nM final), i.e., 10×PACAP27 or 10×VIP, respectively, in a HTRF plate. 20 μl of $Eu^{3+}$ cryptate labeled anti-hu Fc donor and 20 μl of d2-labeled streptavidin acceptor were added to each well and incubated for 1 hour at room temperature. Fluorescence was measured at 620 and 665 nm with a delay of 300 μsec.

Binding data were obtained based on experiments assaying the binding of the subject anti-PACAP antibodies to PACAP38 and to PACAP27. These binding curve data showed that VIP is unable to effectively compete with binding of PACAP38. The lack of effect of VIP on binding to PACAP38 indicated its inability to compete with binding of PACAP38. These results demonstrated that Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, and Ab1.H bind to PACAP38 and PACAP27, but do not bind (or do not appreciably bind) VIP. These results also demonstrated that Ab22 and Ab23 bind to PACAP38, but do not bind (or do not appreciably bind) PACAP27 or VIP.

$EC_{50}$ values, i.e. the concentration of an antibody that yields a response halfway between the baseline and the maximum value within a specified time period, were computed for each antibody based upon their binding curves and are shown in Table 1 below. The results demonstrated that Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab22, Ab23, and Ab1.H bound to and recognized human PACAP38 with high affinity. A humanized form of antibody Ab1 was produced and is identified by an appended ".H", i.e., Ab1.H also bound PACAP38 with high affinity.

TABLE 1

Binding ($EC_{50}$) of PACAP38 by anti-PACAP antibodies

| ANTIBODY | PACAP38-binding $EC_{50}$ (nM) |
|---|---|
| Ab1 | 0.43 |
| Ab2 | 0.35 |
| Ab3 | 0.45 |
| Ab4 | 0.66 |
| Ab5 | 0.60 |
| Ab6 | 0.50 |
| Ab7 | 0.45 |
| Ab8 | 0.48 |
| Ab9 | 0.23 |
| Ab10 | 0.36 |
| Ab11 | 0.53 |
| Ab12 | 0.51 |
| Ab13 | 0.48 |
| Ab14 | 0.57 |
| Ab15 | 0.62 |
| Ab16 | 0.68 |
| Ab17 | 0.46 |
| Ab18 | 0.48 |
| Ab19 | 0.43 |
| Ab1.H | 0.46 |
| Ab22 | 0.57 |
| Ab23 | 0.56 |

Ability of Anti-PACAP Antibodies to Neutralize PACAP38-Induced and PACAP27-Induced cAMP Production The ability of anti-PACAP antibodies to neutralize PACAP38-induced and PACAP27-induced PAC1-R signaling was tested in a cell-based assay.

For Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab22, Ab23, Ab1.H, Ab10.H, Ab3.H, Ab4.H, Ab5.H, Ab9.H and Ab12.H, to identify antibodies that neutralized PACAP38-induced and PACAP27-induced signaling via PAC1-R, antibody solutions were incubated with either PACAP38 or with PACAP27 at 4× the final concentration (100 pM) for 1 hour. While the antibody/antigen complexes were incubated, PAC1-R expressing PC-12 cells (Japanese Collection of Research Bioresources Cell Bank) were washed and re-suspended at $2\times10^6$ cells per ml in cell culture media. Cells (10 μl) and antigen/antibody complex (40 μl) were transferred to an HTRF plate and shaken at room temperature for 30 minutes. Following the incubation, 20 μl of (1:20 diluted) $Eu^{3+}$ cryptate-labeled mAb anti-cAMP and 20 μl of (1:20 diluted) d2-labeled cAMP in lysis buffer were added, and the plate was incubated for 1 hour while shaking. Following incubation, plates were read (excitation 330 nm, emission 620/665 nm), and a ratio of 620:665 signal was determined. The final concentration of PACAP38 and PACAP27 in each well was 0.1 nM.

Inhibition curves were obtained for Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab1.H, Ab10.H, Ab22, Ab23, Ab3.H, Ab4.H, Ab5.H, Ab9.H, and Ab12.H. The inhibition results were quantified for each antibody to yield an $IC_{50}$ value, which are summarized in Table 2 below. These results demonstrated that anti-PACAP antibodies Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab22, Ab23, Ab1.H, Ab10.H, Ab3.H, Ab4.H, Ab5.H, Ab9.H, and Ab12.H inhibited PACAP38-induced cAMP increase in cells expressing PAC1-R. Additionally, these results demonstrated that anti-PACAP antibodies Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab1.H, Ab10.H, Ab3.H, Ab4.H, Ab5.H, Ab9.H, and Ab12.H, but not Ab22 or Ab23, inhibited PACAP27-induced cAMP increase in cells expressing PAC1-R.

TABLE 2

Inhibition ($IC_{50}$) of PACAP38-induced and PACAP27-induced cAMP increase in cells expressing PAC1-R by anti-PACAP antibodies

| ANTIBODY | Inhibition of 0.1 nM PACAP38-induced PAC1-R mediated cAMP increase $IC_{50}$ (pM) | Inhibition of 0.1 nM PACAP27-induced PAC1-R mediated cAMP increase $IC_{50}$ (pM) |
|---|---|---|
| Ab1 | 292.9 | 72.9 |
| Ab2 | 236.6 | 63.0 |
| Ab3 | 227.3 | 90.0 |
| Ab4 | 340.4 | 76.9 |
| Ab5 | 326.9 | 353.3 |
| Ab6 | 51.2 | 380.0 |
| Ab7 | 111.3 | 45.8 |
| Ab8 | 39.3 | 49.0 |
| Ab9 | 987.0 | 2840.0 |
| Ab10 | 180.3 | 227.0 |
| Ab11 | 56.7 | 109.3 |
| Ab12 | 51.1 | 60.4 |
| Ab13 | 82.4 | 74.1 |
| Ab14 | 154.4 | 95.7 |
| Ab15 | 162.0 | 155.5 |
| Ab16 | 211.8 | 192.4 |
| Ab17 | 97.7 | 77.6 |
| Ab18 | 117.7 | 91.6 |
| Ab19 | 100.8 | 87.4 |
| Ab1.H | 259.6 | 57.7 |
| Ab10.H | 163.4 | 84.0 |
| Ab22 | 101.4 | n/a * |
| Ab23 | 114.9 | n/a * |
| Ab3.H | 1320.0 | 1207.0 |
| Ab4.H | 307.0 | 293.6 |
| Ab5.H | 378.4 | 216.8 |
| Ab9.H | 278.0 | 270.5 |
| Ab12.H | 113.9 | 86.3 |

* n/a: not active because these Abs are PACAP38 specific

Example 2: Binding Affinities of Anti-PACAP Antibodies

Binding affinities of monoclonal antibodies for human PACAP were estimated using SPR on the PROTEON™ XPR36 (Bio-Rad, Hercules, CA). Antibody was immobilized to the surface of general amine coupling ("GLC" or "GLM") Chips (Bio-Rad, Hercules, CA). A dilution series of human PACAP38 (SEQ ID NO: 1241) prepared in 1×PBST Buffer (4.3 mM Na Phosphate, 1.4 mM K Phosphate, 135 mM NaCl, 2.7 mM KCl 0.05% Polysorbate-20) purchased from Teknova (Cat #P1192, Teknova, Hollister, CA) and supplemented with 0.25 M arginine (from J.T. BAKER®), 0.2 mg/ml BSA (Jackson Immuno Research Labs, West Grove, PA), and 0.005% sodium azide (VWR International, Radnor, PA) with the pH adjusted to 7 was used to query the antibodies. Antigen (ranging from 1.23 nM to 100 nM) was typically run sequentially with association times of 2-4 minutes and dissociation times of 3-120 minutes grouped with the PROTEON™ Manager Software (v3.1.0.6 (Bio-Rad, Hercules, CA)) and fitted using a 1:1 Langmuir binding model. Surfaces were regenerated between analyte queries using 0.85% Phosphoric Acid. A single $K_D$ was calculated for each antibody with association times limited near the rate of diffusion ($1.0\times10^6$) and dissociation times limited to $1.5\times10^{-5}$ where no discernible dissociation was observed.

The same procedure was used to determine binding affinities of antibodies for human VIP (SEQ ID NO: 1243) and PACAP27 (SEQ ID NO: 1242) though peptide concentrations ranged from 1.23 nM to 1000 nM with association times of 200 seconds and dissociation times of 3-120 minutes.

The measured antibody affinities for PACAP38 are listed in Table 3.

TABLE 3

Antibody affinity constants for PACAP38

| Antibody | ka (1/Ms) | kd (1/s) | $K_D$ (M) |
|---|---|---|---|
| Ab1 | 3.7E+05 | 1.0E−05 | 2.7E−11 |
| Ab2 | 2.3E+05 | 1.0E−05 | 4.4E−11 |
| Ab3 | 2.6E+05 | 4.2E−05 | 1.6E−10 |
| Ab4 | 3.3E+05 | 7.2E−05 | 2.2E−10 |

TABLE 3-continued

| Antibody affinity constants for PACAP38 | | | |
|---|---|---|---|
| Antibody | ka (1/Ms) | kd (1/s) | $K_D$ (M) |
| Ab5 | 2.4E+05 | 1.0E−05 | 4.1E−11 |
| Ab6 | 3.0E+05 | 4.1E−05 | 1.4E−10 |
| Ab7 | 1.8E+05 | 1.0E−05 | 5.6E−11 |
| Ab8 | 3.5E+05 | 1.0E−05 | 2.9E−11 |
| Ab9 | 8.2E+05 | 1.1E−04 | 1.4E−10 |
| Ab10 | 2.6E+05 | 2.0E−05 | 7.5E−11 |
| Ab11 | 2.7E+05 | 3.1E−05 | 1.1E−10 |
| Ab12 | 3.1E+05 | 1.0E−05 | 3.2E−11 |
| Ab13 | 4.2E+05 | 2.7E−05 | 6.4E−11 |
| Ab14 | 3.2E+05 | 1.0E−05 | 3.1E−11 |
| Ab15 | 5.3E+05 | 2.7E−05 | 5.0E−11 |
| Ab16 | 9.1E+05 | 1.0E−05 | 1.1E−11 |
| Ab17 | 5.0E+05 | 1.0E−05 | 2.0E−11 |
| Ab18 | 4.3E+05 | 1.0E−05 | 2.3E−11 |
| Ab19 | 2.7E+05 | 2.5E−05 | 9.3E−11 |
| Ab22 | 3.7E+05 | 1.0E−05 | 2.7E−11 |
| Ab23 | 5.1E+05 | 3.6E−05 | 7.1E−11 |
| Ab1.H | 4.7E+05 | 1.0E−05 | 2.1E−11 |
| Ab3.H | 4.9E+05 | 1.4E−04 | 2.9E−10 |
| Ab4.H | 3.1E+05 | 3.2E−05 | 1.0E−10 |
| Ab5.H | 5.5E+05 | 1.7E−05 | 3.1E−11 |
| Ab9.H | 1.0E+06 | 6.1E−05 | 6.1E−11 |
| Ab10.H | 3.4E+05 | 1.0E−05 | 2.9E−11 |
| Ab12.H | 3.8E+05 | 1.0E−05 | 2.6E−11 |

Examples of antibody affinity constants for VIP are listed in Table 4.

TABLE 4

| Antibody affinity constants for VIP | | | |
|---|---|---|---|
| Antibody | ka (1/Ms) | kd (1/s) | $K_D$ (M) |
| Ab1 | 2.5E+05 | 2.5E−02 | 9.9E−08 |
| Ab2 | 5.8E+05 | 8.4E−02 | 1.4E−07 |
| Ab3 | 1.0E+00 | 1.0E−01 | 1.0E−01 |
| Ab4 | 1.7E+05 | 2.1E−02 | 1.2E−07 |
| Ab5 | 1.2E+05 | 8.6E−01 | 7.2E−06 |
| Ab6 | 3.1E+03 | 1.4E−04 | 4.4E−08 |
| Ab7 | 2.6E+05 | 8.8E−03 | 3.4E−08 |
| Ab8 | 4.8E+05 | 1.0E−01 | 2.1E−07 |
| Ab9 | 1.0E+00 | 1.0E−01 | 1.0E−01 |
| Ab10 | 3.7E+04 | 1.0E−02 | 2.8E−07 |
| Ab11 | 2.0E+05 | 4.7E−02 | 2.3E−07 |
| Ab12 | 2.9E+05 | 2.4E−03 | 8.2E−09 |
| Ab13 | 3.2E+05 | 4.6E−02 | 1.4E−07 |
| Ab14 | 2.7E+05 | 6.7E−02 | 2.5E−07 |
| Ab15 | 1.6E+05 | 1.3E−01 | 8.2E−07 |
| Ab16 | 3.6E+05 | 9.6E−02 | 2.6E−07 |
| Ab17 | 3.1E+05 | 1.7E−02 | 5.5E−08 |
| Ab18 | 3.1E+05 | 1.2E−01 | 4.0E−07 |
| Ab19 | 2.8E+05 | 2.8E−01 | 1.0E−06 |
| Ab22 | 2.7E+05 | 1.8E−01 | 6.9E−07 |
| Ab23 | 4.3E+05 | 3.2E−01 | 7.3E−07 |
| Ab1.H | 3.8E+04 | 1.8E−01 | 4.8E−06 |
| Ab3.H | 1.0E+00 | 1.0E−01 | 1.0E−01 |
| Ab4.H | 3.3E+05 | 2.4E−02 | 7.2E−08 |
| Ab5.H | 1.0E+00 | 1.0E−01 | 1.0E−01 |
| Ab9.H | 9.3E+04 | 1.4E−01 | 1.5E−06 |

TABLE 4-continued

| Antibody affinity constants for VIP | | | |
|---|---|---|---|
| Antibody | ka (1/Ms) | kd (1/s) | $K_D$ (M) |
| Ab10.H | 3.8E+05 | 3.9E−02 | 1.0E−07 |
| Ab12.H | 2.8E+05 | 1.4E−02 | 5.1E−08 |

Examples of antibody affinity constants for PACAP27 are listed in Table 5.

TABLE 5

| Antibody affinity constants for PACAP27 | | | |
|---|---|---|---|
| Antibody | ka (1/Ms) | kd (1/s) | $K_D$ (M) |
| Ab1 | 1.0E+06 | 1.0E−05 | 1.0E−11 |
| Ab2 | 8.3E+05 | 1.0E−05 | 1.2E−11 |
| Ab3 | 3.7E+05 | 1.4E−04 | 3.7E−10 |
| Ab4 | 3.9E+05 | 2.0E−04 | 5.1E−10 |
| Ab5 | 2.5E+05 | 2.4E−05 | 9.6E−11 |
| Ab6 | 3.9E+05 | 8.2E−05 | 2.1E−10 |
| Ab7 | 2.3E+05 | 4.5E−05 | 2.0E−10 |
| Ab8 | 4.4E+05 | 6.0E−05 | 1.4E−10 |
| Ab9 | 9.6E+05 | 3.2E−04 | 3.4E−10 |
| Ab10 | 1.0E+06 | 1.0E−05 | 1.0E−11 |
| Ab11 | 2.6E+05 | 1.1E−04 | 4.2E−10 |
| Ab12 | 2.9E+05 | 2.1E−05 | 7.0E−11 |
| Ab13 | 5.4E+05 | 6.6E−05 | 1.2E−10 |
| Ab14 | 2.7E+05 | 2.0E−05 | 7.4E−11 |
| Ab15 | 4.7E+05 | 7.8E−05 | 1.7E−10 |
| Ab16 | 8.2E+05 | 2.9E−05 | 3.5E−11 |
| Ab17 | 3.7E+05 | 1.0E−05 | 2.7E−11 |
| Ab18 | 4.4E+05 | 1.0E−05 | 2.3E−11 |
| Ab19 | 4.2E+05 | 1.3E−04 | 3.1E−10 |
| Ab22 | 1.0E+00 | 1.0E−01 | 1.0E−01 |
| Ab23 | 8.9E+05 | 3.1E−02 | 3.5E−08 |
| Ab1.H | 7.6E+05 | 1.0E−05 | 1.3E−11 |
| Ab3.H | 3.3E+05 | 3.4E−04 | 1.0E−09 |
| Ab4.H | 3.3E+05 | 1.0E−05 | 3.1E−11 |
| Ab5.H | 2.7E+05 | 1.3E−04 | 4.8E−10 |
| Ab9.H | 6.2E+05 | 7.7E−05 | 1.2E−10 |
| Ab10.H | 5.3E+05 | 1.8E−05 | 3.3E−11 |
| Ab12.H | 2.6E+05 | 7.9E−05 | 3.0E−10 |

The binding affinity results of Tables 3 and 5 present data demonstrating that Ab23 weakly bound to PACAP27 as compared to its binding affinity for PACAP38. Tables 3 and 5 additionally present data demonstrating that Ab22 did not specifically recognize PACAP27, but that Ab22 specifically bound to PACAP38.

Example 3: Inhibition of PACAP38-Induced Signaling Via VPAC1-R

To identify antibodies that neutralize PACAP38-induced signaling via human VPAC1-R, CHO-K1 cells expressing human VPAC1-R were used in a cAMP HTRF cell-based assay. Antibody dilutions were incubated with PACAP38 at 4× the final concentration (5 nM) for 1 hour. While the antibody/antigen complexes were incubated for 1 hour, VPAC1-R expressing CHO-K1 cells (generated at Alder Biopharmaceuticals, by stable transfection of CHO-K1 cells (ATCC, catalog #CCL-61) with human VPAC1-R cDNA; selected clone 1 was used for in vitro cell based assays) were detached with 0.25% trypsin for 4 minutes. The cells were washed and re-suspended at $1\times10^6$ cells per ml culture media. 20 μl of Ab/antigen mixture was mixed with 20 μl of cells in HTRF plates and incubated with shaking for 30 minutes. 20 μl of $Eu^{3+}$ cryptate labeled anti-cAMP mAb (1:20 diluted) and 20 μl of (1:20 diluted) d2-labeled cAMP in lysis buffer were added to each well and incubated for 1 hour with shaking. The final concentration of PACAP38 in each well was 5 nM. Following incubation, plates were read (excitation 330 nm, emission 620/665 nm), and a ratio of 620:665 signal was determined.

Inhibition curves were obtained for Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab1.H, Ab10.H, Ab22, Ab23, Ab3.H, Ab4.H, Ab5.H, Ab9.H, and Ab12.H. The computed $IC_{50}$ values for each antibody, which are shown below in Table 6, demonstrated that Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab1.H, Ab10.H, Ab22, Ab23, Ab3.H, Ab4.H, Ab5.H, Ab9.H, and Ab12.H inhibited PACAP38-induced cAMP increase in cells expressing human VPAC1-R.

TABLE 6

Inhibition ($IC_{50}$) of PACAP38-induced cAMP increase in cells expressing human VPAC1-R by anti-PACAP antibodies

| ANTIBODY | Inhibition of 5 nM PACAP38-induced Human VPAC1-R mediated cAMP increase $IC_{50}$ (pM) |
|---|---|
| Ab1 | 664.7 |
| Ab2 | 688.3 |
| Ab3 | 1736.0 |
| Ab4 | 942.8 |
| Ab5 | 720.7 |
| Ab6 | 797.1 |
| Ab7 | 687.3 |
| Ab8 | 481.2 |
| Ab9 | 4059.0 |
| Ab10 | 649.1 |
| Ab11 | 541.0 |
| Ab12 | 292.2 |
| Ab13 | 2183.0 |
| Ab14 | 2626.0 |
| Ab15 | 3715.0 |
| Ab16 | 3533.0 |
| Ab17 | 780.1 |
| Ab18 | 911.2 |
| Ab19 | 826.8 |
| Ab1.H | 1021.1 |
| Ab10.H | 1336.0 |
| Ab22 | 1300.0 |
| Ab23 | 2667.0 |
| Ab3.H | 7332.0 |
| Ab4.H | 2600.0 |
| Ab5.H | 2772.0 |
| Ab9.H | 2465.0 |
| Ab12.H | 1284.0 |

Example 4: Inhibition of PACAP38-Induced Signaling Via VPAC2-R

To identify antibodies that neutralize PACAP38-induced signaling via human VPAC2-R, CHO-K1 cells expressing human VPAC2-R were used in a cAMP HTRF cell based assay.

Antibody dilutions were incubated with PACAP38 at 4× the final concentration (1 nM) for 1 hr. While the antibody/antigen complexes were incubated for 1 hour, VPAC2-R expressing CHO-K1 cells (generated at Alder Biopharmaceuticals, by stable transfection of CHO-K1 cells (ATCC, catalog #CCL-61) with human VPAC2-R cDNA; selected clone 8 was used for in vitro cell based assays) were detached with 0.25% trypsin for 4 minutes. The cells were washed and re-suspended at $1\times10^6$ cells per ml culture media. 20 μl of Ab/antigen mixture was mixed with 20 11.1 of cells in HTRF plates and incubated with shaking for 30 minutes. 20 μl of $Eu^{3+}$ cryptate labeled anti-cAMP mAb (1:20 diluted) and 20 μl of (1:20 diluted) d2-labeled cAMP in lysis buffer were added to each well and incubated for 1 hour with shaking. The final concentration of PACAP38 in the wells was 1 nM. Following incubation, plates were read (excitation 330 nm, emission 620/665 nm) and, a ratio of 620:665 signal was determined.

Inhibition curves were obtained using this method for Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab1.H, Ab10.H, Ab22, Ab23, Ab3.H, Ab4.H, Ab5.H, Ab9.H, and Ab12.H. The computed $IC_{50}$ values for each antibody, which are shown below in Table 7, demonstrated that Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab1.H, Ab10.H, Ab22, Ab23, Ab3.H, Ab4.H, Ab5.H, Ab9.H, and Ab12.H inhibited PACAP38-induced cAMP increase in cells expressing human VPAC2-R.

TABLE 7

Inhibition ($IC_{50}$) of PACAP38-induced cAMP increase in cells expressing human VPAC2-R by anti-PACAP antibodies

| ANTIBODY | Inhibition of 1 nM PACAP38-induced human VPAC2-R mediated cAMP increase $IC_{50}$ (pM) |
|---|---|
| Ab1 | 146.7 |
| Ab2 | 174.1 |
| Ab3 | 667.4 |
| Ab4 | 217.9 |
| Ab5 | 239.3 |
| Ab6 | 216.9 |
| Ab7 | 162.4 |
| Ab8 | 146.9 |
| Ab9 | 6965.0 |
| Ab10 | 188.5 |
| Ab11 | 265.2 |
| Ab12 | 179.0 |
| Ab13 | 652.2 |
| Ab14 | 840.4 |
| Ab15 | 22850.0 |
| Ab16 | 1146.0 |
| Ab17 | 205.0 |
| Ab18 | 285.4 |
| Ab19 | 953.5 |
| Ab1.H | 983.0 |
| Ab10.H | 988.0 |
| Ab22 | 515.0 |
| Ab23 | 1789.0 |
| Ab3.H | 64240.0 |
| Ab4.H | 4487.0 |
| Ab5.H | 7466.0 |
| Ab9.H | 2649.0 |
| Ab12.H | 653.0 |

Example 5: Inhibition of PACAP38 Binding to PAC1-R-Expressing Cells

To identify antibodies that block PACAP38 binding to PAC1-R-expressing cells, adherent PC-12 cells (ATCC, Manassas, VA) expressing PAC1-R were used in a Europium-based PAC1-R-expressing cells binding assay.

Antibody solutions were incubated with N-terminal biotinylated PACAP38 at 10× the final concentration (100 nM or 30 nM) for 1 hr, then added to PC-12 cells that were plated 24 hrs prior in black clear bottom 96 well plates (COSTAR™, Corning Incorporated, Corning, NY) and further incubated for 1 hr at room temperature. After three washes, the cells were incubated with 20 μl Europium-labeled streptavidin (PerkinElmer, Waltham, MA) for 1 hr at room temperature. Cells were washed three times, then 20 μl DELFIA® Enhancement solution (PerkinElmer, Waltham, MA) was added to each well and incubated for 15 minutes with gentle shaking. Plates were read (Time Resolved Fluorescence ("TRF")) on SPECTRAMAX® (Molecular Devices, Sunnyvale, CA) plate reader.

Inhibition curves were obtained using this method for Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab1.H, Ab10.H, Ab22, Ab23, Ab3.H, Ab4.H, Ab5.H, Ab9.H, and Ab12.H wherein the PAC1-R expressing cells were PC-12 cells. The computed $IC_{50}$ values for each antibody, which are shown below in Table 8, demonstrated that Ab1, Ab2, Ab3, Ab4, Ab5, Ab6, Ab7, Ab8, Ab9, Ab10, Ab11, Ab12, Ab13, Ab14, Ab15, Ab16, Ab17, Ab18, Ab19, Ab1.H, Ab10.H, Ab22, Ab23, Ab3.H, Ab4.H, Ab5.H, Ab9.H, and Ab12.H inhibited PACAP38 binding to PAC1-R expressing cells.

TABLE 8

Inhibition ($IC_{50}$) of PACAP38 binding to PAC1-R-expressing PC-12 cells by anti-PACAP antibodies.

| ANTIBODY | Inhibition of 100 nM biotinylated PACAP38 binding to PAC1R-expressing PC-12 cells $IC_{50}$ (nM) |
|---|---|
| Ab1 | 12.7 |
| Ab2 | 26.6 |
| Ab3 | 17.2 |
| Ab4 | 28.6 |
| Ab5 | 16.3 |
| Ab6 | 7.8 |
| Ab7 | 22.0 |
| Ab8 | 20.3 |
| Ab9 | 33.3 |
| Ab10 | 17.8 |
| Ab11 | 24.6 |
| Ab12 | 22.6 |
| Ab13 | 53.1 |
| Ab14 | 17.9 |
| Ab15 | 36.7 |
| Ab16 | 27.3 |
| Ab17 | 33.1 |
| Ab18 | 30.6 |
| Ab19 | 162 |
| **ANTIBODY** | **Inhibition of 30 nM Biotinylated PACAP38 binding to PAC1R-expressing PC-12 cells $IC_{50}$ (nM)** |
| Ab1.H | 56.3 |
| Ab10.H | 14.5 |
| Ab22 | 13.8 |
| Ab23 | 14.9 |
| Ab3.H | 88.3 |
| Ab4.H | 98.0 |
| Ab5.H | 34.9 |
| Ab9.H | 22.5 |
| Ab12.H | 68.1 |

Example 6: PACAP38-Mediated Binding of Anti-PACAP Antibodies to the Cell Surface of PAC1-R Expressing Cells To identify anti-PACAP antibodies that bind, via PACAP38, to the cell surface of PAC1-R expressing cells, adherent PC-12 cells (Japanese Collection of Research Bioresources Cell Bank) expressing PAC1-R were used in a cell surface binding-based assay. To perform the binding experiment, PAC1-R expressing PC-12 cells were first seeded into Corning 96 well white solid bottom plates (Corning, Corning, NY). Cells were initially seeded at $1\times10^5$ cells/well in a solution of complete RPMI ("cRPMI": RPMI medium supplemented with 10% sterile heat-inactivated FBS and 1% sterile antibiotic/antimycotic)+10% FBS, and the plates were allowed to incubate overnight at 37° C. On the day of the binding assay, antibodies at an initial concentration of 15 μg/ml were diluted at a 1:3 ratio in DELFIA® binding buffer (50 mM Tris, 150 mM NaCl, 0.1% azide, 2% horse serum) (Perkin-Elmer, Waltham, MA) to a total volume of 60 μL in a separate 96 well round bottom plate. PACAP38 was prepared for the binding assay by diluting it in DELFIA® binding buffer to a concentration of 200 nM, and then 60 μl of the diluted PACAP38 was added to each of the antibody-containing wells to form antibody: antigen complexes. Following addition of PACAP38, the antibody:antigen complexes were incubated at room temperature on a shaker for 1 hour. Separately, the PC-12 cells were prepared for addition of antibody:antigen complexes by washing the cells two times with DELFIA® wash buffer (50 mM Tris, 150 mM NaCl, 0.1% Azide) (Perkin-Elmer, Waltham, MA). After washing the cells two times and following the 1 hour room temperature incubation of the antibody:antigen complexes, 50 μl of the antibody:antigen complex was added to each well containing cells. The mixtures of cells and antibody:antigen complexes were then incubated for 30 minutes at room temperature. Following this 30 minute incubation, each mixture was washed two times with DELFIA® wash buffer (Perkin-Elmer, Waltham, MA).

DELFIA® Europium labeled anti-human IgG detection reagent (Cat #1244-330, Perkin-Elmer, Waltham, MA) was diluted to a concentration of 300 ng/ml in DELFIA® Binding Buffer. Following dilution, 50 μl of the anti-human IgG detection reagent was added to each well containing cells, and a 30 minute incubation at room temperature followed this addition of IgG detection reagent. After completion of the 30 minute room temperature incubation, the cells were then washed two times with DELFIA® wash buffer. Next, 50 μl of DELFIA® Enhancement Solution (Cat #1244-105, Perkin-Elmer, Waltham, MA) was added to each well containing cells for a final 15 minute room temperature incubation with shaking. The plates were then read (TRF, excitation 330 nm, emission 620 nm) on a SPECTRAMAX® (Molecular Devices, Sunnyvale, CA) plate reader.

FIGS. 19A-J are representative of the binding curves obtained by this method (results are shown for Ab1.H, Ab3.H, Ab4.H, Ab5.H, Ab9.H, Ab12.H, Ab10, Ab10.H, Ab22, and Ab23, respectively) wherein the PAC1-R expressing cells were PC-12 cells. Ab1.H, Ab3.H, Ab4.H, Ab5.H, Ab9.H, and Ab12.H demonstrated binding to the surface of PAC1-R expressing cells in the presence of PACAP38, while Ab10, Ab10.H, Ab22, and Ab23 did not appear to appreciably bind to the surface of PAC1-R expressing cells using this assay. The binding of Ab1.H, Ab3.H, Ab4.H, Ab5.H, Ab9.H, and Ab12.H to the cell surface of PAC1-R cells was only observed in the presence of PACAP38. Without intent to be bound by theory, it is hypothesized that the binding of the antibodies to the cell surface was mediated by binding of PACAP38 to GAGs that were present on the cell surface, since binding of PACAP38 by GAGs has been previously demonstrated as a PAC1-R receptor independent mechanism of PACAP38 binding and internalization by PC-12 cells (see Doan et al. (2012), Juhász et al. (2014), and Neree et al. (2015)).

Example 7: Inhibition of PACAP38-Induced Dermal Vasodilation in Rabbits by Anti-PACAP Antibody Ab1.H Intradermal injection of PACAP38 has been shown to elicit a localized vasodilation in rabbits and humans (Warren et al., *J. Cardio. Pharmacol.,* 29(1): 83-87 (1992); Seelinger et al., *Am. J. Path.,* 177(5):2563-2575 (2010)). An in vivo efficacy study was conducted to determine the activity of Ab1.H to inhibit a localized dermal vasodilation induced by an intradermal injection of PACAP38 in male New Zealand White rabbits.

Groups of 4 rabbits were dosed with either 90 mg/kg of Ab1.H or with negative control vehicle (25 mM histidine, 250 mM sorbitol, pH 6.0). Injections were performed by IV (ear vein) bolus administration on day 0. Prior to each rabbit PACAP38 challenge, the scapular region of each animal was clipped free of hair and wiped with 20% (v/v) alcohol in water. On day 2, the animals were pre-anesthetized with ketamine hydrochloride and maintained under deep anesthesia with isoflurane gas. Four sites (Region of Interest ("ROI")) for injection were identified on the back of each animal using a SHARPIE® permanent marker. Dermal vasodilation and blood perfusion were monitored using the PeriCam PSI NR system for Laser Speckle Contrast Analysis ("LASCA") imaging (Perimed, Järfälla, Sweden), before (baseline) and for 35 minutes after intradermal PACAP38 challenge. Intradermal PACAP38 challenge was performed as follows: each animal received single intradermal administrations (100 μl/site) of vehicle (one site or ROI) and PACAP38 at 30 pmoles/site (3 sites or 3 ROIs). The blood perfusion rates for each ROI were reported by the PeriCam PSI NR system in Perfusion units ("PU") and analyzed using PIMSoft (Ver. 1.5 (Perimed, Järfälla, Sweden)).

For each treatment group, the relative % PU change following Ab1.H or negative control administration compared to baseline was calculated for each ROI (% PU change for each PACAP38 challenge site−% PU change for the vehicle site). The relative % PU change in the Ab1.H group was compared to the relative % PU change in the Negative control group by performing a two-tailed unpaired t-test statistical evaluation using GraphPad Prism (version 5.0d, GraphPad Software, La Jolla, CA) software.

FIG. 13 demonstrates that Ab1.H inhibited PACAP38-induced dermal vasodilation in rabbits, indicating effectiveness of the antibody at neutralizing PACAP38 activity in vivo.

Example 8: Inhibition of PACAP38-Induced Dermal Vasodilation in Rabbits by Anti-PACAP Antibody Ab10

Intradermal injection of PACAP38 has been shown to elicit a localized vasodilation in rabbits and humans (Warren et al. (1992); Seelinger et al. (2010)). An in vivo efficacy study was conducted to determine the activity of Ab10 to inhibit a localized dermal vasodilation induced by an intradermal injection of PACAP38 in male New Zealand White rabbits.

Groups of 4 rabbits were dosed with either 72 mg/kg of Ab10 or with isotype antibody control. Injections were by (ear vein) bolus intravenous administration on day 0. Prior to each rabbit PACAP38 challenge, the scapular region of each animal was clipped free of hair and wiped with 20% (v/v) alcohol in water. On day 2, the animals were pre-anesthetized with ketamine hydrochloride and maintained under deep anesthesia with isoflurane gas. Four sites (ROIs) for injection were identified on the back of each animal using a SHARPIE® permanent marker. Dermal vasodilation and blood perfusion were monitored using the PeriCam PSI NR system for LASCA imaging (Perimed, Järfälla, Sweden), before (baseline) and for 35 minutes after intradermal PACAP38 challenge. Intradermal PACAP38 challenge was performed as follows: each animal received single intradermal administrations (100 μl/site) of vehicle (one site or ROI) and PACAP38 at 30 pmoles/site (3 sites or 3 ROIs). The blood perfusion rates for each ROI were reported by the PeriCam PSI NR system in PU and analyzed using PIMSoft (Ver. 1.5 (Perimed, Järfälla, Sweden)).

For each treatment group, the relative % PU change following Ab10 or Isotype Ab control administration compared to baseline was calculated for each ROI (% PU change for each PACAP38 challenge site−% PU change for the vehicle site). The relative % PU change in the Ab10 group was compared to the relative % PU change in the Isotype Ab control group by performing a two-tailed unpaired t-test statistical evaluation using GraphPad Prism (version 5.0d, GraphPad Software, La Jolla, CA) software.

Figure 14:
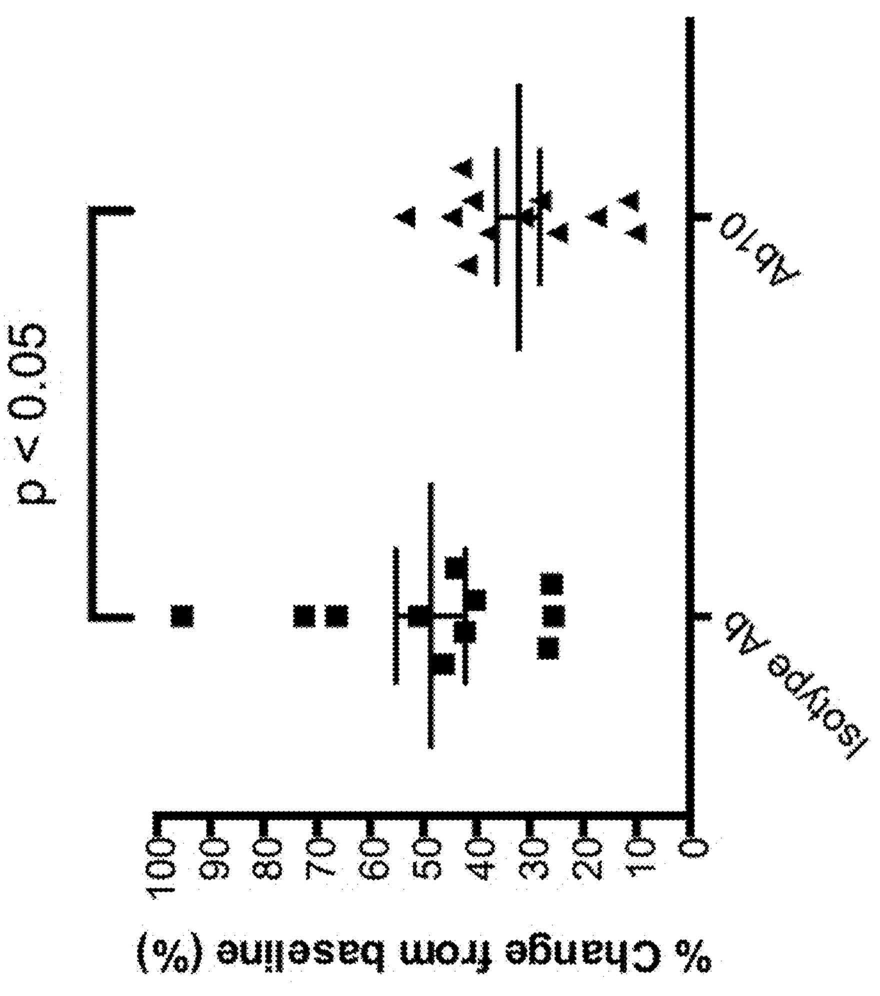
FIG. 14 provides representative data showing a reduction in vasodilation obtained by administering Ab10 following PACAP38 administration in a rabbit model, relative to an isotype antibody control, obtained following the protocol in Example 8 infra.

FIG. 14 demonstrates that Ab10 inhibited PACAP38-induced dermal vasodilation in rabbits, indicating effectiveness of the antibody at neutralizing PACAP38 activity in vivo.

Example 9: Epitope Binning of Anti-PACAP Antibodies, Ab1 and Ab10

Figure 15A:
FIG. 15A provides epitope binning data for labeled Ab1 and unlabeled Ab10 obtained following the protocol in Example 9 infra.
Figure 15B:
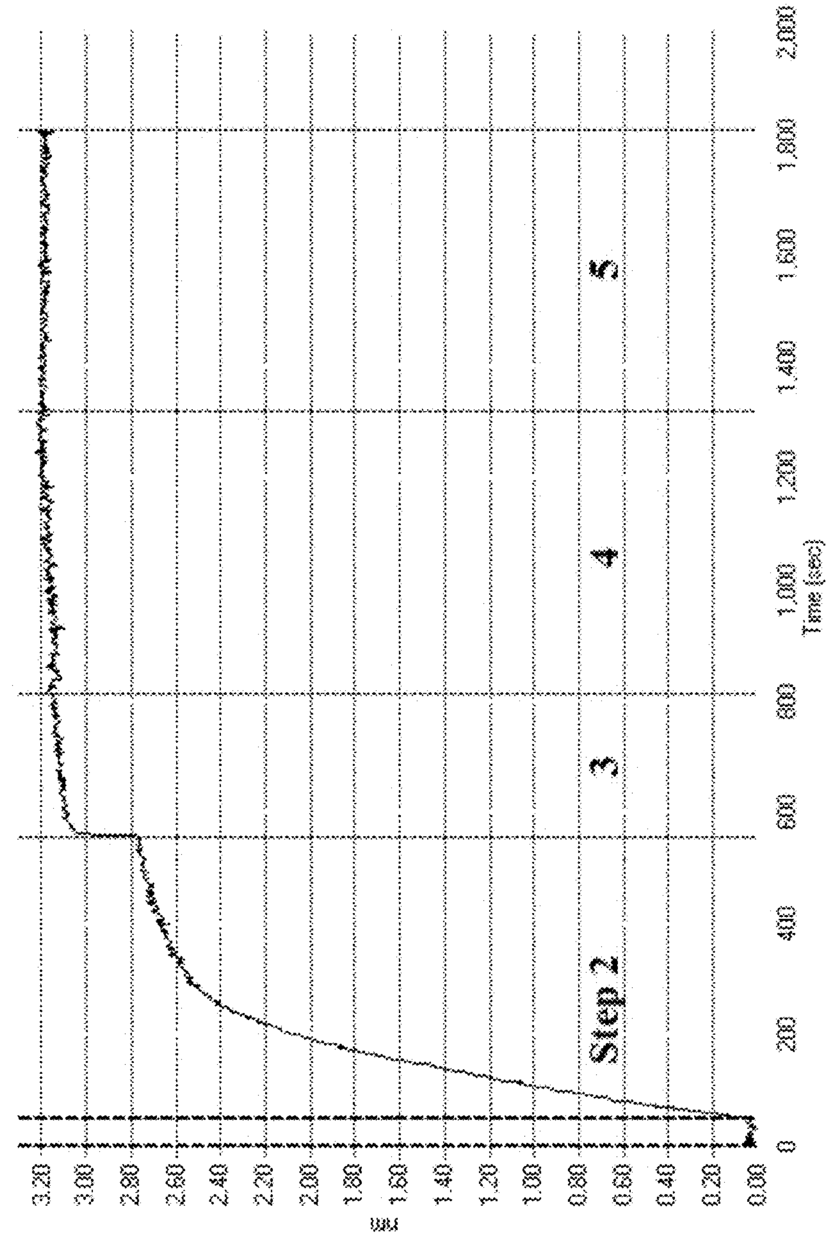
FIG. 15B provides epitope binning data for unlabeled Ab1 and labeled Ab10 obtained following the protocol in Example 9 infra.

Ab1 was biotinylated at a 10:1 molar ratio with biotin (Thermo Fisher Scientific, Waltham, MA) per manufacturer guidelines. A 5 step biolayer interferometry experiment was performed as follows: In step 1, streptavidin biosensors (Pall ForteBio LLC, Menlo Park, CA) were equilibrated for 50 seconds in 1× kinetics buffer (a 1:10 dilution in DBS of Pall ForteBio LLC, Menlo Park, CA, cat #18-5032). In step 2, a 2 μg/ml dilution of biotinylated antibody Ab1 in 1× kinetics buffer was immobilized for 500 seconds onto Streptavidin biosensors. In step 3, the antibody-functionalized biosensors were incubated in a solution of 2 μM unlabeled PACAP peptide (American Peptide Company, Sunnyvale, CA, catalog #34-0-20) in 1× kinetics buffer for 200 seconds. In step 4, the sensors were placed into 67 nM solutions of either unlabeled antibody Ab10 (FIG. 15A) or unlabeled antibody Ab1 as control (FIG. 15B) in 1× kinetics buffer for a 1000 second association step. Stability of binding was monitored during step 5 for a 1000 second dissociation in 1× kinetics buffer. In FIG. 15A, the "sandwich-style" capture of Ab10 via Ab1-captured PACAP indicates simultaneous and non-competitive binding of these two antibodies to PACAP. The control experiment in FIG. 15B shows minimal "sandwich-style" capture of Ab1 via Ab1-captured PACAP. The experiment was conducted on a ForteBio OCTET® QK instrument (Pall ForteBio LLC, Menlo Park, CA) at 30° C. and 1000 RPM.

Example 10: Inhibition of PACAP27 Binding to Human PAC1-R by Anti-PACAP Antibodies To identify antibodies that block PACAP27 binding to PAC1-R, antibodies at an initial concentration of 30 nM were diluted in incubation buffer (50 mM Hepes pH 7.4, 1 mM $CaCl_2$, 5 mM $MgCl_2$, 0.2% BSA) and serial 1:3 dilutions were performed. Antibody dilutions (30 nM, 10 nM, 3 nM, 1 nM, 0.3 nM, 0.1 nM, 0.03 nM, 0.01 nM, 0.003 nM and 0.001 nM) were then mixed and pre-incubated at 25° C. for 30 minutes with 0.1 nM of $^{125}I$-labelled PACAP27 in incubation buffer. The antibody: $^{125}$I-labelled PACAP27 mixture was then added to 0.5 μg aliquots of cell membranes derived from Chem-1 cells expressing human recombinant PAC1-R long isoform in incubation buffer. The mixture was then incubated for 1 hour at 25° C. Following incubation, the samples were filtered and washed. Afterward, the filters were counted to quantitate $^{125}$I-labelled PACAP27. As an experimental control, non-specific binding to the cell membranes was estimated using 0.1 μM of labeled PACAP27. The results indicated that Ab1.H, Ab10.H, and Ab12.H were capable of blocking PACAP27 binding to PAC1-R, thereby demonstrating inhibition of ligand-receptor binding by the tested antibodies presented in Table 9.

TABLE 9

Inhibition ($IC_{50}$) of 0.1 nM $^{125}$I-PACAP27 binding to PAC1-R by anti-PACAP antibodies

| ANTIBODY | $IC_{50}$ (nM) |
|---|---|
| Ab1.H | 0.70 |
| Ab10.H | 0.22 |
| Ab12.H | 0.16 |

Example 11: Effect of Anti-PACAP Antibody on Light Aversion

To examine the effect of anti-PACAP antibodies on photophobia, a mouse model was employed in which mice were administered PACAP to trigger photophobia. Photophobia was detected using a light aversion assay using a light-dark box as described in Kaiser et al., *J. Neurosci.,* 32(44):15439-15449, 2012. Mice were then administered anti-PACAP antibodies Ab1.H or Ab10.H or an unrelated control antibody and their aversion to light quantitated. Results are reflected in FIGS. 16-18.

Light Aversion Assay

As described in Kaiser et al., the testing chambers were a plexiglas open field (27 cm wide×27 cm deep×20.3 cm high) containing three sets of 16 beam infrared arrays (two sets of perpendicular beams cross at a height of 1.0 cm to detect mouse location and locomotion, and the third beam crosses the width of the chamber at a height of 7.3 cm to detect vertical activity). The field was divided in two equal sized zones by a dark insert, which is a five-sided, black-colored plexiglas box with a top, but no floor. The use of infrared light beams allowed tracking in both zones. An opening (5.2 cm×6.8 cm) in the dark insert allowed free movement between zones. While the dark insert blocked direct light, some light could still enter through the opening. Each testing chamber was located inside a sound-attenuating cubicle (56 cm wide×38 cm deep×36 cm high) with a fan for ventilation (Med Associates, Inc.®, St. Albans, VT). A computer using Activity Monitor v6.02 (Med Associated Inc.) was used for recording data from the six chambers.

For each chamber, a LED panel was attached to the ceiling of the sound-attenuating cubicle. The LED panel contains 36 collimated 1 watt LEDs (5500k Daylight White) (LEDwholesalers.com, Burlingame, CA). To control light intensity, each LED panel was connected to a dimmable LED driver (LINEARdrive®; eldoLED America Inc., San Jose, CA) leading to a potential range of light intensity from $3.0\times10^2$ to $2.7\times10^4$ lx. Levels were further attenuated to $5.5\times10^1$ lx using wax paper placed on a clear plexiglass tray below the LEDs. Light intensity was measured with Traceable Dual-Display Light Meter (Control Company, Friendswood, TX) placed on the floor of the testing chamber. At $2.7\times10^4$ lx, LED lights generated some heat in the sound attenuating chamber with the dark zone at ~25° C. and light zone at ~27° C.

On the day of the experiment, mice were transported from animal housing and allowed to acclimate to the testing room (~22° C.) for at least 30 to 60 minutes with standard overhead fluorescent lighting (~200 lx inside the housing cage). Room lights remained on, unless noted otherwise. In addition, all sound-generating equipment were turned on during acclimation and remained on until testing was complete. There was minimal human presence in the room during acclimation. Behavioral testing was performed between 0800 CST and 1400 CST. Any abnormal physical conditions (e.g. missing eye) were noted.

Ten week old male and female CD1 mice were used in the study (strain #022, Charles River, Wilmington, MA, US). Mice were allowed to recover from shipping for one to two weeks prior to testing.

Acclimation

All mice were acclimated in the testing room at least 30 to 60 minutes prior to being placed in the light/dark chamber. The light intensity in the chamber was initially set to $2.7\times10^3$ lx. The mice were tested for thirty minutes in the chamber every day they were exposed to the light/dark chamber. Baseline time in light for each mouse was obtained by exposing the mice to the light/dark chamber twice, with a period of rest of three days between baseline measurements (FIGS. 16 and 18, "Baseline1" and "Baseline2," or "Baseline", respectively).

Treatment

Figure 16:
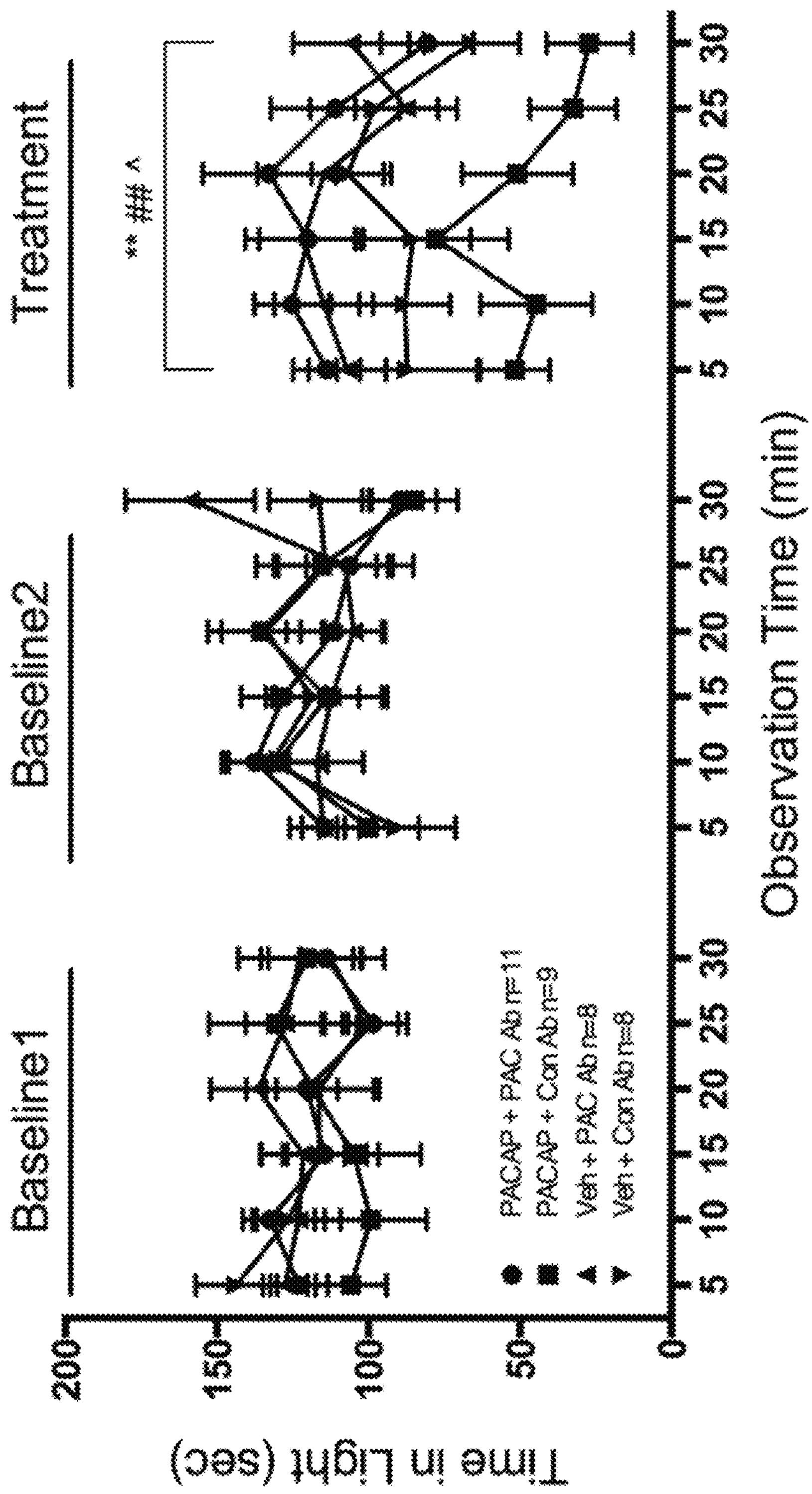
FIG. 16 provides representative data showing the in vivo effect of the administration of PACAP and an anti-PACAP antibody Ab1.H in a rodent photophobia model, which model detects the amount of time treated animals (mice) spend in the light per 5 minute intervals compared to appropriate control animals obtained following the protocol in Example 11 infra.
Figure 18:
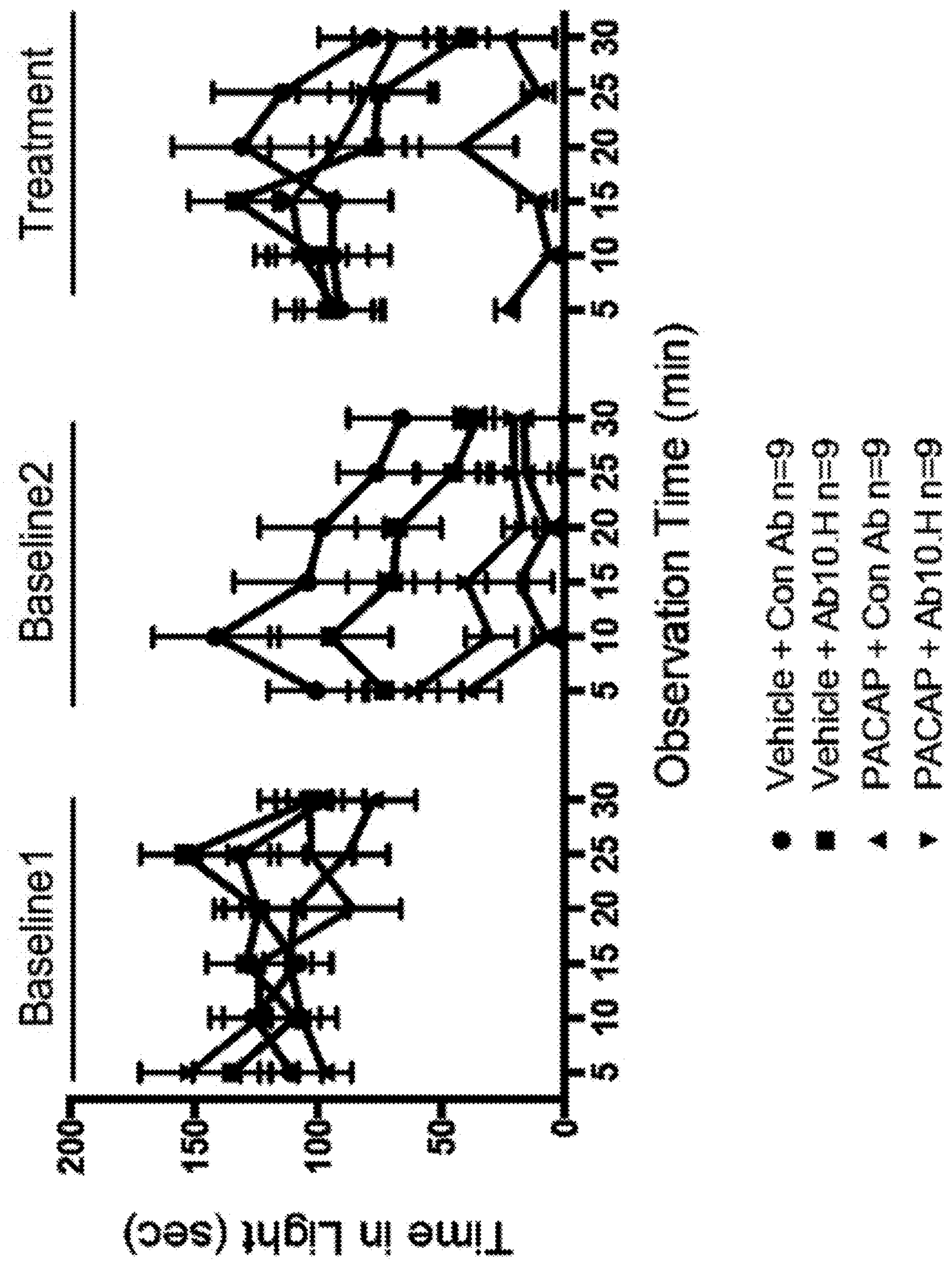
FIG. 18 provides representative data showing the in vivo effect of the administration of PACAP and an anti-PACAP antibody Ab10.H in a rodent photophobia model, which model detects the amount of time treated animals (mice) spend in the light compared to appropriate control animals obtained following the protocol in Example 11 infra.
Figure 19A:
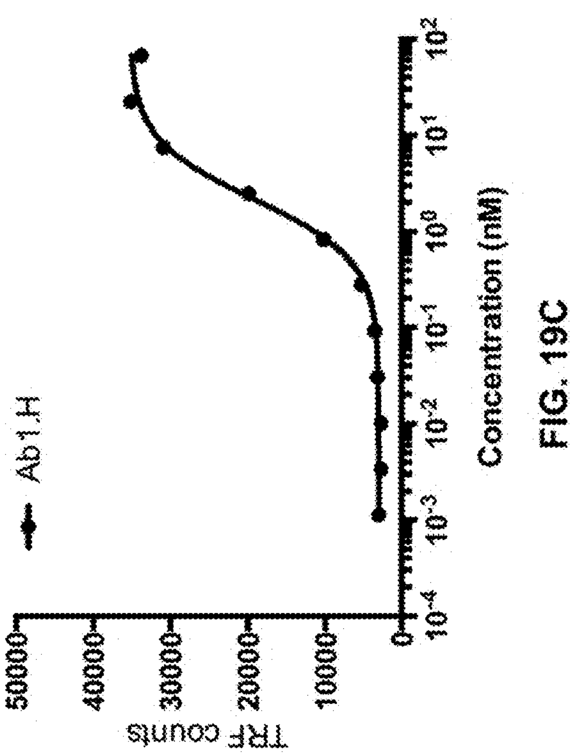
FIG. 19A-J provides representative data showing Ab1.H (FIG. 19A), Ab3.H (FIG. 19B), Ab4.H (FIG. 19C), Ab5.H (FIG. 19D), Ab9.H (FIG. 19E), Ab12.H (FIG. 19F), Ab10 (FIG. 19G), Ab10.H (FIG. 19H), Ab22 (FIG. 19I), and Ab23 (FIG. 19J) binding to PAC1-R-expressing PC-12 cells in the presence of PACAP38 obtained following the protocol in Example 6 infra.
Figure 19B:
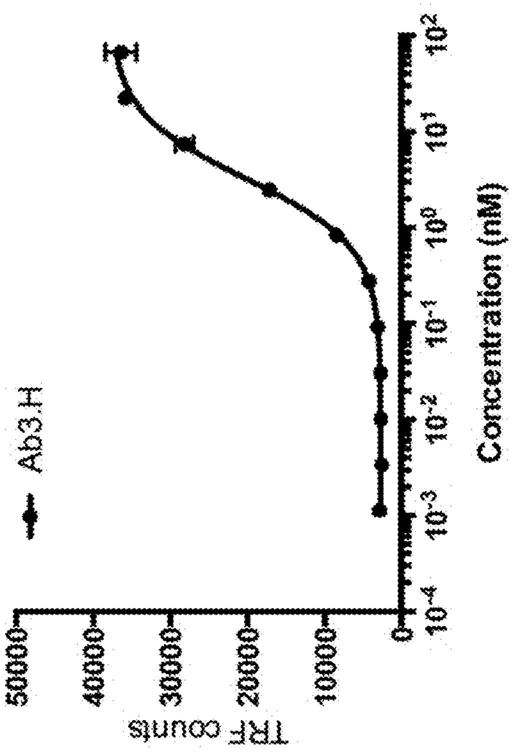
Figure 19C:
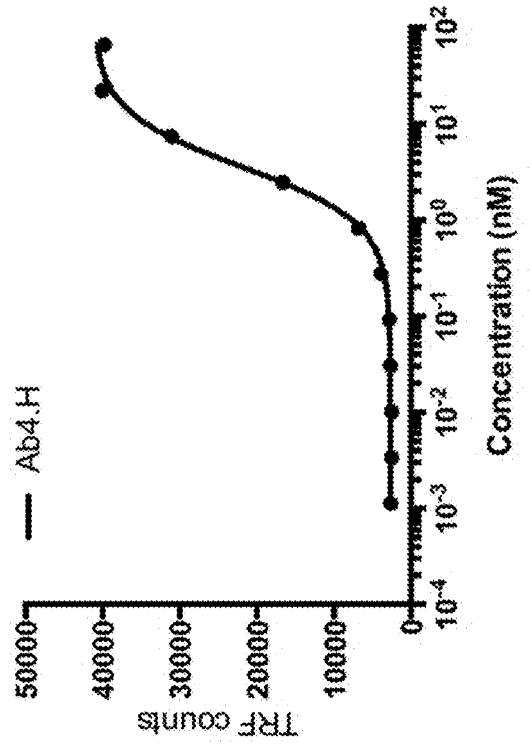
Figure 19D:
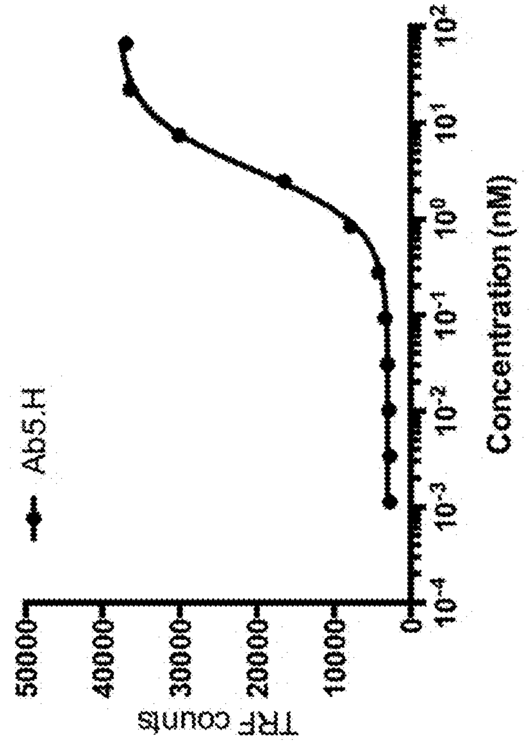
Figure 19F:
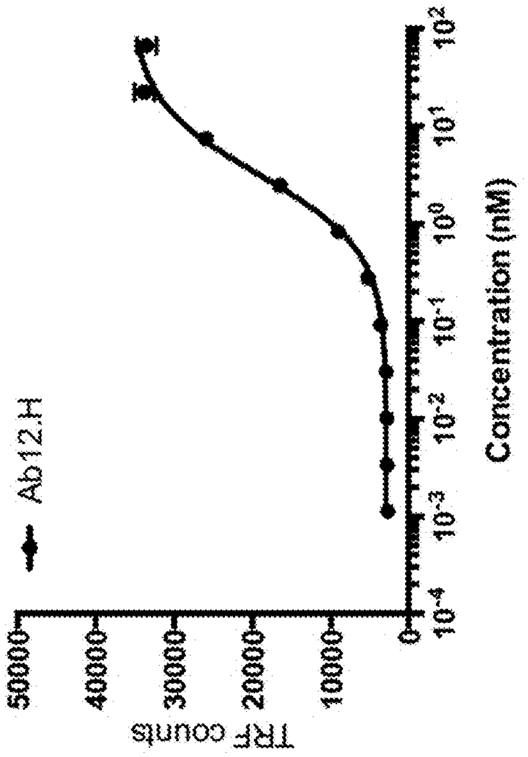
Figure 19E:
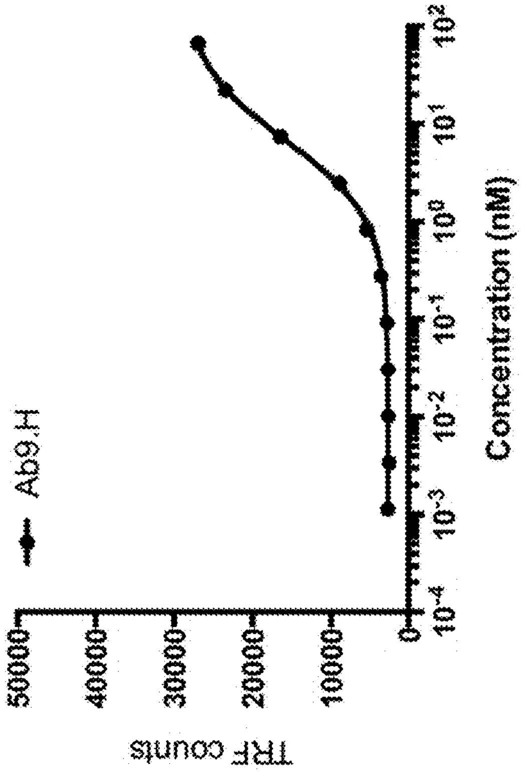
Figure 19H:
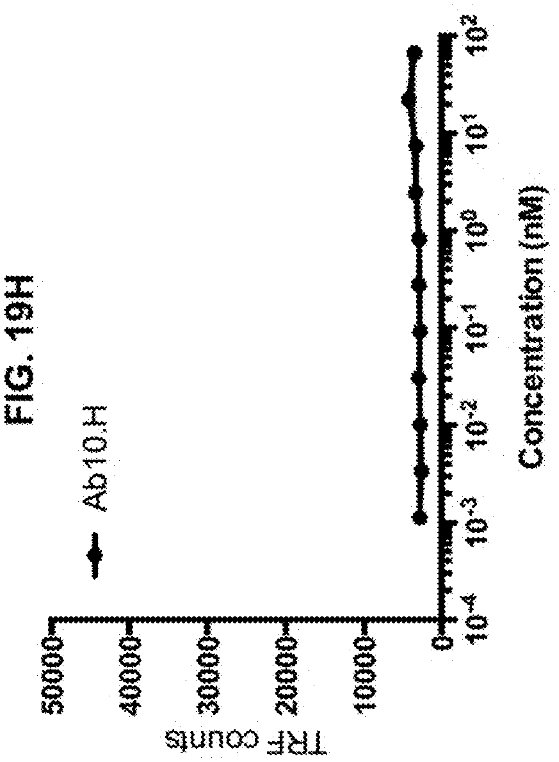
Figure 19G:
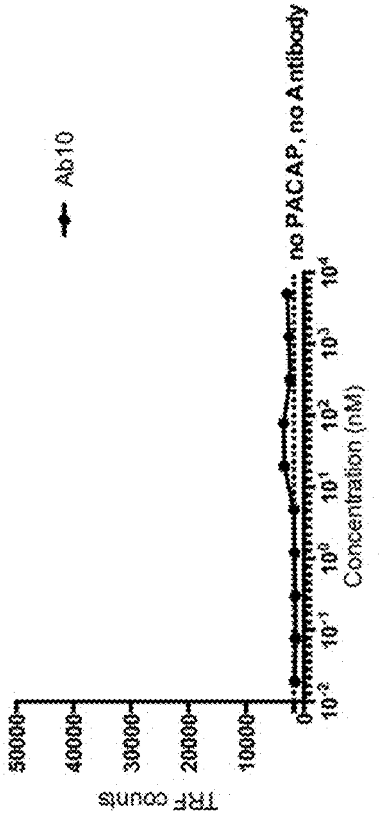
Figure 19J:
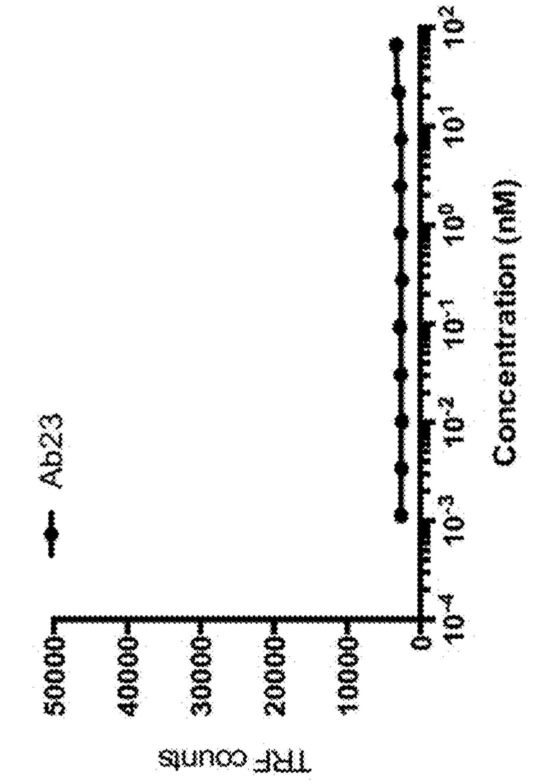
Figure 19I:
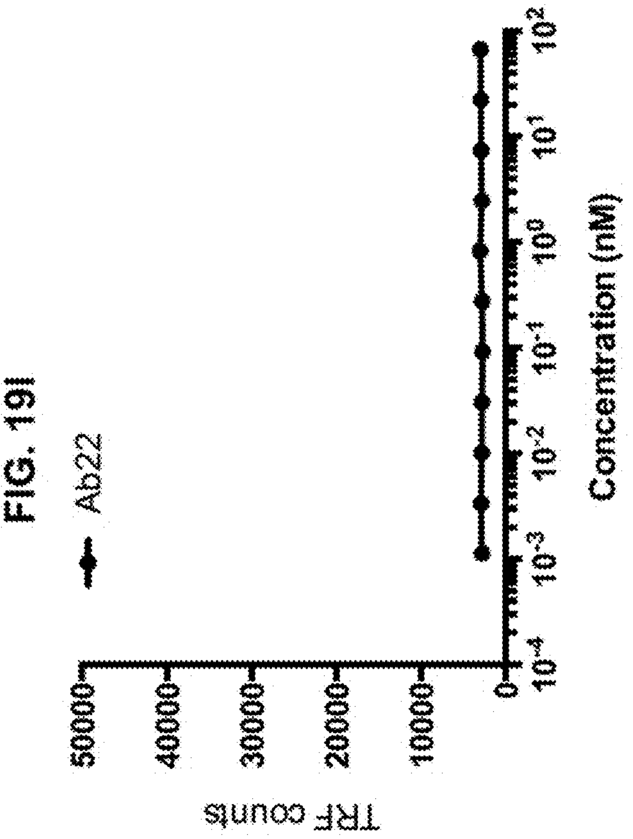

The mice were administered 30 mg/kg of either anti-PACAP antibody or control IgG antibody (negative control antibody having the same framework as the tested antibodies and that recognizes digoxigenin) by i.p. injection. The mice were then returned to their home cage to rest for one day (24 hours) prior to testing. The mice were then administered 0.6 mg/kg PACAP or vehicle by i.p. injection and rested for 30 minutes. The mice were then placed in the light/dark chamber for 30 minutes (FIG. 16 and FIG. 18, "Treatment"). After each mouse was exposed to the light/dark chamber, the light/dark chamber and components were cleaned with germicidal wipes and dried. About 5 to 7 minutes after a mouse was placed in the light/dark chamber, the next mouse to be tested was injected with PACAP or vehicle, as described above. This interval was approximately the amount of time required to clean the light/dark chamber between experiments.

Motility Measurements

Motility was measured at 5 minute intervals over the 30 minute testing period as described in Kaiser et al., *J. Neurosci.,* 2012. Briefly, the number of vertical movements, such as rearing, ambulatory distance (cm, the total distance traveled during ambulatory movement status), transitions, and resting (percentage of time spent breaking no new beams), were measured by light beam. All motility parameters were normalized to the time spent in each zone to account for different amount of time spent in that zone; thus, the raw value for each parameter was divided by the time spent in that zone during the 5 min interval. Time spent in each chamber was analyzed using GraphPad Prism software (GraphPad Software, San Diego, CA), and reported as mean±standard error of the mean ("SEM"). Comparison was calculated by two-way repeated measure ANOVA, with Bonferroni's multiple-comparison test for post-hoc analysis.

Mice were excluded based on three criteria: (1) after the first two exposures to the box the baseline time in light was analyzed and any mouse that spent+/−one standard deviation of mean time in light at baseline was removed from the experiment and not given drug treatment, (2) mice were excluded from analysis if they were identified as statistical outliers (box plot, 10-90%), and (3) mice were excluded if they moved less than 10% of the time (combined light and dark).

Figure 17:
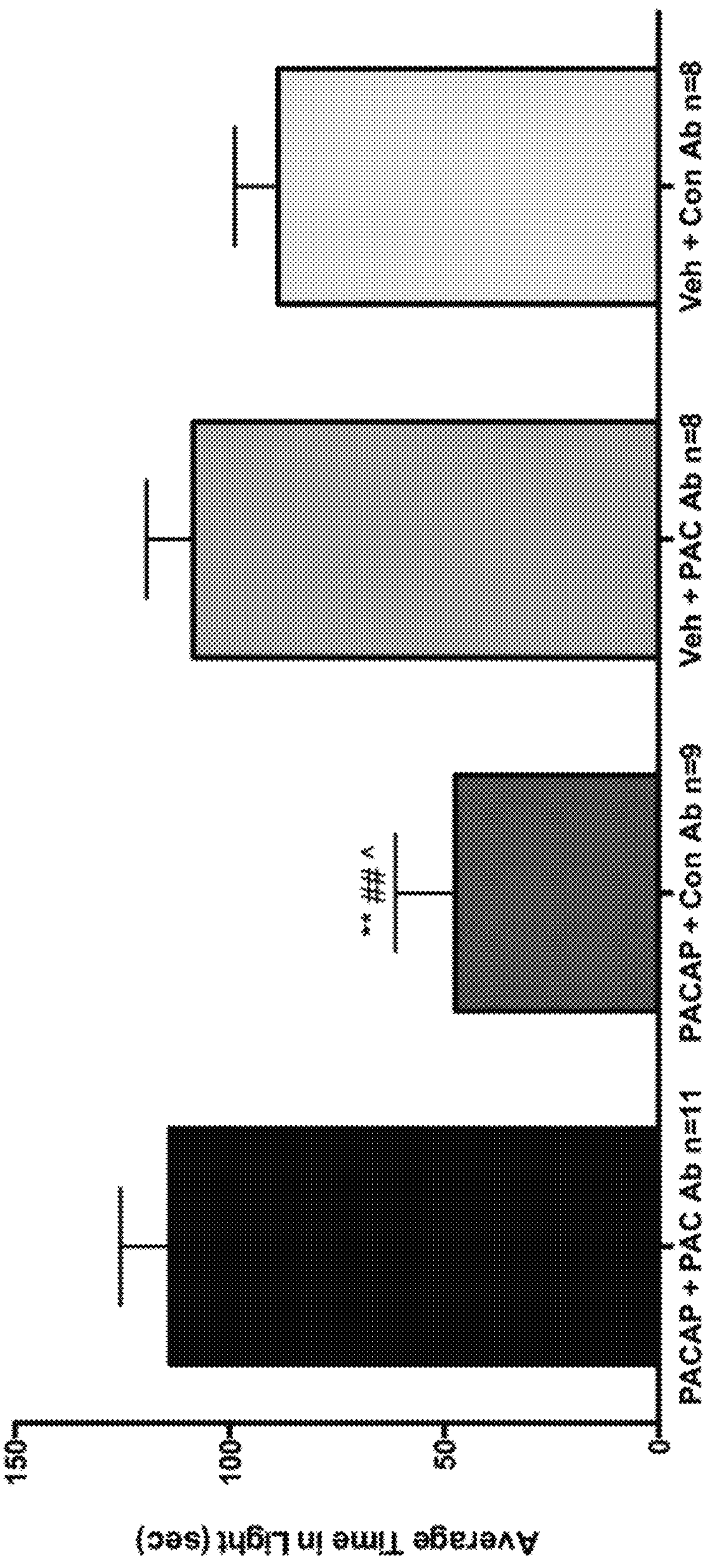
FIG. 17 provides representative data showing the in vivo effect of the administration of PACAP and anti-PACAP antibody Ab1.H in a rodent photophobia animal model, which detects the average amount of time treated animals (mice) spend in the light compared to appropriate control animals obtained following the protocol in Example 11 infra.

In two experiments comparing the response of mice administered either antibody Ab1.H or Ab10.H to control IgG, the results indicate that mice administered either PACAP antibody Ab1.H or Ab10.H spent more time in light as compared to IgG control mice. FIG. 16 shows that mice behaved normally and similarly in both baseline measurements. On the other hand, the data provided in FIG. 16 show that mice treated with control IgG antibody and then PACAP spent statistically less time in light (squares) than mice administered anti-PACAP antibody Ab1.H and then PACAP (circles). (See, FIG. 16, "Treatment"). The data provided in FIG. 18 also show that mice behaved normally and similarly in baseline measurements. On the other hand, the data provided in FIG. 18 show that mice treated with control IgG antibody and then PACAP spent statistically less time in light (triangles) than mice administered anti-PACAP antibody Ab10.H and then PACAP (inverted triangles). (See, FIG. 18, "Treatment"). Time between each measurement was three days. The mean±SEM is provided for each 5-minute interval. Mice administered vehicle only behaved as normal controls. Data provided in FIG. 17 shows that administration of either anti-PACAP antibody Ab1.H, or control IgG, and vehicle ("Veh+PAC Ab" and "Veh+Con Ab," respectively) did not markedly alter mouse behavior. FIG. 17 also shows that the average time of the mouse in light decreased when PACAP and control IgG were administered ("PACAP+Con Ab"), whereas mice administered anti-PACAP antibody Ab1.H and PACAP exhibited normal, non-light-sensitive behavior ("PACAP+PAC Ab").

Example 12: Epitope Mapping of Anti-PACAP Antibodies

In order to determine the epitopes contained within PACAP to which the anti-PACAP antibodies and antigen binding fragments thereof of the invention bind, alanine scanning experiments were used. To perform these experiments, PACAP peptides were synthesized with a single point mutation in each position replacing the native amino acid with an Alanine ("Ala"), and the consequences of a single point mutation as it relates to binding affinity of PACAP and an antibody were measured.

Since an alanine residue already occupies positions 18, 24, and 25 of wild-type PACAP, according to convention, these Ala residues were replaced with Valine ("Val") to determine the possible effects of the removal of the alanine at these positions on the binding of the subject anti-PACAP antibodies to PACAP. Per the usual convention these Ala mutants were labeled according to the position in PACAP 1-38 followed by the letter code for the substituted amino acid, e.g., 10A indicates PACAP 1-38 substituted with alanine at amino acid position 10. Binding of monoclonal antibodies for human PACAP and each mutant peptide was detected using SPR on the PROTEON™ XRP36 (Bio-Rad Laboratories, Hercules, CA). Samples and sample controls were immobilized onto a PROTEON™ GLC sensor chip (Bio-Rad Laboratories, Hercules, CA) at a single density using standard amine coupling. The running buffer used for immobilization was DPBS/modified (HYCLONE™, GE Healthcare Life Sciences, Marlborough, MA) and immobilization was conducted at 25° C. The PROTEON™ GLC sensor chip (Bio-Rad Laboratories, Hercules, CA) was initialized and pre-conditioned per the manufacturer's protocol (bi-directional injections of 0.5% SDS, 50 mM NaOH, 100 mM HCl).

The immobilization process was performed step-wise to ensure a unique antibody on the spots of the PROTEON™ Chip (Bio-Rad Laboratories, Hercules, CA). The surface of the chip was activated with a 1:1 mixture of 1-ethyl-3-(3-dimethylaminopropyl)carbodiimide/N-hydroxysuccinimide ("EDAC/NHS") and flow rate of 30 μL/min×5 minutes. Antibody samples were previously dialyzed or exchanged to 10 mM HEPES 150 mM NaCl pH 7.2, and the antibody concentration was quantified using a NANODROP™ 2000 spectrophotometer (Thermo Fisher Scientific, Waltham, MA). The immobilization targeted 2000-3000 response units ("RU"). Antibody samples (5 μg/ml) in 10 mM sodium acetate, pH 5.5, were flowed at 30×4 minutes. Deactivation was achieved at a flow rate of 30 μL/min for 5 minutes using 0.3 M ethanolamine concomitantly with the next activation.

Following immobilization, the running buffer was changed to 1×PBST (4.3 mM sodium phosphate, 1.4 mM potassium phosphate, 135 mM NaCl, 2.7 mM KCl, 0.05% TWEEN®) with 0.2 M arginine HCl (to reduce non-specific binding), BSA (0.2 mg/ml, as a carrier) and PROCLIN300® (0.005% as a preservative, Sigma Aldrich, St. Louis, MO) and the chip surface was allowed to re-equilibrate with an injection of new running buffer. Stock solutions of human PACAP peptide (1-38) and alanine/valine mutant peptides (Molecular Weight(s): 4.5 kD) at a concentration of 1 mg/ml were added to the running buffer to final concentrations of 0.45 μg/ml (100 nM). These mixtures were then used to query individual spots on the chip surface with flow rates of 100 μL/min×2 minutes and allowed to dissociate for 600 seconds. Chip surfaces were regenerated between analytes by the addition of 0.85% phosphoric acid.

Each of antibodies Ab1, Ab2, Ab13, Ab14, Ab15, Ab16, Ab17, Ab18, Ab19, Ab5, Ab7, Ab11, Ab12, Ab4, Ab3, Ab6, Ab8, Ab9, Ab22, and Ab23 were examined under the same conditions as herein described Sensorgrams representing affinity data of mutant peptide binding to a panel of antibodies were assessed using multiple parameters. A visual inspection was first performed for each sensorgram to assess apparent maximal response ("$R_{max}$") relative to the wild-type PACAP peptide (1-38). Second, a visual inspection of the dissociation phase was performed with an emphasis on the curve shape relative to the wild-type PACAP peptide. Off-rates (dissociation rates) were calculated for wild-type PACAP peptide and the binding of each mutant peptide to the panel of antibodies. Finally, as a control experiment to confirm the integrity of each peptide variant (wild-type or mutant), the binding affinity of each member of the peptide library was individually determined for each member of a panel of antibodies that were known to bind wild-type PACAP, to ensure that each Ala mutant PACAP peptide exhibited binding affinity that was similar to the binding affinity of wild-type PACAP peptide. Collective assessment of all described parameters identified PACAP amino acid residues important for PACAP/antibody binding.

Binding and dissociation data were obtained for binding of antibodies Ab1, Ab2, Ab13, Ab14, Ab15, Ab16, Ab17, Ab18, Ab19, Ab5, Ab7, Ab11, Ab12, Ab4, Ab3, Ab6, Ab8, Ab9, Ab22, and Ab23 to wild-type PACAP and PACAP mutants.

The PACAP residue positions contributing most to antibody binding were interpreted to jointly comprise the epitopes bound by each antibody. Based on data obtained in these alanine scanning studies, the epitopes bound by each antibody were concluded to comprise the following residues:

(i) Ab1: residues 5, 6, 8, 10, and 13 of human PACAP;
(ii) Ab2: residues 5, 6, 8, 9, 10, 13, and 14 of human PACAP;
(iii) Ab13: residues 6, 8, 9, 10, and 13 of human PACAP;
(iv) Ab14: residues 5, 6, 8, 9, 10, and 13 of human PACAP;
(v) Ab15: residues 5, 6, 8, 9, 10, 12, 13, and 14 of human PACAP;
(vi) Ab16: residues 5, 6, 8, 10, and 13 of human PACAP;
(vii) Ab17: residues 5, 6, 8, 10, and 13 of human PACAP;
(viii) Ab18: residues 5, 6, 8, 9, 10, 12, and 13 of human PACAP;
(ix) Ab19: residues 4, 5, 6, 8, 9, 10, 12, 13, 14, and 17 of human PACAP;
(x) Ab5: residues 3, 4, 5, 6, 7, 10, 13, and 14 of human PACAP;
(xi) Ab7: residues 6, 8, 10, 11, 13, 14, and 18 of human PACAP;
(xii) Ab11: residues 6, 8, 10, 11, 13, 14, 18, and 22 of human PACAP;
(xiii) Ab12: residues 6, 8, 10, 11, 13, 14, and 18 of human PACAP;
(xiv) Ab4: residues 8, 9, 10, 13, 14, 17, and 18 of human PACAP;
(xv) Ab3: residues 8, 9, 10, 11, 12, 13, 14, 17, and 21 of human PACAP;
(xvi) Ab6: residues 5, 6, 9, 10, 12, 13, 14, and 17 of human PACAP;
(xvii) Ab8: residues 7, 10, 13, and 14 of human PACAP;
(xviii) Ab9: residues 7, 10, 12, 13, 14, and 17 of human PACAP;
(xix) Ab22: residues 22, 23, 27, 28, and 31 of human PACAP; and
(xx) Ab23: residues 12, 20, 23, 24, 26, 27, and 28 of human PACAP.

It was further noted based on the alanine scanning experimental results that the affinity of each of antibodies Ab1, Ab2, Ab13, Ab14, Ab15, Ab16, Ab17, Ab18, Ab19, Ab5, Ab7, Ab11, Ab12, Ab4, Ab3, Ab6, Ab8, and Ab9 for PACAP involves or depends on residues 10 and/or 13 of human PACAP, and in some instances involves or further depends on residues 8 and/or 14.

Additionally, it was observed that the affinity of each of antibodies Ab22 and Ab23 to PACAP involves or requires specific amino acid residues that are present in human wild-type PACAP38, but which are not present in human wild-type PACAP27, e.g., residues 28 or 31 of PACAP38.

With respect to the foregoing alanine scanning results humanized variants of the subject anti-PACAP antibodies should interact with the identical or substantially identical residues of human PACAP as humanization should not appreciably impact the specificity of the binding of the humanized anti-PACAP antibody to human PACAP compared to the parent (unhumanized) antibody. Particularly, Ab3.H should interact with the same residues on human PACAP as Ab3, Ab4.H should interact with the same residues on human PACAP as Ab4, Ab5.H should interact with the same residues on human PACAP as Ab5, Ab9.H should interact with the same residues on human PACAP Ab9, and Ab12.H should interact with the same residues on human PACAP as Ab12.

Antibodies which bind to the same or overlapping epitopes on human PACAP as the subject antibodies may be produced and identified using method described herein. It is reasonable to anticipate that antibodies which bind to the same or overlapping epitope as any of the antibodies identified herein will likely possess similar biological activity absent a meaningful difference in binding kinetics. Particularly, such antibodies should antagonize one or more of the biological effects elicited by PACAP analogously to the exemplified anti-PACAP antibodies which bind these epitopes. Additionally, antibodies that bind to these same or overlapping epitopes, or a subset of residues thereof, are anticipated to mimic the binding characteristics of the subject antibodies. For example such antibodies are expected to selectively bind to PACAP and not bind or bind with much less affinity (weaker) to VIP or other peptides within this family of neuropeptides.

Having fully described and enabled the invention, the invention is further described by the claims that follow.

What is claimed is:

1. A method of screening for an antibody or antigen binding fragment suitable for use in treating or preventing Pituitary Adenylate Cyclase-Activating Peptide (PACAP)-associated photophobia or light aversion, or precluding the onset of PACAP-associated photophobia or light aversion, in a subject in need thereof, which method comprises:

(i) providing at least one first test subject and at least one second test subject;

(ii) administering PACAP to the at least one first test subject and the at least one second test subject;

(iii) further administering to the at least one first test subject one or more anti-PACAP antibodies, or an antigen binding fragment of any of the foregoing, wherein said one or more antibodies or antigen binding fragments includes one comprising a variable heavy chain polypeptide having the heavy chain CDRs1-3 of SEQ ID NO: 44, 46 and 48 respectively; and a variable light chain polypeptide having the light chain CDRs1-3 of SEQ ID NO: 64, 66 and 68 respectively; or one comprising the variable heavy chain polypeptide of SEQ ID NO: 42 and the variable light chain polypeptide of SEQ ID NO: 62;

(iv) comparing the response of the at least one first test subject and the at least one second test subject to light; and (v) based on this comparison, identifying one or more antibodies or antigen binding fragments thereof that yield a decreased light aversion or decreased photophobia in the at least one first test subject as compared with the at least one second test subject, thereby identifying an antibody or antigen binding fragment suitable for use in treating or preventing PACAP-associated photophobia or light aversion, or precluding the onset of PACAP-associated photophobia or light aversion in a subject in need thereof; or which method comprises:

(i) providing at least one first test subject and at least one second test subject;

(ii) administering to the at least one first test subject one or more anti-PACAP antibodies, or an antigen binding fragment of any of the foregoing, wherein said one or more antibodies or antigen binding fragments thereof includes one comprising a variable heavy chain polypeptide having the heavy chain CDRs1-3 of SEQ ID NO: 44, 46 and 48 respectively; and a variable light chain polypeptide having the light chain CDRs1-3 of SEQ ID NO: 64, 66 and 68 respectively; or one comprising the variable heavy chain polypeptide of SEQ ID NO: 42 and the variable light chain polypeptide of SEQ ID NO: 62;

(iii) administering PACAP to the at least one first test subject and the at least one second test subject;

(iv) comparing the response of the at least one first test subject and the at least one second test subject to light; and (v) based on this comparison, identifying antibodies or antigen binding fragments that yield decreased photophobia or decreased light aversion in the at least one first test subject as compared with the at least one second test subject, identifying an antibody or antigen binding fragment suitable for use in treating or preventing PACAP-associated photophobia or light aversion, or identifying an antibody or antigen binding fragment suitable for precluding the onset of PACAP-associated photophobia or light aversion, in a subject to be treated in need thereof.

2. The method of claim 1, further comprising one or more of the following:

(i) further confirming in a human subject, the efficacy of the one or more antibodies or antigen binding fragments for inhibiting PACAP-associated photophobia or light aversion, or precluding the onset of PACAP-associated photophobia or light aversion;

(ii) the at least one first test subject and/or the at least one second test subject is a mammal;

(iii) the at least one first test subject and/or at least one second test subject is (i) a mouse, monkey, rabbit, human, rat, guinea pig, dog, or hamster, wherein optionally the monkey is a macaque, marmoset, tamarin, spider monkey, owl monkey, vervet monkey, squirrel monkey, or baboon; or (ii) a mouse, optionally a CD1 mouse;

(iv) the identified antibody or antigen binding fragment thereof specifically binds PACAP; and (v) the method further comprises adapting the identified antibody or antigen binding fragment for use in treating a subject who suffers from one or more of migraine, hemiplegic migraines, cluster headaches, migrainous neuralgia, chronic headaches, tension headaches, secondary headaches due to an underlying structural problem in the head or neck, cranial neuralgia, sinus headaches, allergy-induced headaches, headache, or other migraine condition.

3. The method of claim 1, wherein (i) the subject to be treated has an ocular disorder associated with photophobia selected from one or more of achromatopsia, aniridia, photophobia caused by an anticholinergic drug, aphakia (absence of the lens of the eye), buphthalmos (abnormally narrow angle between the cornea and iris), cataracts, cone dystrophy, congenital abnormalities of the eye, viral conjunctivitis ("pink eye"), corneal abrasion, corneal dystrophy, corneal ulcer, disruption of the corneal epithelium, ectopia lentis, endophthalmitis, eye trauma caused by disease, injury, infection, optionally chalazion, episcleritis, glaucoma, keratoconus, optic nerve hypoplasia, hydrophthalmos, congenital glaucoma iritis, optic neuritis, pigment dispersion syndrome, pupillary dilation (naturally or chemically induced), retinal detachment, scarring of the cornea or sclera, and uveitis; or (ii) the subject to be treated has a nervous-system-related or neurological condition associated with photophobia selected from one or more of autism spectrum disorders, chiari malformation, dyslexia, encephalitis including myalgic encephalomyelitis (chronic fatigue syndrome), meningitis, subarachnoid hemorrhage, tumor of the posterior cranial fossa, ankylosing spondylitis, albinism, ariboflavinosis, long term use of benzodiazepines, withdrawal from benzodiazepines, chemotherapy, chikungunya infection, cystinosis, Ehlers-Danlos syndrome, hangover, influenza infection, infectious mononucleosis, magnesium deficiency, mercury poisoning, migraine, rabies, and tyrosinemia type II (Richner-Hanhart syndrome); or (iii) the subject to be treated has a photophobia-associated disorder selected from one or more of migraine (with or without aura), iritis, uveitis, meningitis, depression, bipolar disorder, cluster headache or another trigeminal autonomic cephalalgia or blepharospasm, depression, post-traumatic stress syndrome (PTSD) traumatic brain injury, and agoraphobia; or (iv) the at least one first subject and/or the at least one second subject suffers from migraine headaches.

4. The method of claim 1, wherein (i) the one or more antibodies or antigen binding fragments thereof are for use in combination with another active agent for treating migraine, or are for use as a monotherapy;

(ii) the anti-PACAP antibody or fragment thereof comprises:

an immunoglobulin variable heavy chain having the CDR1 sequence of SEQ ID NO: 44; a CDR2 sequence of SEQ ID NO: 46; and a CDR3 sequence of SEQ ID NO: 48; and an immunoglobulin variable light chain having the CDR1 sequence of SEQ ID NO: 64; a CDR2 sequence of SEQ ID NO: 66; and a CDR3 sequence of SEQ ID NO: 68; and/or (iii) the antibody or fragment thereof is a humanized antibody or fragment thereof;

(iv) the antibody or fragment thereof is a chimeric antibody or fragment thereof;

(v) the antibody or fragment thereof comprises a single chain antibody or fragment thereof;

(vi) the chimeric antibody or fragment thereof comprises a human Fc, optionally a human Fc is derived from IgG1, IgG2, IgG3, or IgG4;

(vii) the anti-PACAP antibody or fragment thereof binds to PACAP with a binding affinity ($K_D$) of less than or equal to $5\times10^{-5}$ M, $10^{-5}$ M, $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, or $10^{-13}$ M, as determined by ELISA, bio-layer interferometry ("BLI"), kinetics exclusion assay, or surface plasmon resonance at 25° C. or 37° C.;

(viii) the anti-PACAP antibody or fragment thereof binds to PACAP with a KD that is less than about 100 nM, less than about 40 nM, less than about 1 nM, less than about 100 pM, less than about 50 pM, or less than about 25 pM;

(ix) the anti-PACAP antibody or fragment thereof binds to PACAP with a KD that is between about 10 pM and about 100 pM;

(x) the antibody or fragment thereof is entirely non-glycosylated, or lacks N-glycosylation, or contains only mannose residues;

(xi) the antibody or fragment thereof contains an Fc region that is modified to alter effector function, half-life, proteolysis, and/or glycosylation;

(xii) the anti-PACAP antibody or fragment thereof specifically binds to circulating soluble PACAP molecules in vivo;

(xiii) the anti-PACAP antibody or fragment thereof specifically binds to PACAP27 and/or PACAP38;

(xiv) the affinity of said anti-PACAP antibody or fragment thereof for PACAP is at least 10-fold, 30-fold, 100-fold, 300-fold, 1000-fold, 3000-fold, 10000-fold, 30000-fold, 100000-fold, 300000-fold, 1000000-fold, 3000000-fold, 10000000-fold, 30000000-fold or more stronger than the affinity of said anti-PACAP antibody and antigen binding fragment to VIP;

(xv) the anti-PACAP antibody or fragment thereof (a) inhibits or neutralizes at least one biological effect elicited by PACAP; (b) neutralizes or inhibits PACAP activation of at least one of PAC1-R, VPAC1-R and/or VPAC2-R; (c) neutralizes or inhibits PACAP activation of each of PAC1-R, VPAC1-R and VPAC2-R; (d) neutralizes or inhibits PACAP activation of PAC1-R; (e) is capable of inhibiting PACAP binding to at least one of PAC1-R, VPAC1-R and/or VPAC2-R; (f) is capable of inhibiting PACAP binding to each of PAC1-R, VPAC1-R and/or VPAC2-R; (g) is capable of inhibiting PACAP binding to PAC1-R; and/or (h) inhibits PACAP-induced cAMP production;

(xvi) the anti-PACAP antibody or fragment thereof inhibits the association of PACAP with one or more PACAP receptors including PAC-1R, VPAC1-R, and/or VPAC2-R;

(xvii) the antibody or fragment thereof is administered intramuscularly, subcutaneously, intravenously, rectally, by infusion, orally, transdermally, or by inhalation;

(xviii) the antibody or fragment thereof is administered intravenously;

(xix) the antibody or fragment thereof is administered with an additional therapeutic agent or regimen selected from anti-histamines, anti-inflammatory agents, and antibiotics;

(xx) the antibody or fragment thereof is directly or indirectly attached to a detectable label or therapeutic agent; or (xxi) the antibody or fragment thereof further comprises an effector moiety optionally a detectable moiety or a functional moiety, further optionally wherein the detectable label is a fluorescent dye, an enzyme, a substrate, a bioluminescent material, a radioactive material, or a chemiluminescent material and the functional moiety is streptavidin, avidin, biotin, a cytotoxin, a cytotoxic agent, or a radioactive material.

5. A method of assessing the potential in vivo efficacy of one or more candidate anti-Pituitary Adenylate Cyclase-Activating Peptide (PACAP) antibodies, or antigen binding fragments thereof, for treating PACAP-associated photophobia or light aversion, comprising determining whether the one or more antibodies or fragments thereof inhibit or diminish light aversion behavior in a first rodent administered PACAP, as compared to a second rodent administered PACAP in the presence of said one or more candidate anti-PACAP antibodies or fragments thereof, wherein said one or more anti-PACAP antibodies or fragments thereof comprise an anti-PACAP antibody or antigen binding fragment thereof which comprises a variable heavy chain polypeptide having the heavy chain CDRs1-3 of SEQ ID NO: 44, 46 and 48 respectively; and a variable light chain polypeptide having the light chain CDRs1-3 of SEQ ID NO: 64, 66 and 68 respectively; or comprise the variable heavy chain polypeptide of SEQ ID NO: 42 and the variable light chain polypeptide of SEQ ID NO: 62.

6. The method of claim 5, wherein this assay is used to assess whether the one or more anti-PACAP antibodies or fragments thereof may be effective for treatment of a neurological condition characterized by increased PACAP levels.

7. The method of claim 5, wherein this assay is used to assess whether the one or more anti-PACAP antibodies or fragments thereof may be effective for treatment of migraine, menstrual migraine, or chronic migraine.

8. The method of claim 5, wherein this assay is used to assess whether the one or more anti-PACAP antibodies or fragments thereof may be effective for treatment of migraines (with or without aura.

9. The method of claim 5, which further comprises administering an active agent to said first and/or second rodent selected from: ibuprofen, naproxen, sumatriptan, paracetamol/acetaminophen, caffeine, a triptan, a corticosteroid, and combinations thereof.

* * * * *